US010450273B2

(12) United States Patent
Azimioara et al.

(10) Patent No.: US 10,450,273 B2
(45) Date of Patent: Oct. 22, 2019

(54) N-(PYRIDIN-2-YL)PYRIDINE-SULFONAMIDE DERIVATIVES AND THEIR USE IN THE TREATMENT OF DISEASE

(71) Applicant: Novartis AG, Basel (CH)

(72) Inventors: Mihai Azimioara, La Jolla, CA (US); Bei Chen, San Diego, CA (US); Robert Epple, Solana Beach, CA (US); Ayako Honda, Cambridge, MA (US); Philip Lam, Somerville, MA (US); Hasnain Ahmed Malik, Boston, MA (US); Casey Jacob Nelson Mathison, San Diego, CA (US); Truc Ngoc Nguyen, San Diego, CA (US); Victor Ivanovich Nikulin, Carlsbad, CA (US); Sejal Patel, Cambridge, MA (US); Dean Paul Phillips, San Diego, CA (US); Rodrigo A. Rodriguez, San Diego, CA (US); Baogen Wu, San Diego, CA (US); Xuefeng Zhu, San Diego, CA (US)

(73) Assignee: Novartis AG, Basel (CH)

( * ) Notice: Subject to any disclaimer, the term of this patent is extended or adjusted under 35 U.S.C. 154(b) by 2 days.

(21) Appl. No.: 15/688,089

(22) Filed: Aug. 28, 2017

(65) Prior Publication Data
US 2018/0072673 A1 Mar. 15, 2018

Related U.S. Application Data

(60) Provisional application No. 62/380,659, filed on Aug. 29, 2016.

(51) Int. Cl.
| | |
|---|---|
| *C07D 213/76* | (2006.01) |
| *C07D 401/14* | (2006.01) |
| *A61K 31/444* | (2006.01) |
| *C07D 401/12* | (2006.01) |
| *A61K 31/4545* | (2006.01) |
| *A61K 31/46* | (2006.01) |
| *A61K 31/496* | (2006.01) |
| *A61K 31/4985* | (2006.01) |
| *A61K 31/5377* | (2006.01) |
| *A61K 45/06* | (2006.01) |
| *C07D 405/14* | (2006.01) |
| *C07D 487/04* | (2006.01) |
| *C07D 487/10* | (2006.01) |
| *C07D 491/107* | (2006.01) |
| *C07D 493/08* | (2006.01) |

(52) U.S. Cl.
CPC ......... *C07D 213/76* (2013.01); *A61K 31/444* (2013.01); *A61K 31/4545* (2013.01); *A61K 31/46* (2013.01); *A61K 31/496* (2013.01); *A61K 31/4985* (2013.01); *A61K 31/5377* (2013.01); *A61K 45/06* (2013.01); *C07D 401/12* (2013.01); *C07D 401/14* (2013.01); *C07D 405/14* (2013.01); *C07D 487/04* (2013.01); *C07D 487/10* (2013.01); *C07D 491/107* (2013.01); *C07D 493/08* (2013.01)

(58) Field of Classification Search
CPC .................................................. C07D 213/76
See application file for complete search history.

(56) References Cited

U.S. PATENT DOCUMENTS

| | | | |
|---|---|---|---|
| 2004/0204422 | A1 | 10/2004 | Braje et al. |
| 2006/0074237 | A1 | 4/2006 | Amrein et al. |
| 2006/0270686 | A1 | 11/2006 | Kelly et al. |
| 2007/0099938 | A1 | 5/2007 | Ohmoto et al. |
| 2008/0280891 | A1 | 11/2008 | Kelly et al. |
| 2009/0197859 | A1 | 8/2009 | Collantes |
| 2011/0118248 | A1 | 5/2011 | Chen et al. |

(Continued)

FOREIGN PATENT DOCUMENTS

| | | |
|---|---|---|
| CN | 104844566 A | 8/2015 |
| WO | 96/09818 A1 | 4/1996 |

(Continued)

OTHER PUBLICATIONS

Quon, Bradley. "New and emerging targeted therapies for cystic fibrosis." BMJ. (2016), vol. 352, pp. 1-29.*

(Continued)

*Primary Examiner* — Andrew D Kosar
*Assistant Examiner* — John S Kenyon
(74) *Attorney, Agent, or Firm* — Daniel E. Raymond; Genomics Institute of the Novartis Research Foundation

(57) ABSTRACT

The invention relates to heterocyclic compounds of the formula (I)

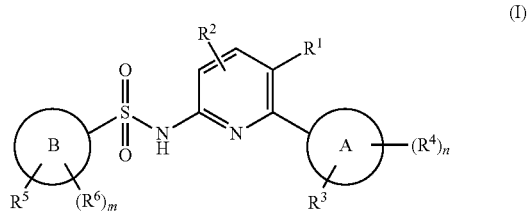

in which all of the variables are as defined in the specification; capable of modulating the activity of CFTR. The invention further provides a method for manufacturing compounds of the invention, and its therapeutic uses. The invention further provides methods to their preparation, to their medical use, in particular to their use in the treatment and management of diseases or disorders including Cystic fibrosis and related disorders.

43 Claims, No Drawings

(56) References Cited

U.S. PATENT DOCUMENTS

| | | |
|---|---|---|
| 2012/0165345 A1 | 6/2012 | Bretschneider et al. |
| 2016/0095858 A1 | 4/2016 | Miller et al. |
| 2017/0101395 A1 | 4/2017 | Zhang et al. |

FOREIGN PATENT DOCUMENTS

| | | | |
|---|---|---|---|
| WO | 98/024782 A2 | 6/1998 | |
| WO | 2003004472 A1 | 1/2003 | |
| WO | 2003087044 A2 | 10/2003 | |
| WO | 2004041789 A1 | 5/2004 | |
| WO | 2004108690 A1 | 12/2004 | |
| WO | 2005097750 A1 | 10/2005 | |
| WO | 2005103022 A1 | 11/2005 | |
| WO | 2006020830 A1 | 2/2006 | |
| WO | 2006024779 A1 | 3/2006 | |
| WO | 2006048331 A1 | 5/2006 | |
| WO | 2006051270 A1 | 5/2006 | |
| WO | 2006106423 A2 | 10/2006 | |
| WO | 2007021941 A2 | 2/2007 | |
| WO | 2007023114 A1 | 3/2007 | |
| WO | 2007085718 A1 | 8/2007 | |
| WO | 2007129044 A1 | 11/2007 | |
| WO | 2008008375 A2 | 1/2008 | |
| WO | 2008022286 A2 | 2/2008 | |
| WO | 2008028937 A1 | 3/2008 | |
| WO | 2008033455 A2 | 3/2008 | |
| WO | 2008157500 A1 | 12/2008 | |
| WO | 2009011850 A2 | 1/2009 | |
| WO | 2009152356 A2 | 12/2009 | |
| WO | 2010029300 A1 | 3/2010 | |
| WO | 2010100475 A1 | 9/2010 | |
| WO | 2010133312 A1 | 11/2010 | |
| WO | 2011082400 A2 | 7/2011 | |
| WO | 2012004293 A2 | 1/2012 | |
| WO | 2012085650 A1 | 6/2012 | |
| WO | 2012125904 A1 | 9/2012 | |
| WO | 2014028968 A1 | 2/2014 | |
| WO | 2014031928 A2 | 2/2014 | |
| WO | 2014160478 A1 | 10/2014 | |
| WO | 2014181287 A1 | 11/2014 | |
| WO | 2015097122 A1 | 7/2015 | |
| WO | 2015138934 A1 | 9/2015 | |
| WO | 2016193812 A1 | 12/2016 | |
| WO | WO-2017137535 A1 * | 8/2017 | ........... C07D 213/76 |
| WO | 2017173274 A1 | 10/2017 | |

OTHER PUBLICATIONS

American Lung Association. "Preventing COPD". © 2018. Available from: < http://www.lung.org/lung-health-and-diseases/lung-disease-lookup/copd/symptoms-causes-risk-factors/preventing-copd.html >.*

Mayo Clinic. "COPD". © 2018. Available from: < https://www.mayoclinic.org/diseases-conditions/copd/diagnosis-treatment/drc-20353685 >.*

Mayo Clinic. "Cystic Fibrosis." © 2018. Available from: < https://www.mayoclinic.org/diseases-conditions/cystic-fibrosis/symptoms-causes/syc-20353700 >.*

American Academy of Allergy, Asthma, and Immunology. "Asthma." © 2018. Available from: < http://www.aaaai.org/conditions-and-treatments/asthma >.*

Mayo Clinic. "Bronchitis." © 2018. Available from: < https://www.mayoclinic.org/diseases-conditions/bronchitis/diagnosis-treatment/drc-20355572 >.*

Yu, Xiaoqiang et al. "Intermolecular Amidation of Quinoline N-oxides with Arylsulfonamides under Metal-Free Conditions." Organic Letters, Nov. 2, 2017, 19(22), pp. 6088-6091.

Wu, Yufeng et al. "Polysubstituted 2-Aminopyrrole Synthesis via Gold-Catalyzed Intermolecular Nitrene Transfer from Vinyl Azide to Ynamide: Reaction Scope and Mechanistic." The Journal of Organic Chemistry, Oct. 27, 2015, 80 (22), pp. 11407-11416.

Waring, Michael J. et al. "Potent, selective small molecule inhibitors of type III phosphatidylinositol signaling cascade and cancer cell proliferation." Chemical Communications, (2014), 50(40), pp. 5388-5390.

Al-Issa, Sihan AbdulRahman. "Synthesis of a New Series of Pyridine and Fused Pyridine Derivatives." Molecules, Sep. 11, 2012, 17, pp. 10902-10915.

Braker, William et al. "Substituted Sulfanilamidopyrimidines." Journal of the American Chemical Society, (1947), 69, pp. 3072-3078.

Van Dyke, H.B. et al. "The Pharmacological Behavior of Some Derivatives of Sulfadiazine." J. Pharmacol. Exp. Ther. Jan. 1945, 83, pp. 203-212.

Siddiqui, Shadab Miyan et al. "Synthesis, characterization of 4,6-disubstituted aminopyrimidines and their sulphonamide derivatives as anti-amoebic agents." Medicinal Chemistry Research (2014), 23(6), pp. 2976-2984.

Bhat, Abdul Roouf et al. "Synthesis, Characterization, and Anti-Amoebic Activity of N-(Pyrimidin-2-yl) benzenesulfonamide Derivatives." Chemistry & Biodiversity (2013), 10(12), pp. 2267-2277.

Parmar, Kokila et al. "Synthesis, characterization and biological evaluation of some novel heterocyclic compounds having sulphamido moiety." Pharma Chemica (2010), 2(5), pp. 358-369.

Chen, Chien-Shu et al. "Structure-Based Discovery of Triphenylmethane Derivatives as Inhibitors of Hepatitis C Virus Helicase." Journal of Medicinal Chemistry (2009), 52(9), pp. 2716-2723.

Wasfy, A.A.F. et al. "Simple Synthesis of Novel Diphenylsulfapyrimidine Acetates from Chalcones and Their Antimicrobial Activity." Folia Microbiologica (Prague, Czech Republic) (2003), 48(1), pp. 51-55.

Bharucha, P.B. et al. "Synthesis and Antibacterial Activity of 2-Amino-4-(2', 4'-Dichloro-5'-Fluorophen-1'-yl)-6-Aryl Pyrimidine Derivatives and Related Compounds." Asian Journal of Chemistry (1999), 11(4), pp. 1553-1555.

Olugbade, T.A. et al. "The Reaction of Amines with Isoflavones. 2. [1]. Formation of Phenolic Sulphonamidopyrimidines." Journal of Heterocyclic Chemistry, Sep.-Oct. 1990, 27(6), pp. 1727-1728.

Pene, Cecile et al. Recherche d'agents antitumoraux. XII. Synthese Directe European Journal of Medicinal Chemistry (1975), 10(4), pp. 340-342.

Sprague, James M. et al. "Sulfonido Derivatives of Pyrimidines." Journal of the American Chemical Society (1941), 61, pp. 3028-3030.

International Search Report and Written Opinion for International Application No. PCT/IB2017/055162 dated Oct. 23, 2017. 13 pages.

* cited by examiner

N-(PYRIDIN-2-YL)PYRIDINE-SULFONAMIDE DERIVATIVES AND THEIR USE IN THE TREATMENT OF DISEASE

This application is a U.S. National Phase filing of International Application Serial No. PCT/IB2017/055162 filed 28 Aug. 2017 and claims priority to U.S. Provisional Application Ser. No. 62/380,659 filed 29 Aug. 2016.

FIELD OF THE INVENTION

The present invention relates to N-(pyridin-2-yl)pyridine-sulfonamide derivatives and pharmaceutically acceptable salts thereof, compositions of these compounds, either alone or in combination with at least one additional therapeutic agent, processes for their preparation, their use in the treatment of diseases, their use, either alone or in combination with at least one additional therapeutic agent and optionally in combination with a pharmaceutically acceptable carrier, for the manufacture of pharmaceutical preparations, use of the pharmaceutical preparations for the treatment of diseases, and a method of treatment of said diseases, comprising administering the N-(pyridin-2-yl)pyridine-sulfonamide derivatives to a warm-blooded animal, especially a human.

BACKGROUND OF THE INVENTION

Cystic fibrosis (CF) is an autosomal genetic disease that affects approximately 30,000 people in the United States and approximately 70,000 people worldwide. Approximately 1,000 new cases of CF are diagnosed each year. Most patients are diagnosed with CF by the age of two, and more than half of the CF population is 18 years in age or older. Despite progress in the treatment of CF, there is no cure.

Cystic fibrosis (CF) is caused by loss-of-function mutations in the CF transmembrane conductance regulator (CFTR) protein, a cAMP-regulated chloride channel expressed primarily at the apical plasma membrane of secretory epithelia in the airways, pancreas, intestine, and other tissues. CFTR is a large, multidomain glycoprotein consisting of two membrane-spanning domains, two nucleotide-binding domains (NBD1 and NBD2) that bind and hydrolyze ATP, and a regulatory (R) domain that gates the channel by phosphorylation. Nearly 2000 mutations in the CFTR gene have been identified that produce the loss-of-function phenotype by impairing its translation, cellular processing, and/or chloride channel gating. The F508del mutation, which is present in at least one allele in ~90% of CF patients, impairs CFTR folding, stability at the endoplasmic reticulum and plasma membrane, and chloride channel gating (Dalemans et al. 1991; Denning et al. 1992; Lukacs et al. 1993; Du et al. 2005). Other mutations primarily alter channel gating (e.g., G551D), conductance (e.g., R117H), or translation (e.g., G542X) (Welsh and Smith 1993). The fundamental premise of CFTR corrector and potentiator therapy for CF is that correction of the underlying defects in the cellular processing and chloride channel function of CF-causing mutant CFTR alleles will be of clinical benefit. Correctors are principally targeted at F508del cellular misprocessing, whereas potentiators are intended to restore cAMP-dependent chloride channel activity to mutant CFTRs at the cell surface. In contrast to current therapies, such as antibiotics, anti-inflammatory agents, mucolytics, nebulized hypertonic saline, and pancreatic enzyme replacement, which treat CF disease manifestations, correctors and potentiators correct the underlying CFTR anion channel defect.

In view of the above, CFTR correctors of formula (I) are considered to be of value in the treatment and/or prevention of CF and related disorders.

SUMMARY OF THE INVENTION

In a first aspect, the invention relates to a compound of formula (I),

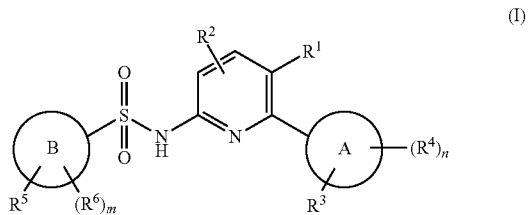

wherein:
ring A is a $C_{6-10}$aryl ring;
ring B is pyridinyl;
$R^1$ and $R^2$ are each independently hydrogen, nitrile, $C_{1-4}$alkoxy, halogen, $C_{1-4}$alkyl, halo-substituted-$C_{1-4}$alkyl, $C_{3-6}$cycloalkyl or halo-substituted-$C_{1-4}$alkoxy;
$R^3$ and $R^4$ are each independently hydrogen, nitrile, $CD_3$, $C_{3-6}$cycloalkyl, $C_{4-6}$heterocycle, $C_{1-4}$alkoxy, halogen, $C_{1-4}$alkyl, halo-substituted-$C_{1-4}$alkyl, hydroxy-substituted-$C_{1-4}$alkyl or halo-substituted-$C_{1-4}$alkoxy;
n is 0, 1 or 2;
$R^5$ is —$NR^7R^8$, —$OR^9$ or $R^{10}$;
$R^6$ is hydrogen, hydroxy, $C_{1-2}$alkyl, $C_{1-2}$alkoxy, hydroxy-substituted-$C_{1-2}$alkyl, halogen or amino;
m is 0, 1 or 2;
$R^7$ is hydrogen, $C_{1-6}$alkyl, $C_{3-6}$cycloalkyl, a fully or partially saturated 4 to 7-membered heterocycle, wherein said 4 to 7-membered heterocycle is optionally substituted with 1 to 4 substituents each independently selected from halogen, hydroxy, $C_{1-4}$alkyl, $C_{1-4}$alkoxy, halo-substituted-$C_{1-4}$alkyl, hydroxy-substituted-$C_{1-4}$alkyl, halo-substituted-$C_{1-4}$alkoxy, oxo, nitrile, $C_{3-6}$cycloalkyl, $C_{4-6}$heterocycle, $NHR^{11}$, —C(O)—$R^{13}$, —C(O)$NHR^{11}$, $C_{1-3}$alkyl-C(O)$NHR^{11}$ and —C(O)O—$R^{12}$;
$R^8$ is hydrogen or $C_{1-4}$alkyl;
$R^9$ is hydrogen, $C_{3-6}$cycloalkyl or a fully or partially saturated 4 to 7-membered heterocycle, each ring is optionally substituted with one to four substituents each independently selected from halogen, hydroxy, $C_{1-4}$alkyl, $C_{1-4}$alkoxy, halo-substituted-$C_{1-4}$alkyl, hydroxy-substituted-$C_{1-4}$alkyl, halo-substituted-$C_{1-4}$alkoxy, oxo, nitrile, $C_{3-6}$cycloalkyl, $C_{4-6}$heterocycle, $NHR^{11}$, —C(O)—$R^{13}$, —C(O)$NHR^{11}$, $C_{1-3}$alkyl-C(O)$NHR^{11}$ and —C(O)O—$R^{12}$;
$R^{10}$ is a fully or partially saturated 4 to 10-membered heterocycle optionally substituted with one to four substituents each independently selected from halogen, hydroxy, $C_{1-4}$alkyl, $C_{1-4}$alkoxy, halo-substituted-$C_{1-4}$alkyl, hydroxy-substituted-$C_{1-4}$alkyl, halo-substituted-$C_{1-4}$alkoxy, oxo, nitrile, $C_{3-6}$cycloalkyl, $C_{4-6}$heterocycle, $NHR^{11}$, —C(O)—$R^{13}$, —C(O)$NHR^{11}$, $C_{1-3}$alkyl-C(O)$NHR^{11}$, —C(O)$C_{1-3}$alkyl-$NHR^{11}$ and —C(O)O—$R^{12}$, wherein said $C_{3-6}$cycloalkyl and $C_{4-6}$heterocycle are optionally substituted with 1 to 3 substituents each independently selected from hydroxy, halogen, amino, —C(O)O—$R^{14}$, $C_{1-4}$alkyl, halo-substituted-$C_{1-4}$alkyl and hydroxy-substituted-$C_{1-4}$alkyl;

$R^{11}$ is hydrogen, $C_{1-4}$alkyl or $C_{0-3}$alkyl-C(O)O—$R^{14}$;

$R^{12}$ is hydrogen, $C_{1-4}$alkyl or $C_{1-3}$alkyl-C(O)—$NHR^{14}$;

$R^{13}$ is $C_{1-4}$alkyl, wherein said alkyl is optionally substituted with amino; and $R^{14}$ is hydrogen or $C_{1-4}$alkyl;

or a pharmaceutically acceptable salt thereof.

Another aspect of the invention relates to pharmaceutical compositions comprising compounds of the invention or pharmaceutically acceptable salts thereof, and a pharmaceutical carrier. Such compositions can be administered in accordance with a method of the invention, typically as part of a therapeutic regimen for treatment or prevention of conditions and disorders related to Cystic Fibrosis Transmembrane Conductance Regulator (CFTR) activity. In a particular aspect, the pharmaceutical compositions may additionally comprise further one or more therapeutically active ingredients suitable for use in combination with the compounds of the invention. In a more particular aspect, the further therapeutically active ingredient is an agent for the treatment of cystic fibrosis.

Another aspect of the invention relates to pharmaceutical combinations comprising compounds of the invention and other therapeutic agents for use as a medicament in the treatment of patients having disorders related to Cystic Fibrosis Transmembrane Conductance Regulator (CFTR) activity. Such combinations can be administered in accordance with a method of the invention, typically as part of a therapeutic regimen for treatment or prevention of CF.

DETAILED DESCRIPTION OF THE INVENTION

The present invention provides compounds and pharmaceutical formulations thereof that may be useful in the treatment or prevention of CFTR mediated diseases, such as cystic fibrosis, and conditions and/or disorders through the mediation of CFTR function.

In a first embodiment, the invention provides a compound of formula (I),

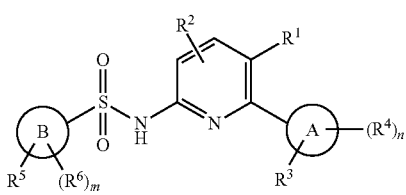

(I)

wherein:

ring A is a $C_{6-10}$aryl ring;

ring B is pyridinyl;

$R^1$ and $R^2$ are each independently hydrogen, nitrile, $C_{1-4}$alkoxy, halogen, $C_{1-4}$alkyl, halo-substituted-$C_{1-4}$alkyl, $C_{3-6}$cycloalkyl or halo-substituted-$C_{1-4}$alkoxy;

$R^3$ and $R^4$ are each independently hydrogen, nitrile, $CD_3$, $C_{3-6}$cycloalkyl, $C_{4-6}$heterocycle, $C_{1-4}$alkoxy, halogen, $C_{1-4}$alkyl, halo-substituted-$C_{1-4}$alkyl, hydroxy-substituted-$C_{1-4}$alkyl or halo-substituted-$C_{1-4}$alkoxy;

n is 0, 1 or 2;

$R^5$ is —$NR^7R^8$, —$OR^9$ or $R^{10}$;

$R^6$ is hydrogen, hydroxy, $C_{1-2}$alkyl, $C_{1-2}$alkoxy, hydroxy-substituted-$C_{1-2}$alkyl, halogen or amino;

m is 0, 1 or 2;

$R^7$ is hydrogen, $C_{1-6}$alkyl, $C_{3-6}$cycloalkyl, a fully or partially saturated 4 to 7-membered heterocycle, wherein said 4 to 7-membered heterocycle is optionally substituted with 1 to 4 substituents each independently selected from halogen, hydroxy, $C_{1-4}$alkyl, $C_{1-4}$alkoxy, halo-substituted-$C_{1-4}$alkyl, hydroxy-substituted-$C_{1-4}$alkyl, halo-substituted-$C_{1-4}$alkoxy, oxo, nitrile, $C_{3-6}$cycloalkyl, $C_{4-6}$heterocycle, $NHR^{11}$, —C(O)—$R^{13}$, —C(O)$NHR^{11}$, $C_{1-3}$alkyl-C(O)$NHR^{11}$ and —C(O)O—$R^{12}$;

$R^8$ is hydrogen or $C_{1-4}$alkyl;

$R^9$ is hydrogen, $C_{3-6}$cycloalkyl or a fully or partially saturated 4 to 7-membered heterocycle each ring is optionally substituted with one to four substituents each independently selected from halogen, hydroxy, $C_{1-4}$alkyl, $C_{1-4}$alkoxy, halo-substituted-$C_{1-4}$alkyl, hydroxy-substituted-$C_{1-4}$alkyl, halo-substituted-$C_{1-4}$alkoxy, oxo, nitrile, $C_{3-6}$cycloalkyl, $C_{4-6}$heterocycle, $NHR^{11}$, —C(O)—$R^{13}$, —C(O)$NHR^{11}$, $C_{1-3}$alkyl-C(O)$NHR^{11}$ and —C(O)O—$R^{12}$;

$R^{10}$ is a fully or partially saturated 4 to 10-membered heterocycle optionally substituted with one to four substituents each independently selected from halogen, hydroxy, $C_{1-4}$alkyl, $C_{1-4}$alkoxy, halo-substituted-$C_{1-4}$alkyl, hydroxy-substituted-$C_{1-4}$alkyl, halo-substituted-$C_{1-4}$alkoxy, oxo, nitrile, $C_{3-6}$cycloalkyl, $C_{4-6}$heterocycle, $NHR^{11}$, —C(O)—$R^{13}$, —C(O)$NHR^{11}$, $C_{1-3}$alkyl-C(O)$NHR^{11}$, —C(O)$C_{1-3}$alkyl-$NHR^{11}$ and —C(O)O—$R^{12}$, wherein said $C_{3-6}$cycloalkyl and $C_{4-6}$heterocycle are optionally substituted with 1 to 3 substituents each independently selected from hydroxy, halogen, amino, —C(O)O—$R^{14}$, $C_{1-4}$alkyl, halo-substituted-$C_{1-4}$alkyl and hydroxy-substituted-$C_{1-4}$alkyl;

$R^{11}$ is hydrogen, $C_{1-4}$alkyl or $C_{0-3}$alkyl-C(O)O—$R^{14}$;

$R^{12}$ is hydrogen, $C_{1-4}$alkyl or $C_{1-3}$alkyl-C(O)—$NHR^{14}$;

$R^{13}$ is $C_{1-4}$alkyl, wherein said alkyl is optionally substituted with amino; and $R^{14}$ is hydrogen or $C_{1-4}$alkyl;

or a pharmaceutically acceptable salt thereof.

A second embodiment of the invention provides a compound according to the first embodiment of formula (Ia), (Ib) or (Ic):

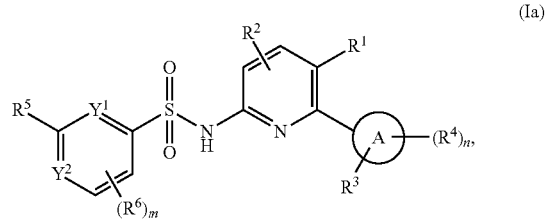

(Ia)

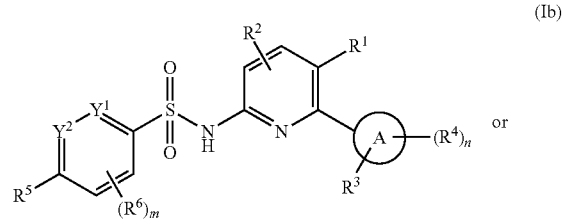

(Ib) or

-continued

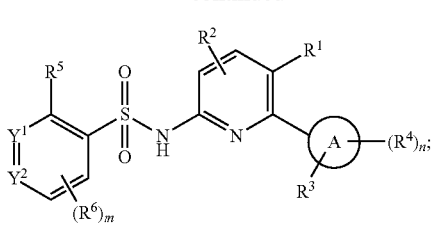

(Ic)

wherein:
at least one of $R^1$ or $R^2$ is not hydrogen;
$Y^1$ is N and $Y^2$ is $CR^6$; or $Y^2$ is N and $Y^1$ is $CR^6$;
or a pharmaceutically acceptable salt thereof.

A third embodiment of the invention provides a compound according to the second embodiment of formula (Ia), (Ib) or (Ic):
$Y^1$ is N and $Y^2$ is $CR^6$;
or a pharmaceutically acceptable salt thereof.

A fourth embodiment of the invention provides a compound according to the second embodiment of formula (Ia), (Ib) or (Ic); wherein:
$Y^1$ is $CR^6$ and $Y^2$ is N; or a pharmaceutically acceptable salt thereof.

A fifth embodiment of any of the preceding embodiments wherein:
m is 0 or 1; and
n is 0 or 1;
or a pharmaceutically acceptable salt thereof.

A sixth embodiment of the invention provides a compound according to the second embodiment of formula (Ia) wherein:
$R^1$ is hydrogen, halogen or $CF_3$;
$R^2$ is hydrogen, halogen, —$OCH_3$ or $CF_3$;
m is 0;
n is 0;
$Y^1$ is N and $Y^2$ is CH; and
ring A is phenyl;
or a pharmaceutically acceptable salt thereof.

A seventh embodiment of the invention provides a compound according to the second embodiment of formula (Ia) wherein:
$R^1$ is selected from hydrogen, halogen and $CF_3$;
$R^2$ is selected from hydrogen, halogen, —$OCH_3$ and $CF_3$;
m is 1;
$R^6$ is selected from hydrogen, hydroxy, $C_{1-2}$alkyl, $C_{1-2}$alkoxy, hydroxy-substituted-$C_{1-2}$alkyl, halogen and amino;
$Y^1$ is N and $Y^2$ is CH; and
ring A is phenyl;
or a pharmaceutically acceptable salt thereof.

An eighth embodiment of the invention provides a compound according to the second embodiment of formula (Ia) wherein:
$R^1$ is selected from hydrogen, halogen and $CF_3$;
$R^2$ is selected from hydrogen, halogen, —$OCH_3$ and $CF_3$;
m is 0 or 1;
$Y^1$ is N and $Y^2$ is CH; and
ring A is phenyl;
or a pharmaceutically acceptable salt thereof.

A ninth embodiment of the invention provides a compound according to any of the previous embodiments, of formula (Ia) wherein:
$R^5$ is $R^{10}$ and $R^{10}$ is a fully or partially saturated 4 to 10-membered heterocycle optionally substituted with one to four substituents each independently selected from halogen, hydroxy, $C_{1-4}$alkyl, $C_{1-4}$alkoxy, halo-substituted-$C_{1-4}$alkyl, hydroxy-substituted-$C_{1-4}$alkyl, halo-substituted-$C_{1-4}$alkoxy, oxo, nitrile, $C_{3-6}$ cycloalkyl, $C_{4-6}$ heterocycle, $NHR^{11}$, —$C(O)$—$R^{13}$, —$C(O)NHR^{11}$, $C_{1-3}$alkyl-$C(O)NHR^{11}$, —$C(O)C_{1-3}$alkyl-$NHR^{11}$ and —$C(O)O$—$R^{12}$, wherein said $C_{3-6}$ cycloalkyl and $C_{4-6}$ heterocycle are optionally substituted with 1 to 3 substituents each independently selected from hydroxy, halogen, amino, $C_{1-4}$alkyl, halo-substituted-$C_{1-4}$alkyl and hydroxy-substituted-$C_{1-4}$alkyl; or a pharmaceutically acceptable salt thereof.

A tenth embodiment of the invention provides a compound according to any of the previous embodiments, of formula (Ia) wherein:
$R^5$ is $R^{10}$ and $R^{10}$ is a fully saturated 4 to 10-membered heterocycle optionally substituted with one to four substituents each independently selected from halogen, hydroxy, $C_{1-4}$alkyl, $C_{1-4}$alkoxy, halo-substituted-$C_{1-4}$alkyl, hydroxy-substituted-$C_{1-4}$alkyl, halo-substituted-$C_{1-4}$ alkoxy, oxo, nitrile, $C_{3-6}$ cycloalkyl, $C_{4-6}$ heterocycle, $NHR^{11}$, —$C(O)$—$R^{13}$, —$C(O)NHR^{11}$, $C_{1-3}$alkyl-$C(O)NHR^{11}$, —$C(O)C_{1-3}$alkyl-$NHR^{11}$ and —$C(O)O$—$R^{12}$, wherein said $C_{3-6}$ cycloalkyl and $C_{4-6}$ heterocycle are optionally substituted with 1 to 3 substituents each independently selected from hydroxy, halogen, amino, $C_{1-4}$alkyl, halo-substituted-$C_{1-4}$alkyl and hydroxy-substituted-$C_{1-4}$alkyl; or a pharmaceutically acceptable salt thereof.

An eleventh embodiment of the invention provides a compound according to the ninth embodiment, wherein:
$R^5$ is $R^{10}$; $R^{10}$ is 4,5,6,7-tetrahydro-3H-imidazo[4,5-c]pyridine, 8-azabicyclo[3.2.1]octan-3-ol, octahydropyrrolo[1,2-a]pyrazine, 6-oxa-1-azaspiro[3.3]heptane, 5,6,7,8-tetrahydroimidazo[1,2-a]pyrazine, 3,8 diazabicyclo[3.2.1]octane, 8-oxa-3-azabicyclo[3.2.1]octane, 2-oxa-6-azaspiro[3.3]heptane, 1H-pyrazole, 2,6-diazaspiro[3.3]heptane, 1,6-diazaspiro[3.3]heptane, 5-oxa-2-azaspiro[3.4]octane, 7-azaspiro[3.5]nonane, 2,6-diazaspiro[3.4]octane, 2,5-diazabicyclo[2.2.1]heptane, 8-azaspiro[4.5]decane, 5-azaspiro[2.5]octane, 4,7-diazaspiro[2.5]octane, 5,6,7,8-tetrahydro-[1,2,4]triazolo[4,3-a]pyrazine or 3-azabicyclo[3.1.0]hexane; wherein $R^{10}$ is optionally substituted by 1 to 3 substituents each independently selected from amino, oxo, halogen, $C_{1-4}$ alkyl, hydroxy-substituted $C_{1-4}$alkyl and halo-substituted $C_{1-4}$alkyl; or a pharmaceutically acceptable salt thereof.

A twelfth embodiment of the invention provides a compound according to the second embodiment of formula (Ia) wherein:
$R^1$ is F, Cl or $CF_3$;
$R^2$ is hydrogen, —$OCH_3$ or $CF_3$;
$Y^1$ is N and $Y^2$ is CH;
m is 0;
n is 0 or 1;
ring A is phenyl;
$R^5$ is —$NR^7R^8$; and
$R^8$ is hydrogen;
or a pharmaceutically acceptable salt thereof.

A thirteenth embodiment of the invention provides a compound according to the second embodiment of formula (Ia) wherein:
$R^1$ is F, Cl or $CF_3$;
$R^2$ is hydrogen, —$OCH_3$ or $CF_3$;
$Y^1$ is N and $Y^2$ is CH;
m is 0;
ring A is phenyl; and
$R^5$ is —$OR^9$;
or a pharmaceutically acceptable salt thereof.

A fourteenth embodiment of the invention provides a compound according to the first embodiment of formula (II):

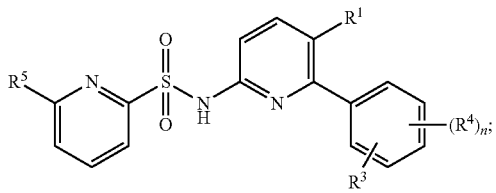

wherein:
$R^1$ is F, Cl or $CF_3$;
or a pharmaceutically acceptable salt thereof.

A fifteenth embodiment of the invention provides a compound according to embodiment fourteen wherein:
$R^1$ is F, Cl or $CF_3$;
$R^5$ is $R^{10}$; and
$R^{10}$ is a fully or partially saturated 4 to 10-membered heterocycle optionally substituted with one to four substituents each independently selected from the group consisting of halogen, hydroxy, $C_{1-4}$alkyl, $C_{1-4}$alkoxy, halo-substituted-$C_{1-4}$alkyl, hydroxy-substituted-$C_{1-4}$alkyl, halo-substituted-$C_{1-4}$alkoxy, oxo, nitrile, $C_{3-6}$ cycloalkyl, $C_{4-6}$ heterocycle, $NHR^{11}$, —C(O)—$R^{13}$, —C(O)$NHR^{11}$, $C_{1-3}$alkyl-C(O)$NHR^{11}$, —C(O)$C_{1-3}$alkyl-$NHR^{11}$ and —C(O)O—$R^{12}$; wherein said $C_{3-6}$ cycloalkyl or $C_{4-6}$ heterocycle, are optionally substituted with 1 to 3 substituents each independently selected from hydroxy, halogen, amino, $C_{1-4}$alkyl, halo-substituted-$C_{1-4}$alkyl and hydroxy-substituted-$C_{1-4}$alkyl;
or a pharmaceutically acceptable salt thereof.

A sixteenth embodiment of the invention provides a compound of the second embodiment of formula (Ia), wherein:
$R^1$ is F, Cl or $CF_3$;
$R^2$ is H;
$Y^1$ is N and $Y^2$ is CH;
m is 0;
n is 0 or 1;
ring A is

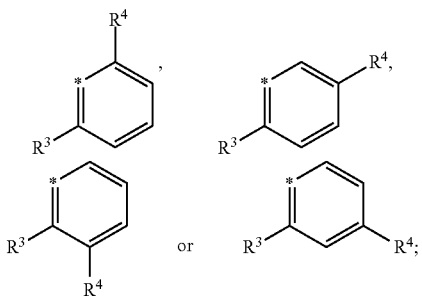

wherein * represents the carbon atom to which ring A is attached to formula (Ia);
$R^3$ and $R^4$ are each independently hydrogen, Cl, F, $CH_3$, $CD_3$, nitrile, cyclopropyl, —$OCH_3$, —$OCF_3$ or $CF_3$, where at least one of $R^3$ or $R^4$ is not hydrogen;
$R^5$ is $R^{10}$;
$R^{11}$ is hydrogen or $C_{1-4}$alkyl;
$R^{12}$ is hydrogen or $C_{1-4}$alkyl; and
$R^{13}$ is $C_{1-4}$alkyl;
or a pharmaceutically acceptable salt thereof.

A seventeenth embodiment of the invention provides a compound of embodiment fifteen wherein $R^3$ is $CH_3$, cyclopropyl, Cl, —$OCH_3$, $CD_3$, —$CF_3$ or —$OCF_3$ and $R^4$ is hydrogen, Cl, —$OCH_3$, F, $CH_3$, $CD_3$, nitrile, or —$CF_3$; or a pharmaceutically acceptable salt thereof.

An eighteenth embodiment of the invention provides a compound of embodiment fifteen, wherein:
$R^1$ is F;
or a pharmaceutically acceptable salt thereof.

A nineteenth embodiment of the invention provides a compound of embodiment fifteen, wherein:
$R^1$ is Cl;
or a pharmaceutically acceptable salt thereof.

A twentieth embodiment of the invention provides a compound of embodiment fifteen, wherein:
$R^1$ is $CF_3$;
or a pharmaceutically acceptable salt thereof.

A twenty-first embodiment of the invention provides a compound of embodiment fifteen, wherein:
n is 0;
or a pharmaceutically acceptable salt thereof.

A twenty-second embodiment of the invention provides a compound of embodiment fifteen, wherein:
$R^{10}$ is

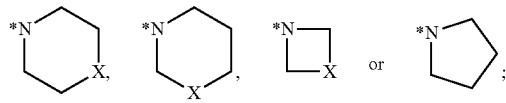

wherein *N represents the ring attachment nitrogen and X is O, C or N;
wherein each $R^{10}$ ring is substituted with 1 or 2 substituents each independently selected from hydrogen, flouro, hydroxy, $C_{1-4}$alkyl, $C_{1-2}$alkoxy, halo-substituted-$C_{1-2}$alkyl, hydroxy-substituted-$C_{1-2}$alkyl, halo-substituted-$C_{1-2}$alkoxy, oxo, nitrile, $C_{3-6}$ cycloalkyl, $C_{4-6}$ heterocycle, $NHR^{11}$, —C(O)$NHR^{11}$, $C_{1-3}$alkyl-C(O)$NHR^{11}$, —C(O)$C_{1-3}$alkyl-$NHR^{11}$ and —C(O)O—$R^{12}$, wherein said $C_{3-6}$ cycloalkyl and $C_{4-6}$ heterocycle are optionally substituted with 1 or 2 substituents each independently selected from hydroxy, halogen, amino, $C_{1-4}$alkyl, halo-substituted-$C_{1-4}$alkyl and hydroxy-substituted-$C_{1-4}$alkyl;
$R^{11}$ is selected from hydrogen and $C_{1-4}$alkyl; and
$R^{12}$ is selected from hydrogen and $C_{1-4}$alkyl;
or the pharmaceutically acceptable salt thereof.

A twenty-third embodiment of the invention provides a compound of embodiment two of formula (Ia), wherein:
$R^1$ is selected from F, Cl or $CF_3$;
$R^2$ is H;
$Y^1$ is N and $Y^2$ is CH;
m is 0;
ring A is

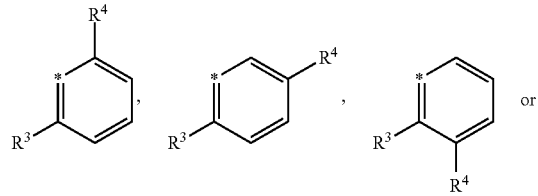

-continued

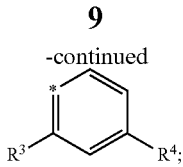

wherein * represents the carbon atom to which ring A is attached to formula (Ia);
R$^3$ and R$^4$ are each independently selected from hydrogen, Cl, F, CH$_3$, CD$_3$, nitrile, cyclopropyl, —OCH$_3$, —OCF$_3$ and CF$_3$; where at least one of R$^3$ or R$^4$ is not hydrogen;
R$^5$ is —NR$^7$R$^8$;
R$^8$ is hydrogen;
—NR$^7$R$^8$ is selected from the group consisting of:

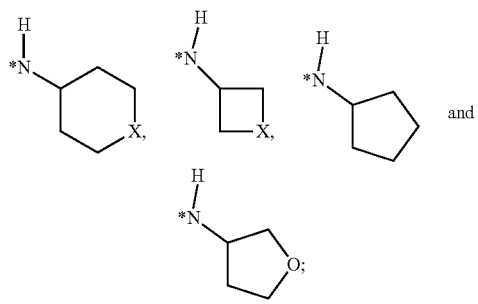

X is O, C or N;
wherein R$^7$ is substituted with 1 to 2 substituents each independently selected from hydrogen, halogen, hydroxy, C$_{1-4}$alkyl, C$_{1-4}$alkoxy, halo-substituted-C$_{1-4}$alkyl, hydroxy-substituted-C$_{1-4}$alkyl, halo-substituted-C$_{1-4}$alkoxy, oxo, nitrile, C$_{3-6}$ cycloalkyl, C$_{4-6}$ heterocycle, NHR$^{11}$, —C(O)—R$^{13}$, —C(O)NHR$^{11}$, C$_{1-3}$alkyl-C(O)NHR$^{11}$ and —C(O)O—R$^{12}$;
R$^{11}$ is selected from hydrogen and C$_{1-4}$alkyl; and
R$^{12}$ is selected from hydrogen and C$_{1-4}$alkyl;
or the pharmaceutically acceptable salt thereof.

A twenty-fourth embodiment of the invention provides a compound of according to embodiment two of formula (Ia), wherein:
R$^1$ is selected from F, Cl and CF$_3$;
R$^2$ is H;
Y$^1$ is N and Y$^2$ is CH;
m is 0;
ring A is

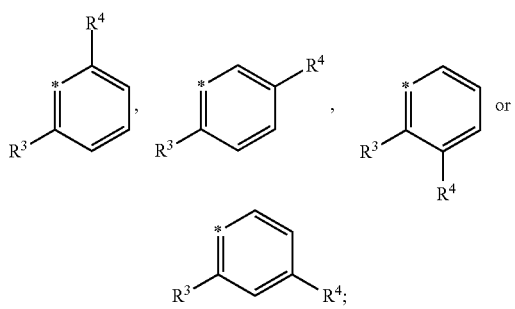

wherein * represents the carbon atom to which ring A is attached to formula (Ia);
R$^3$ and R$^4$ are each independently selected from hydrogen, Cl, F, CH$_3$, CD$_3$, nitrile, cyclopropyl, —OCH$_3$, —OCF$_3$ and CF$_3$; where at least one of R$^3$ or R$^4$ is not hydrogen;
R$^5$ is R$^{10}$;
R$^{10}$ is selected from the group consisting of:

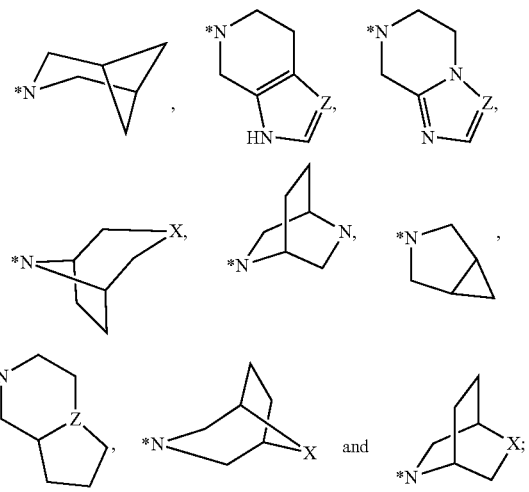

wherein:
*N represents the ring attachment nitrogen:
X is O, C or N;
Z is N, or CH;
wherein said R$^{10}$ heterocycle is substituted with 1 to 2 substituents each independently selected from hydrogen, flouro, hydroxy, C$_{1-4}$alkyl, C$_{1-2}$alkoxy, halo-substituted-C$_{1-2}$alkyl, hydroxy-substituted-C$_{1-2}$alkyl, halo-substituted-C$_{1-2}$alkoxy, oxo, nitrile, C$_{3-6}$ cycloalkyl, C$_{4-6}$ heterocycle, NHR$^{11}$, —C(O)NHR$^{11}$ and —C(O)O—R$^{12}$;
wherein said C$_{3-6}$ cycloalkyl and C$_{4-6}$ heterocycle are optionally substituted with 1 or 2 substituents each independently selected from hydroxy, halogen, amino, C$_{1-4}$alkyl, halo-substituted-C$_{1-4}$alkyl and hydroxy-substituted-C$_{1-4}$alkyl;
R$^{11}$ is selected from hydrogen and C$_{1-4}$alkyl; and
R$^{12}$ is selected from hydrogen and C$_{1-4}$alkyl;
or the pharmaceutically acceptable salt thereof.

A twenty-fifth embodiment of the invention provides a compound according to embodiment fifteen, wherein:
R$^{10}$ is selected from the group consisting of:

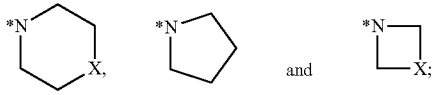

X is O, C or N;
*N represents the ring attachment nitrogen:
wherein said heterocycle is optionally substituted with 1 to 2 substituents each independently selected from hydrogen, fluoro, hydroxy, C$_{1-2}$alkyl, cyclopropyl, oxetane, halo-substituted-C$_{1-2}$alkyl, hydroxy-substituted-C$_{1-2}$alkyl, oxo, NHR$^{11}$, —C(O)NHR$^{11}$, C$_{1-3}$alkyl-C(O)NHR$^{11}$, —C(O)C$_{1-3}$alkyl-NHR$^{11}$ and —C(O)O—R$^{12}$;

$R^{11}$ is selected from hydrogen and $C_{1-4}$alkyl;
$R^{12}$ is selected from hydrogen and $C_{1-4}$alkyl; and
Ring A is

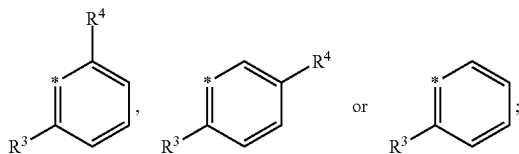

wherein * represents the carbon atom to which ring A is attached to formula (II);
$R^3$ is selected from Cl, $CH_3$ and $CD_3$, and $R^4$ is selected from hydrogen, $CH_3$, Cl and F;
or a pharmaceutically acceptable salt thereof.

A twenty-sixth embodiment of the invention provides a compound according to any of the preceding embodiments wherein:
$R^3$ is $CH_3$, or Cl, and $R^4$ is hydrogen or F;
or a pharmaceutically acceptable salt thereof.

A twenty-seventh embodiment of the invention provides a compound according to embodiment twenty-three, wherein:
said $R^{10}$ heterocycle is substituted with 1 to 2 substituents each independently selected from hydrogen, fluoro, hydroxyl and $C_{1-4}$alkyl;
or a pharmaceutically acceptable salt thereof.

A twenty-eighth embodiment of the invention provides a compound according to embodiment twenty-four, wherein:
said $R^{10}$ heterocycle is substituted with 1 to 2 substituents each independently selected from hydrogen, fluoro, hydroxyl and $C_{1-4}$alkyl;
or a pharmaceutically acceptable salt thereof.

A twenty-ninth embodiment of the invention is a compound selected from the group consisting of:
6-amino-N-(6-(5-fluoro-2-methylphenyl)-5-(trifluoromethyl)pyridin-2-yl)pyridine-2-sulfonamide;
6-Amino-N-(5-chloro-6-(o-tolyl)pyridin-2-yl)pyridine-2-sulfonamide;
6-amino-N-(6-(2,6-dimethylphenyl)-5-(trifluoromethyl)pyridin-2-yl)pyridine-2-sulfonamide;
6-amino-N-(5-bromo-6-(2,6-dimethylphenyl)pyridin-2-yl)pyridine-2-sulfonamide;
2-amino-N-(5-chloro-6-(2,6-dimethylphenyl)pyridin-2-yl)pyridine-4-sulfonamide;
6-amino-N-(6-(2,6-dimethylphenyl)-4-(trifluoromethyl)pyridin-2-yl)pyridine-2-sulfonamide;
6-amino-N-(5-chloro-6-(5-fluoro-2-methylphenyl)pyridin-2-yl)pyridine-2-sulfonamide;
6-amino-N-(6-(3-fluoro-2-methylphenyl)-5-(trifluoromethyl)pyridin-2-yl)pyridine-2-sulfonamide;
6-amino-N-(5-chloro-6-(2,6-dimethylphenyl)-4-(trifluoromethyl)pyridin-2-yl)pyridine-2-sulfonamide;
6-amino-N-(6-(2,6-dimethylphenyl)-5-fluoropyridin-2-yl)pyridine-2-sulfonamide;
6-amino-N-(4-chloro-6-(2,6-dimethylphenyl)pyridin-2-yl)pyridine-2-sulfonamide;
6-amino-N-(5-chloro-6-(2,6-dimethylphenyl)pyridin-2-yl)pyridine-2-sulfonamide;
6-amino-N-(5-chloro-6-(3-fluoro-2-methylphenyl)pyridin-2-yl)pyridine-2-sulfonamide;
6-amino-N-(5-chloro-6-(2-chloro-6-methylphenyl)pyridin-2-yl)pyridine-2-sulfonamide;
6-amino-N-(6-(o-tolyl)-5-(trifluoromethyl)pyridin-2-yl)pyridine-2-sulfonamide;
6-amino-N-(5-chloro-6-(5-chloro-2-cyclopropylphenyl)pyridin-2-yl)pyridine-2-sulfonamide;
6-amino-N-(6-(2-chlorophenyl)-5-(trifluoromethyl)pyridin-2-yl)pyridine-2-sulfonamide;
6-amino-N-(5-(trifluoromethyl)-6-(2-(trifluoromethyl)phenyl)pyridin-2-yl)pyridine-2-sulfonamide;
6-amino-N-(5-chloro-6-(2-cyclopropylphenyl)pyridin-2-yl)pyridine-2-sulfonamide;
6-amino-N-(5-chloro-6-(2-(methyl-d3)phenyl)pyridin-2-yl)pyridine-2-sulfonamide;
6-amino-N-(5-chloro-6-(2-cyclopropyl-5-fluorophenyl)pyridin-2-yl)pyridine-2-sulfonamide;
6-amino-N-(5-chloro-6-(o-tolyl)-4-(trifluoromethyl)pyridin-2-yl)pyridine-2-sulfonamide;
6-amino-N-(5-bromo-6-(o-tolyl)pyridin-2-yl)pyridine-2-sulfonamide;
6-amino-N-(5-chloro-6-(2-chlorophenyl)pyridin-2-yl)pyridine-2-sulfonamide;
2-amino-N-(6-(2,6-dimethylphenyl)-5-(trifluoromethyl)pyridin-2-yl)pyridine-4-sulfonamide;
2-amino-N-(5-chloro-6-(2-(methyl-d3)phenyl)pyridin-2-yl)pyridine-4-sulfonamide;
6-amino-N-(5-chloro-6-(2-cyclopropyl-4-fluorophenyl)pyridin-2-yl)pyridine-2-sulfonamide;
6-amino-N-(6-(2-cyclopropyl-4-fluorophenyl)-5-(trifluoromethyl)pyridin-2-yl)pyridine-2-sulfonamide;
6-amino-N-(5-chloro-6-(2-ethylphenyl)pyridin-2-yl)pyridine-2-sulfonamide;
6-amino-N-(5-chloro-6-(4-fluoro-2,6-dimethylphenyl)pyridin-2-yl)pyridine-2-sulfonamide;
6-amino-N-(5-chloro-6-(2-fluoro-6-methylphenyl)pyridin-2-yl)pyridine-2-sulfonamide;
6-amino-N-(5-chloro-6-mesitylpyridin-2-yl)pyridine-2-sulfonamide;
6-amino-N-(5-chloro-6-(o-tolyl)pyridin-2-yl)-3-fluoropyridine-2-sulfonamide;
6-amino-N-(5-chloro-6-(2-methyl-3-(trifluoromethyl)phenyl)pyridin-2-yl)pyridine-2-sulfonamide;
6-amino-N-(5-fluoro-6-(2-isopropylphenyl)pyridin-2-yl)pyridine-2-sulfonamide;
6-amino-5-methyl-N-(6-(o-tolyl)-5-(trifluoromethyl)pyridin-2-yl)pyridine-2-sulfonamide;
6-amino-N-(5-chloro-6-(4-fluoro-2-methylphenyl)pyridin-2-yl)pyridine-2-sulfonamide;
6-amino-N-(5-chloro-6-(6-chloro-2-fluoro-3-methylphenyl)pyridin-2-yl)pyridine-2-sulfonamide;
6-amino-N-(5-chloro-6-(2-chloro-6-fluorophenyl)pyridin-2-yl)pyridine-2-sulfonamide;
6-amino-N-(5-chloro-6-(o-tolyl)pyridin-2-yl)pyridine-3-sulfonamide;
6-amino-N-(6-(2-chloro-4-fluorophenyl)-5-(trifluoromethyl)pyridin-2-yl)pyridine-2-sulfonamide;
2-amino-N-(6-(5-fluoro-2-methylphenyl)-5-(trifluoromethyl)pyridin-2-yl)pyridine-4-sulfonamide;
6-amino-N-(5-chloro-6-(2-chloro-5-(trifluoromethyl)phenyl)pyridin-2-yl)pyridine-2-sulfonamide;
6-amino-N-(5-chloro-6-(5-fluoro-2-methylphenyl)pyridin-2-yl)pyridine-3-sulfonamide;
6-amino-N-(5-chloro-6-(2-isopropylphenyl)pyridin-2-yl)pyridine-3-sulfonamide;
2-amino-N-(5-chloro-6-(5-fluoro-2-methylphenyl)pyridin-2-yl)pyridine-4-sulfonamide;
6-amino-N-(5-chloro-6-(2,6-dimethylphenyl)pyridin-2-yl)pyridine-3-sulfonamide;

6-amino-N-(5-chloro-6-(2-(1,1-difluoroethyl)phenyl)pyridin-2-yl)pyridine-2-sulfonamide;
2-amino-N-(5-chloro-6-(2-methyl-5-(trifluoromethyl)phenyl)pyridin-2-yl)pyridine-4-sulfonamide;
6-amino-N-(5-chloro-6-(2-isopropylphenyl)pyridin-2-yl)pyridine-2-sulfonamide;
6-amino-N-(5-chloro-6-(2-methyl-5-(trifluoromethyl)phenyl)pyridin-2-yl)pyridine-2-sulfonamide;
6-amino-N-(5-chloro-6-(2-chloro-6-(trifluoromethyl)phenyl)pyridin-2-yl)pyridine-2-sulfonamide;
6-amino-N-(5-chloro-6-(2-methyl-6-(trifluoromethyl)phenyl)pyridin-2-yl)pyridine-2-sulfonamide;
6-amino-N-(5-chloro-6-(2-cyclopropylphenyl)pyridin-2-yl)pyridine-3-sulfonamide;
6-amino-N-(5-chloro-6-(2-(trifluoromethyl)phenyl)pyridin-2-yl)pyridine-2-sulfonamide;
6-amino-N-(5-chloro-6-(2-chloro-4-fluorophenyl)pyridin-2-yl)pyridine-2-sulfonamide;
2-amino-N-(5-chloro-6-(o-tolyl)pyridin-2-yl)pyridine-4-sulfonamide;
6-amino-N-(5-chloro-6-(2-chloro-6-fluoro-3-methylphenyl)pyridin-2-yl)pyridine-2-sulfonamide;
6-amino-N-(5-chloro-6-(2-(trifluoromethoxy)phenyl)pyridin-2-yl)pyridine-2-sulfonamide;
6-amino-N-(5-chloro-6-(2-fluoro-6-methylphenyl)pyridin-2-yl)pyridine-3-sulfonamide;
2-amino-N-(5-chloro-6-(2-(trifluoromethyl)phenyl)pyridin-2-yl)pyridine-4-sulfonamide;
6-amino-N-(5-chloro-6-(5-fluoro-2-methoxyphenyl)pyridin-2-yl)pyridine-2-sulfonamide;
6-amino-N-(6-(2,6-dimethylphenyl)-4-methylpyridin-2-yl)pyridine-2-sulfonamide;
2-amino-N-(6-(5-cyano-2-methylphenyl)-5-(trifluoromethyl)pyridin-2-yl)pyridine-4-sulfonamide;
6-amino-N-(5-chloro-6-(2-(difluoromethyl)phenyl)pyridin-2-yl)pyridine-2-sulfonamide;
6-amino-N-(5-cyclopropyl-6-(o-tolyl)pyridin-2-yl)pyridine-2-sulfonamide;
6-amino-N-(5-chloro-6-(3-cyano-2-methyl phenyl)pyridin-2-yl)pyridine-2-sulfonamide;
6-amino-N-(6-(2,6-dimethylphenyl)pyridin-2-yl)pyridine-2-sulfonamide;
6-amino-N-(5-chloro-6-(2-fluorophenyl)pyridin-2-yl)pyridine-2-sulfonamide;
6-amino-N-(5-fluoro-6-(o-tolyl)pyridin-2-yl)pyridine-2-sulfonamide;
6-amino-N-(5-chloro-6-(4-fluoro-2-methylphenyl)pyridin-2-yl)pyridine-3-sulfonamide;
6-amino-N-(6-(2,6-dimethylphenyl)-5-methoxypyridin-2-yl)pyridine-2-sulfonamide;
6-amino-N-(5-chloro-6-(3-(trifluoromethyl)phenyl)pyridin-2-yl)pyridine-2-sulfonamide;
2-amino-N-(5-chloro-6-(2,6-dimethylphenyl)pyridin-2-yl)pyridine-3-sulfonamide;
6-amino-N-(5-methyl-6-(o-tolyl)pyridin-2-yl)pyridine-2-sulfonamide;
6-amino-N-(5-chloro-6-(2-methoxyphenyl)pyridin-2-yl)pyridine-2-sulfonamide;
6-amino-N-(6-(2-chlorophenyl)-5-methylpyridin-2-yl)pyridine-2-sulfonamide;
6-amino-N-(5-chloro-6-(2,3,6-trifluorophenyl)pyridin-2-yl)pyridine-2-sulfonamide;
6-amino-N-(5-(trifluoromethyl)-6-(3-(trifluoromethyl)phenyl)pyridin-2-yl)pyridine-2-sulfonamide;
6-amino-N-(5-chloro-6-(2,6-difluorophenyl)pyridin-2-yl)pyridine-2-sulfonamide;
6-amino-5-bromo-N-(5-chloro-6-(2,6-dimethylphenyl)pyridin-2-yl)pyridine-2-sulfonamide;
6-amino-N-(6-(2-methyl-5-(trifluoromethoxy)phenyl)-5-(trifluoromethyl)pyridin-2-yl)pyridine-2-sulfonamide;
6-amino-N-(6-(5-cyano-2-methylphenyl)-5-(trifluoromethyl)pyridin-2-yl)pyridine-2-sulfonamide;
6-amino-N-(5-chloro-6-(5-cyano-2-methyl phenyl)pyridin-2-yl)pyridine-2-sulfonamide;
2-amino-N-(5-chloro-6-(5-cyano-2-methyl phenyl)pyridin-2-yl)pyridine-4-sulfonamide;
6-amino-N-(5-chloro-6-(2,4,6-trifluorophenyl)pyridin-2-yl)pyridine-2-sulfonamide;
2-amino-N-(5-chloro-6-(3-cyano-2-methyl phenyl)pyridin-2-yl)pyridine-4-sulfonamide;
2-amino-N-(5-chloro-6-(o-tolyl)pyridin-2-yl)pyridine-3-sulfonamide;
6-amino-N-(5-chloro-6-(2-methyl-5-(trifluoromethoxy)phenyl)pyridin-2-yl)pyridine-2-sulfonamide;
6-amino-N-(5-chloro-6-(2-cyanophenyl)pyridin-2-yl)pyridine-2-sulfonamide;
6-amino-N-(5-chloro-6-(4-cyano-2-methyl phenyl)pyridin-2-yl)pyridine-2-sulfonamide;
2-amino-N-(5-chloro-6-(4-cyano-2-methylphenyl)pyridin-2-yl)pyridine-4-sulfonamide;
6-amino-N-(6-(2,6-dimethylphenyl)-3-fluoropyridin-2-yl)pyridine-2-sulfonamide;
6-amino-N-(5-chloro-6-(4-(trifluoromethyl)phenyl)pyridin-2-yl)pyridine-2-sulfonamide;
6-amino-N-(5-chloro-6-(2,6-dimethylphenyl)-3-fluoropyridin-2-yl)pyridine-2-sulfonamide;
6-amino-N-(3-chloro-6-(2,6-dimethylphenyl)pyridin-2-yl)pyridine-2-sulfonamide;
(R)-6-(3-aminopiperidin-1-yl)-N-(6-(o-tolyl)-5-(trifluoromethyl)pyridin-2-yl)pyridine-2-sulfonamide;
(S)-6-(3-aminopiperidin-1-yl)-N-(6-(o-tolyl)-5-(trifluoromethyl)pyridin-2-yl)pyridine-2-sulfonamide;
(R)-6-(piperidin-3-ylamino)-N-(6-(o-tolyl)-5-(trifluoromethyl)pyridin-2-yl)pyridine-2-sulfonamide;
(S)-6-(piperidin-3-ylamino)-N-(6-(o-tolyl)-5-(trifluoromethyl)pyridin-2-yl)pyridine-2-sulfonamide;
6-(((3R,4S)-4-methoxypiperidin-3-yl)amino)-N-(6-(o-tolyl)-5-(trifluoromethyl)pyridin-2-yl)pyridine-2-sulfonamide;
6-(6-amino-3-azabicyclo[3.1.0]hexan-3-yl)-N-(6-(o-tolyl)-5-(trifluoromethyl)pyridin-2-yl)pyridine-2-sulfonamide;
6-(4-aminopiperidin-1-yl)-N-(6-(o-tolyl)-5-(trifluoromethyl)pyridin-2-yl)pyridine-2-sulfonamide;
6-(4-(methylamino)piperidin-1-yl)-N-(6-(o-tolyl)-5-(trifluoromethyl)pyridin-2-yl)pyridine-2-sulfonamide;
6-(4-amino-4-methylpiperidin-1-yl)-N-(6-(o-tolyl)-5-(trifluoromethyl)pyridin-2-yl)pyridine-2-sulfonamide;
6-((3S,4R)-4-amino-3-fluoropiperidin-1-yl)-N-(6-(o-tolyl)-5-(trifluoromethyl)pyridin-2-yl)pyridine-2-sulfonamide;
6-(piperidin-4-ylamino)-N-(6-(o-tolyl)-5-(trifluoromethyl)pyridin-2-yl)pyridine-2-sulfonamide;
6-(((3S,4R)-3-hydroxypiperidin-4-yl)amino)-N-(6-(o-tolyl)-5-(trifluoromethyl)pyridin-2-yl)pyridine-2-sulfonamide;
6-(((3R,4R)-3-hydroxypiperidin-4-yl)amino)-N-(6-(o-tolyl)-5-(trifluoromethyl)pyridin-2-yl)pyridine-2-sulfonamide;
6-(((3S,4R)-3-methoxypiperidin-4-yl)amino)-N-(6-(o-tolyl)-5-(trifluoromethyl)pyridin-2-yl)pyridine-2-sulfonamide;
6-(((3R,4R)-3-methoxypiperidin-4-yl)amino)-N-(6-(o-tolyl)-5-(trifluoromethyl)pyridin-2-yl)pyridine-2-sulfonamide;

6-(((3S,4R)-3-fluoropiperidin-4-yl)amino)-N-(6-(o-tolyl)-5-(trifluoromethyl)pyridin-2-yl)pyridine-2-sulfonamide;
6-((3'S,4'S)-4'-hydroxy-[1,3'-bipyrrolidin]-1'-yl)-N-(6-(o-tolyl)-5-(trifluoromethyl)pyridin-2-yl)pyridine-2-sulfonamide;
(R)-6-(3-aminopyrrolidin-1-yl)-N-(6-(o-tolyl)-5-(trifluoromethyl)pyridin-2-yl)pyridine-2-sulfonamide;
(S)-6-(3-aminopyrrolidin-1-yl)-N-(6-(o-tolyl)-5-(trifluoromethyl)pyridin-2-yl)pyridine-2-sulfonamide;
(R)-6-(3-(methylamino)pyrrolidin-1-yl)-N-(6-(o-tolyl)-5-(trifluoromethyl)pyridin-2-yl)pyridine-2-sulfonamide;
(S)-6-(3-(methylamino)pyrrolidin-1-yl)-N-(6-(o-tolyl)-5-(trifluoromethyl)pyridin-2-yl)pyridine-2-sulfonamide;
(R)-6-(pyrrolidin-3-ylamino)-N-(6-(o-tolyl)-5-(trifluoromethyl)pyridin-2-yl)pyridine-2-sulfonamide;
(S)-6-(pyrrolidin-3-ylamino)-N-(6-(o-tolyl)-5-(trifluoromethyl)pyridin-2-yl)pyridine-2-sulfonamide;
N-(5-chloro-6-(2-(trifluoromethyl)phenyl)pyridin-2-yl)-6-(((3S,4R)-4-hydroxytetrahydrofuran-3-yl)amino)pyridine-2-sulfonamide;
N-(5-chloro-6-(2-(trifluoromethyl)phenyl)pyridin-2-yl)-6-(((3R,4S)-4-hydroxytetrahydrofuran-3-yl)amino)pyridine-2-sulfonamide;
N-(5-chloro-6-(5-fluoro-2-methylphenyl)pyridin-2-yl)-6-(((3R,4S)-4-hydroxytetrahydrofuran-3-yl)amino)pyridine-2-sulfonamide;
N-(5-chloro-6-(5-fluoro-2-methylphenyl)pyridin-2-yl)-6-(((1S,2R,3R,4R)-3-(hydroxymethyl)-7-oxabicyclo[2.2.1]heptan-2-yl)amino)pyridine-2-sulfonamide;
(1S,4S)-4-((6-(N-(5-chloro-6-(2,6-dimethylphenyl)pyridin-2-yl)sulfamoyl)pyridin-2-yl)oxy)cyclohexane-1-carboxylic acid;
(1R,4R)-4-((6-(N-(5-chloro-6-(2,6-dimethylphenyl)pyridin-2-yl)sulfamoyl)pyridin-2-yl)oxy)cyclohexane-1-carboxylic acid;
N-(5-chloro-6-(2,6-dimethylphenyl)pyridin-2-yl)-6-(3-oxopiperazin-1-yl)pyridine-2-sulfonamide;
tert-butyl 4-(6-(N-(6-(2,6-dimethylphenyl)-4-(trifluoromethyl)pyridin-2-yl)sulfamoyl)pyridin-2-yl)piperazine-1-carboxylate;
N-(6-(2,6-dimethylphenyl)-4-(trifluoromethyl)pyridin-2-yl)-6-(piperazin-1-yl)pyridine-2-sulfonamide;
N-(5-chloro-6-(5-fluoro-2-methylphenyl)pyridin-2-yl)-6-((7S,8aR)-7-fluorohexahydropyrrolo[1,2-a]pyrazin-2(1H)-yl)pyridine-2-sulfonamide;
N-(5-chloro-6-(5-fluoro-2-methylphenyl)pyridin-2-yl)-6-((1S,7S)-7-fluoro-1-methylhexahydropyrrolo[1,2-a]pyrazin-2(1H)-yl)pyridine-2-sulfonamide;
(S)-6-(7,7-difluorohexahydropyrrolo[1,2-a]pyrazin-2(1H)-yl)-N-(6-(o-tolyl)-5-(trifluoromethyl)pyridin-2-yl)pyridine-2-sulfonamide;
6-((7S,8aS)-7-fluorohexahydropyrrolo[1,2-a]pyrazin-2(1H)-yl)-N-(6-(o-tolyl)-5-(trifluoromethyl)pyridin-2-yl)pyridine-2-sulfonamide;
6-((7S,8aR)-7-fluorohexahydropyrrolo[1,2-a]pyrazin-2(1H)-yl)-N-(6-(o-tolyl)-5-(trifluoromethyl)pyridin-2-yl)pyridine-2-sulfonamide;
N-(6-(2,6-dimethylphenyl)-4-methoxypyridin-2-yl)-6-(piperazin-1-yl)pyridine-2-sulfonamide;
6-(4-(tert-butyl)piperazin-1-yl)-N-(5-chloro-6-(3-fluoro-2-methylphenyl)pyridin-2-yl)pyridine-2-sulfonamide;
N-(5-chloro-6-(3-fluoro-2-methylphenyl)pyridin-2-yl)-6-(4-cyclopropylpiperazin-1-yl)pyridine-2-sulfonamide;
6-(4-(tert-butyl)piperazin-1-yl)-N-(6-(3-fluoro-2-methylphenyl)-5-(trifluoromethyl)pyridin-2-yl)pyridine-2-sulfonamide;
6-(4-(tert-butyl)piperazin-1-yl)-N-(6-(5-fluoro-2-methylphenyl)-5-(trifluoromethyl)pyridin-2-yl)pyridine-2-sulfonamide;
6-(4-cyclopropylpiperazin-1-yl)-N-(6-(3-fluoro-2-methylphenyl)-5-(trifluoromethyl)pyridin-2-yl)pyridine-2-sulfonamide;
6-(4-cyclopropylpiperazin-1-yl)-N-(6-(5-fluoro-2-methylphenyl)-5-(trifluoromethyl)pyridin-2-yl)pyridine-2-sulfonamide;
N-(5-chloro-6-(3-fluoro-2-methylphenyl)pyridin-2-yl)-6-(5,6-dihydro-[1,2,4]triazolo[4,3-a]pyrazin-7(8H)-yl)pyridine-2-sulfonamide;
tert-butyl 4-(6-(N-(6-(2-cyclopropylphenyl)-5-(trifluoromethyl)pyridin-2-yl)sulfamoyl)pyridin-2-yl)piperazine-1-carboxylate;
N-(6-(2-cyclopropylphenyl)-5-(trifluoromethyl)pyridin-2-yl)-6-(piperazin-1-yl)pyridine-2-sulfonamide;
6-(4-(tert-butyl)piperazin-1-yl)-N-(6-(5-fluoro-2-methoxyphenyl)-5-(trifluoromethyl)pyridin-2-yl)pyridine-2-sulfonamide;
N-(6-(2-chlorophenyl)-5-(trifluoromethyl)pyridin-2-yl)-6-(piperazin-1-yl)pyridine-2-sulfonamide;
N-(6-(3-fluoro-2-methylphenyl)-5-(trifluoromethyl)pyridin-2-yl)-6-(piperazin-1-yl)pyridine-2-sulfonamide;
N-(6-(5-fluoro-2-methylphenyl)-5-(trifluoromethyl)pyridin-2-yl)-6-(piperazin-1-yl)pyridine-2-sulfonamide;
N-(6-(2-chloro-4-fluorophenyl)-5-(trifluoromethyl)pyridin-2-yl)-6-(piperazin-1-yl)pyridine-2-sulfonamide;
N-(6-(2-chloro-5-methoxyphenyl)-5-(trifluoromethyl)pyridin-2-yl)-6-(piperazin-1-yl)pyridine-2-sulfonamide;
N-(6-(2-chloro-3-fluorophenyl)-5-(trifluoromethyl)pyridin-2-yl)-6-(piperazin-1-yl)pyridine-2-sulfonamide;
N-(5-chloro-6-(2-chlorophenyl)pyridin-2-yl)-6-(piperazin-1-yl)pyridine-2-sulfonamide;
N-(5-chloro-6-(2-chloro-4-fluorophenyl)pyridin-2-yl)-6-(piperazin-1-yl)pyridine-2-sulfonamide;
N-(5-chloro-6-(2-chloro-5-methoxyphenyl)pyridin-2-yl)-6-(piperazin-1-yl)pyridine-2-sulfonamide;
N-(5-chloro-6-(2-chloro-3-fluorophenyl)pyridin-2-yl)-6-(piperazin-1-yl)pyridine-2-sulfonamide;
6-(piperazin-1-yl)-N-(6-(o-tolyl)-5-(trifluoromethyl)pyridin-2-yl)pyridine-2-sulfonamide;
tert-butyl 4-(6-(N-(6-(o-tolyl)-5-(trifluoromethyl)pyridin-2-yl)sulfamoyl)pyridin-2-yl)piperazine-1-carboxylate;
tert-butyl 4-(6-(N-(5-chloro-6-(2,6-dimethylphenyl)pyridin-2-yl)sulfamoyl)pyridin-2-yl)piperazine-1-carboxylate;
N-(5-chloro-6-(2,6-dimethylphenyl)pyridin-2-yl)-6-(piperazin-1-yl)pyridine-2-sulfonamide;
tert-butyl (R)-2-(hydroxymethyl)-4-(6-(N-(6-(o-tolyl)-5-(trifluoromethyl)pyridin-2-yl)sulfamoyl)pyridin-2-yl)piperazine-1-carboxylate;
(R)-6-(3-(hydroxymethyl)piperazin-1-yl)-N-(6-(o-tolyl)-5-(trifluoromethyl)pyridin-2-yl)pyridine-2-sulfonamide;
tert-butyl (R)-2-methyl-4-(6-(N-(6-(o-tolyl)-5-(trifluoromethyl)pyridin-2-yl)sulfamoyl)pyridin-2-yl)piperazine-1-carboxylate;
(R)-6-(3-methylpiperazin-1-yl)-N-(6-(o-tolyl)-5-(trifluoromethyl)pyridin-2-yl)pyridine-2-sulfonamide;
tert-butyl 4-(6-(N-(5-chloro-6-(2-methyl-5-(trifluoromethyl)phenyl)pyridin-2-yl)sulfamoyl)pyridin-2-yl)piperazine-1-carboxylate;
N-(5-chloro-6-(2-methyl-5-(trifluoromethyl)phenyl)pyridin-2-yl)-6-(piperazin-1-yl)pyridine-2-sulfonamide;
(S)-6-(2-methylpiperazin-1-yl)-N-(6-(o-tolyl)-5-(trifluoromethyl)pyridin-2-yl)pyridine-2-sulfonamide;
(R)-6-(2-methylpiperazin-1-yl)-N-(6-(o-tolyl)-5-(trifluoromethyl)pyridin-2-yl)pyridine-2-sulfonamide;

(R)—N-(6-(2,6-dimethylphenyl)-5-(trifluoromethyl)pyridin-2-yl)-6-(3-(hydroxymethyl)piperazin-1-yl)pyridine-2-sulfonamide;
(S)—N-(6-(2,6-dimethylphenyl)-5-(trifluoromethyl)pyridin-2-yl)-6-(3-(hydroxymethyl)piperazin-1-yl)pyridine-2-sulfonamide;
(R)—N-(6-(5-fluoro-2-methylphenyl)-5-(trifluoromethyl)pyridin-2-yl)-6-(3-(hydroxymethyl)piperazin-1-yl)pyridine-2-sulfonamide;
(S)—N-(6-(5-fluoro-2-methylphenyl)-5-(trifluoromethyl)pyridin-2-yl)-6-(3-(hydroxymethyl)piperazin-1-yl)pyridine-2-sulfonamide;
(R)—N-(6-(5-fluoro-2-methylphenyl)-5-(trifluoromethyl)pyridin-2-yl)-6-(3-methylpiperazin-1-yl)pyridine-2-sulfonamide;
(S)—N-(6-(5-fluoro-2-methylphenyl)-5-(trifluoromethyl)pyridin-2-yl)-6-(3-methylpiperazin-1-yl)pyridine-2-sulfonamide;
6-((3S,5R)-3,5-dimethylpiperazin-1-yl)-N-(6-(5-fluoro-2-methylphenyl)-5-(trifluoromethyl)pyridin-2-yl)pyridine-2-sulfonamide;
N-(6-(5-fluoro-2-methylphenyl)-5-(trifluoromethyl)pyridin-2-yl)-6-(4-methylpiperazin-1-yl)pyridine-2-sulfonamide;
6-(4-acetylpiperazin-1-yl)-N-(6-(5-fluoro-2-methylphenyl)-5-(trifluoromethyl)pyridin-2-yl)pyridine-2-sulfonamide;
6-(3,8-diazabicyclo[3.2.1]octan-3-yl)-N-(6-(o-tolyl)-5-(trifluoromethyl)pyridin-2-yl)pyridine-2-sulfonamide;
6-(4-(2-hydroxyethyl)piperazin-1-yl)-N-(6-(o-tolyl)-5-(trifluoromethyl)pyridin-2-yl)pyridine-2-sulfonamide;
2-(4-(6-(N-(6-(o-tolyl)-5-(trifluoromethyl)pyridin-2-yl)sulfamoyl)pyridin-2-yl)piperazin-1-yl)acetamide;
4-(6-(N-(6-(o-tolyl)-5-(trifluoromethyl)pyridin-2-yl)sulfamoyl)pyridin-2-yl)piperazine-1-carboxamide;
6-(4-(2,2-difluoroethyl)piperazin-1-yl)-N-(6-(o-tolyl)-5-(trifluoromethyl)pyridin-2-yl)pyridine-2-sulfonamide;
N-(6-(o-tolyl)-5-(trifluoromethyl)pyridin-2-yl)-6-(4-(2,2,2-trifluoroethyl)piperazin-1-yl)pyridine-2-sulfonamide;
6-(4-(oxetan-3-yl)piperazin-1-yl)-N-(6-(o-tolyl)-5-(trifluoromethyl)pyridin-2-yl)pyridine-2-sulfonamide;
tert-butyl 4-(6-(N-(5-chloro-6-(2,6-dimethylphenyl)pyridin-2-yl)sulfamoyl)pyridin-2-yl)-3-oxopiperazine-1-carboxylate
6-(4-methylpiperazin-1-yl)-N-(6-(o-tolyl)-5-(trifluoromethyl)pyridin-2-yl)pyridine-2-sulfonamide;
6-(3-oxopiperazin-1-yl)-N-(6-(o-tolyl)-5-(trifluoromethyl)pyridin-2-yl)pyridine-2-sulfonamide;
6-(4-glycylpiperazin-1-yl)-N-(6-(o-tolyl)-5-(trifluoromethyl)pyridin-2-yl)pyridine-2-sulfonamide;
N-(5-chloro-6-(2,6-dimethylphenyl)pyridin-2-yl)-6-(2-oxopiperazin-1-yl)pyridine-2-sulfonamide;
N-(5-chloro-6-(5-fluoro-2-methylphenyl)pyridin-2-yl)-6-(piperazin-1-yl)pyridine-2-sulfonamide;
N-[5-chloro-6-(3-fluoro-2-methylphenyl)pyridin-2-yl]-6-(piperazin-1-yl)pyridine-2-sulfonamide;
N-(5-chloro-6-(o-tolyl)pyridin-2-yl)-6-(piperazin-1-yl)pyridine-2-sulfonamide;
6-(4-methyl-3-oxopiperazin-1-yl)-N-(6-(o-tolyl)-5-(trifluoromethyl)pyridin-2-yl)pyridine-2-sulfonamide;
N-(5-chloro-6-(2,6-dimethylphenyl)pyridin-2-yl)-6-(4-methyl-2-oxopiperazin-1-yl)pyridine-2-sulfonamide;
N-(5-chloro-6-(2,6-dimethylphenyl)pyridin-2-yl)-6-(5,6-dihydroimidazo[1,2-a]pyrazin-7(8H)-yl)pyridine-2-sulfonamide;
N-(5-chloro-6-(2,6-dimethylphenyl)pyridin-2-yl)-6-(2-(trifluoromethyl)-5,6-dihydroimidazo[1,2-a]pyrazin-7(8H)-yl)pyridine-2-sulfonamide;
6-((1S,4S)-2,5-diazabicyclo[2.2.2]octan-2-yl)-N-(6-(5-fluoro-2-methylphenyl)-5-(trifluoromethyl)pyridin-2-yl)pyridine-2-sulfonamide;
6-(2,5-diazabicyclo[2.2.2]octan-2-yl)-N-(6-(5-fluoro-2-methylphenyl)-5-(trifluoromethyl)pyridin-2-yl)pyridine-2-sulfonamide;
6-((5S)-1,4-diazabicyclo[3.2.1]octan-4-yl)-N-(6-(5-fluoro-2-methylphenyl)-5-(trifluoromethyl)pyridin-2-yl)pyridine-2-sulfonamide;
6-((1S,4S)-2,5-diazabicyclo[2.2.1]heptan-2-yl)-N-(6-(o-tolyl)-5-(trifluoromethyl)pyridin-2-yl)pyridine-2-sulfonamide;
6-(3-hydroxy-3-(trifluoromethyl)azetidin-1-yl)-N-(6-(o-tolyl)-5-(trifluoromethyl)pyridin-2-yl)pyridine-2-sulfonamide;
N-(6-(2,6-dimethylphenyl)-4-(trifluoromethyl)pyridin-2-yl)-6-(3-hydroxyazetidin-1-yl)pyridine-2-sulfonamide;
N-(6-(2,6-dimethylphenyl)-4-methoxypyridin-2-yl)-6-(3-hydroxy-3-methylazetidin-1-yl)pyridine-2-sulfonamide;
N-(5-bromo-6-(o-tolyl)pyridin-2-yl)-6-(3-hydroxy-3-methylazetidin-1-yl)pyridine-2-sulfonamide;
N-(6-(2-cyclopropylphenyl)-5-(trifluoromethyl)pyridin-2-yl)-6-(3-hydroxyazetidin-1-yl)pyridine-2-sulfonamide;
N-(6-(5-fluoro-2-methoxyphenyl)-5-(trifluoromethyl)pyridin-2-yl)-6-(3-hydroxyazetidin-1-yl)pyridine-2-sulfonamide;
N-(5-chloro-6-(2,6-dimethylphenyl)pyridin-2-yl)-6-(3-hydroxy-3-methylazetidin-1-yl)pyridine-2-sulfonamide;
N-(5-chloro-6-(2,6-dimethylphenyl)pyridin-2-yl)-6-(3-cyclopropyl-3-hydroxyazetidin-1-yl)pyridine-2-sulfonamide;
N-(5-chloro-6-(2-methyl-5-(trifluoromethyl)phenyl)pyridin-2-yl)-6-(3-hydroxy-3-methylazetidin-1-yl)pyridine-2-sulfonamide;
N-(5-chloro-6-(2-chloro-4-fluorophenyl)pyridin-2-yl)-6-(3-hydroxy-3-methylazetidin-1-yl)pyridine-2-sulfonamide;
N-(5-chloro-6-(2-chloro-4-fluorophenyl)pyridin-2-yl)-6-(3-hydroxyazetidin-1-yl)pyridine-2-sulfonamide;
N-(6-(3-fluoro-2-methylphenyl)-5-(trifluoromethyl)pyridin-2-yl)-6-(3-hydroxy-3-methylazetidin-1-yl)pyridine-2-sulfonamide;
N-(6-(3-fluoro-2-methylphenyl)-5-(trifluoromethyl)pyridin-2-yl)-6-(3-hydroxyazetidin-1-yl)pyridine-2-sulfonamide;
N-(6-(4-fluoro-2-methylphenyl)-5-(trifluoromethyl)pyridin-2-yl)-6-(3-hydroxy-3-methylazetidin-1-yl)pyridine-2-sulfonamide;
N-(6-(4-fluoro-2-methylphenyl)-5-(trifluoromethyl)pyridin-2-yl)-6-(3-hydroxyazetidin-1-yl)pyridine-2-sulfonamide;
N-(6-(5-fluoro-2-methylphenyl)-5-(trifluoromethyl)pyridin-2-yl)-6-(3-hydroxy-3-methylazetidin-1-yl)pyridine-2-sulfonamide;
N-(6-(5-fluoro-2-methylphenyl)-5-(trifluoromethyl)pyridin-2-yl)-6-(3-hydroxyazetidin-1-yl)pyridine-2-sulfonamide;
N-(6-(2-chlorophenyl)-5-(trifluoromethyl)pyridin-2-yl)-6-(3-hydroxy-3-methylazetidin-1-yl)pyridine-2-sulfonamide;
N-(6-(2-chlorophenyl)-5-(trifluoromethyl)pyridin-2-yl)-6-(3-hydroxyazetidin-1-yl)pyridine-2-sulfonamide;
N-(5-chloro-6-(2-methyl-5-(trifluoromethyl)phenyl)pyridin-2-yl)-6-(3-hydroxyazetidin-1-yl)pyridine-2-sulfonamide;
6-(3-hydroxyazetidin-1-yl)-N-(5-(trifluoromethyl)-6-(2-(trifluoromethyl)phenyl)pyridin-2-yl)pyridine-2-sulfonamide;
N-(6-(2-chloro-4-fluorophenyl)-5-(trifluoromethyl)pyridin-2-yl)-6-(3-hydroxyazetidin-1-yl)pyridine-2-sulfonamide;

N-(6-(2-chloro-5-methoxyphenyl)-5-(trifluoromethyl)pyridin-2-yl)-6-(3-hydroxyazetidin-1-yl)pyridine-2-sulfonamide;
N-(5-chloro-6-(2-chlorophenyl)pyridin-2-yl)-6-(3-hydroxyazetidin-1-yl)pyridine-2-sulfonamide;
N-(5-chloro-6-(2-chloro-5-methoxyphenyl)pyridin-2-yl)-6-(3-hydroxyazetidin-1-yl)pyridine-2-sulfonamide;
N-(5-chloro-6-(2-chloro-3-fluorophenyl)pyridin-2-yl)-6-(3-hydroxyazetidin-1-yl)pyridine-2-sulfonamide;
N-(6-(2-chloro-3-fluorophenyl)-5-(trifluoromethyl)pyridin-2-yl)-6-(3-hydroxyazetidin-1-yl)pyridine-2-sulfonamide;
N-(5-chloro-6-(2,6-dimethylphenyl)pyridin-2-yl)-6-(3-hydroxyazetidin-1-yl)pyridine-2-sulfonamide;
N-(5-chloro-6-(3-fluoro-2-methylphenyl)pyridin-2-yl)-6-(3-hydroxyazetidin-1-yl)pyridine-2-sulfonamide;
6-(3-hydroxyazetidin-1-yl)-N-(6-(o-tolyl)-5-(trifluoromethyl)pyridin-2-yl)pyridine-2-sulfonamide;
N-(5-chloro-6-(5-fluoro-2-methylphenyl)pyridin-2-yl)-6-(3-hydroxyazetidin-1-yl)pyridine-2-sulfonamide;
N-(5-chloro-6-(5-fluoro-2-methylphenyl)pyridin-2-yl)-6-(3-hydroxy-3-(hydroxymethyl)azetidin-1-yl)pyridine-2-sulfonamide;
methyl 1-(6-(N-(6-(2-cyclopropylphenyl)-5-(trifluoromethyl)pyridin-2-yl)sulfamoyl)pyridin-2-yl)-4-methylpiperidine-4-carboxylate;
1-(6-(N-(6-(2-cyclopropylphenyl)-5-(trifluoromethyl)pyridin-2-yl)sulfamoyl)pyridin-2-yl)-4-methylpiperidine-4-carboxylic acid;
1-(6-(N-(6-(2-chlorophenyl)-5-(trifluoromethyl)pyridin-2-yl)sulfamoyl)pyridin-2-yl)-4-methylpiperidine-4-carboxylic acid;
1-(6-(N-(5-chloro-6-(2-chlorophenyl)pyridin-2-yl)sulfamoyl)pyridin-2-yl)-4-methylpiperidine-4-carboxylic acid;
1-(6-(N-(6-(2-chloro-4-fluorophenyl)-5-(trifluoromethyl)pyridin-2-yl)sulfamoyl)pyridin-2-yl)-4-methylpiperidine-4-carboxylic acid;
1-(6-(N-(6-(2-chloro-5-methoxyphenyl)-5-(trifluoromethyl)pyridin-2-yl)sulfamoyl)pyridin-2-yl)-4-methylpiperidine-4-carboxylic acid;
1-(6-(N-(6-(2-chloro-3-fluorophenyl)-5-(trifluoromethyl)pyridin-2-yl)sulfamoyl)pyridin-2-yl)-4-methylpiperidine-4-carboxylic acid;
1-(6-(N-(5-chloro-6-(2-chloro-4-fluorophenyl)pyridin-2-yl)sulfamoyl)pyridin-2-yl)-4-methylpiperidine-4-carboxylic acid;
1-(6-(N-(5-chloro-6-(2-chloro-5-methoxyphenyl)pyridin-2-yl)sulfamoyl)pyridin-2-yl)-4-methylpiperidine-4-carboxylic acid;
1-(6-(N-(5-chloro-6-(2-chloro-3-fluorophenyl)pyridin-2-yl)sulfamoyl)pyridin-2-yl)-4-methylpiperidine-4-carboxylic acid;
methyl 1-(6-(N-(5-chloro-6-(2,6-dimethylphenyl)pyridin-2-yl)sulfamoyl)pyridin-2-yl)piperidine-4-carboxylate;
1-(6-(N-(5-chloro-6-(2,6-dimethylphenyl)pyridin-2-yl)sulfamoyl)pyridin-2-yl)piperidine-4-carboxylic acid;
1-(6-(N-(5-chloro-6-(2,6-dimethylphenyl)pyridin-2-yl)sulfamoyl)pyridin-2-yl)-4-ethylpiperidine-4-carboxylic acid;
ethyl 1-(6-(N-(5-chloro-6-(2,6-dimethylphenyl)pyridin-2-yl)sulfamoyl)pyridin-2-yl)-4-methylpiperidine-4-carboxylate;
1-(6-(N-(5-chloro-6-(2,6-dimethylphenyl)pyridin-2-yl)sulfamoyl)pyridin-2-yl)-4-methylpiperidine-4-carboxylic acid;
ethyl 1-(6-(N-(6-(5-fluoro-2-methylphenyl)-5-(trifluoromethyl)pyridin-2-yl)sulfamoyl)pyridin-2-yl)-4-methylpiperidine-4-carboxylate;
ethyl 1-(6-(N-(5-chloro-6-(3-fluoro-2-methylphenyl)pyridin-2-yl)sulfamoyl)pyridin-2-yl)-4-methylpiperidine-4-carboxylate;
1-(6-(N-(5-chloro-6-(3-fluoro-2-methylphenyl)pyridin-2-yl)sulfamoyl)pyridin-2-yl)-4-methylpiperidine-4-carboxylic acid;
ethyl 1-(6-(N-(5-chloro-6-(o-tolyl)pyridin-2-yl)sulfamoyl)pyridin-2-yl)-4-methylpiperidine-4-carboxylate;
1-(6-(N-(5-chloro-6-(o-tolyl)pyridin-2-yl)sulfamoyl)pyridin-2-yl)-4-methylpiperidine-4-carboxylic acid;
ethyl 1-(6-(N-(5-chloro-6-(5-fluoro-2-methylphenyl)pyridin-2-yl)sulfamoyl)pyridin-2-yl)-4-methylpiperidine-4-carboxylate;
1-(6-{[5-chloro-6-(5-fluoro-2-methylphenyl)pyridin-2-yl]sulfamoyl}pyridin-2-yl)-4-methylpiperidine-4-carboxylic acid;
ethyl 1-(6-{[6-(3-fluoro-2-methylphenyl)-5-(trifluoromethyl)pyridin-2-yl]sulfamoyl}pyridin-2-yl)-4-methylpiperidine-4-carboxylate;
ethyl 4-methyl-1-(6-{[6-(2-methylphenyl)-5-(trifluoromethyl)pyridin-2-yl]sulfamoyl}pyridin-2-yl)piperidine-4-carboxylate;
methyl 1-(6-{[5-chloro-6-(2,6-dimethylphenyl)pyridin-2-yl]sulfamoyl}pyridin-2-yl)-4-hydroxypiperidine-4-carboxylate;
1-(6-{[5-chloro-6-(2,6-dimethylphenyl)pyridin-2-yl]sulfamoyl}pyridin-2-yl)-4-hydroxypiperidine-4-carboxylic acid;
1-(6-{[6-(5-fluoro-2-methylphenyl)-5-(trifluoromethyl)pyridin-2-yl]sulfamoyl}pyridin-2-yl)-4-methylpiperidine-4-carboxylic acid;
1-(6-(N-(6-(3-fluoro-2-methylphenyl)-5-(trifluoromethyl)pyridin-2-yl)sulfamoyl)pyridin-2-yl)-4-methylpiperidine-4-carboxylic acid;
4-methyl-1-(6-(N-(6-(o-tolyl)-5-(trifluoromethyl)pyridin-2-yl)sulfamoyl)pyridin-2-yl)piperidine-4-carboxylic acid;
1-(6-{[6-(3-fluoro-2-methylphenyl)-5-(trifluoromethyl)pyridin-2-yl]sulfamoyl}pyridin-2-yl)-4-methylpiperidine-4-carboxylic acid;
4-methyl-1-(6-{[6-(2-methylphenyl)-5-(trifluoromethyl)pyridin-2-yl]sulfamoyl}pyridin-2-yl)piperidine-4-carboxylic acid;
1-(6-{[6-(2,6-dimethylphenyl)-5-(trifluoromethyl)pyridin-2-yl]sulfamoyl}pyridin-2-yl)-4-methylpiperidine-4-carboxylic acid;
ethyl 1-(6-{[6-(2,6-dimethylphenyl)-5-(trifluoromethyl)pyridin-2-yl]sulfamoyl}pyridin-2-yl)-4-methylpiperidine-4-carboxylate;
methyl 4-{[(tert-butoxy)carbonyl]amino}-1-(6-{[5-chloro-6-(2,6-dimethylphenyl)pyridin-2-yl]sulfamoyl}pyridin-2-yl)piperidine-4-carboxylate;
4-{[(tert-butoxy)carbonyl]amino}-1-(6-{[5-chloro-6-(2,6-dimethylphenyl)pyridin-2-yl]sulfamoyl}pyridin-2-yl)piperidine-4-carboxylic acid;
4-amino-1-(6-{[5-chloro-6-(2,6-dimethylphenyl)pyridin-2-yl]sulfamoyl}pyridin-2-yl)piperidine-4-carboxylic acid;
methyl 4-amino-1-(6-{[5-chloro-6-(2,6-dimethylphenyl)pyridin-2-yl]sulfamoyl}pyridin-2-yl)piperidine-4-carboxylate;
N-[5-chloro-6-(2,6-dimethylphenyl)pyridin-2-yl]-6-[(oxan-4-yl)amino]pyridine-2-sulfonamide;
rac-N-[5-chloro-6-(5-fluoro-2-methylphenyl)pyridin-2-yl]-6-{[(3R,4R)-3-hydroxyoxan-4-yl]amino}pyridine-2-sulfonamide;

N-[5-chloro-6-(5-fluoro-2-methyl phenyl)pyridin-2-yl]-6-{[(3S,4R)-3-hydroxyoxan-4-yl]amino}pyridine-2-sulfonamide;

rac-6-{[(3R,4R)-3-hydroxyoxan-4-yl]amino}-N-[6-(2-methylphenyl)-5-(trifluoromethyl)pyridin-2-yl]pyridine-2-sulfonamide;

6-{[(3S,4R)-3-hydroxyoxan-4-yl]amino}-N-[6-(2-methylphenyl)-5-(trifluoromethyl)pyridin-2-yl]pyridine-2-sulfonamide;

6-{[(3R,4R)-3-hydroxyoxan-4-yl]amino}-N-[6-(2-methylphenyl)-5-(trifluoromethyl)pyridin-2-yl]pyridine-2-sulfonamide;

6-{[(3S,4S)-3-hydroxyoxan-4-yl]amino}-N-[6-(2-methylphenyl)-5-(trifluoromethyl)pyridin-2-yl]pyridine-2-sulfonamide;

N-[5-chloro-6-(5-fluoro-2-methyl phenyl)pyridin-2-yl]-6-{[(3R,4R)-4-hydroxyoxan-3-yl]amino}pyridine-2-sulfonamide;

6-{[(3R,4R)-4-hydroxyoxan-3-yl]amino}-N-[6-(2-methylphenyl)-5-(trifluoromethyl)pyridin-2-yl]pyridine-2-sulfonamide;

rac-6-{[(3R,4S)-4-hydroxyoxan-3-yl]amino}-N-[6-(2-methylphenyl)-5-(trifluoromethyl)pyridin-2-yl]pyridine-2-sulfonamide;

6-{[(3S,4S)-4-hydroxyoxan-3-yl]amino}-N-[6-(2-methylphenyl)-5-(trifluoromethyl)pyridin-2-yl]pyridine-2-sulfonamide;

6-{[(3S,4R)-4-hydroxyoxan-3-yl]amino}-N-[6-(2-methylphenyl)-5-(trifluoromethyl)pyridin-2-yl]pyridine-2-sulfonamide;

N-[6-(2-methylphenyl)-5-(trifluoromethyl)pyridin-2-yl]-6-{[(1 s, 3s)-3-hydroxycyclobutyl]amino}pyridine-2-sulfonamide;

N-[6-(2-methylphenyl)-5-(trifluoromethyl)pyridin-2-yl]-6-{[(1r,3r)-3-hydroxycyclobutyl]amino}pyridine-2-sulfonamide;

N-[5-chloro-6-(2,6-dimethylphenyl)pyridin-2-yl]-6-{[(1r, 3s)-3-hydroxy-3-methylcyclobutyl]amino}pyridine-2-sulfonamide;

N-[5-chloro-6-(2,6-dimethylphenyl)pyridin-2-yl]-6-{[(1s, 3s)-3-hydroxycyclobutyl]amino}pyridine-2-sulfonamide;

N-[5-chloro-6-(2,6-dimethylphenyl)pyridin-2-yl]-6-{[(1r, 3r)-3-hydroxycyclobutyl]amino}pyridine-2-sulfonamide;

N-[5-chloro-6-(2,6-dimethylphenyl)pyridin-2-yl]-6-{[(3S, 5S)-5-(hydroxymethyl)oxolan-3-yl]oxy}pyridine-2-sulfonamide;

N-[5-chloro-6-(5-fluoro-2-methylphenyl)pyridin-2-yl]-6-{[(3R,4S)-4-hydroxyoxolan-3-yl]oxy}pyridine-2-sulfonamide;

rac-N-[5-chloro-6-(2,6-dimethylphenyl)pyridin-2-yl]-6-{[(3R,4S)-4-hydroxyoxolan-3-yl]oxy}pyridine-2-sulfonamide;

rac-6-{[(3RS,4SR)-4-hydroxyoxolan-3-yl]oxy}-N-[6-(2-methyl phenyl)-5-(trifluoromethyl)pyridin-2-yl]pyridine-2-sulfonamide;

rac-N-[6-(2-methylphenyl)-5-(trifluoromethyl)pyridin-2-yl]-6-[(4-oxooxolan-3-yl)oxy]pyridine-2-sulfonamide;

rac-6-{[(3RR,4SR)-4-hydroxy-4-methyl oxolan-3-yl]oxy}-N-[6-(2-methyl phenyl)-5-(trifluoromethyl)pyridin-2-yl] pyridine-2-sulfonamide;

6-{[(3R,4R)-4-hydroxy-4-methyloxolan-3-yl]oxy}-N-[6-(2-methylphenyl)-5-(trifluoromethyl)pyridin-2-yl]pyridine-2-sulfonamide;

6-{[(3R,4S)-4-hydroxy-4-methyloxolan-3-yl]oxy}-N-[6-(2-methylphenyl)-5-(trifluoromethyl)pyridin-2-yl]pyridine-2-sulfonamide;

6-{[(3R,4S)-4-hydroxyoxolan-3-yl]oxy}-N-[6-(2-methylphenyl)-5-(trifluoromethyl)pyridin-2-yl]pyridine-2-sulfonamide;

ethyl 1-(4-(6-(N-(6-(5-fluoro-2-methylphenyl)-5-(trifluoromethyl)pyridin-2-yl)sulfamoyl)pyridin-2-yl)piperazin-1-yl)cyclopropane-1-carboxylate;

tert-butyl 4-(6-(N-(5-chloro-6-(5-fluoro-2-methylphenyl)pyridin-2-yl)sulfamoyl)pyridin-2-yl)piperazine-1-carboxylate;

N-(6-(5-cyano-2-methylphenyl)-5-(trifluoromethyl)pyridin-2-yl)-6-(3-hydroxy-3-methylazetidin-1-yl)pyridine-2-sulfonamide;

1-(6-(N-(6-(5-fluoro-2-methylphenyl)-5-(trifluoromethyl)pyridin-2-yl)sulfamoyl)pyridin-2-yl)pyrrolidine-3-carboxylic acid;

tert-butyl 1-(6-(N-(6-(o-tolyl)-5-(trifluoromethyl)pyridin-2-yl)sulfamoyl)pyridin-2-yl)-1,6-diazaspiro[3.3]heptane-6-carboxylate;

6-(4,7-diazaspiro[2.5]octan-7-yl)-N-(6-(o-tolyl)-5-(trifluoromethyl)pyridin-2-yl)pyridine-2-sulfonamide;

6-(8-amino-5-oxa-2-azaspiro[3.4]octan-2-yl)-N-(6-(o-tolyl)-5-(trifluoromethyl)pyridin-2-yl)pyridine-2-sulfonamide;

(R)-6-(1-amino-8-azaspiro[4.5]decan-8-yl)-N-(6-(o-tolyl)-5-(trifluoromethyl)pyridin-2-yl)pyridine-2-sulfonamide;

N-(5-chloro-6-(5-cyano-2-methylphenyl)pyridin-2-yl)-6-(3-hydroxy-3-methylazetidin-1-yl)pyridine-2-sulfonamide;

(S)-6-(1-amino-7-azaspiro[3.5]nonan-7-yl)-N-(6-(o-tolyl)-5-(trifluoromethyl)pyridin-2-yl)pyridine-2-sulfonamide;

6-((1R)-1-amino-2-(hydroxymethyl)-8-azaspiro[4.5]decan-8-yl)-N-(6-(o-tolyl)-5-(trifluoromethyl)pyridin-2-yl)pyridine-2-sulfonamide;

N-(6-(3-cyano-2-methylphenyl)-5-(trifluoromethyl)pyridin-2-yl)-6-(3-hydroxy-3-methylazetidin-1-yl)pyridine-2-sulfonamide;

N-(5-chloro-6-(3-cyano-2-methylphenyl)pyridin-2-yl)-6-(3-hydroxy-3-methylazetidin-1-yl)pyridine-2-sulfonamide;

N-(5-chloro-6-(5-fluoro-2-methylphenyl)pyridin-2-yl)-6-(1, 6-diazaspiro[3.3]heptan-1-yl)pyridine-2-sulfonamide;

N-(6-(5-cyano-2-methylphenyl)-5-(trifluoromethyl)pyridin-2-yl)-6-(piperazin-1-yl)pyridine-2-sulfonamide;

N-(5-chloro-6-(5-cyano-2-methylphenyl)pyridin-2-yl)-6-(piperazin-1-yl)pyridine-2-sulfonamide;

6-(1,6-diazaspiro[3.3]heptan-1-yl)-N-(6-(o-tolyl)-5-(trifluoromethyl)pyridin-2-yl)pyridine-2-sulfonamide;

6-((2R,3S)-3-hydroxy-2-methylpyrrolidin-1-yl)-N-(6-(o-tolyl)-5-(trifluoromethyl)pyridin-2-yl)pyridine-2-sulfonamide;

1-(6-(N-(6-(5-fluoro-2-methylphenyl)-5-(trifluoromethyl)pyridin-2-yl)sulfamoyl)pyridin-2-yl)-3-hydroxypyrrolidine-2-carboxylic acid;

6-{[(3S,4R)-4-hydroxyoxolan-3-yl]oxy}-N-[6-(2-methylphenyl)-5-(trifluoromethyl)pyridin-2-yl]pyridine-2-sulfonamide;

N-(6-(5-cyano-2-methylphenyl)-5-(trifluoromethyl)pyridin-2-yl)-2-(3-hydroxy-3-methylazetidin-1-yl)pyridine-4-sulfonamide;

(R)—N-(5-chloro-6-(5-fluoro-2-methylphenyl)pyridin-2-yl)-2-(3-methylmorpholino)pyridine-4-sulfonamide;

(R)—N-(5-chloro-6-(3-fluoro-2-methylphenyl)pyridin-2-yl)-2-(3-methylmorpholino)pyridine-4-sulfonamide;

N-(6-(5-fluoro-2-methylphenyl)-5-(trifluoromethyl)pyridin-2-yl)-2-(3-hydroxy-3-methylazetidin-1-yl)pyridine-4-sulfonamide;

(R)—N-(6-(5-fluoro-2-methylphenyl)-5-(trifluoromethyl)pyridin-2-yl)-2-(3-methylmorpholino)pyridine-4-sulfonamide;

N-(5-chloro-6-(5-fluoro-2-methylphenyl)pyridin-2-yl)-2-(3-hydroxyazetidin-1-yl)pyridine-4-sulfonamide;

N-(5-chloro-6-(3-fluoro-2-methylphenyl)pyridin-2-yl)-2-(3-hydroxyazetidin-1-yl)pyridine-4-sulfonamide;

N-(6-(5-fluoro-2-methylphenyl)-5-(trifluoromethyl)pyridin-2-yl)-2-(3-hydroxyazetidin-1-yl)pyridine-4-sulfonamide;

2-(3-hydroxyazetidin-1-yl)-N-(5-(trifluoromethyl)-6-(2-(trifluoromethyl)phenyl)pyridin-2-yl)pyridine-4-sulfonamide;

N-(6-(5-fluoro-2-methylphenyl)-5-(trifluoromethyl)pyridin-2-yl)-2-(piperazin-1-yl)pyridine-4-sulfonamide;

N-(5-chloro-6-(5-fluoro-2-methylphenyl)pyridin-2-yl)-2-(piperazin-1-yl)pyridine-4-sulfonamide;

(R)-1-(6-(N-(6-(2-ethoxyphenyl)-5-(trifluoromethyl)pyridin-2-yl)sulfamoyl)pyridin-2-yl)-3-methylpiperidine-3-carboxylic acid;

(R)-3-methyl-1-(6-(N-(6-(2-propoxyphenyl)-5-(trifluoromethyl)pyridin-2-yl)sulfamoyl)pyridin-2-yl)piperidine-3-carboxylic acid;

1-(6-(N-(6-(o-tolyl)-5-(trifluoromethyl)pyridin-2-yl)sulfamoyl)pyridin-2-yl)azetidine-3-carboxylic acid;

3-((6-(N-(6-(o-tolyl)-5-(trifluoromethyl)pyridin-2-yl)oxy)cyclobutanecarboxylic acid;

(3R)-1-(6-{[6-(2-methylphenyl)-5-(trifluoromethyl)pyridin-2-yl]sulfamoyl}pyridin-2-yl)piperidine-3-carboxylic acid;

(3S)-1-(6-{[6-(2-methylphenyl)-5-(trifluoromethyl)pyridin-2-yl]sulfamoyl}pyridin-2-yl)piperidine-3-carboxylic acid;

(2S)-1-[(tert-butoxy)carbonyl]-4-(6-{[6-(2-methylphenyl)-5-(trifluoromethyl)pyridin-2-yl]sulfamoyl}pyridin-2-yl)piperazine-2-carboxylic acid;

(2S)-4-(6-{[6-(2-methylphenyl)-5-(trifluoromethyl)pyridin-2-yl]sulfamoyl}pyridin-2-yl)piperazine-2-carboxylic acid;

3-methyl-1-(6-{[6-(2-methylphenyl)-5-(trifluoromethyl)pyridin-2-yl]sulfamoyl}pyridin-2-yl)pyrrolidine-3-carboxylic acid;

3-methyl-1-(6-{[6-(2-methylphenyl)-5-(trifluoromethyl)pyridin-2-yl]sulfamoyl}pyridin-2-yl)piperidine-3-carboxylic acid;

(2R)-1-[(tert-butoxy)carbonyl]-4-(6-{[6-(2-methylphenyl)-5-(trifluoromethyl)pyridin-2-yl]sulfamoyl}pyridin-2-yl)piperazine-2-carboxylic acid;

(2R)-4-(6-{[6-(2-methylphenyl)-5-(trifluoromethyl)pyridin-2-yl]sulfamoyl}pyridin-2-yl)morpholine-2-carboxylic acid;

(1R,2S,5S)-3-(6-{[6-(2-methylphenyl)-5-(trifluoromethyl)pyridin-2-yl]sulfamoyl}pyridin-2-yl)-3-azabicyclo[3.1.0]hexane-2-carboxylic acid;

(2R)-4-(6-{[6-(2-methylphenyl)-5-(trifluoromethyl)pyridin-2-yl]sulfamoyl}pyridin-2-yl)piperazine-2-carboxylic acid;

4-((6-(N-(6-(o-tolyl)-5-(trifluoromethyl)pyridin-2-yl)sulfamoyl)pyridin-2-yl)oxy)cyclohexanecarboxylic acid;

4-methyl-1-(6-(N-(6-(2-morpholinophenyl)-5-(trifluoromethyl)pyridin-2-yl)sulfamoyl)pyridin-2-yl)piperidine-4-carboxylic acid;

1-(6-{[6-(2-methylphenyl)-5-(trifluoromethyl)pyridin-2-yl]sulfamoyl}pyridin-2-yl)piperidine-4-carboxylic acid;

9-(6-{[6-(2-methylphenyl)-5-(trifluoromethyl)pyridin-2-yl]sulfamoyl}pyridin-2-yl)-9-azabicyclo[3.3.1]nonane-3-carboxylic acid;

8-(6-{[6-(2-methylphenyl)-5-(trifluoromethyl)pyridin-2-yl]sulfamoyl}pyridin-2-yl)-8-azabicyclo[3.2.1]octane-3-carboxylic acid;

(2R)-4-[(tert-butoxy)carbonyl]-1-(6-{[6-(2-methylphenyl)-5-(trifluoromethyl)pyridin-2-yl]sulfamoyl}pyridin-2-yl)piperazine-2-carboxylic acid;

(3S)-1-(6-{[6-(2-methylphenyl)-5-(trifluoromethyl)pyridin-2-yl]sulfamoyl}pyridin-2-yl)pyrrolidine-3-carboxylic acid;

(3R)-1-(6-{[6-(2-methylphenyl)-5-(trifluoromethyl)pyridin-2-yl]sulfamoyl}pyridin-2-yl)pyrrolidine-3-carboxylic acid;

(2S)-4-[(tert-butoxy)carbonyl]-1-(6-{[6-(2-methylphenyl)-5-(trifluoromethyl)pyridin-2-yl]sulfamoyl}pyridin-2-yl)piperazine-2-carboxylic acid;

1-(6-{[6-(2-ethylphenyl)-5-(trifluoromethyl)pyridin-2-yl]sulfamoyl}pyridin-2-yl)-4-propylpiperidine-4-carboxylic acid;

1-(6-{[6-(2-ethylphenyl)-5-(trifluoromethyl)pyridin-2-yl]sulfamoyl}pyridin-2-yl)-3-propylpiperidine-3-carboxylic acid;

(2R)-1-(6-{[6-(2-methylphenyl)-5-(trifluoromethyl)pyridin-2-yl]sulfamoyl}pyridin-2-yl)piperazine-2-carboxylic acid;

(2S)-1-(6-{[6-(2-methylphenyl)-5-(trifluoromethyl)pyridin-2-yl]sulfamoyl}pyridin-2-yl)piperazine-2-carboxylic acid;

(1r,3r)-3-((6-(N-(6-(o-tolyl)-5-(trifluoromethyl)pyridin-2-yl)sulfamoyl)pyridin-2-yl)amino)cyclobutanecarboxylic acid;

(1s,3s)-1-methyl-3-((6-(N-(6-(o-tolyl)-5-(trifluoromethyl)pyridin-2-yl)sulfamoyl)pyridin-2-yl)amino)cyclobutanecarboxylic acid;

(3R)-1-(6-{[6-(5-fluoro-2-methylphenyl)-5-(trifluoromethyl)pyridin-2-yl]sulfamoyl}pyridin-2-yl)piperidine-3-carboxylic acid;

(3R)-1-(6-{[6-(3-fluoro-2-methylphenyl)-5-(trifluoromethyl)pyridin-2-yl]sulfamoyl}pyridin-2-yl)piperidine-3-carboxylic acid;

(3S)-1-(6-{[6-(5-fluoro-2-methylphenyl)-5-(trifluoromethyl)pyridin-2-yl]sulfamoyl}pyridin-2-yl)piperidine-3-carboxylic acid;

(3S)-1-(6-{[6-(3-fluoro-2-methylphenyl)-5-(trifluoromethyl)pyridin-2-yl]sulfamoyl}pyridin-2-yl)piperidine-3-carboxylic acid;

1-(6-{[6-(5-fluoro-2-methylphenyl)-5-(trifluoromethyl)pyridin-2-yl]sulfamoyl}pyridin-2-yl)-3-methylpiperidine-3-carboxylic acid;

1-(6-{[6-(3-fluoro-2-methylphenyl)-5-(trifluoromethyl)pyridin-2-yl]sulfamoyl}pyridin-2-yl)-3-methylpiperidine-3-carboxylic acid;

1-(6-(N-(6-(2-cyclobutylphenyl)-5-(trifluoromethyl)pyridin-2-yl)-4-methylpiperidine-4-carboxylic acid;

(1r,4r)-4-((6-(N-(6-(o-tolyl)-5-(trifluoromethyl)pyridin-2-yl)sulfamoyl)pyridin-2-yl)amino)cyclohexanecarboxylic acid;

(1r,3s)-1-methyl-3-[(6-{[6-(2-methylphenyl)-5-(trifluoromethyl)pyridin-2-yl]sulfamoyl}pyridin-2-yl)amino]cyclobutane-1-carboxylic acid;

(R)-1-(6-(N-(6-(2-cyclobutylphenyl)-5-(trifluoromethyl)pyridin-2-yl)sulfamoyl)pyridin-2-yl)piperidine-3-carboxylic acid;

(S)-1-(6-(N-(6-(2-cyclobutylphenyl)-5-(trifluoromethyl)pyridin-2-yl)sulfamoyl)pyridin-2-yl)piperidine-3-carboxylic acid;

1-(6-(N-(6-(2-cyclobutylphenyl)-5-(trifluoromethyl)pyridin-2-yl)-3-methylpiperidine-3-carboxylic acid;

(R)-1-(6-(N-(6-(2-ethylphenyl)-5-(trifluoromethyl)pyridin-2-yl)sulfamoyl)pyridin-2-yl)piperidine-3-carboxylic acid;

(S)-1-(6-(N-(6-(2-ethylphenyl)-5-(trifluoromethyl)pyridin-2-yl)sulfamoyl)pyridin-2-yl)piperidine-3-carboxylic acid;
1-(6-(N-(6-(2-ethylphenyl)-5-(trifluoromethyl)pyridin-2-yl)sulfamoyl)pyridin-2-yl)-3-methylpiperidine-3-carboxylic acid;
4-((6-(N-(6-(o-tolyl)-5-(trifluoromethyl)pyridin-2-yl)amino)cyclohexanecarboxylic acid;
(S)-1-(6-(N-(6-(2-cyclobutylphenyl)-5-(trifluoromethyl)pyridin-2-yl)sulfamoyl)pyridin-2-yl)-3-methylpiperidine-3-carboxylic acid;
1-(4-(N-(6-(2-ethylphenyl)-5-(trifluoromethyl)pyridin-2-yl)sulfamoyl)pyridin-2-yl)-4-methylpiperidine-4-carboxylic acid;
(R)-1-(6-(N-(6-(2-isopropylphenyl)-5-(trifluoromethyl)pyridin-2-yl)sulfamoyl)pyridin-2-yl)piperidine-3-carboxylic acid;
(S)-1-(6-(N-(6-(2-isopropylphenyl)-5-(trifluoromethyl)pyridin-2-yl)sulfamoyl)pyridin-2-yl)piperidine-3-carboxylic acid;
1-(6-(N-(6-(2-isopropylphenyl)-5-(trifluoromethyl)pyridin-2-yl)sulfamoyl)pyridin-2-yl)-3-methylpiperidine-3-carboxylic acid;
1-(4-(N-(6-(2-cyclobutylphenyl)-5-(trifluoromethyl)pyridin-2-yl)-4-methylpiperidine-4-carboxylic acid;
1-(6-(N-(6-(2-cyclopentylphenyl)-5-(trifluoromethyl)pyridin-2-yl)-4-methylpiperidine-4-carboxylic acid;
1-(6-(6-(2-ethylphenyl)-5-(trifluoromethyl)pyridine-2-sulfonamido)pyridin-2-yl)-4-methylpiperidine-4-carboxylic acid;
4-methyl-1-(6-(N-(6-(2-(2,2,2-trifluoroethoxy)phenyl)-5-(trifluoromethyl)pyridin-2-yl)sulfamoyl)pyridin-2-yl)piperidine-4-carboxylic acid;
1-(6-(N-(6-(2-isobutoxyphenyl)-5-(trifluoromethyl)pyridin-2-yl)sulfamoyl)pyridin-2-yl)-4-methylpiperidine-4-carboxylic acid;
(R)-1-(6-(N-(6-(2-cyclobutylphenyl)-5-(trifluoromethyl)pyridin-2-yl)sulfamoyl)pyridin-2-yl)-3-methylpiperidine-3-carboxylic acid;
(R)-1-(6-(N-(6-(2-isopropylphenyl)-5-(trifluoromethyl)pyridin-2-yl)sulfamoyl)pyridin-2-yl)-3-methylpiperidine-3-carboxylic acid;
(S)-1-(6-(N-(6-(2-isopropylphenyl)-5-(trifluoromethyl)pyridin-2-yl)sulfamoyl)pyridin-2-yl)-3-methylpiperidine-3-carboxylic acid;
1-(6-(N-(6-(2-isobutoxyphenyl)-5-(trifluoromethyl)pyridin-2-yl)sulfamoyl)pyridin-2-yl)-3-methylpiperidine-3-carboxylic acid;
1-(6-(N-(5-chloro-6-(2-ethylphenyl)pyridin-2-yl)sulfamoyl)pyridin-2-yl)-3-methylpiperidine-3-carboxylic acid;
1-(6-(N-(5-chloro-6-(2-isopropylphenyl)pyridin-2-yl)sulfamoyl)pyridin-2-yl)-3-methylpiperidine-3-carboxylic acid;
1-(6-(N-(5-chloro-6-(2-cyclobutylphenyl)pyridin-2-yl)sulfamoyl)pyridin-2-yl)-3-methylpiperidine-3-carboxylic acid;
1-(6-(N-(6-(2-(tert-butyl)phenyl)-5-chloropyridin-2-yl)sulfamoyl)pyridin-2-yl)-3-methylpiperidine-3-carboxylic acid;
(R)-1-(6-(N-(5-chloro-6-(2-cyclobutylphenyl)pyridin-2-yl)sulfamoyl)pyridin-2-yl)-3-methylpiperidine-3-carboxylic acid;
(R)-1-(6-(N-(5-chloro-6-(2-isopropylphenyl)pyridin-2-yl)sulfamoyl)pyridin-2-yl)-3-methylpiperidine-3-carboxylic acid;
(R)-1-(6-(N-(5-chloro-6-(2-ethylphenyl)pyridin-2-yl)sulfamoyl)pyridin-2-yl)-3-methylpiperidine-3-carboxylic acid;
(R)-1-(6-(N-(6-(2-ethylphenyl)-5-(trifluoromethyl)pyridin-2-yl)sulfamoyl)pyridin-2-yl)-3-methylpiperidine-3-carboxylic acid;
rac-(1RS,3RS,4SR)-3-((6-(N-(6-(o-tolyl)-5-(trifluoromethyl)pyridin-2-yl)sulfamoyl)pyridin-2-yl)amino)-7-oxabicyclo[2.2.1]heptane-1-carboxylic acid;
(R)-1-(6-(N-(6-(2-isobutoxyphenyl)-5-(trifluoromethyl)pyridin-2-yl)sulfamoyl)pyridin-2-yl)-3-methylpiperidine-3-carboxylic acid;
1-(6-(N-(5-chloro-6-(2-isobutoxyphenyl)pyridin-2-yl)sulfamoyl)pyridin-2-yl)-4-methylpiperidine-4-carboxylic acid;
4-methyl-1-(6-(N-(6-(2-propylphenyl)-5-(trifluoromethyl)pyridin-2-yl)sulfamoyl)pyridin-2-yl)piperidine-4-carboxylic acid;
1-(6-(N-(6-(2-chlorophenyl)-5-(trifluoromethyl)pyridin-2-yl)sulfamoyl)pyridin-2-yl)-3-methylpiperidine-3-carboxylic acid;
1-(6-(N-(5-chloro-6-(2-isobutoxyphenyl)pyridin-2-yl)sulfamoyl)pyridin-2-yl)-3-methylpiperidine-3-carboxylic acid;
3-methyl-1-(6-(N-(6-(2-propylphenyl)-5-(trifluoromethyl)pyridin-2-yl)sulfamoyl)pyridin-2-yl)piperidine-3-carboxylic acid;
1-(6-(N-(6-(2-cyclopropylphenyl)-5-(trifluoromethyl)pyridin-2-yl)sulfamoyl)pyridin-2-yl)-3-methylpiperidine-3-carboxylic acid;
rac-(1RS,3RS,4SR)-3-((6-(N-(6-(2-isopropylphenyl)-5-(trifluoromethyl)pyridin-2-yl)sulfamoyl)pyridin-2-yl)amino)-7-oxabicyclo[2.2.1]heptane-1-carboxylic acid;
rac-(1SR,5RS,6RS,7SR)-5-propyl-2-(6-(N-(6-(o-tolyl)-5-(trifluoromethyl)pyridin-2-yl)sulfamoyl)pyridin-2-yl)-2-azabicyclo[4.2.0]octane-7-carboxylic acid;
(R)-1-(6-(N-(6-(2-cyclopropylphenyl)pyridin-2-yl)sulfamoyl)pyridin-2-yl)-3-methylpiperidine-3-carboxylic acid;
(R)-1-(6-(N-(6-(2-cyclopropylphenyl)-5-methylpyridin-2-yl)sulfamoyl)pyridin-2-yl)-3-methylpiperidine-3-carboxylic acid;
(R)-1-(6-(N-(5-cyclopropyl-6-(2-cyclopropylphenyl)pyridin-2-yl)sulfamoyl)pyridin-2-yl)-3-methylpiperidine-3-carboxylic acid;
(R)-3-methyl-1-(6-(N-(5-methyl-6-(o-tolyl)pyridin-2-yl)sulfamoyl)pyridin-2-yl)piperidine-3-carboxylic acid;
R)-1-(6-(N-(5-methoxy-6-(o-tolyl)pyridin-2-yl)sulfamoyl)pyridin-2-yl)-3-methylpiperidine-3-carboxylic acid;
R)-1-(6-(N-(5-methoxy-6-(o-tolyl)pyridin-2-yl)sulfamoyl)pyridin-2-yl)-3-methylpiperidine-3-carboxylic acid;
(R)-3-methyl-1-(6-(N-(6-(o-tolyl)pyridin-2-yl)sulfamoyl)pyridin-2-yl)piperidine-3-carboxylic acid;
(R)-1-(6-(N-(6-(2-cyclopropylphenyl)-5-(trifluoromethyl)pyridin-2-yl)sulfamoyl)pyridin-2-yl)-3-methylpiperidine-3-carboxylic acid;
1-(6-(N-(6-(2-chloro-5-methoxyphenyl)-5-(trifluoromethyl)pyridin-2-yl)sulfamoyl)pyridin-2-yl)-3-methylpiperidine-3-carboxylic acid;
(3R)-3-methyl-1-(6-{[6-(2-methylphenyl)-5-(trifluoromethyl)pyridin-2-yl]sulfamoyl}pyridin-2-yl)piperidine-3-carboxylic acid;
(3R)-1-(6-{[6-(5-fluoro-2-methylphenyl)-5-(trifluoromethyl)pyridin-2-yl]sulfamoyl}pyridin-2-yl)-3-methylpiperidine-3-carboxylic acid;

(3R)-1-(6-{[6-(3-fluoro-2-methylphenyl)-5-(trifluoromethyl)pyridin-2-yl]sulfamoyl}pyridin-2-yl)-3-methylpiperidine-3-carboxylic acid;
(1S,3S)-3-((6-(N-(6-(2-isopropylphenyl)-5-(trifluoromethyl)pyridin-2-yl)sulfamoyl)pyridin-2-yl)amino)cyclohexanecarboxylic acid;
5-(6-(N-(6-(o-tolyl)-5-(trifluoromethyl)pyridin-2-yl)sulfamoyl)pyridin-2-yl)-5-azaspiro[2.4]heptane-1-carboxylic acid;
5-(6-(N-(6-(2-cyclopropylphenyl)-5-(trifluoromethyl)pyridin-2-yl)sulfamoyl)pyridin-2-yl)-5-azaspiro[2.4]heptane-1-carboxylic acid;
(R)-1-(6-(N-(6-(2-chlorophenyl)-5-(trifluoromethyl)pyridin-2-yl)sulfamoyl)pyridin-2-yl)-3-methylpiperidine-3-carboxylic acid;
(R)-1-(6-(N-(5-chloro-6-(2-isobutoxyphenyl)pyridin-2-yl)sulfamoyl)pyridin-2-yl)-3-methylpiperidine-3-carboxylic acid;
(R)-3-methyl-1-(6-(N-(6-(2-propylphenyl)-5-(trifluoromethyl)pyridin-2-yl)sulfamoyl)pyridin-2-yl)piperidine-3-carboxylic acid;
(R)-1-(6-(N-(6-(2-chloro-5-methoxyphenyl)-5-(trifluoromethyl)pyridin-2-yl)sulfamoyl)pyridin-2-yl)-3-methylpiperidine-3-carboxylic acid;
(S)-3-methyl-1-(6-(N-(6-(2-propylphenyl)-5-(trifluoromethyl)pyridin-2-yl)sulfamoyl)pyridin-2-yl)piperidine-3-carboxylic acid;
1-(6-(N-(6-(5-chloro-2-methoxyphenyl)-5-(trifluoromethyl)pyridin-2-yl)sulfamoyl)pyridin-2-yl)-4-methylpiperidine-4-carboxylic acid;
1-(6-(N-(6-(5-chloro-2-isopropoxyphenyl)-5-(trifluoromethyl)pyridin-2-yl)sulfamoyl)pyridin-2-yl)-4-methylpiperidine-4-carboxylic acid;
(3S)-3-methyl-1-(6-{[6-(2-methylphenyl)-5-(trifluoromethyl)pyridin-2-yl]sulfamoyl}pyridin-2-yl)piperidine-3-carboxylic acid;
(S)-1-(6-(N-(6-(2-cyclopropylphenyl)-5-(trifluoromethyl)pyridin-2-yl)sulfamoyl)pyridin-2-yl)-3-methylpiperidine-3-carboxylic acid;
1-(6-(N-(5-chloro-6-(2-cyclopropylphenyl)pyridin-2-yl)sulfamoyl)pyridin-2-yl)-4-methylpiperidine-4-carboxylic acid;
1-(6-(N-(5-chloro-6-(2-cyclopropylphenyl)pyridin-2-yl)sulfamoyl)pyridin-2-yl)-3-methylpiperidine-3-carboxylic acid;
1-(6-(N-(6-(5-chloro-2-methoxyphenyl)-5-(trifluoromethyl)pyridin-2-yl)sulfamoyl)pyridin-2-yl)-3-methylpiperidine-3-carboxylic acid;
1-(6-(N-(6-(5-chloro-2-isopropoxyphenyl)-5-(trifluoromethyl)pyridin-2-yl)sulfamoyl)pyridin-2-yl)-3-methylpiperidine-3-carboxylic acid;
rac-(1SR,5RS,6RS,7SR)-2-(6-(N-(3-chloro-2'-isopropyl-[2,3'-bipyridin]-6-yl)sulfamoyl)pyridin-2-yl)-5-propyl-2-azabicyclo[4.2.0]octane-7-carboxylic acid;
(3S)-1-(6-{[6-(5-fluoro-2-methylphenyl)-5-(trifluoromethyl)pyridin-2-yl]sulfamoyl}pyridin-2-yl)-3-methylpiperidine-3-carboxylic acid;
(3S)-1-(6-{[6-(3-fluoro-2-methylphenyl)-5-(trifluoromethyl)pyridin-2-yl]sulfamoyl}pyridin-2-yl)-3-methylpiperidine-3-carboxylic acid;
(R)-1-(6-(N-(5-chloro-6-(2-cyclopropylphenyl)pyridin-2-yl)sulfamoyl)pyridin-2-yl)-3-methylpiperidine-3-carboxylic acid;
rac-(1RS,3RS,4SR)-3-((6-(N-(6-(2-cyclopropylphenyl)-5-(trifluoromethyl)pyridin-2-yl)sulfamoyl)pyridin-2-yl)amino)-7-oxabicyclo[2.2.1]heptane-1-carboxylic acid;
5-(6-(N-(6-(5-fluoro-2-methylphenyl)-5-(trifluoromethyl)pyridin-2-yl)sulfamoyl)pyridin-2-yl)-5-azaspiro[2.5]octane-1-carboxylic acid;
5-(6-(N-(6-(3-fluoro-2-methylphenyl)-5-(trifluoromethyl)pyridin-2-yl)sulfamoyl)pyridin-2-yl)-5-azaspiro[2.5]octane-1-carboxylic acid;
5-(6-(N-(6-(o-tolyl)-5-(trifluoromethyl)pyridin-2-yl)sulfamoyl)pyridin-2-yl)-5-azaspiro[2.5]octane-1-carboxylic acid;
rac-(1SR,6RS,7SR)-2-(6-(N-(6-(2-isopropylphenyl)-5-(trifluoromethyl)pyridin-2-yl)sulfamoyl)pyridin-2-yl)-2-azabicyclo[4.2.0]octane-7-carboxylic acid;
rac-(1SR,6RS,7SR)-2-(6-(N-(6-(o-tolyl)-5-(trifluoromethyl)pyridin-2-yl)sulfamoyl)pyridin-2-yl)-2-azabicyclo[4.2.0]octane-7-carboxylic acid;
1-(6-(N-(6-(2-(hydroxymethyl)phenyl)-5-(trifluoromethyl)pyridin-2-yl)sulfamoyl)pyridin-2-yl)-3-methylpiperidine-3-carboxylic acid;
1-(6-(N-(6-(2-(2-hydroxyethyl)phenyl)-5-(trifluoromethyl)pyridin-2-yl)sulfamoyl)pyridin-2-yl)-3-methylpiperidine-3-carboxylic acid;
7-(6-(N-(6-(o-tolyl)-5-(trifluoromethyl)pyridin-2-yl)sulfamoyl)pyridin-2-yl)-7-azaspiro[3.5]nonane-2-carboxylic acid;
(R)-1-(6-(N-(5-chloro-6-(o-tolyl)pyridin-2-yl)sulfamoyl)pyridin-2-yl)-3-methylpiperidine-3-carboxylic acid;
(R)-1-(6-(N-(5-chloro-6-(2,6-dimethylphenyl)pyridin-2-yl)sulfamoyl)pyridin-2-yl)-3-methylpiperidine-3-carboxylic acid;
(R)-1-(6-(N-(6-(2-chloro-5-methoxyphenyl)-5-(trifluoromethyl)pyridin-2-yl)sulfamoyl)pyridin-2-yl)piperidine-3-carboxylic acid;
(R)-1-(6-(N-(6-(5-chloro-2-methylphenyl)-5-(trifluoromethyl)pyridin-2-yl)sulfamoyl)pyridin-2-yl)-3-methylpiperidine-3-carboxylic acid;
1-(6-(N-(6-(5-chloro-2-methylphenyl)-5-(trifluoromethyl)pyridin-2-yl)sulfamoyl)pyridin-2-yl)-4-methylpiperidine-4-carboxylic acid;
1-(6-(N-(5-chloro-6-(o-tolyl)pyridin-2-yl)sulfamoyl)pyridin-2-yl)-3-ethylpiperidine-3-carboxylic acid;
1-(6-(N-(5-chloro-6-(2,6-dimethylphenyl)pyridin-2-yl)sulfamoyl)pyridin-2-yl)-3-ethylpiperidine-3-carboxylic acid;
3-ethyl-1-(6-(N-(6-(o-tolyl)-5-(trifluoromethyl)pyridin-2-yl)sulfamoyl)pyridin-2-yl)piperidine-3-carboxylic acid;
(R)-1-(6-(N-(6-(5-chloro-2-methoxyphenyl)-5-(trifluoromethyl)pyridin-2-yl)sulfamoyl)pyridin-2-yl)-3-methylpiperidine-3-carboxylic acid;
1-(6-(N-(5-chloro-6-(o-tolyl)pyridin-2-yl)sulfamoyl)pyridin-2-yl)-3-propylpiperidine-3-carboxylic acid;
1-(6-(N-(5-chloro-6-(2,6-dimethylphenyl)pyridin-2-yl)sulfamoyl)pyridin-2-yl)-3-propylpiperidine-3-carboxylic acid;
3-propyl-1-(6-(N-(6-(o-tolyl)-5-(trifluoromethyl)pyridin-2-yl)sulfamoyl)pyridin-2-yl)piperidine-3-carboxylic acid;
3-((6-(N-(6-(o-tolyl)-5-(trifluoromethyl)pyridin-2-yl)sulfamoyl)pyridin-2-yl)amino)cyclopentanecarboxylic acid;
3-((6-(N-(6-(o-tolyl)-5-(trifluoromethyl)pyridin-2-yl)amino)cyclohexanecarboxylic acid;
(1,3-cis)-3-((6-(N-(6-(o-tolyl)-5-(trifluoromethyl)pyridin-2-yl)sulfamoyl)pyridin-2-yl)amino)cyclohexanecarboxylic acid;
(1S,2S,4R)-7-(6-(N-(6-(o-tolyl)-5-(trifluoromethyl)pyridin-2-yl)sulfamoyl)pyridin-2-yl)-7-azabicyclo[2.2.1]heptane-2-carboxylic acid;

(1,3-trans)-3-((6-(N-(6-(o-tolyl)-5-(trifluoromethyl)pyridin-2-yl)sulfamoyl)pyridin-2-yl)amino)cyclohexanecarboxylic acid;

(3R,6S)-6-methyl-1-(6-(N-(6-(o-tolyl)-5-(trifluoromethyl)pyridin-2-yl)sulfamoyl)pyridin-2-yl)piperidine-3-carboxylic acid; and (R)-1-(6-(N-(6-(2,6-dimethylphenyl)-5-(trifluoromethyl)pyridin-2-yl)sulfamoyl)pyridin-2-yl)-3-methylpiperidine-3-carboxylic acid;

or a pharmaceutically acceptable salt thereof.

A thirtieth embodiment of the invention is a pharmaceutical composition comprising a compound according to any one of the first through twenty-ninth embodiments, or a pharmaceutically acceptable salt thereof and one or more pharmaceutically acceptable carriers, or diluents.

A thirty-first embodiment of the invention is a pharmaceutical composition comprising a compound according embodiment thirty, or a pharmaceutically acceptable salt thereof and one or more pharmaceutically acceptable carriers, or diluents.

A thirty-second embodiment of the invention is a pharmaceutical composition comprising a compound according embodiment thirty-one, wherein the additional pharmaceutical agent(s) is selected from a mucolytic agent, nebulized hypertonic saline, bronchodilator, an antibiotic, an anti-infective agent, a CFTR modulator, and an anti-inflammatory agent or a pharmaceutically acceptable salt thereof and one or more pharmaceutically acceptable carriers, or diluents.

A thirty-third embodiment of the invention is a pharmaceutical composition comprising a compound according embodiment thirty-one, wherein the additional pharmaceutical agent(s) is selected from a CFTR modulator, or a pharmaceutically acceptable salt thereof and one or more pharmaceutically acceptable carriers, or diluents.

A thirty-fourth embodiment of the invention is a pharmaceutical composition comprising a compound according embodiment thirty-one, wherein the additional pharmaceutical agent(s) is selected from a CFTR corrector, or a pharmaceutically acceptable salt thereof and one or more pharmaceutically acceptable carriers, or diluents.

A thirty-fifth embodiment of the invention is a pharmaceutical composition comprising a compound according embodiment thirty-one, wherein the additional pharmaceutical agent(s) is selected from a CFTR potentiator, or a pharmaceutically acceptable salt thereof and one or more pharmaceutically acceptable carriers, or diluents.

A thirty-sixth embodiment of the invention is a pharmaceutical composition comprising a compound according embodiment thirty-one, wherein the additional pharmaceutical agents are a CFTR modulator, and a CFTR potentiator, or a pharmaceutically acceptable salt thereof and one or more pharmaceutically acceptable carriers, or diluents.

A thirty-seventh embodiment of the invention is a method of treating a CFTR mediated disease in a subject comprising administering to the subject a compound a pharmaceutically acceptable salt thereof of any one of embodiments 1 to 29 or the pharmaceutical composition of any one of embodiments 30 to 36.

A thirty-eighth embodiment of the invention comprising a method of treatment according to embodiment thirty-seven, wherein the CFTR mediated disease is selected from cystic fibrosis, asthma, COPD and chronic bronchitis.

A thirty-ninth embodiment of the invention comprising a method of treatment according to embodiment thirty-seven or thirty-eight, wherein the CFTR mediated disease is selected from cystic fibrosis, COPD and emphysema.

A fortieth embodiment of the invention comprising a method of treatment according to embodiment thirty-seven or thirty-eight, wherein the CFTR mediated disease is cystic fibrosis.

A forty-first embodiment of the invention comprising a method of treatment according to embodiment thirty-seven, further comprising administering to the subject one or more additional pharmaceutical agent(s) prior to, concurrent with, or subsequent to the compound of any one of embodiments 1 to 29 or the pharmaceutical composition of any one of embodiments 30 to 36.

A forty-second embodiment of the invention comprising a method of treatment according to embodiment forty-one, wherein the additional pharmaceutical agent(s) is selected from a mucolytic agent, nebulized hypertonic saline, bronchodilator, an antibiotic, an anti-infective agent, a CFTR modulator, and an anti-inflammatory agent.

A forty-third embodiment of the invention comprising a method of treatment according to embodiment forty-one, wherein the additional pharmaceutical agent(s) is selected from a CFTR modulator.

A forty-fourth embodiment of the invention comprising a method of treatment according to embodiment forty-one, wherein the additional pharmaceutical agent(s) is selected from a CFTR potentiator.

A forty-fifth embodiment of the invention comprising a method of treatment according to embodiment forty-one, wherein the additional pharmaceutical agent(s) is selected from a CFTR modulator and a CFTR potentiator.

A forty-sixth embodiment of the invention comprising the use of a compound of formula (I) in the manufacture of a medicament for treating a disease in an animal in which CFTR modulation contributes to the pathology and/or symptomology of a disease.

A forty-seventh embodiment of the invention comprising a compound according to any one of the first through twenty-ninth embodiments, or a pharmaceutically acceptable salt thereof, for use in the treatment of a CFTR mediated disease which is selected from cystic fibrosis, asthma, COPD and chronic bronchitis.

A forty-eighth embodiment of the invention comprising a compound according to any one of the first through twenty-ninth embodiments, or a pharmaceutically acceptable salt thereof, for use in the treatment of a CFTR mediated disease which is selected from cystic fibrosis, COPD and emphysema.

A forty-ninth embodiment of the invention comprising a compound according to any one of the first through twenty-ninth embodiments, or a pharmaceutically acceptable salt thereof, for use in the treatment of a CFTR mediated disease which is cystic fibrosis.

In certain embodiments, the present invention relates to the aforementioned methods, wherein said compound is administered parenterally.

In certain embodiments, the present invention relates to the aforementioned methods, wherein said compound is administered intramuscularly, intravenously, subcutaneously, orally, pulmonary, intrathecally, topically or intranasally.

In certain embodiments, the present invention relates to the aforementioned methods, wherein said compound is administered systemically.

In certain embodiments, the present invention relates to the aforementioned methods, wherein said subject is a mammal.

In certain embodiments, the present invention relates to the aforementioned methods, wherein said subject is a primate.

In certain embodiments, the present invention relates to the aforementioned methods, wherein said subject is a human.

The compounds and intermediates described herein may be isolated and used as the compound per se. Alternatively, when a moiety is present that is capable of forming a salt, the compound or intermediate may be isolated and used as its corresponding salt. As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfornate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The salts can be synthesized by conventional chemical methods from a compound containing a basic or acidic moiety. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed. For example, the compound of the present invention can exist in a deuterated form as shown below:

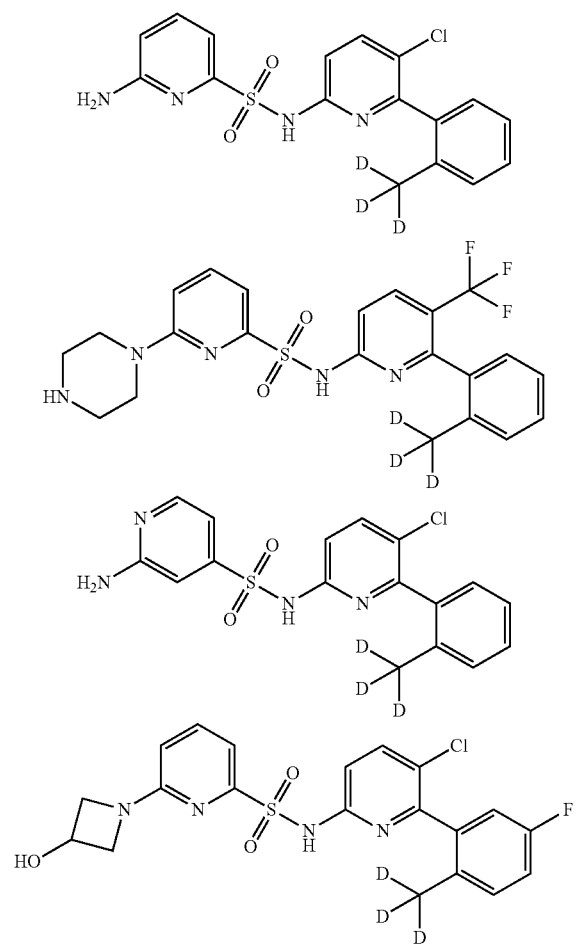

Pharmaceutically acceptable solvates in accordance with the invention include those wherein the solvent of crystallization may be isotopically substituted, e.g. $D_2O$, $d_6$-acetone, $d_6$-DMSO.

It will be recognized by those skilled in the art that the compounds of the present invention may contain chiral centers and as such may exist in different stereoisomeric forms. As used herein, the term "an optical isomer" or "a stereoisomer" refers to any of the various stereo isomeric configurations which may exist for a given compound of the present invention. It is understood that a substituent may be attached at a chiral center of a carbon atom. Therefore, the invention includes enantiomers, diastereomers or racemates of the compound.

"Enantiomers" are a pair of stereoisomers that are non-superimposable mirror images of each other. A 1:1 mixture of a pair of enantiomers is a "racemic" mixture. The term is used to designate a racemic mixture where appropriate. When designating the stereochemistry for the compounds of the present invention, a single stereoisomer with known relative and absolute configuration of the two chiral centers is designated using the conventional RS system (e.g., (1S, 2S)); a single stereoisomer with known relative configuration but unknown absolute configuration is designated with stars (e.g., (1R*,2R*)); and a racemate with two letters (e.g, (1RS,2RS) as a racemic mixture of (1R,2R) and (1S,2S); (1RS,2SR) as a racemic mixture of (1R,2S) and (1S,2R)). "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Alternatively, the resolved compounds can be defined by the respective retention times for the corresponding enantiomers/diastereomers via chiral HPLC.

Certain of the compounds described herein contain one or more asymmetric centers or axes and may thus give rise to enantiomers, diastereomers, and other stereoisomeric forms that may be defined, in terms of absolute stereochemistry, as (R)- or (S)-.

Unless specified otherwise, the compounds of the present invention are meant to include all such possible stereoisomers, including racemic mixtures, optically pure forms and intermediate mixtures. Optically active (R)- and (S)-stereoisomers may be prepared using chiral synthons or chiral reagents, or resolved using conventional techniques (e.g., separated on chiral SFC or HPLC chromatography columns, such as CHIRALPAK® and CHIRALCEL® available from DAICEL Corp. using the appropriate solvent or mixture of solvents to achieve good separation). If the compound contains a double bond, the substituent may be E or Z configuration. If the compound contains a disubstituted cycloalkyl, the cycloalkyl substituent may have a cis- or trans-configuration. All tautomeric forms are also intended to be included.

Pharmacology and Utility

Compounds of the present invention have been found to modulate CFTR activity and may be beneficial for the treatment of cystic fibrosis and additional diseases not directly caused by mutations in CFTR, such as secretory diseases and other protein folding diseases mediated by CFTR. These include, but are not limited to, chronic obstructive pulmonary disease (COPD), dry eye disease, and Sjogren's Syndrome.

COPD is characterized by airflow limitation that is progressive and not fully reversible. The airflow limitation is due to mucus hypersecretion, emphysema, and bronchiolitis. Activators of mutant or wild-type CFTR offer a potential treatment of mucus hypersecretion and impaired mucociliary clearance that is common in COPD. Specifically, increasing anion secretion across CFTR may facilitate fluid transport into the airway surface liquid to hydrate the mucus and optimized periciliary fluid viscosity. This would lead to enhanced mucociliary clearance and a reduction in the symptoms associated with COPD.

Dry eye disease is characterized by a decrease in tear aqueous production and abnormal tear film lipid, protein and mucin profiles. There are many causes of dry eye, some of which include age, Lasik eye surgery, arthritis, medications, chemical/thermal burns, allergies, and diseases, such as cystic fibrosis and Sjogrens's syndrome. Increasing anion secretion via CFTR would enhance fluid transport from the corneal endothelial cells and secretory glands surrounding the eye to increase corneal hydration. This would help to alleviate the symptoms associated with dry eye disease.

Sjogrens's syndrome is an autoimmune disease in which the immune system attacks moisture-producing glands throughout the body, including the eye, mouth, skin, respiratory tissue, liver, vagina, and gut. Symptoms, include, dry eye, mouth, and vagina, as well as lung disease. The disease is also associated with rheumatoid arthritis, systemic lupus, systemic sclerosis, and polymypositis/dermatomyositis. Defective protein trafficking is believed to cause the disease, for which treatment options are limited. Augmenters or inducers of CFTR activity may hydrate the various organs afflicted by the disease and help to elevate the associated symptoms.

Another aspect of the invention provides a method for treating or lessening the severity of a disease, disorder, or condition associated with the modulation of CFTR in a subject, which comprises administering to the subject a compound of formula (I) or a pharmaceutically acceptable salt thereof.

In certain embodiments, the present invention provides a method of treating a condition, disease, or disorder implicated by a deficiency of the CFTR activity, the method comprising administering a composition comprising a compound of formula (I) to a subject, preferably a mammal, in need of treatment thereof.

In certain embodiments, the present invention provides a method of treating diseases associated with reduced CFTR function due to mutations in the gene encoding CFTR or environmental factors (e.g., smoke). These diseases include, cystic fibrosis, chronic bronchitis, recurrent bronchitis, acute bronchitis, male infertility caused by congenital bilateral absence of the vas deferens (CBAVD), female infertility caused by congenital absence of the uterus and vagina (CAUV), idiopathic chronic pancreatitis (ICP), idiopathic recurrent pancreatitis, idiopathic acute pancreatitis, chronic rhinosinusitis, primary sclerosing cholangitis, allergic bronchopulmonary aspergillosis, diabetes, dry eye, constipation, allergic bronchopulmonary aspergillosis (ABPA), bone diseases (e.g., osteoporosis), and asthma.

In certain embodiments, the present invention provides a method for treating diseases associated with normal CFTR function. These diseases include, chronic obstructive pulmonary disease (COPD), chronic bronchitis or dyspnea associated therewith, recurrent bronchitis, acute bronchitis, rhinosinusitis, constipation, pancreatitis including chronic pancreatitis, recurrent pancreatitis, and acute pancreatitis, pancreatic insufficiency, male infertility caused by congenital bilateral absence of the vas deferens (CBAVD), mild pulmonary disease, idiopathic pancreatitis, liver disease, emphysema, hereditary emphysema, gallstones, gastroesophageal reflux disease, gastrointestinal malignancies, inflammatory bowel disease, constipation, diabetes, arthritis, osteoporosis, and osteopenia.

According to an alternative preferred embodiment, the present invention provides a method of treating cystic fibrosis comprising the step of administering to a mammal a composition comprising the step of administering to said mammal a composition comprising a compound of formula (I) or a pharmaceutically acceptable salt thereof.

According to the invention an "effective dose" or an "effective amount" of the compound or pharmaceutical composition is that amount effective for treating or lessening the severity of one or more of the diseases, disorders or conditions as recited above.

The compounds and compositions, according to the methods of the present invention, may be administered using any amount and any route of administration effective for treating or lessening the severity of one or more of the diseases, disorders or conditions recited above.

The compounds of the present invention are typically used as a pharmaceutical composition (e.g., a compound of the present invention and at least one pharmaceutically acceptable carrier). As used herein, the term "pharmaceutically acceptable carrier" includes generally recognized as safe (GRAS) solvents, dispersion media, surfactants, antioxidants, preservatives (e.g., antibacterial agents, antifungal agents), isotonic agents, salts, preservatives, drug stabilizers, buffering agents (e.g., maleic acid, tartaric acid, lactic acid, citric acid, acetic acid, sodium bicarbonate, sodium phosphate, and the like), and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated. For purposes of this invention, solvates and hydrates are considered pharmaceutical compositions comprising a compound of the present invention and a solvent (i.e., solvate) or water (i.e., hydrate).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The pharmaceutical composition comprising a compound of the present invention is generally formulated for use as a parenteral or oral administration.

For example, the pharmaceutical oral compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with
a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

The parenteral compositions (e.g, intravenous (IV) formulation) are aqueous isotonic solutions or suspensions. The parenteral compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are generally prepared according to conventional mixing, granulating or coating methods, respectively, and contain about 0.1-75%, or contain about 1-50%, of the active ingredient.

The compound of the present invention or pharmaceutical composition thereof for use in a subject (e.g., human) is typically administered orally or parenterally at a therapeutic dose of less than or equal to about 100 mg/kg, 75 mg/kg, 50 mg/kg, 25 mg/kg, 10 mg/kg, 7.5 mg/kg, 5.0 mg/kg, 3.0 mg/kg, 1.0 mg/kg, 0.5 mg/kg, 0.05 mg/kg or 0.01 mg/kg, but preferably not less than about 0.0001 mg/kg. When administered intravenously via infusion, the dosage may depend upon the infusion rate at which an iv formulation is administered. In general, the therapeutically effective dosage of a compound, the pharmaceutical composition, or the combinations thereof, is dependent on the species of the subject, the body weight, age and individual condition, the disorder or disease or the severity thereof being treated. A physician, pharmacist, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations.

Combination Therapy

In certain instances, it may be advantageous to administer the compound of the present invention in combination with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by CFTR. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by CFTR, wherein the medicament is prepared for administration with another therapeutic agent. The invention also provides the use of another therapeutic agent for treating a disease or condition mediated by CFTR, wherein the medicament is administered with a compound of formula (I).

The invention also provides a compound of formula (I) for use in a method of treating a disease or condition mediated by CFTR, wherein the compound of formula (I) is prepared for administration with another therapeutic agent. The invention also provides another therapeutic agent for use in a method of treating a disease or condition mediated by CFTR, wherein the other therapeutic agent is prepared for administration with a compound of formula (I). The invention also provides a compound of formula (I) for use in a method of treating a disease or condition mediated by CFTR, wherein the compound of formula (I) is administered with another therapeutic agent. The invention also provides another therapeutic agent for use in a method of treating a disease or condition mediated by CFTR, wherein the other therapeutic agent is administered with a compound of formula (I).

The invention also provides the use of a compound of formula (I) for treating a disease or condition mediated by CFTR, wherein the patient has previously (e.g. within 24 hours) been treated with another therapeutic agent. The invention also provides the use of another therapeutic agent for treating a disease or condition mediated by CFTR, wherein the patient has previously (e.g. within 24 hours) been treated with a compound of formula (I).

In one embodiment, the other therapeutic agent is selected from osmotic agents, ion channel modulating agents, mucolytic agents, bronchodilators, antihistamines, antibiotics, anti-inflammatory agents and CFTR modulators.

In another embodiment the other therapeutic agent is an osmotic agent, for example, nebulized hypertonic saline, dextran, mannitol or Xylitol.

In another embodiment the other therapeutic agent is a mucolytic agent, for example, Pulmozyme™.

In another embodiment, the other therapeutic agent is a bronchodilator, for example, albuterol, metaprotenerol sulfate, pirbuterol acetate, salmeterol, indacaterol or tetrabuline sulfate; suitable bronchodilatory agents also include anticholinergic and antimuscarinic agents, in particular, ipratropium bromide, oxitropium bromide, glycopyrronium salts or tiotropium salts.

In another embodiment, the other therapeutic agent is an antihistamine, for example, cetirizine hydrochloride, clemastine fumarate, promethazine, loratidine, desloratidine, diphenhydramine fexofenadine hydrochloride, activastine, astemizole, azelastine, ebastine, epinastine, mizolastine or tefenadine In another embodiment the other therapeutic agent is an antibiotic, for example tobramycin, including tobramycin inhaled powder, azithromycin, cayston, aztreonam, including the aerosolized for of aztreonam, amikacin, including liposomal formulations thereof, ciprofloxacin, including formulations thereof suitable of administration by inhalation, levofloxacin, including aerosolized formulations thereof and combinations of two antibiotics, for example, fosfomycin and tobramycin.

In another embodiment the other therapeutic agent is an anti-inflammatory agent, for example ibuprofen, docosahexanoic acid, sildenafil, inhaled glutathione, pioglitazone, hydroxychloroquine or simavastatin; a steroid, for example, glucocorticosteroids, such as budesonide, beclamethasone dipropionate, fluticasone propionate, ciclesonide or mometasone furoate; an LTD4 antagonist, such as montelukast or zafirlukast; a PDE4 inhibitor, such as Enprofylline, Theophylline, Roflumilaste, Ariflo (Cilomilaste), Tofimilaste, Pumafentrine, Lirimilaste, Apremilaste, Arofylline, Atizorame, Oglemilasturn, or Tetomilaste.

In another embodiment the other therapeutic agent is a CFTR modulator. In another embodiment the other therapeutic agent is a CFTR potentiator. In another embodiment the other therapeutic agent is a CFTR corrector. Exemplary CFTR modulators include N-(2-(5-chloro-2-methoxy-phenylamino)-4'-methyl-[4,5']bithiazolyl-2'-yl)-benzamide (Corr-4a), N-(2,4-di-tert-butyl-5-hydroxyphenyl)-1,4-dihydro-4-oxoquinoline-3-carboxamide (Ivacaftor), N-[2-(1,1-Dinmethythyl)-4-[1,1-di(methyl-dc)ethyl-2,2,2-$d_3$]-5-hydroxyphenyl]-1,4-dihydro-4-oxo-3-quinolinecarboxamide (CTP-656), (((3-((3-carbamoyl-5,5,7,7-tetramethyl-4,7-dihydro-5H-thieno[2,3-c]pyran-2-yl)carbamoyl)-1H-pyrazol-1-yl)methoxy)methyl)phosphonic acid (GLPG1833), 3-[6-({[1-(2,2-difluoro-1,3-benzodioxol-5-yl)cyclopropyl]carbonyl}amino)-3-methylpyridin-2-yl]benzoic acid (Lumacaftor), N-(3-carbamoyl-5,5,7,7-tetramethyl-4,7-dihydro-5H-thieno[2,3-c]pyran-2-yl)-1H-pyrazole-3-carboxamide, 1-(2,2-difluoro-1,3-benzodioxol-5-yl)-N-[1-[(2R)-2,3-dihydroxypropyl]-6-fluoro-2-(2-hydroxy-1,1-dimethylethyl)-1H-indol-5-yl]-cyclopropanecarboxamide (VX-661), 4-((2R,4R)-4-(1-(2,2-difluorobenzo[d][1,3]dioxol-5-yl)cyclopropane-1-carboxamido)-7-(difluoromethoxy)chroman-2-yl)benzoic acid (GLPG2222), 4-(3-(1-(2,2-difluorobenzo[d][1,3]dioxol-5-yl)cyclopropane-1-carboxamido)isoquinolin-1-yl)benzoic acid, N-(4-(7-azabicyclo[2.2.1]heptan-7-yl)-2-(trifluoromethyl)phenyl)-4-oxo-5-(trifluromethyl)-1,4-dihydroquinoline-3-carboxamide, 3-[5-(2-fluorophenyl)-1,2,4-oxadiazol-3-yl]benzoic acid (Ataluren), 5,7-Dihydroxy-3-(4-hydroxyphenyl)chromen-4-one (Genistein), N-(2-(tert-butyl)-5-hydroxy-4-(2-(methyl-$d_3$)propan-2-yl-1,1,1,3,3,3-$d_6$)phenyl)-4-oxo-1,4-dihydroquinoline-3-carboxamide (CTP-656), N-(3-carbamoyl-5,5,7,7-tetramethyl-4,7-dihydro-5H-thieno[2,3-c]pyran-2-yl)-1H-pyrazole-5-carboxamide (GLPG1837), 3-Chloro-4-(6-hydroxyquinolin-2-yl)benzoic acid (N-91115) and (S)-3-amino-6-methoxy-N-(3,3,3-trifluoro-2-hydroxy-2-methylpropyl)-5-(trifluoromethyl)picolinamide.

In one embodiment of the invention, there is provided a product comprising a compound of formula (I) or a pharmaceutically acceptable salt thereof and a CFTR modulator as a combined preparation for simultaneous, separate or sequential use in therapy. In another embodiment, there is provided a product comprising a compound of formula (I) and a CFTR potentiator as a combined preparation for simultaneous, separate or sequential use in therapy. In another embodiment there is provided a product comprising a compound of formula (I), a CFTR potentiator and a CFTR corrector as a combined preparation for simultaneous, separate or sequential use in therapy.

In another embodiment there is provided a product comprising a compound of formula (I) or a pharmaceutically acceptable salt thereof and (S)-3-amino-6-methoxy-N-(3,3,3-trifluoro-2-hydroxy-2-methylpropyl)-5-(trifluoromethyl)picolinamide or a pharmaceutically acceptable salt thereof as a combined preparation for simultaneous, separate or sequential use in therapy.

In another embodiment there is provided a product comprising 6-(4-cyclopropylpiperazin-1-yl)-N-(6-(3-fluoro-2-methylphenyl)-5-(trifluoromethyl)pyridin-2-yl)pyridine-2-sulfonamide or a pharmaceutically acceptable salt thereof and (S)-3-amino-6-methoxy-N-(3,3,3-trifluoro-2-hydroxy-2-methylpropyl)-5-(trifluoromethyl)picolinamide or a pharmaceutically acceptable salt thereof as a combined preparation for simultaneous, separate or sequential use in therapy.

In another embodiment there is provided a product comprising N-(5-chloro-6-(5-fluoro-2-methylphenyl)pyridin-2-yl)-6-(((3R,4R)-4-hydroxytetrahydro-2H-pyran-3-yl)amino)pyridine-2-sulfonamide or a pharmaceutically acceptable salt thereof and (S)-3-amino-6-methoxy-N-(3,3,3-trifluoro-2-hydroxy-2-methylpropyl)-5-(trifluoromethyl)picolinamide as a combined preparation for simultaneous, separate or sequential use in therapy.

In another embodiment there is provided a product comprising 6-(((1s,3s)-3-hydroxycyclobutyl)amino)-N-(6-(o-tolyl)-5-(trifluoromethyl)pyridin-2-yl)pyridine-2-sulfonamide or a pharmaceutically acceptable salt thereof and (S)-3-amino-6-methoxy-N-(3,3,3-trifluoro-2-hydroxy-2-methylpropyl)-5-(trifluoromethyl)picolinamide or a pharmaceutically acceptable salt thereof as a combined preparation for simultaneous, separate or sequential use in therapy.

In another embodiment there is provided a product comprising (1s,4s)-4-((6-(N-(5-chloro-6-(2,6-dimethylphenyl)pyridin-2-yl)sulfamoyl)pyridin-2-yl)oxy)cyclohexane-1-carboxylic acid or a pharmaceutically acceptable salt thereof and (S)-3-amino-6-methoxy-N-(3,3,3-trifluoro-2-hydroxy-2-methylpropyl)-5-(trifluoromethyl)picolinamide or a pharmaceutically acceptable salt thereof as a combined preparation for simultaneous, separate or sequential use in therapy.

In another embodiment there is provided a product comprising N-(5-chloro-6-(2,6-dimethylphenyl)pyridin-2-yl)-6-(3-cyclopropyl-3-hydroxyazetidin-1-yl)pyridine-2-sulfonamide or a pharmaceutically acceptable salt thereof and (S)-3-amino-6-methoxy-N-(3,3,3-trifluoro-2-hydroxy-2-methylpropyl)-5-(trifluoromethyl)picolinamide or a pharmaceutically acceptable salt thereof as a combined preparation for simultaneous, separate or sequential use in therapy.

In another embodiment there is provided a product comprising (R)-6-(piperidin-3-ylamino)-N-(6-(o-tolyl)-5-(trifluoromethyl)pyridin-2-yl)pyridine-2-sulfonamide or a pharmaceutically acceptable salt thereof and (S)-3-amino-6-methoxy-N-(3,3,3-trifluoro-2-hydroxy-2-methylpropyl)-5-(trifluoromethyl)picolinamide or a pharmaceutically acceptable salt thereof as a combined preparation for simultaneous, separate or sequential use in therapy.

In another embodiment there is provided a product comprising 6-amino-N-(5-chloro-6-(2,6-dimethylphenyl)pyridin-2-yl)pyridine-2-sulfonamide or a pharmaceutically acceptable salt thereof and (S)-3-amino-6-methoxy-N-(3,3,3-trifluoro-2-hydroxy-2-methylpropyl)-5-(trifluoromethyl)

picolinamide or a pharmaceutically acceptable salt thereof as a combined preparation for simultaneous, separate or sequential use in therapy.

In another embodiment there is provided a product comprising 6-(piperazin-1-yl)-N-(6-(o-tolyl)-5-(trifluoromethyl)pyridin-2-yl)pyridine-2-sulfonamide or a pharmaceutically acceptable salt thereof and (S)-3-amino-6-methoxy-N-(3,3,3-trifluoro-2-hydroxy-2-methylpropyl)-5-(trifluoromethyl)picolinamide or a pharmaceutically acceptable salt thereof as a combined preparation for simultaneous, separate or sequential use in therapy.

In another embodiment there is provided a product comprising N-(5-chloro-6-(5-fluoro-2-methylphenyl)pyridin-2-yl)-6-(3-hydroxyazetidin-1-yl)pyridine-2-sulfonamide or a pharmaceutically acceptable salt thereof and (S)-3-amino-6-methoxy-N-(3,3,3-trifluoro-2-hydroxy-2-methylpropyl)-5-(trifluoromethyl)picolinamide or a pharmaceutically acceptable salt thereof as a combined preparation for simultaneous, separate or sequential use in therapy.

In another embodiment there is provided a product comprising a compound of formula (I) or a pharmaceutically acceptable salt thereof and N-(2,4-di-tert-butyl-5-hydroxyphenyl)-1,4-dihydro-4-oxoquinoline-3-carboxamide or a pharmaceutically acceptable salt thereof as a combined preparation for simultaneous, separate or sequential use in therapy.

In another embodiment there is provided a product comprising 6-(4-cyclopropylpiperazin-1-yl)-N-(6-(3-fluoro-2-methylphenyl)-5-(trifluoromethyl)pyridin-2-yl)pyridine-2-sulfonamide or a pharmaceutically acceptable salt thereof and N-(2,4-di-tert-butyl-5-hydroxyphenyl)-1,4-dihydro-4-oxoquinoline-3-carboxamide or a pharmaceutically acceptable salt thereof as a combined preparation for simultaneous, separate or sequential use in therapy.

In another embodiment there is provided a product comprising N-(5-chloro-6-(5-fluoro-2-methylphenyl)pyridin-2-yl)-6-(((3R,4R)-4-hydroxytetrahydro-2H-pyran-3-yl)amino)pyridine-2-sulfonamide or a pharmaceutically acceptable salt thereof and N-(2,4-di-tert-butyl-5-hydroxyphenyl)-1,4-dihydro-4-oxoquinoline-3-carboxamide as a combined preparation for simultaneous, separate or sequential use in therapy.

In another embodiment there is provided a product comprising 6-(((1s,3s)-3-hydroxycyclobutyl)amino)-N-(6-(o-tolyl)-5-(trifluoromethyl)pyridin-2-yl)pyridine-2-sulfonamide or a pharmaceutically acceptable salt thereof and N-(2,4-di-tert-butyl-5-hydroxyphenyl)-1,4-dihydro-4-oxoquinoline-3-carboxamide or a pharmaceutically acceptable salt thereof as a combined preparation for simultaneous, separate or sequential use in therapy.

In another embodiment there is provided a product comprising (1s,4s)-4-((6-(N-(5-chloro-6-(2,6-dimethylphenyl)pyridin-2-yl)sulfamoyl)pyridin-2-yl)oxy)cyclohexane-1-carboxylic acid or a pharmaceutically acceptable salt thereof and N-(2,4-di-tert-butyl-5-hydroxyphenyl)-1,4-dihydro-4-oxoquinoline-3-carboxamide or a pharmaceutically acceptable salt thereof as a combined preparation for simultaneous, separate or sequential use in therapy.

In another embodiment there is provided a product comprising N-(5-chloro-6-(2,6-dimethylphenyl)pyridin-2-yl)-6-(3-cyclopropyl-3-hydroxyazetidin-1-yl)pyridine-2-sulfonamide or a pharmaceutically acceptable salt thereof and N-(2,4-di-tert-butyl-5-hydroxyphenyl)-1,4-dihydro-4-oxoquinoline-3-carboxamide or a pharmaceutically acceptable salt thereof as a combined preparation for simultaneous, separate or sequential use in therapy.

In another embodiment there is provided a product comprising (R)-6-(piperidin-3-ylamino)-N-(6-(o-tolyl)-5-(trifluoromethyl)pyridin-2-yl)pyridine-2-sulfonamide or a pharmaceutically acceptable salt thereof and N-(2,4-di-tert-butyl-5-hydroxyphenyl)-1,4-dihydro-4-oxoquinoline-3-carboxamide or a pharmaceutically acceptable salt thereof as a combined preparation for simultaneous, separate or sequential use in therapy.

In another embodiment there is provided a product comprising 6-amino-N-(5-chloro-6-(2,6-dimethylphenyl)pyridin-2-yl)pyridine-2-sulfonamide or a pharmaceutically acceptable salt thereof and N-(2,4-di-tert-butyl-5-hydroxyphenyl)-1,4-dihydro-4-oxoquinoline-3-carboxamide or a pharmaceutically acceptable salt thereof as a combined preparation for simultaneous, separate or sequential use in therapy.

In another embodiment there is provided a product comprising 6-(piperazin-1-yl)-N-(6-(o-tolyl)-5-(trifluoromethyl)pyridin-2-yl)pyridine-2-sulfonamide or a pharmaceutically acceptable salt thereof and N-(2,4-di-tert-butyl-5-hydroxyphenyl)-1,4-dihydro-4-oxoquinoline-3-carboxamide or a pharmaceutically acceptable salt thereof as a combined preparation for simultaneous, separate or sequential use in therapy.

In another embodiment there is provided a product comprising N-(5-chloro-6-(5-fluoro-2-methylphenyl)pyridin-2-yl)-6-(3-hydroxyazetidin-1-yl)pyridine-2-sulfonamide or a pharmaceutically acceptable salt thereof and N-(2,4-di-tert-butyl-5-hydroxyphenyl)-1,4-dihydro-4-oxoquinoline-3-carboxamide or a pharmaceutically acceptable salt thereof as a combined preparation for simultaneous, separate or sequential use in therapy.

In another embodiment there is provided a product comprising a compound of formula (I) or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and 3-[6-({[1-(2,2-difluoro-1,3-benzodioxol-5-yl)cyclopropyl]carbonyl}amino)-3-methylpyridin-2-yl]benzoic acid or a pharmaceutically acceptable salt thereof as a combined preparation for simultaneous, separate or sequential use in therapy.

In another embodiment there is provided a product comprising 6-(4-cyclopropylpiperazin-1-yl)-N-(6-(3-fluoro-2-methylphenyl)-5-(trifluoromethyl)pyridin-2-yl)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and 3-[6-({[1-(2,2-difluoro-1,3-benzodioxol-5-yl)cyclopropyl]carbonyl}amino)-3-methylpyridin-2-yl]benzoic acid or a pharmaceutically acceptable salt thereof as a combined preparation for simultaneous, separate or sequential use in therapy.

In another embodiment there is provided a product comprising N-(5-chloro-6-(5-fluoro-2-methylphenyl)pyridin-2-yl)-6-(((3R,4R)-4-hydroxytetrahydro-2H-pyran-3-yl)amino)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and 3-[6-({[1-(2,2-difluoro-1,3-benzodioxol-5-yl)cyclopropyl]carbonyl}amino)-3-methylpyridin-2-yl]benzoic acid or a pharmaceutically acceptable salt thereof as a combined preparation for simultaneous, separate or sequential use in therapy.

In another embodiment there is provided a product comprising 6-(((1S,3S)-3-hydroxycyclobutyl)amino)-N-(6-(o-tolyl)-5-(trifluoromethyl)pyridin-2-yl)pyridine-2-sulfonamide or a pharmaceutically acceptable salt thereof, N-(2,4- di-tert-butyl-5-hydroxyphenyl)-1,4-dihydro-4-oxoquinoline-3-carboxamide or a pharmaceutically acceptable salt thereof and 3-[6-({[1-(2,2-difluoro-1,3-benzodioxol-5-yl)cyclopropyl]carbonyl}amino)-3-methylpyridin-2-yl]benzoic acid or a pharmaceutically acceptable salt thereof as a combined preparation for simultaneous, separate or sequential use in therapy.

In another embodiment there is provided a product comprising (1S,4S)-4-((6-(N-(5-chloro-6-(2,6-dimethylphenyl)pyridin-2-yl)sulfamoyl)pyridin-2-yl)oxy)cyclohexane-1-carboxylic acid or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and 3-[6-({[1-(2,2-difluoro-1,3-benzodioxol-5-yl)cyclopropyl]carbonyl}amino)-3-methylpyridin-2-yl]benzoic acid or a pharmaceutically acceptable salt thereof as a combined preparation for simultaneous, separate or sequential use in therapy.

In another embodiment there is provided a product comprising N-(5-chloro-6-(2,6-dimethylphenyl)pyridin-2-yl)-6-(3-cyclopropyl-3-hydroxyazetidin-1-yl)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and 3-[6-({[1-(2,2-difluoro-1,3-benzodioxol-5-yl)cyclopropyl]carbonyl}amino)-3-methylpyridin-2-yl]benzoic acid or a pharmaceutically acceptable salt thereof as a combined preparation for simultaneous, separate or sequential use in therapy.

In another embodiment there is provided a product comprising (R)-6-(piperidin-3-ylamino)-N-(6-(o-tolyl)-5-(trifluoromethyl)pyridin-2-yl)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and 3-[6-({[1-(2,2-difluoro-1,3-benzodioxol-5-yl)cyclopropyl]carbonyl}amino)-3-methylpyridin-2-yl]benzoic acid or a pharmaceutically acceptable salt thereof as a combined preparation for simultaneous, separate or sequential use in therapy.

In another embodiment there is provided a product comprising 6-amino-N-(5-chloro-6-(2,6-dimethylphenyl)pyridin-2-yl)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and 3-[6-({[1-(2,2-difluoro-1,3-benzodioxol-5-yl)cyclopropyl]carbonyl}amino)-3-methylpyridin-2-yl]benzoic acid or a pharmaceutically acceptable salt thereof as a combined preparation for simultaneous, separate or sequential use in therapy.

In another embodiment there is provided a product comprising 6-(piperazin-1-yl)-N-(6-(o-tolyl)-5-(trifluoromethyl)pyridin-2-yl)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and 3-[6-({[1-(2,2-difluoro-1,3-benzodioxol-5-yl)cyclopropyl]carbonyl}amino)-3-methylpyridin-2-yl]benzoic acid or a pharmaceutically acceptable salt thereof as a combined preparation for simultaneous, separate or sequential use in therapy.

In another embodiment there is provided a product comprising N-(5-chloro-6-(5-fluoro-2-methylphenyl)pyridin-2-yl)-6-(3-hydroxyazetidin-1-yl)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and 3-[6-({[1-(2,2-difluoro-1,3-benzodioxol-5-yl)cyclopropyl]carbonyl}amino)-3-methylpyridin-2-yl]benzoic acid or a pharmaceutically acceptable salt thereof as a combined preparation for simultaneous, separate or sequential use in therapy.

In another embodiment there is provided a product comprising a compound of formula (I) or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and 1-(2,2-difluoro-1,3-benzodioxol-5-yl)-N-[1-[(2R)-2,3-dihydroxypropyl]-6-fluoro-2-(2-hydroxy-1,1-dimethylethyl)-1H-indol-5-yl]-cyclopropanecarboxamide or a pharmaceutically acceptable salt thereof as a combined preparation for simultaneous, separate or sequential use in therapy.

In another embodiment there is provided a product comprising 6-(4-cyclopropylpiperazin-1-yl)-N-(6-(3-fluoro-2-methylphenyl)-5-(trifluoromethyl)pyridin-2-yl)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and 1-(2,2-difluoro-1,3-benzodioxol-5-yl)-N-[1-[(2R)-2,3-dihydroxypropyl]-6-fluoro-2-(2-hydroxy-1,1-dimethylethyl)-1H-indol-5-yl]-cyclopropanecarboxamide or a pharmaceutically acceptable salt thereof as a combined preparation for simultaneous, separate or sequential use in therapy.

In another embodiment there is provided a product comprising N-(5-chloro-6-(5-fluoro-2-methylphenyl)pyridin-2-yl)-6-(((3R,4R)-4-hydroxytetrahydro-2H-pyran-3-yl)amino)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and 1-(2,2-difluoro-1,3-benzodioxol-5-yl)-N-[1-[(2R)-2,3-dihydroxypropyl]-6-fluoro-2-(2-hydroxy-1,1-dimethylethyl)-1H-indol-5-yl]-cyclopropanecarboxamide or a pharmaceutically acceptable salt thereof as a combined preparation for simultaneous, separate or sequential use in therapy.

In another embodiment there is provided a product comprising 6-(((1S,3S)-3-hydroxycyclobutyl)amino)-N-(6-(o-tolyl)-5-(trifluoromethyl)pyridin-2-yl)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and 1-(2,2-difluoro-1,3-benzodioxol-5-yl)-N-[1-[(2R)-2,3-dihydroxypropyl]-6-fluoro-2-(2-hydroxy-1,1-dimethylethyl)-1H-indol-5-yl]-cyclopropanecarboxamide or a pharmaceutically acceptable salt thereof as a combined preparation for simultaneous, separate or sequential use in therapy.

In another embodiment there is provided a product comprising (1S,4S)-4-((6-(N-(5-chloro-6-(2,6-dimethylphenyl)pyridin-2-yl)sulfamoyl)pyridin-2-yl)oxy)cyclohexane-1-carboxylic acid or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and 1-(2,2-difluoro-1,3-benzodioxol-5-yl)-N-[1-[(2R)-2,3-dihydroxypropyl]-6-fluoro-2-(2-hydroxy-1,1-dimethylethyl)-1H-indol-5-yl]-cyclopropanecarboxamide or a pharmaceutically acceptable salt thereof as a combined preparation for simultaneous, separate or sequential use in therapy.

In another embodiment there is provided a product comprising N-(5-chloro-6-(2,6-dimethylphenyl)pyridin-2-yl)-6-(3-cyclopropyl-3-hydroxyazetidin-1-yl)pyridine-2-sulfonamide or a pharmaceutically acceptable salt thereof, N-(2,4-di-tert-butyl-5-hydroxyphenyl)-1,4-dihydro-4- oxoquinoline-3-carboxamide or a pharmaceutically acceptable salt thereof and 1-(2,2-difluoro-1,3-benzodioxol-5-yl)-N-[1-[(2R)-2,3-dihydroxypropyl]-6-fluoro-2-(2-hydroxy-1,1-dimethylethyl)-1H-indol-5-yl]-cyclopropanecarboxamide or a pharmaceutically acceptable salt thereof as a combined preparation for simultaneous, separate or sequential use in therapy.

In another embodiment there is provided a product comprising (R)-6-(piperidin-3-ylamino)-N-(6-(o-tolyl)-5-(trifluoromethyl)pyridin-2-yl)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and 1-(2,2-difluoro-1,3-benzodioxol-5-yl)-N-[1-[(2R)-2,3-dihydroxypropyl]-6-fluoro-2-(2-hydroxy-1,1-dimethylethyl)-1H-indol-5-yl]-cyclopropanecarboxamide or a pharmaceutically acceptable salt thereof as a combined preparation for simultaneous, separate or sequential use in therapy.

In another embodiment there is provided a product comprising 6-amino-N-(5-chloro-6-(2,6-dimethylphenyl)pyridin-2-yl)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and 1-(2,2-difluoro-1,3-benzodioxol-5-yl)-N-[1-[(2R)-2,3-dihydroxypropyl]-6-fluoro-2-(2-hydroxy-1,1-dimethylethyl)-1H-indol-5-yl]-cyclopropanecarboxamide or a pharmaceutically acceptable salt thereof as a combined preparation for simultaneous, separate or sequential use in therapy.

In another embodiment there is provided a product comprising 6-(piperazin-1-yl)-N-(6-(o-tolyl)-5-(trifluoromethyl)pyridin-2-yl)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and 1-(2,2-difluoro-1,3-benzodioxol-5-yl)-N-[1-[(2R)-2,3-dihydroxypropyl]-6-fluoro-2-(2-hydroxy-1,1-dimethylethyl)-1H-indol-5-yl]-cyclopropanecarboxamide or a pharmaceutically acceptable salt thereof as a combined preparation for simultaneous, separate or sequential use in therapy.

In another embodiment there is provided a product comprising N-(5-chloro-6-(5-fluoro-2-methylphenyl)pyridin-2-yl)-6-(3-hydroxyazetidin-1-yl)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and 1-(2,2-difluoro-1,3-benzodioxol-5-yl)-N-[1-[(2R)-2,3-dihydroxypropyl]-6-fluoro-2-(2-hydroxy-1,1-dimethylethyl)-1H-indol-5-yl]-cyclopropanecarboxamide or a pharmaceutically acceptable salt thereof as a combined preparation for simultaneous, separate or sequential use in therapy.

In another embodiment, there is provided a pharmaceutical composition comprising a compound of formula (I) or a pharmaceutically acceptable salt thereof, a CFTR modulator and a pharmaceutically acceptable carrier.

In another embodiment there is provided a pharmaceutical composition comprising a compound of formula (I), a CFTR potentiator and a pharmaceutically acceptable carrier. In yet another embodiment there is provided a pharmaceutical composition comprising a compound of formula (I) a CFTR corrector and a pharmaceutically acceptable carrier.

In another embodiment, there is provided a pharmaceutical composition comprising a compound of formula (I) or a pharmaceutically acceptable salt thereof, (S)-3-amino-6-methoxy-N-(3,3,3-trifluoro-2-hydroxy-2-methylpropyl)-5-(trifluoromethyl)picolinamide or a pharmaceutically acceptable salt thereof and a pharmaceutically acceptable carrier.

In another embodiment, there is provided a pharmaceutical composition comprising 6-(4-cyclopropylpiperazin-1-yl)-N-(6-(3-fluoro-2-methylphenyl)-5-(trifluoromethyl)pyridin-2-yl)pyridine-2-sulfonamide or a pharmaceutically acceptable salt thereof, (S)-3-amino-6-methoxy-N-(3,3,3-trifluoro-2-hydroxy-2-methylpropyl)-5-(trifluoromethyl)picolinamide or a pharmaceutically acceptable salt thereof and a pharmaceutically acceptable carrier.

In another embodiment, there is provided a pharmaceutical composition comprising N-(5-chloro-6-(5-fluoro-2-methylphenyl)pyridin-2-yl)-6-(((3R,4R)-4-hydroxytetrahydro-2H-pyran-3-yl)amino)pyridine-2-sulfonamide or a pharmaceutically acceptable salt thereof, (S)-3-amino-6-methoxy-N-(3,3,3-trifluoro-2-hydroxy-2-methylpropyl)-5-(trifluoromethyl)picolinamide or a pharmaceutically acceptable salt thereof and a pharmaceutically acceptable carrier.

In another embodiment, there is provided a pharmaceutical composition comprising 6-(((1S,3S)-3-hydroxycyclobutyl)amino)-N-(6-(o-tolyl)-5-(trifluoromethyl)pyridin-2-yl)pyridine-2-sulfonamide or a pharmaceutically acceptable salt thereof, (S)-3-amino-6-methoxy-N-(3,3,3-trifluoro-2-hydroxy-2-methylpropyl)-5-(trifluoromethyl)picolinamide or a pharmaceutically acceptable salt thereof and a pharmaceutically acceptable carrier.

In another embodiment, there is provided a pharmaceutical composition comprising (1S,4S)-4-((6-(N-(5-chloro-6-(2,6-dimethylphenyl)pyridin-2-yl)sulfamoyl)pyridin-2-yl)oxy)cyclohexane-1-carboxylic acid or a pharmaceutically acceptable salt thereof, (S)-3-amino-6-methoxy-N-(3,3,3-trifluoro-2-hydroxy-2-methylpropyl)-5-(trifluoromethyl)picolinamide or a pharmaceutically acceptable salt thereof and a pharmaceutically acceptable carrier.

In another embodiment, there is provided a pharmaceutical composition comprising N-(5-chloro-6-(2,6-dimethylphenyl)pyridin-2-yl)-6-(3-cyclopropyl-3-hydroxyazetidin-1-yl)pyridine-2-sulfonamide or a pharmaceutically acceptable salt thereof, (S)-3-amino-6-methoxy-N-(3,3,3-trifluoro-2-hydroxy-2-methylpropyl)-5-(trifluoromethyl)picolinamide or a pharmaceutically acceptable salt thereof and a pharmaceutically acceptable carrier.

In another embodiment, there is provided a pharmaceutical composition comprising (R)-6-(piperidin-3-ylamino)-N-(6-(o-tolyl)-5-(trifluoromethyl)pyridin-2-yl)pyridine-2-sulfonamide or a pharmaceutically acceptable salt thereof, (S)-3-amino-6-methoxy-N-(3,3,3-trifluoro-2-hydroxy-2-methylpropyl)-5-(trifluoromethyl)picolinamide or a pharmaceutically acceptable salt thereof and a pharmaceutically acceptable carrier.

In another embodiment, there is provided a pharmaceutical composition comprising 6-amino-N-(5-chloro-6-(2,6-dimethylphenyl)pyridin-2-yl)pyridine-2-sulfonamide or a pharmaceutically acceptable salt thereof, (S)-3-amino-6-methoxy-N-(3,3,3-trifluoro-2-hydroxy-2-methylpropyl)-5-(trifluoromethyl)picolinamide or a pharmaceutically acceptable salt thereof and a pharmaceutically acceptable carrier.

In another embodiment, there is provided a pharmaceutical composition comprising 6-(piperazin-1-yl)-N-(6-(o-tolyl)-5-(trifluoromethyl)pyridin-2-yl)pyridine-2-sulfonamide or a pharmaceutically acceptable salt thereof, (S)-3-amino-6-methoxy-N-(3,3,3-trifluoro-2-hydroxy-2-methylpropyl)-5-(trifluoromethyl)picolinamide or a pharmaceutically acceptable salt thereof and a pharmaceutically acceptable carrier.

In another embodiment, there is provided a pharmaceutical composition comprising N-(5-chloro-6-(5-fluoro-2- methylphenyl)pyridin-2-yl)-6-(3-hydroxyazetidin-1-yl)pyridine-2-sulfonamide or a pharmaceutically acceptable salt thereof, (S)-3-amino-6-methoxy-N-(3,3,3-trifluoro-2-hydroxy-2-methylpropyl)-5-(trifluoromethyl)picolinamide or a pharmaceutically acceptable salt thereof and a pharmaceutically acceptable carrier.

In another embodiment, there is provided a pharmaceutical composition comprising a compound of formula (I) or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and a pharmaceutically acceptable carrier.

In another embodiment, there is provided a pharmaceutical composition comprising 6-(4-cyclopropylpiperazin-1-yl)-N-(6-(3-fluoro-2-methylphenyl)-5-(trifluoromethyl)pyridin-2-yl)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and a pharmaceutically acceptable carrier.

In another embodiment, there is provided a pharmaceutical composition comprising N-(5-chloro-6-(5-fluoro-2-methylphenyl)pyridin-2-yl)-6-(((3R,4R)-4-hydroxytetrahydro-2H-pyran-3-yl)amino)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and a pharmaceutically acceptable carrier.

In another embodiment, there is provided a pharmaceutical composition comprising 6-(((1S,3S)-3-hydroxycyclobutyl)amino)-N-(6-(o-tolyl)-5-(trifluoromethyl)pyridin-2-yl)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and a pharmaceutically acceptable carrier.

In another embodiment, there is provided a pharmaceutical composition comprising (1S,4S)-4-((6-(N-(5-chloro-6-(2,6-dimethylphenyl)pyridin-2-yl)sulfamoyl)pyridin-2-yl)oxy)cyclohexane-1-carboxylic acid or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and a pharmaceutically acceptable carrier.

In another embodiment, there is provided a pharmaceutical composition comprising N-(5-chloro-6-(2,6-dimethylphenyl)pyridin-2-yl)-6-(3-cyclopropyl-3-hydroxyazetidin-1-yl)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and a pharmaceutically acceptable carrier.

In another embodiment, there is provided a pharmaceutical composition comprising (R)-6-(piperidin-3-ylamino)-N-(6-(o-tolyl)-5-(trifluoromethyl)pyridin-2-yl)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and a pharmaceutically acceptable carrier.

In another embodiment, there is provided a pharmaceutical composition comprising 6-amino-N-(5-chloro-6-(2,6-dimethylphenyl)pyridin-2-yl)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and a pharmaceutically acceptable carrier.

In another embodiment, there is provided a pharmaceutical composition comprising 6-(piperazin-1-yl)-N-(6-(o-tolyl)-5-(trifluoromethyl)pyridin-2-yl)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and a pharmaceutically acceptable carrier.

In another embodiment, there is provided a pharmaceutical composition comprising N-(5-chloro-6-(5-fluoro-2-methylphenyl)pyridin-2-yl)-6-(3-hydroxyazetidin-1-yl)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof and a pharmaceutically acceptable carrier.

In another embodiment, there is provided a pharmaceutical composition comprising a compound of formula (I) or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof, 3-[6-({[1-(2,2-difluoro-1,3-benzodioxol-5-yl)cyclopropyl]carbonyl}amino)-3-methylpyridin-2-yl]benzoic acid or a pharmaceutically acceptable salt thereof and a pharmaceutically acceptable carrier.

In another embodiment, there is provided a pharmaceutical composition comprising 6-(4-cyclopropylpiperazin-1-yl)-N-(6-(3-fluoro-2-methylphenyl)-5-(trifluoromethyl)pyridin-2-yl)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof, 3-[6-({[1-(2,2-difluoro-1,3-benzodioxol-5-yl)cyclopropyl]carbonyl}amino)-3-methylpyridin-2-yl]benzoic acid or a pharmaceutically acceptable salt thereof and a pharmaceutically acceptable carrier.

In another embodiment, there is provided a pharmaceutical composition comprising N-(5-chloro-6-(5-fluoro-2-methylphenyl)pyridin-2-yl)-6-(((3R,4R)-4-hydroxytetrahydro-2H-pyran-3-yl)amino)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof, 3-[6-({[1-(2,2-difluoro-1,3-benzodioxol-5-yl)cyclopropyl]carbonyl}amino)-3-methylpyridin-2-yl]benzoic acid or a pharmaceutically acceptable salt thereof and a pharmaceutically acceptable carrier.

In another embodiment, there is provided a pharmaceutical composition comprising 6-(((1S,3S)-3-hydroxycyclobutyl)amino)-N-(6-(o-tolyl)-5-(trifluoromethyl)pyridin-2-yl)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof, 3-[6-({[1-(2,2-difluoro-1,3-benzodioxol-5-yl)cyclopropyl]carbonyl}amino)-3-methylpyridin-2-yl]benzoic acid or a pharmaceutically acceptable salt thereof and a pharmaceutically acceptable carrier.

In another embodiment, there is provided a pharmaceutical composition comprising (1S,4S)-4-((6-(N-(5-chloro-6-(2,6-dimethylphenyl)pyridin-2-yl)sulfamoyl)pyridin-2-yl)oxy)cyclohexane-1-carboxylic acid or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof, 3-[6-({[1-(2,2-difluoro-1,3-benzodioxol-5-yl)cyclopropyl]carbonyl}amino)-

3-methylpyridin-2-yl]benzoic acid or a pharmaceutically acceptable salt thereof and a pharmaceutically acceptable carrier.

In another embodiment, there is provided a pharmaceutical composition comprising N-(5-chloro-6-(2,6-dimethylphenyl)pyridin-2-yl)-6-(3-cyclopropyl-3-hydroxyazetidin-1-yl)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof, 3-[6-({[1-(2,2-difluoro-1,3-benzodioxol-5-yl)cyclopropyl]carbonyl}amino)-3-methylpyridin-2-yl]benzoic acid or a pharmaceutically acceptable salt thereof and a pharmaceutically acceptable carrier.

In another embodiment, there is provided a pharmaceutical composition comprising (R)-6-(piperidin-3-ylamino)-N-(6-(o-tolyl)-5-(trifluoromethyl)pyridin-2-yl)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof, 3-[6-({[1-(2,2-difluoro-1,3-benzodioxol-5-yl)cyclopropyl]carbonyl}amino)-3-methylpyridin-2-yl]benzoic acid or a pharmaceutically acceptable salt thereof and a pharmaceutically acceptable carrier.

In another embodiment, there is provided a pharmaceutical composition comprising 6-amino-N-(5-chloro-6-(2,6-dimethylphenyl)pyridin-2-yl)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof, 3-[6-({[1-(2,2-difluoro-1,3-benzodioxol-5-yl)cyclopropyl]carbonyl}amino)-3-methylpyridin-2-yl]benzoic acid or a pharmaceutically acceptable salt thereof and a pharmaceutically acceptable carrier.

In another embodiment, there is provided a pharmaceutical composition comprising 6-(piperazin-1-yl)-N-(6-(o-tolyl)-5-(trifluoromethyl)pyridin-2-yl)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof, 3-[6-({[1-(2,2-difluoro-1,3-benzodioxol-5-yl)cyclopropyl]carbonyl}amino)-3-methylpyridin-2-yl]benzoic acid or a pharmaceutically acceptable salt thereof and a pharmaceutically acceptable carrier.

In another embodiment, there is provided a pharmaceutical composition comprising N-(5-chloro-6-(5-fluoro-2-methylphenyl)pyridin-2-yl)-6-(3-hydroxyazetidin-1-yl)pyridine-2-sulfonamide or a pharmaceutically acceptable salt thereof, N-(2,4-di-tert-butyl-5-hydroxyphenyl)-1,4-dihydro-4-oxoquinoline-3-carboxamide or a pharmaceutically acceptable salt thereof, 3-[6-({[1-(2,2-difluoro-1,3-benzodioxol-5-yl)cyclopropyl]carbonyl}amino)-3-methylpyridin-2-yl]benzoic acid or a pharmaceutically acceptable salt thereof and a pharmaceutically acceptable carrier.

In another aspect of the present invention, kits that include one or more compound of the present invention and a combination partner as disclosed herein are provided. Representative kits include (a) a compound of the present invention or a pharmaceutically acceptable salt thereof, (b) at least one combination partner, e.g., as indicated above, whereby such kit may comprise a package insert or other labeling including directions for administration.

In the combination therapies of the invention, the compound of the present invention and the other therapeutic agent may be manufactured and/or formulated by the same or different manufacturers. Moreover, the compound of the present invention and the other therapeutic (or pharmaceutical agent) may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

Definitions

As used herein, "CFTR" stands for cystic fibrosis transmembrane conductance regulator.

As used herein, "mutations" can refer to mutations in the CFTR gene or the CFTR protein. A "CFTR mutation" refers to a mutation in the CFTR gene, and a "CFTR mutation" refers to a mutation in the CFTR protein. A genetic defect or mutation, or a change in the nucleotides in a gene in general results in a mutation in the CFTR protein translated from that gene.

As used herein, a "F508del mutation" or "F508del" is a specific mutation within the CFTR protein. The mutation is a deletion of the three nucleotides that comprise the codon for amino acid phenylalanine at position 508, resulting in CFTR protein that lacks this phenylalanine residue.

The term "CFTR gating mutation" as used herein means a CFTR mutation that results in the production of a CFTR protein for which the predominant defect is a low channel open probability compared to normal CFTR (Van Goor, F., Hadida S. and Grootenhuis P., "Pharmacological Rescue of Mutant CFTR function for the Treatment of Cystic Fibrosis", Top. Med. Chem. 3: 91-120 (2008)). Gating mutations include, but are not limited to, G551D, G178R, S549N, S549R, G551S, G970R, G1244E, S1251N, S1255P, and G1349D.

As used herein, a patient who is ""homozygous" for a particular mutation, e.g. F508del, has the same mutation on each allele.

As used herein, a patient who is "heterozygous" for a particular mutation, e.g. F508del, has this mutation on one allele, and a different mutation on the other allele.

As used herein, the term "modulator" refers to a compound that increases the activity of a biological compound such as a protein. For example, a CFTR modulator is a compound that increases the activity of CFTR. The increase in activity resulting from a CFTR modulator may be through a corrector mechanism or a potentiator mechanism as described below.

As used herein, the term "CFTR corrector" refers to a compound that increases the amount of functional CFTR protein at the cell surface, resulting in enhanced ion transport.

As used herein, the term "CFTR potentiator" refers to a compound that increases the channel activity of CFTR protein located at the cell surface, resulting in enhanced ion transport.

As used herein, the term "modulating" as used herein means increasing or decreasing by a measurable amount.

As used herein, the term "inducing," as in inducing CFTR activity, refers to increasing CFTR activity, whether by the corrector, potentiator, or other mechanism.

As used herein "Asthma" includes both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g., of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".) Prophylactic efficacy in the treatment of asthma will be evidenced by reduced frequency or severity of symptomatic attack, e.g., of acute asthmatic or bronchoconstrictor attack, improvement in lung function or improved airways hyper-reactivity. It may further be evidenced by reduced requirement for other, symptomatic therapy, i.e., therapy for or intended to restrict or abort symptomatic attack when it occurs, e.g., anti-inflammatory (e.g., cortico-steroid) or bronchodilatory. Prophylactic benefit in asthma may, in particular, be apparent in subjects prone to "morning dipping". "Morning dipping" is a recognized asthmatic syndrome, common to a substantial percentage of asthmatics and characterized by asthma attack, e.g., between the hours of about 4-6 am, i.e., at a time normally substantially distant from any previously administered symptomatic asthma therapy.

A "patient," "subject" or "individual" are used interchangeably and refer to either a human or non-human animal. The term includes mammals such as humans. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. Preferably, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder, refers to the management and care of a patient for the purpose of combating the disease, condition, or disorder and includes the administration of a compound of the present invention to prevent the onset of the symptoms or complications, alleviating the symptoms or complications, or eliminating the disease, condition or disorder.

As used herein, the terms "treatment," "treating," and the like generally mean the improvement of CF or its symptoms or lessening the severity of CF or its symptoms in a subject. "Treatment," as used herein, includes, but is not limited to, the following: (i) to ameliorating the disease or disorder (i.e., slowing or arresting or reducing the development of the disease or at least one of the clinical symptoms thereof); (ii) to alleviating or ameliorating at least one physical parameter including those which may not be discernible by the patient; or (iii) to preventing or delaying the onset or development or progression of the disease or disorder. (iiii) increased growth of the subject, increased weight gain, reduction of mucus in the lungs, improved pancreatic and/or liver function, reduced cases of chest infections, and/or reduced instances of coughing or shortness of breath. Improvements in or lessening the severity of any of these conditions can be readily assessed according to standard methods and techniques known in the art.

As used herein, a subject is "in need of" a treatment if such subject would benefit biologically, medically or in quality of life from such treatment (preferably, a human).

As used herein the term "co-administer" refers to the presence of two active agents in the blood of an individual. Active agents that are co-administered can be concurrently or sequentially delivered.

The term "combination therapy" or "in combination with" or "pharmaceutical combination" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. Powders and/or liquids may be reconstituted or diluted to a desired dose prior to administration. In addition, such administration also encompasses use of each type of therapeutic agent being administered prior to, concurrent with, or sequentially to each other with no specific time limits. In each case, the treatment regimen will provide beneficial effects of the drug combination in treating the conditions or disorders described herein.

As used herein, the phrase "optionally substituted" is used interchangeably with the phrase "substituted or unsubstituted." In general the term "optionally substituted" refers to the replacement of hydrogen radicals in a given structure with the radical of a specified substituent. Specific substituents are described in the definitions and in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position.

As used herein, the term "$C_{1-6}$alkyl" refers to a fully saturated branched or unbranched hydrocarbon moiety having 1 to 6 carbon atoms. The terms "$C_{1-6}$alkyl", "$C_{1-4}$alkyl" and "$C_{1-2}$ alkyl" are to be construed accordingly. Representative examples of $C_{1-6}$alkyl include, but are not limited to, methyl, ethyl, n-propyl, iso-propyl, n-butyl, sec-butyl, iso-butyl, tert-butyl, n-pentyl, isopentyl, neopentyl and n-hexyl. Similarly, the alkyl portion (i.e., alkyl moiety) of an alkoxy have the same definition as above. When indicated as being "optionally substituted", the alkane radical or alkyl moiety may be unsubstituted or substituted with one or more substituents (generally, one to three substituents except in the case of halogen substituents such as perchloro or perfluoroalkyls). "Halo-substituted alkyl" refers to an alkyl group having at least one halogen substitution.

As used herein, the term "$C_{1-4}$ alkoxy" refers to an alkyl moiety attached through an oxygen bridge (i.e. a —O—$C_{1-4}$ alkyl group wherein $C_{1-4}$ alkyl is as defined herein). Representative examples of alkoxy include, but are not limited to, methoxy, ethoxy, propoxy, 2-propoxy, butoxy, tert-butoxy and the like. Preferably, alkoxy groups have about 1-4 carbons, more preferably about 1-2 carbons.

As used herein, the term "$C_{1-4}$ alkoxy" refers to a fully saturated branched or unbranched hydrocarbon moiety having 1 to 4 carbon atoms. The term "$C_{1-2}$alkoxy" is to be construed accordingly.

"Halogen" or "halo" may be fluorine, chlorine, bromine or iodine (preferred halogens as substituents are fluorine and chlorine).

As used herein, the term "halo-substituted-$C_{1-4}$alkyl" or "halo-$C_{1-4}$alkyl" refers to a $C_{1-4}$alkyl group as defined herein, wherein at least one of the hydrogen atoms is replaced by a halo atom. The halo-$C_{1-4}$alkyl group can be monohalo-$C_{1-4}$alkyl, dihalo-$C_{1-4}$alkyl or polyhalo-$C_{1-4}$ alkyl including perhalo-$C_{1-4}$alkyl. A monohalo-$C_{1-4}$alkyl can have one iodo, bromo, chloro or fluoro within the alkyl group. Dihalo-$C_{1-4}$alkyl and polyhalo-$C_{1-4}$alkyl groups can have two or more of the same halo atoms or a combination of different halo groups within the alkyl. Typically the polyhalo-$C_{1-4}$alkyl group contains up to 9, or 8, or 7, or 6, or 5, or 4, or 3, or 2 halo groups. Non-limiting examples of halo-$C_{1-4}$alkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhalo-$C_{1-4}$alkyl group refers to a $C_{1-4}$alkyl group having all hydrogen atoms replaced with halo atoms.

As used herein, the term "halo-substituted-$C_{1-4}$alkoxy" or "halo-$C_{1-4}$alkoxy" refers to $C_{1-4}$ alkoxy group as defined herein above wherein at least one of the hydrogen atoms is replaced by a halo atom. Non-limiting examples of halo-substituted-$C_{1-4}$alkoxy include fluoromethoxy, difluoromethoxy, trifluoromethoxy, chloromethoxy, dichloromethoxy, trichloromethoxy, difluorochloromethoxy, dichlorofluoromethoxy, difluoroethoxy, difluoropropoxy, dichloroethoxy and dichloropropoxy and the like.

As used herein, the term "hydroxy-substituted-$C_{1-4}$alkyl" refers to a $C_{1-4}$alkyl group as defined herein, wherein at least one of the hydrogen atoms is replaced by a hydroxyl group. The hydroxy-substituted-$C_{1-4}$alkyl group can be monohydroxy-$C_{1-4}$alkyl, dihydroxy-$C_{1-4}$alkyl or polyhydroxy-$C_{1-4}$alkyl including perhydroxy-$C_{1-4}$alkyl. A monohydroxy-$C_{1-4}$alkyl can have one hydroxyl group within the alkyl group. Dihydroxy-$C_{1-4}$alkyl and polyhydroxy-$C_{1-4}$alkyl groups can have two or more of the same hydroxyl groups or a combination of different hydroxyl groups within the alkyl. Typically the polyhydroxy-$C_{1-4}$alkyl group contains up to 9, or 8, or 7, or 6, or 5, or 4, or 3, or 2 hydroxy groups. Non-limiting examples of hydroxy substituted —$C_{1-4}$alkyl include hydroxy-methyl, dihydroxy-methyl, pentahydroxyethyl, dihydroxyethyl, and dihydroxypropyl. A perhydroxy-$C_{1-4}$alkyl group refers to a $C_{1-4}$alkyl group having all hydrogen atoms replaced with hydroxy atoms.

The term "oxo" (=O) refers to an oxygen atom connected to a carbon or sulfur atom by a double bond. Examples include carbonyl, sulfinyl, or sulfonyl groups (—C(O)—, —S(O)— or —S(O)$_2$—) such as, a ketone, aldehyde, or part of an acid, ester, amide, lactone, or lactam group and the like.

The term "aryl or $C_{6-10}$aryl" refers to 6- to 10-membered aromatic carbocyclic moieties having a single (e.g., phenyl) or a fused ring system (e.g., naphthalene.). A typical aryl group is phenyl group.

The term "$C_{3-6}$ cycloalkyl" refers to a carbocyclic ring which is fully saturated (e.g., cyclopropyl, cyclobutyl, cyclopentyl, and cyclohexyl).

The term "$C_{4-6}$ heterocycle" refers to a monocyclic ring which is fully saturated which has 4 to 6 ring atoms which contains 1 to 2 heteroatoms, independently selected from sulfur, oxygen and/or nitrogen. A typical "$C_{4-6}$ heterocycle" group includes oxtanyl, tetrahydrofuranyl, dihydrofuranyl, 1,4-dioxanyl, morpholinyl, 1,4-dithianyl, piperazinyl, piperidinyl, 1,3-dioxolanyl, pyrrolinyl, pyrrolidinyl, tetrahydropyranyl, oxathiolanyl, dithiolanyl, 1,3-dioxanyl, 1,3-dithianyl, oxathianyl, thiomorpholinyl, thiomorpholinyl 1,1 dioxide, tetrahydro-thiopyran 1,1-dioxide, 1,4-diazepanyl.

The term "fully or partially saturated heterocycle" refers to a nonaromatic ring that is either partially or fully saturated and may exist as a single ring, bicyclic ring (including fused heterocyclic rings) or a spiral ring. Unless specified otherwise, the heterocyclic ring is generally a 4- to 10-membered ring containing 1 to 4 heteroatoms (preferably 1, 2 or 3 heteroatoms) independently selected from sulfur, oxygen and/or nitrogen. A partially saturated heterocyclic ring also includes groups wherein the heterocyclic ring is fused to an aryl or heteroaryl ring (e.g., 2,3-dihydrobenzofuranyl, indolinyl (or 2,3-dihydroindolyl), 2,3-dihydrobenzothiophenyl, 2,3-dihydrobenzothiazolyl, 1,2,3,4-tetrahydroquinolinyl, 1,2,3,4-tetrahydroisoquinolinyl, 5,6,7,8-tetrahydropyrido[3,4-b]pyrazinyl). As used herein the term "spiral" or "spiro" means a two ring system wherein both rings share one common atom. Examples of spiral rings include 2,6-diazaspiro[3.3]heptanyl, -oxa-6-azaspiro[3.3]heptane, 2,2,6-diazaspiro[3.3]heptane, 3-azaspiro[5.5]undecanyl, 3,9-diazaspiro[5.5]undecanyl, 7-azaspiro[3.5]nonane, 2,6-diazaspiro[3.4]octane, 8-azaspiro[4.5]decane, 1,6-diazaspiro[3.3]heptane, 5-azaspiro[2.5]octane, 4,7-diazaspiro[2.5]octane, 5-oxa-2-azaspiro[3.4]octane, 6-oxa-1-azaspiro[3.3]heptane, 3-azaspiro[5.5]undecanyl, 3,9-diazaspiro[5.5]undecanyl, and the like.

Partially saturated or fully saturated heterocyclic rings include groups such as epoxy, aziridinyl, azetidinyl, tetrahydrofuranyl, dihydrofuranyl, dihydropyridinyl, pyrrolidinyl, imidazolidinyl, imidazolinyl, 1H-dihydroimidazolyl, hexahydropyrimidinyl, piperidinyl, piperazinyl, pyrazolidinyl, 2H-pyranyl, 4H-pyranyl, oxazinyl, morpholino, thiomorpholino, tetrahydrothienyl, tetrahydrothienyl 1,1-dioxide, oxazolidinyl, thiazolidinyl, 7-oxabicyclo[2.2.1]heptane, and the like.

The term "Fused heterocycle or 8 to 10 membered fused heterocycle" rings include fully or partially saturated groups such as 4,5,6,7-tetrahydro-3H-imidazo[4,5-c]pyridine, 8-azabicyclo[3.2.1]octan-3-ol, octahydropyrrolo[1,2-a]pyrazine, 5,6,7,8-tetrahydroimidazo[1,2-a]pyrazine, 3,8 diazabicyclo[3.2.1]octane, 8-oxa-3-azabicyclo[3.2.1]octane, 7-oxabicyclo[2.2.1]heptane, 1H-pyrazole, 2,5-diazabicyclo[2.2.1]heptane, 5,6,7,8-tetrahydro-[1,2,4]triazolo[4,3-a]pyrazine or 3-azabicyclo[3.1.0]hexane. A partially saturated heterocyclic ring also includes groups wherein the heterocyclic ring is fused to an aryl or heteroaryl ring (e.g., 2,3-dihydrobenzofuranyl, indolinyl (or 2,3-dihydroindolyl), 2,3-dihydrobenzothiophenyl, 2,3-dihydrobenzothiazolyl, 1,2,3,4-tetrahydroquinolinyl, 1,2,3,4-tetrahydroisoquinolinyl, 5,6,7,8-tetrahydropyrido[3,4-b]pyrazinyl, and the like).

The term "heteroaryl" refers to aromatic moieties containing at least one heteroatom (e.g., oxygen, sulfur, nitrogen or combinations thereof) within a 5- to 6-membered aromatic ring system (e.g., pyrrolyl, pyridyl, pyrazolyl, indolyl, indazolyl, thienyl, furanyl, benzofuranyl, oxazolyl, imidazolyl, tetrazolyl, triazinyl, pyrimidyl, pyrazinyl, thiazolyl, and the like.)

The phrase "pharmaceutically acceptable" indicates that the substance, composition or dosage form must be compatible chemically and/or toxicologically, with the other ingredients comprising a formulation, and/or the mammal being treated therewith.

Unless specified otherwise, the term "compounds of the present invention" refers to compounds of formula (I), as well as all stereoisomers (including diastereoisomers and enantiomers), rotamers, tautomers, isotopically labeled compounds (including deuterium substitutions), and inherently formed moieties (e.g., polymorphs, solvates and/or hydrates). When a moiety is present that is capable of forming a salt, then salts are included as well, in particular pharmaceutically acceptable salts.

As used herein, the term "a," "an," "the" and similar terms used in the context of the present invention (especially in the context of the claims) are to be construed to cover both the singular and plural unless otherwise indicated herein or clearly contradicted by the context. The use of any and all examples, or exemplary language (e.g. "such as") provided herein is intended merely to better illuminate the invention and does not pose a limitation on the scope of the invention otherwise claimed.

In one Embodiment, there is provided a compound of the Examples as an isolated stereoisomer wherein the compound has one stereocenter and the stereoisomer is in the R configuration.

In one Embodiment, there is provided a compound of the Examples as an isolated stereoisomer wherein the compound has one stereocenter and the stereoisomer is in the S configuration.

In one Embodiment, there is provided a compound of the Examples as an isolated stereoisomer wherein the compound has two stereocenters and the stereoisomer is in the R R configuration.

In one Embodiment, there is provided a compound of the Examples as an isolated stereoisomer wherein the compound has two stereocenters and the stereoisomer is in the R S configuration.

In one Embodiment, there is provided a compound of the Examples as an isolated stereoisomer wherein the compound has two stereocenters and the stereoisomer is in the S R configuration.

In one Embodiment, there is provided a compound of the Examples as an isolated stereoisomer wherein the compound has two stereocenters and the stereoisomer is in the S S configuration.

In one Embodiment, there is provided a compound of the Examples, wherein the compound has one or two stereocenters, as a racemic mixture.

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons.

In one Embodiment, the invention relates to a compound of the formula (I) as defined herein, in free form. In another Embodiment, the invention relates to a compound of the formula (I) as defined herein, in salt form. In another Embodiment, the invention relates to a compound of the formula (I) as defined herein, in acid addition salt form. In a further Embodiment, the invention relates to a compound of the formula (I) as defined herein, in pharmaceutically acceptable salt form. In yet a further Embodiment, the invention relates to a compound of the formula (I) as defined herein, in pharmaceutically acceptable acid addition salt form. In yet a further Embodiment, the invention relates to any one of the compounds of the Examples in free form. In yet a further Embodiment, the invention relates to any one of the compounds of the Examples in salt form. In yet a further Embodiment, the invention relates to any one of the compounds of the Examples in acid addition salt form. In yet a further Embodiment, the invention relates to any one of the compounds of the Examples in pharmaceutically acceptable salt form. In still another Embodiment, the invention relates to any one of the compounds of the Examples in pharmaceutically acceptable acid addition salt form.

Furthermore, the compounds of the present invention, including their salts, may also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

The compounds of the present invention, including salts, hydrates and solvates thereof, may inherently or by design form polymorphs.

Compounds of the present invention may be synthesized by synthetic routes that include processes analogous to those well-known in the chemical arts, particularly in light of the description contained herein. The starting materials are generally available from commercial sources such as Sigma-Aldrich or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin, including supplements (also available via the Beilstein online database)).

The further optional reduction, oxidation or other functionalization of compounds of formula (I) may be carried out according to methods well known to those skilled in the art. Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J.

Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, and in H.-D. Jakubke and H. Jeschkeit, "Aminosäuren, Peptide, Proteine" (Amino acids, Peptides, Proteins), Verlag Chemie, Weinheim, Deerfield Beach, and Basel 1982. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, acid addition salts of compounds of the present invention are obtained in customary manner, e.g. by treating the compounds with an acid or a suitable anion exchange reagent. Salts can be converted into the free compounds in accordance with methods known to those skilled in the art. Acid addition salts can be converted, for example, by treatment with a suitable basic agent.

Any resulting mixtures of isomers can be separated on the basis of the physicochemical differences of the constituents, into the pure or substantially pure geometric or optical isomers, diastereomers, racemates, for example, by chromatography and/or fractional crystallization.

For those compounds containing an asymmetric carbon atom, the compounds exist in individual optically active isomeric forms or as mixtures thereof, e.g. as racemic or diastereomeric mixtures. Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Enantiomers can also be separated by use of a commercially available chiral HPLC column.

The invention further includes any variant of the present processes, in which the reaction components are used in the form of their salts or optically pure material. Compounds of the invention and intermediates can also be converted into each other according to methods generally known to those skilled in the art.

For illustrative purposes, the reaction schemes depicted below provide potential routes for synthesizing the compounds of the present invention as well as key intermediates. For a more detailed description of the individual reaction steps, see the Examples section below. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

General Synthetic Methods

The following examples of compounds of the present invention illustrate the invention. Methods for preparing such compounds are described hereinafter.

Abbreviations

Abbreviations used are those conventional in the art or the following:

| | |
|---|---|
| Ac: Acetyl | Min(s): minute(s) |
| AcOH, HOAc: acetic acid | Me: methyl |
| aq.: aqueous | m/z: mass to charge ratio |
| app. q: apparent quartet | Alloc: allyloxycarbonyl protecting group |
| Ar: aromatic | M and mM: molar and millimolar |
| ADME: absorption, distribution, metabolism and excretion | mg: milligram |
| BPR: backpressure regulator | EDCl: 1-ethyl-3-(3-dimethylaminopropyl)carbodiimide |
| br: broad | BOP: (Benzotriazol-1-yloxy)tris(dimethylamino)phosphonium hexafluorophosphate |
| DCC: dicyclohexylcarbodiimide | µL, mL and L: microliter, milliliter and liter |
| PyBOP: (Benzotriazol-1-yloxy)tripyrrolidinophosphonium hexafluorophosphate | N: equivalent per liter |
| calc: calculated | n-BuLi: n-butyllitium |
| d: doublet; dd: doublet of doublets | NMR: nuclear magnetic resonance |
| DCM: dichloromethane | o/n: over night |
| Diox: Dioxane | PFA: perfluoroalkoxy (fluoropolymer) |
| DMF: N,N-dimethylformamide | ppm: parts per million |
| DMSO: dimethylsulfoxide | Ph: phenyl |
| DIPEA: N,N-diisopropylethylamine | q: quartet |
| dppp: 1,3-bis(diphenylphosphino)propane | rt: room temperature |
| ESI-MS: electrospray ionization mass spectrometry | rpm: revolutions per minute |
| Et and EtOAc: ethyl and ethyl acetate | s: singlet |
| HATU: O-(7-azobenzotriazol-1-yl)-1,1,3,3-tetramethyluroniumhexafluorophosphate | SFC: supercritical fluid chromatography |
| HOAt: 1-hydroxy-7-azabenzotriazole | t: triplet |
| HPLC: high pressure liquid chromatography | TEA: triethylamine |
| h, hr: hour(s) | THF: tetrahydrofuran |
| HRMS: high resolution mass spectrometry | 2-MeTHF: 2-methyltetrahydrofuran |
| LC and LCMS: liquid chromatography and liquid chromatography-mass spectrometry | TFA: trifluoroacetic acid |
| NMU: N-nitroso-N-methylurea | HEK293: Human Embryonic Kidney 293 cells |

| | |
|---|---|
| MeOH: methanol | DMEM: Dulbecco's modified eagle medium |
| HEPES: 4-(2-hydroxyethyl)-1-piperazineethanesulfonic acid | wt: weight |
| EGTA: ethylene glycol tetraacetic acid | TBME: tert-butyl methy ether |
| PBS: Phosphate Buffered Saline, pH7.4 | TFAA: Trifluoroacetic acid |
| MS: mass | UHP: urea-hydrogen peroxide |
| m: multiplet | |

Analytical Methods

ESI-MS data (also reported herein as simply MS) were recorded using Waters System (Acquity UPLC and a Micromass ZQ mass spectrometer); all masses reported are the m/z of the protonated parent ions unless recorded otherwise.

LC/MS:

The sample is dissolved in suitable solvent such as MeCN, DMSO or MeOH and is injected directly into the column using an automated sample handler. The analysis is performed using one of the following methods:

HPLC Conditions:

Condition 1:
Waters Acquity UPLC system:
Acquity Binary Gradient Manager with Degasser
Acquity Diode Array Detector
Leap Technologies HTS Pal Autosampler
Waters Waters SQD Mass Spectrometer
HPLC Column: Waters Acquity C18 1.7 um 2.1×30 mm
Mobile Phase: (A) H2O+0.05% TFA and (B) Acetonitrile+0.05% TFA
Gradient:
  1 mL/minute, initial 5% B for 0.1 minutes, ramp to 95% B over 1.5 minutes, hold until 1.6 minutes then to 100% B at 1.7 and return to 5% B to at 1.9 minutes until end of run at 2.25.
MS Scan: 180 to 800 amu in 0.4 seconds
Diode Array Detector: 214 nm-400 nm Condition 2:
Waters Acquity UPLC system:
Acquity Binary Gradient Manager with Degasser
Acquity Column Compartment set at 50° C.
Acquity Diode Array Detector
Leap Technologies HTS Pal Autosampler
Antek Chemiluminescent Nitrogen Detector (CLND)
Waters ZQ2000 Mass Spectrometer
HPLC Column: Thermo Syncronis C18 30×2.1 mm
Mobile Phase: (A) 95% H2O/5% MeOH/IPA (75/25, v/v)+0.05% formic acid, (B) MeOH/IPA (75/25, v/v)+0.035% formic acid
Gradient:
  0.4 mL/minute, initial 2% B for 1.0 minutes, ramp to 95% B over 2.5 minutes, until 4.0 minutes, return to 2% B to at 4.25 minutes until end of run at 5.0.
MS Scan: 150 to 1000 amu in 1 second
Diode Array Detector: 190 nm-400 nm Condition 3:
Waters Acquity UPLC system
Waters Acquity UPLC BEH C18 1.7 um, 2.1×30 mm (Part #: 186002349)
Flow rate: 1 mL/min
Temperature: 55° C. (column temp)
Mobile Phase Compositions:
A: 0.05% formic acid in water.
B: 0.04% formic acid in methanol.
Gradient:

| Time (min) | Flow (mL/min) | % A | % B |
|---|---|---|---|
| 0 | 1.000 | 95.0 | 5.0 |
| 0.10 | 1.000 | 95.0 | 5.0 |
| 0.50 | 1.000 | 20.0 | 80.0 |
| 0.60 | 1.000 | 5.0 | 95.0 |
| 0.80 | 1.000 | 5.0 | 95.0 |
| 0.90 | 1.000 | 95.0 | 5.0 |
| 1.15 | 1.000 | 95.0 | 5.0 |

Condition 4: (SQ4)
Waters Acquity UPLC system:
Acquity Binary Gradient Manager with Degasser
Acquity Diode Array Detector
Waters Sample Manager
Waters SQD Mass Spectrometer
HPLC Column: Waters ACQUITY UPLC BEH C18, 130 Å, 1.7 μm, 2.1 mm×50 mm-50° C.
Mobile Phase: (A) H2O+0.1 Formic Acid and (B) Acetonitrile+0.1 Formic Acid
Diode Array Detector: 214 nm-400 nm
Gradient:

| Time (min) | Flow (mL/min) | % A | % B |
|---|---|---|---|
| 0 | 1.000 | 98.0 | 2.0 |
| 0.06 | 1.000 | 98.0 | 2.0 |
| 1.76 | 1.000 | 2.0 | 98.0 |
| 2.06 | 1.000 | 2.0 | 98.0 |
| 2.50 | 1.000 | 98.0 | 2.0 |

Condition 5: (LCT02)
Waters Acquity UPLC system:
Acquity Binary Gradient Manager with Degasser
Acquity Diode Array Detector
Waters Sample Manager
Waters LCT Premier Time of Flight Mass Spectrometer
HPLC Column: ACQUITY UPLC BEH C18, 130 Å, 1.7 um, 2.1 mm×50 mm-50° C.
Mobile Phase: (A) H2O+0.1 Formic Acid and (B) Acetonitrile+0.1 Formic Acid
MS Scan: 180 to 800 amu in 0.4 seconds
Diode Array Detector: 214 nm-400 nm
Gradient:

| Time (min) | Flow (mL/min) | % A | % B |
|---|---|---|---|
| 0 | 1.000 | 98.0 | 2.0 |
| 7.50 | 1.000 | 2.0 | 98.0 |
| 7.90 | 1.000 | 2.0 | 98.0 |
| 8.05 | 1.000 | 98.0 | 2.0 |

Condition 6: (SQ4 RxnMon Basic)
Waters Acquity UPLC system:
Acquity Binary Gradient Manager with Degasser
Acquity Diode Array Detector
Waters Sample Manager
Waters SQD Mass Spectrometer
HPLC Column: Waters ACQUITY UPLC BEH C18, 130 Å, 1.7 μm, 2.1 mm×50 mm-50° C.
Mobile Phase: (A) H2O+5 mM ammonium hydroxide and (B) Acetonitrile+5 mM ammonium hydroxide
Diode Array Detector: 214 nm-400 nm
Gradient:

| Time (min) | Flow (mL/min) | % A | % B |
| --- | --- | --- | --- |
| 0 | 2.000 | 2.0 | 98.0 |
| 1.00 | 2.000 | 98.0 | 2.0 |
| 1.30 | 2.000 | 98.0 | 2.0 |

Condition 7:
Agilent 1200 Series HPLC system:
Agilent Binary Gradient Manager with Degasser
Agilent Diode Array Detector
Agilent 6140 Quadrupole LC/MS
SoftA ELS Detector
HPLC column: Waters Acquity HSS T3 C18 1.8 um, 2.1×50 mm
Flow rate: 0.9 mL/min
Temperature: 60° C. (column temp)
Mobile Phase Compositions:
A: 0.05% trifluoroacetic acid in water.
B: 0.035% trifluoroacetic acid in acetonitrile.
Gradient:

| Time (min) | Flow (mL/min) | % A | % B |
| --- | --- | --- | --- |
| 0 | 0.9 | 10 | 90 |
| 0.15 | 0.9 | 10 | 90 |
| 1.50 | 0.9 | 0 | 100 |
| 1.95 | 0.9 | 0 | 100 |
| 2 | 0.9 | 10 | 90 |
| 2.25 | 0.9 | 10 | 90 |

NMR:

Proton spectra are recorded on one of the following instruments: Bruker AVANCE II 400 MHz with 5 mm QNP Cryoprobe; Bruker AVANCE III 500 MHz with 5 mm QNP probe; or Bruker Avance 600 MHz with TCI cryoprobe. Chemical shifts are reported in ppm relative to dimethyl sulfoxide-$d_5$ (δ 2.50), chloroform (δ 7.26), methanol-$d_2$ (δ 3.34), dichloromethane-d (δ 5.32) or tetramethylsilane (δ 0.0).

Fluorine spectra are recorded on one of the following instruments: at 376.5 MHz on a Bruker AVANCE II 400 MHz with 5 mm QNP Cryoprobe or at 470.6 MHz on a Bruker AVANCE III 500 MHz with 5 mm QNP probe. The spectra are run with $^1$H-decoupling using appropriate composite pulse decoupling, unless specified. Chemical shifts are reported in ppm relative to an external $CFCl_3$ standard (b 0.0).

Spectra were acquired using a small amount of the dry sample (2-5 mg) dissolved in an appropriate deuterated solvent (1 mL).

HPLC Purification Methods:
Condition 1:
Waters Prep HPLC:
Waters 2767 Autosampler
Waters 2545 Binary Gradient Module
Waters Diode Array Detector
Waters Mass Spectrometer
Waters 515 HPLC Pump
HPLC Column: Waters XBridge C18 5 um 30×50 mm
Mobile Phase: Water/Acetonitrile with 10 mM NH4OH 75 mL/min 1.5 mL injection
  Water/Acetonitrile with 0.1% Formic Acid 75 mL/min 1.5 mL injection
PDA: 200 nm to 600 nm
Mass Range: 100-1250
Gradient:
Method 1: 5% to 20% ACN 3.5 min gradient
Method 2: 10% to 30% ACN 3.5 min gradient
Method 3: 15% to 40% ACN 3.5 min gradient
Method 4: 25% to 50% ACN 3.5 min gradient
Method 5: 35% to 60% ACN 3.5 min gradient
Method 6: 45% to 70% ACN 3.5 min gradient
Method 7: 55% to 80% ACN 3.5 min gradient
Method 8: 65% to 95% ACN 3.5 min gradient
Condition 2:
Agilent technologies 1200 series systems for prep HPLC
Binary Gradient with Degasser
Photo Diode Array Detector
Agilent 1200 Auto sampler with 1290-Infinity 8 valve Auto collection.
Shimadzu LC2020 Single Quad Mass Spectrometer, and API 2000 and API 3000 Triple Quad Mass Spectrometers.
HPLC Column: Phenomenox Gemini NX 5μ C18 110A AXIA 21.2 mm×150 mm
Mobile Phase 1: 0.05% Formic Acid in Water (A) and Acetonitrile (B)
Mobile Phase 2: 0.1% Formic Acid in Water (A) and Acetonitrile (B)
Gradient Time: 2 mL/minute Initial 30% B 0.5 min 30% 2.5 min 95% and 3.0 min 30% (3.0 min run time)
MS Scan: 100 to 1000 0.4 Seconds
Diode Array Detector: 214 nm-400 nm
Condition 3:
Agilent technologies 1200 series systems for prep HPLC
Binary Gradient with Degasser
Photo Diode Array Detector
Agilent 1200 Auto sampler with 1290-Infinity 8 valve Auto collection.
Shimadzu LC2020 Single Quad Mass Spectrometer, and API 2000 and API 3000 Triple Quad Mass Spectrometers.
HPLC Column: Agilent Eclipse Zorbax XDB C18 150×4.6 mm 5 um
Mobile Phase 1: 0.05% Formic Acid in Water (A) and Acetonitrile (B)
Mobile Phase 2: 0.2% ammonium acetate in Water (A) and Acetonitrile (B)
Gradient Time: 2 mL/minute Initial 30% B 0.5 min 30% 2.5 min 95% and 3.0 min 30% (3.0 min run time)
MS Scan: 100 to 1000 0.4 Seconds
Diode Array Detector: 214 nm-400 nm
Condition 4:
Agilent technologies 1200 series systems for prep HPLC
Binary Gradient with Degasser
Photo Diode Array Detector
Agilent 1200 Auto sampler with 1290-Infinity 8 valve Auto collection.
Shimadzu LC2020 Single Quad Mass Spectrometer, and API 2000 and API 3000 Triple Quad Mass Spectrometers.
HPLC Column: Phenominex Luna C18 250×4.6 mm 5 um Mobile Phase: 0.05% Formic Acid in Water (A) and Acetonitrile (B)
Gradient Time: 2 mL/minute Initial 30% B 0.5 min 30% 2.5 min 95% and 3.0 min 30% (3.0 min run time)
MS Scan: 100 to 1000 0.4 Seconds
Diode Array Detector: 214 nm-400 nm
Condition 5:
Agilent technologies 1200 series systems for prep HPLC
Binary Gradient with Degasser
Photo Diode Array Detector
Agilent 1200 Auto sampler with 1290-Infinity 8 valve Auto collection.
Shimadzu LC2020 Single Quad Mass Spectrometer, and API 2000 and API 3000 Triple Quad Mass Spectrometers.
HPLC Column: Kinetex Evo C18 150×4.6 mm 5 um
Mobile Phase: 0.1% Formic Acid in Water (A) and Acetonitrile (B)
Gradient Time: 2 mL/minute Initial 30% B 0.5 min 30% 2.5 min 95% and 3.0 min 30% (3.0 min run time)
MS Scan: 100 to 1000 0.4 Seconds
Diode Array Detector: 214 nm-400 nm
Schemes Scheme I and II provide potential routes for making compounds of formula (I).

ing block D are combined to form intermediate E. Intermediate E is then converted in to the target compound following removal of the protecting group, typically the tert-butylcarbamate. In summary the combination of various building blocks and intermediates can then be applied to yield compounds 1-96 of formula (I).

PREPARATION OF INTERMEDIATES

Intermediate (D): Procedure 1, Scheme 1

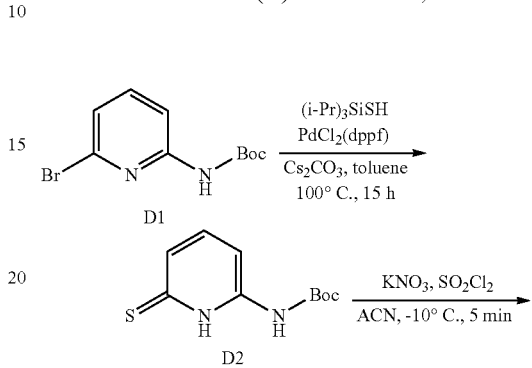

Scheme 1:

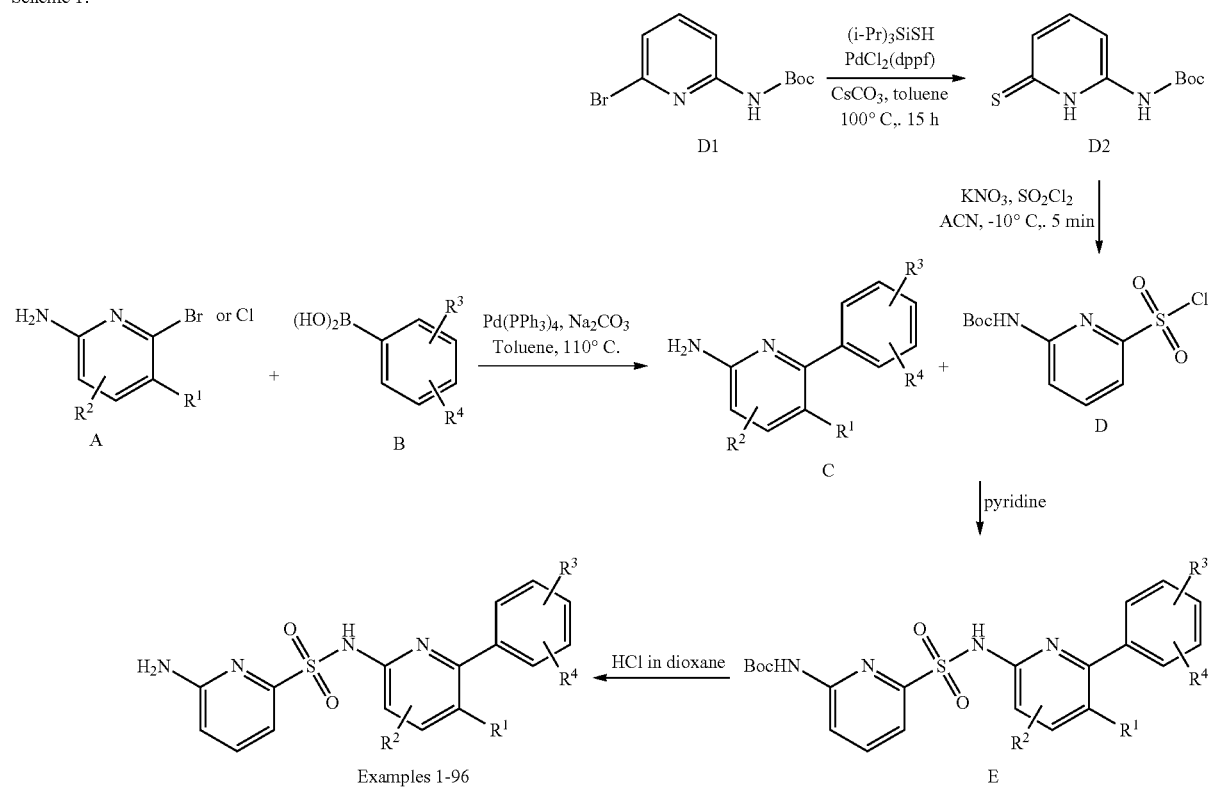

Examples 1-96

The starting materials for the above reaction scheme are commercially available or can be prepared according to methods known to one skilled in the art or by methods disclosed herein. In general, compounds 1-96 of the invention are prepared in the above reaction Scheme I as follows: Suzuki cross-coupling of building block A with building block B provides intermediate C. Separately, building block D1 is converted into intermediate D2 which is subsequently converted into building block D. Intermediate C and build- -continued

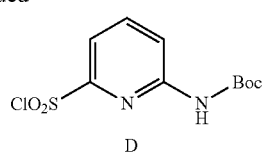

Step 1

A 250 mL round bottom flask was charged with tert-butyl (6-bromopyridin-2-yl)carbamate (D1) (9.83 g, 36 mmol)), $PdCl_2(dppf) \cdot CH_2Cl_2$ adduct (1.47 g, 1.8 mmol), $Cs_2CO_3$ (15.25 g, 46.8 mmol), triisopropylsilanethiol (10.05 mL, 46.8 mmol), and toluene (150 mL). The reaction mixture was filled with nitrogen and stirred at 100° C. for 15 h. The reaction mixture was filtered through Celite, washed with DCM and concentrated. The product was purified by silica gel chromatography (330 g silica gel column, 0-60% EA-hex) to give tert-butyl (6-thioxo-1,6-dihydropyridin-2-yl)carbamate (D2) (5.89 g, 72% yield), yellow crystals. The product was partially oxidized into di-tert-butyl (6,6'-disulfanediylbis(pyridine-6,2-diyl))dicarbamate. LCMS: m/z 227.1 $[M+H]^+$. $^1H$ NMR (400 MHz, DMSO-$d_6$) δ 12.63 (s, 1H), 10.48 (s, 1H), 7.38 (m, 1H), 6.87 (d, J=8.4 Hz, 1H), 6.51 (d, J=7.8 Hz, 1H), 1.50 (s, 9H).

Step 2

To a solution of tert-butyl (6-thioxo-1,6-dihydropyridin-2-yl)carbamate (D2) (1.70 g, 7.51 mmol) in acetonitrile (60 mL) was added $KNO_3$ (1.90 g, 18.8 mmol). The flask was cooled to −10° C. in ice water salt bath and $SO_2Cl_2$ (1.53 mL, 18.8 mmol) was added dropwise at the same temperature and stirred for 5 min. The mixture was diluted with ice-water and extracted with DCM (×3). The organic layer was dried over $Na_2SO_4$, filtered, concentrated at RT in vacuo and dried to give tert-butyl (6-(chlorosulfonyl)pyridin-2-yl)carbamate (D) (2.0 g, 5.47 mmol, 91% yield) as white solid. LCMS m/z 315.0 $[M+Na]^+$ $^1H$ NMR (400 MHz, DMSO-$d_6$) δ 10.61 (s, 1H), 7.96 (dd, J=8.4, 7.6 Hz, 1H), 7.66 (dd, J=8.5, 0.8 Hz, 1H), 7.46 (dd, J=7.5, 0.9 Hz, 1H), 1.48 (s, 9H).

Intermediate (D): Procedure 2, Scheme 1

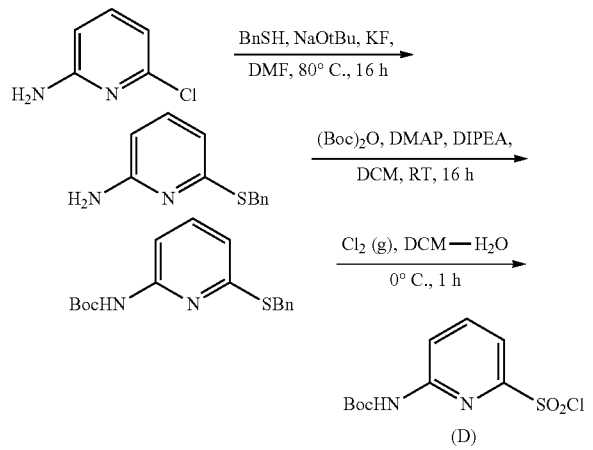

Step 1

To dry DMF (300 mL) taken in a sealed tube, was added NaOtBu (74.8 g, 777.85 mmol) followed by phenylmethanethiol (91.1 mL, 777.85 mmol) at rt and stirred for 30 min. Then 6-chloropyridin-2-amine (50.0 g, 388.92 mmol) was added in portions for 15 min at rt, followed by KF (45.2 g, 777.85 mmol). The reaction was sealed and heated at 80-90° C. for 36 h. Then the reaction was quenched with water (1.5 L) and extracted with $Et_2O$ thrice. The combined organic portion was washed with brine solution, dried over $Na_2SO_4$, and concentrated in vacuo to yield the crude compound, which was purified by column chromatography on silica gel (60-120 mesh size) (15-20% EtOAc in Hexane) to afford 6-(benzylthio)pyridin-2-amine as yellowish oil (67.5 g, 80.2%). LC/MS, ESI-MS (+): 217.4. $^1H$ NMR (300 MHz, $CDCl_3$) δ ppm 7.42-7.39 (m, 2H), 7.33-7.23 (m, 4H), 7.55 (d, J=7.8 Hz, 1H), 7.21 (d, J=8.1 Hz, 1H), 4.44 (brs, 2H), 4.36 (s, 2H).

Step 2

To the stirred solution of 6-(benzylthio)pyridin-2-amine (135 g, 624.13 mmol), DMAP (7.61 g, 62.38 mmol), and R3 DIPEA (128 mL, 748.95 mmol) in DCM (5.5 L), Boc anhydride dissolved in DCM (1.5 L) was added dropwise by addition funnel over 6 h at 0° C. The reaction mixture was stirred at rt for 16 h. The reaction mixture was diluted with water and extracted with DCM twice. The combined organic portion was washed with brine solution, dried over $Na_2SO_4$ and concentrated in vacuo to yield the crude compound. The crude was purified by column chromatography on silica gel (60-120 mesh size) (5-10% EtOAc in Hexane) to afford tert-butyl (6-(benzylthio)pyridin-2-yl)carbamate as a white solid (110 g, 55.7%). LC/MS, ESI-MS (+) 317.0. $^1H$ NMR (300 MHz, $CDCl_3$) δ ppm 7.62 (d, J=8.1 Hz, 1H), 7.46 (t, J=8.1 Hz, 1H), 7.40-7.37 (m, 2H), 7.34-7.22 (m, 3H), 7.16 (brs, 1H), 6.84 (dd, J=7.8, 0.9 Hz, 1H), 4.36 (s, 2H), 1.54 (s, 9H).

Step 3

To a two-necked round bottom flask containing tert-butyl (6-(benzylthio)pyridin-2-yl)carbamate (84 g, 265.47 mmol) was added DCM (800 mL) and water (200 mL) at room temperature. The content was then cool to 0° C. with an ice bath. Chlorine gas (generated from $KMnO_4$-con HCl) was purged for 30 min and reaction mixture stirred for additional 30 min at 0° C. After completion of the reaction, $N_2$ was purged for 20 min, reaction mixture was diluted with water (1000 mL). The organic portion was extracted with DCM thrice. The combined organic portion was washed with brine solution, dried over anhydrous $Na_2SO_4$ and concentrated in vacuo (at 40° C.) to afford a brown oily residue. The residue was purified by Si-gel (60-120 mesh size) column chromatography (1-30% EtOAc in Hexane) to afford tert-butyl (6-(chlorosulfonyl)pyridin-2-yl)carbamate (D): as a white solid (63 g, 81%). $^1H$ NMR (300 MHz, $CDCl_3$) δ ppm 8.36 (dd, J=8.4, 0.8 Hz, 1H), 7.96 (t, J=8.1 Hz, 1H), 7.72 (dd, J=7.5, 0.8 Hz, 1H), 7.55 (brs, 1H), 1.54 (s, 9H).

Intermediate (D): Scheme 1

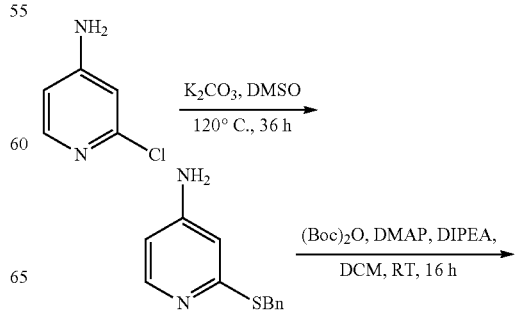

-continued

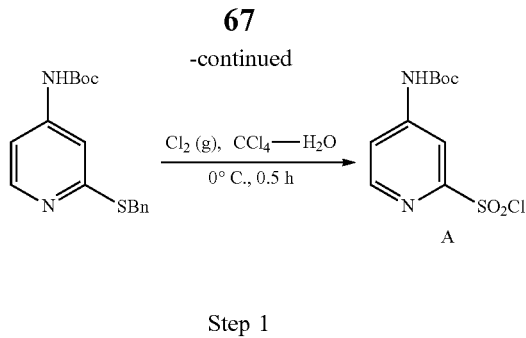

Step 1

To dry DMSO (100 mL) taken in a sealed tube, was added phenylmethanethiol (18.2 mL, 155.56 mmol) followed by $K_2CO_3$ (21.49 g, 155.56 mmol) at rt and stirred for 15 min. Then 2-chloropyridin-4-amine (10.0 g, 77.78 mmol) was added at rt and the reaction mass was heated at 120° C. for 36 h. Then the reaction was quenched with water (1 L) and extracted with EtOAc thrice. The combined organic portion was washed with brine solution, dried over $Na_2SO_4$, and concentrated in vacuo to yield the crude compound, which was purified by column chromatography on silica gel (60-120 mesh size) (20-25% EtOAc in Hexane) to afford 2-(benzylthio)pyridin-4-amine as a yellowish solid (8.0 g, 47.6%). LC/MS, ESI-MS ($^+$): 217.15. $^1$H NMR (300 MHz, DMSO-d6) δ ppm 7.88 (d, J=5.7 Hz, 1H), 7.38-7.35 (m, 2H), 7.31-3.21 (m, 3H), 6.35-6.34 (m, 1H), 6.26 (dd, J=5.4, 1.8 Hz, 1H), 6.04 (brs, 2H), 4.31 (s, 2H).

Step 2

To the stirred solution of 2-(benzylthio)pyridin-4-amine (6.0 g, 27.73 mmol), DMAP (0.34 g, 2.77 mmol) and DIPEA (5.81 mL, 33.28 mmol) in DCM (300 mL), Boc anhydride (6.69 mL, 29.12 mmol) dissolved in DCM (100 mL) was added dropwise by addition funnel at 0° C. The reaction mixture was stirred at rt for 16 h. The reaction mixture was diluted with water and extracted with DCM twice. The combined organic portion was washed with brine solution, dried over $Na_2SO_4$ and concentrated in vacuo to yield the crude compound. The crude was purified by column chromatography on silica gel (60-120 mesh size) (0-10% EtOAc in Hexane) to afford tert-butyl (2-(benzylthio)pyridin-4-yl)carbamate as a white solid (4.0 g, 52.8%). LC/MS, ESI-MS ($^+$) 317.15. $^1$H NMR (300 MHz, CDCl$_3$) δ ppm 8.28 (d, J=6.0 Hz, 1H), 7.42-7.39 (m, 2H), 7.32-7.23 (m, 4H), 6.97 (dd, J=5.7, 2.1 Hz, 1H), 6.54 (brs, 1H), 4.42 (s, 2H), 1.52 (s, 9H).

Step 3

A mixture of tert-butyl (2-(benzylthio)pyridin-4-yl)carbamate (2.0 g, 6.32 mmol) in CCl$_4$ (80 mL) and water (20 mL) was cooled to 0° C. with an ice-water bath. Chlorine gas (generated from KMnO$_4$-conc HCl) was purged into the reaction mixture at 0° C. for 30 min. After reaction completion, N$_2$ was purged into the reaction mixture for 20 min. The reaction mixture was then diluted with water (40 mL). The organic portion was extracted with DCM thrice. The combined organic portion was washed with brine solution, dried over anhydrous Na$_2$SO$_4$ and concentrated in vacuo at 40° C. to afford a crude oil. The crude was purified by combi flash using 12 g SiliCycle column (15-20% EtOAc in Hexane) to afford tert-butyl (2-(chlorosulfonyl)pyridin-4-yl)carbamate as a white solid (1.38 g, 74.5%). $^1$H NMR (400 MHz, DMSO-d$_6$) δ ppm 11.17 (s, 1H), 8.44 (d, J=6.8 Hz, 1H), 8.17 (s, 1H), 7.84-7.83 (m, 1H), 1.52 (s, 9H).

Intermediate (D): Scheme 1

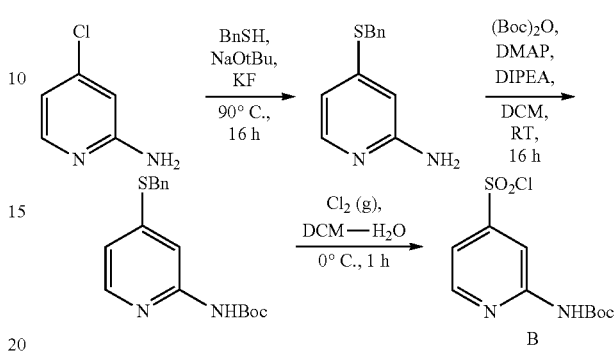

Step 1

To dry DMF (300 mL) taken in a sealed tube, was added phenylmethanethiol (73.0 mL, 622.27 mmol) followed by NaOtBu (65.78 g, 684.50 mmol) at rt and stirred for 30 min. Then 4-chloropyridin-2-amine (40.0 g, 311.13 mmol) was added in portions at rt, followed by KF (36.14 g, 622.27 mmol). The reaction was sealed and heated at 90° C. for 16 h. Then the reaction was poured into ice cold water and stirred for 30 min. The solid precipitated was filtered, washed with water and dried in vacuo. The isolated solid was stirred in hexane for 30 min, solid was collected by filtration and dried in vacuo to afford 4-(benzylthio)pyridin-2-amine as a white solid (36.0 g, 53.4%). LC/MS, ESI-MS ($^+$): 217.15. $^1$H NMR (400 MHz, DMSO-d6) δ ppm 7.71 (d, J=5.2 Hz, 1H), 7.41 (d, J=7.2 Hz, 1H), 7.32 (t, J=7.4 Hz, 2H), 7.26 (d, J=7.2 Hz, 2H), 6.40 (dd, J=5.2, 1.6 Hz, 1H), 6.33 (d, J=1.2 Hz, 1H), 5.89 (brs, 2H), 4.22 (s, 2H).

Step 2

To the stirred solution of 4-(benzylthio)pyridin-2-amine (36 g, 166.43 mmol), DMAP (2.03 g, 16.64 mmol) and DIPEA (34.88 mL, 199.72 mmol) in DCM (1.2 L), Boc anhydride (49.7 mL, 216.36 mmol) dissolved in DCM (0.6 L) was added dropwise by addition funnel at over 2 h 0° C. The reaction mixture was stirred at rt for 16 h. The reaction mixture was diluted with water and extracted with DCM twice. The combined organic portion was washed with brine solution, dried over Na$_2$SO$_4$ and concentrated in vacuo to yield the crude compound. To the crude compound Et$_2$O was added and stirred for 30 min. The solid separated was collected by filtration and dried in vacuo to afford tert-butyl (4-(benzylthio)pyridin-2-yl)carbamate as a pale yellow solid (42.0 g, 79.8%). LC/MS, ESI-MS ($^+$) 317.1. $^1$H NMR (300 MHz, DMSO-d6) δ ppm 9.77 (s, 1H), 8.02 (d, J=5.4 Hz, 1H), 7.73 (d, J=1.5 Hz, 1H), 7.44 (d, J=7.2 Hz, 2H), 7.33-7.22 (m, 3H), 6.94 (dd, J=7.2, 1.5 Hz, 1H), 4.31 (s, 2H), 1.45 (s, 9H).

Step 3

A mixture of tert-butyl (4-(benzylthio)pyridin-2-yl)carbamate (22.0 g, 69.52 mmol) in DCM (600 mL) and water (200 mL) was cooled to 0° C. with an ice-water bath.

Chlorine gas (generated from KMnO$_4$-conc HCl) was purged into the reaction mixture at 0° C. for 1 h. After reaction completion, N$_2$ was purged into the reaction mixture for 20 min. The reaction mixture was then diluted with water (100 mL). The organic portion was extracted with DCM thrice. The combined organic portion was washed with brine solution, dried over anhydrous Na$_2$SO$_4$ and concentrated in vacuo at 40° C. to afford a crude compound. To the crude compound DCM (50 mL) was added and stirred at 0° C. for 30 min. The solid separated was filtered, washed with cold DCM and dried in vacuo to afford tert-butyl (4-(chlorosulfonyl)pyridin-2-yl)carbamate as a white solid (13.0 g, 63.8%). $^1$H NMR (400 MHz, DMSO-d6) δ ppm 11.72 (s, 1H), 8.32 (d, J=6.4 Hz, 1H), 7.70 (d, J=1.2 Hz, 1H), 7.49 (dd, J=6.0, 1.6 Hz, 1H), 1.53 (s, 9H).

Intermediate (D): Scheme 1

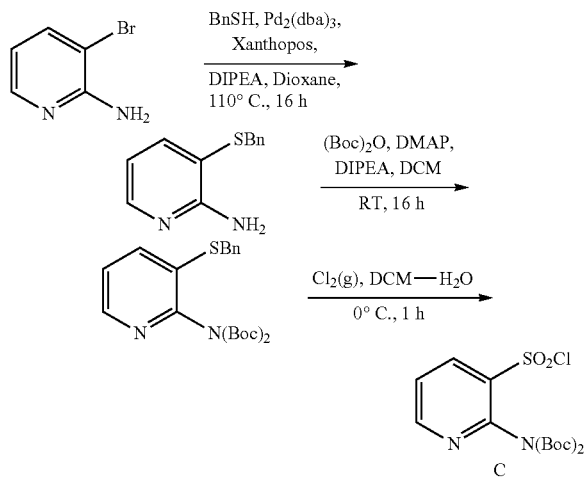

Step 1

The stirred solution of 3-bromopyridin-2-amine (5.0 g, 28.90 mmol), phenylmethanethiol (5.08 mL, 43.35 mmol), Pd$_2$(dba)$_3$ (1.32 g, 1.45 mmol), Xanthophos (1.67 g, 2.89 mmol) and DIPEA (10.0 mL, 57.80 mmol) in 1,4-dioxane (100 mL) was degassed with argon for 15 min. The resulting reaction mixture was heated at reflux for 16 h under argon atmosphere. The reaction mixture was cooled to rt, filtered through celite bed. The celite bed was washed with EtOAc and the combined filtrate was concentrated to dryness under reduced pressure. The crude residue was purified by column chromatography on silica gel (60-120 mesh size) (30-40% EtOAc in Hexane) to afford 3-(benzylthio)pyridin-2-amine as a yellow solid (5.0 g, 80%). LC/MS, ESI-MS (+): 217.0. $^1$H NMR (300 MHz, CDCl$_3$) δ ppm 7.99 (dd, J=4.8, 1.5 Hz, 1H), 7.33 (dd, J=7.5, 1.8 Hz, 1H), 7.26-7.21 (m, 3H), 7.13-7.11 (m, 2H), 6.53-6.49 (m, 1H), 5.06 (brs, 2H), 3.91 (s, 2H).

Step 2

To the stirred solution of 3-(benzylthio)pyridin-2-amine (5.0 g, 23.11 mmol), DMAP (0.28 g, 2.31 mmol) and DIPEA (4.74 mL, 27.73 mmol) in DCM (120 mL), Boc anhydride (6.9 mL, 30.05 mmol) dissolved in DCM (80 mL) was added dropwise by addition funnel at 0° C. The reaction mixture was stirred at rt for 16 h. The reaction mixture was diluted with water and extracted with DCM twice. The combined organic portion was washed with brine solution, dried over Na$_2$SO$_4$ and concentrated in vacuo to yield the crude compound. The crude was purified by column chromatography on silica gel (60-120 mesh size) (25-30% EtOAc in Hexane) to afford (3-(benzylthio)pyridin-2-yl) bis(tert-butyl carbamate) as a pale yellow solid (5.5 g, 57.1%). LC/MS, ESI-MS (+) 417.0. $^1$H NMR (400 MHz, CDCl$_3$) δ ppm 8.33 (dd, J=4.8, 1.6 Hz, 1H), 7.51 (dd, J=8.0, 2.0 Hz, 1H), 7.31-7.25 (m, 5H), 7.14 (dd, J=7.6, 4.4 Hz, 1H), 4.10 (s, 2H), 1.42 (s, 18H).

Step 3

A mixture of (3-(benzylthio)pyridin-2-yl) bis(tert-butyl carbamate) (5.5 g, 13.20 mmol) in DCM (240 mL) and water (60 mL) was cool to 0° C. with an ice-water bath. Chlorine gas (generated from KMnO$_4$-conc HCl) was purged into the reaction mixture for 1 h at 0° C. After reaction completion, N$_2$ was purged into the reaction mixture for 20 min. The reaction mixture was diluted with water (100 mL) and the organic portion was extracted with DCM thrice. The combined organic portion was washed with brine solution, dried over anhydrous Na$_2$SO$_4$ and concentrated in vacuo at 40° C. to afford a crude oil. The crude residue was purified by combi flash using 24 g SiliCycle column (10-15% EtOAc in Hexane) to provide (3-(chlorosulfonyl)pyridin-2-yl) bis(tert-butyl carbamate) as pale yellow oil (4.4 g, 84.9%). $^1$H NMR (400 MHz, CDCl$_3$) δ ppm 8.90-8.88 (m, 1H), 8.50 (dd, J=7.6, 1.2 Hz, 1H), 7.61 (dd, J=8.0, 4.8 Hz, 1H), 1.44 (s, 18H).

Intermediate (D): Scheme 1

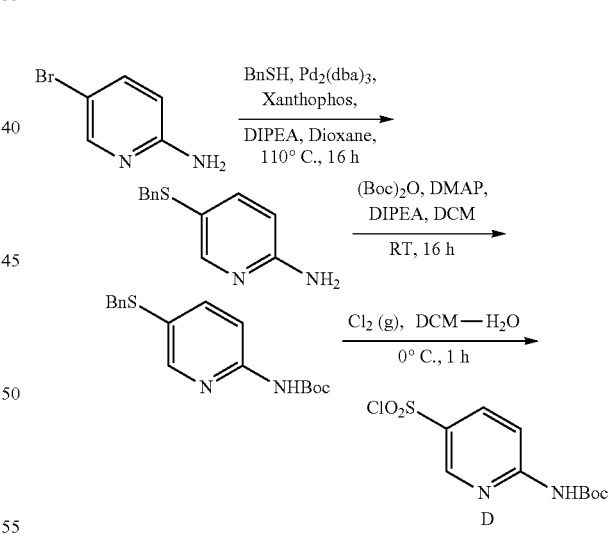

Step 1

The stirred solution of 5-bromopyridin-2-amine (50.0 g, 289.00 mmol), phenylmethanethiol (50.88 mL, 433.50 mmol), Pd$_2$(dba)$_3$ (13.23 g, 14.45 mmol), Xanthophos (16.72 g, 28.90 mmol) and DIPEA (100.9 mL, 578.00 mmol) in 1,4-dioxane (750 mL) was degassed with argon for 15 min. The resulting reaction mixture was heated at reflux for 16 h under argon atmosphere. The reaction mixture was cooled to rt, filtered through celite bed. The celite bed was washed with EtOAc and the combined filtrate was concentrated to dryness under reduced pressure. The crude residue was purified by column chromatography on silica gel (60-120 mesh size) (35-50% EtOAc in Hexane) to afford tert-butyl (5-(benzylthio)pyridin-2-amine as a yellow solid (60.5 g, 96.7%). LC/MS, ESI-MS (+): 216.95. $^1$H NMR (400 MHz, CDCl$_3$) δ ppm 7.99-7.98 (m, 1H), 7.31-7.21 (m, 4H), 7.15-7.13 (m, 2H), 6.36 (dd, J=8.4, 0.8 Hz, 1H), 4.51 (brs, 2H), 3.88 (s, 2H).

Step 2

To the stirred solution of 5-(benzylthio)pyridin-2-amine (59.0 g, 272.76 mmol), DMAP (3.33 g, 27.27 mmol) and DIPEA (55.96 mL, 327.32 mmol) in DCM (1.5 L), Boc anhydride (75.19 mL, 327.32 mmol) dissolved in DCM (500 mL) was added dropwise by addition funnel over 2 h at 0° C. The reaction mixture was stirred at rt for 16 h. The reaction mixture was diluted with water and extracted with DCM twice. The combined organic portion was washed with brine solution, dried over Na$_2$SO$_4$ and concentrated in vacuo to yield the crude compound. The crude was stirred with Et$_2$O (180 mL) for 30 min. The solid separated was filtered and dried in vacuo to afford tert-butyl (5-(benzylthio)pyridin-2-yl)carbamate as a pale yellow solid (60.0 g, 69.5%). LC/MS, ESI-MS (+) 317.0. $^1$H NMR (300 MHz, CDCl$_3$) δ ppm 8.81 (brs, 1H), 8.23 (d, J=1.8 Hz, 1H), 7.89 (d, J=9.0 Hz, 1H), 7.55 (dd, J=9.0, 2.4 Hz, 1H), 7.28-7.22 (m, 3H), 7.16-7.13 (m, 2H), 3.95 (s, 2H), 1.53 (s, 9H).

Step 3

A mixture of tert-butyl (5-(benzylthio)pyridin-2-yl)carbamate (60.0 g, 189.62 mmol) in DCM (1.6 L) and water (0.4 L) was cool to 0° C. with an ice-water bath. Chlorine gas (generated from KMnO$_4$-conc HCl) was purged into the reaction mixture for 1 h and 30 min at 0° C. After reaction completion, N$_2$ was purged into the reaction mixture for 20 min. The reaction mixture was diluted with water (500 mL). The organic portion was extracted with DCM thrice. The combined organic portion was washed with brine solution, dried over anhydrous Na$_2$SO$_4$ and concentrated in vacuo at 40° C. to afford a crude product. To the crude compound, DCM (120 mL) was added and stirred at 0° C. for 30 min. The solid separated was filtered, washed with cold DCM and dried in vacuo to afford tert-butyl (5-(chlorosulfonyl)pyridin-2-yl)carbamate as a white solid (48.0 g, 86.4%). $^1$H NMR (400 MHz, DMSO-d6) δ ppm 11.48 (s, 1H), 8.40 (d, J=1.5 Hz, 1H), 8.28 (dd, J=9.2, 2.0 Hz, 1H), 7.51 (d, J=8.8 Hz, 1H), 1.52 (s, 9H).

Building Block (C):
5-Chloro-6-(o-tolyl)pyridin-2-amine

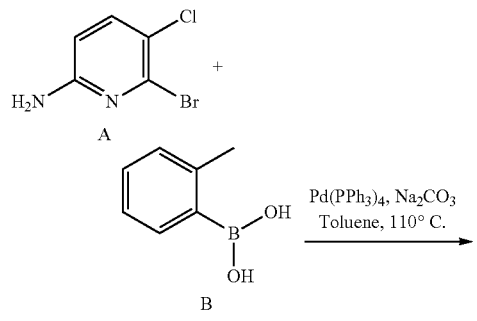

Step 1

Reaction flask was charged with o-tolylboronic acid (B) (1.357 g, 9.98 mmol), 6-bromo-5-chloropyridin-2-amine (A) (2.070 g, 9.98 mmol) in dioxane (60 mL), and 2 M Na$_2$CO$_3$ (15 mL). It was degassed and filled with nitrogen, then Pd(PPh$_3$)$_4$ (557 mg, 0.499 mmol) was added, and degassed again. The reaction mixture was heated at 100° C. for 12 h and cooled down to room temperature. DCM (100 mL) was added and the mixture was washed with brine, dried over sodium sulfate, filtered, and concentrated. The crude material was purified on silica gel (80 g silica gel chromatography column, EtOAc:Hexanes gradient 0-35%) to give the desired product (C) (1.96 g, 85%). LCMS m/z 219.2 [M+H]$^+$ $^1$H NMR (400 MHz, Methylene Chloride-d$_2$) δ 7.49 (d, J=8.7 Hz, 1H), 7.36-7.13 (m, 4H), 6.48 (d, J=8.7 Hz, 1H), 4.59 (s, 2H), 2.16 (s, 3H).

(2-(Methyl-d$_3$)phenyl)boronic Acid: Intermediate (B) Used in Ex. 20 and 26

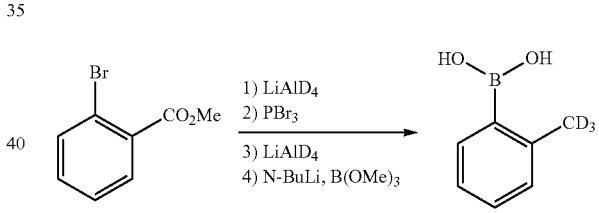

Step 1

(2-Bromophenyl)methan-d$_2$-ol (J. Am. Chem. Soc. 1981, 103, 6308-6313)

To a slurry of lithium aluminumdeuteride (1.278 g, 30.5 mmol) in anhydrous THF (100 mL) was slowly added dropwise within 1 h a solution of methyl 2-bromobenzoate (10.75 g, 50 mmol) in anhydrous THF (100 mL) and stirred at rt for 1 h under nitrogen atmosphere. The reaction mixture was quenched by the slow addition of sat. Na$_2$SO$_4$ (8.5 mL) followed by stirring for 1 h. The resulting mixture was filtered through celite, washed with THF (100 mL), dried over Na$_2$SO$_4$, and the solvent was removed in vacuo. The crude product was recrystallized under hexanes to give the desired compound (6.50 g, 34.4 mmol, 68.8% yield) as white crystals. LCMS: m/z 171.1 [M−OH]$^+$. $^1$H NMR (400 MHz, CDCl$_3$) δ 7.55 (dd, J=8.0, 1.2 Hz, 1H), 7.48 (dd, J=7.6, 1.7 Hz, 1H), 7.34 (td, J=7.5, 1.2 Hz, 1H), 7.17 (td, J=7.7, 1.7 Hz, 1H).

Step 2

1-Bromo-2-(bromomethyl-d$_2$)benzene (J. Am. Chem. Soc. 1981, 103, 6308-6313)

To a solution of (2-bromophenyl)methan-d$_2$-ol (6.50 g, 34.4 mmol) in anhydrous ether (60 mL) PBr$_3$ (1.946 mL, 20.6 mmol) was added slowly. The reaction mixture was refluxed for 2 h, cooled to rt, washed with water, saturated NaHCO$_3$ and dried over Na$_2$SO$_4$. Evaporation gave the desired compound (8.20 g, 32.5 mmol, 95% yield) as crystals. LCMS: no mass detected. $^1$H NMR (400 MHz, CDCl$_3$) δ 7.58 (dd, J=8.0, 1.2 Hz, 1H), 7.46 (dd, J=7.6, 1.7 Hz, 1H), 7.30 (td, J=7.5, 1.3 Hz, 1H), 7.17 (m, 1H).

Step 3

1-Bromo-2-(methyl-d$_3$)benzene (J. Am. Chem. Soc. 1981, 103, 6308-6313)

To a slurry of LAD (1.120 g, 26.7 mmol) in anhydrous THF (80 mL) was added dropwise a solution of 1-bromo-2-(bromomethyl-d$_2$)benzene (8.20 g, 32.5 mmol) in anhydrous THF (80 mL) over period of 1 h with stirring under nitrogen atmosphere. The reaction was refluxed for 3 h, cooled and then carefully quenched by the slow addition of saturated Na$_2$SO$_4$ (2.5 mL) followed by stirring for 1 h. Filtered through celite, washed with THF and dried over Na$_2$SO$_4$, and the solvent was removed in vacuo to yield the desired product (7.33 g, 31.6 mmol, 97% yield) as transparent liquid. LCMS: m/z 171.1 [M−OH]$^+$. $^1$H NMR (400 MHz, CDCl$_3$) δ 7.52 (dd, J=7.9, 1.1 Hz, 1H), 7.21 (m, 2H), 7.04 (ddd, J=7.9, 6.9, 2.2 Hz, 1H). D content 97% (by $^1$H NMR, 2.37 (p, J=2.2 Hz, 0.03H).

Step 4

2-(Methyl-d$_3$)phenyl)boronic acid was obtained following the procedure for 2-methylphenylboronic acid (Sleveland, Dagfinn and Bjoersvik, Hans-Rene. Organic Process Research & Development, 16(5), 1121-1130; 2012)

To a cooled mixture of 1-bromo-2-(methyl-d$_3$)benzene (7.33 g, 31.6 mmol) in dry THF (105 mL) at −78° C. was added n-BuLi (16.42 mL, 41.1 mmol). The reaction mixture was stirred at −78° C. for 30 minutes prior to the addition of B(OMe)$_3$ (5.99 mL, 53.7 mmol). The reaction mixture was stirred at −78° C. for 30 min. After the solution reached rt, it was stirred at rt for 1.5 h. 120 mL of saturated NH$_4$Cl solution was added and THF was evaporated. The aqueous phase was acidified with 3 M HCl until the pH<4. The reaction mixture was extracted with DCM (×3), and the combined organic layers were washed with brine, dried over Na$_2$SO$_4$, filtered and concentrated. The crude solid was triturated under hexanes, and white crystals were filtered, yield 1.13 g (26%). LCMS: Rt no mass detected. $^1$H NMR (400 MHz, CDCl$_3$) δ 8.22 (dd, J=7.4, 1.2 Hz, 1H), 7.46 (td, J=7.5, 1.6 Hz, 1H), 7.30 (m, 2H). D content 97% (by $^1$H NMR, 2.79 (p, J=Hz, 0.03H).

PREPARATION OF EXAMPLES

Example 14: 6-Amino-N-(5-chloro-6-(o-tolyl)pyridin-2-yl)pyridine-2-sulfonamide

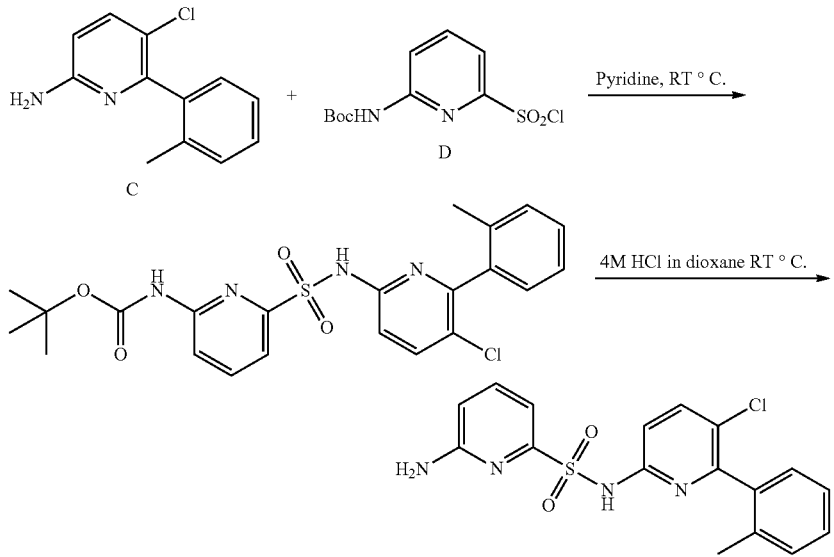

Ex. 14

Step 1

To a solution of 5-chloro-6-(o-tolyl)pyridin-2-amine (C) (1.006 g, 4.60 mmol) in pyridine (20 mL) was added tert-butyl (6-(chlorosulfonyl)pyridin-2-yl)carbamate (D) (2.02 g, 6.90 mmol) and stirred at RT o/n. Water was added and stirred for 30 min. Brine was added, the mixture was extracted with DCM (×3), and dried over sodium sulfate. The solution was filtered, concentrated and evaporated with toluene twice to remove pyridine. Purification on silica gel chromatography, 80 g column, 0-40% EA-hex afforded tert-Butyl (6-(N-(5-chloro-6-(o-tolyl)pyridin-2-yl)sulfamoyl)pyridin-2-yl)carbamate (2.18 g, 100%). LCMS m/z 475.2 [M+H]$^+$. $^1$H NMR (400 MHz, DMSO-d$_6$) δ 11.36 (s, 1H), 10.18 (s, 1H), 7.98 (m, 1H), 7.92 (m, 2H), 7.54 (dd, J=7.4, 0.8 Hz, 1H), 7.25 (m, 4H), 6.98 (d, J=7.3 Hz, 1H), 1.88 (s, 3H), 1.47 (s, 9H).

Step 2 tert-Butyl (6-(N-(5-chloro-6-(o-tolyl)pyridin-2-yl)sulfamoyl)pyridin-2-yl)carbamate (2.18 g, 4.59 mmol) was dissolved in 4 M HCl in dioxane (33 mL, 132 mmol) and stirred at RT o/n. A precipitate resulted. Ether (33 mL) was added, stirred for 30 min, filtered, and washed with ether. The white crystals were partitioned between DCM and sat. NaHCO$_3$ and extracted with DCM (×3). The combined extracts were washed with brine and dried over Na$_2$SO$_4$. The solution was filtered, evaporated and dried in high vac. at 60° C. o/n to afford 6-Amino-N-(5-chloro-6-(o-tolyl)pyridin-2-yl)pyridine-2-sulfonamide (Ex. 14) (1.54 g, 89%) as white crystals. Condition 2, LCMS: m/z 375.1 [M+H]$^+$, $^1$H NMR (400 MHz, DMSO-d$_6$) δ 11.16 (s, 1H), 7.89 (d, J=8.8 Hz, 1H), 7.51 (dd, J=8.3, 7.4 Hz, 1H), 7.31 (td, J=7.4, 1.4 Hz, 1H), 7.23 (m, 3H), 7.02 (m, 2H), 6.62 (dd, J=8.4, 0.6 Hz, 1H), 6.45 (s, 2H), 1.91 (s, 3H).

The following examples were prepared using a combination of various building blocks and intermediates as indicated within the general synthetic methods.

Example 1: 6-amino-N-(6-(5-fluoro-2-methylphenyl)-5-(trifluoromethyl)pyridin-2-yl)pyridine-2-sulfonamide Condition 2, LCMS: m/z 427.1 [M+H]$^+$, 13.04 min. $^1$H NMR (500 MHz, DMSO-d$_6$) δ 11.61 (s, 1H), 8.16 (d, J=8.9 Hz, 1H), 7.49 (dd, J=8.4, 7.3 Hz, 1H), 7.37 (d, J=8.7 Hz, 1H), 7.28 (dd, J=8.5, 5.8 Hz, 1H), 7.17 (td, J=8.6, 2.8 Hz, 1H), 7.02 (dd, J=7.3, 0.7 Hz, 1H), 6.96 (d, J=6.9 Hz, 1H), 6.63 (dd, J=8.4, 0.7 Hz, 1H), 6.45 (s, 2H), 5.76 (s, 1H), 1.76 (s, 3H).

Example 2: 6-amino-N-(6-(2,6-dimethylphenyl)-5-(trifluoromethyl)pyridin-2-yl)pyridine-2-sulfonamide Condition 2, LCMS: m/z 423.1 [M+H]$^+$ 3.05 min. $^1$H NMR (400 MHz, Methanol-d$_4$) δ 8.07 (d, J=8.9 Hz, 1H), 7.51-7.37 (m, 1H), 7.20 (d, J=7.6 Hz, 1H), 7.15 (dd, J=7.4, 0.7 Hz, 1H), 7.06 (d, J=7.6 Hz, 2H), 6.66 (d, J=8.4 Hz, 1H), 1.85 (s, 6H).

Example 3: 6-amino-N-(5-bromo-6-(2,6-dimethylphenyl)pyridin-2-yl)pyridine-2-sulfonamide Condition 2, LCMS: m/z 433.1 [M+H]$^+$, 3.04 min. $^1$H NMR 400 MHz (DMSO-d$_6$) δ 11.11 (s, 1H), 8.04 (d, J=8.8 Hz, 1H), 7.47 (dd, J=8.3, 7.4, 1H), 7.22-7.13 (m, 2H), 7.07 (d, J=7.6, 2H), 6.98 (dd, J=7.3, 0.6 Hz, 1H), 6.61 (dd, J=8.4, 0.7 Hz, 1H), 6.41 (s, 2H), 1.78 (s, 6H).

Example 4: 2-amino-N-(5-chloro-6-(2,6-dimethylphenyl)pyridin-2-yl)pyridine-4-sulfonamide Condition 2, LCMS: m/z 389.1 [M+H]$^+$, 2.80 min. $^1$H NMR (400 MHz, Methanol-d$_4$) δ 7.83 (d, J=5.5 Hz, 1H), 7.70 (d, J=8.7 Hz, 1H), 7.11-7.04 (m, 2H), 6.96 (d, J=7.6 Hz, 2H), 6.82 (d, J=1.5 Hz, 1H), 6.78 (dd, J=1.6, 5.5 Hz, 1H), 1.74 (s, 6H).

Example 5: 6-amino-N-(6-(2,6-dimethylphenyl)-4-(trifluoromethyl)pyridin-2-yl)pyridine-2-sulfonamide Condition 2, LCMS: m/z 423.1 [M+H]$^+$, 3.21 min. $^1$H NMR (400 MHz, Methanol-d$_4$) δ 7.60-7.44 (m, 2H), 7.18 (d, J=7.4 Hz, 2H), 7.14-7.02 (m, 3H), 6.66 (d, J=8.4 Hz, 1H), 1.93 (s, 6H).

Example 6: 6-amino-N-(5-chloro-6-(5-fluoro-2-methylphenyl)pyridin-2-yl)pyridine-2-sulfonamide Condition 2, LCMS: m/z 393.1 [M+H]$^+$, 3.01 min. $^1$H NMR (400 MHz, DMSO-d$_6$) δ 11.21 (s, 1H), 7.92 (d, J=8.8 Hz, 1H), 7.50 (t, J=7.8 Hz, 1H), 7.30 (dd, J=8.3, 5.9 Hz, 1H), 7.22 (d, J=8.8 Hz, 1H), 7.16 (td, J=8.7, 2.6 Hz, 1H), 7.02 (d, J=7.3 Hz, 1H), 6.90 (dd, J=9.3, 2.4 Hz, 1H), 6.62 (d, J=8.4 Hz, 1H), 6.46 (s, 2H), 1.88 (s, 3H). $^{19}$F NMR (376 MHz, DMSO-d$_6$) δ −117.93 (s).

Example 7: 6-amino-N-(6-(3-fluoro-2-methylphenyl)-5-(trifluoromethyl)pyridin-2-yl)pyridine-2-sulfonamide Condition 2, LCMS: m/z 427.1 [M+H]$^+$, 3.07 min. $^1$H NMR (400 MHz, Methylene Chloride-d$_2$) δ 7.99 (d, J=8.9 Hz, 1H), 7.63-7.55 (m, 1H), 7.53 (d, J=4.3 Hz, 1H), 7.34 (d, J=7.3 Hz, 1H), 7.23 (q, J=7.3 Hz, 1H), 7.13 (t, J=8.7 Hz, 1H), 6.97 (d, J=5.9 Hz, 1H), 6.66 (d, J=8.4 Hz, 1H), 4.74 (d, J=47.8 Hz, 2H), 1.92 (s, 3H). 19F NMR (376 MHz, Methylene Chloride-d2) δ −58.93 (s, 3F), −117.28 (d, J=74.2 Hz, 1F).

Example 8: 6-amino-N-(5-chloro-6-(2,6-dimethylphenyl)-4-(trifluoromethyl)pyridin-2-yl)pyridine-2-sulfonamide Condition 2, LCMS: m/z 457.1 [M+H]$^+$, 3.32 min. $^1$H NMR (500 MHz, Methanol-d$_4$) δ 7.65 (s, 1H), 7.50 (dd, J=8.4, 7.3 Hz, 2H), 7.29-7.13 (m, 1H), 7.11-7.03 (m, 1H), 6.69 (dd, J=8.4, 0.6 Hz, 2H), 1.85 (s, 6H).

Example 9: 6-amino-N-(6-(2,6-dimethylphenyl)-5-fluoropyridin-2-yl)pyridine-2-sulfonamide Condition 2, LCMS: m/z 373.1 [M+H]$^+$, 2.89 min. $^1$H NMR (400 MHz, Methanol-d$_4$) δ 7.58 (d, J=8.6 Hz, 1H), 7.48 (dd, J=8.4, 7.3 Hz, 1H), 7.37 (dd, J=8.9, 3.2 Hz, 1H), 7.22-7.11 (m, 2H), 7.06 (d, J=7.6 Hz, 2H), 6.65 (d, J=8.4 Hz, 1H), 1.91 (s, 6H).

Example 10: 6-amino-N-(4-chloro-6-(2,6-dimethylphenyl)pyridin-2-yl)pyridine-2-sulfonamide Condition 2, LCMS: m/z 389.1 [M+H]$^+$, 3.02 min. $^1$H NMR (400 MHz, Methanol-d$_4$) δ 7.54 (t, J=7.9 Hz, 1H), 7.37 (s, 1H), 7.20 (dd, J=13.1, 7.4 Hz, 2H), 7.11 (d, J=7.7 Hz, 2H), 6.92 (d, J=1.9 Hz, 1H), 6.66 (d, J=8.4 Hz, 1H), 2.04 (d, J=18.7 Hz, 6H).

Example 11: 6-amino-N-(5-chloro-6-(2,6-dimethylphenyl)pyridin-2-yl)pyridine-2-sulfonamide Condition 2, LCMS: m/z 389.1 [M+H]$^+$. 3.01 min. $^1$H NMR (400 MHz, DMSO-d$_6$) δ 11.12 (s, 1H), 7.92 (d, J=8.8 Hz, 1H), 7.47 (dd, J=8.3, 7.4 Hz, 1H), 7.20 (m, 2H), 7.07 (d, J=7.6 Hz, 2H), 6.97 (dd, J=7.3, 0.6 Hz, 1H), 6.59 (dd, J=8.4, 0.7 Hz, 1H), 6.43 (s, 2H), 1.77 (s, 6H).

Example 12: 6-amino-N-(5-chloro-6-(3-fluoro-2-methylphenyl)pyridin-2-yl)pyridine-2-sulfonamide Condition 2, LCMS: m/z 393.1 [M+H]$^+$, 3.02 min. $^1$H NMR (400 MHz, DMSO-d$_6$) δ 11.22 (s, 1H), 7.93 (d, J=8.8 Hz, 1H), 7.52 (dd, J=7.4, 8.3 Hz, 1H), 7.33-7.18 (m, 3H), 7.02 (dd, J=0.6, 7.3 Hz, 1H), 6.92 (dd, J=1.1, 7.4 Hz, 1H), 6.65-6.60 (m, 1H), 6.46 (s, 2H), 1.81 (d, J=2.1 Hz, 3H).

Example 13: 6-amino-N-(5-chloro-6-(2-chloro-6-methylphenyl)pyridin-2-yl)pyridine-2-sulfonamide Condition 2, LCMS: m/z 409.0 [M+H]$^+$, 3.26 min. $^1$H NMR (400 MHz, Methanol-d$_4$) δ 7.82 (d, J=8.7 Hz, 1H), 7.49 (t, J=7.8 Hz, 1H), 7.36 (d, J=8.8 Hz, 1H), 7.28 (d, J=4.4 Hz, 2H), 7.20 (t, J=4.5 Hz, 1H), 7.15 (d, J=7.3 Hz, 1H), 6.66 (d, J=8.4 Hz, 1H), 1.90 (s, 3H).

Example 15: 6-amino-N-(6-(o-tolyl)-5-(trifluoromethyl)pyridin-2-yl)pyridine-2-sulfonamide Condition 2, LCMS: m/z 409.1 [M+H]$^+$, 2.98 min. $^1$H NMR (400 MHz, Methanol-d$_4$) δ 8.05 (d, J=8.8 Hz, 1H), 7.49 (dd, J=8.4, 7.3 Hz, 1H), 7.42 (d, J=8.9 Hz, 1H), 7.32 (d, J=7.5 Hz, 1H), 7.27-7.19 (m, 2H), 7.17 (d, J=7.6 Hz, 1H), 7.08 (d, J=7.6 Hz, 1H), 6.66 (d, J=8.4 Hz, 1H), 1.94 (s, 3H).

Example 16: 6-amino-N-(5-chloro-6-(5-chloro-2-cyclopropylphenyl)pyridin-2-yl)pyridine-2-sulfonamide Condition 2, LCMS: m/z 409.1 [M+H]$^+$, 2.98 min. $^1$H NMR (400 MHz, DMSO-d$_6$) 11.20 (s, 1H), 7.92 (d, J=8.7 Hz, 1H), 7.51 (dd, J=8.3, 7.4 Hz, 1H), 7.36 (dd, J=8.4, 2.3 Hz, 1H), 7.23 (d, J=8.8 Hz, 1H), 7.05-7.01 (m, 2H), 6.98 (d, J=8.5 Hz, 1H), 6.62 (d, J=8.3 Hz, 1H), 6.45 (s, 2H), 1.41-1.33 (m, 1H), 0.70-0.62 (m, 2H), 0.51 (brs, 2H).

Example 17: 6-amino-N-(6-(2-chlorophenyl)-5-(trifluoromethyl)pyridin-2-yl)pyridine-2-sulfonamide Condition 2, LCMS: m/z 429.1 [M+H]$^+$, 2.96 min. $^1$H NMR (400 MHz, Methylene Chloride-d$_2$) δ 7.99 (d, J=8.9 Hz, 1H), 7.58 (dt, J=6.8, 8.2 Hz, 2H), 7.47 (dd, J=1.2, 8.0 Hz, 1H), 7.43 (dt, J=1.9, 6.8 Hz, 1H), 7.39 (dd, J=1.6, 12.2 Hz, 1H), 7.34 (dd, J=1.7, 7.3 Hz, 2H), 7.27 (d, J=7.3 Hz, 1H), 4.85 (s, 2H).

Example 18: 6-amino-N-(5-(trifluoromethyl)-6-(2-(trifluoromethyl)phenyl)pyridin-2-yl)pyridine-2-sulfonamide Condition 2, LCMS: m/z 463.1 [M+H]$^+$, 3.00 min. $^1$H NMR (400 MHz, Methylene Chloride-d$_2$) δ 7.98 (d, J=8.8 Hz, 1H), 7.74 (dq, J=3.1, 3.7, 6.4 Hz, 1H), 7.66-7.52 (m, 4H), 7.31 (dd, J=6.3, 12.1 Hz, 2H), 6.73-6.60 (m, 1H), 4.80 (s, 2H); $^{19}$F NMR (376 MHz, Methylene Chloride-d$_2$) δ −58.42 (s, 3F).

Example 19: 6-amino-N-(5-chloro-6-(2-cyclopropylphenyl)pyridin-2-yl)pyridine-2-sulfonamide Condition 2, LCMS: m/z 401.1 [M+H]$^+$, 3.04 min. $^1$H NMR (400 MHz, DMSO-d$_6$) δ 11.14 (s, 1H), 7.90 (d, J=8.8 Hz, 1H), 7.51 (dd, J=8.3, 7.4 Hz, 1H), 7.35-7.28 (m, 1H), 7.24 (d, J=8.8 Hz, 1H), 7.22-7.15 (m, 1H), 7.05-6.98 (m, 2H), 6.97 (d, J=7.7 Hz, 1H), 6.64-6.58 (m, 1H), 6.45 (s, 2H), 1.46-1.36 (m, 1H), 0.68-0.58 (m, 2H), 0.49 (s, 2H).

Example 20: 6-amino-N-(5-chloro-6-(2-(methyl-d3)phenyl)pyridin-2-yl)pyridine-2-sulfonamide Condition 2, LCMS: m/z 378.1 [M+H]$^+$, 2.94 min. $^1$H NMR (400 MHz, DMSO-d$_6$) δ 11.16 (s, 1H), 7.89 (d, J=8.8 Hz, 1H), 7.51 (dd, J=8.3, 7.4 Hz, 1H), 7.31 (td, J=7.4, 1.4 Hz, 1H), 7.23 (m, 3H), 7.03 (m, 2H), 6.62 (d, J=8.1 Hz, 1H), 6.45 (s, 2H).

Example 21: 6-amino-N-(5-chloro-6-(2-cyclopropyl-5-fluorophenyl)pyridin-2-yl)pyridine-2-sulfonamide Condition 2, LCMS: m/z 419.1 [M+H]$^+$, 3.13 min. $^1$H NMR (400 MHz, DMSO-d$_6$) δ d$_6$) 11.19 (s, 1H), 7.92 (d, J=8.8 Hz, 1H), 7.50 (dd, J=7.3, 8.4 Hz, 1H), 7.25 (d, J=8.8 Hz, 1H), 7.15 (td, J=2.8, 8.7 Hz, 1H), 7.05-6.98 (m, 2H), 6.88 (dd, J=2.8, 9.3 Hz, 1H), 6.61 (dd, J=0.6, 8.4 Hz, 1H), 6.45 (s, 2H), 1.37 (ddd, J=5.5, 8.5, 13.7 Hz, 1H), 0.59 (d, J=8.4 Hz, 2H), 0.45 (s, 2H).

Example 22: 6-amino-N-(5-chloro-6-(o-tolyl)-4-(trifluoromethyl)pyridin-2-yl)pyridine-2-sulfonamide Condition 2, LCMS: m/z 443.1 [M+H]$^+$, 3.26 min. $^1$H NMR (500 MHz, Chloroform-d) δ 7.86 (s, 1H), 7.51 (dd, J=8.3, 7.4 Hz, 1H), 7.29 (dd, J=11.3, 7.5 Hz, 2H), 7.22-7.16 (m, 3H), 7.09 (d, J=7.3 Hz, 1H), 6.57 (d, J=8.3 Hz, 1H), 4.5 (s, 2H) 2.02 (s, 3H).

Example 23: 6-amino-N-(5-bromo-6-(o-tolyl)pyridin-2-yl)pyridine-2-sulfonamide Condition 2, LCMS: m/z 419.1 [M+H]$^+$, 2.95 min. $^1$H NMR (500 MHz, DMSO-d$_6$) δ 11.21 (s, 1H), 7.84 (d, J=8.8 Hz, 1H), 7.44-7.37 (m, 1H), 7.25-7.11 (m, 3H), 7.01 (d, J=8.8 Hz, 1H), 6.97-6.90 (m, 2H), 6.51 (d, J=8.4 Hz, 1H), 6.28 (s, 2H), 1.84 (s, 3H).

Example 24: 6-amino-N-(5-chloro-6-(2-chlorophenyl)pyridin-2-yl)pyridine-2-sulfonamide Condition 2, LCMS: m/z 395.0 [M+H]$^+$, 2.92 min. $^1$H NMR (400 MHz, DMSO-d$_6$) δ 11.25 (s, 1H), 7.92 (d, J=8.8 Hz, 1H), 7.57-7.52 (m, 2H), 7.50-7.45 (m, 1H), 7.44-7.39 (m, 1H), 7.30 (d, J=8.8 Hz, 1H), 7.21 (dd, J=1.7, 7.5 Hz, 1H), 7.05 (d, J=0.6, 7.3 Hz, 1H), 6.64 (dd, J=0.7, 8.4 Hz, 1H), 6.48 (s, 2H).

Example 25: 2-amino-N-(6-(2,6-dimethylphenyl)-5-(trifluoromethyl)pyridin-2-yl)pyridine-4-sulfonamide Condition 2, LCMS: m/z 423.1 [M+H]$^+$, 2.90 min. $^1$H NMR (400 MHz, Methanol-d$_4$) δ 8.09 (d, J=8.8 Hz, 1H), 7.94 (d, J=5.5 Hz, 1H), 7.23 (s, 2H), 7.08 (d, J=7.6 Hz, 2H), 7.00-6.77 (m, 2H), 3.67 (s, 2H), 1.82 (s, 6H).

Example 26: 2-amino-N-(5-chloro-6-(2-(methyl-d3)phenyl)pyridin-2-yl)pyridine-4-sulfonamide Condition 2, LCMS: m/z 378.1 [M+H]$^+$, 2.67 min. $^1$H NMR (400 MHz, DMSO-d$_6$) δ 11.45 (s, 1H), 8.02 (m, 1H), 7.97 (d, J=8.7 Hz, 1H), 7.32 (m, 1H), 7.25 (m, 2H), 7.13 (d, J=8.8 Hz, 1H), 7.07 (dd, J=7.5, 1.1 Hz, 1H), 6.79 (dd, J=1.6, 0.6 Hz, 1H), 6.72 (dd, J=5.3, 1.6 Hz, 1H), 6.50 (s, 2H).

Example 27: 6-amino-N-(5-chloro-6-(2-cyclopropyl-4-fluorophenyl)pyridin-2-yl)pyridine-2-sulfonamide Condition 2, LCMS: m/z 419.1 [M+H]+, 3.13 min. $^1$H NMR (400 MHz, DMSO-d$_6$) δ 11.17 (s, 1H), 7.91 (d, J=8.8 Hz, 1H), 7.52 (dd, J=8.3, 7.4 Hz, 1H), 7.25 (d, J=8.8 Hz, 1H), 7.08-6.97 (m, 3H), 6.77 (dd, J=10.8, 2.3 Hz, 1H), 6.61 (d, J=8.3 Hz, 1H), 6.45 (s, 2H), 1.40 (ddd, J=13.0, 8.0, 5.6 Hz, 1H), 0.71-0.65 (m, 2H), 0.57 (brs, 2H).

Example 28: 6-amino-N-(6-(2-cyclopropyl-4-fluorophenyl)-5-(trifluoromethyl)pyridin-2-yl)pyridine-2-sulfonamide Condition 2, LCMS: m/z 435.1 [M+H]+, 3.13 min. $^1$H NMR (400 MHz, DMSO-d$_6$) δ 11.45 (s, 1H), 8.02 (m, 1H), 7.97 (d, J=8.7 Hz, 1H), 7.32 (m, 1H), 7.25 (m, 2H), 7.13 (d, J=8.8 Hz, 1H), 7.07 (dd, J=7.5, 1.1 Hz, 1H), 6.79 (dd, J=1.6, 0.6 Hz, 1H), 6.72 (dd, J=5.3, 1.6 Hz, 1H), 6.50 (s, 2H).

Example 29: 6-amino-N-(5-chloro-6-(2-ethylphenyl)pyridin-2-yl)pyridine-2-sulfonamide Condition 2, LCMS: m/z 389.1 [M+H]+, 3.03 min+. $^1$H NMR (400 MHz, DMSO-d$_6$) δ 11.15 (s, 1H), 7.90 (d, J=8.8 Hz, 1H), 7.50 (dd, J=8.3, 7.4 Hz, 1H), 7.38-7.32 (m, 1H), 7.31-7.26 (m, 1H), 7.26-7.19 (m, 2H), 7.05 (dd, J=7.6, 1.1 Hz, 1H), 7.01 (dd, J=7.3, 0.6 Hz, 1H), 6.62 (dd, J=8.4, 0.6 Hz, 1H), 6.46 (s, 2H), 2.21 (brs, 2H), 0.86 (t, J=7.6 Hz, 3H).

Example 30: 6-amino-N-(5-chloro-6-(4-fluoro-2,6-dimethylphenyl)pyridin-2-yl)pyridine-2-sulfonamide Condition 2, LCMS: m/z 407.2 [M+H]+, 3.09 min. $^1$H NMR (500 MHz, Acetonitrile-d$_3$) δ 8.39 (s, 1H), 7.81 (d, J=8.8 Hz, 1H), 7.52 (dd, J=7.4, 8.4 Hz, 1H), 7.36 (d, J=8.8 Hz, 1H), 7.15 (d, J=7.3 Hz, 1H), 6.87 (d, J=9.8 Hz, 2H), 6.66 (d, J=8.4 Hz, 1H), 5.20 (s, 2H), 1.85 (s, 6H).

Example 31: 6-amino-N-(5-chloro-6-(2-fluoro-6-methylphenyl)pyridin-2-yl)pyridine-2-sulfonamide LCMS: m/z 393.1

Example 32: 6-amino-N-(5-chloro-6-mesitylpyridin-2-yl)pyridine-2-sulfonamide Condition 2, LCMS: m/z 403.1 [M+H]+, 3.13 min. $^1$H NMR (400 MHz, Methanol-d$_4$) δ 7.81 (d, J=8.8 Hz, 1H), 7.52-7.43 (m, 1H), 7.32 (d, J=8.8 Hz, 1H), 7.15 (d, J=7.3 Hz, 1H), 6.89 (s, 2H), 6.65 (d, J=8.4 Hz, 1H), 3.74 (d, J=5.8 Hz, 0H), 3.67 (d, J=5.5 Hz, 1H), 3.59 (d, J=5.2 Hz, 0H), 2.30 (s, 3H), 1.84 (s, 6H).

Example 33: 6-amino-N-(5-chloro-6-(o-tolyl)pyridin-2-yl)-3-fluoropyridine-2-sulfonamide Condition 2, LCMS: m/z 393.1 [M+H]+, 2.90 min. $^1$H NMR (400 MHz, DMSO-d$_6$) δ 11.45 (s, 1H), 7.92 (d, J=8.8 Hz, 1H), 7.47 (t, J=9.3 Hz, 1H), 7.31 (td, J=7.5, 1.3 Hz, 1H), 7.22 (m, 2H), 7.10 (d, J=8.7 Hz, 1H), 7.01 (d, J=7.4 Hz, 1H), 6.67 (dd, J=9.0, 2.8 Hz, 1H), 6.32 (s, 2H), 1.90 (s, 3H). $^{19}$F NMR (376 MHz, DMSO-d$_6$) δ −135.96 (s).

Example 34: 6-amino-N-(5-chloro-6-(2-methyl-3-(trifluoromethyl)phenyl)pyridin-2-yl)pyridine-2-sulfonamide Condition 2, LCMS: m/z 443.1 [M+H]+, 3.16 min. $^1$H NMR (400 MHz, Methylene Chloride-d$_2$) δ 7.76 (d, J=8.8 Hz, 1H), 7.71 (d, J=7.2 Hz, 1H), 7.57 (dd, J=7.4, 8.3 Hz, 1H), 7.47 (d, J=8.8 Hz, 1H), 7.42-7.28 (m, 3H), 6.66 (d, J=8.4 Hz, 1H), 4.78 (s, 2H), 2.22-2.04 (m, 3H); $^{19}$F NMR (376 MHz, Methylene Chloride-d$_2$) δ −61.26 (s, 3F).

Example 35: 6-amino-N-(5-fluoro-6-(2-isopropylphenyl)pyridin-2-yl)pyridine-2-sulfonamide Condition 2, LCMS: m/z 387.1 [M+H]+, 3.03 min. $^1$H NMR (400 MHz, Methanol-d$_4$) δ 7.61-7.47 (m, 2H), 7.41-7.34 (m, 3H), 7.24-7.14 (m, 2H), 7.08 (d, J=7.6 Hz, 1H), 6.66 (dd, J=8.5, 0.7 Hz, 1H), 3.67 (d, J=5.6 Hz, 3H), 1.08 (d, J=6.8 Hz, 7H).

Example 36: 6-amino-5-methyl-N-(6-(o-tolyl)-5-(trifluoromethyl)pyridin-2-yl)pyridine-2-sulfonamide Condition 2, LCMS: m/z 423.2 [M+H]+, 3.12 min. $^1$H NMR (400 MHz, DMSO-d$_6$) δ 11.47 (s, 1H), 8.08 (d, J=8.9 Hz, 1H), 7.37-7.24 (m, 3H), 7.23-7.12 (m, 2H), 7.01 (d, J=7.4 Hz, 1H), 6.96 (d, J=7.4 Hz, 1H), 6.23 (s, 2H), 2.02 (s, 3H), 1.74 (s, 3H).

Example 37: 6-amino-N-(5-chloro-6-(4-fluoro-2-methylphenyl)pyridin-2-yl)pyridine-2-sulfonamide Condition 2, LCMS: m/z 393.1 [M+H]+, 3.00 min. $^1$H NMR (400 MHz, Methanol-d$_4$) δ 7.79 (dd, J=8.8, 1.3 Hz, 1H), 7.50 (dd, J=8.5, 7.3 Hz, 1H), 7.30 (dd, J=8.8, 1.3 Hz, 1H), 7.17 (dd, J=7.3, 1.4 Hz, 1H), 7.10 (dd, J=8.3, 6.1 Hz, 1H), 7.03-6.89 (m, 2H), 6.67 (dd, J=8.5, 1.4 Hz, 1H), 3.79-3.71 (m, 1H), 3.71-3.63 (m, 2H), 3.59 (dd, J=5.2, 1.3 Hz, 1H), 2.02 (s, 3H).

Example 38: 6-amino-N-(5-chloro-6-(6-chloro-2-fluoro-3-methylphenyl)pyridin-2-yl)pyridine-2-sulfonamide Condition 2, LCMS: m/z 427.0 [M+H]+, 3.01 min. $^1$H NMR (400 MHz, Methanol-d$_4$) δ 7.83 (d, J=8.8 Hz, 1H), 7.53 (dd, J=8.5, 7.3 Hz, 1H), 7.38 (d, J=8.8 Hz, 1H), 7.31 (s, 1H), 7.23-7.11 (m, 2H), 6.70 (d, J=8.5 Hz, 1H), 2.27 (d, J=2.2 Hz, 4H).

Example 39: 6-amino-N-(5-chloro-6-(2-chloro-6-fluorophenyl)pyridin-2-yl)pyridine-2-sulfonamide Condition 2, LCMS: m/z 413.0 [M+H]+, 2.88 min. $^1$H NMR (400 MHz, Methanol-d$_4$) δ 7.83 (d, J=8.8 Hz, 1H), 7.51 (dd, J=8.4, 7.3 Hz, 1H), 7.46-7.37 (m, 2H), 7.32 (d, J=8.1 Hz, 1H), 7.21-7.12 (m, 2H), 6.67 (d, J=8.4 Hz, 1H).

Example 40: 6-amino-N-(5-chloro-6-(o-tolyl)pyridin-2-yl)pyridine-3-sulfonamide Condition 2, LCMS: m/z 375.1 [M+H]+, 2.82 min. $^1$H NMR (400 MHz, DMSO-d$_6$) δ 11.02 (s, 1H), 8.28 (m, 1H), 7.91 (d, J=8.7 Hz, 1H), 7.64 (dd, J=8.9, 2.6 Hz, 1H), 7.34

(td, J=7.4, 1.4 Hz, 1H), 7.27 (m, 2H), 7.10 (dd, J=7.5, 1.1 Hz, 1H), 7.05 (d, J=8.7 Hz, 1H), 6.95 (s, 2H), 6.37 (dd, J=8.9, 0.5 Hz, 1H), 1.95 (s, 3H).

Example 41: 6-amino-N-(6-(2-chloro-4-fluorophenyl)-5-(trifluoromethyl)pyridin-2-yl)pyridine-2-sulfonamide Condition 2, LCMS: m/z 447.2 [M+H]$^+$, 3.06 min. $^1$H NMR (400 MHz, Methylene Chloride-d$_2$) δ 8.00 (d, J=8.8 Hz, 1H), 7.66-7.56 (m, 2H), 7.35 (d, J=7.4 Hz, 1H), 7.30-7.20 (m, 2H), 7.08 (td, J=2.5, 8.4 Hz, 1H), 6.67 (d, J=8.4 Hz, 1H), 4.81 (s, 2H); $^{19}$F NMR (376 MHz, Methylene Chloride-d$_2$) δ −59.27 (s, 3F), −110.80 (s, 1F).

Example 42: 2-amino-N-(6-(5-fluoro-2-methylphenyl)-5-(trifluoromethyl)pyridin-2-yl)pyridine-4-sulfonamide Condition 2, LCMS: m/z 427.1 [M+H]$^+$, 2.87 mi. $^1$H NMR (400 MHz, DMSO-d$_6$) δ 8.25 (d, J=8.9 Hz, 1H), 8.03 (d, J=6.3 Hz, 2H), 7.35-7.25 (m, 2H), 7.22 (td, J=8.6, 2.8 Hz, 2H). 7.09-6.95 (m, 1H), 6.92 (dd, J=6.3, 1.7 Hz, 1H), 1.78 (s, 3H).

Example 43: 6-amino-N-(5-chloro-6-(2-chloro-5-(trifluoromethyl)phenyl)pyridin-2-yl)pyridine-2-sulfonamide Condition 2, LCMS: m/z 463.0 [M+H]$^+$, 3.18 min. $^1$H NMR (400 MHz, Methylene Chloride-d$_2$) δ 7.77 (d, J=8.8 Hz, 1H), 7.66 (dd, J=1.7, 8.5 Hz, 1H), 7.62 (d, J=8.5 Hz, 1H), 7.60-7.54 (m, 1H), 7.51 (d, J=8.9 Hz, 2H), 7.32 (d, J=7.3 Hz, 1H), 6.68 (d, J=8.4 Hz, 1H), 4.88 (s, 2H); $^{19}$F NMR (376 MHz, Methylene Chloride-d$_2$) δ −62.83 (s, 3F).

Example 44: 6-amino-N-(5-chloro-6-(5-fluoro-2-methylphenyl)pyridin-2-yl)pyridine-3-sulfonamide Condition 2, LCMS: m/z 393.1 [M+H]$^+$, 2.89 min. $^1$H NMR (400 MHz, DMSO-d$_6$) δ 11.07 (s, 1H), 8.27 (d, J=2.5 Hz, 1H), 7.90 (d, J=8.8 Hz, 1H), 7.64 (dd, J=8.9, 2.6 Hz, 1H), 7.33 (dd, J=8.5, 5.8 Hz, 1H), 7.19 (td, J=8.6, 2.8 Hz, 1H), 7.04 (d, J=8.8 Hz, 1H), 6.99 (dd, J=9.3, 2.8 Hz, 1H), 6.92 (s, 2H), 6.36 (m, 1H), 1.92 (s, 3H). $^{19}$F NMR (376 MHz, DMSO-d$_6$) δ −117.72 (s).

Example 45: 6-amino-N-(5-chloro-6-(2-isopropylphenyl)pyridin-2-yl)pyridine-3-sulfonamide Condition 2, LCMS: m/z 403.2 [M+H]$^+$, 3.04 min. $^1$H NMR (400 MHz, DMSO-d$_6$) δ 10.99 (s, 1H), 8.26 (d, J=2.4 Hz, 1H), 7.93 (d, J=8.7 Hz, 1H), 7.62 (dd, J=8.9, 2.6 Hz, 1H), 7.41 (d, J=3.7 Hz, 2H), 7.28-7.21 (m, 1H), 7.13 (d, J=8.8 Hz, 1H), 7.04 (d, J=7.5 Hz, 1H), 6.94 (s, 2H), 6.36 (d, J=8.9 Hz, 1H), 2.49-2.46 (m, 1H), 1.11-0.92 (m, 6H).

Example 46: 2-amino-N-(5-chloro-6-(5-fluoro-2-methylphenyl)pyridin-2-yl)pyridine-4-sulfonamide Condition 2, LCMS: m/z 393.1 [M+H]$^+$, 2.80 min. $^1$H NMR (400 MHz, DMSO-d$_6$) δ 11.48 (s, 1H), 8.02 (dd, J=5.3, 0.5 Hz, 1H), 7.99 (d, J=8.8 Hz, 1H), 7.31 (dd, J=8.5, 5.8 Hz, 1H), 7.17 (m, 2H), 6.97 (dd, J=9.3, 2.8 Hz, 1H), 6.79 (dd, J=1.6, 0.6 Hz, 1H), 6.72 (dd, J=5.3, 1.6 Hz, 1H), 6.51 (s, 2H), 1.84 (s, 3H).

Example 47: 6-amino-N-(5-chloro-6-(2,6-dimethylphenyl)pyridin-2-yl)pyridine-3-sulfonamide Condition 2, LCMS: m/z 389.1 [M+H]$^+$, 2.92 min. $^1$H NMR (400 MHz, DMSO-d$_6$) δ 10.98 (s, 1H), 8.23 (m, 1H), 7.94 (d, J=8.7 Hz, 1H), 7.60 (dd, J=8.9, 2.6 Hz, 1H), 7.21 (m, 1H), 7.09 (m, 3H), 6.93 (s, 2H), 6.34 (dd, J=8.9, 0.5 Hz, 1H), 1.78 (s, 6H).

Example 48: 6-amino-N-(5-chloro-6-(2-(1,1-difluoroethyl)phenyl)pyridin-2-yl)pyridine-2-sulfonamide Condition 2, LCMS: m/z 425.1 [M+H]$^+$, 2.93 min. $^1$H NMR (400 MHz, DMSO-d$_6$) δ 11.15 (s, 1H), 7.88 (d, J=8.8 Hz, 1H), 7.51 (m, 4H), 7.25 (d, J=8.8 Hz, 1H), 7.16 (m, 1H), 6.99 (dd, J=7.3, 0.6 Hz, 1H), 6.60 (m, 1H), 6.46 (s, 2H), 1.78 (t, J=19.1 Hz, 3H). $^{19}$F NMR (376 MHz, DMSO-d$_6$) δ −82.35 (d, J=240.6 Hz), −85.68 (d, J=240.8 Hz).

Example 49: 2-amino-N-(5-chloro-6-(2-methyl-5-(trifluoromethyl)phenyl)pyridin-2-yl)pyridine-4-sulfonamide Condition 2, LCMS: m/z 443.1 [M+H]$^+$, 3.07 min. $^1$H NMR (400 MHz, Methylene Chloride-d$_2$) δ 8.17 (s, 1H), 7.79 (d, J=8.8 Hz, 1H), 7.64-7.56 (m, 1H), 7.43-7.39 (m, 2H), 7.36 (d, J=8.8 Hz, 1H), 6.94-6.85 (m, 2H), 5.12 (s, 2H), 2.10 (s, 3H).

Example 50: 6-amino-N-(5-chloro-6-(2-isopropylphenyl)pyridin-2-yl)pyridine-2-sulfonamide Condition 2, LCMS: m/z 403.1 [M+H]$^+$, 3.15 min. $^1$H NMR (400 MHz, DMSO-d$_6$) δ 11.15 (s, 1H), 7.90 (d, J=8.8 Hz, 1H), 7.50 (dd, J=8.4, 7.3 Hz, 1H), 7.39 (dd, J=4.8, 1.3 Hz, 2H), 7.26 (d, J=8.8 Hz, 1H), 7.22 (ddd, J=7.7, 5.1, 3.5 Hz, 1H), 7.02-6.98 (m, 2H), 6.61 (dd, J=8.4, 0.6 Hz, 1H), 6.47 (s, 2H), 1.04 (s, 3H), 0.96 (s, 3H).

Example 51: 6-amino-N-(5-chloro-6-(2-methyl-5-(trifluoromethyl)phenyl)pyridin-2-yl)pyridine-2-sulfonamide Condition 2, LCMS: m/z 443.1 [M+H]$^+$, 3.17 min. $^1$H NMR (400 MHz, Methanol-d$_4$) δ 7.83 (d, J=8.8 Hz, 1H), 7.60 (dd, J=2.0, 8.2 Hz, 1H), 7.52-7.43 (m, 2H), 7.36-7.34 (m, 1H), 7.32 (d, J=8.8 Hz, 1H), 7.16 (d, J=7.3 Hz, 1H), 6.69-6.64 (m, 1H), 2.10 (s, 3H).

Example 52: 6-amino-N-(5-chloro-6-(2-chloro-6-(trifluoromethyl)phenyl)pyridin-2-yl)pyridine-2-sulfonamide Condition 2, LCMS: m/z 462.9 [M+H]$^+$, 3.00 min. $^1$H NMR (400 MHz, Methanol-d$_4$) δ 7.82 (d, J=8.8 Hz, 1H), 7.75 (t, J=7.3 Hz, 2H), 7.63 (d, J=8.0 Hz, 1H), 7.51-7.40 (m, 2H), 7.13 (d, J=7.3 Hz, 1H), 6.66 (d, J=8.4 Hz, 1H).

Example 53: 6-amino-N-(5-chloro-6-(2-methyl-6-(trifluoromethyl)phenyl)pyridin-2-yl)pyridine-2-sulfonamide Condition 2, LCMS: m/z 443.1 [M+H]$^+$, 3.03 min. $^1$H NMR (400 MHz, DMSO-d$_6$) δ 11.17 (s, 1H), 7.93 (d, J=8.8 Hz, 1H), 7.60 (m, 3H), 7.43 (dd, J=7.4, 8.3 Hz, 1H), 7.27 (d, J=8.8 Hz, 1H), 6.94 (dd, J=0.7, 7.3 Hz, 1H), 6.59 (dd, J=0.6, 8.4 Hz, 1H), 6.43 (s, 2H), 1.79 (s, 3H). $^{19}$F NMR (376 MHz, DMSO-d$_6$) δ −57.96 (s).

Example 54: 6-amino-N-(5-chloro-6-(2-cyclopropylphenyl)pyridin-2-yl)pyridine-3-sulfonamide Condition 2, LCMS: m/z 401.1 [M+H]$^+$, 2.97 min. $^1$H NMR (400 MHz, DMSO-d$_6$) δ 10.99 (s, 1H), 8.28 (d, J=2.3 Hz, 1H), 7.92 (d, J=8.7 Hz, 1H), 7.65 (dd, J=8.9, 2.6 Hz, 1H), 7.37-7.30 (m, 1H), 7.26-7.19 (m, 1H), 7.11 (d, J=8.7 Hz, 1H), 7.08 (dd, J=7.6, 1.3 Hz, 1H), 7.00 (d, J=7.7 Hz, 1H), 6.95 (s, 2H), 6.36 (d, J=9.0 Hz, 1H), 1.50-1.37 (m, 1H), 0.70-0.57 (m, 2H), 0.51 (brs, 2H).

Example 55: 6-amino-N-(5-chloro-6-(2-(trifluoromethyl)phenyl)pyridin-2-yl)pyridine-2-sulfonamide Condition 2, LCMS: m/z 429.1 [M+H]$^+$, 2.96 min. $^1$H NMR (400 MHz, DMSO-d$_6$) δ 11.20 (s, 1H), 7.92 (d, J=8.8 Hz, 1H), 7.83 (d, J=7.5 Hz, 1H), 7.75 (t, J=7.2 Hz, 1H), 7.68 (t, J=7.5 Hz, 1H), 7.49 (dd, J=7.4, 8.3 Hz, 1H), 7.35-7.32 (m, 2H), 7.02-6.98 (m, 1H), 6.62 (d, J=8.4 Hz, 1H), 6.47 (s, 2H).

Example 56: 6-amino-N-(5-chloro-6-(2-chloro-4-fluorophenyl)pyridin-2-yl)pyridine-2-sulfonamide Condition 2, LCMS: m/z 413.2 [M+H]$^+$, 3.02 min. $^1$H NMR (500 MHz, DMSO-d$_6$) δ 11.24 (s, 1H), 7.92 (d, J=8.8 Hz, 1H), 7.56 (dd, J=3.2, 5.7 Hz, 1H), 7.53 (d, J=8.4 Hz, 1H), 7.36-7.24 (m, 3H), 7.05 (d, J=7.3 Hz, 1H), 6.64 (d, J=8.4 Hz, 1H), 6.45 (s, 2H); $^{19}$F NMR (471 MHz, DMSO-d$_6$) δ −110.57 (s, 1F).

Example 57: 2-amino-N-(5-chloro-6-(o-tolyl)pyridin-2-yl)pyridine-4-sulfonamide Condition 2, LCMS: m/z 374.9 [M+H]$^+$, 2.69 min. $^1$H NMR (400 MHz, Methylene Chloride-d$_2$) δ 8.12 (d, J=5.4 Hz, 1H), 7.78 (d, J=8.8 Hz, 1H), 7.35 (td, J=1.5, 7.5 Hz, 1H), 7.31-7.19 (m, 3H), 7.14 (dd, J=1.4, 7.6 Hz, 1H), 6.93 (dd, J=1.6, 5.4 Hz, 1H), 6.91-6.89 (m, 1H), 2.04 (s, 3H).

Example 58: 6-amino-N-(5-chloro-6-(2-chloro-6-fluoro-3-methylphenyl)pyridin-2-yl)pyridine-2-sulfonamide Condition 2, LCMS: m/z 427.0 [M+H]$^+$, 3.00 min. $^1$H NMR (400 MHz, Methanol-d$_4$) δ 7.84 (d, J=8.9 Hz, 1H), 7.57 (dd, J=8.5, 7.3 Hz, 1H), 7.36 (d, J=8.8 Hz, 1H), 7.20 (d, J=7.2 Hz, 1H), 7.07 (s, 1H), 6.74 (d, J=8.4 Hz, 1H), 2.37 (s, 3H).

Example 59: 6-amino-N-(5-chloro-6-(2-(trifluoromethoxy)phenyl)pyridin-2-yl)pyridine-2-sulfonamide Condition 2, LCMS: m/z 445.0 [M+H]$^+$, 3.02 min. $^1$H NMR (400 MHz, DMSO-d$_6$) δ 11.25 (s, 1H), 7.92 (d, J=8.8 Hz, 1H), 7.63-7.57 (m, 1H), 7.54-7.43 (m, 3H), 7.29-7.24 (m, 2H), 7.04 (dd, J=7.3, 0.6 Hz, 1H), 6.65-6.61 (m, 1H), 6.47 (s, 2H).

Example 60: 6-amino-N-(5-chloro-6-(2-fluoro-6-methylphenyl)pyridin-2-yl)pyridine-3-sulfonamide Condition 2, LCMS: m/z 393.1 [M+H]$^+$, 2.79 min. $^1$H NMR (400 MHz, Methanol-d$_4$) δ 8.33 (d, J=2.5 Hz, 1H), 7.82 (d, J=8.7 Hz, 1H), 7.75 (dd, J=9.0, 2.5 Hz, 1H), 7.33 (d, J=5.8 Hz, 1H), 7.11 (dd, J=10.3, 8.2 Hz, 2H), 6.99 (s, 1H), 6.44 (d, J=8.9 Hz, 1H), 1.94 (s, 3H).

Example 61: 2-amino-N-(5-chloro-6-(2-(trifluoromethyl)phenyl)pyridin-2-yl)pyridine-4-sulfonamide Condition 2, LCMS: m/z 429.0 [M+H]$^+$, 2.72 min. $^1$H NMR (400 MHz, Methanol-d$_4$) δ 7.97 (d, J=4.7 Hz, 1H), 7.83 (d, J=8.8 Hz, 1H), 7.77 (d, J=7.4 Hz, 1H), 7.66 (dt, J=15.4, 7.5 Hz, 3H), 7.31-7.24 (m, 2H), 6.94 (s, 1H), 6.88 (dd, J=5.5, 1.6 Hz, 1H).

Example 62: 6-amino-N-(5-chloro-6-(5-fluoro-2-methoxyphenyl)pyridin-2-yl)pyridine-2-sulfonamide Condition 2, LCMS: m/z 409.1 [M+H]$^+$, 2.84 min. $^1$H NMR (400 MHz, DMSO-d$_6$) δ 11.21 (s, 1H), 7.84 (d, J=8.8 Hz, 1H), 7.55 (dd, J=8.3, 7.4 Hz, 1H), 7.30-7.22 (m, 1H), 7.20 (d, J=8.8 Hz, 1H), 7.10 (dd, J=9.2, 4.4 Hz, 1H), 7.07 (dd, J=7.3, 0.6 Hz, 1H), 6.75 (dd, J=8.6, 3.1 Hz, 1H), 6.69-6.62 (m, 1H), 6.49 (s, 2H), 3.70 (s, 3H).

Example 63: 6-amino-N-(6-(2,6-dimethylphenyl)-4-methylpyridin-2-yl)pyridine-2-sulfonamide Condition 2, LCMS: m/z 369.2 [M+H]$^+$, 2.64 min. $^1$H NMR (400 MHz, Methanol-d$_4$) δ 7.59 (dd, J=8.4, 7.3 Hz, 1H), 7.33 (dd, J=8.2, 7.0 Hz, 1H), 7.24-7.17 (m, 3H), 7.13 (s, 1H), 6.74 (d, J=1.5 Hz, 1H), 6.64 (d, J=8.4 Hz, 1H), 2.43 (s, 3H), 2.15 (s, 6H).

Example 64: 2-amino-N-(6-(5-cyano-2-methylphenyl)-5-(trifluoromethyl)pyridin-2-yl)pyridine-4-sulfonamide Condition 2, LCMS: m/z 434.1 [M+H]$^+$, 2.86 min. $^1$H NMR (400 MHz, Chloroform-d) δ 7.95 (m, 1H), 7.68 (m, 1H), 7.62 (m, 1H), 7.54-7.48 (m, 1H), 7.42 (m, 1H), 7.37 (m, 1H), 7.32 (m, 1H), 6.74 (m, 1H), 2.15 (s, 3H).

Example 65: 6-amino-N-(5-chloro-6-(2-(difluoromethyl)phenyl)pyridin-2-yl)pyridine-2-sulfonamide Condition 2, LCMS: m/z 411.0 [M+H]$^+$, 2.91 min. $^1$H NMR (400 MHz, Acetonitrile-d$_3$) δ 7.86 (d, J=8.8 Hz, 1H), 7.79-7.73 (m, 1H), 7.64-7.59 (m, 2H), 7.55 (dd, J=8.4, 7.3 Hz, 1H), 7.41 (d, J=8.8 Hz, 2H), 7.21 (dd, J=7.4, 0.7 Hz, 1H), 6.70-6.68 (m, 1H), 5.29 (s, 2H).

Example 66: 6-amino-N-(5-cyclopropyl-6-(o-tolyl)pyridin-2-yl)pyridine-2-sulfonamide Condition 2, LCMS: m/z 381.1 [M+H]$^+$, 2.73 min. $^1$H NMR (500 MHz, DMSO-d$_6$) δ 10.81 (s, 1H), 7.41 (dd, J=8.3, 7.3 Hz, 1H), 7.25-7.11 (m, 3H), 7.02 (dd, J=14.7, 8.0 Hz, 2H), 6.94 (dd, J=7.3, 0.7 Hz, 2H), 6.50 (dd, J=8.3, 0.6 Hz, 1H), 6.23 (s, 2H), 1.90 (s, 3H), 1.30 (ddd, J=13.6, 8.4, 5.2 Hz, 1H), 0.68-0.57 (m, 2H), 0.48 (dt, J=6.3, 3.1 Hz, 2H).

Example 67: 6-amino-N-(5-chloro-6-(3-cyano-2-methylphenyl)pyridin-2-yl)pyridine-2-sulfonamide Condition 2, LCMS: m/z 400.0 [M+H]$^+$, 2.80 min. $^1$H NMR (400 MHz, Methanol-d$_4$) δ 7.84 (m, 1H), 7.78-7.66 (m, 1H), 7.59-7.24 (m, 4H), 7.16 (m, 1H), 6.69 (m, 1H), 5.50 (s, 1H), 2.17 (s, 3H).

Example 68: 6-amino-N-(6-(2,6-dimethylphenyl) pyridin-2-yl)pyridine-2-sulfonamide Condition 2, LCMS: m/z 400.0 [M+H]⁺, 2.57 min. ¹H NMR (400 MHz, Methanol-d₄) δ 7.89 (t, J=8.0 Hz, 1H), 7.56 (t, J=7.9 Hz, 1H), 7.25 (dd, J=46.7, 8.0 Hz, 4H), 6.85 (d, J=7.2 Hz, 1H), 6.63 (d, J=8.4 Hz, 1H), 2.11 (s, 6H).

Example 69: 6-amino-N-(5-chloro-6-(2-fluorophenyl)pyridin-2-yl)pyridine-2-sulfonamide Condition 2, LCMS: m/z 379.0 [M+H]⁺, 2.83 min. ¹H NMR (400 MHz, Methanol-d₄) δ 7.78 (d, J=8.8 Hz, 1H), 7.54 (dd, J=8.4, 7.3 Hz, 1H), 7.49-7.41 (m, 1H), 7.31 (d, J=8.8 Hz, 1H), 7.26-7.19 (m, 3H), 7.18-7.11 (m, 1H), 6.71-6.64 (m, 1H), 3.67 (s, 3H).

Example 70: 6-amino-N-(5-fluoro-6-(o-tolyl)pyridin-2-yl)pyridine-2-sulfonamide Condition 2, LCMS: m/z 359.1 [M+H]⁺, 2.82 min. ¹H NMR (400 MHz, Methanol-d₄) δ 7.61-7.48 (m, 2H), 7.36-7.12 (m, 6H), 6.67 (dd, J=8.4, 0.8 Hz, 1H), 2.12 (s, 3H).

Example 71: 6-amino-N-(5-chloro-6-(4-fluoro-2-methylphenyl)pyridin-2-yl)pyridine-3-sulfonamide Condition 2, LCMS: m/z 393.0 [M+H]⁺, 2.92 min. ¹H NMR (400 MHz, Methanol-d₄) δ 8.33 (d, J=2.4 Hz, 1H), 7.84-7.66 (m, 2H), 7.11 (d, J=5.9 Hz, 1H), 7.06 (d, J=8.7 Hz, 1H), 7.03-6.92 (m, 2H), 6.44 (d, J=8.9 Hz, 1H), 2.02 (s, 3H).

Example 72: 6-amino-N-(6-(2,6-dimethylphenyl)-5-methoxypyridin-2-yl)pyridine-2-sulfonamide Hydrochloride Condition 2, LCMS: m/z 385.1 [M+H]⁺, 2.63 min. ¹H NMR (500 MHz, Methanol-d₄) δ 8.04 (d, J=9.3 Hz, 1H), 7.90 (dd, J=8.9, 7.2 Hz, 1H), 7.52 (d, J=9.2 Hz, 1H), 7.38-7.29 (m, 2H), 7.24-7.19 (m, 2H), 7.03 (dd, J=8.9, 0.9 Hz, 1H), 3.89 (s, 3H), 2.05 (s, 6H).

Example 73: 6-amino-N-(5-chloro-6-(3-(trifluoromethyl)phenyl)pyridin-2-yl)pyridine-2-sulfonamide Condition 2, LCMS: m/z 429.0 [M+H]⁺ 3.18 min. ¹H NMR (400 MHz, Methylene Chloride-d₂) δ 7.90 (m, 2H), 7.78-7.63 (m, 2H), 7.56 (m, 2H), 7.36 (m, 3H), 6.63 (m, 1H), 4.78 (m, 2H).

Example 74: 2-amino-N-(5-chloro-6-(2,6-dimethylphenyl)pyridin-2-yl)pyridine-3-sulfonamide Condition 2, LCMS: m/z 389.2 [M+H]⁺, 3.14 min. ¹H NMR (400 MHz, DMSO-d₆) δ 8.20 (dd, J=5.3, 1.8 Hz, 1H), 8.03 (d, J=7.4 Hz, 1H), 7.98 (d, J=8.8 Hz, 1H), 7.58-7.31 (m, 2H), 7.28-7.19 (m, 2H), 7.11 (d, J=7.4 Hz, 3H), 6.66 (dd, J=7.6, 5.4 Hz, 1H), 1.77 (s, 6H).

Example 75: 6-amino-N-(5-methyl-6-(o-tolyl)pyridin-2-yl)pyridine-2-sulfonamide Condition 2, LCMS: m/z 355.1 [M+H]⁺, 2.52 min. ¹H NMR (400 MHz, Methanol-d₄) δ 7.83-7.70 (m, 1H), 7.56 (dd, J=8.4, 7.3 Hz, 1H), 7.50-7.28 (m, 4H), 7.25 (d, J=8.9 Hz, 1H), 7.18 (d, J=7.2 Hz, 1H), 6.62 (d, J=8.4 Hz, 1H), 2.13 (d, J=27.4 Hz, 3H), 2.02 (s, 3H).

Example 76: 6-amino-N-(5-chloro-6-(2-methoxyphenyl)pyridin-2-yl)pyridine-2-sulfonamide Condition 2, LCMS: m/z 391.1 [M+H]⁺, 2.75 min. ¹H NMR (400 MHz, DMSO-d₆) δ 11.16 (s, 1H), 7.81 (d, J=8.8 Hz, 1H), 7.57 (dd, J=8.3, 7.4 Hz, 1H), 7.42 (ddd, J=8.4, 7.4, 1.9 Hz, 1H), 7.18 (d, J=8.7 Hz, 1H), 7.13-7.04 (m, 2H), 7.02-6.95 (m, 1H), 6.92 (d, J=6.8 Hz, 1H), 6.66 (d, J=8.0 Hz, 1H), 6.48 (s, 2H), 3.71 (s, 3H).

Example 77: 6-amino-N-(6-(2-chlorophenyl)-5-methylpyridin-2-yl)pyridine-2-sulfonamide Hydrochloride Condition 2, LCMS: m/z 375.1 [M+H]⁺, 2.66 min. ¹H NMR (500 MHz, Methanol-d₄) δ 8.14-8.08 (m, 2H), 7.64-7.57 (m, 1H), 7.52 (t, J=7.7 Hz, 2H), 7.30-7.22 (m, 2H), 7.12 (d, J=7.6 Hz, 2H), 1.90 (s, 6H).

Example 78: 6-amino-N-(5-chloro-6-(2,3,6-trifluorophenyl)pyridin-2-yl)pyridine-2-sulfonamide Condition 2, LCMS: m/z 415.2 [M+H]⁺, 2.87 min. ¹H NMR (500 MHz, Acetonitrile-d₃) δ 8.49 (s, 1H), 7.79 (d, J=9.0 Hz, 1H), 7.47 (dd, J=7.3, 8.4 Hz, 1H), 7.40 (d, J=8.9 Hz, 1H), 7.34 (qd, J=4.9, 9.3 Hz, 1H), 7.13 (d, J=7.3 Hz, 1H), 7.00 (tdd, J=2.2, 3.8, 8.9 Hz, 1H), 6.61 (d, J=8.4 Hz, 1H), 5.15 (s, 2H); ¹⁹F NMR (471 MHz, Acetonitrile-d₃) δ −119.26 (d, J=15.3 Hz, 1F), −137.72 (d, J=20.8 Hz, 1F), −143.81 (dd, J=15.2, 21.0 Hz, 1F).

Example 79: 6-amino-N-(5-(trifluoromethyl)-6-(3-(trifluoromethyl)phenyl)pyridin-2-yl)pyridine-2-sulfonamide Condition 2, LCMS: m/z 463.1 [M+H]⁺, 3.20 min. ¹H NMR (400 MHz, Methylene Chloride-d₂) δ 8.00 (m, 1H), 7.73 (m, 1H), 7.70-7.63 (m, 2H), 7.63-7.54 (m, 2H), 7.52 (m, 1H), 7.43-7.31 (m, 1H), 6.72-6.62 (m, 1H).

Example 80: 6-amino-N-(5-chloro-6-(2,6-difluorophenyl)pyridin-2-yl)pyridine-2-sulfonamide Condition 2, LCMS: m/z 397.1 [M+H]⁺, 2.81 min. ¹H NMR (500 MHz, Acetonitrile-d₃) δ 8.54 (s, 1H), 7.85 (d, J=8.9 Hz, 1H), 7.60-7.49 (m, 2H), 7.46 (d, J=8.8 Hz, 1H), 7.24-7.19 (m, 1H), 7.13-7.05 (m, 2H), 6.69 (d, J=8.4 Hz, 1H), 5.23 (s, 2H); ¹⁹F NMR (471 MHz, Acetonitrile-d₃) δ −114.53 (s, 2F).

Example 81: 6-amino-5-bromo-N-(5-chloro-6-(2,6-dimethylphenyl)pyridin-2-yl)pyridine-2-sulfonamide Condition 2, LCMS: m/z 467.0 [M+H]⁺, 3.30 min. ¹H NMR (400 MHz, DMSO-d₆) δ 11.26 (s, 1H), 7.93 (d, J=8.8 Hz, 1H), 7.81 (d, J=7.9 Hz, 1H), 7.19 (m, 2H), 7.07 (d, J=7.6 Hz, 2H), 6.89 (d, J=7.9 Hz, 1H), 6.75 (s, 2H), 1.74 (s, 6H).

Example 82: 6-amino-N-(6-(2-methyl-5-(trifluoromethoxy)phenyl)-5-(trifluoromethyl)pyridin-2-yl)pyridine-2-sulfonamide Condition 2, LCMS: m/z 493.2 [M+H]⁺, 3.30 min. ¹H NMR (400 MHz, Methylene Chloride-d₂) δ 7.99 (d, J=8.9

Hz, 1H), 7.57 (dd, J=7.4, 8.3 Hz, 1H), 7.50 (d, J=8.4 Hz, 1H), 7.39-7.30 (m, 1H), 7.19 (d, J=8.3 Hz, 1H), 7.15 (s, 1H), 7.11 (d, J=8.3 Hz, 1H), 6.65 (d, J=8.3 Hz, 1H), 4.72 (s, 2H), 2.03 (s, 3H); $^{19}$F NMR (376 MHz, Methylene Chloride-d$_2$) δ −58.06 (s, 1F), −58.90 (s, 1F).

Example 83: 6-amino-N-(6-(5-cyano-2-methylphenyl)-5-(trifluoromethyl)pyridin-2-yl)pyridine-2-sulfonamide Condition 2, LCMS: m/z 434.1 [M+H]$^+$, 2.68 min. $^1$H NMR (400 MHz, Methanol-d$_4$) δ 8.00 (m, 1H), 7.85 (m, 1H), 7.60 (dd, J=7.9, 1.8 Hz, 1H), 7.39-7.30 (m, 2H), 7.15-7.08 (m, 1H), 6.83 (m, 1H), 6.80-6.74 (m, 1H), 1.84 (s, 3H).

Example 84: 6-amino-N-(5-chloro-6-(5-cyano-2-methylphenyl)pyridin-2-yl)pyridine-2-sulfonamide Condition 2, LCMS: m/z 400.1 [M+H]$^+$, 2.80 min. $^1$H NMR (400 MHz, Methanol-d$_4$) δ 7.88-7.83 (m, 1H), 7.68 (dd, J=8.0, 1.8 Hz, 1H), 7.59 (dd, J=8.5, 7.3 Hz, 1H), 7.46 (d, J=8.0 Hz, 1H), 7.39 (d, J=1.7 Hz, 1H), 7.30-7.24 (m, 1H), 7.19 (dd, J=7.3, 0.7 Hz, 1H), 6.76 (dd, J=8.5, 0.7 Hz, 1H), 2.10 (s, 3H).

Example 85: 2-amino-N-(5-chloro-6-(5-cyano-2-methylphenyl)pyridin-2-yl)pyridine-4-sulfonamide Condition 2, LCMS: m/z 400.1 [M+H]$^+$, 2.58 min. $^1$H NMR (400 MHz, Chloroform-d) δ 8.18 (m, 1H), 7.77 (m, 1H), 7.61 (m, 1H), 7.45 (m, 1H), 7.39 (m, 2H), 7.32-7.25 (m, 1H), 6.94-6.85 (m, 2H), 5.52 (s, 2H), 2.12 (s, 3H).

Example 86: 6-amino-N-(5-chloro-6-(2,4,6-trifluorophenyl)pyridin-2-yl)pyridine-2-sulfonamide Condition 2, LCMS: m/z 415.2 [M+H]$^+$, 2.93 min. $^1$H NMR (500 MHz, Acetonitrile-d$_3$) δ 8.56 (s, 1H), 7.85 (d, J=8.9 Hz, 1H), 7.55 (dd, J=7.3, 8.4 Hz, 1H), 7.46 (d, J=8.8 Hz, 1H), 7.21 (dd, J=0.7, 7.3 Hz, 1H), 7.02-6.88 (m, 2H), 6.69 (dd, J=0.8, 8.4 Hz, 1H), 5.45 (s, 1H), 5.22 (s, 2H); $^{19}$F NMR (471 MHz, Acetonitrile-d$_3$) δ −107.52 (t, J=6.9 Hz, 1F), −111.29 (d, J=7.2 Hz, 2F).

Example 87: 2-amino-N-(5-chloro-6-(3-cyano-2-methylphenyl)pyridin-2-yl)pyridine-4-sulfonamide Condition 2, LCMS: m/z 400.1 [M+H]$^+$, 2.58 min. $^1$H NMR (400 MHz, Methanol-d$_4$) δ 7.99 (dd, J=5.5, 0.6 Hz, 1H), 7.91-7.81 (m, 1H), 7.75 (dd, J=7.5, 1.7 Hz, 1H), 7.51-7.33 (m, 2H), 7.19 (d, J=8.8 Hz, 1H), 6.93 (m, 1H), 6.90-6.86 (m, 1H), 2.15 (s, 3H).

Example 88: 2-amino-N-(5-chloro-6-(o-tolyl)pyridin-2-yl)pyridine-3-sulfonamide Condition 2, LCMS: m/z 375.1. $^1$H NMR (400 MHz, DMSO-d$_6$) δ 11.44 (s, 1H), 8.17 (dd, J=4.7, 1.8 Hz, 1H), 7.92 (d, J=8.7 Hz, 1H), 7.88 (dd, J=7.8, 1.8 Hz, 1H), 7.38-7.22 (m, 3H), 7.07 (d, J=7.6 Hz, 1H), 7.04 (d, J=8.8 Hz, 1H), 6.67 (s, 2H), 6.57 (dd, J=7.8, 4.8 Hz, 1H), 1.94 (s, 3H).

Example 89: 6-amino-N-(5-chloro-6-(2-methyl-5-(trifluoromethoxy)phenyl)pyridin-2-yl)pyridine-2-sulfonamide Condition 2, LCMS: m/z 459.2 [M+H]$^+$, 3.25 min. $^1$H NMR (400 MHz, Methylene Chloride-d$_2$) a 8.75-7.80 (m, 1H), 7.72 (d, J=8.8 Hz, 1H), 7.58-7.47 (m, 1H), 7.39 (d, J=8.8 Hz, 1H), 7.29 (d, J=7.3 Hz, 1H), 7.20 (d, J=8.3 Hz, 1H), 7.16-7.04 (m, 2H), 6.63 (d, J=8.3 Hz, 1H), 4.84 (s, 2H), 2.07 (s, 3H); $^{19}$F NMR (376 MHz, Methylene Chloride-d$_2$) δ −58.02 (s, 3F).

Example 90: 6-amino-N-(5-chloro-6-(2-cyanophenyl)pyridin-2-yl)pyridine-2-sulfonamide Condition 2, LCMS: m/z 386.0 [M+H]$^+$. $^1$H NMR (400 MHz, Chloroform-d) δ 7.85-7.75 (m, 1H), 7.75-7.70 (m, 1H), 7.69-7.62 (m, 1H), 7.60-7.48 (m, 4H), 7.35 (m, 1H), 6.68 (m, 1H), 4.78 (brs, 2H).

Example 91: 6-amino-N-(5-chloro-6-(4-cyano-2-methylphenyl)pyridin-2-yl)pyridine-2-sulfonamide Condition 2, LCMS: m/z 400.1 [M+H]$^+$, 2.85 min. $^1$H NMR (400 MHz, Chloroform-d) δ 7.83 (d, J=8.8 Hz, 1H), 7.67-7.62 (m, 1H), 7.62-7.57 (m, 1H), 7.50 (dd, J=8.4, 7.3 Hz, 1H), 7.35-7.29 (m, 1H), 7.27 (m, 1H), 7.16 (dd, J=7.3, 0.7 Hz, 1H), 6.70-6.63 (m, 1H), 2.06 (s, 3H)

Example 92: 2-amino-N-(5-chloro-6-(4-cyano-2-methylphenyl)pyridin-2-yl)pyridine-4-sulfonamide Condition 2, 400.1, 2.62 min. $^1$H NMR (400 MHz, Chloroform-d) δ 8.10 (m, 1H), 7.71 (m, 1H), 7.48 (m, 3H), 7.31 (m, 1H), 7.17 (s, 1H), 6.89-6.78 (m, 2H), 4.87 (m, 2H), 2.06 (s, 3H).

Example 93: 6-amino-N-(6-(2,6-dimethylphenyl)-3-fluoropyridin-2-yl)pyridine-2-sulfonamide Condition 2, 373.6, 2.63 min.

Example 94: 6-amino-N-(5-chloro-6-(4-(trifluoromethyl)phenyl)pyridin-2-yl)pyridine-2-sulfonamide Condition 2, LCMS: m/z 429.0 [M+H]$^+$, 3.25 min. $^1$H NMR (400 MHz, Methylene Chloride-d$_2$) δ 7.74 (m, 4H), 7.63-7.52 (m, 1H), 7.45-7.30 (m, 2H), 6.66 (m, 1H), 4.78 (m, 2H).

Example 95: 6-amino-N-(5-chloro-6-(2,6-dimethylphenyl)-3-fluoropyridin-2-yl)pyridine-2-sulfonamide Condition 2, LCMS: m/z 407.1 [M+H]$^+$, 3.02 min. $^1$H NMR (400 MHz, Methanol-d$_4$) δ 7.79 (d, J=9.5 Hz, 1H), 7.34 (t, J=7.8 Hz, 1H), 7.20-7.12 (m, 1H), 7.03 (dd, J=7.4, 2.0 Hz, 3H), 6.62 (d, J=8.3 Hz, 1H), 1.77 (s, 6H).

Example 96: 6-amino-N-(3-chloro-6-(2,6-dimethylphenyl)pyridin-2-yl)pyridine-2-sulfonamide Condition 2, LCMS: m/z 389.1 [M+H]$^+$, 2.74 min. $^1$H NMR (400 MHz, Methanol-d$_4$) δ 8.00 (s, 1H), 7.62-7.00 (m, 4H), 6.90 (d, J=7.9 Hz, 1H), 6.60 (d, J=8.4 Hz, 1H), 2.06 (s, 6H).

| Ex. No. | Product |
|---|---|
| 1 | 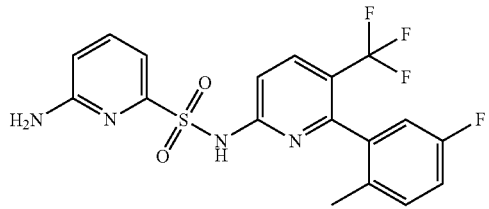 [SMILES: Cc1ccc(F)cc1-c1nc(NS(=O)(=O)c2cccc(N)n2)ccc1C(F)(F)F] |
| 2 | 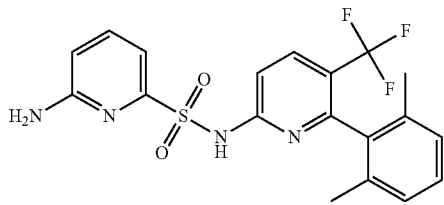 [SMILES: Cc1cccc(C)c1-c1nc(NS(=O)(=O)c2cccc(N)n2)ccc1C(F)(F)F] |
| 3 | 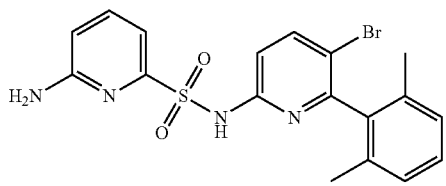 |
| 4 | 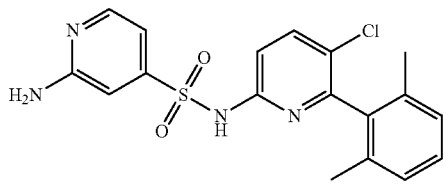 [SMILES: Cc1cccc(C)c1-c1nc(NS(=O)(=O)c2ccnc(N)c2)ccc1Cl] |
| 5 | 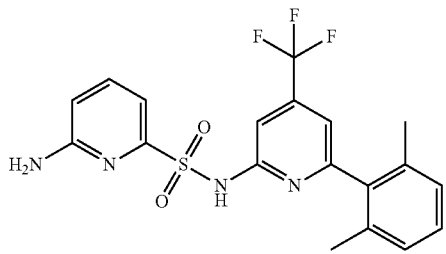 [SMILES: Cc1cccc(C)c1-c1cc(C(F)(F)F)cc(NS(=O)(=O)c2cccc(N)n2)n1] |
| 6 | 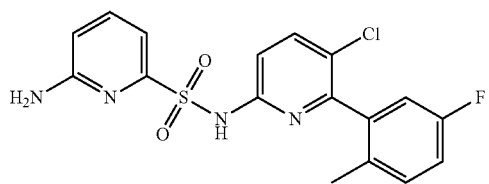 [SMILES: Cc1ccc(F)cc1-c1nc(NS(=O)(=O)c2cccc(N)n2)ccc1Cl] |
| 7 | 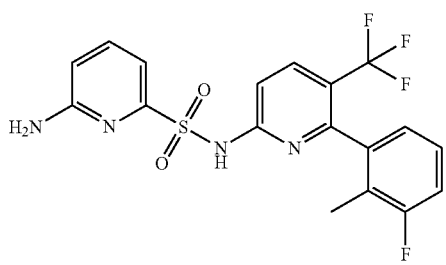 [SMILES: Cc1c(F)cccc1-c1nc(NS(=O)(=O)c2cccc(N)n2)ccc1C(F)(F)F] |
-continued
| Ex. No. | Product |
|---|---|
| 8 | 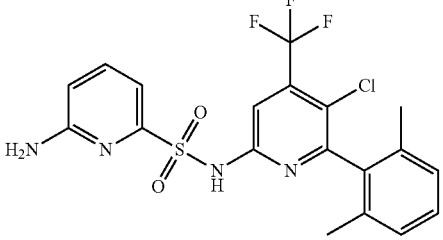 |
| 9 |  |
| 10 | 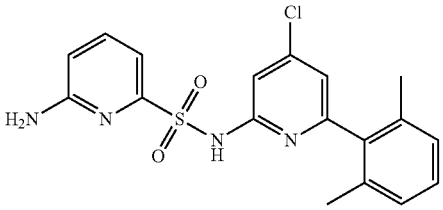 [SMILES: Cc1cccc(C)c1-c1cc(Cl)cc(NS(=O)(=O)c2cccc(N)n2)n1] |
| 11 | 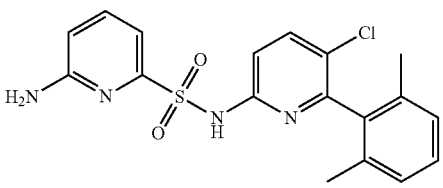 |
| 12 | 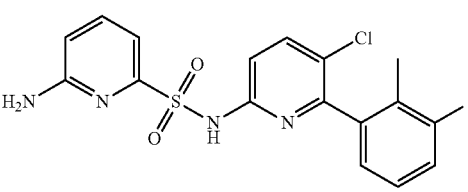 |
| 13 | 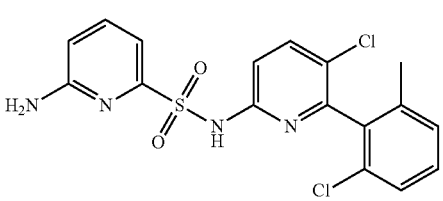 [SMILES: Cc1cccc(Cl)c1-c1nc(NS(=O)(=O)c2cccc(N)n2)ccc1Cl] |
| 14 | 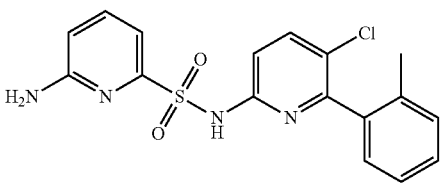 [SMILES: Cc1ccccc1-c1nc(NS(=O)(=O)c2cccc(N)n2)ccc1Cl] |

91
-continued
| Ex. No. | Product |
|---|---|
| 15 | |
| 16 | |
| 17 | |
| 18 | |
| 19 | |
| 20 | |
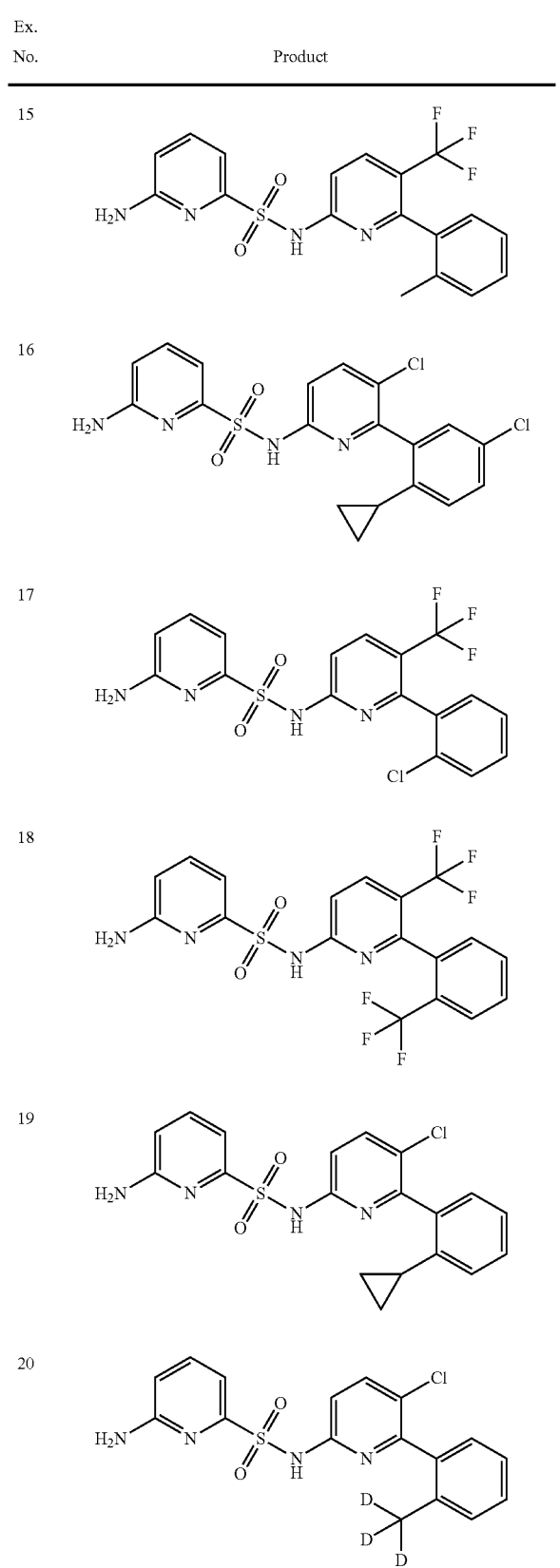
92
-continued
| Ex. No. | Product |
|---|---|
| 21 | |
| 22 | |
| 23 | |
| 24 | |
| 25 | |
| 26 | |
| 27 | |
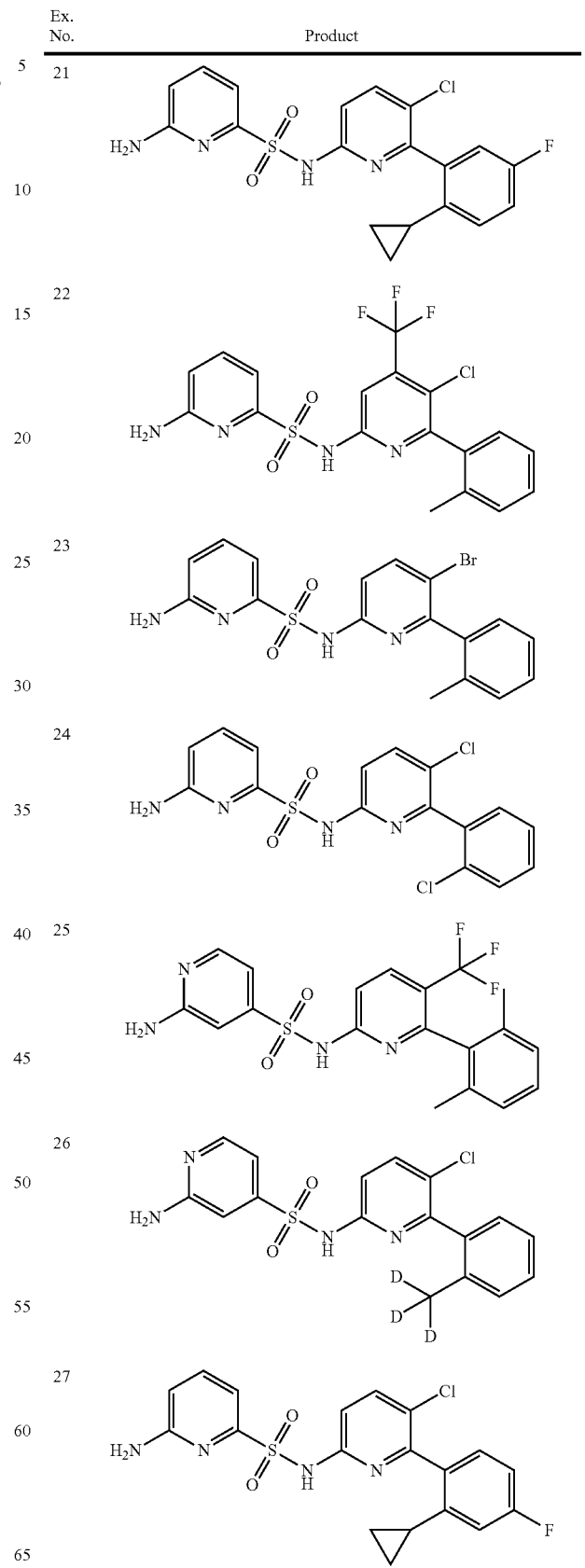

| Ex. No. | Product |
|---|---|
| 28 | 6-amino-N-(5-(trifluoromethyl)-6-(2-cyclopropylphenyl)pyridin-2-yl)pyridine-2-sulfonamide |
| 29 | 6-amino-N-(5-chloro-6-(2-ethylphenyl)pyridin-2-yl)pyridine-2-sulfonamide |
| 30 | 6-amino-N-(5-chloro-6-(4-fluoro-2,6-dimethylphenyl)pyridin-2-yl)pyridine-2-sulfonamide |
| 31 | 6-amino-N-(5-chloro-6-(2-fluoro-6-methylphenyl)pyridin-2-yl)pyridine-2-sulfonamide |
| 32 | 6-amino-N-(5-chloro-6-mesitylpyridin-2-yl)pyridine-2-sulfonamide |
| 33 | 6-amino-3-fluoro-N-(5-chloro-6-(o-tolyl)pyridin-2-yl)pyridine-2-sulfonamide |
| 34 | 6-amino-N-(5-chloro-6-(2-methyl-3-(trifluoromethyl)phenyl)pyridin-2-yl)pyridine-2-sulfonamide |
| 35 | 6-amino-N-(5-fluoro-6-(2-isopropylphenyl)pyridin-2-yl)pyridine-2-sulfonamide |
| 36 | 6-amino-5-methyl-N-(6-(o-tolyl)-5-(trifluoromethyl)pyridin-2-yl)pyridine-2-sulfonamide |
| 37 | 6-amino-N-(5-chloro-6-(4-fluoro-2-methylphenyl)pyridin-2-yl)pyridine-2-sulfonamide |
| 38 | 6-amino-N-(5-chloro-6-(6-chloro-2-fluoro-3-methylphenyl)pyridin-2-yl)pyridine-2-sulfonamide |
| 39 | 6-amino-N-(5-chloro-6-(2-chloro-6-fluorophenyl)pyridin-2-yl)pyridine-2-sulfonamide |
| 40 | 6-amino-N-(5-chloro-6-(o-tolyl)pyridin-2-yl)pyridine-3-sulfonamide |
| 41 | 6-amino-N-(6-(2-chloro-4-fluorophenyl)-5-(trifluoromethyl)pyridin-2-yl)pyridine-3-sulfonamide |

| Ex. No. | Product |
|---|---|
| 42 | |
| 43 | |
| 44 | |
| 45 | |
| 46 | |
| 47 | |
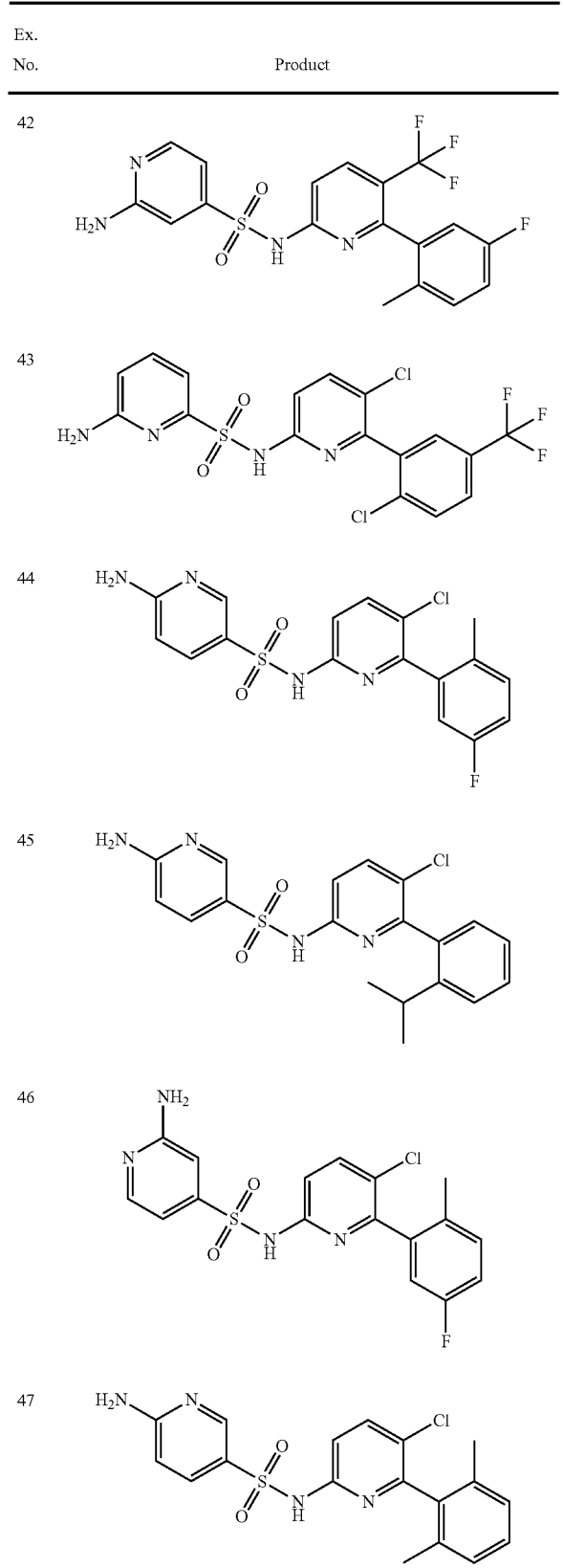
| Ex. No. | Product |
|---|---|
| 48 | |
| 49 | |
| 50 | |
| 51 | |
| 52 | |
| 53 | |
| 54 | |
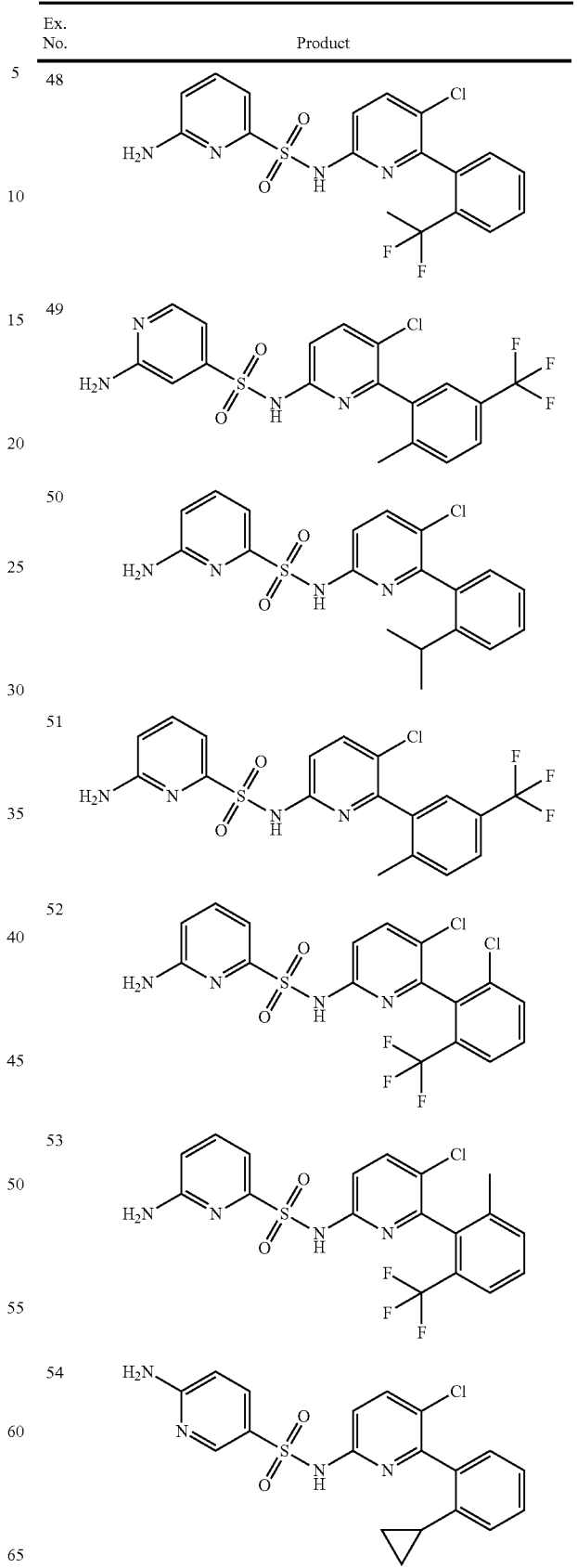

| Ex. No. | Product |
|---|---|
| 55 | 6-amino-N-[5-chloro-6-[2-(trifluoromethyl)phenyl]pyridin-2-yl]pyridine-2-sulfonamide |
| 56 | 6-amino-N-[5-chloro-6-(2-chloro-4-fluorophenyl)pyridin-2-yl]pyridine-2-sulfonamide |
| 57 | 6-amino-N-[5-chloro-6-(2-methylphenyl)pyridin-2-yl]pyridine-4-sulfonamide |
| 58 | 6-amino-N-[5-chloro-6-(2-chloro-6-fluoro-3-methylphenyl)pyridin-2-yl]pyridine-2-sulfonamide |
| 59 | 6-amino-N-[5-chloro-6-[2-(trifluoromethoxy)phenyl]pyridin-2-yl]pyridine-2-sulfonamide |
| 60 | 6-amino-N-[5-chloro-6-(2-fluoro-6-methylphenyl)pyridin-2-yl]pyridine-3-sulfonamide |
| 61 | 6-amino-N-[5-chloro-6-[2-(trifluoromethyl)phenyl]pyridin-2-yl]pyridine-3-sulfonamide |
| 62 | 6-amino-N-[5-chloro-6-(5-fluoro-2-methoxyphenyl)pyridin-2-yl]pyridine-2-sulfonamide |
| 63 | 6-amino-N-[6-(2,6-dimethylphenyl)-4-methylpyridin-2-yl]pyridine-2-sulfonamide |
| 64 | 6-amino-N-[6-(5-cyano-2-methylphenyl)-5-(trifluoromethyl)pyridin-2-yl]pyridine-4-sulfonamide |
| 65 | 6-amino-N-[5-chloro-6-[2-(difluoromethyl)phenyl]pyridin-2-yl]pyridine-2-sulfonamide |
| 66 | 6-amino-N-[5-cyclopropyl-6-(2-methylphenyl)pyridin-2-yl]pyridine-2-sulfonamide |
| 67 | 6-amino-N-[5-chloro-6-(3-cyano-2-methylphenyl)pyridin-2-yl]pyridine-2-sulfonamide |
| 68 | 6-amino-N-[6-(2,6-dimethylphenyl)pyridin-2-yl]pyridine-2-sulfonamide |

| Ex. No. | Product |
|---|---|
| 69 | 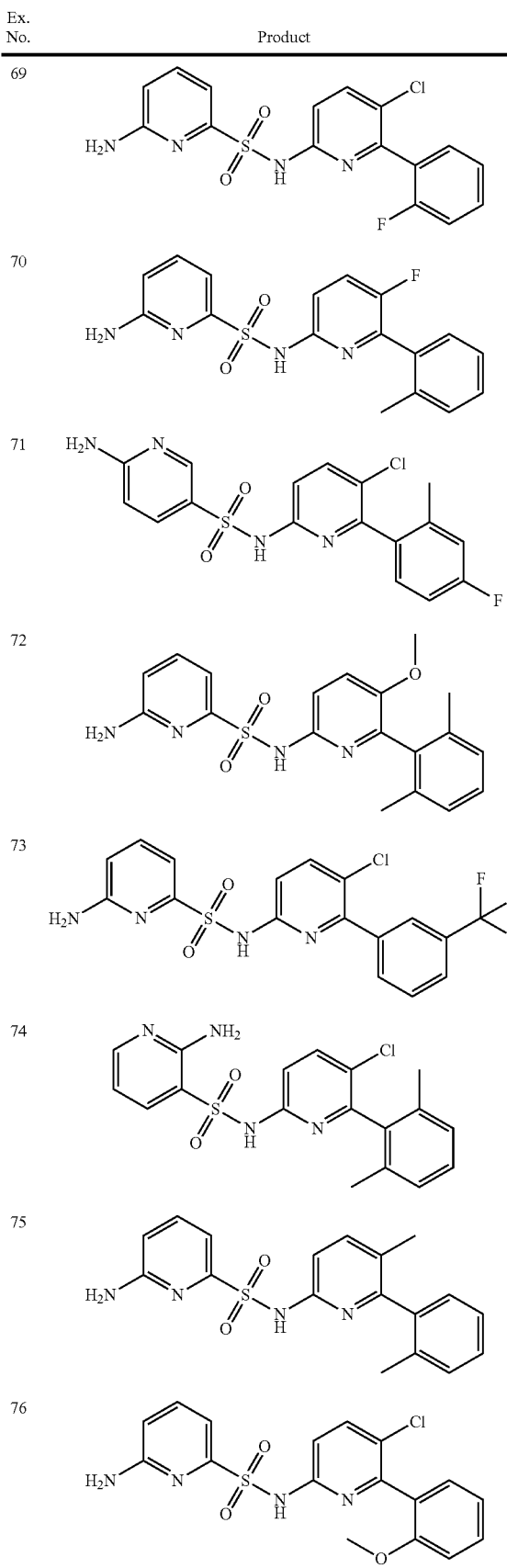 |
| 70 | |
| 71 | |
| 72 | |
| 73 | |
| 74 | |
| 75 | |
| 76 | |
| Ex. No. | Product |
|---|---|
| 77 | 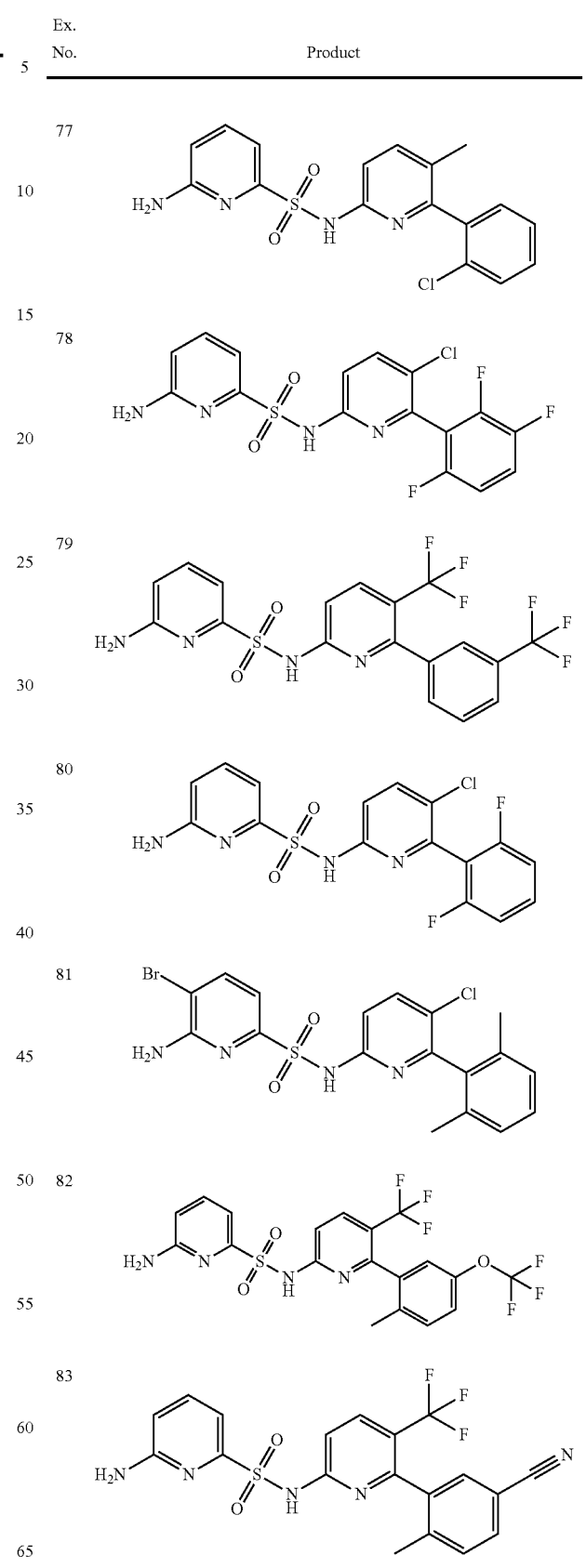 |
| 78 | |
| 79 | |
| 80 | |
| 81 | |
| 82 | |
| 83 | |

| Ex. No. | Product | Ex. No. | Product |
|---|---|---|---|
| 84 | 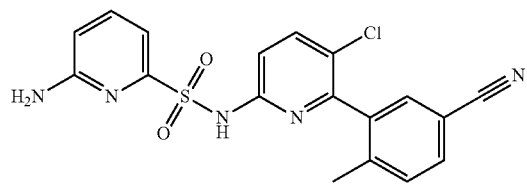 [SMILES: Cc1ccc(C#N)cc1-c1nc(NS(=O)(=O)c2cccc(N)n2)ccc1Cl] | 91 | 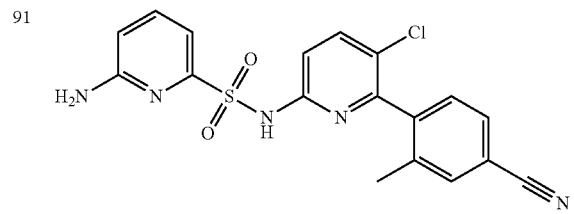 |
| 85 | 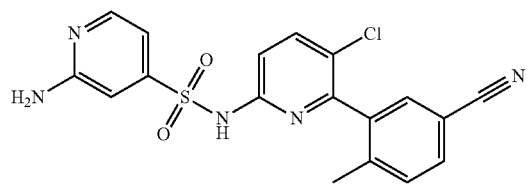 [SMILES: Cc1ccc(C#N)cc1-c1nc(NS(=O)(=O)c2ccnc(N)c2)ccc1Cl] | 92 | 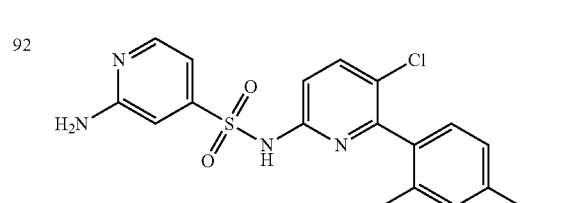 |
| 86 | 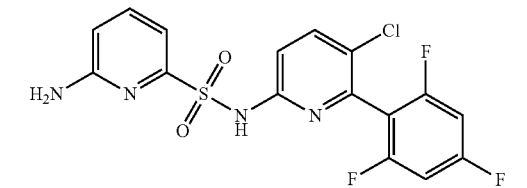 [SMILES: Nc1cccc(S(=O)(=O)Nc2ccc(Cl)c(-c3c(F)cc(F)cc3F)n2)n1] | 93 | 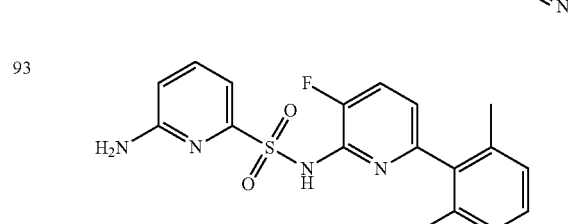 |
| 87 | 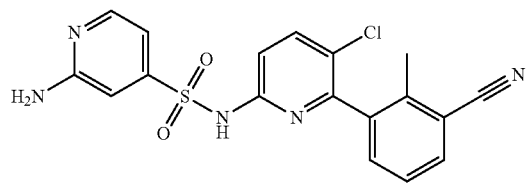 [SMILES: Cc1c(C#N)cccc1-c1nc(NS(=O)(=O)c2ccnc(N)c2)ccc1Cl] | 94 | 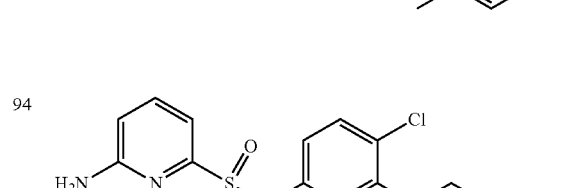 |
| 88 | 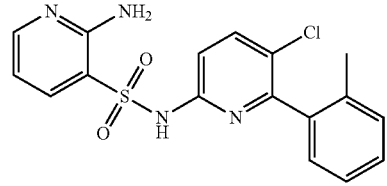 [SMILES: Cc1ccccc1-c1nc(NS(=O)(=O)c2cccnc2N)ccc1Cl] | 95 | 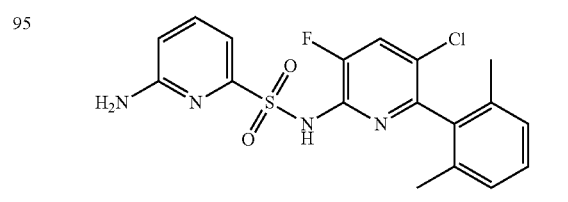 |
| 89 | 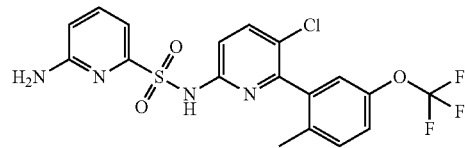 [SMILES: Cc1ccc(OC(F)(F)F)cc1-c1nc(NS(=O)(=O)c2cccc(N)n2)ccc1Cl] | 96 | 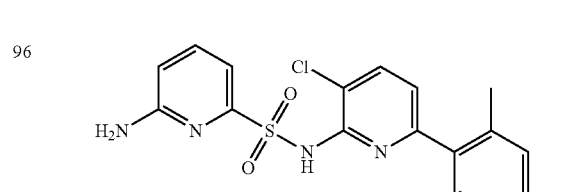 |
| 90 | 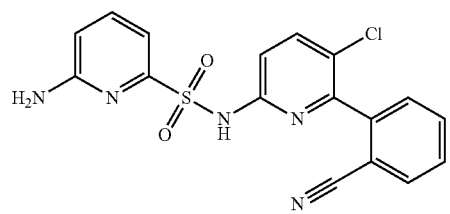 [SMILES: N#Cc1ccccc1-c1nc(NS(=O)(=O)c2cccc(N)n2)ccc1Cl] | | |

Scheme II:

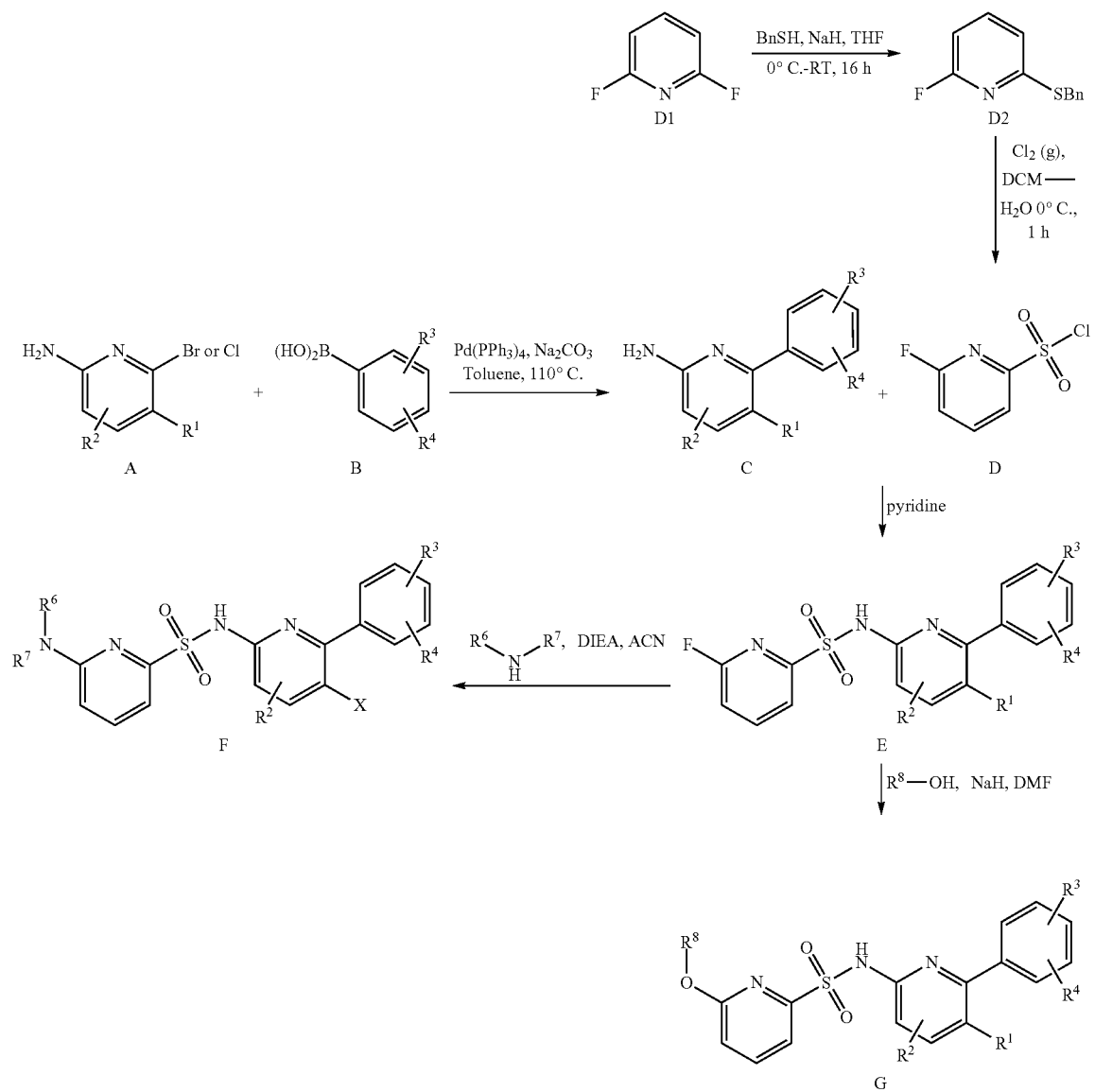

The starting materials for the above reaction scheme are commercially available or can be prepared according to methods known to one skilled in the art or by methods disclosed herein. In general, the compounds of the invention are prepared in the above reaction Scheme II as follows: Suzuki cross-coupling of building block A with building block B provides intermediate C. Separately, building block D1 is converted into intermediate D2 which is subsequently converted into building block D. Intermediate C and building block D are combined to form intermediate E. Intermediate E can then be converted into F with an appropriate building block amine of the subtype NHR⁶R⁷ to give target compound F. Alternatively, intermediate E can be combined with the appropriate building block alcohol R⁸OH in the presence of a strong base to yield target compound G. The combination of various building blocks and intermediates can then be applied to yield compounds 102-327 of formula (I).

Intermediate (2)

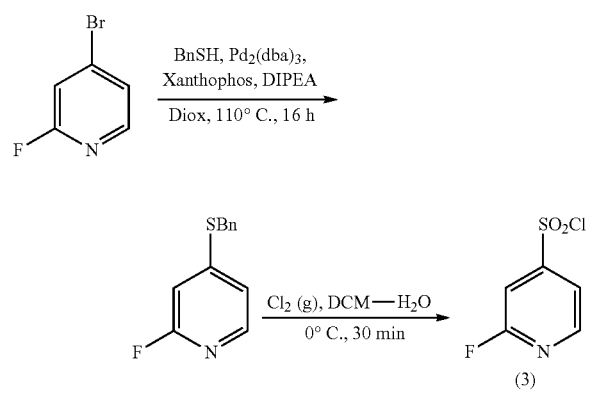

Step 1. Synthesis of 4-(benzylthio)-2-fluoropyridine

The stirred solution of 4-bromo-2-fluoropyridine (10.0 g, 56.82 mmol), phenylmethanethiol (7.3 mL, 62.50 mmol), Pd$_2$(dba)$_3$ (2.60 g, 2.84 mmol), Xanthophos (3.28 g, 5.68 mmol) and DIPEA (19.4 mL, 113.64 mmol) in dioxane (150 mL) was degassed with argon for 15 min. The resulting reaction mixture was heated to reflux for 16 h under argon atmosphere. The reaction mixture was cooled to rt, filtered through celite bed, the celite bed was washed with EtOAc and the combined filtrate was concentrated to dryness under reduced pressure. The crude was purified by flash column chromatography (40 g SiliCycle column, 2-3% EtOAc in Hexane elution) to provide the title compound as yellow oil (12.0 g, 96.3%). LC/MS, ESI-MS (+): 219.5. $^1$H NMR (400 MHz, CDCl$_3$) δ ppm 7.99 (d, J=5.2 Hz, 1H), 7.43-7.30 (m, 5H), 7.00-6.98 (m, 1H), 6.74-6.73 (m, 1H).

Step 2. Synthesis of 2-fluoropyridine-4-sulfonyl Chloride

To a two-necked round bottom flask containing 4-(benzylthio)-2-fluoropyridine (7.0 g, 31.92 mmol) was added DCM (160 mL) and water (40 mL) at rt. The content was then cool to 0° C. with an ice bath. Chlorine gas (generated from KMnO$_4$-con HCl) was purged for 15 min and the reaction mixture was stirred at 0° C. for additional 15 min. After completion of the reaction, N$_2$ was purged for 20 min, reaction mixture was diluted with water (50 mL). The organic portion was extracted with DCM thrice. The combined organic portion was washed with brine solution, dried over anhydrous Na$_2$SO$_4$ and concentrated in vacuo (at 40° C.) to yield a crude oil. The crude was purified by flash column chromatography (40 g SiliCycle column, 2-10% EtOAc in Hexane elution) to afforded Intermediate (3): as pale yellow oil (5.0 g, 80%). $^1$H NMR (300 MHz, CDCl$_3$) δ ppm 8.62 (d, J=5.4 Hz, 1H), 7.80 (dt, J=5.1, 1.5 Hz, 1H), 7.56-7.54 (m, 1H).

Intermediate (6)

Route 1

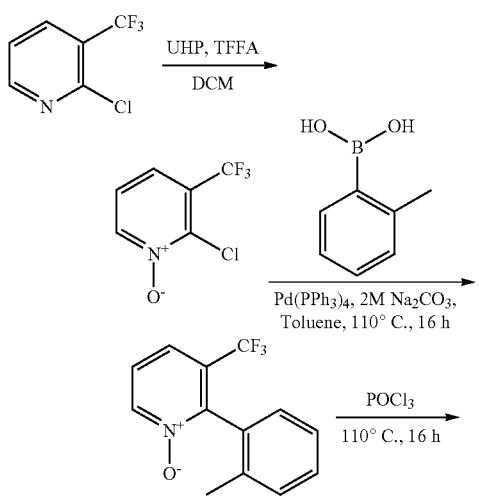

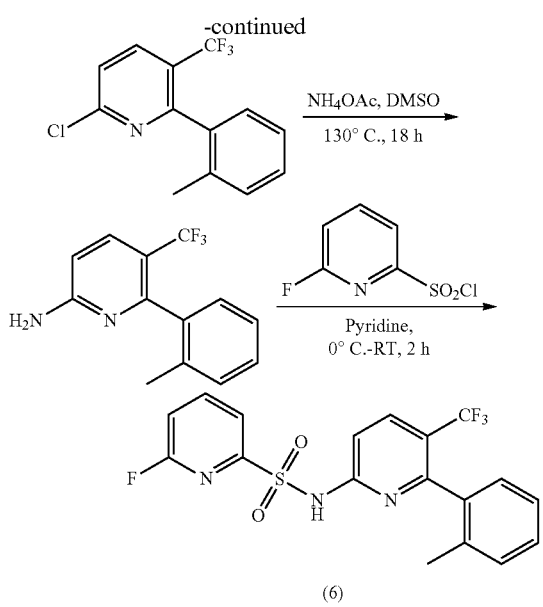

Step 1. Synthesis of 2-chloro-3-(trifluoromethyl)pyridine 1-oxide

The title compound was prepared analogous to the literature procedure (US2008/0275057). To a stirred solution of 2-chloro-3-(trifluoromethyl)pyridine (75.0 g, 413.13 mmol) in DCM (750 mL) was added UHP (79.7 g, 846.92 mmol). The solution was cooled to 0° C. with ice-bath and TFAA (114.0 mL, 913.02 mmol) was added dropwise. After completion of addition, reaction mixture was stirred at rt for 16 h. Then the reaction mixture was diluted with ice-water and neutralized with Na$_2$CO$_3$, organic portion was separated and the aqueous portion was extracted with DCM twice. The combined organic portion was washed with brine solution, dried over anhydrous Na$_2$SO$_4$ and concentrated. The crude mass was triturated with 5% DCM in hexane, solid separated was collected by filtration and dried under vacuum to afford the product as a white solid (76.3 g, 93.5%). LC/MS, ESI-MS (+): 197.9. $^1$H NMR (400 MHz, CDCl$_3$) δ ppm 8.72 (dd, J=6.8, 1.2 Hz, 1H), 7.80 (d, J=8.4 Hz, 1H), 7.60 (t, J=7.2 Hz, 1H).

Step 2. Synthesis of 2-(o-tolyl)-3-(trifluoromethyl)pyridine 1-oxide

The title compound was prepared analogous to the literature procedure (US2008/0275057). A solution of 2-chloro-3-(trifluoromethyl)pyridine 1-oxide (30.0 g, 151.87 mmol) in toluene (450 mL) and water (300 mL) was added o-tolylboronic acid (20.7 g, 151.87 mmol), Na$_2$CO$_3$ (62.8 g, 597.61 mmol) and stirred under N$_2$ for 10 min. Then Pd(PPh$_3$)$_4$ (8.8 g, 7.61 mmol) was added and the reaction mixture was stirred under reflux in a N$_2$ atmosphere for 16 h. Reaction mixture was cooled to rt, diluted with EtOAc-water, organic portion was separated and the aqueous portion was extracted with EtOAc twice. Combined organic portion was washed with brine solution, dried over anhydrous Na$_2$SO$_4$ and concentrated. The crude mass was crystallized from EtOAc-Hexane to afford 27 g (70%) product as an off white solid. LC/MS, ESI-MS (+): 254.05.

Step 3. Synthesis of 6-chloro-2-(o-tolyl)-3-(trifluoromethyl)pyridine

A solution of 2-(o-tolyl)-3-(trifluoromethyl)pyridine 1-oxide (8.25 g, 41.76 mmol) in POCl$_3$ (70 mL) was heated at 100° C. for 16 h. Then the reaction mixture was cooled, and concentrated under reduced pressure. The residue was poured into ice-water and extracted with EtOAc thrice. The combined organic portion was washed with sat. NaHCO$_3$, dried over Na$_2$SO$_4$ and concentrated to afford a crude oil. The crude mass was purified by flash column chromatography (40 g RediSep Column, Hexane elution) to afford the title compound as colorless oil (4.9 g, 62%). LC/MS, ESI-MS (+): 272.2. $^1$H NMR (400 MHz, CDCl$_3$) δ ppm 8.04 (d, J=8.4 Hz, 1H), 7.47 (d, J=8.0 Hz, 1H), 7.34 (td, J=8.0, 1.6 Hz, 1H), 7.28-7.22 (m, 2H), 7.16 (d, J=7.6 Hz, 1H).

Step 4. Synthesis of 6-(o-tolyl)-5-(trifluoromethyl)pyridin-2-amine

To a solution of 6-chloro-2-(o-tolyl)-3-(trifluoromethyl)pyridine (4.9 g, 18.04 mmol) in DMSO (10 mL) was added NH$_4$OAc (7.0 g, 90.2 mmol), the reaction vessel was closed and heated at 130° C. for 18 h. After completion, cooled reaction mixture was partitioned between ice-water and EtOAc. Separated organic portion was washed with brine solution, dried over Na$_2$SO$_4$ and concentrated under reduced pressure to give crude residue. The crude mass was purified by flash column chromatography (12 g RediSep Column, 20% EtOAc in Hexane elution) to afford the product as a white solid (3.3 g, 72%). LC/MS, ESI-MS (+): 253.2. $^1$H NMR (300 MHz, CDCl$_3$) δ ppm 7.75 (d, J=8.4 Hz, 1H), 7.33-7.16 (m, 4H), 6.48 (d, J=9.0 Hz, 1H).

Step 5. Synthesis of 6-fluoro-N-(6-(o-tolyl)-5-(trifluoromethyl)pyridin-2-yl)pyridine-2-sulfonamide The solution of 6-(o-tolyl)-5-(trifluoromethyl)pyridin-2-amine (5.3 g, 21.01 mmol) in pyridine (15 mL) was cooled to 0° C. and 6-fluoropyridine-2-sulfonyl chloride (5.75 g, 29.42 mmol) was added dropwise. Reaction mixture was stirred at rt. After 2 h, reaction was quenched with water and extracted with EtOAc thrice. The combined organic portion was washed with brine, dried over Na$_2$SO$_4$ and concentrated to afford an oily residue, which was purified by combi flash using 40 g RediSep column (30-35% EtOAc in Hexane) to yield Intermediate (6): as a white solid (6.9 g, 79%). LC/MS, ESI-MS (+): 411.9. $^1$H NMR (300 MHz, CD$_3$OD) δ ppm 8.08 (d, J=8.7 Hz, 1H), 8.01-7.94 (m, 1H), 7.86 (dd, J=7.2, 1.5 Hz, 1H), 7.35-7.30 (m, 2H), 7.27-7.17 (m, 4H), 7.01 (d, J=7.2 Hz, 1H), 1.89 (s, 3H).

Intermediate (6)

Route 2

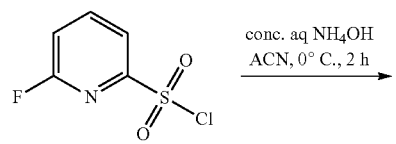

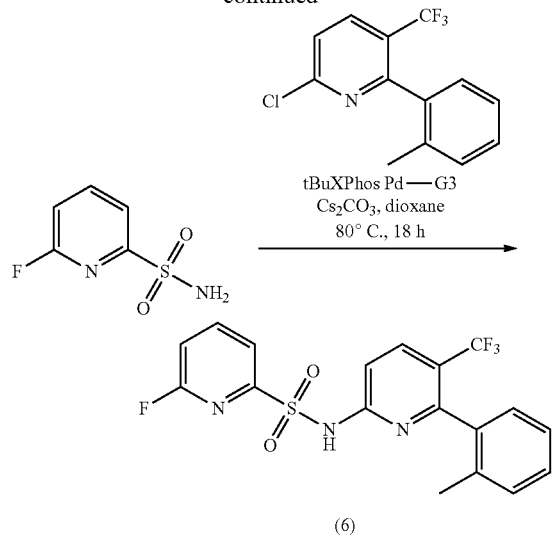

Route 2; Step 1. Synthesis of 6-fluoropyridine-2-sulfonamide

To a solution of 6-fluoropyridine-2-sulfonyl chloride (2.0875 g, 10.67 mmol) was dissolved in MeCN (50 mL) cooled to 0° C., concentrated aqueous ammonium hydroxide (70 mL, 539 mmol) was added dropwise. The resulting reaction mixture was stirred at 0° C. for 30 minutes, then warmed to room temperature and allowed to stir at room temperature for 2 hours. The solution was concentrated by vacuum to remove some of the acetonitrile and dried by lyophilization to yield the desired product as a dark gray solid (95% yield). LC/MS, ESI-MS (+): 177.0. $^1$H NMR (400 MHz, DMSO-d6) δ 8.26 (q, J=7.9 Hz, 1H), 7.88 (ddd, J=7.5, 2.3, 0.6 Hz, 1H), 7.63 (s, 2H), 7.48 (ddd, J=8.3, 2.4, 0.6 Hz, 1H).

Synthesis of 6-fluoropyridine-2-sulfonamide Alternate Route

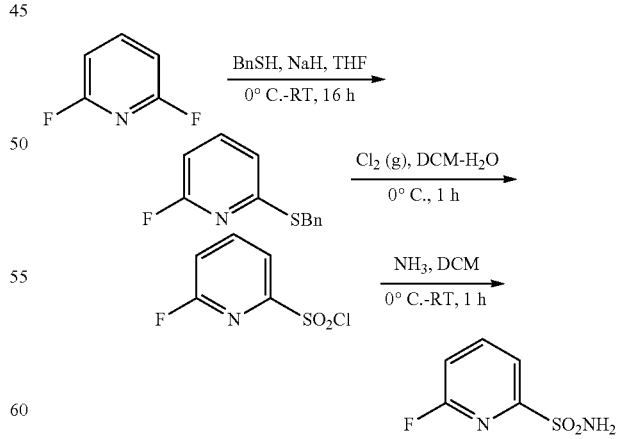

Step 1. Synthesis of 2-(benzylthio)-6-fluoropyridine

To a two-necked round bottom flask containing anhydrous tetrahydrofuran (500 ml) cooled at 00° C. was added sodium hydride (60% suspension in oil) (19.2 g, 477.93 mmol) in portions. A solution of phenylmethanethiol (51.0 mL, 434.48 mmol) in tetrahydrofuran (100 mL) was added dropwise via an additional funnel and stirred at 0° C. After 30 min, 2,6-difluoropyridine (50 g, 434.48 mmol) in tetrahydrofuran (100 mL) was added dropwise via additional funnel maintaining the reaction temperature at 0° C. The reaction mixture was stirred at rt for 16 h. Then cooled to 00° C., quenched with ice-water and extracted with EtOAc thrice. The combined organic portion was washed with brine solution, dried over anhydrous Na$_2$SO$_4$ and concentrated to afford a crude oil. The crude residue was purified by column chromatography on silica gel (60-120 mesh size) (0-3% EtOAc in Hexane) to yield the title compound as yellowish viscous oil (88 g, 92%). LC/MS, ESI-MS (-): 218.0. $^1$H NMR (400 MHz, CDCl$_3$) δ ppm 7.61-7.55 (m, 1H), 7.45-7.43 (m, 2H), 7.35-7.31 (m, 2H), 7.29-7.25 (m, 1H), 7.24 (dt, J=7.6, 1.2 Hz, 1H), 7.62 (dt, J=8.0, 1.2 Hz, 1H), 4.43 (s, 2H).

Step 2. Synthesis of 6-fluoropyridine-2-sulfonyl Chloride

A mixture of 2-(benzylthio)-6-fluoropyridine (60 g, 273.62 mmol) in DCM (2000 mL) and water (400 mL) was cooled to 00° C. with an ice-water bath. Chlorine gas (generated from KMnO$_4$-conc HCl) was purged into the reaction mixture for 1 h and 15 min at 0° C. After reaction completion, N$_2$ was purged into the reaction mixture for 20 min. The reaction mixture was then diluted with water (1000 mL). The organic portion was extracted with DCM thrice. The combined organic portion was washed with brine solution, dried over anhydrous Na$_2$SO$_4$ and concentrated in vacuo at 40° C. to afford a crude oil. The crude was purified by Si-gel (60-120 mesh size) column chromatography (10-15% EtOAc in Hexane) to afford the desired product as yellowish viscous oil (51 g, 95%). $^1$H NMR (400 MHz, CDCl$_3$) δ ppm 8.23-8.15 (m, 1H), 8.04-8.01 (m, 1H), 7.39-7.36 (m, 1H).

Step 3. Synthesis of 6-fluoropyridine-2-sulfonamide

A solution of 6-fluoropyridine-2-sulfonyl chloride (3 g, 15.34 mmol) in DCM (50 mL) was cooled to 0° C. with an ice-water bath. Ammonia gas was purged into the reaction mixture for 10 min and then the reaction mixture was stirred at rt for 1 h. The reaction mixture was filtered through a pad of Celite to remove the solid, and the filtrate was concentrated in vacuo to yield the crude product, which was triturated with hexane, filtered and dried in vacuo to obtain the product as an off white solid (2.6 g, 87%). LCMS: m/z 174.90 [M+H]$^+$. $^1$H NMR (300 MHz, DMSO-d6) δ ppm 8.30-8.22 (m, 1H), 7.88 (dd, J=7.5, 2.1 Hz, 1H), 7.67 (brs, 2H), 7.48 (dd, J=8.1, 2.1 Hz, 1H).

Route 2. Step 2: Synthesis of 6-fluoro-N-(6-(o-tolyl)-5-(trifluoromethyl)pyridin-2-yl)pyridine-2-sulfonamide To a suspension of 6-chloro-2-(o-tolyl)-3-(trifluoromethyl)pyridine (800 mg, 2.94 mmol), 6-fluoropyridine-2-sulfonamide (778 mg, 4.42 mmol), and cesium carbonate (1439 mg, 4.42 mmol) in Dioxane (30 mL), tBuXPhos palladacycle G3 (234 mg, 0.294 mmol) was added. The reaction mixture was purged with nitrogen and then was stirred at 80° C. for 3 h. The reaction was diluted with DCM, then was washed twice with saturated aqueous ammonium chloride solution followed by brine, dried over magnesium sulfate, concentrated in vacuo. The crude product was purified by an ISCO silica gel chromatography [40 g RediSep column, eluted with 100% heptane to 50% EtOAc/heptane to 100% EtOAc] to yield Intermediate (6): as a creamy pale yellow solid (828 mg, 68%). LCMS: m/z 412.0 [M+H]$^+$.

Intermediate (7)

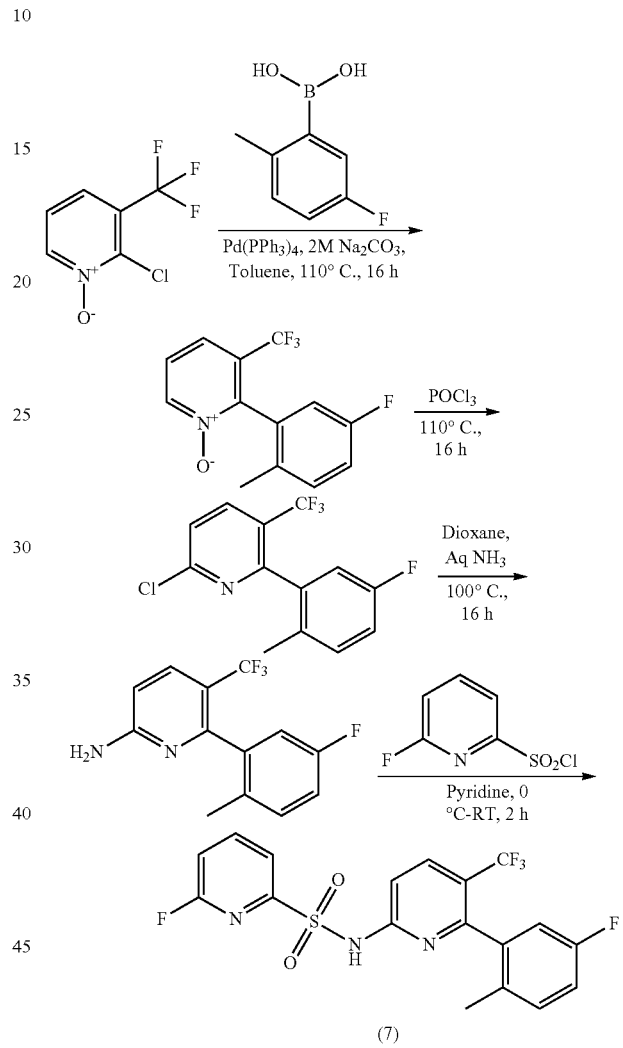

Step 1. Synthesis of 2-(5-fluoro-2-methylphenyl)-3-(trifluoromethyl)pyridine 1-oxide The title compound was prepared analogous to the literature procedure (US2008/0275057). A solution of 2-chloro-3-(trifluoromethyl)pyridine 1-oxide (15.0 g, 75.93 mmol) in toluene (210 mL) and water (114 mL) was added (5-fluoro-2-methylphenyl)boronic acid (11.7 g, 75.93 mmol), Na$_2$CO$_3$ (24.2 g, 227.80 mmol) and stirred under N$_2$ for 10 min. Then Pd(PPh$_3$)$_4$ (4.4 g, 3.80 mmol) was added and the reaction mixture was stirred under reflux in a N$_2$ atmosphere for 16 h. Reaction mixture was cooled to rt, diluted with EtOAc-water, organic portion was separated and the aqueous portion was extracted with EtOAc twice. Combined organic portion was washed with brine solution, dried over anhydrous Na$_2$SO$_4$ and concentrated. The crude mass was purified by flash column chromatography (40 g SiliCycle column, 60-70% EtOAc in Hexane elution) to afford 19.51 g (94%) of product as a white solid. LC/MS, ESI-MS (⁺): 272.2.

Step 2. Synthesis of 6-chloro-2-(5-fluoro-2-methylphenyl)-3-(trifluoromethyl)pyridine A solution of 2-(5-fluoro-2-methylphenyl)-3-(trifluoromethyl)pyridine 1-oxide (19.5 g, 71.90 mmol) in POCl₃ (130 mL) was heated at 90° C. for 18 h. Then the reaction mixture was cooled, and concentrated under reduced pressure. The residue was poured into ice-water and extracted with EtOAc thrice. The combined organic portion was washed with sat. NaHCO₃, dried over Na₂SO₄ and concentrated to afford a crude oil. The crude mass was purified by flash chromatography (40 g RediSep column, Hexane elution) to afford the title compound as colorless oil (11.0 g, 52.8%). LC/MS, ESI-MS (⁺): 289.95. ¹H NMR (400 MHz, CDCl₃) δ ppm 8.05 (d, J=8.4 Hz, 1H), 7.50 (d, J=8.4 Hz, 1H), 7.42-7.21 (m, 1H), 7.07-7.01 (m, 1H), 6.91 (dd, J=8.4, 2.0 Hz, 1H).

Step 3. Synthesis of 6-(5-fluoro-2-methylphenyl)-5-(trifluoromethyl)pyridin-2-amine To a stirred solution of 6-chloro-2-(5-fluoro-2-methylphenyl)-3-(trifluoromethyl)pyridine (9.0 g, 31.07 mmol) in dioxane (100 mL) was added aq. NH₃ (150 mL, 30%), the reaction vessel was closed and heated at 100° C. for 16 h. Reaction mixture was cooled to rt and extracted with EtOAc thrice. The combined organic portion was dried over Na₂SO₄ and concentrated under reduced pressure to give crude residue. The residue was purified by flash column chromatography (40 g SiliCycle column, 30-35% EtOAc in Hexane elution) to yield 2.0 g (66%, based on starting material conversion; 6.0 g starting material recovered) product as a white solid. LC/MS, ESI-MS (⁺): 271.0.

Step 4. Synthesis of 6-fluoro-N-(6-(5-fluoro-2-methylphenyl)-5-(trifluoromethyl)pyridin-2-yl)pyridine-2-sulfonamide The solution of 6-(5-fluoro-2-methylphenyl)-5-(trifluoromethyl)pyridin-2-amine (2.0 g, 7.40 mmol) in pyridine (5 mL) was cooled to 0° C. and 6-fluoropyridine-2-sulfonyl chloride (2.03 g, 10.36 mmol) was added dropwise. Reaction mixture was allowed to stir at rt for 2 h. Then the reaction was quenched with water and extracted with EtOAc thrice. The combined organic portion was washed with brine, dried over Na₂SO₄ and concentrated to afford an oily residue, which was purified by flash column chromatography (24 g SiliCycle column, 30-35% EtOAc in Hexane elution) to provide Intermediate (7): as an off white solid (1.95 g, 61%). LC/MS, ESI-MS (⁺): 429.0. ¹H NMR (300 MHz, CD₃OD) δ ppm 8.08 (d, J=8.7 Hz, 1H), 8.04-7.96 (m, 1H), 7.86 (dd, J=7.5, 2.1 Hz, 1H), 7.29-7.20 (m, 3H), 7.08-7.02 (m, 1H), 7.75 (d, J=8.7 Hz, 1H), 1.82 (s, 3H).

Intermediate (8)

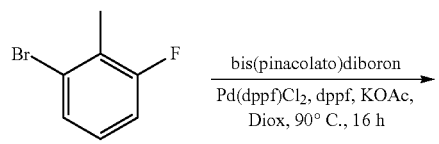

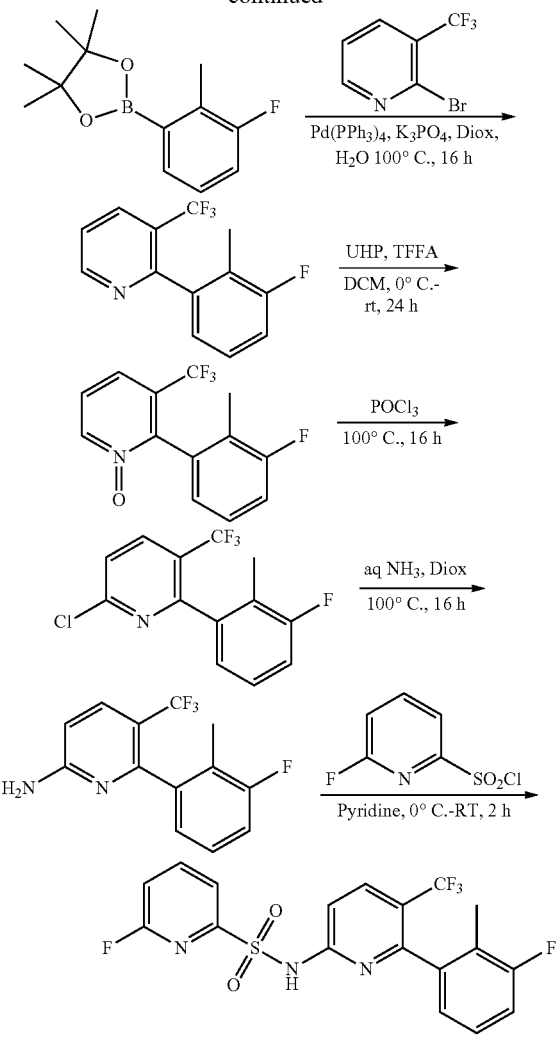

Step 1. Synthesis of 2-(3-fluoro-2-methylphenyl)-4,4,5,5-tetramethyl-1,3,2-dioxaborolane A solution of 1-bromo-3-fluoro-2-methylbenzene (24.0 g, 126.96 mmol) and bis(pinacolato)diboron (38.68 g, 152.35 mmol) and KOAc (37.38 g, 380.89 mmol) in dioxane was stirred under N₂ for 10 min. Then Pd(dppf)Cl₂.DCM (5.18 g, 6.35 mmol) and 1,1'-bis(diphenylphosphino)ferrocene (2.11 g, 3.808 mmol) were added and the reaction mixture was stirred at 90° C. for 16 h. After cooling to rt, the reaction mixture was diluted with water and extracted with EtOAc thrice. The combined organic portion was washed with water followed by brine solution, then dried over Na₂SO₄ and concentrated under reduced pressure. The residue was purified by column chromatography on silica gel (60-120 mesh size) (1-5% EtOAc in Hexane) to afford the title compound as a colorless oil (28 g, 93%). ¹H NMR (300 MHz, CD₃OD) δ ppm 7.52 (dd, J=6.9, 1.2 Hz, 1H), 7.17-7.03 (m, 2H), 1.35 (s, 12H).

Step 2. Synthesis of 2-(3-fluoro-2-methylphenyl)-3-(trifluoromethyl)pyridine

A solution of 2-bromo-3-(trifluoromethyl)pyridine (16.0 g, 70.79 mmol), 2-(3-fluoro-2-methylphenyl)-4,4,5,5-tetramethyl-1,3,2-dioxaborolane (20.0 g, 84.95 mmol) and K₃PO₄ (30.0 g, 141.59 mmol) in dioxane-water (240 mL:60 mL) stirred under argon for 15 min. Then Pd(PPh₃)₄ (8.18 g, 7.08 mmol) was added, degassed and stirred at 100° C. for 16 h. Then the reaction mixture was cooled to rt, diluted with water and extracted with EtOAc twice. Combined organic portion was washed with brine solution, dried over anhydrous Na₂SO₄ and concentrated. The residue was purified by flash column chromatography (40 g SiliCycle column, 5-7% EtOAc in Hexane elution) to yield the title compound as a pale yellow oil (14.5 g, 80%). LC/MS, ESI-MS (⁺): 256.05.

Step 3. Synthesis of 2-(3-fluoro-2-methylphenyl)-3-(trifluoromethyl)pyridine 1-oxide To a stirred solution of 2-(3-fluoro-2-methylphenyl)-3-(trifluoromethyl)pyridine (14.5 g, 56.81 mmol) in DCM (150 mL) was added UHP (10.95 g, 116.40 mmol). The solution was cooled to 0° C. with ice-bath and TFAA (15.7 mL, 125.76 mmol) was added dropwise. After completion of addition, reaction mixture was stirred at rt for 24 h. Then the reaction mixture was diluted with ice-water and neutralized with Na₂CO₃, organic layer was separated and the aqueous portion was extracted with DCM twice. The combined organic portion was washed with brine solution, dried over anhydrous Na₂SO₄ and concentrated. The crude mass was stirred with hexane for 15 min, the solid separated was collected by filtration and dried in vacuo to afford the product as a pale yellow solid (13.2 g, 85.7%). LC/MS, ESI-MS (⁺): 272.05. ¹H NMR (300 MHz, CDCl₃) δ ppm 8.49 (d, J=6.6 Hz, 1H), 7.64 (d, J=8.4 Hz, 1H), 7.45 (t, J=7.2 Hz, 1H), 7.32-7.25 (m, 1H), 7.17 (d, J=8.4 Hz, 1H), 6.95 (d, J=7.5 Hz, 1H), 2.03 (s, 3H).

Step 4. Synthesis of 6-chloro-2-(3-fluoro-2-methylphenyl)-3-(trifluoromethyl)pyridine A solution of 2-(3-fluoro-2-methylphenyl)-3-(trifluoromethyl)pyridine 1-oxide (14.0 g, 51.62 mmol) in POCl₃ (100 mL) was heated at 100° C. for 16 h. Then the reaction mixture was cooled, and concentrated under reduced pressure. The residue was poured into ice-water and extracted with EtOAc thrice. The combined organic portion was washed with sat. NaHCO₃, dried over Na₂SO₄ and concentrated to afford a crude oil. The crude mass was purified by flash column chromatography (40 g RediSep column, Hexane elution) to provide the title compound as colorless oil (10.5 g, 70%). LC/MS, ESI-MS (⁺): 290.0. ¹H NMR (400 MHz, CDCl₃) δ ppm 8.05 (d, J=8.4 Hz, 1H), 7.50 (d, J=8.4, 1H), 7.24-7.20 (m, 1H), 7.11 (t, J=8.8 Hz, 1H), 6.97 (d, J=8.0 Hz, 1H), 1.99 (s, 3H).

Step 5. Synthesis of 6-(3-fluoro-2-methylphenyl)-5-(trifluoromethyl)pyridin-2-amine To a stirred solution of 6-chloro-2-(3-fluoro-2-methylphenyl)-3-(trifluoromethyl)pyridine (4.3 g, 14.84 mmol) in dioxane (200 mL) was added aq. NH₃ (200 mL, 30%), the reaction vessel was closed and heated at 100° C. for 16 h. Reaction mixture was cooled to rt and extracted with EtOAc thrice. The combined organic portion dried over Na₂SO₄ and concentrated under reduced pressure to give crude residue. The residue was purified by flash column chromatography (40 g RediSep column, 10-50% EtOAC in Hexane elution) to afford 1.85 g (94%, based on starting material conversion; 2.2 g starting material recovered) product as a pale yellow solid. LC/MS, ESI-MS (⁺): 271.2.

Step 6. Synthesis of 6-fluoro-N-(6-(3-fluoro-2-methylphenyl)-5-(trifluoromethyl)pyridin-2-yl)pyridine-2-sulfonamide The solution of 6-(3-fluoro-2-methylphenyl)-5-(trifluoromethyl)pyridin-2-amine (1.9 g, 7.03 mmol) in pyridine (15 mL) was cooled to 0° C. and 6-fluoropyridine-2-sulfonyl chloride (1.92 g, 9.84 mmol) was added dropwise. Reaction mixture was allowed to stir at rt for 16 h. Then the reaction was quenched with water and extracted with DCM thrice. The combined organic portion was washed with brine, dried over Na₂SO₄ and concentrated to afford an oily residue, which was purified by flash column chromatography (24 g SiliCycle, 25-30% EtOAc in Hexane elution) to afford Intermediate (8): as an off white solid (1.99 g, 65.9%). LC/MS, ESI-MS (⁺): 430.2. ¹H NMR (400 MHz, CDCl₃) δ ppm 8.03-7.49 (m, 3H), 7.44 (d, J=8.8 Hz, 1H), 7.24-7.21 (m, 1H), 7.16-7.12 (m, 1H), 6.99 (d, J=7.6 Hz, 1H), 2.00 (s, 3H).

Intermediate (9)

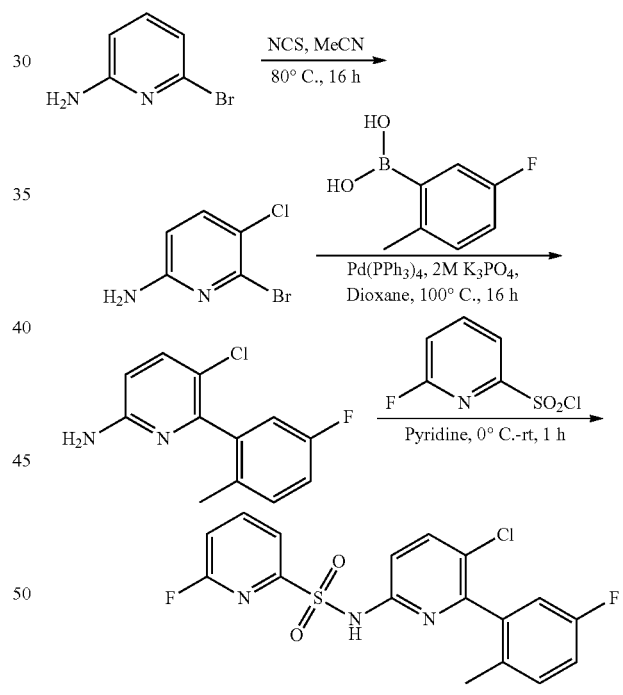

(9)

Step 1. Synthesis of 6-bromo-5-chloropyridin-2-amine

The title compound was prepared analogous to the literature procedure (WO2015/97122). A solution of 6-bromopyridin-2-amine (20.0 g, 115.60 mmol) and N-chlorosuccinimide (15.43 g, 115.60 mmol) in acetonitrile (250 mL) was heated at 80° C. for 16 h. Reaction mixture was cooled, concentrated under reduced pressure. The residue was diluted with sat. NaHCO₃ solution (100 mL) and extracted with EtOAc thrice. The combined organic portion was washed with brine, dried over anhydrous Na$_2$SO$_4$, and concentrated under reduce pressure. The crude product mass was stirred with hexane, the solid separated was collected by filtration and dried in vacuo to yield the title compound as an off white solid (16.0 g, 61%). LC/MS, ESI-MS (+): 210.9.

Step 2. Synthesis of 5-chloro-6-(5-fluoro-2-methylphenyl)pyridin-2-amine

To a stirred solution of 6-bromo-5-chloropyridin-2-amine (7.5 g, 36.15 mmol) in dioxane (120 mL) were added (5-fluoro-2-methylphenyl)boronic acid (6.7 g, 43.38 mmol) and 2M K$_3$PO$_4$ solution (55 mL) under N$_2$. Then Pd(PPh$_3$)$_4$ (4.2 g, 3.62 mmol) was added, degassed and the reaction mixture was stirred at 100° C. for 16 h. The reaction mixture was cooled to rt, filtered through a celite bed, which was thoroughly washed with EtOAc. The organic portion was separated and washed with 10% HCl solution thrice. The combined (acidic) aqueous portion was basified with saturated NaHCO$_3$ solution and extracted with EtOAC thrice. The combined EtOAc extract was washed with brine solution, dried over anhydrous Na$_2$SO$_4$ and concentrated. The residue was stirred with hexane, filtered and solid collected was dried in vacuo to yield 7.2 g (84%) product as an off white solid. LC/MS, ESI-MS (+): 237.0. $^1$H NMR (300 MHz, CDCl$_3$) δ ppm 7.50 (d, J=8.7 Hz, 1H), 7.24-7.19 (m, 1H), 7.03-6.94 (m, 2H), 6.49 (d, J=8.7 Hz, 1H), 4.55 (brs, 2H), 2.15 (s, 3H).

Step 3. Synthesis of N-(5-chloro-6-(5-fluoro-2-methylphenyl)pyridin-2-yl)-6-fluoropyridine-2-sulfonamide The solution of 5-chloro-6-(5-fluoro-2-methylphenyl)pyridin-2-amine (5.0 g, 21.12 mmol) in pyridine (10 mL) was cooled to 0° C. and 6-fluoropyridine-2-sulfonyl chloride (4.95 g, 25.35 mmol) was added dropwise. Reaction mixture was allowed to stir at rt for 16 h. The reaction was quenched with ice and stirred for 2 h. the solid separated was filtered, washed with water and hexane. And then dried in vacuo to yield Intermediate (9): as a pale brown solid (5.5 g, 65.8%). LC/MS, ESI-MS (+): 396.0. $^1$H NMR (400 MHz, CD$_3$OD) δ ppm 8.06-8.00 (m, 1H), 7.89 (dd, J=7.6, 2.4 Hz, 1H), 7.82 (d, J=8.8 Hz, 1H), 7.28-7.20 (m, 3H), 7.03 (td, J=8.8, 3.2 Hz, 1H), 6.72 (dd, J=9.2, 2.8 Hz, 1H), 1.92 (s, 3H).

Intermediate (10)

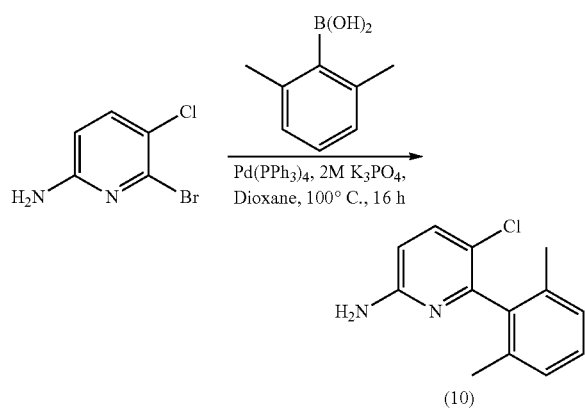

To a stirred solution of 6-bromo-5-chloropyridin-2-amine (5.0 g, 24.10 mmol) in dioxane (60 mL) were added (2,6-dimethylphenyl)boronic acid (5.42 g, 36.15 mmol) and 2M K$_3$PO$_4$ solution (36.3 mL) under N$_2$. Then Pd(PPh$_3$)$_4$ (2.8 g, 2.41 mmol) was added, degassed and the reaction mixture was stirred at 100° C. for 16 h. Then the reaction mixture was cooled to rt, diluted with water and extracted with EtOAc twice. Combined organic portion was washed with brine solution, dried over anhydrous Na$_2$SO$_4$ and concentrated. The residue was purified by flash column chromatography (12 g SiliCycle column, 14% EtOAc in Hexane elution) to afford Intermediate (10): as an off white solid. LC/MS, ESI-MS (+): 233.2. $^1$H NMR (300 MHz, CDCl$_3$) δ ppm 7.52 (d, J=8.4 Hz, 1H), 7.21-7.17 (m, 1H), 7.10-7.08 (m, 2H), 6.47 (d, J=8.7 Hz, 1H), 4.54 (brs, 2H), 2.06 (s, 3H)

Intermediate (11): 6-fluoro-N-(6-(2-isopropylphenyl)-5-(trifluoromethyl)pyridin-2-yl)pyridine-2-sulfonamide

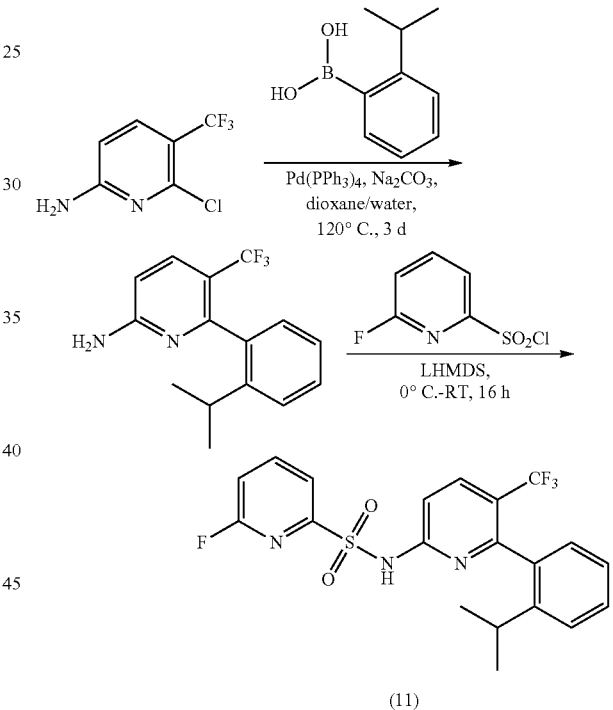

Step 1. Synthesis of 6-(2-isopropylphenyl)-5-(trifluoromethyl)pyridin-2-amine

In a vial, 6-chloro-5-(trifluoromethyl)pyridin-2-amine (2.0 g, 10.18 mmol), (2-isopropylphenyl)boronic acid (2.003 g, 12.21 mmol), sodium carbonate (3.24 g, 30.5 mmol), and Pd(Ph$_3$P)$_4$ (1.176 g, 1.018 mmol) were taken up in dioxane (Volume: 20 mL, Ratio: 6.67) and water (Volume: 3 mL, Ratio: 1.000), the mixture was sparged with argon, then the reaction was heated to 120° C. for 3 d. The crude reaction material was evaporated on silica gel and purified by flash column chromatography (ISCO, 80 g silica gel column, 0-6% MeOH/DCM, dry loading) to give the product 6-(2-isopropylphenyl)-5-(trifluoromethyl)pyridin-2-amine (2.6102 g, 9.31 mmol, 92% yield) as a light yellow solid.

Step 2. Synthesis of 6-fluoro-N-(6-(2-isopropylphenyl)-5-(trifluoromethyl)pyridin-2-yl)pyridine-2-sulfonamide In a flask, 6-(2-isopropylphenyl)-5-(trifluoromethyl)pyridin-2-amine (2.61 g, 9.31 mmol) was taken up in THF (Volume: 100 mL) and the solution was cooled to 0° C. To the solution was added 1.0 M LHMDS in THF (18.62 mL, 18.62 mmol), then a solution of 6-fluoropyridine-2-sulfonyl chloride (3.64 g, 18.62 mmol) that had been dissolved in THF (5 mL). After stirring overnight the reaction was quenched with 1 M HCl and extracted into EtOAc (25 mL×3). The organics were then washed with water and brine, dried over MgSO$_4$, and concentrated in vacuo. The crude material was purified by flash column chromatography (ISCO, 220 g silica gel column, 0-80% EtOAc/heptanes) to give the title product Intermediate (11): 6-fluoro-N-(6-(2-isopropylphenyl)-5-(trifluoromethyl)pyridin-2-yl)pyridine-2-sulfonamide (3.3088 g, 7.53 mmol, 81% yield) as a light tan solid. LC/MS, ESI-MS (+): 440.1, RT: 1.84 min. $^1$H NMR (400 MHz, DMSO-d$_6$) δ 12.12 (s, 1H), 8.19 (d, J=8.9 Hz, 1H), 8.10 (q, J=7.8 Hz, 1H), 7.83 (dd, J=7.4, 2.1 Hz, 1H), 7.48 (ddd, J=8.3, 2.4, 0.7 Hz, 1H), 7.43-7.34 (m, 2H), 7.29 (s, 1H), 7.17 (ddd, J=7.6, 6.7, 1.8 Hz, 1H), 6.89 (d, J=7.6 Hz, 1H), 2.34-2.27 (m, 1H), 1.01 (d, J=6.8 Hz, 3H), 0.91 (d, J=6.8 Hz, 3H).

Intermediate (12): rac-ethyl (1SR,3SR,4RS)-3-(((benzyloxy)carbonyl)amino)-7-oxabicyclo[2.2.1]heptane-1-carboxylate

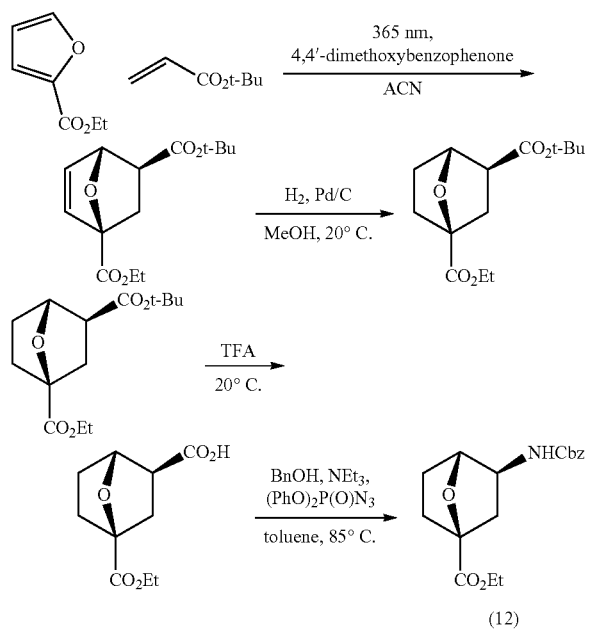

(12)

Step 1. Synthesis of rac-3-(tert-butyl) 1-ethyl (1RS,3SR,4RS)-7-oxabicyclo[2.2.1]hept-5-ene-1,3-dicarboxylate A solution of ethyl 2-furoate (12 g, 86 mmol), tert-butyl acrylate (62.1 mL, 428 mmol) and 4,4'-dimethoxybenzophenone (2.075 g, 8.56 mmol) in acetonitrile (428 mL) was passed through a flow photoreactor (reactor volume 0.9 mL; PFA tubing 0.04" ID, 0.0625" ID; irradiated area 20 cm$^2$; 365 nm LED; 11 W radiant flux) equipped with 8-bar back pressure regulator at a rate of 0.4 mL per minute (Vapourtec R-Series pump). The solvent was then removed and the material was purified by flash column chromatography (ISCO, 220 g silica gel column, 0-60% EtOAc/hexanes) to afford rac-3-(tert-butyl) 1-ethyl (1RS,3SR,4RS)-7-oxabicyclo[2.2.1]hept-5-ene-1,3-dicarboxylate (7.05 g, 21.02 mmol, 25% yield), contaminated with a small amount of sensitizer. LC/MS, ESI-MS (M+Na$^+$): 291.2 observed. $^1$H NMR (400 MHz, Chloroform-d) δ 6.48 (d, J=5.6 Hz, 1H), 6.45 (dd, J=5.7, 1.7 Hz, 1H), 5.23 (d, J=1.7 Hz, 1H), 4.33 (q, J=7.3 Hz, 2H), 2.47 (dd, J=8.5, 4.0 Hz, 1H), 2.29 (dd, J=11.5, 4.0 Hz, 1H), 1.88 (dd, J=11.5, 8.5 Hz, 1H), 1.47 (s, 9H), 1.35 (t, J=7.1 Hz, 3H). $^{13}$C NMR (101 MHz, CDCl3) δ 171.5, 169.5, 136.6, 135.6, 87.0, 82.1, 81.2, 61.7, 45.5, 32.8, 28.1, 14.2.

Step 2. Synthesis of rac-3-(tert-butyl) 1-ethyl (1SR,3SR,4RS)-7-oxabicyclo[2.2.1]heptane-1,3-dicarboxylate A solution of rac-3-(tert-butyl) 1-ethyl (1RS,3SR,4RS)-7-oxabicyclo[2.2.1]hept-5-ene-1,3-dicarboxylate (7.05 g, 26.3 mmol) in methanol (10 mL) was added to a vial containing palladium on carbon, 10% (0.125 g, 0.118 mmol). The atmosphere in the vial was exchanged for hydrogen and the reaction was stirred under hydrogen overnight. The atmosphere was then exchanged for nitrogen and the catalyst was removed by filtration. The solvent was removed, and the residue was purified by flash column chromatography to afford rac-3-(tert-butyl) 1-ethyl (1SR,3SR,4RS)-7-oxabicyclo[2.2.1]heptane-1,3-dicarboxylate (5.84 g, 20.52 mmol, 78% yield).

Step 3. Synthesis of rac-(1RS,2SR,4SR)-4-(ethoxycarbonyl)-7-oxabicyclo[2.2.1]heptane-2-carboxylic Acid A sample of rac-3-(tert-butyl) 1-ethyl (1SR,3SR,4RS)-7-oxabicyclo[2.2.1]heptane-1,3-dicarboxylate (2.82 g, 8.35 mmol) was treated with trifluoroacetic acid (10 mL, 130 mmol) and aged for 2 hours. The solvent was then removed and the residue was co-evaporated with toluene 3 times to afford rac-(1RS,2SR,4SR)-4-(ethoxycarbonyl)-7-oxabicyclo[2.2.1]heptane-2-carboxylic acid (2.1 g, 9.80 mmol, quantitative yield). LC/MS, ESI-MS (+): 215.1 observed. $^1$H NMR (400 MHz, Chloroform-d) δ 5.01 (d, J=4.9 Hz, 1H), 4.31 (qd, J=7.2, 3.1 Hz, 2H), 2.84 (dd, J=9.1, 4.9 Hz, 1H), 2.42-2.34 (m, 2H), 2.18 (dd, J=12.6, 9.1 Hz, 1H), 2.09-1.89 (m, 3H), 1.77-1.66 (m, 1H), 1.35 (t, J=7.1 Hz, 3H).

Step 4. Synthesis of rac-ethyl (1SR,3SR,4RS)-3-(((benzyloxy)carbonyl)amino)-7-oxabicyclo[2.2.1]heptane-1-carboxylate A solution of rac-(1RS,2SR,4SR)-4-(ethoxycarbonyl)-7-oxabicyclo[2.2.1]heptane-2-carboxylic acid (1.789 g, 8.35 mmol), DPPA (3.45 g, 12.53 mmol) and triethylamine (3.49 mL, 25.05 mmol) in toluene (15 mL) was heated to 85° C. for 1 hour. The reaction was then treated with the benzyl alcohol (1.736 mL, 16.70 mmol) and stirred at 85° C. for 4 hours. The reaction was then cooled to room temperature, diluted with ethyl acetate, washed with 1 M aqueous NaOH twice, 1 M aqueous HCl twice, and water once, dried over MgSO$_4$, filtered, evaporated, and purified by flash column chromatography (ISCO, 80 g silica gel column, 0-60% EtOAc/hexanes) to afford the title compound Intermediate (12): rac-ethyl (1SR,3SR,4RS)-3-(((benzyloxy)carbonyl) amino)-7-oxabicyclo[2.2.1]heptane-1-carboxylate (1.67 g, 4.97 mmol, 60% yield) as a colorless oil that solidified upon standing. LC/MS, ESI-MS (+): 320.2 observed. $^1$H NMR (400 MHz, Chloroform-d) δ 7.39-7.28 (m, 5H), 5.08 (s, 2H), 4.47 (d, J=5.0 Hz, 1H), 4.27 (qd, J=7.1, 1.0 Hz, 2H), 3.99 (td, J=8.3, 3.1 Hz, 1H), 2.38 (dd, J=13.3, 8.0 Hz, 1H), 1.85 (dddd, J=17.9, 8.9, 7.7, 3.8 Hz, 3H), 1.71-1.58 (m, 3H), 1.31 (t, J=7.1 Hz, 3H). $^{13}$C NMR (101 MHz, CDCl3) δ 170.87, 155.76, 136.47, 128.66, 128.62, 128.27, 128.13, 128.09, 84.18, 82.75, 66.86, 61.61, 55.37, 43.49, 32.94, 26.68, 14.30.

Intermediate (13): rac-tert-butyl (1SR,6RS,7SR)-3-oxo-2-azabicyclo[4.2.0]oct-4-ene-7-carboxylate and Intermediate (14): rac-tert-butyl (1SR,5RS,6RS, 7SR)-5-allyl-2-azabicyclo[4.2.0]octane-7-carboxylate

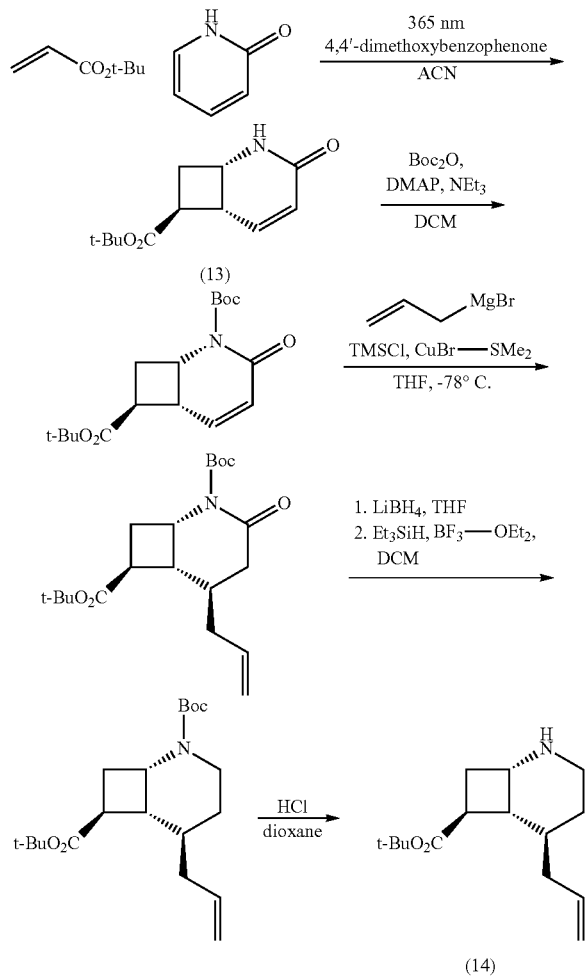

Step 1. Synthesis of rac-tert-butyl (1SR,6RS,7SR)-3-oxo-2-azabicyclo[4.2.0]oct-4-ene-7-carboxylate A solution of tert-butyl acrylate (51.3 mL, 350 mmol), 4,4'-dimethoxybenzophenone (0.848 g, 3.50 mmol) and pyridin-2(1H)-one (3.328 g, 35.0 mmol) in acetonitrile (350 mL) was passed through the flow photoreactor (reactor volume 0.9 mL; PFA tubing 0.04" ID, 0.0625" ID; irradiated area 20 cm$^2$; 365 nm LED; 11 W radiant flux) equipped with 8-bar back pressure regulator at a rate of 0.50 mL per minute (Vapourtec R-Series pump). The solvent was removed and the resulting residue was purified by flash column chromatography (ISCO, 220 g silica gel column, 0-100% EtOAc/hexanes) to afford Intermediate (13): rac-tert-butyl (1SR, 6RS,7SR)-3-oxo-2-azabicyclo[4.2.0]oct-4-ene-7-carboxylate (2.87 g, 12.21 mmol, 35% yield). LC/MS, ESI-MS (+): 224.2 observed. $^1$NMR (400 MHz, Chloroform-d) δ 6.55 (ddd, J=10.0, 4.1, 0.8 Hz, 1H), 5.91 (dt, J=10.1, 1.4 Hz, 1H), 4.28 (tt, J=7.3, 3.8 Hz, 1H), 3.42-3.34 (m, 1H), 2.94 (dtd, J=9.5, 5.0, 1.2 Hz, 1H), 2.59-2.43 (m, 2H), 1.46 (s, 9H). $^{13}$NMR (101 MHz, CDCl$_3$) δ 173.23, 164.18, 141.25, 123.35, 81.39, 46.37, 43.49, 37.25, 34.71, 28.22, 28.19, 28.15, 28.12.

Step 2. Synthesis of rac-di-tert-butyl (1SR,6RS, 7SR)-3-oxo-2-azabicyclo[4.2.0]oct-4-ene-2,7-dicarboxylate A solution of Intermediate (13): rac-tert-butyl (1SR,6RS, 7SR)-3-oxo-2-azabicyclo[4.2.0]oct-4-ene-7-carboxylate (2.00 g, 8.96 mmol), BOC-anhydride (4.16 mL, 17.92 mmol), DMAP (1.642 g, 13.44 mmol) and TEA (2.497 mL, 17.92 mmol) in dichloromethane (Volume: 10 mL) was stirred at room temperature for 2.5 hours. The reaction was diluted with ethyl acetate and washed with water followed by saturated sodium bicarbonate and brine. The organics were dried over MgSO$_4$, filtered, evaporated and purified by flash column chromatography (ISCO, 80 g silica gel column, 0-50% EtOAc/toluene) to afford rac-di-tert-butyl (1SR,6RS, 7SR)-3-oxo-2-azabicyclo[4.2.0]oct-4-ene-2,7-dicarboxylate (2.675 g, 8.19 mmol, 91% yield) as a colorless oil that solidified upon standing under vacuum overnight. LC/MS, ESI-MS (M-tBu+H$^+$): 268.0 observed. $^1$H NMR (400 MHz, Chloroform-d) δ 6.60 (ddd, J=9.9, 3.8, 0.9 Hz, 1H), 5.96 (dd, J=9.9, 1.8 Hz, 1H), 4.91 (tdd, J=9.1, 7.6, 1.0 Hz, 1H), 3.48 (dddt, J=7.5, 3.7, 1.9, 1.0 Hz, 1H), 2.83 (dtd, J=10.3, 3.8, 1.1 Hz, 1H), 2.62 (dddd, J=11.8, 8.0, 3.7, 2.7 Hz, 1H), 2.53 (dddd, J=12.3, 10.3, 8.2, 1.0 Hz, 1H), 1.52 (s, 9H), 1.48 (s, 9H). $^{13}$C NMR (101 MHz, CDCl$_3$) δ 172.92, 162.18, 151.66, 141.67, 125.00, 83.23, 81.52, 49.34, 41.96, 38.62, 33.62, 28.15.

Step 3. Synthesis of rac-di-tert-butyl (1SR,5RS, 6RS,7SR)-5-allyl-3-oxo-2-azabicyclo[4.2.0]octane-2,7-dicarboxylate A suspension of copper(I) bromide-dimethyl sulfide complex (8.50 g, 41.4 mmol) in THF (75 mL) was cooled in a dry ice/acetone bath and treated with allylmagnesium bromide (41.4 mL, 41.4 mmol). The resulting mixture was stirred at −78° C. for 1 hour. A solution of rac-di-tert-butyl (1SR,6RS,7SR)-3-oxo-2-azabicyclo[4.2.0]oct-4-ene-2,7-dicarboxylate (2.675 g, 8.27 mmol) in THF (120 mL) was cooled in a dry ice/acetone bath and treated with TMS-Cl (2.115 mL, 16.54 mmol). The solution of enone was then transferred by cannula to the stirring cuprate solution and the resulting mixture was stirred at −78° C. for 1 hour. The reaction was quenched by addition of saturated ammonium chloride solution and allowed to warm to room temperature. The reaction was diluted with ethyl acetate and water. The organics were isolated and washed once with water, dried over MgSO4, filtered, evaporated and purified by flash column chromatography (ISCO, 80 g silica gel column, 0-50% EtOAc/heptane) to afford rac-di-tert-butyl (1SR,5RS, 6RS,7SR)-5-allyl-3-oxo-2-azabicyclo[4.2.0]octane-2,7-dicarboxylate (2.708 g, 7.04 mmol, 85% yield). LC/MS, ESI-MS (M-tBu+H⁺): 310.2 observed. $^1$H NMR (400 MHz, Chloroform-d) δ 5.78-5.65 (m, 1H), 5.09 (s, 1H), 5.08-5.04 (m, 1H), 4.52-4.44 (m, 1H), 2.77-2.65 (m, 2H), 2.65-2.58 (m, 1H), 2.52 (tt, J=9.1, 2.8 Hz, 1H), 2.31-2.21 (m, 2H), 2.11-1.95 (m, 3H), 1.50 (s, 9H), 1.47 (s, 9H). $^{13}$C NMR (101 MHz, CDCl₃) δ 173.79, 171.13, 150.97, 134.40, 118.15, 83.15, 81.00, 50.28, 42.11, 39.19, 39.06, 37.45, 35.14, 32.73, 28.18, 28.15.

Step 4. Synthesis of rac-di-tert-butyl (1SR,5RS, 6RS,7SR)-5-allyl-2-azabicyclo[4.2.0]octane-2,7-dicarboxylate A solution of rac-di-tert-butyl (1SR,5RS,6RS,7SR)-5-allyl-3-oxo-2-azabicyclo[4.2.0]octane-2,7-dicarboxylate (2.40 g, 6.57 mmol) in THF (20 mL) was cooled to −20° C. in an ice/salt bath and treated with LiBH₄ (0.5 M in ether) (13.13 mL, 6.57 mmol). After stirring for 1.5 hours, the reaction was quenched by addition of saturated ammonium chloride solution. The reaction was then diluted with ethyl acetate and water. The organics were separated, washed with water, dried over MgSO₄, filtered, and concentrated. The resulting oil was treated with triethylsilane (2.291 g, 19.70 mmol) and dissolved in DCM (20.00 mL), cooled in a dry ice/acetone bath and treated with BF₃—OEt₂ (2.497 mL, 19.70 mmol). After stirring for 1.5 hours, the reaction was quenched by addition of saturated sodium bicarbonate solution. The organics were separated and the aqueous layer was extracted with dichloromethane twice. The combined organics were dried over MgSO₄, filtered, evaporated, and purified by flash column chromatography (ISCO, 80 g Gold silica column, 5-50% EtOAc/heptane) to afford rac-di-tert-butyl (1SR,5RS,6RS,7SR)-5-allyl-2-azabicyclo[4.2.0]octane-2,7-dicarboxylate (1.935 g, 5.51 mmol, 84% yield). LC/MS, ESI-MS (M-tBu+H⁺): 296.2 observed. $^1$H NMR (400 MHz, Chloroform-d) δ 5.78 (dddd, J=16.9, 10.2, 7.8, 6.6 Hz, 1H), 5.07-5.03 (m, 1H), 5.03-5.00 (m, 1H), 4.68-4.46 (m, 1H), 3.79 (d, J=11.7 Hz, 1H), 2.98 (t, J=11.6 Hz, 1H), 2.60-2.51 (m, 1H), 2.49-2.24 (m, 3H), 2.19 (dt, J=12.6, 6.1 Hz, 1H), 1.99 (dt, J=14.1, 7.7 Hz, 1H), 1.82-1.69 (m, 1H), 1.64-1.53 (m, 2H), 1.46 (s, 9H), 1.44 (s, 9H), 1.08 (dtd, J=13.5, 11.7, 4.0 Hz, 1H). $^{13}$C NMR (101 MHz, CDCl3) δ 136.16, 116.90, 80.38, 79.56, 46.60, 43.77, 40.99, 40.60, 39.11, 37.81, 30.10, 28.60, 28.20.

Step 5. Synthesis of rac-tert-butyl (1SR,5RS,6RS, 7SR)-5-allyl-2-azabicyclo[4.2.0]octane-7-carboxylate A solution of rac-di-tert-butyl (1SR,5RS,6RS,7SR)-5-allyl-2-azabicyclo[4.2.0]octane-2,7-dicarboxylate (1.83 g, 5.21 mmol) in HCl (2M in diethyl ether) (2 mL, 4.00 mmol) was aged for 6.5 hours. The solvent was removed and the reaction was partitioned between ethyl acetate and 1 M NaOH. The aqueous phase was isolated and extracted once with ethyl acetate. The combined organics were dried over MgSO₄, filtered and evaporated to afford the title compound Intermediate (14): rac-tert-butyl (1SR,5RS,6RS,7SR)-5-allyl-2-azabicyclo[4.2.0]octane-7-carboxylate (840 mg, 3.27 mmol, 62.9% yield) as an oil.

Intermediate (15): N-(3-chloro-2'-isopropyl-[2,3'-bipyridin]-6-yl)-6-fluoropyridine-2-sulfonamide

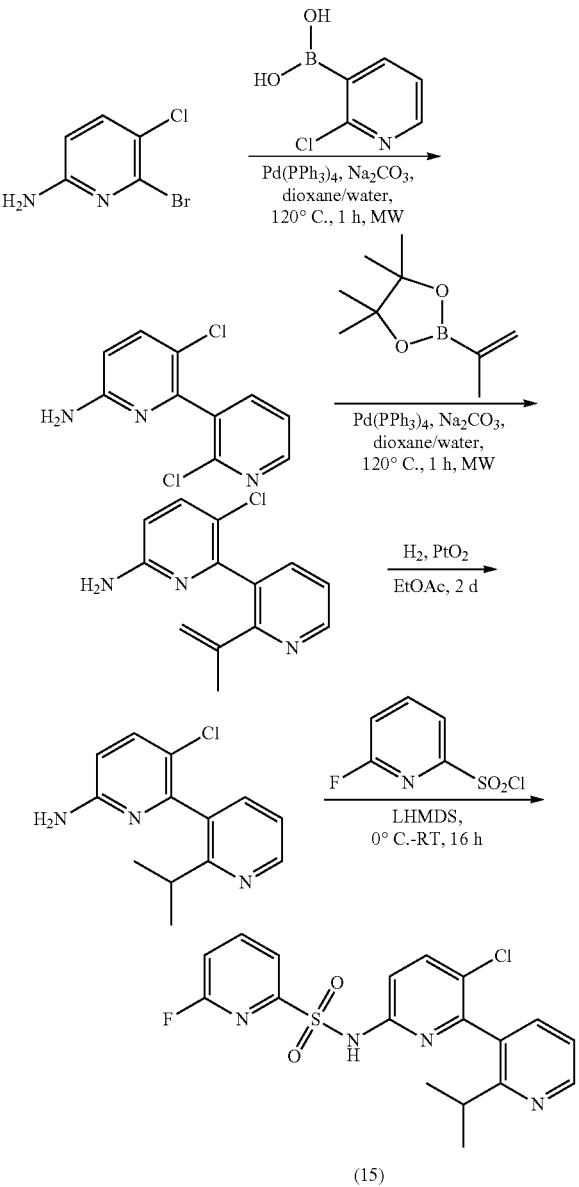

(15)

Step 1. Synthesis of 2',3-dichloro-[2,3'-bipyridin]-6-amine

In a microwave vial, 6-bromo-5-chloropyridin-2-ylamine (2.2 g, 10.60 mmol), 2-chloropyridine-3-boronic acid (2.003 g, 12.73 mmol), sodium carbonate (3.37 g, 31.8 mmol), and Pd(Ph₃P)₄ (1.225 g, 1.060 mmol) were taken up in dioxane (Volume: 12 mL, Ratio: 6.00) and water (Volume: 2 mL, Ratio: 1.000), the solution was sparged with argon, then the reaction was heated in the microwave to 120° C. for 1 h. The crude reaction material was evaporated on silica gel and purified by flash column chromatography (ISCO, 80 g silica gel column, 0-6% MeOH/DCM, dry loading) to give the product 2',3-dichloro-[2,3'-bipyridin]-6-amine (2.1941 g, 9.14 mmol, 86% yield) as a light orange solid.

Step 2. Synthesis of 3-chloro-2'-(prop-1-en-2-yl)-[2,3'-bipyridin]-6-amine

In a microwave vial, 2',3-dichloro-[2,3'-bipyridin]-6-amine (1.19 g, 4.96 mmol), 2-isopropenylboronic acid, pinacol ester (1.118 mL, 5.95 mmol), sodium carbonate (1.576 g, 14.87 mmol), and Pd(Ph$_3$P)$_4$ (0.573 g, 0.496 mmol) were taken up in dioxane (Volume: 12 mL, Ratio: 6.00) and water (Volume: 2 mL, Ratio: 1.000), the solution was sparged with Ar, then the reaction was heated in the microwave to 120° C. for 1 h. The crude reaction material was evaporated on silica gel and purified by flash column chromatography (ISCO, 80 g silica gel column, 0-8% MeOH/DCM, dry loading) to give the product 3-chloro-2'-(prop-1-en-2-yl)-[2,3'-bipyridin]-6-amine (489 mg, 1.99 mmol, 40% yield) as a yellow solid.

Step 3. Synthesis of 3-chloro-2'-isopropyl-[2,3'-bipyridin]-6-amine

In a vial, 3-chloro-2'-(prop-1-en-2-yl)-[2,3'-bipyridin]-6-amine (489 mg, 1.990 mmol) was taken up in EtOAc (Volume: 5 mL) and platinum(IV) oxide (48.8 mg, 0.199 mmol) was added, then the suspension was sparged with hydrogen and allowed to stir for 2 d. The reaction was filtered and the resulting solution was concentrated in vacuo to give the product 3-chloro-2'-isopropyl-[2,3'-bipyridin]-6-amine (579.3 mg) that was taken on directly to the next reaction with no purification. LC/MS, ESI-MS (+): 248.1, RT: 1.01 min. $^1$H NMR (400 MHz, Methanol-d$_4$) (8.55 (dd, J=4.9, 1.8 Hz, 1H), 7.60 (dd, J=7.7, 1.8 Hz, 1H), 7.56 (d, J=8.9 Hz, 1H), 7.33 (dd, J=7.7, 4.9 Hz, 1H), 6.62 (d, J=8.9 Hz, 1H), 2.92 (hept, J=6.8 Hz, 1H), 1.24-1.11 (m, 6H).

Step 4. Synthesis of N-(3-chloro-2'-isopropyl-[2,3'-bipyridin]-6-yl)-6-fluoropyridine-2-sulfonamide In a vial, 3-chloro-2'-isopropyl-[2,3'-bipyridin]-6-amine (579.3 mg, 2.338 mmol) was taken up in THF (Volume: 20 mL) and the solution was cooled to 0° C. To the solution was added 1.0 M LHMDS in THF (4.68 mL, 4.68 mmol), then a solution of 6-fluoropyridine-2-sulfonyl chloride (915 mg, 4.68 mmol) that had been dissolved in THF (2 mL). After stirring overnight the reaction was quenched with sat. aq. NH$_4$Cl and extracted into EtOAc (10 mL×3). The organics were then washed with water and brine, dried over MgSO$_4$, and concentrated in vacuo. The crude material was purified by flash column chromatography (ISCO, 12 g silica gel column, 0-5% MeOH/DCM) to give the title product Intermediate (15): N-(3-chloro-2'-isopropyl-[2,3'-bipyridin]-6-yl)-6-fluoropyridine-2-sulfonamide (716.1 mg, 1.760 mmol, 75% yield) as a yellow solid. LC/MS, ESI-MS (+): 407.0, RT: 1.21 min. $^1$H NMR (400 MHz, Methanol-d$_4$) δ 8.53 (dd, J=4.9, 1.8 Hz, 1H), 8.04 (dt, J=8.3, 7.5 Hz, 1H), 7.89 (ddd, J=7.3, 2.1, 0.7 Hz, 1H), 7.86 (d, J=8.8 Hz, 1H), 7.43 (dd, J=7.7, 1.8 Hz, 1H), 7.32-7.24 (m, 3H), 2.72 (hept, J=6.8 Hz, 1H), 1.08 (d, J=44.1 Hz, 6H).

Intermediate (16): rac-tert-butyl (1SR,6RS,7SR)-2-azabicyclo[4.2.0]octane-7-carboxylate

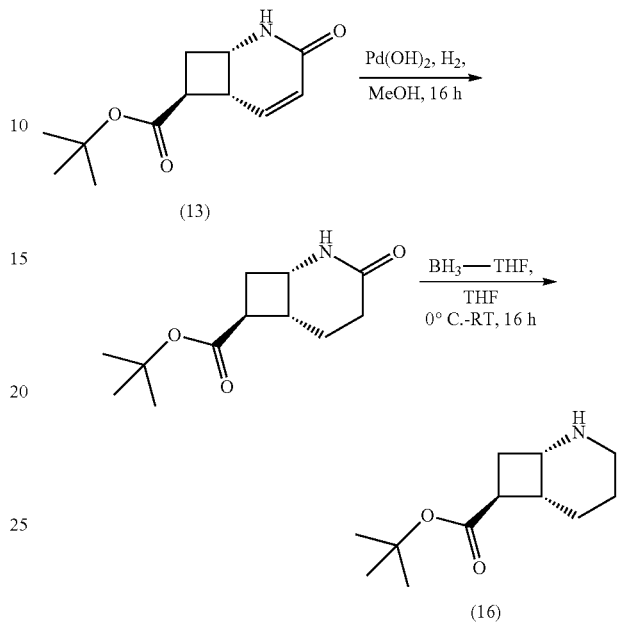

Step 1. Synthesis of rac-tert-butyl (1SR,6RS,7SR)-3-oxo-2-azabicyclo[4.2.0]octane-7-carboxylate In a vial, Intermediate (13): rac-tert-butyl (1SR,6RS,7SR)-3-oxo-2-azabicyclo[4.2.0]oct-4-ene-7-carboxylate (500 mg, 2.239 mmol) was taken up in MeOH (Volume: 10 mL), then 20% Pd(OH)$_2$ on carbon (629 mg, 0.896 mmol) was added and the reaction mixture was sparged with hydrogen. After stirring for 16 h, the reaction was filtered and the solution was concentrated in vacuo to give the crude product rac-tert-butyl (1SR,6RS,7SR)-3-oxo-2-azabicyclo[4.2.0]octane-7-carboxylate (476.2 mg, 2.114 mmol, 94% yield) as a white solid that was taken on directly to the next reaction.

Step 2. Synthesis of rac-tert-butyl (1SR,6RS,7SR)-2-azabicyclo[4.2.0]octane-7-carboxylate In a vial, crude rac-tert-butyl (1SR,6RS,7SR)-3-oxo-2-azabicyclo[4.2.0]octane-7-carboxylate (476.2 mg, 2.114 mmol) was taken up in THF (Volume: 10 mL), the solution was cooled to 0° C., then BH$_3$-THF (2.54 mL, 2.54 mmol) was added and the reaction was allowed to warm to RT for 16 h. No anticipated product was observed by LMCS, likely due to poor quality BH$_3$-THF. The reaction was cooled to 0° C., and additional BH$_3$-THF (2.54 mL, 2.54 mmol) was added from a new bottle, and the reaction was allowed to warm to RT. After stirring for 3 d, reaction was again cooled to 0° C. and a third portion of BH$_3$-THF (2.54 mL, 2.54 mmol) was added. After stirring for 16 h, the reaction was cooled to 0° C., quenched with AcOH, and concentrated. The resulting residue was dissolved in EtOAc and the organics were washed with sat. aq. NaHCO$_3$ and brine, dried over MgSO$_4$, and concentrated in vacuo to give the crude title product Intermediate (16): rac-tert-butyl (1SR,6RS, 7SR)-2-azabicyclo[4.2.0]octane-7-carboxylate that was used directly without purification.

Intermediate (17): 6-fluoro-N-(6-(2-(hydroxymethyl)phenyl)-5-(trifluoromethyl)pyridin-2-yl)pyridine-2-sulfonamide

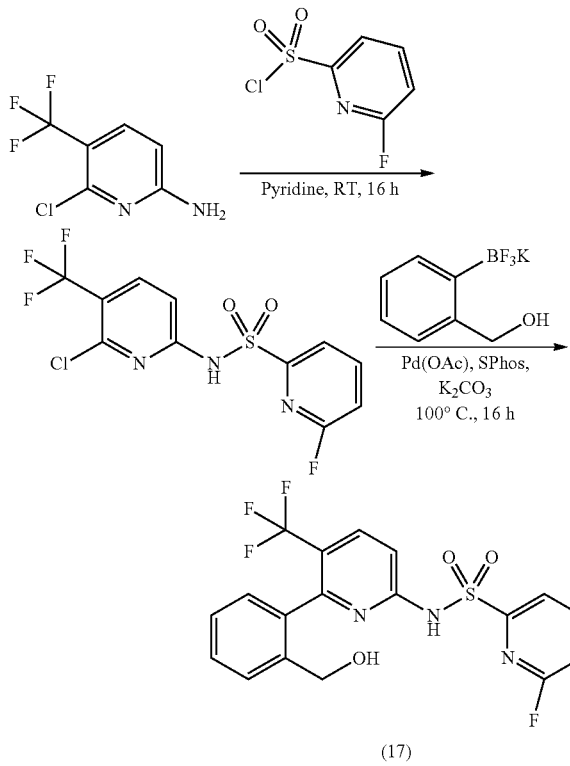

(17)

Step 1. Synthesis of N-(6-chloro-5-(trifluoromethyl)pyridin-2-yl)-6-fluoropyridine-2-sulfonamide 6-chloro-5-(trifluoromethyl)pyridin-2-amine (100 mg, 1.02 mmol) was suspended in pyridine (1 mL) and 6-fluoropyridine-2-sulfonyl chloride (219 mg, 1.12 mmol) was added. The reaction mixture was stirred at RT for 16 h. Pyridine was removed in vacuo and the resulting residue was dissolved in ethyl acetate. The organics were then washed with brine and water, dried over $Na_2SO_4$, filtered, and concentrated. The crude material was then subjected to flash column chromatography (ISCO, 24 g silica gel column, 0-60% EtOAc/heptane) to give the product N-(6-chloro-5-(trifluoromethyl)pyridin-2-yl)-6-fluoropyridine-2-sulfonamide (312 mg, 0.834 mmol, 82% yield) as light yellow solid. LC/MS, ESI-MS ($^+$): 356.0, RT: 1.69 min. $^1$H NMR (600 MHz, DMSO-$d_6$) δ 12.34 (s, 1H), 8.36 (dt, J=8.3, 7.6 Hz, 1H), 8.19-8.10 (m, 2H), 7.53 (ddd, J=8.3, 2.3, 0.7 Hz, 1H), 7.21-7.12 (m, 1H).

Step 2. Synthesis of 6-fluoro-N-(6-(2-(hydroxymethyl)phenyl)-5-(trifluoromethyl)pyridin-2-yl)pyridine-2-sulfonamide In a microwave vial, N-(6-chloro-5-(trifluoromethyl)pyridin-2-yl)-6-fluoropyridine-2-sulfonamide (100 mg, 0.28 mmol), (2-(trifluoro-l4-boranyl)phenyl)methanol, potassium salt (47 mg, 0.225 mmol), potassium carbonate (78 mg, 0.56 mmol), Pd(OAc)$_2$ (6 mg, 0.028 mmol) and 2-dicyclohexylphosphino-2',6'-dimethoxy-1,1'-biphenyl (Sphos) (23 mg, 0.056 mmol) were taken up in dioxane (Volume: 4 mL, Ratio: 4.00) and water (Volume: 1 mL, Ratio: 1.000), the solution was sparged with $N_2$, then the reaction was heated in the microwave to 120° C. for 1 h. The crude reaction material was evaporated on silica gel and purified by flash column chromatography (ISCO, 12 g silica gel column, 0-8% MeOH/DCM, dry loading) to give the product Intermediate (17): 6-fluoro-N-(6-(2-(hydroxymethyl)phenyl)-5-(trifluoromethyl)pyridin-2-yl)pyridine-2-sulfonamide (78 mg, 0.183 mmol, 65% yield) as a yellow solid. LC/MS, ESI-MS ($^+$): 428.1, RT: 1.54 min. $^1$H NMR (400 MHz, Methanol-$d_4$) δ 8.09 (d, J=8.8 Hz, 1H), 7.96 (dtd, J=9.1, 7.5, 1.6 Hz, 1H), 7.89-7.82 (m, 1H), 7.61-7.39 (m, 2H), 7.37-7.16 (m, 3H), 7.03 (d, J=7.6 Hz, 1H), 4.26 (d, J=11.8 Hz, 2H).

PREPARATION OF EXAMPLES

Example 129: (1s,4s)-4-((6-(N-(5-chloro-6-(2,6-dimethylphenyl)pyridin-2-yl)sulfamoyl)pyridin-2-yl)oxy)cyclohexane-1-carboxylic Acid

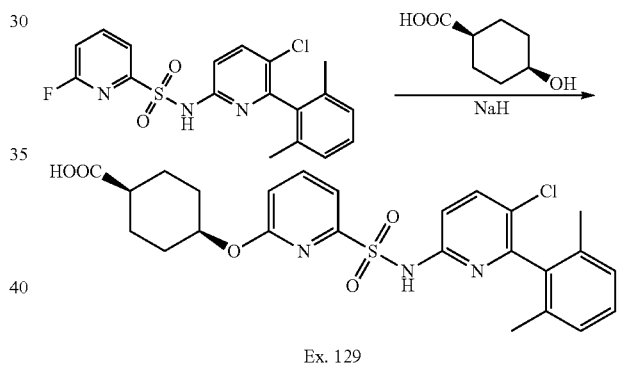

Ex. 129

Step 1

To a solution of cis-4-hydroxycyclohexanecarboxylic acid (33.1 mg, 0.23 mmol) in N-methylpyrrolidone (0.8 mL) was added sodium hydride (18 mg, 0.77 mmol). The mixture was stirred at rt for 30 min. Solid N-(5-chloro-6-(2,6-dimethylphenyl)pyridin-2-yl)-6-fluoropyridine-2-sulfonamide (30 mg, 0.077 mmol) was added and stirred at rt o/n. Quenched with water, acidified with 1 N HCl to pH 3-4, taken into ethyl acetate, washed twice with water, four washes with brine, dried over sodium sulfate, filtered, and concentrated. Purification by flash silica gel chromatography using 0-70% hexanes/ethyl acetate gradient afforded (1s,4s)-4-((6-(N-(5-chloro-6-(2,6-dimethylphenyl)pyridin-2-yl)sulfamoyl)pyridin-2-yl)oxy)cyclohexane-1-carboxylic acid (35.9 mg, 86% yield) as white solid: LCMS: Rt 1.56 min; m/z 516.2 [M+H]$^+$. $^1$H NMR (400 MHz, DMSO-$d_6$) δ 12.14 (s, 1H), 11.37 (s, 1H), 7.99 (d, J=8.8 Hz, 1H), 7.86 (dd, J=7.4, 8.3 Hz, 1H), 7.48 (dd, J=0.6, 7.3 Hz, 1H), 7.31 (d, J=8.2 Hz, 1H), 7.17 (m, 1H), 7.04 (m, 3H), 4.89 (m, 1H), 2.35 (m, 1H), 1.62 (m, 14H).

Example 249: 1-(6-(N-(5-chloro-6-(2,6-dimethylphenyl)pyridin-2-yl)sulfamoyl)pyridin-2-yl)-4-methylpiperidine-4-carboxylic Acid

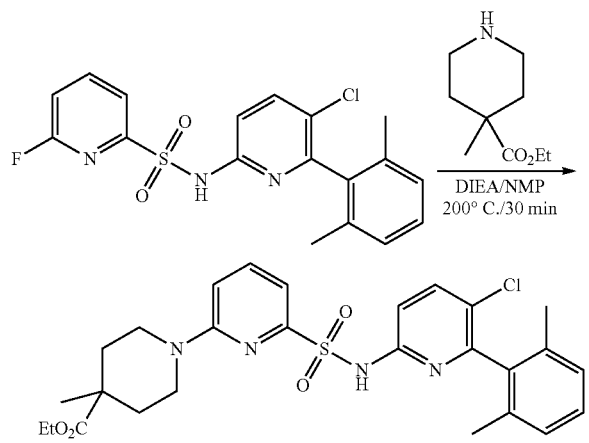

Ex. 249

Step 1

The mixture of methyl 4-hydroxypiperidine-4-carboxylate (172 mg, 0.829 mmol), N-(5-chloro-6-(2,6-dimethylphenyl)pyridin-2-yl)-6-fluoropyridine-2-sulfonamide (65 mg, 0.166 mmol) and Huenig's Base (0.290 mL, 1.659 mmol) in NMP (Volume: 1.5 mL) was microwaved at 200° C. for 30 min. LC-MS indicated that the reaction was complete. Aqueous work-up followed by ISCO purification (solid loading, 0-100% EtOAc in hexane) to yield the product ethyl 1-(6-(N-(5-chloro-6-(2,6-dimethylphenyl)pyridin-2-yl)sulfamoyl)pyridin-2-yl)-4-methylpiperidine-4-carboxylate (86 mg, 0.150 mmol, 91% yield) as a white solid. LC/MS, m/z 543.2 (M+H+), RT 1.82 min. $^1$H NMR (400 MHz, DMSO-d6) δ 11.15 (s, 1H), 7.96 (d, J=8.8 Hz, 1H), 7.67 (dd, J=8.7, 7.3 Hz, 1H), 7.33 (d, J=8.8 Hz, 1H), 7.21-7.14 (m, 1H), 7.10-7.01 (m, 4H), 4.09 (q, J=7.1 Hz, 2H), 3.85-3.76 (m, 2H), 3.05-2.94 (m, 2H), 1.91-1.81 (m, 2H), 1.27-1.20 (m, 2H), 1.17 (t, J=7.1 Hz, 3H), 1.10 (s, 3H).

Example 250: 1-(6-(N-(5-chloro-6-(2,6-dimethylphenyl)pyridin-2-yl)sulfamoyl)pyridin-2-yl)-4-methylpiperidine-4-carboxylic Acid

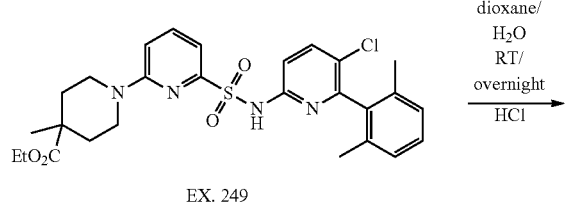

EX. 249

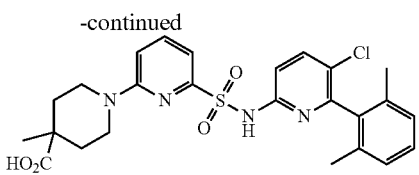

EX. 250

Step 1

To the solution of Example 249: ethyl 1-(6-(N-(5-chloro-6-(2,6-dimethylphenyl)pyridin-2-yl)sulfamoyl)pyridin-2-yl)-4-methylpiperidine-4-carboxylate (70 mg, 0.129 mmol) in Dioxane (Volume: 3 mL, Ratio: 1.000) was added a solution of LiOH (61.7 mg, 2.58 mmol) in Water (Volume: 3.00 mL, Ratio: 1.000). The resulting mixture was stirred at room temperature for overnight, LC-MS indicated that the reaction was complete. The reaction then was neutralized with 1N HCl at room temperature. The resulting mixture was then extracted with EtOAc. The combined organic phases were dried over Na2SO4, evaporated to yield Example 250: 1-(6-(N-(5-chloro-6-(2,6-dimethylphenyl)pyridin-2-yl)sulfamoyl)pyridin-2-yl)-4-methylpiperidine-4-carboxylic acid (69 mg, 0.127 mmol, 99% yield) as a white solid. LC/MS, m/z 515.2 (M+H+), RT 1.62 min.
$^1$H NMR (400 MHz, DMSO-d6) δ 7.93 (d, J=8.8 Hz, 1H), 7.66 (dd, J=8.6, 7.3 Hz, 1H), 7.33 (d, J=8.8 Hz, 1H), 7.20-7.13 (m, 1H), 7.09-6.98 (m, 4H), 3.87-3.74 (m, 2H), 3.07-2.95 (m, 2H), 1.85 (d, J=13.7 Hz, 2H), 1.75 (s, 6H), 1.21-1.11 (m, 2H), 1.09 (s, 3H).

Example 160: tert-butyl 4-(6-(N-(6-(o-tolyl)-5-(trifluoromethyl)pyridin-2-yl)sulfamoyl)pyridin-2-yl)piperazine-1-carboxylate

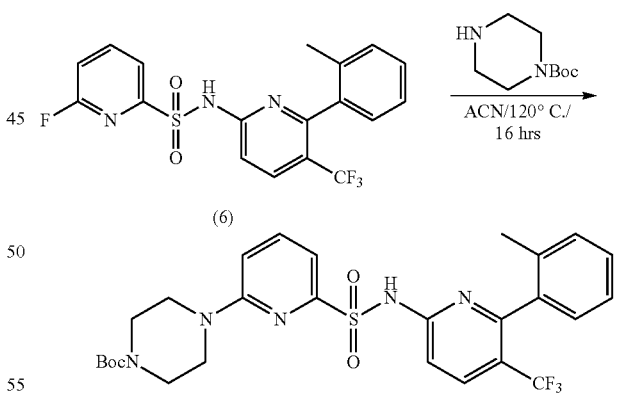

Ex. 160

The mixture of Intermediate (6) 6-fluoro-N-(6-(o-tolyl)-5-(trifluoromethyl)pyridin-2-yl)pyridine-2-sulfonamide (2000 mg, 4.86 mmol), tert-butyl piperazine-1-carboxylate (4528 mg, 24.31 mmol) and Acetonitrile (Volume: 60 mL) was stirred at 120° C. in a pressure tube for overnight. LC-MS indicated that the reaction was complete. Aqueous work-up followed by ISCO purification (0-100% EtOAc/hexane) to yield Example 160: tert-butyl 4-(6-(N-(6-(o-tolyl)-5-(trifluoromethyl)pyridin-2-yl)sulfamoyl)pyridin-2- yl)piperazine-1-carboxylate (2779 mg, 4.81 mmol, 98% yield) as a white solid. LC/MS, m/z 578.3 (M+H+), RT 1.77 min.

Example 161: 6-(piperazin-1-yl)-N-(6-(o-tolyl)-5-(trifluoromethyl)pyridin-2-yl)pyridine-2-sulfonamide (HCl Salt)

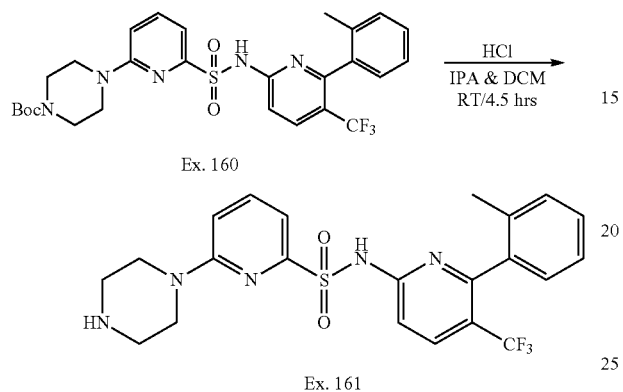

Ex. 160

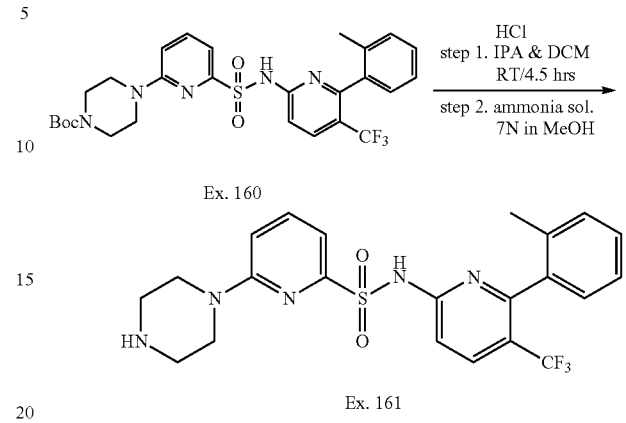

Example 161: 6-(piperazin-1-yl)-N-(6-(o-tolyl)-5-(trifluoromethyl)pyridin-2-yl)pyridine-2-sulfonamide Ex. 161

To Example 160: Tert-butyl 4-(6-(N-(6-(o-tolyl)-5-(trifluoromethyl)pyridin-2-yl)sulfamoyl)pyridin-2-yl)piperazine-1-carboxylate (2479 mg, 4.29 mmol) was added DCM (Volume: 20 mL) and 6 N HCl in IPA (20 mL, 120 mmol). The resulting solution was stirred at room temperature for 4 hrs 30 min. LC-MS indicated that the reaction was complete. Evaporation to remove the solvents, the residue was dried under vacuum for overnight. Then diethyl ether was added, filtration to yield Example 161: 6-(piperazin-1-yl)-N-(6-(o-tolyl)-5-(trifluoromethyl)pyridin-2-yl)pyridine-2-sulfonamide (HCl salt) (2.14 g, 3.96 mmol, 92% yield) as a white solid. LC/MS, m/z 478.2 3 (M+H+), RT 1.34 min. $^1$H NMR (400 MHz, Methanol-d4) δ 8.09 (d, J=8.9 Hz, 1H), 7.74 (dd, J=8.6, 7.4 Hz, 1H), 7.53 (d, J=8.8 Hz, 1H), 7.37 (d, J=7.3 Hz, 1H), 7.32 (td, J=7.5, 1.3 Hz, 1H), 7.27-7.16 (m, 2H), 7.10 (d, J=8.6 Hz, 1H), 7.05 (d, J=7.5 Hz, 1H), 3.82-3.73 (m, 4H), 3.27-3.20 (m, 4H), 1.93 (s, 3H).

To Example 160: To a solution of tert-butyl 4-(6-(N-(6-(o-tolyl)-5-(trifluoromethyl)pyridin-2-yl)sulfamoyl)pyridin-2-yl)piperazine-1-carboxylate (1.1323 g, 1.960 mmol) in dioxane (2.5 mL), 4N HCl in dioxane (12.25 mL, 49.0 mmol) was added, and the reaction mixture was stirred at rt for 18 h. The reaction mixture was concentrated in vacuo, then excess HCl was azeotroped twice with DCM and diethyl ether. The resulting yellow salt was triturated twice with diethyl ether, then was suspended in THF. The resulting solution was basified with a 7N ammonia in MeOH solution. The mixture was concentrated in vacuo, then was triturated twice with diethyl ether and DCM, followed by trituration with DI water The resulting white solid was dried over high vacuum at rt for 78 h, then at 50° C. for 18 h to yield 6-(piperazin-1-yl)-N-(6-(o-tolyl)-5-(trifluoromethyl)pyridin-2-yl)pyridine-2-sulfonamide as a white solid (784 mg, 84% yield). Condition 4, LCMS: R$_t$ 1.64 min; m/z 477.8 [M+H]$^+$. $^1$H NMR (400 MHz, DMSO-d6) δ 7.79 (d, J=8.9 Hz, 1H), 7.69 (dd, J=8.6, 7.3 Hz, 1H), 7.28-7.22 (m, 2H), 7.17 (d, J=8.8 Hz, 1H), 7.13-7.04 (m, 2H), 6.92 (d, J=7.3 Hz, 1H), 6.84 (d, J=8.6 Hz, 1H), 5.75 (s, 1H), 3.44 (s, 4H), 2.94 (d, J=3.7 Hz, 4H), 1.64 (s, 3H).

Example 291: rac-6-{[(3RS,4SR)-4-hydroxyoxolan-3-yl]oxy}-N-[6-(2-methylphenyl)-5-(trifluoromethyl)pyridin-2-yl]pyridine-2-sulfonamide

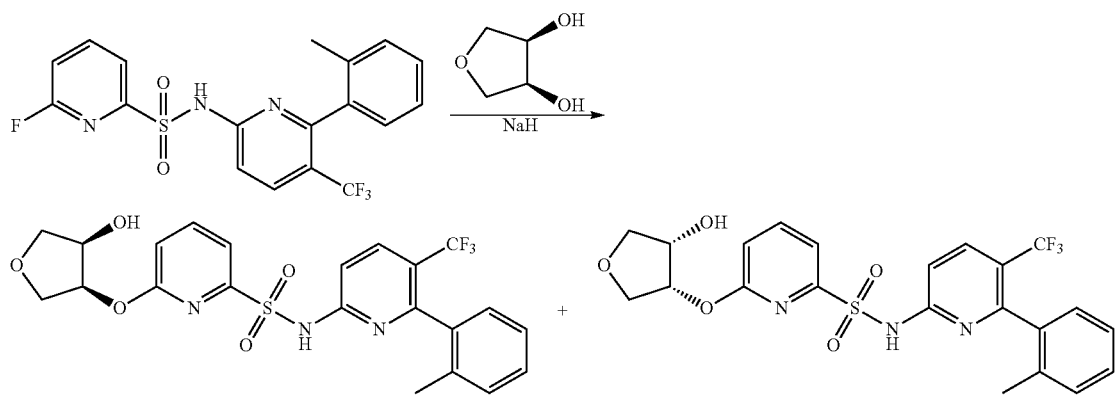

Ex. 291

Step 1

To a solution of (3R,4S)-tetrahydrofuran-3,4-diol (260 mg, 2.5 mmol) and 6-fluoro-N-(6-(o-tolyl)-5-(trifluoromethyl)pyridin-2-yl)pyridine-2-sulfonamide (206 mg, 0.5 mmol) in DMF (Volume: 20 mL) was added NaH (240 mg, 10 mmol) under nitrogen atmosphere. The mixture stirred at rt for 5 h and quenched with aq. citric acid, ethyl acetate added, washed with 10% citric acid, water, aq. NaHCO$_3$, brine (×3), and dried (Na$_2$SO$_4$). The crude material was purified by flash silica gel chromathotography (hexanes/ethyl acetate 0-100% gradient) to afford rac-6-{[(3RS,4SR)-4-hydroxyoxolan-3-yl]oxy}-N-[6-(2-methylphenyl)-5-(trifluoromethyl)pyridin-2-yl]pyridine-2-sulfonamide (180 mg, 71% yield) as white crystals. LCMS: Rt 1.47 min; m/z 496.2 [M+H]$^+$. $^1$H NMR (400 MHz, DMSO-d$_6$) δ 11.81 (s, 1H), 8.21 (d, J=8.9 Hz, 1H), 7.91 (m, 1H), 7.56 (dd, J=0.6, 7.3 Hz, 1H), 7.47 (s, 1H), 7.32 (t, J=7.3 Hz, 1H), 7.22 (m, 2H), 7.11 (d, J=8.3 Hz, 1H), 7.05 (m, 1H), 5.07 (dd, J=5.2, 14.7 Hz, 1H), 4.95 (m, 1H), 4.21 (m, 1H), 3.82 (m, 2H), 3.54 (m, 2H), 1.79 (m, 3H).
$^{19}$F NMR (376 MHz, DMSO-d$_6$) δ −57.17 (s).

Example 293: rac-6-{[(3RR,4SR)-4-hydroxy-4-methyloxolan-3-yl]oxy}-N-[6-(2-methylphenyl)-5-(trifluoromethyl)pyridin-2-yl]pyridine-2-sulfonamide

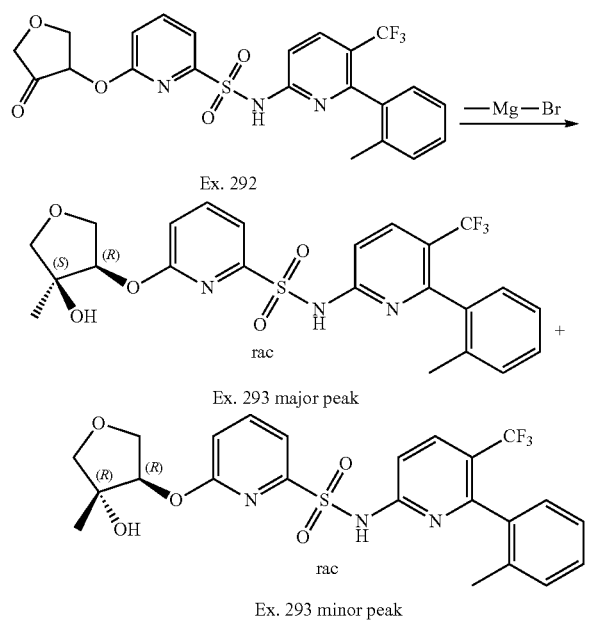

Ex. 292

Ex. 293 major peak

Ex. 293 minor peak

To a solution of Example 292: 6-((4-oxotetrahydrofuran-3-yl)oxy)-N-(6-(o-tolyl)-5-(trifluoromethyl)pyridin-2-yl)pyridine-2-sulfonamide (49.3 mg, 0.1 mmol) in DCM (Volume: 2 ml) was added at −78° C. 3 M MeMgBr in ether (0.167 ml, 0.500 mmol) under nitrogen atmosphere. The mixture was stirred at −78° C. for 2 h. Complete. Reaction mixture was quenched with 1N HCl, and EtOAc was added. Organic layer was washed with 10% citric acid, water, aq. NaHCO$_3$, brine (×3), and dried over Na$_2$SO$_4$. The crude material was purified by silica gel column, (EtOAc/Hexanes 0-70%) to afford rac-6-{[(3RR,4SR)-4-hydroxy-4-methyloxolan-3-yl]oxy}-N-[6-(2-methylphenyl)-5-(trifluoromethyl)pyridin-2-yl]pyridine-2-sulfonamide. Condition 2, LCMS: m/z 510.2 [M+H]$^+$, 3.07 min. $^1$H NMR (400 MHz, DMSO-d$_6$) δ 11.83 (s, 1H), 8.22 (d, J=8.9 Hz, 1H), 7.91 (dd, J=7.4, 8.3 Hz, 1H), 7.55 (d, J=7.3 Hz, 1H), 7.45 (m, 1H), 7.32 (t, J=7.4 Hz, 1H), 7.21 (m, 2H), 7.11 (d, J=8.3 Hz, 1H), 7.02 (m, 1H), 4.97 (m, 1H), 4.73 (m, 1H), 3.93 (dd, J=5.7, 9.5 Hz, 1H), 3.60 (d, J=8.5 Hz, 1H), 3.49 (d, J=8.5 Hz, 1H), 3.42 (m, 1H), 1.76 (m, 3H), 1.17 (m, 3H). $^{19}$F NMR (376 MHz, DMSO-d$_6$) δ −57.15 (m).

The following examples were prepared using the specified intermediates and general procedures as indicated within the general synthetic methods section.

Example 102: (R)-6-(3-aminopiperidin-1-yl)-N-(6-(o-tolyl)-5-(trifluoromethyl)pyridin-2-yl)pyridine-2-sulfonamide Hydrochloride Condition 2, LCMS: m/z 492.2 [M+H]$^+$ 2.53 min. $^1$H NMR (400 MHz, DMSO-d$_6$) δ 11.61 (s, 1H), 8.21 (d, J=8.9 Hz, 1H), 8.13 (s, 3H), 7.78-7.71 (m, 1H), 7.55 (s, 1H), 7.38-7.29 (m, 1H), 7.28-7.19 (m, 2H), 7.18 (d, J=7.3 Hz, 1H), 7.11-7.02 (m, 2H), 4.17-4.03 (m, 1H), 3.79 (d, J=12.4 Hz, 1H), 3.21-3.06 (m, 2H), 3.00 (q, J=11.7 Hz, 1H), 1.95 (s, 1H), 1.81 (d, J=18.6 Hz, 3H), 1.72-1.52 (m, 2H), 1.41-1.23 (m, 1H).

Example 103: (S)-6-(3-aminopiperidin-1-yl)-N-(6-(o-tolyl)-5-(trifluoromethyl)pyridin-2-yl)pyridine-2-sulfonamide Hydrochloride Condition 2, LCMS: m/z 492.2 [M+H]$^+$, 2.52 min. $^1$H NMR (400 MHz, DMSO-d$_6$) δ 11.61 (s, 1H), 8.21 (d, J=8.9 Hz, 1H), 8.10 (s, 3H), 7.79-7.71 (m, 1H), 7.55 (s, 1H), 7.38-7.29 (m, 1H), 7.29-7.19 (m, 2H), 7.18 (d, J=7.3 Hz, 1H), 7.07 (d, J=8.7 Hz, 2H), 4.16-4.03 (m, 1H), 3.79 (d, J=12.4 Hz, 1H), 3.21-3.07 (m, 2H), 3.08-2.93 (m, 1H), 1.95 (s, 1H), 1.81 (d, J=19.1 Hz, 3H), 1.73-1.52 (m, 2H), 1.34 (s, 1H).

Example 104: (R)-6-(piperidin-3-ylamino)-N-(6-(o-tolyl)-5-(trifluoromethyl)pyridin-2-yl)pyridine-2-sulfonamide Hydrochloride Condition 2, LCMS: m/z 492.2 [M+H]$^+$, 2.44 min. $^1$H NMR (400 MHz, DMSO-d$_6$) δ 11.56 (s, 1H), 8.83 (s, 2H), 8.22 (d, J=8.9 Hz, 1H), 7.59 (t, J=7.9 Hz, 1H), 7.53 (d, J=6.6 Hz, 1H), 7.33 (dd, J=13.1, 6.0 Hz, 2H), 7.28-7.17 (m, 2H), 7.10 (d, J=7.2 Hz, 1H), 7.03 (s, 1H), 6.73 (d, J=8.5 Hz, 1H), 3.89 (s, 1H), 3.21 (s, 1H), 3.12 (s, 1H), 2.97-2.77 (m, 2H), 1.88-1.54 (m, 6H), 1.51-1.30 (m, 1H).

Example 105: (S)-6-(piperidin-3-ylamino)-N-(6-(o-tolyl)-5-(trifluoromethyl)pyridin-2-yl)pyridine-2-sulfonamide Hydrochloride Condition 2, LCMS: m/z 492.2 [M+H]$^+$, 2.45 min. $^1$H NMR (400 MHz, DMSO-d$_6$) δ 11.56 (s, 1H), 8.68 (s, 2H), 8.25-8.17 (m, 1H), 7.59 (t, J=7.9 Hz, 1H), 7.51 (d, J=7.2 Hz, 1H), 7.37-7.15 (m, 4H), 7.09 (dd, J=15.2, 7.8 Hz, 2H), 6.73 (d, J=8.3 Hz, 1H), 3.86 (s, 1H), 3.22 (d, J=7.0 Hz, 1H), 3.13 (s, 1H), 2.97-2.81 (m, 2H), 1.87-1.55 (m, 6H), 1.38 (s, 1H).

Example 106: 6-(((3R,4S)-4-methoxypiperidin-3-yl)amino)-N-(6-(o-tolyl)-5-(trifluoromethyl)pyridin-2-yl)pyridine-2-sulfonamide Hydrochloride Condition 2, LCMS: m/z 522.2 [M+H]$^+$, 2.44 min. $^1$H NMR (400 MHz, DMSO-d$_6$) δ 11.59 (s, 1H), 8.88 (s, 1H), 8.66 (s, 1H), 8.21 (d, J=8.8 Hz, 1H), 7.59 (d, J=7.8 Hz, 1H), 7.45 (s, 1H), 7.32 (t, J=7.5 Hz, 1H), 7.22 (d, J=7.1 Hz, 3H), 7.13-6.91 (m, 2H), 6.85 (d, J=8.0 Hz, 1H), 4.13 (s, 1H), 3.17-2.91 (m, 8H), 2.02 (s, 1H), 1.89-1.60 (m, 4H).

Example 107: 6-(6-amino-3-azabicyclo[3.1.0]hexan-3-yl)-N-(6-(o-tolyl)-5-(trifluoromethyl)pyridin-2-yl)pyridine-2-sulfonamide Hydrochloride Condition 2, LCMS: m/z 490.2 [M+H]$^+$, 2.57 min. $^1$H NMR (400 MHz, DMSO-d$_6$) δ 11.57 (s, 1H), 8.29-8.19 (m, 4H), 7.68 (dd, J=8.5, 7.4 Hz, 1H), 7.58 (d, J=6.8 Hz, 1H), 7.38-7.30 (m, 1H), 7.24 (dd, J=13.5, 7.1 Hz, 2H), 7.15 (d, J=7.3 Hz, 1H), 7.08 (d, J=7.2 Hz, 1H), 6.73 (d, J=8.5 Hz, 1H), 3.61-3.52 (m, 2H), 3.28 (d, J=10.2 Hz, 2H), 2.43-2.35 (m, 1H), 2.06 (s, 2H), 1.83 (s, 3H).

Example 108: 6-(4-aminopiperidin-1-yl)-N-(6-(o-tolyl)-5-(trifluoromethyl)pyridin-2-yl)pyridine-2-sulfonamide Hydrochloride Condition 2, LCMS: m/z 492.3 [M+H]$^+$, 2.48 min. $^1$H NMR (400 MHz, DMSO-d$_6$) δ 11.59 (s, 1H), 8.22 (d, J=9.0 Hz, 1H), 8.02-7.87 (m, 3H), 7.73 (dd, J=8.7, 7.3 Hz, 1H), 7.57 (d, J=7.5 Hz, 1H), 7.38-7.30 (m, 1H), 7.24 (dd, J=15.8, 7.6 Hz, 2H), 7.16 (d, J=7.2 Hz, 1H), 7.12 (d, J=8.7 Hz, 1H), 7.09 (d, J=7.4 Hz, 1H), 4.13 (d, J=12.6 Hz, 2H), 3.34-3.20 (m, 1H), 2.84 (t, J=12.4 Hz, 2H), 1.85 (s, 5H), 1.34 (d, J=11.8 Hz, 2H).

Example 109: 6-(4-(methylamino)piperidin-1-yl)-N-(6-(o-tolyl)-5-(trifluoromethyl)pyridin-2-yl)pyridine-2-sulfonamide Hydrochloride Condition 2, LCMS: m/z 506.3 [M+H]$^+$, 2.41 min. $^1$H NMR (400 MHz, DMSO-d$_6$) δ 11.61 (s, 1H), 8.96-8.78 (m, 2H), 8.22 (d, J=8.9 Hz, 1H), 7.73 (dd, J=8.6, 7.3 Hz, 1H), 7.55 (d, J=8.4 Hz, 1H), 7.38-7.29 (m, 1H), 7.24 (dd, J=14.3, 7.3 Hz, 2H), 7.15 (dd, J=9.8, 8.0 Hz, 2H), 7.09 (d, J=7.5 Hz, 1H), 4.20 (d, J=13.2 Hz, 2H), 3.57 (s, 3H), 3.27-3.13 (m, 1H), 2.79 (t, J=11.0 Hz, 2H), 1.97 (d, J=10.4 Hz, 2H), 1.83 (s, 3H), 1.44-1.28 (m, 2H).

Example 110: 6-(4-amino-4-methylpiperidin-1-yl)-N-(6-(o-tolyl)-5-(trifluoromethyl)pyridin-2-yl)pyridine-2-sulfonamide Hydrochloride Condition 2, LCMS: m/z 506.2 [M+H]$^+$, 2.51 min. $^1$H NMR (400 MHz, DMSO-d$_6$) δ 11.59 (s, 1H), 8.22 (d, J=9.0 Hz, 1H), 8.09 (s, 3H), 7.73 (dd, J=8.7, 7.3 Hz, 1H), 7.56 (d, J=7.6 Hz, 1H), 7.37-7.31 (m, 1H), 7.24 (dd, J=15.4, 7.5 Hz, 2H), 7.15 (dd, J=15.7, 8.0 Hz, 2H), 7.08 (d, J=7.2 Hz, 1H), 3.81 (d, J=12.4 Hz, 2H), 3.22 (ddd, J=13.1, 9.1, 3.2 Hz, 2H), 1.84 (s, 3H), 1.68-1.51 (m, 4H), 1.31 (s, 3H).

Example 111: 6-((3S,4R)-4-amino-3-fluoropiperidin-1-yl)-N-(6-(o-tolyl)-5-(trifluoromethyl)pyridin-2-yl)pyridine-2-sulfonamide Hydrochloride Condition 2, LCMS: m/z 510.2 [M+H]$^+$, 2.47 min. $^1$H NMR (400 MHz, DMSO-d$_6$) δ 11.62 (s, 1H), 8.35-8.24 (m, 3H), 8.22 (d, J=9.0 Hz, 1H), 7.73 (dd, J=8.6, 7.4 Hz, 1H), 7.57 (d, J=7.0 Hz, 1H), 7.34-7.29 (m, 1H), 7.24 (dd, J=16.1, 7.8 Hz, 2H), 7.16 (dd, J=8.0, 5.7 Hz, 2H), 7.13-7.05 (m, 1H), 4.95 (d, J=49.2 Hz, 1H), 4.57 (t, J=13.1 Hz, 1H), 4.23 (d, J=12.4 Hz, 1H), 3.66-3.50 (m, 1H), 3.26-3.06 (m, 1H), 2.88 (t, J=12.4 Hz, 1H), 1.84 (s, 3H), 1.76 (d, J=10.1 Hz, 1H), 1.71-1.56 (m, 1H).

Example 112: 6-(piperidin-4-ylamino)-N-(6-(o-tolyl)-5-(trifluoromethyl)pyridin-2-yl)pyridine-2-sulfonamide Hydrochloride Condition 2, LCMS: m/z 492.3 [M+H]$^+$, 2.41 min. $^1$H NMR (400 MHz, DMSO-d$_6$) δ 11.52 (s, 1H), 8.81 (s, 2H), 8.21 (d, J=8.9 Hz, 1H), 7.56 (dd, J=8.5, 7.3 Hz, 1H), 7.49 (d, J=8.6 Hz, 1H), 7.36 (brs, 1H), 7.40-7.28 (m, 2H), 7.25-7.18 (m, 2H), 7.05 (t, J=7.9 Hz, 2H), 6.74-6.69 (m, 1H), 3.28-3.09 (m, 2H), 2.87 (s, 2H), 1.93-1.76 (m, 2H), 1.75 (s, 3H), 1.63-1.41 (m, 2H).

Example 113: 6-(((3S,4R)-3-hydroxypiperidin-4-yl)amino)-N-(6-(o-tolyl)-5-(trifluoromethyl)pyridin-2-yl)pyridine-2-sulfonamide Hydrochloride Condition 2, LCMS: m/z 508.2 [M+H]$^+$, 2.43 min. mixture of cis isomer: $^1$H NMR (400 MHz, DMSO-d$_6$) δ 11.52 (s, 1H), 8.81 (s, 2H), 8.21 (d, J=8.9 Hz, 1H), 7.56 (dd, J=8.5, 7.3 Hz, 1H), 7.49 (d, J=8.6 Hz, 1H), 7.36 (brs, 1H), 7.40-7.28 (m, 2H), 7.25-7.18 (m, 2H), 7.05 (t, J=7.9 Hz, 2H), 6.74-6.69 (m, 1H), 3.28-3.09 (m, 2H), 2.87 (s, 2H), 1.93-1.76 (m, 2H), 1.75 (s, 3H), 1.63-1.41 (m, 2H).

Example 114: 6-(((3R,4R)-3-hydroxypiperidin-4-yl)amino)-N-(6-(o-tolyl)-5-(trifluoromethyl)pyridin-2-yl)pyridine-2-sulfonamide Hydrochloride Condition 2, LCMS: m/z 508.2 [M+H]$^+$, 2.42 min. mixture of trans isomer: $^1$H NMR (400 MHz, DMSO-d$_6$) δ 11.49 (s, 1H), 8.91 (s, 1H), 8.65 (s, 1H), 8.19 (d, J=8.9 Hz, 1H), 7.62-7.47 (m, 2H), 7.34 (dd, J=16.4, 7.8 Hz, 2H), 7.28-7.17 (m, 2H), 7.13-7.00 (m, 2H), 6.78 (d, J=8.5 Hz, 1H), 5.61 (s, 1H), 3.74 (dd, J=7.0, 3.2 Hz, 2H), 3.26 (s, 1H), 3.07 (s, 1H), 2.87 (s, 1H), 2.77 (dt, J=10.9, 6.0 Hz, 1H), 1.96 (s, 1H), 1.86-1.69 (m, 3H), 1.51-1.29 (m, 1H).

Example 115: 6-(((3S,4R)-3-methoxypiperidin-4-yl)amino)-N-(6-(o-tolyl)-5-(trifluoromethyl)pyridin-2-yl)pyridine-2-sulfonamide Hydrochloride Condition 2, LCMS: m/z 522.2 [M+H]$^+$, 2.55 min. mixture of cis isomer: $^1$H NMR (400 MHz, DMSO-d$_6$) δ 11.54 (s, 1H), 9.08 (s, 1H), 8.31 (d, J=8.1 Hz, 1H), 8.21 (d, J=8.8 Hz, 1H), 7.62-7.49 (m, 1H), 7.39 (d, J=15.7 Hz, 1H), 7.34-7.29 (m, 1H), 7.29-7.14 (m, 3H), 7.10-6.90 (m, 2H), 6.80 (t, J=8.2 Hz, 1H), 3.94 (s, 1H), 3.38-3.33 (m, 1H), 3.23-2.82 (m, 6H), 1.88-1.53 (m, 5H).

Example 116: 6-(((3R,4R)-3-methoxypiperidin-4-yl)amino)-N-(6-(o-tolyl)-5-(trifluoromethyl)pyridin-2-yl)pyridine-2-sulfonamide Hydrochloride Condition 2, LCMS: m/z 522.2 [M+H]$^+$, 2.42 min. mixture of trans isomer: $^1$H NMR (400 MHz, DMSO-d$_6$) δ 11.52 (s, 1H), 8.92 (s, 1H), 8.52 (s, 1H), 8.18 (d, J=8.9 Hz, 1H), 7.58 (t, J=7.8 Hz, 1H), 7.51 (s, 1H), 7.43 (d, J=7.2 Hz, 1H), 7.33 (t, J=7.5 Hz, 1H), 7.22 (dd, J=14.3, 7.2 Hz, 2H), 7.11-6.99 (m, 2H), 6.78 (d, J=8.4 Hz, 1H), 3.84 (s, 1H), 3.34-3.23 (m, 4H), 3.17-2.86 (m, 3H), 1.99-1.71 (m, 4H), 1.63-1.42 (m, 1H).

Example 117: 6-(((3S,4R)-3-fluoropiperidin-4-yl) amino)-N-(6-(o-tolyl)-5-(trifluoromethyl)pyridin-2-yl)pyridine-2-sulfonamide Hydrochloride Condition 2, LCMS: m/z 510.2 [M+H]$^+$, 2.54 min. mixture of cis isomer: $^1$H NMR (400 MHz, DMSO-d$_6$) δ 11.52 (s, 1H), 9.19 (d, J=7.4 Hz, 1H), 8.65 (q, J=9.3, 8.6 Hz, 1H), 8.21 (d, J=8.9 Hz, 1H), 7.60 (t, J=7.8 Hz, 1H), 7.51-7.37 (m, 2H), 7.37-7.28 (m, 1H), 7.27-7.18 (m, 2H), 7.12 (d, J=7.2 Hz, 1H), 7.03 (d, J=6.5 Hz, 1H), 6.80 (d, J=8.4 Hz, 1H), 4.99-4.62 (m, 1H), 3.99 (d, J=31.0 Hz, 1H), 3.53-3.30 (m, 1H), 3.32-3.13 (m, 2H), 3.04-2.91 (m, 1H), 1.88-1.63 (m, 5H).

Example 118: 6-((3'S,4'S)-4'-hydroxy-[1,3'-bipyrrolidin]-1'-yl)-N-(6-(o-tolyl)-5-(trifluoromethyl)pyridin-2-yl)pyridine-2-sulfonamide Condition 2, LCMS: m/z 548.2 [M+H]$^+$, 2.39 min. $^1$H NMR (400 MHz, DMSO-d$_6$) δ 11.27 (s, 1H), 7.97 (d, J=8.7 Hz, 1H), 7.44 (dd, J=8.5, 7.4 Hz, 2H), 7.11 (t, J=7.4 Hz, 1H), 7.01 (dd, J=16.5, 7.9 Hz, 2H), 6.93-6.83 (m, 2H), 6.46 (d, J=8.6 Hz, 1H), 5.00 (s, 1H), 4.02 (s, 1H), 3.22 (s, 2H), 3.18 (s, 2H), 3.05 (m, 1H), 2.87 (d, J=9.8 Hz, 1H), 2.29 (m, 5H), 1.62 (d, J=14.2 Hz, 3H), 1.43 (s, 3H).

Example 119: (R)-6-(3-aminopyrrolidin-1-yl)-N-(6-(o-tolyl)-5-(trifluoromethyl)pyridin-2-yl)pyridine-2-sulfonamide Hydrochloride Condition 2, LCMS: m/z 478.2 [M+H]$^+$, 2.46 min. $^1$H NMR (400 MHz, DMSO-d$_6$) δ 11.65 (s, 1H), 8.22 (d, J=9.0 Hz, 1H), 8.19 (s, 3H), 7.70 (dd, J=8.5, 7.4 Hz, 1H), 7.58 (s, 1H), 7.37-7.31 (m, 1H), 7.29-7.19 (m, 2H), 7.16 (d, J=7.2 Hz, 1H), 7.07 (d, J=7.3 Hz, 1H), 6.76 (d, J=8.5 Hz, 1H), 3.92 (s, 1H), 3.62-3.54 (m, 1H), 3.50-3.30 (m, 3H), 2.32-2.21 (m, 1H), 2.11-2.01 (m, 1H), 1.85 (s, 3H).

Example 120: (S)-6-(3-aminopyrrolidin-1-yl)-N-(6-(o-tolyl)-5-(trifluoromethyl)pyridin-2-yl)pyridine-2-sulfonamide Hydrochloride Condition 2, LCMS: m/z 478.2 [M+H]$^+$, 2.50 min. $^1$H NMR (400 MHz, DMSO-d$_6$) δ 11.65 (s, 1H), 8.30-8.16 (m, 4H), 7.70 (dd, J=8.5, 7.4 Hz, 1H), 7.59 (s, 1H), 7.37-7.31 (m, 1H), 7.29-7.19 (m, 2H), 7.15 (d, J=7.2 Hz, 1H), 7.07 (d, J=7.4 Hz, 1H), 6.75 (d, J=8.5 Hz, 1H), 3.96-3.86 (m, 1H), 3.63-3.53 (m, 1H), 3.49-3.30 (m, 3H), 2.27 (m, 1H), 2.07 (m, 1H), 1.85 (s, 3H).

Example 121: (R)-6-(3-(methylamino)pyrrolidin-1-yl)-N-(6-(o-tolyl)-5-(trifluoromethyl)pyridin-2-yl)pyridine-2-sulfonamide Hydrochloride Condition 2, LCMS: m/z 492.2 [M+H]$^+$, 2.45 min. $^1$H NMR (400 MHz, DMSO-d$_6$) δ 11.64 (s, 1H), 9.12-8.90 (m, 2H), 8.24 (d, J=9.0 Hz, 1H), 7.72 (dd, J=8.5, 7.4 Hz, 1H), 7.61 (d, J=6.1 Hz, 1H), 7.38-7.30 (m, 1H), 7.29-7.19 (m, 2H), 7.17 (d, J=7.2 Hz, 1H), 7.08 (d, J=7.2 Hz, 1H), 6.77 (d, J=8.5 Hz, 1H), 3.88-3.80 (m, 1H), 3.67-3.57 (m, 1H), 3.35-3.27 (m, 1H), 2.60 (t, J=5.3 Hz, 3H), 2.33-2.26 (m, 1H), 2.20-2.10 (m, 1H), 1.86 (s, 3H).

Example 122: (S)-6-(3-(methylamino)pyrrolidin-1-yl)-N-(6-(o-tolyl)-5-(trifluoromethyl)pyridin-2-yl)pyridine-2-sulfonamide Hydrochloride Condition 2, LCMS: m/z 492.2 [M+H]$^+$, 2.47 min. $^1$H NMR (400 MHz, DMSO-d$_6$) δ 11.65 (s, 1H), 9.28-9.03 (m, 2H), 8.24 (d, J=9.0 Hz, 1H), 7.71 (dd, J=8.5, 7.4 Hz, 1H), 7.61 (d, J=7.5 Hz, 1H), 7.37-7.31 (m, 1H), 7.29-7.20 (m, 2H), 7.16 (d, J=7.2 Hz, 1H), 7.08 (d, J=7.3 Hz, 1H), 6.77 (d, J=8.5 Hz, 1H), 3.89-3.79 (m, 1H), 3.65-3.60 (m, 1H), 3.55-3.50 (m, 1H), 3.49-3.43 (m, 1H), 3.35-3.25 (m, 1H), 2.59 (t, J=5.3 Hz, 3H), 2.32-2.25 (m, 1H), 2.22-2.12 (m, 1H), 1.86 (s, 3H).

Example 123: (R)-6-(pyrrolidin-3-ylamino)-N-(6-(o-tolyl)-5-(trifluoromethyl)pyridin-2-yl)pyridine-2-sulfonamide Hydrochloride Condition 2, LCMS: m/z 478.2 [M+H]$^+$, 2.47 min. $^1$H NMR (400 MHz, DMSO-d$_6$) δ 11.64 (s, 1H), 9.09 (s, 1H), 9.01 (s, 1H), 8.22 (d, J=8.9 Hz, 1H), 7.60 (dd, J=8.4, 7.3 Hz, 1H), 7.56 (s, 1H), 7.48 (d, J=8.2 Hz, 1H), 7.36-7.30 (m, 1H), 7.27-7.19 (m, 2H), 7.14 (d, J=7.2 Hz, 1H), 7.06 (d, J=6.7 Hz, 1H), 6.74 (d, J=8.2 Hz, 1H), 4.15 (s, 1H), 3.38-3.23 (m, 2H), 3.18 (s, 1H), 3.04-2.87 (m, 1H), 2.15-1.99 (m, 1H), 1.80 (s, 4H).

Example 124: (S)-6-(pyrrolidin-3-ylamino)-N-(6-(o-tolyl)-5-(trifluoromethyl)pyridin-2-yl)pyridine-2-sulfonamide Hydrochloride Condition 2, LCMS: m/z 478.2 [M+H]$^+$, 2.43 min. $^1$H NMR (400 MHz, DMSO-d$_6$) δ 11.63 (s, 1H), 9.10 (s, 1H), 9.02 (s, 1H), 8.22 (d, J=8.9 Hz, 1H), 7.60 (dd, J=8.4, 7.3 Hz, 1H), 7.56 (s, 1H), 7.48 (d, J=8.7 Hz, 1H), 7.38-7.29 (m, 1H), 7.28-7.18 (m, 2H), 7.17-7.10 (m, 1H), 7.06 (d, J=6.6 Hz, 1H), 6.74 (d, J=8.1 Hz, 1H), 4.14 (s, 1H), 3.37-3.24 (m, 2H), 3.18 (s, 1H), 3.04-2.86 (m, 1H), 2.16-1.98 (m, 1H), 1.80 (s, 4H).

Example 125: N-(5-chloro-6-(2-(trifluoromethyl)phenyl)pyridin-2-yl)-6-(((3S,4R)-4-hydroxytetrahydrofuran-3-yl)amino)pyridine-2-sulfonamide Condition 2, LCMS: m/z 515.1 [M+H]$^+$, 2.97 min. $^1$H NMR (400 MHz, DMSO-d$_6$) δ 11.14 (s, 1H), 7.93 (d, J=8.9 Hz, 1H), 7.82 (d, J=7.3 Hz, 1H), 7.77-7.65 (m 2H), 7.54 (dd, J=8.4, 7.3 Hz, 1H), 7.45 (d, J=8.9 Hz, 1H), 7.40-7.27 (m, 2H), 7.06 (d, J=7.2 Hz, 1H), 6.71 (d, J=8.4 Hz, 1H), 5.21-5.09 (m, 1H), 4.06 (s, 1H), 3.94-3.80 (m, 3H), 3.48 (d, J=9.6 Hz, 1H), 3.43-3.36 (m, 1H).

Example 126: N-(5-chloro-6-(2-(trifluoromethyl)phenyl)pyridin-2-yl)-6-(((3R,4S)-4-hydroxytetrahydrofuran-3-yl)amino)pyridine-2-sulfonamide Condition 2, LCMS: m/z 515.1 [M+H]$^+$, 2.97 min. $^1$H NMR (400 MHz, DMSO-d$_6$) δ 11.15 (s, 1H), 7.93 (d, J=8.9 Hz, 1H), 7.82 (d, J=7.5 Hz, 1H), 7.79-7.70 (m, 1H), 7.68 (t, J=7.5 Hz, 1H), 7.54 (dd, J=8.4, 7.3 Hz, 1H), 7.45 (d, J=8.9 Hz, 1H), 7.41-7.27 (m, 2H), 7.06 (d, J=7.1 Hz, 1H), 6.71 (d, J=8.5 Hz, 1H), 5.21-5.11 (m, 1H), 4.06 (s, 1H), 3.90 (s, 1H), 3.87-3.80 (m, 2H), 3.49 (d, J=9.5 Hz, 1H), 3.43-3.36 (m, 1H).

Example 127: N-(5-chloro-6-(5-fluoro-2-methylphenyl)pyridin-2-yl)-6-(((3R,4S)-4-hydroxytetrahydrofuran-3-yl)amino)pyridine-2-sulfonamide Condition 2, LCMS: m/z 479.2 [M+H]$^+$, 3.04 min. $^1$H NMR (400 MHz, DMSO-d$_6$) δ 11.16 (s, 1H), 7.93 (d, J=8.8 Hz, 1H), 7.55 (dd, J=7.3, 8.4 Hz, 1H), 7.34 (m, 2H), 7.29 (dd, J=5.9, 8.5 Hz, 1H), 7.16 (td, J=2.8, 8.6 Hz, 1H), 7.07

(m, 1H), 6.90 (dd, J=2.4, 9.3 Hz, 1H), 6.70 (m, 1H), 5.15 (d, J=3.6 Hz, 1H), 4.04 (m, 1H), 3.84 (m, 3H), 3.47 (dd, J=2.3, 9.4 Hz, 1H), 3.31 (m, 1H), 1.86 (s, 3H). $^{19}$F NMR (376 MHz, DMSO-d$_6$) δ −117.86 (s).

Example 128: N-(5-chloro-6-(5-fluoro-2-methylphenyl)pyridin-2-yl)-6-(((1S,2R,3R,4R)-3-(hydroxymethyl)-7-oxabicyclo[2.2.1]heptan-2-yl)amino)pyridine-2-sulfonamide Condition 2, LCMS: m/z 519.2 [M+H]$^+$, 3.11 min. $^1$H NMR (400 MHz, DMSO-d$_6$) δ 11.10 (s, 1H), 7.99 (d, J=8.9 Hz, 1H), 7.50 (m, 2H), 7.30 (dd, J=5.8, 8.5 Hz, 1H), 7.16 (td, J=2.8, 8.6 Hz, 1H), 7.10 (d, J=8.6 Hz, 1H), 6.98 (m, 2H), 6.71 (d, J=8.4 Hz, 1H), 4.44 (d, J=4.0 Hz, 1H), 4.41 (t, J=4.7 Hz, 1H), 4.10 (d, J=4.3 Hz, 1H), 3.88 (t, J=8.2 Hz, 1H), 3.17 (td, J=5.3, 10.8 Hz, 1H), 2.85 (m, 1H), 1.91 (s, 3H), 1.78 (m, 1H), 1.53 (m, 2H), 1.37 (m, 2H). $^{19}$F NMR (376 MHz, DMSO-d$_6$) δ −117.87 (s).

Example 129: (1s,4s)-4-((6-(N-(5-chloro-6-(2,6-dimethylphenyl)pyridin-2-yl)sulfamoyl)pyridin-2-yl)oxy)cyclohexane-1-carboxylic Acid Condition 2, LCMS: m/z 516.2 [M+H]$^+$, 3.23 min. $^1$H NMR (400 MHz, DMSO-d$_6$) δ 12.14 (s, 1H), 11.37 (s, 1H), 7.99 (d, J=8.8 Hz, 1H), 7.86 (dd, J=7.4, 8.3 Hz, 1H), 7.48 (dd, J=0.6, 7.3 Hz, 1H), 7.31 (d, J=8.2 Hz, 1H), 7.17 (m, 1H), 7.04 (m, 3H), 4.89 (m, 1H), 2.35 (m, 1H), 1.62 (m, 14H).

Example 130: (1r,4r)-4-((6-(N-(5-chloro-6-(2,6-dimethylphenyl)pyridin-2-yl)sulfamoyl)pyridin-2-yl)oxy)cyclohexane-1-carboxylic Acid Condition 2, LCMS: m/z 516.2 [M+H]$^+$, 3.32 min. $^1$H NMR (400 MHz, DMSO-d$_6$) δ 12.14 (s, 1H), 11.38 (s, 1H), 7.96 (d, J=8.8 Hz, 1H), 7.86 (dd, J=7.4, 8.3 Hz, 1H), 7.47 (m, 1H), 7.27 (d, J=7.9 Hz, 1H), 7.17 (m, 1H), 7.04 (d, J=7.6 Hz, 2H), 6.98 (d, J=8.3 Hz, 1H), 4.69 (tt, J=3.9, 10.2 Hz, 1H), 2.22 (tt, J=3.3, 11.7 Hz, 1H), 1.83 (m, 4H), 1.67 (s, 6H), 1.42 (m, 2H), 1.27 (m, 2H).

Example 131: N-(5-chloro-6-(2,6-dimethylphenyl)pyridin-2-yl)-6-(3-oxopiperazin-1-yl)pyridine-2-sulfonamide Condition 2, LCMS: m/z 472.2 [M+H]$^+$, 3.00 min. $^1$H NMR (400 MHz, DMSO-d$_6$) δ 11.31 (s, 1H), 8.18 (s, 1H), 8.01 (d, J=8.8 Hz, 1H), 7.78 (dd, J=8.6, 7.3 Hz, 1H), 7.38 (d, J=8.9 Hz, 1H), 7.29-7.21 (m, 2H), 7.13 (d, J=7.6 Hz, 2H), 7.09 (d, J=8.6 Hz, 1H), 3.98 (s, 2H), 3.72-3.61 (m, 2H), 3.25 (t, J=6.5 Hz, 2H), 1.81 (s, 6H).

Example 132: tert-butyl 4-(6-(N-(6-(2,6-dimethylphenyl)-4-(trifluoromethyl)pyridin-2-yl)sulfamoyl)pyridin-2-yl)piperazine-1-carboxylate Condition 2, LCMS: m/z 592.3 [M+H]$^+$, 3.58 min. $^1$H NMR (400 MHz, DMSO-d$_6$) δ 11.49 brs, 1H), 7.76 (dd, J=8.7, 7.3 Hz, 1H), 7.69 (brs, 1H), 7.34 (s, 1H), 7.20 (dd, J=7.3, 3.2 Hz, 2H), 7.09 (d, J=8.3 Hz, 3H), 3.34 (brs, 4H), 3.25 (dd, J=6.4, 3.3 Hz, 4H), 1.84 (s, 6H), 1.40 (s, 9H).

Example 133: N-(6-(2,6-dimethylphenyl)-4-(trifluoromethyl)pyridin-2-yl)-6-(piperazin-1-yl)pyridine-2-sulfonamide Hydrochloride Condition 2, LCMS: m/z 492.2 [M+H]$^+$, 2.65 min. $^1$H NMR (600 MHz, DMSO-d$_6$) δ 11.59 (s, 1H), 8.94 (s, 2H), 7.81 (dd, J=8.7, 7.4 Hz, 1H), 7.59 (s, 1H), 7.34 (s, 1H), 7.28 (d, J=7.2 Hz, 1H), 7.24-7.18 (m, 1H), 7.17 (d, J=8.6 Hz, 1H), 7.10 (d, J=7.6 Hz, 2H), 3.63-3.59 (m, 4H), 3.08 (s, 4H), 1.84 (s, 6H).

Example 134: N-(5-chloro-6-(5-fluoro-2-methylphenyl)pyridin-2-yl)-6-((7S,8aR)-7-fluorohexahydropyrrolo[1,2-a]pyrazin-2(1H)-yl)pyridine-2-sulfonamide Condition 2, LCMS: m/z 520.1 [M+H]$^+$, 2.58 min. $^1$H NMR (400 MHz, DMSO-d$_6$) δ 11.19 (s, 1H), 7.98 (d, J=8.8 Hz, 1H), 7.72 (dd, J=8.7, 7.3 Hz, 1H), 7.41 (d, J=8.8 Hz, 1H), 7.30 (dd, J=8.5, 5.8 Hz, 1H), 7.20-7.13 (m, 2H), 7.09 (d, J=8.7 Hz, 1H), 6.89 (dd, J=9.3, 2.8 Hz, 1H), 5.40-5.09 (m, 1H), 4.23 (d, J=11.0 Hz, 1H), 4.07 (d, J=11.6 Hz, 1H), 3.52 (ddd, J=16.6, 10.5, 6.3 Hz, 1H), 2.92 (d, J=11.1 Hz, 1H), 2.78 (td, J=12.5, 3.1 Hz, 1H), 2.42-2.34 (m, 1H), 2.28-2.09 (m, 3H), 1.99-1.89 (m, 1H), 1.87 (s, 3H).

Example 135: N-(5-chloro-6-(5-fluoro-2-methylphenyl)pyridin-2-yl)-6-((1S,7S)-7-fluoro-1-methylhexahydropyrrolo[1,2-a]pyrazin-2(1H)-yl)pyridine-2-sulfonamide Condition 2, LCMS: m/z 534.1 [M+H]$^+$, 2.64 min. $^1$H NMR (400 MHz, DMSO-d$_6$) δ 11.16 (d, J=2.3 Hz, 1H), 7.99 (d, J=8.8 Hz, 1H), 7.72 (dd, J=8.7, 7.3 Hz, 1H), 7.43 (d, J=8.8 Hz, 1H), 7.30 (dd, J=8.5, 5.8 Hz, 1H), 7.18 (dd, J=8.6, 2.8 Hz, 1H), 7.14 (d, J=7.2 Hz, 1H), 7.04 (d, J=8.7 Hz, 1H), 6.87 (dd, J=9.3, 2.6 Hz, 1H), 5.47-5.17 (m, 1H), 4.37 (s, 1H), 4.06 (d, J=10.4 Hz, 1H), 3.53 (ddd, J=15.8, 10.4, 6.4 Hz, 1H), 2.84 (d, J=10.6 Hz, 1H), 2.35-2.26 (m, 1H), 2.17-2.08 (m, 1H), 1.87 (s, 3H), 1.68-1.57 (m, 1H), 1.48-1.35 (m, 1H), 0.98 (d, J=6.4 Hz, 3H).

Example 136: (S)-6-(7,7-difluorohexahydropyrrolo[1,2-a]pyrazin-2(1H)-yl)-N-(6-(o-tolyl)-5-(trifluoromethyl)pyridin-2-yl)pyridine-2-sulfonamide Condition 2, LCMS: m/z 554.2 [M+H]$^+$, 3.30 min. $^1$H NMR (400 MHz, DMSO-d$_6$) δ 11.70 (s, 1H), 8.21 (d, J=8.9 Hz, 1H), 7.72 (dd, J=8.6, 7.4 Hz, 1H), 7.52 (s, 1H), 7.36-7.28 (m, 1H), 7.22 (dd, J=13.5, 7.0 Hz, 2H), 7.16 (d, J=7.2 Hz, 1H), 7.10 (d, J=8.7 Hz, 1H), 7.06 (s, 1H), 4.26 (t, J=13.3 Hz, 1H), 4.15-4.05 (m, 1H), 3.41 (td, J=12.3, 10.9, 2.8 Hz, 1H), 2.90 (t, J=10.7 Hz, 1H), 2.35-2.13 (m, 2H), 2.13-2.03 (m, 1H), 1.91 (dd, J=20.6, 14.0 Hz, 1H), 1.87-1.69 (m, 4H).

Example 137: 6-((7S,8aS)-7-fluorohexahydropyrrolo[1,2-a]pyrazin-2(1H)-yl)-N-(6-(o-tolyl)-5-(trifluoromethyl)pyridin-2-yl)pyridine-2-sulfonamide Condition 2, LCMS: m/z 536.3 [M+H]$^+$, 2.60 min. $^1$H NMR (400 MHz, DMSO-d$_6$) δ 11.62 (s, 1H), 8.22 (d, J=8.9 Hz, 1H), 7.71 (dd, J=8.7, 7.3 Hz, 1H), 7.53 (d, J=8.7 Hz, 1H), 7.32 (td, J=7.5, 1.3 Hz, 1H), 7.22 (dd, J=13.2, 7.0 Hz, 2H), 7.14 (d, J=7.2 Hz, 1H), 7.09 (d, J=8.7 Hz, 1H), 7.05 (d, J=7.5 Hz, 1H), 5.17 (d, J=55.8 Hz, 1H), 4.23 (s, 1H), 4.08 (d, J=12.7 Hz, 1H), 3.16 (dd, J=21.9, 11.4 Hz, 1H), 2.96 (d, J=10.5 Hz, 1H), 2.84 (t, J=12.1 Hz, 1H), 2.40-2.26 (m, 1H), 2.16 (ddd, J=34.9, 11.3, 4.8 Hz, 1H), 1.92 (d, J=5.7 Hz, 1H), 1.78 (brs, 4H), 1.57-1.35 (m, 1H).

Example 138: 6-((7S,8aR)-7-fluorohexahydropyrrolo[1,2-a]pyrazin-2(1H)-yl)-N-(6-(o-tolyl)-5-(trifluoromethyl)pyridin-2-yl)pyridine-2-sulfonamide Condition 2, LCMS: m/z 536.3 [M+H]$^+$, 2.58 min. $^1$H NMR (400 MHz, DMSO-d$_6$) δ 11.65 (s, 1H), 8.20 (d, J=8.9

Hz, 1H), 7.71 (dd, J=8.7, 7.3 Hz, 1H), 7.53 (d, J=8.6 Hz, 1H), 7.32 (td, J=7.5, 1.3 Hz, 1H), 7.22 (dd, J=13.2, 7.1 Hz, 2H), 7.14 (d, J=7.2 Hz, 1H), 7.09 (d, J=8.7 Hz, 1H), 7.05 (d, J=7.4 Hz, 1H), 5.36-5.11 (m, 1H), 4.26 (t, J=10.8 Hz, 1H), 4.06 (brs, 1H), 3.52 (ddd, J=16.7, 10.5, 6.3 Hz, 1H), 2.89 (d, J=10.4 Hz, 1H), 2.78 (t, J=11.9 Hz, 1H), 2.39 (t, J=11.3 Hz, 1H), 2.29-2.03 (m, 3H), 1.96-1.81 (m, 1H), 1.78 (d, J=6.9 Hz, 3H).

Example 139: N-(6-(2,6-dimethylphenyl)-4-methoxypyridin-2-yl)-6-(piperazin-1-yl)pyridine-2-sulfonamide Condition 2, LCMS: m/z 454.3 [M+H]⁺, 2.14 min. ¹H NMR (400 MHz, DMSO-d₆) δ 9.00 (s, 1H), 7.78 (dd, J=8.6, 7.4 Hz, 1H), 7.24 (t, J=6.3 Hz, 2H), 7.11 (dd, J=13.0, 8.0 Hz, 4H), 6.44 (s, 1H), 3.84 (s, 3H), 3.73-3.68 (m, 2H), 3.54-3.45 (m, 2H), 3.13 (s, 4H), 2.02 (s, 6H).

Example 140: 6-(4-(tert-butyl)piperazin-1-yl)-N-(5-chloro-6-(3-fluoro-2-methylphenyl)pyridin-2-yl)pyridine-2-sulfonamide Condition 2, LCMS: m/z 518.2 [M+H]⁺, 2.52 min. ¹H NMR (400 MHz, Methylene Chloride-d₂) δ 7.72 (m, 1H), 7.63-7.52 (m, 2H), 7.28-7.12 (m, 2H), 7.14-7.03 (m, 1H), 6.96 (dd, J=7.6, 1.2 Hz, 1H), 6.75 (m, 1H), 3.40 (m, 4H), 2.57 (m, 4H), 1.97 (d, J=2.3 Hz, 3H), 1.06 (s, 9H).

Example 141: N-(5-chloro-6-(3-fluoro-2-methylphenyl)pyridin-2-yl)-6-(4-cyclopropylpiperazin-1-yl)pyridine-2-sulfonamide Condition 2, LCMS: m/z 502.2 [M+H]⁺, 2.62 min. ¹H NMR (400 MHz, Methylene Chloride-d₂) δ 7.74 (m, 1H), 7.63-7.54 (m, 2H), 7.22 (q, J=7.2 Hz, 2H), 7.09 (t, J=8.9 Hz, 1H), 6.97 (m, 1H), 6.78 (m, 1H), 3.38 (m, 4H), 2.57 (m, 4H), 1.96 (m, 3H), 1.56 (m, 1H), 0.45 (m, 4H).

Example 142: 6-(4-(tert-butyl)piperazin-1-yl)-N-(6-(3-fluoro-2-methylphenyl)-5-(trifluoromethyl)pyridin-2-yl)pyridine-2-sulfonamide Condition 2, LCMS: m/z 552.3 [M+H]⁺, 2.55 min. ¹H NMR (400 MHz, Methylene Chloride-d₂) δ 12.70 (m, 1H), 7.89 (m, 1H), 7.60 (dd, J=7.3, 8.6 Hz, 2H), 7.30 (m, 1H), 7.21 (td, J=5.5, 7.9 Hz, 1H), 7.10 (m, 1H), 6.92 (m, 1H), 6.68 (m, 1H), 3.52 (m, 4H), 2.73 (m, 4H), 1.90 (m, 3H), 1.17 (s, 9H).

Example 143: 6-(4-(tert-butyl)piperazin-1-yl)-N-(6-(5-fluoro-2-methylphenyl)-5-(trifluoromethyl)pyridin-2-yl)pyridine-2-sulfonamide Condition 2, LCMS: m/z 552.3 [M+H]⁺, 2.59 min. ¹H NMR (400 MHz, Methylene Chloride-d₂) δ 7.81 (d, J=8.9 Hz, 1H), 7.59 (dd, J=7.3, 8.6 Hz, 1H), 7.50 (d, J=8.9 Hz, 1H), 7.33 (d, J=7.2 Hz, 1H), 7.23 (dd, J=5.6, 8.5 Hz, 1H), 7.04 (td, J=2.8, 8.5 Hz, 1H), 6.82 (dd, J=2.8, 9.1 Hz, 1H), 6.64 (d, J=8.6 Hz, 1H), 3.74-3.50 (m, 4H), 2.83 (t, J=5.2 Hz, 4H), 1.95 (s, 3H), 1.22 (s, 9H).

Example 144: 6-(4-cyclopropylpiperazin-1-yl)-N-(6-(3-fluoro-2-methylphenyl)-5-(trifluoromethyl)pyridin-2-yl)pyridine-2-sulfonamide Condition 2, LCMS: m/z 536.3 [M+H]⁺, 2.71 min. ¹H NMR (400 MHz, Methylene Chloride-d₂) δ 8.10 (m, 1H), 7.66 (dd, J=8.7, 7.3 Hz, 1H), 7.60 (m, 1H), 7.25-7.17 (m, 2H), 7.11 (t, J=9.0 Hz, 1H), 6.97 (m, 1H), 6.90 (m, 1H), 3.52-3.39 (m, 4H), 2.65-2.54 (m, 4H), 1.81 (d, J=2.1 Hz, 3H), 1.65 (m, 1H), 0.59-0.39 (m, 4H).

Example 145: 6-(4-cyclopropylpiperazin-1-yl)-N-(6-(5-fluoro-2-methylphenyl)-5-(trifluoromethyl)pyridin-2-yl)pyridine-2-sulfonamide Condition 2, LCMS: m/z 536.2 [M+H]⁺, 2.69 min. ¹H NMR (400 MHz, Methylene Chloride-d₂) δ 7.99 (m, 1H), 7.69 (m, 1H), 7.60 (dd, J=8.7, 7.2 Hz, 1H), 7.29-7.17 (m, 2H), 7.04 (td, J=8.5, 2.8 Hz, 1H), 6.89-6.75 (m, 2H), 3.41-3.33 (m, 4H), 2.60-2.52 (m, 4H), 1.94 (s, 3H), 1.65-1.55 (m, 1H), 0.51-0.37 (m, 4H).

Example 146: N-(5-chloro-6-(3-fluoro-2-methylphenyl)pyridin-2-yl)-6-(5,6-dihydro-[1,2,4]triazolo[4,3-a]pyrazin-7(8H)-yl)pyridine-2-sulfonamide Condition 2, LCMS: m/z 500.1 [M+H]⁺, 2.92 min. ¹H NMR (400 MHz, Methylene Chloride-d₂) δ 12.67 (m, 1H), 8.68 (m, 1H), 7.77-7.66 (m, 2H), 7.45 (m, 1H), 7.37 (m, 1H), 7.17 (m, 1H), 7.05 (t, J=8.8 Hz, 1H), 6.98 (m, 1H), 6.83 (m, 1H), 4.25 (m, 2H), 4.07 (m, 2H), 1.86 (m, 2H), 1.26 (s, 3H).

Example 147: tert-butyl 4-(6-(N-(6-(2-cyclopropylphenyl)-5-(trifluoromethyl)pyridin-2-yl)sulfamoyl)pyridin-2-yl)piperazine-1-carboxylate Condition 1, LCMS: m/z 604.2 [M+H]⁺, 1.37 min. ¹H NMR (400 MHz, Methylene Chloride-d₂) δ 8.02 (m, 1H), 7.72-7.61 (m, 2H), 7.38-7.27 (m, 2H), 7.20 (td, J=7.5, 1.2 Hz, 1H), 7.09 (m, 1H), 6.97 (m, 1H), 6.81 (m, 1H), 3.41 (m, 8H), 1.45 (s, 9H), 1.42-1.36 (m, 1H), 0.70-0.47 (m, 4H).

Example 148: N-(6-(2-cyclopropylphenyl)-5-(trifluoromethyl)pyridin-2-yl)-6-(piperazin-1-yl)pyridine-2-sulfonamide Condition 2, LCMS: m/z 504.2 [M+H]⁺, 2.54 min. ¹H NMR (400 MHz, Methylene Chloride-d₂) δ 7.89 (m, 1H), 7.65 (dd, J=8.6, 7.4 Hz, 1H), 7.48-7.38 (m, 2H), 7.32 (td, J=7.7, 1.3 Hz, 1H), 7.16 (td, J=7.5, 1.0 Hz, 1H), 7.07 (m, 1H), 6.88 (m, 1H), 6.72 (m, 1H), 3.64 (m, 4H), 3.12 (m, 4H), 1.42-1.29 (m, 1H), 0.67-0.42 (m, 4H).

Example 149: 6-(4-(tert-butyl)piperazin-1-yl)-N-(6-(5-fluoro-2-methoxyphenyl)-5-(trifluoromethyl)pyridin-2-yl)pyridine-2-sulfonamide Condition 2, LCMS: m/z 568.3 [M+H]⁺, 2.38 min. ¹H NMR (400 MHz, Methylene Chloride-d₂) δ 7.95 (m, 1H), 7.74 (m, 1H), 7.58 (t, J=7.9 Hz, 1H), 7.49 (m, 1H), 7.29 (m, 1H), 7.10 (td, J=8.6, 3.1 Hz, 1H), 6.88 (m, 2H), 6.65 (m, 1H), 3.70 (s, 3H), 3.50-3.44 (m, 2H), 3.37-3.30 (m, 2H), 2.75 (m, 2H), 2.54 (m, 2H), 1.06 (s, 9H).

Example 150: N-(6-(2-chlorophenyl)-5-(trifluoromethyl)pyridin-2-yl)-6-(piperazin-1-yl)pyridine-2-sulfonamide Hydrochloride Condition 2, LCMS: m/z 498.1 [M+H]⁺, 2.38 min. ¹H NMR (400 MHz, Acetonitrile-d₃) δ 9.37 (s, 2H), 8.11 (d, J=9.0 Hz, 1H), 7.73 (dd, J=7.3, 8.7 Hz, 1H), 7.64 (d, J=8.9 Hz, 1H), 7.54-7.41 (m, 2H), 7.41 (td, J=1.8, 7.3 Hz, 1H), 7.34-7.25 (m, 2H), 6.99 (d, J=8.7 Hz, 1H), 3.80 (t, J=4.7 Hz, 4H), 3.15 (s, 4H); $^{19}$F NMR (376 MHz, Acetonitrile-$d_3$) δ −59.30 (s, 3F).

Example 151: N-(6-(3-fluoro-2-methylphenyl)-5-(trifluoromethyl)pyridin-2-yl)-6-(piperazin-1-yl)pyridine-2-sulfonamide Hydrochloride Condition 2, LCMS: m/z 496.1 [M+H]$^+$, 2.53 min. $^1$H NMR (400 MHz, Acetonitrile-$d_3$) δ 9.11 (s, 2H), 8.30 (d, J=9.1 Hz, 1H), 7.86 (d, J=9.0 Hz, 1H), 7.81-7.69 (m, 1H), 7.36 (d, J=7.3 Hz, 1H), 7.37-7.28 (m, 2H), 7.23 (t, J=9.0 Hz, 1H), 7.08 (s, 1H), 7.05 (d, J=8.9 Hz, 1H), 3.85 (d, J=4.7 Hz, 4H), 3.19 (s, 4H), 1.90 (d, J=1.6 Hz, 3H); $^{19}$F NMR (376 MHz, Acetonitrile-$d_3$) δ −59.12 (s, 3F), −117.47 (s, 1F).

Example 152: N-(6-(5-fluoro-2-methylphenyl)-5-(trifluoromethyl)pyridin-2-yl)-6-(piperazin-1-yl)pyridine-2-sulfonamide Hydrochloride Condition 2, LCMS: m/z 496.1 [M+H]$^+$, 2.48 min. $^1$H NMR (400 MHz, Acetonitrile-$d_3$) δ 8.85 (s, 2H), 8.37 (s, 1H), 7.95 (s, 1H), 7.79 (dd, J=7.3, 8.7 Hz, 1H), 7.43-7.32 (m, 2H), 7.21 (td, J=2.8, 8.7 Hz, 1H), 7.12-7.01 (m, 2H), 3.86 (t, J=5.0 Hz, 4H), 3.21 (q, J=4.7 Hz, 4H), 2.01 (d, J=2.2 Hz, 3H); $^{19}$F NMR (376 MHz, Acetonitrile-$d_3$) δ −59.25 (s, 3F), −118.89 (s, 1F).

Example 153: N-(6-(2-chloro-4-fluorophenyl)-5-(trifluoromethyl)pyridin-2-yl)-6-(piperazin-1-yl)pyridine-2-sulfonamide Hydrochloride Condition 2, LCMS: m/z 516.1 [M+H]$^+$, 2.41 min. $^1$H NMR (400 MHz, DMSO-$d_6$) δ 11.78 (s, 1H), 8.77 (s, 2H), 8.26 (d, J=8.9 Hz, 1H), 7.81 (dd, J=7.4, 8.6 Hz, 1H), 7.61 (d, J=8.6 Hz, 1H), 7.56 (dd, J=2.5, 8.9 Hz, 1H), 7.45-7.36 (m, 1H), 7.31 (td, J=2.5, 8.5 Hz, 1H), 7.27 (d, J=7.3 Hz, 1H), 7.17 (d, J=8.7 Hz, 1H), 3.62 (s, 4H), 3.10 (s, 4H); $^{19}$F NMR (376 MHz, DMSO-$d_6$) δ −57.49 (s, 3F), −110.30 (s, 1F).

Example 154: N-(6-(2-chloro-5-methoxyphenyl)-5-(trifluoromethyl)pyridin-2-yl)-6-(piperazin-1-yl)pyridine-2-sulfonamide Hydrochloride Condition 2, LCMS: m/z 528.1 [M+H]$^+$, 2.41 min. $^1$H NMR (400 MHz, DMSO-$d_6$) δ 11.75 (s, 1H), 9.26 (s, 2H), 8.25 (d, J=8.9 Hz, 1H), 7.81 (t, J=8.0 Hz, 1H), 7.62 (d, J=8.7 Hz, 1H), 7.42 (d, J=8.9 Hz, 1H), 7.28 (d, J=7.3 Hz, 1H), 7.18 (d, J=8.7 Hz, 1H), 7.06 (dd, J=3.0, 8.9 Hz, 1H), 6.89 (d, J=2.6 Hz, 1H), 3.76 (s, 3H), 3.70-3.62 (m, 4H), 3.09 (s, 4H); $^{19}$F NMR (376 MHz, DMSO-$d_6$) δ −57.39 (s, 1F).

Example 155: N-(6-(2-chloro-3-fluorophenyl)-5-(trifluoromethyl)pyridin-2-yl)-6-(piperazin-1-yl)pyridine-2-sulfonamide Hydrochloride Condition 2, LCMS: m/z 516.1 [M+H]$^+$, 2.44 min. $^1$H NMR (400 MHz, DMSO-$d_6$) δ 11.80 (s, 1H), 9.18 (s, 2H), 8.29 (d, J=9.0 Hz, 1H), 7.81 (t, J=8.0 Hz, 1H), 7.62 (d, J=8.8 Hz, 1H), 7.58-7.51 (m, 1H), 7.48 (td, J=5.4, 8.0 Hz, 1H), 7.26 (d, J=7.3 Hz, 1H), 7.22 (s, 1H), 7.19 (d, J=8.8 Hz, 1H), 3.65 (s, 6H), 3.09 (s, 4H); $^{19}$F NMR (376 MHz, DMSO-$d_6$) δ −57.47 (s, 3F), −115.40 (dd, J=5.5, 9.0 Hz, 1F).

Example 156: N-(5-chloro-6-(2-chlorophenyl)pyridin-2-yl)-6-(piperazin-1-yl)pyridine-2-sulfonamide Condition 2, LCMS: m/z 464.1 [M+H]$^+$, 2.32 min. $^1$H NMR (400 MHz, DMSO-$d_6$) δ 7.75 (d, J=8.9 Hz, 1H), 7.69 (dd, J=7.3, 8.6 Hz, 1H), 7.50 (dd, J=1.2, 8.0 Hz, 1H), 7.43 (td, J=1.7, 7.7 Hz, 1H), 7.37-7.28 (m, 2H), 7.21-7.14 (m, 2H), 6.94 (d, J=8.7 Hz, 1H), 3.46-3.40 (m, 4H), 2.90-2.80 (m, 4H).

Example 157: N-(5-chloro-6-(2-chloro-4-fluorophenyl)pyridin-2-yl)-6-(piperazin-1-yl)pyridine-2-sulfonamide Condition 2, LCMS: m/z 482.1 [M+H]$^+$, 2.42 min. $^1$H NMR (400 MHz, DMSO-$d_6$) δ 7.74 (d, J=8.9 Hz, 1H), 7.72-7.67 (m, 1H), 7.49 (d, J=8.6 Hz, 1H), 7.30 (d, J=8.9 Hz, 1H), 7.20 (dd, J=3.2, 6.9 Hz, 3H), 6.94 (d, J=8.6 Hz, 1H), 3.45 (d, J=4.8 Hz, 4H), 2.90 (s, 4H); $^{19}$F NMR (376 MHz, DMSO-$d_6$) δ −111.03 (s, 1F).

Example 158: N-(5-chloro-6-(2-chloro-5-methoxyphenyl)pyridin-2-yl)-6-(piperazin-1-yl)pyridine-2-sulfonamide Hydrochloride Condition 2, LCMS: m/z 494.1 [M+H]$^+$, 2.38 min. $^1$H NMR (400 MHz, DMSO-$d_6$) δ 11.33 (s, 1H), 8.85 (s, 2H), 7.99 (d, J=8.8 Hz, 1H), 7.82 (t, J=8.0 Hz, 1H), 7.45 (dd, J=6.2, 8.8 Hz, 2H), 7.28 (d, J=7.3 Hz, 1H), 7.18 (d, J=8.7 Hz, 1H), 7.05 (dd, J=3.0, 8.9 Hz, 1H), 6.80 (d, J=2.9 Hz, 1H), 3.76 (s, 4H), 3.65 (s, 6H), 3.11 (s, 4H).

Example 159: N-(5-chloro-6-(2-chloro-3-fluorophenyl)pyridin-2-yl)-6-(piperazin-1-yl)pyridine-2-sulfonamide Hydrochloride Condition 1, LCMS: m/z 482.1 [M+H]$^+$, 0.71 min. $^1$H NMR (400 MHz, DMSO-$d_6$) δ 11.37 (s, 1H), 8.85 (s, 2H), 8.03 (d, J=8.9 Hz, 1H), 7.87-7.77 (m, 1H), 7.58-7.43 (m, 3H), 7.27 (d, J=7.3 Hz, 1H), 7.18 (d, J=8.7 Hz, 1H), 7.14 (d, J=7.2 Hz, 1H), 3.64 (s, 6H), 3.12 (s, 5H); $^{19}$F NMR (376 MHz, DMSO-$d_6$) δ −114.95 (dd, J=5.6, 9.0 Hz, 1F).

Example 160: tert-butyl 4-(6-(N-(6-(o-tolyl)-5-(trifluoromethyl)pyridin-2-yl)sulfamoyl)pyridin-2-yl)piperazine-1-carboxylate Condition 2, LCMS: m/z 577.6 [M+H]$^+$, 3.41 min.

Example 161: 6-(piperazin-1-yl)-N-(6-(o-tolyl)-5-(trifluoromethyl)pyridin-2-yl)pyridine-2-sulfonamide Hydrochloride Condition 2, LCMS: m/z 478.2 [M+H]$^+$, 2.47 min. $^1$H NMR (400 MHz, DMSO-$d_6$) δ 11.68 (s, 1H), 9.05 (s, 2H), 8.23 (d, J=8.9 Hz, 1H), 7.79 (dd, J=8.6, 7.4 Hz, 1H), 7.51 (d, J=6.6 Hz, 1H), 7.38-7.29 (m, 1H), 7.28-7.19 (m, 3H), 7.17 (d, J=8.7 Hz, 1H), 7.08 (d, J=7.4 Hz, 1H), 3.68-3.62 (m, 4H), 3.10 (s, 4H), 1.81 (s, 3H).

Example 162: tert-butyl 4-(6-(N-(5-chloro-6-(2,6-dimethylphenyl)pyridin-2-yl)sulfamoyl)pyridin-2-yl)piperazine-1-carboxylate Condition 1, LCMS: m/z 558.3 [M+H]$^+$, 1.34 min.

Example 163: N-(5-chloro-6-(2,6-dimethylphenyl)pyridin-2-yl)-6-(piperazin-1-yl)pyridine-2-sulfonamide Hydrochloride Condition 2, LCMS: m/z 458.2 [M+H]$^+$, 2.48 min. $^1$H NMR (400 MHz, DMSO-$d_6$) δ 11.27 (s, 1H), 8.93 (s, 2H), 7.98 (d, J=8.8 Hz, 1H), 7.78 (dd, J=8.6, 7.4 Hz, 1H), 7.33 (d, J=8.7 Hz, 1H), 7.24-7.17 (m, 2H), 7.15 (d, J=8.6 Hz, 1H), 7.08 (d, J=7.6 Hz, 2H), 3.67-3.62 (m, 4H), 3.11 (s, 4H), 1.76 (s, 6H).

Example 164: tert-butyl (R)-2-(hydroxymethyl)-4-(6-(N-(6-(o-tolyl)-5-(trifluoromethyl)pyridin-2-yl)sulfamoyl)pyridin-2-yl)piperazine-1-carboxylate Condition 1, LCMS: m/z 608.3 [M+H]$^+$, 1.22 min.

Example 165: (R)-6-(3-(hydroxymethyl)piperazin-1-yl)-N-(6-(o-tolyl)-5-(trifluoromethyl)pyridin-2-yl)pyridine-2-sulfonamide Hydrochloride Condition 2, LCMS: m/z 508.2 [M+H]$^+$, 2.48 min. $^1$H NMR (400 MHz, DMSO-d$_6$) δ 11.67 (s, 1H), 9.16 (s, 1H), 8.86 (s, 1H), 8.22 (d, J=8.9 Hz, 1H), 7.80 (dd, J=8.6, 7.4 Hz, 1H), 7.53 (s, 1H), 7.34 (t, J=7.5 Hz, 1H), 7.28-7.16 (m, 4H), 7.08 (d, J=6.9 Hz, 1H), 5.55 (t, J=4.7 Hz, 1H), 4.21 (t, J=13.4 Hz, 2H), 3.69-3.62 (m, 1H), 3.55-3.50 (m, 1H), 3.29-3.15 (m, 2H), 3.09 (t, J=11.7 Hz, 1H), 3.04-2.89 (m, 2H), 1.80 (s, 3H).

Example 166: tert-butyl (R)-2-methyl-4-(6-(N-(6-(o-tolyl)-5-(trifluoromethyl)pyridin-2-yl)sulfamoyl)pyridin-2-yl)piperazine-1-carboxylate Condition 1, LCMS: m/z 592.3 [M+H]$^+$, 1.35 min.

Example 167: (R)-6-(3-methylpiperazin-1-yl)-N-(6-(o-tolyl)-5-(trifluoromethyl)pyridin-2-yl)pyridine-2-sulfonamide Hydrochloride Condition 2, LCMS: m/z 492.3 [M+H]$^+$, 2.51 min. $^1$H NMR (400 MHz, DMSO-d$_6$) δ 11.65 (s, 1H), 9.08 (d, J=6.3 Hz, 1H), 8.83 (d, J=9.0 Hz, 1H), 8.23 (d, J=8.9 Hz, 1H), 7.80 (dd, J=8.6, 7.4 Hz, 1H), 7.55 (d, J=6.9 Hz, 1H), 7.34 (t, J=7.5 Hz, 1H), 7.28-7.17 (m, 4H), 7.08 (d, J=7.0 Hz, 1H), 4.19 (d, J=13.5 Hz, 2H), 3.20 (s, 1H), 3.12-3.02 (m, 1H), 3.01-2.89 (m, 1H), 2.88-2.76 (m, 1H), 1.81 (s, 3H), 1.20 (d, J=6.5 Hz, 3H).

Example 168: tert-butyl 4-(6-(N-(5-chloro-6-(2-methyl-5-(trifluoromethyl)phenyl)pyridin-2-yl)sulfamoyl)pyridin-2-yl)piperazine-1-carboxylate Condition 1, LCMS: m/z 612.2 [M+H]$^+$, 1.38 min.

Example 169: N-(5-chloro-6-(2-methyl-5-(trifluoromethyl)phenyl)pyridin-2-yl)-6-(piperazin-1-yl)pyridine-2-sulfonamide Hydrochloride Condition 2, LCMS: m/z 512.2 [M+H]$^+$, 2.64 min. $^1$H NMR (400 MHz, DMSO-d$_6$) δ 11.35 (s, 1H), 9.00 (s, 2H), 8.02 (d, J=8.8 Hz, 1H), 7.78 (dd, J=8.6, 7.4 Hz, 1H), 7.75-7.67 (m, 1H), 7.54 (d, J=8.1 Hz, 1H), 7.41-7.34 (m, 2H), 7.25 (d, J=7.3 Hz, 1H), 7.17 (d, J=8.7 Hz, 1H), 3.69-3.63 (m, 4H), 3.11 (s, 4H), 2.01 (s, 3H).

Example 170: (S)-6-(2-methylpiperazin-1-yl)-N-(6-(o-tolyl)-5-(trifluoromethyl)pyridin-2-yl)pyridine-2-sulfonamide Hydrochloride Condition 2, LCMS: m/z 492.2 [M+H]$^+$, 2.52 min. $^1$H NMR (400 MHz, DMSO-d$_6$) δ 11.66 (s, 1H), 9.23 (s, 1H), 8.75 (s, 1H), 8.23 (d, J=8.9 Hz, 1H), 7.79 (dd, J=8.5, 7.5 Hz, 1H), 7.52 (s, 1H), 7.33 (t, J=7.5 Hz, 1H), 7.23 (q, J=9.6, 7.8 Hz, 3H), 7.11 (d, J=8.7 Hz, 1H), 7.09-6.97 (m, 1H), 4.60 (s, 1H), 4.15-4.04 (m, 1H), 3.30-3.20 (m, 2H), 3.18-2.85 (m, 3H), 1.79 (d, J=17.2 Hz, 3H), 1.07-0.95 (m, 3H).

Example 171: (R)-6-(2-methylpiperazin-1-yl)-N-(6-(o-tolyl)-5-(trifluoromethyl)pyridin-2-yl)pyridine-2-sulfonamide Hydrochloride Condition 2, LCMS: m/z 492.2 [M+H]$^+$, 2.55 min. $^1$H NMR (400 MHz, DMSO-d$_6$) δ 11.66 (s, 1H), 9.18 (s, 1H), 8.70 (s, 1H), 8.23 (d, J=8.9 Hz, 1H), 7.79 (dd, J=8.5, 7.5 Hz, 1H), 7.52 (s, 1H), 7.38-7.29 (m, 1H), 7.28-7.18 (m, 3H), 7.11 (d, J=8.7 Hz, 1H), 7.08-6.91 (m, 1H), 4.59 (s, 1H), 4.16-4.03 (m, 1H), 3.30-3.21 (m, 2H), 3.18-2.87 (m, 3H), 1.79 (d, J=16.3 Hz, 3H), 1.08-0.93 (m, 3H).

Example 172: (R)—N-(6-(2,6-dimethylphenyl)-5-(trifluoromethyl)pyridin-2-yl)-6-(3-(hydroxymethyl)piperazin-1-yl)pyridine-2-sulfonamide Hydrochloride Condition 2, LCMS: m/z 522.2 [M+H]$^+$, 2.58 min. $^1$H NMR (400 MHz, DMSO-d$_6$) δ 11.69 (s, 1H), 9.14 (d, J=10.3 Hz, 1H), 8.82 (q, J=9.6, 8.8 Hz, 1H), 8.23 (d, J=8.9 Hz, 1H), 7.78 (dd, J=8.6, 7.4 Hz, 1H), 7.49 (s, 1H), 7.25-7.15 (m, 3H), 7.07 (d, J=7.6 Hz, 2H), 5.55 (s, 1H), 4.22 (t, J=10.7 Hz, 2H), 3.69-3.62 (m, 1H), 3.57-3.51 (m, 1H), 3.28 (d, J=11.8 Hz, 1H), 3.17 (s, 1H), 3.12-2.98 (m, 1H), 2.99-2.87 (m, 2H), 1.73 (s, 6H).

Example 173: (S)—N-(6-(2,6-dimethylphenyl)-5-(trifluoromethyl)pyridin-2-yl)-6-(3-(hydroxymethyl)piperazin-1-yl)pyridine-2-sulfonamide Hydrochloride Condition 2, LCMS: m/z 522.2 [M+H]$^+$, 2.58 min. $^1$H NMR (400 MHz, DMSO-d$_6$) δ 11.69 (s, 1H), 9.13 (s, 1H), 8.82 (d, J=9.7 Hz, 1H), 8.23 (d, J=8.9 Hz, 1H), 7.78 (dd, J=8.6, 7.4 Hz, 1H), 7.48 (s, 1H), 7.26-7.14 (m, 3H), 7.07 (d, J=7.6 Hz, 2H), 5.55 (s, 1H), 4.22 (t, J=10.8 Hz, 2H), 3.71-3.61 (m, 1H), 3.59-3.52 (m, 1H), 3.32-3.24 (m, 1H), 3.18 (s, 1H), 3.06 (t, J=11.7 Hz, 1H), 3.01-2.88 (m, 2H), 1.73 (s, 6H).

Example 174: (R)—N-(6-(5-fluoro-2-methylphenyl)-5-(trifluoromethyl)pyridin-2-yl)-6-(3-(hydroxymethyl)piperazin-1-yl)pyridine-2-sulfonamide Hydrochloride Condition 2, LCMS: m/z 526.2 [M+H]$^+$, 2.54 min. $^1$H NMR (400 MHz, DMSO-d$_6$) δ 11.74 (s, 1H), 9.21 (d, J=9.2 Hz, 1H), 8.90 (q, J=9.2 Hz, 1H), 8.24 (d, J=8.9 Hz, 1H), 7.80 (dd, J=8.6, 7.4 Hz, 1H), 7.54 (d, J=8.4 Hz, 1H), 7.29 (dd, J=8.5, 5.8 Hz, 1H), 7.26 (d, J=7.3 Hz, 1H), 7.22-7.16 (m, 2H), 6.98 (d, J=8.3 Hz, 1H), 5.55 (s, 1H), 4.22 (t, J=12.5 Hz, 2H), 3.69-3.62 (m, 1H), 3.59-3.53 (m, 1H), 3.26 (d, J=12.3 Hz, 1H), 3.19 (s, 1H), 3.14-3.04 (m, 1H), 3.03-2.90 (m, 2H), 1.76 (s, 3H).

Example 175: (S)—N-(6-(5-fluoro-2-methylphenyl)-5-(trifluoromethyl)pyridin-2-yl)-6-(3-(hydroxymethyl)piperazin-1-yl)pyridine-2-sulfonamide Hydrochloride Condition 2, LCMS: m/z 526.2 [M+H]$^+$, 2.55 min. $^1$H NMR (400 MHz, DMSO-d$_6$) δ 11.74 (s, 1H), 9.19 (s, 1H), 8.89 (s, 1H), 8.24 (d, J=8.9 Hz, 1H), 7.80 (dd, J=8.6, 7.4 Hz, 1H), 7.54 (d, J=8.2 Hz, 1H), 7.29 (dd, J=8.5, 5.8 Hz, 1H), 7.26 (d, J=7.3 Hz, 1H), 7.23-7.15 (m, 2H), 6.98 (d, J=8.2 Hz, 1H), 5.55 (t, J=4.6 Hz, 1H), 4.21 (t, J=12.6 Hz, 2H), 3.69-3.62 (m, 1H), 3.59-3.51 (m, 1H), 3.26 (d, J=12.4 Hz, 1H), 3.19 (s, 1H), 3.15-3.03 (m, 1H), 3.03-2.90 (m, 2H), 1.76 (s, 3H).

Example 176: (R)—N-(6-(5-fluoro-2-methylphenyl)-5-(trifluoromethyl)pyridin-2-yl)-6-(3-methylpiperazin-1-yl)pyridine-2-sulfonamide Hydrochloride Condition 2, LCMS: m/z 510.3 [M+H]$^+$, 2.56 min. $^1$H NMR (400 MHz, DMSO-d$_6$) δ 11.72 (s, 1H), 9.16 (d, J=8.5 Hz, 1H), 9.02-8.85 (m, 1H), 8.25 (d, J=8.9 Hz, 1H), 7.80 (dd, J=8.6, 7.4 Hz, 1H), 7.55 (d, J=8.2 Hz, 1H), 7.30 (dd, J=8.5, 5.8 Hz, 1H), 7.26 (d, J=7.3 Hz, 1H), 7.23-7.16 (m, 2H), 6.97 (d, J=8.5 Hz, 1H), 4.19 (d, J=13.6 Hz, 2H), 3.20 (s, 1H), 3.15-3.03 (m, 1H), 3.02-2.88 (m, 1H), 2.89-2.76 (m, 1H), 1.76 (s, 3H), 1.21 (d, J=6.5 Hz, 3H).

Example 177: (S)—N-(6-(5-fluoro-2-methylphenyl)-5-(trifluoromethyl)pyridin-2-yl)-6-(3-methylpiperazin-1-yl)pyridine-2-sulfonamide Hydrochloride Condition 2, LCMS: m/z 510.3 [M+H]$^+$, 2.56 min. $^1$H NMR (400 MHz, DMSO-d$_6$) δ 11.72 (s, 1H), 9.22 (d, J=9.3 Hz, 1H), 9.00 (q, J=7.5 Hz, 1H), 8.25 (d, J=8.9 Hz, 1H), 7.79 (dd, J=8.6, 7.4 Hz, 1H), 7.55 (d, J=8.8 Hz, 1H), 7.30 (dd, J=8.5, 5.7 Hz, 1H), 7.25 (d, J=7.3 Hz, 1H), 7.22-7.16 (m, 2H), 6.97 (d, J=7.5 Hz, 1H), 4.19 (d, J=13.1 Hz, 2H), 3.31 (d, J=12.4 Hz, 1H), 3.19 (s, 1H), 3.14-3.04 (m, 1H), 3.01-2.77 (m, 2H), 1.76 (s, 3H), 1.21 (d, J=6.5 Hz, 3H).

Example 178: 6-((3S,5R)-3,5-dimethylpiperazin-1-yl)-N-(6-(5-fluoro-2-methylphenyl)-5-(trifluoromethyl)pyridin-2-yl)pyridine-2-sulfonamide Hydrochloride Condition 2, LCMS: m/z 524.3 [M+H]$^+$, 2.56 min. $^1$H NMR (400 MHz, DMSO-d$_6$) δ 11.69 (s, 1H), 9.21-9.08 (m, 1H), 8.68 (q, J=10.5 Hz, 1H), 8.26 (d, J=8.9 Hz, 1H), 7.81 (dd, J=8.6, 7.4 Hz, 1H), 7.59 (d, J=8.0 Hz, 1H), 7.30 (dd, J=8.5, 5.8 Hz, 1H), 7.26 (d, J=7.3 Hz, 1H), 7.27-7.15 (m, 2H), 6.97 (d, J=8.0 Hz, 1H), 4.28 (d, J=13.9 Hz, 2H), 3.19 (s, 2H), 2.74-2.60 (m, 2H), 1.77 (s, 3H), 1.22 (d, J=6.5 Hz, 6H).

Example 179: N-(6-(5-fluoro-2-methylphenyl)-5-(trifluoromethyl)pyridin-2-yl)-6-(4-methylpiperazin-1-yl)pyridine-2-sulfonamide Condition 2, LCMS: m/z 510.2 [M+H]$^+$, 2.55 min. $^1$H NMR (400 MHz, DMSO-d$_6$) δ 11.53 (s, 1H), 8.21-8.13 (m, 1H), 7.69 (dd, J=8.7, 7.3 Hz, 1H), 7.48 (d, J=8.8 Hz, 1H), 7.27 (dd, J=8.5, 5.8 Hz, 1H), 7.21-7.13 (m, 2H), 7.05 (d, J=8.6 Hz, 1H), 6.93 (dd, J=9.2, 2.4 Hz, 1H), 3.46-3.37 (m, 4H), 2.33-2.22 (m, 4H), 2.20 (s, 3H), 1.75 (s, 3H).

Example 180: 6-(4-acetylpiperazin-1-yl)-N-(6-(5-fluoro-2-methylphenyl)-5-(trifluoromethyl)pyridin-2-yl)pyridine-2-sulfonamide Condition 2, LCMS: m/z 538.3 [M+H]$^+$, 3.10 min. $^1$H NMR (400 MHz, DMSO-d$_6$) δ 11.67 (s, 1H), 8.25 (d, J=8.9 Hz, 1H), 7.73 (dd, J=8.6, 7.3 Hz, 1H), 7.52 (d, J=8.4 Hz, 1H), 7.28 (dd, J=8.5, 5.8 Hz, 1H), 7.21-7.14 (m, 2H), 7.10 (d, J=8.7 Hz, 1H), 6.96 (d, J=7.9 Hz, 1H), 3.50-3.44 (m, 2H), 3.44-3.36 (m, 6H), 2.02 (s, 3H), 1.75 (s, 3H).

Example 181: 6-(3,8-diazabicyclo[3.2.1]octan-3-yl)-N-(6-(o-tolyl)-5-(trifluoromethyl)pyridin-2-yl)pyridine-2-sulfonamide Hydrochloride Condition 2, LCMS: m/z 504.3 [M+H]$^+$, 2.51 min. $^1$H NMR (400 MHz, DMSO-d$_6$) δ 11.67 (s, 1H), 9.17 (d, J=10.0 Hz, 1H), 9.08 (d, J=10.7 Hz, 1H), 8.23 (d, J=8.9 Hz, 1H), 7.78 (dd, J=8.6, 7.4 Hz, 1H), 7.52 (s, 1H), 7.38-7.29 (m, 1H), 7.27-7.19 (m, 3H), 7.10-7.02 (m, 2H), 4.10 (s, 2H), 4.00 (d, J=12.9 Hz, 2H), 3.13 (d, J=13.0 Hz, 2H), 1.96-1.83 (m, 2H), 1.76 (s, 3H), 1.61 (d, J=7.7 Hz, 2H).

Example 182: 6-(4-(2-hydroxyethyl)piperazin-1-yl)-N-(6-(o-tolyl)-5-(trifluoromethyl)pyridin-2-yl)pyridine-2-sulfonamide Hydrochloride Condition 2, LCMS: m/z 522.3 [M+H]$^+$, 2.51 min. $^1$H NMR (600 MHz, DMSO-d$_6$) δ 11.69 (s, 1H), 10.08 (s, 1H), 8.22 (d, J=9.0 Hz, 1H), 7.80 (dd, J=8.6, 7.4 Hz, 1H), 7.49 (s, 1H), 7.33 (t, J=7.4 Hz, 1H), 7.31-7.17 (m, 4H), 7.08 (s, 1H), 5.40 (brs, 1H), 4.26 (d, J=13.6 Hz, 2H), 3.80-3.74 (m, 2H), 3.52 (d, J=11.4 Hz, 2H), 3.27-3.17 (m, 4H), 3.08-2.99 (m, 2H), 1.81 (s, 3H).

Example 183: 2-(4-(6-(N-(6-(o-tolyl)-5-(trifluoromethyl)pyridin-2-yl)sulfamoyl)pyridin-2-yl)piperazin-1-yl)acetamide Condition 2, LCMS: m/z 535.3 [M+H]$^+$, 2.58 min. $^1$H NMR (600 MHz, DMSO-d$_6$) δ 11.55 (s, 1H), 8.20 (d, J=8.6 Hz, 1H), 7.70 (dd, J=8.5, 7.5 Hz, 1H), 7.50 (s, 1H), 7.35-7.29 (m, 1H), 7.26-7.19 (m, 3H), 7.16 (s, 1H), 7.13 (d, J=7.3 Hz, 1H), 7.05 (d, J=8.5 Hz, 2H), 3.42 (s, 4H), 2.85 (s, 2H), 2.37 (s, 4H), 1.79 (s, 3H).

Example 184: 4-(6-(N-(6-(o-tolyl)-5-(trifluoromethyl)pyridin-2-yl)sulfamoyl)pyridin-2-yl)piperazine-1-carboxamide Condition 2, LCMS: m/z 521.2 [M+H]$^+$, 3.01 min. $^1$H NMR (600 MHz, DMSO-d$_6$) δ 11.59 (s, 1H), 8.18 (s, 1H), 7.70 (t, J=7.9 Hz, 1H), 7.44 (s, 1H), 7.31 (t, J=7.4 Hz, 1H), 7.25-7.18 (m, 2H), 7.15 (d, J=7.3 Hz, 1H), 7.10-7.02 (m, 2H), 6.06 (s, 2H), 3.39-3.36 (m, 4H), 3.29-3.25 (m, 4H), 1.78 (s, 3H).

Example 185: 6-(4-(2,2-difluoroethyl)piperazin-1-yl)-N-(6-(o-tolyl)-5-(trifluoromethyl)pyridin-2-yl)pyridine-2-sulfonamide Condition 2, LCMS: m/z 542.3 [M+H]$^+$, 3.20 min. $^1$H NMR (500 MHz, DMSO-d$_6$) δ 11.55 (s, 1H), 8.20 (d, J=8.9 Hz, 1H), 7.71 (dd, J=8.7, 7.3 Hz, 1H), 7.50 (d, J=9.1 Hz, 1H), 7.35-7.29 (m, 1H), 7.27-7.18 (m, 2H), 7.15 (d, J=7.2 Hz, 1H), 7.09-7.02 (m, 2H), 6.27-6.00 (m, 1H), 3.42-3.35 (m, 4H), 2.78-2.67 (m, 2H), 2.50-2.44 (m, 4H), 1.80 (s, 3H). 11.55 (s, 1H), 8.20 (d, J=8.9 Hz, 1H), 7.71 (dd, J=8.7, 7.3 Hz, 1H), 7.50 (d, J=9.1 Hz, 1H), 7.35-7.29 (m, 1H), 7.23 (dd, J=17.5, 7.4 Hz, 2H), 7.15 (d, J=7.2 Hz, 1H), 7.06 (t, J=7.7 Hz, 2H), 6.14 (tt, J=55.8, 4.3 Hz, 1H), 3.42-3.35 (m, 4H), 2.78-2.67 (m, 2H), 2.50-2.44 (m, 4H), 1.80 (s, 3H).

Example 186: N-(6-(o-tolyl)-5-(trifluoromethyl)pyridin-2-yl)-6-(4-(2,2,2-trifluoroethyl)piperazin-1-yl)pyridine-2-sulfonamide Condition 2, LCMS: m/z 560.2 [M+H]$^+$, 3.40 min. $^1$H NMR (500 MHz, DMSO-d$_6$) δ 11.53 (s, 1H), 8.21 (d, J=8.9 Hz, 1H), 7.72 (dd, J=8.6, 7.3 Hz, 1H), 7.52 (d, J=6.5 Hz, 1H), 7.36-7.29 (m, 1H), 7.28-7.18 (m, 2H), 7.16 (d, J=7.2 Hz, 1H), 7.10-7.03 (m, 2H), 3.43-3.36 (m, 4H), 3.24-3.12 (m, 2H), 2.58-2.53 (m, 4H), 1.81 (s, 3H).

Example 187: 6-(4-(oxetan-3-yl)piperazin-1-yl)-N-(6-(o-tolyl)-5-(trifluoromethyl)pyridin-2-yl)pyridine-2-sulfonamide Condition 2, LCMS: m/z 534.3 [M+H]$^+$, 2.77 min. $^1$H NMR (500 MHz, DMSO-d$_6$) δ 11.59 (s, 1H), 8.18 (d, J=8.7 Hz, 1H), 7.70 (dd, J=8.6, 7.4 Hz, 1H), 7.50 (d, J=8.8 Hz, 1H), 7.35-7.30 (m, 1H), 7.27-7.19 (m, 2H), 7.14 (d, J=7.2 Hz, 1H), 7.08-7.02 (m, 2H), 4.53 (t, J=6.5 Hz, 2H), 4.43 (t, J=6.1 Hz, 2H), 3.44-3.39 (m, 4H), 3.38-3.32 (m, 1H), 2.18 (t, J=4.7 Hz, 4H), 1.80 (s, 3H).

Example 188: tert-butyl 4-(6-(N-(5-chloro-6-(2,6-dimethylphenyl)pyridin-2-yl)sulfamoyl)pyridin-2-yl)-3-oxopiperazine-1-carboxylate Condition 2, LCMS: m/z 572.3 [M+H]$^+$, 3.38 min. $^1$H NMR (400 MHz, DMSO-d$_6$) δ 11.47 (s, 1H), 8.15 (d, J=8.2 Hz, 1H), 8.05-7.97 (m, 2H), 7.73 (d, J=7.5 Hz, 1H), 7.31 (s, 1H), 7.22-7.14 (m, 1H), 7.07 (d, J=7.6 Hz, 2H), 4.15 (s, 2H), 3.81-3.72 (m, 2H), 3.57-3.51 (m, 2H), 1.72 (s, 6H), 1.43 (s, 9H).

Example 189: 6-(4-methylpiperazin-1-yl)-N-(6-(o-tolyl)-5-(trifluoromethyl)pyridin-2-yl)pyridine-2-sulfonamide Condition 2, LCMS: m/z 492.3 [M+H]$^+$, 2.50 min. $^1$H NMR (400 MHz, DMSO-d$_6$) δ 11.56 (s, 1H), 8.17 (d, J=8.9 Hz, 1H), 7.70 (dd, J=8.7, 7.3 Hz, 1H), 7.49 (d, J=8.8 Hz, 1H), 7.35-7.29 (m, 1H), 7.26-7.18 (m, 2H), 7.14 (d, J=7.2 Hz, 1H), 7.07-7.02 (m, 2H), 3.42-3.37 (m, 4H), 2.31-2.23 (m, 4H), 2.19 (s, 3H), 1.79 (s, 3H).

Example 190: 6-(3-oxopiperazin-1-yl)-N-(6-(o-tolyl)-5-(trifluoromethyl)pyridin-2-yl)pyridine-2-sulfonamide Condition 2, LCMS: m/z 492.2 [M+H]$^+$, 2.98 min. $^1$H NMR (400 MHz, DMSO-d$_6$) δ 11.65 (s, 1H), 8.19 (d, J=8.7 Hz, 1H), 8.12 (s, 1H), 7.73 (dd, J=8.6, 7.4 Hz, 1H), 7.56-7.41 (m, 1H), 7.32 (t, J=7.5 Hz, 1H), 7.27-7.20 (m, 2H), 7.19 (d, J=7.2 Hz, 1H), 7.08 (d, J=7.2 Hz, 1H), 7.04 (d, J=8.7 Hz, 1H), 3.91 (s, 2H), 3.63-3.55 (m, 2H), 3.22-3.14 (m, 2H), 1.80 (s, 3H).

Example 191: 6-(4-glycylpiperazin-1-yl)-N-(6-(o-tolyl)-5-(trifluoromethyl)pyridin-2-yl)pyridine-2-sulfonamide Hydrochloride Condition 2, LCMS: m/z 535.3 [M+H]$^+$, 2.52 min. $^1$H NMR (500 MHz, DMSO-d$_6$) δ 11.62 (s, 1H), 8.23 (d, J=9.0 Hz, 1H), 8.06 (t, J=4.7 Hz, 3H), 7.75 (dd, J=8.7, 7.3 Hz, 1H), 7.53 (s, 1H), 7.37-7.30 (m, 1H), 7.24 (dd, J=10.2, 8.0 Hz, 2H), 7.20 (d, J=7.2 Hz, 1H), 7.12 (d, J=8.7 Hz, 1H), 7.07 (d, J=7.3 Hz, 1H), 3.91 (q, J=5.5 Hz, 2H), 3.56-3.47 (m, 4H), 1.81 (s, 3H).

Example 192: N-(5-chloro-6-(2,6-dimethylphenyl)pyridin-2-yl)-6-(2-oxopiperazin-1-yl)pyridine-2-sulfonamide Hydrochloride Condition 2, LCMS: m/z 472.2 [M+H]$^+$, 2.41 min. $^1$H NMR (400 MHz, DMSO-d$_6$) δ 11.59 (s, 1H), 9.42 (s, 2H), 8.12 (dd, J=8.4, 0.8 Hz, 1H), 8.07-7.94 (m, 2H), 7.76 (dd, J=7.5, 0.7 Hz, 1H), 7.26-7.16 (m, 2H), 7.08 (d, J=7.6 Hz, 2H), 3.99 (s, 2H), 3.96-3.90 (m, 2H), 3.53-3.45 (m, 2H), 1.70 (s, 6H).

Example 193: N-(5-chloro-6-(5-fluoro-2-methylphenyl)pyridin-2-yl)-6-(piperazin-1-yl)pyridine-2-sulfonamide Hydrochloride Condition 2, LCMS: m/z 462.2 [M+H]$^+$, 2.43 min. $^1$H NMR (400 MHz, DMSO-d$_6$) δ 11.32 (s, 1H), 8.92 (s, 2H), 7.99 (d, J=8.8 Hz, 1H), 7.80 (dd, J=8.6, 7.4 Hz, 1H), 7.38 (d, J=8.8 Hz, 1H), 7.32 (dd, J=8.5, 5.8 Hz, 1H), 7.26 (d, J=7.3 Hz, 1H), 7.21-7.14 (m, 2H), 6.92 (dd, J=9.3, 2.7 Hz, 1H), 3.69-3.61 (m, 4H), 3.11 (s, 4H), 1.88 (s, 3H).

Example 194: N-[5-chloro-6-(3-fluoro-2-methylphenyl)pyridin-2-yl]-6-(piperazin-1-yl)pyridine-2-sulfonamide Hydrochloride Condition 2, LCMS: m/z 462.2 [M+H]$^+$, 2.42 min. $^1$H NMR (400 MHz, DMSO-d$_6$) δ 11.32 (s, 1H), 9.02 (s, 2H), 8.00 (d, J=8.8 Hz, 1H), 7.81 (dd, J=8.6, 7.4 Hz, 1H), 7.38 (d, J=8.8 Hz, 1H), 7.34-7.20 (m, 3H), 7.17 (d, J=8.6 Hz, 1H), 6.94 (d, J=6.6 Hz, 1H), 3.69-3.63 (m, 4H), 3.11 (s, 4H), 1.81 (d, J=2.0 Hz, 3H).

Example 195: N-(5-chloro-6-(o-tolyl)pyridin-2-yl)-6-(piperazin-1-yl)pyridine-2-sulfonamide Hydrochloride Condition 2, LCMS: m/z 444.2 [M+H]$^+$, 2.29 min. $^1$H NMR (400 MHz, DMSO-d$_6$) δ 11.26 (s, 1H), 9.01 (s, 2H), 7.98 (d, J=8.8 Hz, 1H), 7.80 (dd, J=8.6, 7.4 Hz, 1H), 7.40-7.30 (m, 2H), 7.30-7.21 (m, 3H), 7.17 (d, J=8.6 Hz, 1H), 7.07 (d, J=7.5 Hz, 1H), 3.68-3.62 (m, 4H), 3.11 (s, 4H), 1.92 (s, 3H).

Example 196: 6-(4-methyl-3-oxopiperazin-1-yl)-N-(6-(o-tolyl)-5-(trifluoromethyl)pyridin-2-yl)pyridine-2-sulfonamide Condition 2, LCMS: m/z 506.2 [M+H]$^+$, 3.06 min. $^1$H NMR (400 MHz, DMSO-d$_6$) δ 11.67 (s, 1H), 8.19 (d, J=8.9 Hz, 1H), 7.74 (dd, J=8.6, 7.3 Hz, 1H), 7.45 (d, J=6.3 Hz, 1H), 7.32 (t, J=7.5 Hz, 1H), 7.26-7.17 (m, 3H), 7.11-7.04 (m, 2H), 3.98 (s, 2H), 3.71 (t, J=5.4 Hz, 2H), 3.32-3.27 (m, 2H), 2.85 (s, 3H), 1.76 (s, 3H).

Example 197: N-(5-chloro-6-(2,6-dimethylphenyl)pyridin-2-yl)-6-(4-methyl-2-oxopiperazin-1-yl)pyridine-2-sulfonamide Condition 2, LCMS: m/z 486.2 [M+H]$^+$, 2.67 min. $^1$H NMR (400 MHz, DMSO-d$_6$) δ 11.49 (s, 1H), 8.17-8.12 (m, 1H), 8.02-7.96 (m, 2H), 7.72 (dd, J=7.5, 0.6 Hz, 1H), 7.31

(d, J=8.8 Hz, 1H), 7.22-7.16 (m, 1H), 7.07 (d, J=7.6 Hz, 2H), 3.62-3.55 (m, 2H), 3.19 (s, 2H), 2.69-2.62 (m, 2H), 2.27 (s, 3H), 1.72 (s, 6H).

Example 198: N-(5-chloro-6-(2,6-dimethylphenyl) pyridin-2-yl)-6-(5,6-dihydroimidazo[1,2-a]pyrazin-7 (8H)-yl)pyridine-2-sulfonamide Condition 2, LCMS: m/z 495.0 [M+H]$^+$, 2.49 min. $^1$H NMR (400 MHz, DMSO-d$_6$) δ 11.34 (s, 1H), 7.96 (d, J=8.8 Hz, 1H), 7.76 (dd, J=8.6, 7.3 Hz, 1H), 7.31 (d, J=8.8 Hz, 1H), 7.24-7.18 (m, 2H), 7.18-7.13 (m, 1H), 7.06 (d, J=1.2 Hz, 1H), 7.03 (d, J=7.7 Hz, 2H), 6.88 (d, J=1.2 Hz, 1H), 4.64 (s, 2H), 3.95 (s, 4H), 1.68 (s, 6H).

Example 199: N-(5-chloro-6-(2,6-dimethylphenyl) pyridin-2-yl)-6-(2-(trifluoromethyl)-5,6-dihydroimidazo[1,2-a]pyrazin-7(8H)-yl)pyridine-2-sulfonamide Condition 2, LCMS: m/z 563.0 [M+H]$^+$ 3.36 min. $^1$H NMR (400 MHz, DMSO-d$_6$) δ 11.31 (s, 1H), 7.95 (d, J=8.8 Hz, 1H), 7.78 (dd, J=8.6, 7.3 Hz, 1H), 7.75 (d, J=1.3 Hz, 1H), 7.29 (d, J=8.7 Hz, 1H), 7.24 (d, J=8.6 Hz, 1H), 7.21 (d, J=7.3 Hz, 1H), 7.19-7.11 (m, 1H), 7.02 (d, J=7.6 Hz, 2H), 4.72 (s, 2H), 4.01 (dd, J=12.2, 4.4 Hz, 4H), 1.66 (s, 6H).

Example 200: 6-((1S,4S)-2,5-diazabicyclo[2.2.2] octan-2-yl)-N-(6-(5-fluoro-2-methylphenyl)-5-(trifluoromethyl)pyridin-2-yl)pyridine-2-sulfonamide Hydrochloride Condition 2, LCMS: m/z 522.1 [M+H]$^+$, 2.58 min. $^1$H NMR (400 MHz, DMSO-d$_6$) δ 11.70 (s, 1H), 8.85 (s, 2H), 8.25 (d, J=9.0 Hz, 1H), 7.81-7.73 (m, 1H), 7.60 (d, J=8.0 Hz, 1H), 7.33-7.27 (m, 1H), 7.23-7.16 (m, 2H), 6.96 (d, J=8.3 Hz, 1H), 6.88 (d, J=8.0 Hz, 1H), 4.54 (s, 1H), 3.84 (s, 1H), 3.66 (d, J=11.7 Hz, 1H), 3.48-3.41 (m, 1H), 3.29-3.13 (m, 2H), 2.02 (s, 1H), 1.83-1.65 (m, 6H).

Example 201: 6-(2,5-diazabicyclo[2.2.2]octan-2-yl)-N-(6-(5-fluoro-2-methylphenyl)-5-(trifluoromethyl) pyridin-2-yl)pyridine-2-sulfonamide Hydrochloride Condition 2, LCMS: m/z 522.3 [M+H]$^+$, 2.58 min. $^1$H NMR (400 MHz, DMSO-d$_6$) δ 11.70 (s, 1H), 9.14 (s, 2H), 8.25 (d, J=8.9 Hz, 1H), 7.80-7.71 (m, 1H), 7.59 (d, J=7.9 Hz, 1H), 7.30 (dd, J=8.5, 5.9 Hz, 1H), 7.23-7.15 (m, 2H), 6.96 (d, J=8.0 Hz, 1H), 6.87 (d, J=8.0 Hz, 1H), 4.55 (s, 1H), 3.83 (s, 1H), 3.68 (s, 1H), 3.44 (d, J=11.7 Hz, 1H), 3.29-3.13 (m, 2H), 2.06 (s, 1H), 1.85-1.62 (m, 6H).

Example 202: 6-((5S)-1,4-diazabicyclo[3.2.1]octan-4-yl)-N-(6-(5-fluoro-2-methylphenyl)-5-(trifluoromethyl)pyridin-2-yl)pyridine-2-sulfonamide Condition 2, LCMS: m/z 522.2 [M+H]$^+$, 2.50 min. $^1$H NMR (400 MHz, Methylene Chloride-d$_2$) δ 7.92 (d, J=8.9 Hz, 1H), 7.67-7.54 (m, 2H), 7.34 (d, J=7.2 Hz, 1H), 7.20 (s, 2H), 7.03 (td, J=2.7, 8.5 Hz, 1H), 6.81 (d, J=7.0 Hz, 1H), 6.71 (d, J=8.6 Hz, 1H), 4.92 (s, 0H), 3.59 (d, J=11.2 Hz, 1H), 3.23 (s, 1H), 3.13-3.02 (m, 1H), 2.92 (d, J=10.9 Hz, 3H), 2.76 (s, 1H); $^{19}$F NMR (376 MHz, Methylene Chloride-d$_2$) δ −58.78 (s, 3F), −118.63 (s, 1F).

Example 203: 6-((1S,4S)-2,5-diazabicyclo[2.2.1] heptan-2-yl)-N-(6-(o-tolyl)-5-(trifluoromethyl)pyridin-2-yl)pyridine-2-sulfonamide Hydrochloride Condition 2, LCMS: m/z 490.2 [M+H]$^+$, 2.50 min. $^1$H NMR (400 MHz, DMSO-d$_6$) δ 11.67 (s, 1H), 9.24 (s, 1H), 8.67 (s, 1H), 8.24 (d, J=8.9 Hz, 1H), 7.75 (t, J=7.9 Hz, 1H), 7.59 (s, 1H), 7.34 (t, J=7.5 Hz, 1H), 7.30-7.17 (m, 3H), 7.08 (s, 1H), 6.86 (d, J=8.5 Hz, 1H), 4.71 (d, J=11.7 Hz, 1H), 4.47 (s, 1H), 3.50 (s, 2H), 3.19-3.07 (m, 1H), 2.98 (s, 1H), 2.08 (d, J=10.9 Hz, 1H), 1.94-1.77 (m, 4H).

Example 204: 6-(3-hydroxy-3-(trifluoromethyl)azetidin-1-yl)-N-(6-(o-tolyl)-5-(trifluoromethyl)pyridin-2-yl)pyridine-2-sulfonamide Condition 2, LCMS: m/z 533 [M+H]$^+$, 3.28 min. $^1$H NMR (400 MHz, Methanol-d$_4$) δ 8.07 (d, J=8.9 Hz, 1H), 7.66 (dd, J=8.4, 7.4 Hz, 1H), 7.57 (s, 1H), 7.31 (d, J=7.4 Hz, 2H), 7.26-7.13 (m, 2H), 7.07 (d, J=7.5 Hz, 1H), 6.70-6.57 (m, 1H), 4.16 (d, J=9.8 Hz, 2H), 3.89 (d, J=9.7 Hz, 2H), 1.93 (d, J=6.8 Hz, 3H).

Example 205: N-(6-(2,6-dimethylphenyl)-4-(trifluoromethyl)pyridin-2-yl)-6-(3-hydroxyazetidin-1-yl) pyridine-2-sulfonamide Condition 2, LCMS: m/z 479.2 [M+H]$^+$, 3.25 min. $^1$H NMR (400 MHz, DMSO-d$_6$) δ 11.49 (s, 1H), 7.69 (dd, J=8.4, 7.4 Hz, 1H), 7.33 (s, 1H), 7.18 (dd, J=15.7, 7.3 Hz, 2H), 7.10 (d, J=7.6 Hz, 2H), 6.60 (d, J=8.3 Hz, 1H), 5.68 (d, J=6.4 Hz, 1H), 4.59-4.37 (m, 1H), 4.02 (dd, J=10.3, 5.3 Hz, 2H), 3.55 (dt, J=9.1, 4.1 Hz, 2H), 1.87 (s, 6H).

Example 206: N-(6-(2,6-dimethylphenyl)-4-methoxypyridin-2-yl)-6-(3-hydroxy-3-methylazetidin-1-yl)pyridine-2-sulfonamide Condition 2, LCMS: m/z 455.2 [M+H]$^+$, 2.83 min. $^1$H NMR (400 MHz, DMSO-d$_6$) δ 12.65 (s, 1H), 7.65 (dd, J=8.3, 7.4 Hz, 1H), 7.27 (d, J=7.2 Hz, 1H), 7.14 (d, J=6.9 Hz, 4H), 6.51 (d, J=8.1 Hz, 1H), 6.38 (s, 1H), 5.58 (s, 1H), 3.86 (s, 2H), 3.69 (s, 5H), 2.10 (s, 6H), 1.38 (s, 3H).

Example 207: N-(5-bromo-6-(o-tolyl)pyridin-2-yl)-6-(3-hydroxy-3-methylazetidin-1-yl)pyridine-2-sulfonamide Condition 2, LCMS: m/z 489.1 [M+H]$^+$, 3.06 min. $^1$H NMR (400 MHz, DMSO-d$_6$) δ 11.18 (s, 1H), 8.09 (d, J=8.8 Hz, 1H), 7.66 (dd, J=8.4, 7.4 Hz, 1H), 7.36-7.29 (m, 2H), 7.24 (dd, J=14.9, 7.3 Hz, 2H), 7.14 (d, J=6.9 Hz, 1H), 7.04 (d, J=7.5 Hz, 1H), 6.60 (d, J=8.2 Hz, 1H), 5.62 (s, 1H), 3.72 (q, J=8.6 Hz, 4H), 1.92 (s, 3H), 1.38 (s, 3H).

Example 208: N-(6-(2-cyclopropylphenyl)-5-(trifluoromethyl)pyridin-2-yl)-6-(3-hydroxyazetidin-1-yl)pyridine-2-sulfonamide Condition 2, LCMS: m/z 491.2 [M+H]$^+$, 3.18 min. $^1$H NMR (400 MHz, Methylene Chloride-d$_2$) δ 7.99 (m, 1H), 7.66 (m, 1H), 7.55 (dd, J=8.5, 7.3 Hz, 1H), 7.34 (td, J=7.6, 1.5 Hz, 1H), 7.26 (dd, J=7.3, 0.7 Hz, 1H), 7.18 (td, J=7.5, 1.2 Hz, 1H), 7.15-7.07 (m, 1H), 6.96 (dd, J=8.0, 1.2 Hz, 1H), 6.41 (dd, J=8.4, 0.7 Hz, 1H), 4.67 (m, 1H), 4.17-4.02 (m, 2H), 3.75-3.66 (m, 2H), 1.44 (m, 1H), 0.67 (m, 3H), 0.58-0.47 (m, 1H).

Example 209: N-(6-(5-fluoro-2-methoxyphenyl)-5-(trifluoromethyl)pyridin-2-yl)-6-(3-hydroxyazetidin-1-yl)pyridine-2-sulfonamide Condition 2, LCMS: m/z 499.2 [M+H]$^+$, 2.95 min. $^1$H NMR (400 MHz, Methylene Chloride-d$_2$) δ 7.95 (m, 1H), 7.70 (m, 1H), 7.59 (dd, J=7.3, 8.5 Hz, 1H), 7.27 (dd, J=0.8, 7.3 Hz, 1H), 7.12 (m, 1H), 6.91 (dt, J=3.9, 7.9 Hz, 2H), 6.45 (dd, J=0.7, 8.5 Hz, 1H), 4.72 (m, 1H), 4.16 (m, 2H), 3.74 (m, 2H), 3.69 (s, 3H), 3.42 (s, 1H).

Example 210: N-(5-chloro-6-(2,6-dimethylphenyl)pyridin-2-yl)-6-(3-hydroxy-3-methylazetidin-1-yl)pyridine-2-sulfonamide Condition 2, LCMS: m/z 459.0 [M+H]$^+$, 3.13 min. $^1$H NMR (400 MHz, Methylene Chloride-d$_2$) δ 7.75 (d, J=8.8 Hz, 1H), 7.61-7.48 (m, 2H), 7.28-7.16 (m, 2H), 7.08 (d, J=7.6 Hz, 2H), 6.41 (d, J=8.4 Hz, 1H), 3.85 (d, J=9.0 Hz, 2H), 3.80 (d, J=8.8 Hz, 2H), 1.90 (s, 6H), 1.51 (s, 3H).

Example 211: N-(5-chloro-6-(2,6-dimethylphenyl)pyridin-2-yl)-6-(3-cyclopropyl-3-hydroxyazetidin-1-yl)pyridine-2-sulfonamide Condition 2, LCMS: m/z 485.0 [M+H]$^+$, 3.23 min. $^1$H NMR (400 MHz, Acetonitrile-d$_3$) δ 8.46 (s, 1H), 7.82 (d, J=8.8 Hz, 1H), 7.59 (dd, J=7.4, 8.4 Hz, 1H), 7.47 (d, J=8.8 Hz, 1H), 7.26-7.17 (m, 1H), 7.15 (d, J=7.3 Hz, 1H), 7.09 (d, J=7.6 Hz, 2H), 6.50 (d, J=8.4 Hz, 1H), 3.73 (d, J=9.1 Hz, 2H), 3.66 (d, J=9.2 Hz, 2H), 3.53 (s, 1H), 1.83 (s, 6H), 0.88 (t, J=6.8 Hz, 1H), 0.51-0.41 (m, 2H), 0.30 (q, J=5.2 Hz, 2H).

Example 212: N-(5-chloro-6-(2-methyl-5-(trifluoromethyl)phenyl)pyridin-2-yl)-6-(3-hydroxy-3-methylazetidin-1-yl)pyridine-2-sulfonamide Condition 2, LCMS: m/z 513.0 [M+H]$^+$, 3.29 min. $^1$H NMR (400 MHz, Methylene Chloride-d$_2$) δ 7.78 (d, J=8.8 Hz, 1H), 7.62 (d, J=8.8 Hz, 1H), 7.58 (dd, J=7.3, 8.4 Hz, 2H), 7.42 (d, J=7.1 Hz, 2H), 7.26 (d, J=7.3 Hz, 1H), 6.46 (d, J=8.4 Hz, 1H), 3.88 (d, J=9.0 Hz, 2H), 3.84 (d, J=8.9 Hz, 2H), 2.17 (s, 3H), 1.54 (s, 4H); $^{19}$F NMR (376 MHz, Methylene Chloride-d$_2$) δ -62.53 (s, 3F).

Example 213: N-(5-chloro-6-(2-chloro-4-fluorophenyl)pyridin-2-yl)-6-(3-hydroxy-3-methylazetidin-1-yl)pyridine-2-sulfonamide Condition 2, LCMS: m/z 483.0 [M+H]$^+$, 3.15 min. $^1$H NMR (400 MHz, Methylene Chloride-d$_2$) δ 7.77 (d, J=8.8 Hz, 1H), 7.65 (d, J=8.8 Hz, 1H), 7.59 (dd, J=7.3, 8.4 Hz, 1H), 7.29 (dd, J=6.0, 8.6 Hz, 1H), 7.27-7.21 (m, 2H), 7.11 (td, J=2.5, 8.3 Hz, 1H), 6.46 (d, J=8.4 Hz, 1H), 3.91 (d, J=9.0 Hz, 2H), 3.86 (d, J=8.9 Hz, 2H), 1.55 (s, 3H); $^{19}$F NMR (376 MHz, Methylene Chloride-d$_2$) δ -110.81--110.92 (m, 1F).

Example 214: N-(5-chloro-6-(2-chloro-4-fluorophenyl)pyridin-2-yl)-6-(3-hydroxyazetidin-1-yl)pyridine-2-sulfonamide Condition 2, LCMS: m/z 469.0 [M+H]$^+$, 3.10 min. $^1$H NMR (400 MHz, Methylene Chloride-d$_2$) δ 7.75 (d, J=8.8 Hz, 1H), 7.65 (d, J=8.8 Hz, 1H), 7.58 (dd, J=7.3, 8.4 Hz, 1H), 7.29 (dd, J=6.0, 8.6 Hz, 1H), 7.26-7.20 (m, 2H), 7.10 (td, J=2.5, 8.3 Hz, 1H), 6.44 (d, J=8.4 Hz, 1H), 4.73 (tt, J=4.3, 6.5 Hz, 1H), 4.25-4.14 (m, 2H), 3.83-3.70 (m, 2H); $^{19}$F NMR (376 MHz, Methylene Chloride-d$_2$) δ -111.01 (q, J=8.1 Hz, 1F).

Example 215: N-(6-(3-fluoro-2-methylphenyl)-5-(trifluoromethyl)pyridin-2-yl)-6-(3-hydroxy-3-methylazetidin-1-yl)pyridine-2-sulfonamide Condition 2, LCMS: m/z 497.0 [M+H]$^+$, 3.17 min. $^1$H NMR (400 MHz, Methylene Chloride-d$_2$) δ 8.00 (d, J=8.8 Hz, 1H), 7.71 (d, J=8.1 Hz, 1H), 7.59 (dd, J=7.3, 8.4 Hz, 1H), 7.28 (d, J=7.3 Hz, 1H), 7.16-7.07 (m, 1H), 6.99 (dd, J=2.4, 9.8 Hz, 1H), 6.93 (td, J=2.6, 8.5 Hz, 1H), 6.46 (d, J=8.4 Hz, 1H), 3.85 (d, J=8.7 Hz, 2H), 3.81 (d, J=8.7 Hz, 2H), 2.01 (s, 3H), 1.54 (s, 3H); $^{19}$F NMR (376 MHz, Methylene Chloride-d$_2$) δ -58.90 (s, 3F), -114.17 (s, 1F).

Example 216: N-(6-(3-fluoro-2-methylphenyl)-5-(trifluoromethyl)pyridin-2-yl)-6-(3-hydroxyazetidin-1-yl)pyridine-2-sulfonamide Condition 2, LCMS: m/z 483.0 [M+H]$^+$, 3.13 min. $^1$H NMR (400 MHz, Methylene Chloride-d$_2$) δ 8.02 (d, J=8.9 Hz, 1H), 7.74 (d, J=8.8 Hz, 1H), 7.59 (dd, J=7.3, 8.5 Hz, 1H), 7.28 (d, J=7.3 Hz, 1H), 7.25-7.17 (m, 1H), 7.11 (t, J=8.9 Hz, 1H), 6.95 (d, J=7.6 Hz, 1H), 6.47 (d, J=8.4 Hz, 1H), 4.75 (ddd, J=4.3, 6.5, 10.8 Hz, 1H), 4.28-4.16 (m, 1H), 3.87 (q, J=8.7 Hz, 1H), 3.79 (dd, J=4.0, 9.2 Hz, 1H), 1.91 (d, J=2.1 Hz, 4H); $^{19}$F NMR (376 MHz, Methylene Chloride-d$_2$) δ -58.91 (d, J=3.9 Hz, 3F), -117.04 (s, 1F).

Example 217: N-(6-(4-fluoro-2-methylphenyl)-5-(trifluoromethyl)pyridin-2-yl)-6-(3-hydroxy-3-methylazetidin-1-yl)pyridine-2-sulfonamide Condition 2, LCMS: m/z 497.0 [M+H]$^+$, 3.19 min. $^1$H NMR (400 MHz, Methylene Chloride-d$_2$) δ 8.02 (d, J=8.9 Hz, 1H), 7.74 (d, J=8.8 Hz, 1H), 7.59 (dd, J=7.3, 8.4 Hz, 1H), 7.28 (d, J=7.2 Hz, 1H), 7.21 (td, J=5.6, 7.9 Hz, 1H), 7.16-7.04 (m, 1H), 6.95 (d, J=7.5 Hz, 1H), 6.47 (d, J=8.3 Hz, 1H), 3.87 (d, J=8.6 Hz, 2H), 3.83 (d, J=8.7 Hz, 2H), 1.90 (d, J=2.1 Hz, 3H), 1.55 (s, 3H); $^{19}$F NMR (376 MHz, Methylene Chloride-d$_2$) δ -58.90 (s, 3F), -117.06 (s, 1F).

Example 218: N-(6-(4-fluoro-2-methylphenyl)-5-(trifluoromethyl)pyridin-2-yl)-6-(3-hydroxyazetidin-1-yl)pyridine-2-sulfonamide Condition 2, LCMS: m/z 483.0 [M+H]$^+$, 3.13 min. $^1$H NMR (400 MHz, Methylene Chloride-d$_2$) δ 8.00 (d, J=8.9 Hz, 1H), 7.71 (d, J=8.8 Hz, 1H), 7.59 (dd, J=7.3, 8.4 Hz, 1H), 7.28 (d, J=7.3 Hz, 1H), 7.17-7.07 (m, 1H), 6.99 (dd, J=2.5, 9.8 Hz, 1H), 6.93 (td, J=2.6, 8.5 Hz, 1H), 6.46 (d, J=8.4 Hz, 1H), 4.74 (tt, J=4.3, 6.5 Hz, 1H), 4.25-4.13 (m, 2H), 3.76 (dd, J=4.2, 9.8 Hz, 2H), 2.01 (s, 4H); $^{19}$F NMR (376 MHz, Methylene Chloride-d$_2$) δ -58.91 (s, 3F), -113.92 (s, 1F)

Example 219: N-(6-(5-fluoro-2-methylphenyl)-5-(trifluoromethyl)pyridin-2-yl)-6-(3-hydroxy-3-methylazetidin-1-yl)pyridine-2-sulfonamide Condition 2, LCMS: m/z 497.0 [M+H]$^+$, 3.16 min. $^1$H NMR (400 MHz, Methylene Chloride-d$_2$) δ 8.03 (d, J=8.8 Hz, 1H), 7.73 (d, J=8.8 Hz, 1H), 7.60 (dd, J=7.4, 8.4 Hz, 1H), 7.28 (d, J=7.3 Hz, 1H), 7.24 (dd, J=5.7, 8.5 Hz, 1H), 7.06 (td, J=2.7, 8.5 Hz, 1H), 6.87 (dd, J=2.5, 9.0 Hz, 1H), 6.48 (d, J=8.5 Hz, 1H), 3.90 (d, J=8.8 Hz, 2H), 3.85 (d, J=8.9 Hz, 2H), 1.97 (s, 4H), 1.55 (s, 4H); $^{19}$F NMR (376 MHz, Methylene Chloride-d$_2$) δ -58.95 (s, 3F), -118.76 (s, 1F).

Example 220: N-(6-(5-fluoro-2-methylphenyl)-5-(trifluoromethyl)pyridin-2-yl)-6-(3-hydroxyazetidin-1-yl)pyridine-2-sulfonamide Condition 2, LCMS: m/z 483.0 [M+H]$^+$, 3.09 min. $^1$H NMR (400 MHz, Methylene Chloride-d$_2$) δ 8.02 (d, J=8.8

Hz, 1H), 7.74 (d, J=8.8 Hz, 1H), 7.59 (dd, J=7.4, 8.4 Hz, 1H), 7.28 (d, J=7.3 Hz, 1H), 7.24 (dd, J=5.7, 8.5 Hz, 1H), 7.06 (td, J=2.7, 8.5 Hz, 1H), 6.87 (dd, J=2.6, 9.0 Hz, 1H), 6.47 (d, J=8.5 Hz, 1H), 4.75 (ddd, J=4.3, 6.5, 10.8 Hz, 1H), 4.21 (dd, J=6.6, 9.2 Hz, 2H), 3.78 (dd, J=4.1, 9.3 Hz, 2H), 1.96 (s, 3H); $^{19}$F NMR (376 MHz, Methylene Chloride-d$_2$) δ −58.97 (s, 3F), −118.81 (s, 1F).

Example 221: N-(6-(2-chlorophenyl)-5-(trifluoromethyl)pyridin-2-yl)-6-(3-hydroxy-3-methylazetidin-1-yl)pyridine-2-sulfonamide Condition 2, LCMS: m/z 499.0 [M+H]$^+$, 3.12 min. $^1$H NMR (400 MHz, Methylene Chloride-d$_2$) δ 8.02 (d, J=8.8 Hz, 1H), 7.76 (d, J=8.8 Hz, 1H), 7.59 (dd, J=7.3, 8.5 Hz, 1H), 7.46 (dd, J=1.4, 8.0 Hz, 1H), 7.41 (td, J=1.7, 7.6 Hz, 1H), 7.35 (td, J=1.5, 7.4 Hz, 1H), 7.27 (dd, J=2.6, 7.3 Hz, 2H), 6.47 (d, J=8.5 Hz, 1H), 3.96-3.78 (m, 4H), 1.54 (s, 3H); $^{19}$F NMR (376 MHz, Methylene Chloride-d$_2$) ä −59.18 (s, 3F).

Example 222: N-(6-(2-chlorophenyl)-5-(trifluoromethyl)pyridin-2-yl)-6-(3-hydroxyazetidin-1-yl)pyridine-2-sulfonamide Condition 2, LCMS: m/z 485.0 [M+H]$^+$, 3.05 min. $^1$H NMR (400 MHz, Methylene Chloride-d$_2$) δ 8.01 (d, J=8.8 Hz, 1H), 7.78 (d, J=8.8 Hz, 1H), 7.59 (dd, J=7.4, 8.4 Hz, 1H), 7.46 (dd, J=1.4, 8.0 Hz, 1H), 7.41 (td, J=1.7, 7.6 Hz, 1H), 7.35 (td, J=1.4, 7.4 Hz, 1H), 7.27 (dd, J=2.4, 7.2 Hz, 2H), 6.45 (d, J=8.4 Hz, 1H), 4.72 (tt, J=4.3, 6.5 Hz, 1H), 4.20 (d, J=8.8 Hz, 1H), 4.16 (d, J=8.7 Hz, 1H), 3.80-3.73 (m, 2H); $^{19}$F NMR (376 MHz, Methylene Chloride-d$_2$) δ −59.18 (s, 3F).

Example 223: N-(5-chloro-6-(2-methyl-5-(trifluoromethyl)phenyl)pyridin-2-yl)-6-(3-hydroxyazetidin-1-yl)pyridine-2-sulfonamide Condition 2, LCMS: m/z 499.0 [M+H]$^+$, 3.23 min. $^1$H NMR (400 MHz, Methylene Chloride-d$_2$) δ 7.76 (d, J=8.8 Hz, 1H), 7.62 (d, J=8.8 Hz, 1H), 7.60-7.52 (m, 2H), 7.41 (d, J=8.1 Hz, 2H), 7.24 (d, J=7.2 Hz, 1H), 6.44 (d, J=8.4 Hz, 1H), 4.72 (tt, J=4.3, 6.5 Hz, 1H), 4.18 (ddd, J=0.9, 6.5, 9.1 Hz, 2H), 3.76 (ddd, J=0.9, 4.3, 9.3 Hz, 2H), 2.16 (s, 3H); $^{19}$F NMR (376 MHz, Methylene Chloride-d$_2$) δ −62.54 (s, 3F).

Example 224: 6-(3-hydroxyazetidin-1-yl)-N-(5-(trifluoromethyl)-6-(2-(trifluoromethyl)phenyl)pyridin-2-yl)pyridine-2-sulfonamide Condition 2, LCMS: m/z 519.0 [M+H]$^+$, 3.06 min. $^1$H NMR (400 MHz, Acetonitrile-d$_3$) δ 8.82 (d, J=43.4 Hz, 1H), 8.09 (d, J=8.9 Hz, 1H), 7.84-7.77 (m, 1H), 7.75 (d, J=8.9 Hz, 1H), 7.70-7.63 (m, 2H), 7.61 (dd, J=7.4, 8.4 Hz, 1H), 7.39-7.30 (m, 1H), 7.18 (d, J=7.3 Hz, 1H), 6.52 (d, J=8.5 Hz, 1H), 4.70-4.52 (m, 1H), 4.21-4.02 (m, 2H), 3.65 (dt, J=4.7, 9.2 Hz, 2H); $^{19}$F NMR (376 MHz, Acetonitrile-d$_3$) δ −58.50 (d, J=2.2 Hz, 3F), −58.55--58.66 (m, 3F).

Example 225: N-(6-(2-chloro-4-fluorophenyl)-5-(trifluoromethyl)pyridin-2-yl)-6-(3-hydroxyazetidin-1-yl)pyridine-2-sulfonamide Condition 2, LCMS: m/z 503.1 [M+H]$^+$, 3.13 min. $^1$H NMR (400 MHz, Chloroform-d) δ 8.00 (d, J=8.8 Hz, 1H), 7.84 (d, J=8.8 Hz, 1H), 7.58 (dd, J=7.4, 8.3 Hz, 1H), 7.31 (d, J=7.3 Hz, 1H), 7.28-7.24 (m, 1H), 7.21 (dd, J=2.5, 8.5 Hz, 1H), 7.06 (td, J=2.5, 8.3 Hz, 1H), 6.44 (d, J=8.4 Hz, 1H), 4.76 (tt, J=4.3, 6.5 Hz, 1H), 4.20 (dd, J=8.8, 16.6 Hz, 2H), 3.79 (d, J=8.6 Hz, 2H); $^{19}$F NMR (376 MHz, Chloroform-d) δ −58.88 (s, 3F), −109.92 (s, 1F).

Example 226: N-(6-(2-chloro-5-methoxyphenyl)-5-(trifluoromethyl)pyridin-2-yl)-6-(3-hydroxyazetidin-1-yl)pyridine-2-sulfonamide Condition 2, LCMS: m/z 515.1 [M+H]$^+$, 3.01 min. $^1$H NMR (400 MHz, Chloroform-d) δ 8.00 (d, J=8.9 Hz, 1H), 7.81 (d, J=8.8 Hz, 1H), 7.57 (dd, J=7.4, 8.4 Hz, 1H), 7.34 (d, J=8.9 Hz, 1H), 7.31 (d, J=7.3 Hz, 1H), 6.94 (dd, J=3.0, 8.9 Hz, 1H), 6.82 (d, J=2.9 Hz, 1H), 6.42 (d, J=8.4 Hz, 1H), 4.74 (tt, J=4.3, 6.5 Hz, 1H), 4.27-4.15 (m, 2H), 3.81 (s, 3H), 3.80-3.75 (m, 2H); $^{19}$F NMR (376 MHz, Chloroform-d) δ −58.85 (s, 3F).

Example 227: N-(5-chloro-6-(2-chlorophenyl)pyridin-2-yl)-6-(3-hydroxyazetidin-1-yl)pyridine-2-sulfonamide Condition 2, LCMS: m/z 451.0 [M+H]$^+$, 2.96 min. $^1$H NMR (400 MHz, Chloroform-d) δ 7.74 (d, J=8.8 Hz, 1H), 7.70 (d, J=8.8 Hz, 1H), 7.56 (dd, J=7.4, 8.3 Hz, 1H), 7.50-7.46 (m, 1H), 7.43-7.39 (m, 1H), 7.38-7.34 (m, 1H), 7.33-7.30 (m, 1H), 7.30-7.26 (m, 2H), 6.41 (d, J=8.4 Hz, 1H), 4.79-4.67 (m, 1H), 4.20 (dd, J=6.8, 9.4 Hz, 2H), 3.79 (dd, J=4.3, 9.8 Hz, 2H), 2.29 (s, 1H).

Example 228: N-(5-chloro-6-(2-chloro-5-methoxyphenyl)pyridin-2-yl)-6-(3-hydroxyazetidin-1-yl)pyridine-2-sulfonamide Condition 2, LCMS: m/z 481.0 [M+H]$^+$, 2.98 min. $^1$H NMR (400 MHz, Chloroform-d) δ 7.70 (s, 1H), 7.69 (s, 1H), 7.54 (dd, J=7.4, 8.4 Hz, 1H), 7.48 (dd, J=2.7, 7.2 Hz, 1H), 7.35 (d, J=8.8 Hz, 1H), 7.26 (d, J=2.3 Hz, 1H), 6.92 (dd, J=3.0, 8.9 Hz, 1H), 6.82 (d, J=3.0 Hz, 1H), 6.39 (d, J=8.4 Hz, 1H), 4.72 (s, 1H), 4.19 (dd, J=6.9, 9.4 Hz, 2H), 3.81 (s, 3H), 3.77 (dd, J=4.6, 9.7 Hz, 2H), 2.22 (d, J=11.7 Hz, 1H).

Example 229: N-(5-chloro-6-(2-chloro-3-fluorophenyl)pyridin-2-yl)-6-(3-hydroxyazetidin-1-yl)pyridine-2-sulfonamide Condition 2, LCMS: m/z 469.0 [M+H]$^+$, 2.99 min. $^1$H NMR (400 MHz, Chloroform-d) δ 7.75 (s, 1H), 7.74 (s, 1H), 7.57 (dd, J=7.4, 8.4 Hz, 1H), 7.53 (s, 1H), 7.35 (td, J=5.1, 8.0 Hz, 1H), 7.29 (d, J=4.6 Hz, 2H), 7.25 (td, J=1.5, 8.6 Hz, 1H), 7.13 (dt, J=1.2, 7.6 Hz, 1H), 6.43 (d, J=8.4 Hz, 1H), 4.75 (s, 1H), 4.26-4.17 (m, 2H), 3.85-3.77 (m, 2H), 2.22 (d, J=5.8 Hz, 1H); $^{19}$F NMR (376 MHz, Chloroform-d) δ −113.69 (dd, J=5.2, 8.6 Hz, 1F).

Example 230: N-(6-(2-chloro-3-fluorophenyl)-5-(trifluoromethyl)pyridin-2-yl)-6-(3-hydroxyazetidin-1-yl)pyridine-2-sulfonamide Condition 2, LCMS: m/z 503.1 [M+H]$^+$, 3.04 min. $^1$H NMR (400 MHz, Chloroform-d) δ 8.02 (d, J=8.8 Hz, 1H), 7.87 (d, J=8.8 Hz, 1H), 7.69 (s, 1H), 7.59 (dd, J=7.4, 8.4 Hz, 1H), 7.33 (td, J=4.5, 7.1, 7.7 Hz, 2H), 7.25 (dd, J=1.5, 8.5 Hz, 1H), 7.11 (d, J=7.5 Hz, 1H), 6.45 (d, J=8.4 Hz, 1H), 4.77

(d, J=4.1 Hz, 1H), 4.28-4.18 (m, 2H), 3.81 (dd, J=4.1, 9.6 Hz, 2H); $^{19}$F NMR (376 MHz, Chloroform-d) δ −58.86 (s, 3F), −113.97 (s, 1F).

Example 231: N-(5-chloro-6-(2,6-dimethylphenyl) pyridin-2-yl)-6-(3-hydroxyazetidin-1-yl)pyridine-2-sulfonamide Condition 2, LCMS: m/z 445.2 [M+H]$^+$, 3.08 min. $^1$H NMR (400 MHz, DMSO-d$_6$) δ 11.19 (s, 1H), 7.97 (d, J=8.8 Hz, 1H), 7.64 (dd, J=7.4, 8.4 Hz, 1H), 7.37 (d, J=8.8 Hz, 1H), 7.23-7.15 (m, 1H), 7.11-7.07 (m, 3H), 6.58 (d, J=8.3 Hz, 1H), 5.68 (d, J=6.4 Hz, 1H), 4.57-4.48 (m, 1H), 4.10-4.03 (m, 2H), 3.58 (dd, J=4.7, 9.4 Hz, 2H), 1.79 (s, 6H).

Example 232: N-(5-chloro-6-(3-fluoro-2-methylphenyl)pyridin-2-yl)-6-(3-hydroxyazetidin-1-yl)pyridine-2-sulfonamide Condition 2, LCMS: m/z 449.1 [M+H]$^+$, 3.06 min. $^1$H NMR (400 MHz, DMSO-d$_6$) δ 11.26 (s, 1H), 7.98 (d, J=8.8 Hz, 1H), 7.67 (dd, J=8.4, 7.4 Hz, 1H), 7.41 (d, J=8.8 Hz, 1H), 7.33-7.20 (m, 2H), 7.14 (d, J=6.9 Hz, 1H), 6.94 (d, J=7.5 Hz, 1H), 6.60 (d, J=8.4 Hz, 1H), 5.69 (d, J=6.5 Hz, 1H), 4.59-4.48 (m, 1H), 4.07 (dd, J=9.0, 6.8 Hz, 2H), 3.59 (dd, J=9.3, 4.6 Hz, 2H), 1.83 (d, J=2.0 Hz, 3H).

Example 233: 6-(3-hydroxyazetidin-1-yl)-N-(6-(o-tolyl)-5-(trifluoromethyl)pyridin-2-yl)pyridine-2-sulfonamide Condition 2, LCMS: m/z 465.2 [M+H]$^+$, 3.04 min. $^1$H NMR (400 MHz, DMSO-d$_6$) δ 11.60 (s, 1H), 8.21 (d, J=8.9 Hz, 1H), 7.65 (dd, J=8.4, 7.4 Hz, 1H), 7.52 (s, 1H), 7.37-7.28 (m, 1H), 7.28-7.19 (m, 2H), 7.13 (d, J=7.0 Hz, 1H), 7.08 (d, J=7.3 Hz, 1H), 6.60 (d, J=8.3 Hz, 1H), 5.69 (d, J=6.5 Hz, 1H), 4.59-4.47 (m, 1H), 4.06 (t, J=7.6 Hz, 2H), 3.58 (dd, J=9.1, 4.7 Hz, 2H), 1.82 (s, 3H).

Example 234: N-(5-chloro-6-(5-fluoro-2-methylphenyl)pyridin-2-yl)-6-(3-hydroxyazetidin-1-yl)pyridine-2-sulfonamide Condition 2, LCMS: m/z 449.1 [M+H]$^+$, 3.05 min. $^1$H NMR (400 MHz, DMSO-d$_6$) δ 11.25 (s, 1H), 7.98 (d, J=8.8 Hz, 1H), 7.66 (dd, J=8.4, 7.4 Hz, 1H), 7.41 (d, J=8.8 Hz, 1H), 7.31 (dd, J=8.5, 5.8 Hz, 1H), 7.20-7.12 (m, 2H), 6.93 (dd, J=9.3, 2.7 Hz, 1H), 6.60 (dd, J=8.4, 0.5 Hz, 1H), 5.70 (d, J=6.5 Hz, 1H), 4.58-4.47 (m, 1H), 4.08 (dd, J=9.0, 6.8 Hz, 2H), 3.59 (dd, J=9.3, 4.6 Hz, 2H), 1.90 (s, 3H).

Example 235: N-(5-chloro-6-(5-fluoro-2-methylphenyl)pyridin-2-yl)-6-(3-hydroxy-3-(hydroxymethyl)azetidin-1-yl)pyridine-2-sulfonamide Condition 2, LCMS: m/z 479.2 [M+H]$^+$, 2.99 min. $^1$H NMR (400 MHz, DMSO-d$_6$) δ 11.18 (s, 1H), 7.90 (d, J=7.9 Hz, 1H), 7.52 (dd, J=7.3, 8.4 Hz, 1H), 7.41 (d, J=8.6 Hz, 1H), 7.29 (dd, J=5.9, 8.5 Hz, 1H), 7.15 (m, 2H), 7.03 (d, J=7.2 Hz, 1H), 6.91 (dd, J=2.6, 9.4 Hz, 1H), 6.79 (d, J=8.5 Hz, 1H), 5.89 (s, 1H), 4.33 (d, J=6.6 Hz, 2H), 4.26 (d, J=6.6 Hz, 2H), 3.39 (d, J=5.7 Hz, 2H), 1.90 (s, 3H). 19F NMR (376 MHz, DMSO-d$_6$) δ −117.92 (s).

Example 236: methyl 1-(6-(N-(6-(2-cyclopropylphenyl)-5-(trifluoromethyl)pyridin-2-yl)sulfamoyl) pyridin-2-yl)-4-methylpiperidine-4-carboxylate Condition 2, LCMS: m/z 575.2 [M+H]$^+$, 3.50 min. $^1$H NMR (400 MHz, Methylene Chloride-d$_2$) δ 8.01 (m, 1H), 7.69 (m, 1H), 7.59 (dd, J=7.3, 8.7 Hz, 1H), 7.35 (td, J=1.4, 7.6 Hz, 1H), 7.28-7.15 (m, 2H), 7.10 (m, 1H), 6.96 (dd, J=1.2, 7.8 Hz, 1H), 6.80 (dd, J=0.6, 8.8 Hz, 1H), 3.83-3.73 (m, 1H), 3.68 (s, 3H), 3.42 (s, 1H), 3.02 (m, 2H), 2.11-1.99 (m, 2H), 1.53-1.20 (m, 4H), 1.18 (s, 3H), 0.71-0.57 (m, 3H).

Example 237: 1-(6-(N-(6-(2-cyclopropylphenyl)-5-(trifluoromethyl)pyridin-2-yl)sulfamoyl)pyridin-2-yl)-4-methylpiperidine-4-carboxylic Acid Condition 1, LCMS: m/z 561.2 [M+H]$^+$, 1.19 min. $^1$H NMR (400 MHz, Methylene Chloride-d$_2$) δ 7.99 (m, 1H), 7.67-7.51 (m, 2H), 7.36-7.23 (m, 2H), 7.14 (t, J=7.4 Hz, 1H), 7.05 (m, 1H), 6.91 (m, 1H), 6.73 (m, 1H), 3.86 (m, 2H), 3.42 (m, 1H), 2.82 (m, 2H), 1.95 (m, 2H), 1.41-1.19 (m, 5H), 0.67-0.43 (m, 4H).

Example 238: 1-(6-(N-(6-(2-chlorophenyl)-5-(trifluoromethyl)pyridin-2-yl)sulfamoyl)pyridin-2-yl)-4-methylpiperidine-4-carboxylic Acid Condition 2, LCMS: m/z 555.1 [M+H]$^+$, 3.19 min. $^1$H NMR (400 MHz, Methylene Chloride-d$_2$) δ 8.07 (d, J=9.0 Hz, 1H), 7.87-7.80 (m, 1H), 7.66-7.59 (m, 1H), 7.49-7.40 (m, 2H), 7.35 (ddd, J=2.1, 5.4, 8.7 Hz, 1H), 7.27 (dd, J=7.4, 10.3 Hz, 2H), 6.83 (d, J=8.7 Hz, 1H), 3.85 (dd, J=5.0, 13.4 Hz, 2H), 3.02 (t, J=12.2 Hz, 2H), 2.02 (d, J=9.4 Hz, 3H), 1.37 (ddd, J=3.8, 9.1, 14.4 Hz, 2H), 1.22 (s, 3H); $^{19}$F NMR (376 MHz, DMSO-d$_6$) δ −56.10 (s, 3F).

Example 239: 1-(6-(N-(5-chloro-6-(2-chlorophenyl)pyridin-2-yl)sulfamoyl)pyridin-2-yl)-4-methylpiperidine-4-carboxylic Acid Condition 2, LCMS: m/z 521.1 [M+H]$^+$, 3.16 min. $^1$H NMR (400 MHz, DMSO-d$_6$) δ 12.39 (s, 1H), 11.19 (s, 1H), 7.99 (d, J=8.9 Hz, 1H), 7.70 (dd, J=7.3, 8.6 Hz, 1H), 7.54 (dd, J=1.2, 8.0 Hz, 1H), 7.50-7.43 (m, 2H), 7.41 (td, J=1.3, 7.4 Hz, 1H), 7.17 (dd, J=1.7, 7.5 Hz, 1H), 7.11 (d, J=7.2 Hz, 1H), 7.07 (d, J=8.7 Hz, 1H), 3.87-3.73 (m, 2H), 3.35 (s, 1H), 3.09-2.93 (m, 2H), 1.85 (d, J=13.6 Hz, 2H), 1.21-1.11 (m, 3H), 1.08 (s, 3H).

Example 240: 1-(6-(N-(6-(2-chloro-4-fluorophenyl)-5-(trifluoromethyl)pyridin-2-yl)sulfamoyl)pyridin-2-yl)-4-methylpiperidine-4-carboxylic Acid Condition 2, LCMS: m/z 573.1 [M+H]$^+$, 3.29 min. $^1$H NMR (400 MHz, Chloroform-d) δ 7.92 (d, J=8.9 Hz, 1H), 7.68 (d, J=8.8 Hz, 1H), 7.52 (dd, J=7.3, 8.6 Hz, 1H), 7.23 (d, J=7.2 Hz, 1H), 7.15 (dd, J=6.0, 8.5 Hz, 1H), 7.10 (dd, J=2.4, 8.4 Hz, 1H), 6.96 (td, J=2.5, 8.3 Hz, 1H), 6.71 (d, J=8.7 Hz, 1H), 3.89-3.75 (m, 2H), 2.89 (t, J=12.4 Hz, 2H), 2.01-1.89 (m, 2H), 1.35-1.21 (m, 2H), 1.15 (s, 3H); $^{19}$F NMR (376 MHz, Chloroform-d) δ −58.92 (s, 3F), −109.61 (d, J=6.1 Hz, 1F).

Example 241: 1-(6-(N-(6-(2-chloro-5-methoxyphenyl)-5-(trifluoromethyl)pyridin-2-yl)sulfamoyl)pyridin-2-yl)-4-methylpiperidine-4-carboxylic Acid Condition 2, LCMS: m/z 585.2 [M+H]$^+$, 3.19 min. $^1$H NMR (400 MHz, Chloroform-d) δ 7.91 (d, J=8.9 Hz, 1H), 7.66 (d, J=8.8 Hz, 1H), 7.51 (dd, J=7.3, 8.7 Hz, 1H), 7.23 (d, J=2.6 Hz, 1H), 7.21 (d, J=4.3 Hz, 1H), 6.84 (dd, J=3.0, 8.9 Hz, 1H), 6.74-6.66 (m, 2H), 3.88-3.75 (m, 2H), 3.68 (s, 3H), 2.89 (t, J=12.5 Hz, 2H), 1.97 (d, J=7.9 Hz, 3H), 1.28 (t, J=12.6 Hz, 2H), 1.15 (s, 3H); $^{19}$F NMR (376 MHz, Chloroform-d) δ −58.88 (s, 3F).

Example 242: 1-(6-(N-(6-(2-chloro-3-fluorophenyl)-5-(trifluoromethyl)pyridin-2-yl)sulfamoyl)pyridin-2-yl)-4-methylpiperidine-4-carboxylic Acid Condition 2, LCMS: m/z 573.2 [M+H]$^+$, 3.20 min. $^1$H NMR (400 MHz, Chloroform-d) δ 7.94 (d, J=8.9 Hz, 1H), 7.69 (d, J=8.9 Hz, 1H), 7.52 (dd, J=7.3, 8.7 Hz, 1H), 7.23 (td, J=2.4, 5.0 Hz, 2H), 7.18-7.11 (m, 1H), 6.99 (d, J=7.5 Hz, 1H), 6.72 (d, J=8.7 Hz, 1H), 3.93-3.73 (m, 2H), 2.90 (dt, J=9.7, 18.4 Hz, 2H), 2.01-1.89 (m, 2H), 1.39-1.22 (m, 2H), 1.14 (s, 3H); $^{19}$F NMR (376 MHz, Chloroform-d) δ −58.89 (s, 3F), −114.06 (dd, J=5.2, 8.5 Hz, 1F).

Example 243: 1-(6-(N-(5-chloro-6-(2-chloro-4-fluorophenyl)pyridin-2-yl)sulfamoyl)pyridin-2-yl)-4-methylpiperidine-4-carboxylic Acid Condition 2, LCMS: m/z 539.1 [M+H]$^+$, 3.25 min. $^1$H NMR (400 MHz, Chloroform-d) δ 7.67 (d, J=8.9 Hz, 1H), 7.59 (d, J=8.9 Hz, 1H), 7.50 (dd, J=7.4, 8.6 Hz, 1H), 7.22-7.14 (m, 2H), 7.12 (dd, J=2.5, 8.5 Hz, 1H), 6.98 (td, J=2.5, 8.3 Hz, 1H), 6.70 (d, J=8.7 Hz, 1H), 3.80 (dt, J=3.5, 13.3 Hz, 2H), 3.03-2.84 (m, 2H), 1.99 (d, J=10.3 Hz, 2H), 1.37-1.24 (m, 2H), 1.16 (s, 3H); $^{19}$F NMR (376 MHz, Chloroform-d) δ −109.71 (s, 1F).

Example 244: 1-(6-(N-(5-chloro-6-(2-chloro-5-methoxyphenyl)pyridin-2-yl)sulfamoyl)pyridin-2-yl)-4-methylpiperidine-4-carboxylic Acid Condition 2, LCMS: m/z 551.1 [M+H]$^+$, 3.18 min. $^1$H NMR (400 MHz, Chloroform-d) δ 7.68 (d, J=8.9 Hz, 1H), 7.59 (d, J=8.9 Hz, 1H), 7.50 (dd, J=7.3, 8.6 Hz, 1H), 7.25 (d, J=8.9 Hz, 1H), 7.21 (d, J=7.4 Hz, 1H), 6.84 (dd, J=3.0, 8.9 Hz, 1H), 6.75-6.67 (m, 2H), 3.84-3.75 (m, 2H), 3.71 (s, 3H), 3.02-2.89 (m, 2H), 1.99 (d, J=13.0 Hz, 2H), 1.37-1.25 (m, 2H), 1.15 (s, 3H).

Example 245: 1-(6-(N-(5-chloro-6-(2-chloro-3-fluorophenyl)pyridin-2-yl)sulfamoyl)pyridin-2-yl)-4-methylpiperidine-4-carboxylic Acid Condition 2, LCMS: m/z 539.1 [M+H]$^+$, 3.18 min. $^1$H NMR (400 MHz, Chloroform-d) δ 7.67 (d, J=8.9 Hz, 1H), 7.59 (d, J=8.9 Hz, 1H), 7.50 (dd, J=7.3, 8.7 Hz, 1H), 7.24 (td, J=5.1, 8.0 Hz, 1H), 7.19 (d, J=7.1 Hz, 1H), 7.15 (td, J=1.5, 8.6 Hz, 1H), 7.00 (d, J=7.6 Hz, 1H), 6.70 (d, J=8.7 Hz, 1H), 3.89-3.74 (m, 2H), 3.04-2.84 (m, 2H), 2.02-1.93 (m, 2H), 1.38-1.24 (m, 2H), 1.15 (s, 3H); $^{19}$F NMR (376 MHz, Chloroform-d) δ −113.68 (dd, J=5.2, 8.6 Hz, 1F).

Example 246: methyl 1-(6-(N-(5-chloro-6-(2,6-dimethylphenyl)pyridin-2-yl)sulfamoyl)pyridin-2-yl)piperidine-4-carboxylate Condition 2, LCMS: m/z 515.2 [M+H]$^+$, 3.31 min. $^1$H NMR (400 MHz, DMSO-d$_6$) δ 11.16 (s, 1H), 7.95 (d, J=8.8 Hz, 1H), 7.67 (dd, J=7.3, 8.7 Hz, 1H), 7.33 (d, J=8.8 Hz, 1H), 7.18 (m, 1H), 7.06 (m, 4H), 4.07 (m, 2H), 3.58 (s, 3H), 2.89 (m, 2H), 2.61 (tt, J=3.8, 11.1 Hz, 1H), 1.73 (s, 8H), 1.31 (m, 2H).

Example 247: 1-(6-(N-(5-chloro-6-(2,6-dimethylphenyl)pyridin-2-yl)sulfamoyl)pyridin-2-yl)piperidine-4-carboxylic Acid Condition 2, LCMS: m/z 501.2 [M+H]$^+$, 3.16 min. $^1$H NMR (400 MHz, DMSO-d$_6$) δ 12.23 (s, 1H), 11.16 (s, 1H), 7.95 (d, J=8.8 Hz, 1H), 7.67 (dd, J=7.3, 8.7 Hz, 1H), 7.35 (d, J=8.7 Hz, 1H), 7.18 (m, 1H), 7.06 (m, 4H), 4.05 (m, 2H), 2.88 (m, 2H), 2.46 (m, 1H), 1.75 (m, 8H), 1.31 (m, 2H)

Example 248: 1-(6-(N-(5-chloro-6-(2,6-dimethylphenyl)pyridin-2-yl)sulfamoyl)pyridin-2-yl)-4-ethyl-piperidine-4-carboxylic Acid Condition 2, LCMS: m/z 529.2 [M+H]$^+$, 3.35 min. $^1$H NMR (400 MHz, DMSO-d$_6$) δ 12.48 (s, 1H), 11.14 (s, 1H), 7.97 (d, J=8.8 Hz, 1H), 7.66 (dd, J=7.3, 8.6 Hz, 1H), 7.33 (d, J=8.8 Hz, 1H), 7.18 (m, 1H), 7.06 (m, 3H), 7.02 (d, J=8.7 Hz, 1H), 3.95 (m, 2H), 2.87 (m, 2H), 1.89 (m, 2H), 1.73 (s, 6H), 1.40 (q, J=7.5 Hz, 2H), 1.08 (m, 2H), 0.75 (t, J=7.5 Hz, 3H).

Example 249: ethyl 1-(6-(N-(5-chloro-6-(2,6-dimethylphenyl)pyridin-2-yl)sulfamoyl)pyridin-2-yl)-4-methylpiperidine-4-carboxylate Condition 2, LCMS: m/z 543.2 [M+H]$^+$, 3.51 min. $^1$H NMR (400 MHz, DMSO-d$_6$) δ 11.15 (s, 1H), 7.96 (d, J=8.8 Hz, 1H), 7.67 (dd, J=8.7, 7.3 Hz, 1H), 7.33 (d, J=8.8 Hz, 1H), 7.21-7.14 (m, 1H), 7.10-7.01 (m, 4H), 4.09 (q, J=7.1 Hz, 2H), 3.85-3.76 (m, 2H), 3.05-2.94 (m, 2H), 1.91-1.81 (m, 2H), 1.27-1.20 (m, 2H), 1.17 (t, J=7.1 Hz, 3H), 1.10 (s, 3H).

Example 250: 1-(6-(N-(5-chloro-6-(2,6-dimethylphenyl)pyridin-2-yl)sulfamoyl)pyridin-2-yl)-4-methylpiperidine-4-carboxylic Acid Condition 2, LCMS: m/z 515.2 [M+H]$^+$, 3.28 min. $^1$H NMR (400 MHz, DMSO-d$_6$) δ 7.93 (d, J=8.8 Hz, 1H), 7.66 (dd, J=8.6, 7.3 Hz, 1H), 7.33 (d, J=8.8 Hz, 1H), 7.20-7.13 (m, 1H), 7.09-6.98 (m, 4H), 3.87-3.74 (m, 2H), 3.07-2.95 (m, 2H), 1.85 (d, J=13.7 Hz, 2H), 1.75 (s, 6H), 1.21-1.11 (m, 2H), 1.09 (s, 3H).

Example 251: ethyl 1-(6-(N-(6-(5-fluoro-2-methylphenyl)-5-(trifluoromethyl)pyridin-2-yl)sulfamoyl)pyridin-2-yl)-4-methylpiperidine-4-carboxylate Condition 2, LCMS: m/z 581.2 [M+H]$^+$, 3.53 min. $^1$H NMR (400 MHz, DMSO-d$_6$) δ 11.58 (s, 1H), 8.23 (d, J=8.9 Hz, 1H), 7.69 (dd, J=8.7, 7.3 Hz, 1H), 7.51 (d, J=8.5 Hz, 1H), 7.27 (dd, J=8.5, 5.8 Hz, 1H), 7.17 (td, J=8.6, 2.8 Hz, 1H), 7.11 (d, J=7.2 Hz, 1H), 7.07 (d, J=8.7 Hz, 1H), 6.92 (d, J=9.0 Hz, 1H), 4.08 (q, J=7.1 Hz, 2H), 3.84-3.67 (m, 2H), 3.03-2.91 (m, 2H), 1.88-1.76 (m, 2H), 1.70 (s, 3H), 1.25-1.13 (m, 5H), 1.08 (s, 3H).

Example 252: ethyl 1-(6-(N-(5-chloro-6-(3-fluoro-2-methylphenyl)pyridin-2-yl)sulfamoyl)pyridin-2-yl)-4-methylpiperidine-4-carboxylate Condition 2, LCMS: m/z 547.1 [M+H]$^+$, 3.53 min. $^1$H NMR (400 MHz, DMSO-d$_6$) δ 11.19 (s, 1H), 7.98 (d, J=8.8 Hz, 1H), 7.70 (dd, J=8.7, 7.3 Hz, 1H), 7.36 (d, J=8.8 Hz, 1H), 7.31-7.18 (m, 2H), 7.10 (d, J=7.2 Hz, 1H), 7.06 (d, J=8.7 Hz, 1H), 6.87 (d, J=6.5 Hz, 1H), 4.09 (q, J=7.1

2H), 3.83-3.71 (m, 2H), 3.04-2.93 (m, 2H), 1.89-1.80 (m, 2H), 1.77 (d, J=1.9 Hz, 3H), 1.26-1.18 (m, 2H), 1.16 (t, J=7.1 Hz, 3H), 1.09 (s, 3H).

Example 253: 1-(6-(N-(5-chloro-6-(3-fluoro-2-methylphenyl)pyridin-2-yl)sulfamoyl)pyridin-2-yl)-4-methylpiperidine-4-carboxylic Acid Condition 2, LCMS: m/z 519.1 [M+H]$^+$, 3.24 min. $^1$H NMR (400 MHz, DMSO-d$_6$) δ 12.41 (s, 1H), 11.18 (s, 1H), 7.98 (d, J=8.8 Hz, 1H), 7.69 (dd, J=8.7, 7.3 Hz, 1H), 7.38 (d, J=8.8 Hz, 1H), 7.31-7.18 (m, 2H), 7.10 (d, J=7.2 Hz, 1H), 7.06 (d, J=8.7 Hz, 1H), 6.91-6.84 (m, 1H), 3.83-3.72 (m, 2H), 3.06-2.94 (m, 2H), 1.88-1.80 (m, 2H), 1.78 (d, J=2.0 Hz, 3H), 1.18-1.09 (m, 2H), 1.07 (s, 3H).

Example 254: ethyl 1-(6-(N-(5-chloro-6-(o-tolyl)pyridin-2-yl)sulfamoyl)pyridin-2-yl)-4-methylpiperidine-4-carboxylate Condition 2, LCMS: m/z 529.1 [M+H]$^+$, 3.51 min. $^1$H NMR (400 MHz, DMSO-d$_6$) δ 11.13 (s, 1H), 7.95 (d, J=8.8 Hz, 1H), 7.69 (dd, J=8.7, 7.3 Hz, 1H), 7.35 (d, J=8.8 Hz, 1H), 7.31 (td, J=7.5, 1.3 Hz, 1H), 7.27-7.17 (m, 2H), 7.10 (d, J=7.2 Hz, 1H), 7.06 (d, J=8.7 Hz, 1H), 7.00 (d, J=7.4 Hz, 1H), 4.09 (q, J=7.1 Hz, 2H), 3.83-3.71 (m, 2H), 3.05-2.92 (m, 2H), 1.94-1.79 (m, 5H), 1.26-1.19 (m, 2H), 1.17 (d, J=7.1 Hz, 3H), 1.09 (s, 3H).

Example 255: 1-(6-(N-(5-chloro-6-(o-tolyl)pyridin-2-yl)sulfamoyl)pyridin-2-yl)-4-methylpiperidine-4-carboxylic Acid Condition 2, LCMS: m/z 501.1 [M+H]$^+$, 3.20 min. $^1$H NMR (400 MHz, DMSO-d$_6$) δ 12.41 (s, 1H), 11.12 (s, 1H), 7.95 (d, J=8.8 Hz, 1H), 7.69 (dd, J=8.7, 7.3 Hz, 1H), 7.36 (d, J=8.8 Hz, 1H), 7.30 (dd, J=7.3, 1.3 Hz, 1H), 7.27-7.18 (m, 2H), 7.09 (d, J=7.2 Hz, 1H), 7.05 (d, J=8.7 Hz, 1H), 7.01 (d, J=7.5 Hz, 1H), 3.85-3.70 (m, 2H), 3.07-2.93 (m, 2H), 1.89 (s, 3H), 1.87-1.79 (m, 2H), 1.18-1.10 (m, 2H), 1.08 (s, 3H).

Example 256: ethyl 1-(6-(N-(5-chloro-6-(5-fluoro-2-methylphenyl)pyridin-2-yl)sulfamoyl)pyridin-2-yl)-4-methylpiperidine-4-carboxylate Condition 2, LCMS: m/z 547.1 M+H]$^+$, 3.52 min. $^1$H NMR (400 MHz, DMSO-d$_6$) δ 11.18 (s, 1H), 7.97 (d, J=8.8 Hz, 1H), 7.69 (dd, J=8.7, 7.3 Hz, 1H), 7.36 (d, J=8.8 Hz, 1H), 7.29 (dd, J=8.5, 5.8 Hz, 1H), 7.16 (td, J=8.6, 2.8 Hz, 1H), 7.11 (d, J=7.2 Hz, 1H), 7.06 (d, J=8.7 Hz, 1H), 6.83 (dd, J=9.3, 2.7 Hz, 1H), 4.09 (q, J=7.1 Hz, 2H), 3.82-3.72 (m, 2H), 3.04-2.95 (m, 2H), 1.89-1.80 (m, 5H), 1.24-1.13 (m, 5H), 1.09 (s, 3H).

Example 257: 1-(6-{[5-chloro-6-(5-fluoro-2-methylphenyl)pyridin-2-yl]sulfamoyl}pyridin-2-yl)-4-methylpiperidine-4-carboxylic Acid Condition 2, LCMS: m/z 519.2 [M+H]$^+$, 3.28 min. $^1$H NMR (400 MHz, DMSO-d$_6$) δ 12.39 (s, 1H), 11.18 (s, 1H), 7.97 (d, J=8.8 Hz, 1H), 7.68 (dd, J=8.7, 7.3 Hz, 1H), 7.36 (d, J=8.8 Hz, 1H), 7.29 (dd, J=8.6, 5.9 Hz, 1H), 7.16 (td, J=8.6, 2.8 Hz, 1H), 7.10 (d, J=7.2 Hz, 1H), 7.06 (d, J=8.7 Hz, 1H), 6.84 (dd, J=9.3, 2.7 Hz, 1H), 3.84-3.73 (m, 2H), 3.06-2.95 (m, 2H), 1.88-1.77 (m, 5H), 1.18-1.11 (m, 2H), 1.07 (s, 3H).

Example 258: ethyl 1-(6-{[6-(3-fluoro-2-methylphenyl)-5-(trifluoromethyl)pyridin-2-yl]sulfamoyl}pyridin-2-yl)-4-methylpiperidine-4-carboxylate Condition 2, LCMS: m/z 581.2 [M+H]$^+$, 3.53 min. $^1$H NMR (400 MHz, DMSO-d$_6$) δ 11.59 (s, 1H), 8.23 (d, J=8.9 Hz, 1H), 7.69 (dd, J=8.7, 7.3 Hz, 1H), 7.51 (d, J=8.6 Hz, 1H), 7.30-7.19 (m, 2H), 7.10 (d, J=7.2 Hz, 1H), 7.07 (d, J=8.7 Hz, 1H), 6.92 (d, J=6.9 Hz, 1H), 4.09 (q, J=7.1 Hz, 2H), 3.82-3.68 (m, 2H), 3.04-2.90 (m, 2H), 1.88-1.76 (m, 2H), 1.63 (s, 3H), 1.25-1.11 (m, 5H), 1.08 (s, 3H).

Example 259: ethyl 4-methyl-1-(6-{[6-(2-methylphenyl)-5-(trifluoromethyl)pyridin-2-yl]sulfamoyl}pyridin-2-yl)piperidine-4-carboxylate Condition 2, LCMS: m/z 563.2 [M+H]$^+$, 3.51 min. $^1$H NMR (400 MHz, DMSO-d$_6$) δ 11.52 (s, 1H), 8.21 (d, J=8.9 Hz, 1H), 7.69 (dd, J=8.7, 7.3 Hz, 1H), 7.50 (d, J=8.2 Hz, 1H), 7.31 (t, J=7.5 Hz, 1H), 7.21 (dd, J=14.0, 7.2 Hz, 2H), 7.10 (d, J=7.2 Hz, 1H), 7.05 (t, J=8.4 Hz, 2H), 4.09 (q, J=7.1 Hz, 2H), 3.84-3.68 (m, 2H), 3.03-2.90 (m, 2H), 1.89-1.78 (m, 2H), 1.75 (s, 3H), 1.25-1.11 (m, 5H), 1.08 (s, 3H).

Example 260: methyl 1-(6-{[5-chloro-6-(2,6-dimethylphenyl)pyridin-2-yl]sulfamoyl}pyridin-2-yl)-4-hydroxypiperidine-4-carboxylate Condition 2, LCMS: m/z 531.2 [M+H]$^+$, 3.28 min. $^1$H NMR (400 MHz, DMSO-d$_6$) δ 8.03 (d, J=8.9 Hz, 1H), 7.72-7.64 (m, 2H), 7.22-7.16 (m, 1H), 7.11-7.03 (m, 4H), 3.90-3.71 (m, 2H), 3.33 (s, 3H), 3.19-3.05 (m, 2H), 1.79 (s, 6H), 1.74-1.65 (m, 2H), 1.59-1.50 (m, 2H).

Example 261: 1-(6-{[5-chloro-6-(2,6-dimethylphenyl)pyridin-2-yl]sulfamoyl}pyridin-2-yl)-4-hydroxypiperidine-4-carboxylic Acid Condition 2, LCMS: m/z 517.2 [M+H]$^+$, 3.06 min. $^1$H NMR (400 MHz, DMSO-d$_6$) δ 11.17 (s, 1H), 7.94 (dd, J=8.8, 0.9 Hz, 1H), 7.70-7.62 (m, 1H), 7.38-7.29 (m, 1H), 7.20-7.14 (m, 1H), 7.09-7.03 (m, 4H), 4.06-3.85 (m, 2H), 3.19-3.07 (m, 2H), 1.75 (s, 6H), 1.66-1.46 (m, 2H), 1.46-1.29 (m, 2H).

Example 262: 1-(6-{[6-(5-fluoro-2-methylphenyl)-5-(trifluoromethyl)pyridin-2-yl]sulfamoyl}pyridin-2-yl)-4-methylpiperidine-4-carboxylic Acid Condition 2, LCMS: m/z 553.1 [M+H]$^+$, 3.25 min. $^1$H NMR (400 MHz, DMSO-d$_6$) δ 12.41 (s, 1H), 11.58 (s, 1H), 8.22 (d, J=8.9 Hz, 1H), 7.68 (dd, J=8.7, 7.3 Hz, 1H), 7.50 (d, J=8.7 Hz, 1H), 7.27 (dd, J=8.5, 5.8 Hz, 1H), 7.17 (td, J=8.6, 2.8 Hz, 1H), 7.10 (d, J=7.2 Hz, 1H), 7.06 (d, J=8.7 Hz, 1H), 6.92 (d, J=7.6 Hz, 1H), 3.86-3.68 (m, 2H), 3.06-2.93 (m, 2H), 1.86-1.75 (m, 2H), 1.70 (s, 3H), 1.16-1.07 (m, 2H), 1.06 (s, 3H).

Example 263: 1-(6-(N-(6-(3-fluoro-2-methylphenyl)-5-(trifluoromethyl)pyridin-2-yl)sulfamoyl)pyridin-2-yl)-4-methylpiperidine-4-carboxylic Acid Condition 2, LCMS: m/z 553.2 [M+H]$^+$, 3.27 min. $^1$H NMR (400 MHz, DMSO-d$_6$) δ 12.41 (s, 1H), 11.58 (s, 1H), 8.23 (d, J=8.8 Hz, 1H), 7.69 (dd, J=8.6, 7.3 Hz, 1H), 7.51 (d, J=8.7 Hz, 1H), 7.30-7.19 (m, 2H), 7.10 (d, J=7.2 Hz, 1H), 7.06 (d, J=8.7 Hz, 1H), 6.92 (d, J=7.1 Hz, 1H), 3.77 (t, J=13.4 Hz, 2H), 3.06-2.93 (m, 2H), 1.81 (d, J=11.2 Hz, 2H), 1.63 (s, 3H), 1.18-1.08 (m, 2H), 1.06 (s, 3H).

Example 264: 4-methyl-1-(6-(N-(6-(o-tolyl)-5-(trifluoromethyl)pyridin-2-yl)sulfamoyl)pyridin-2-yl)piperidine-4-carboxylic acid LCMS: m/z 535.2 [M+H]$^+$, 3.22 min. $^1$H NMR (400 MHz, DMSO-d$_6$) δ 12.41 (s, 1H), 11.52 (s, 1H), 8.20 (d, J=8.8 Hz, 1H), 7.68 (dd, J=8.7, 7.3 Hz, 1H), 7.50 (d, J=8.1 Hz, 1H), 7.34-7.27 (m, 1H), 7.21 (dd, J=13.0, 7.0 Hz, 2H), 7.09 (d, J=7.2 Hz, 1H), 7.07-7.00 (m, 2H), 3.84-3.69 (m, 2H), 3.06-2.92 (m, 2H), 1.81 (d, J=12.7 Hz, 2H), 1.75 (s, 3H), 1.18-1.08 (m, 2H), 1.06 (s, 3H).

Example 265: 1-(6-{[6-(2,6-dimethylphenyl)-5-(trifluoromethyl)pyridin-2-yl]sulfamoyl}pyridin-2-yl)-4-methylpiperidine-4-carboxylic Acid Condition 2, LCMS: m/z 549.2 [M+H]$^+$, 3.32 min. $^1$H NMR (400 MHz, DMSO-d$_6$) δ 12.43 (s, 1H), 11.56 (s, 1H), 8.21 (d, J=8.9 Hz, 1H), 7.67 (dd, J=8.7, 7.3 Hz, 1H), 7.48 (s, 1H), 7.19 (t, J=7.6 Hz, 1H), 7.07 (d, J=7.2 Hz, 1H), 7.06-7.01 (m, 3H), 3.86-3.74 (m, 2H), 3.06-2.93 (m, 2H), 1.87-1.76 (m, 2H), 1.71 (s, 6H), 1.15-1.07 (m, 2H), 1.06 (s, 3H).

Example 266: ethyl 1-(6-{[6-(2,6-dimethylphenyl)-5-(trifluoromethyl)pyridin-2-yl]sulfamoyl}pyridin-2-yl)-4-methylpiperidine-4-carboxylate Condition 2, LCMS: m/z 577.2 [M+H]$^+$, 3.54 min. $^1$H NMR (400 MHz, DMSO-d$_6$) δ 11.56 (s, 1H), 8.21 (d, J=8.9 Hz, 1H), 7.67 (dd, J=8.6, 7.3 Hz, 1H), 7.54-7.40 (m, 1H), 7.19 (t, J=7.6 Hz, 1H), 7.10-7.00 (m, 4H), 4.08 (q, J=7.1 Hz, 2H), 3.84-3.73 (m, 2H), 3.03-2.90 (m, 2H), 1.89-1.78 (m, 2H), 1.70 (s, 6H), 1.21-1.13 (m, 5H), 1.08 (s, 3H).

Example 267: methyl 4-{[(tert-butoxy)carbonyl]amino}-1-(6-{[5-chloro-6-(2,6-dimethylphenyl)pyridin-2-yl]sulfamoyl}pyridin-2-yl)piperidine-4-carboxylate Condition 2, LCMS: m/z 630.2 [M+H]$^+$, 3.35 min. $^1$H NMR (400 MHz, DMSO-d$_6$) δ 11.16 (s, 1H), 7.92 (d, J=8.8 Hz, 1H), 7.68 (dd, J=8.6, 7.3 Hz, 1H), 7.42 (s, 1H), 7.35-7.25 (m, 1H), 7.21-7.14 (m, 1H), 7.09 (d, J=7.2 Hz, 1H), 7.08-7.01 (m, 3H), 3.95-3.78 (m, 2H), 3.56 (s, 3H), 3.13-2.98 (m, 2H), 1.93-1.80 (m, 2H), 1.73 (s, 6H), 1.65-1.54 (m, 2H), 1.37 (s, 9H).

Example 268: 4-{[(tert-butoxy)carbonyl]amino}-1-(6-{[5-chloro-6-(2,6-dimethylphenyl)pyridin-2-yl]sulfamoyl}pyridin-2-yl)piperidine-4-carboxylic Acid Condition 2, LCMS: m/z 616.2 [M+H]$^+$, 3.26 min, $^1$H NMR (400 MHz, DMSO-d$_6$) δ 12.37 (s, 1H), 11.16 (s, 1H), 7.92 (d, J=8.8 Hz, 1H), 7.67 (dd, J=8.6, 7.3 Hz, 1H), 7.43-7.21 (m, 2H), 7.20-7.15 (m, 1H), 7.09 (d, J=7.2 Hz, 1H), 7.07-7.02 (m, 3H), 3.94-3.77 (m, 2H), 3.14-2.96 (m, 2H), 1.95-1.84 (m, 2H), 1.75 (s, 6H), 1.68-1.58 (m, 2H), 1.38 (s, 9H).

Example 269: 4-amino-1-(6-{[5-chloro-6-(2,6-dimethylphenyl)pyridin-2-yl]sulfamoyl}pyridin-2-yl)piperidine-4-carboxylic Acid Hydrochloride Condition 2, LCMS: m/z 516.2 [M+H]$^+$, 2.80 min. $^1$H NMR (400 MHz, Methanol-d$_4$) δ 7.83 (d, J=8.8 Hz, 1H), 7.69 (dd, J=8.6, 7.4 Hz, 1H), 7.45 (d, J=8.8 Hz, 1H), 7.26 (d, J=7.3 Hz, 1H), 7.21-7.13 (m, 1H), 7.05 (dd, J=8.3, 2.3 Hz, 3H), 3.88-3.77 (m, 2H), 3.74-3.63 (m, 2H), 2.25-2.15 (m, 2H), 1.86 (s, 6H), 1.81 (dt, J=8.6, 4.5 Hz, 2H).

Example 270: methyl 4-amino-1-(6-{[5-chloro-6-(2,6-dimethylphenyl)pyridin-2-yl]sulfamoyl}pyridin-2-yl)piperidine-4-carboxylate Condition 2, LCMS: m/z 530.1 [M+H]$^+$, 2.54 min. $^1$H NMR (400 MHz, DMSO-d$_6$) δ 7.92 (d, J=8.8 Hz, 1H), 7.66 (dd, J=8.7, 7.3 Hz, 1H), 7.32 (d, J=8.8 Hz, 1H), 7.18 (dd, J=8.0, 7.1 Hz, 1H), 7.10-7.00 (m, 4H), 3.73-3.64 (m, 2H), 3.58 (s, 3H), 3.44-3.36 (m, 2H), 1.74 (s, 6H), 1.67-1.55 (m, 2H), 1.43-1.38 (m, 2H).

Example 271: N-[5-chloro-6-(2,6-dimethylphenyl)pyridin-2-yl]-6-[(oxan-4-yl)amino]pyridine-2-sulfonamide Condition 2, LCMS: m/z 473.2 [M+H]$^+$, 3.17 min. $^1$H NMR (400 MHz, Methylene Chloride-d$_2$) δ 7.76 (d, J=8.8 Hz, 1H), 7.59-7.41 (m, 2H), 7.26-7.15 (m, 2H), 7.09 (d, J=7.6 Hz, 2H), 6.54 (d, J=8.5 Hz, 1H), 3.88-3.66 (m, 3H), 3.39 (td, J=2.2, 11.6 Hz, 2H), 1.98-1.80 (m, 7H), 1.54 (s, 2H), 1.47-1.31 (m, 2H).

Example 272: N-[5-chloro-6-(5-fluoro-2-methylphenyl)pyridin-2-yl]-6-{[(3R,4R)-3-hydroxyoxan-4-yl]amino}pyridine-2-sulfonamide Condition 2, LCMS: m/z 493.2 [M+H]$^+$, 3.04 min. $^1$H NMR (400 MHz, DMSO-d$_6$) δ 11.08 (s, 1H), 8.00 (d, J=8.8 Hz, 1H), 7.52 (dd, J=7.2, 8.5 Hz, 1H), 7.42 (d, J=8.8 Hz, 1H), 7.29 (dd, J=5.8, 8.5 Hz, 1H), 7.16 (td, J=2.8, 8.6 Hz, 1H), 7.01 (m, 1H), 6.87 (m, 2H), 6.82 (d, J=8.5 Hz, 1H), 4.84 (d, J=5.0 Hz, 1H), 3.68 (m, 3H), 3.47 (d, J=0.7 Hz, 1H), 3.33 (m, 1H), 3.27 (m, 1H), 1.87 (s, 3H), 1.67 (m, 1H), 1.28 (m, 1H). $^{19}$F NMR (376 MHz, DMSO-d$_6$) δ −117.85 (s).

Example 273: N-[5-chloro-6-(5-fluoro-2-methylphenyl)pyridin-2-yl]-6-{[(3S,4R)-3-hydroxyoxan-4-yl]amino}pyridine-2-sulfonamide Condition 2, LCMS: m/z 493.2 [M+H]$^+$, 3.08 min. $^1$H NMR (400 MHz, DMSO-d$_6$) δ 11.11 (s, 1H), 7.97 (d, J=8.8 Hz, 1H), 7.52 (dd, J=7.2, 8.5 Hz, 1H), 7.41 (d, J=8.8 Hz, 1H), 7.29 (dd, J=5.8, 8.5 Hz, 1H), 7.16 (td, J=2.8, 8.6 Hz, 1H), 7.07 (d, J=7.0 Hz, 1H), 7.01 (m, 1H), 6.89 (d, J=7.9 Hz, 1H), 6.70 (d, J=8.3 Hz, 1H), 4.92 (d, J=5.0 Hz, 1H), 3.79 (dd, J=4.7, 11.0 Hz, 1H), 3.63 (m, 1H), 3.48 (m, 1H), 3.35 (m, 1H), 3.20 (m, 1H), 2.98 (dd, J=9.7, 10.9 Hz, 1H), 1.88 (s, 3H), 1.66 (m, 1H), 1.13 (m, 1H). $^{19}$F NMR (376 MHz, DMSO-d$_6$) δ −117.89 (s, 1F).

Example 274: 6-(((3S,4R)-3-hydroxytetrahydro-2H-pyran-4-yl)amino)-N-(6-(o-tolyl)-5-(trifluoromethyl)pyridin-2-yl)pyridine-2-sulfonamide Condition 2, LCMS: m/z 509.2 [M+H]$^+$, 3.06 min. 1H NMR (400 MHz, DMSO-d6) δ 11.48 (s, 1H), 8.19 (d, J=8.9 Hz, 1H), 7.52 (m, 2H), 7.31 (t, J=7.3 Hz, 1H), 7.20 (m, 2H), 7.05 (m, 3H), 6.70 (d, J=8.3 Hz, 1H), 4.91 (d, J=13.7 Hz, 1H), 3.79 (m, 1H), 3.54 (m, 2H), 3.34 (m, 1H), 3.16 (m, 1H), 2.96 (m, 1H), 1.80 (m, 3H), 1.55 (m, 1H). $^{19}$F NMR (376 MHz, DMSO-d6) δ −57.06 (s).

Example 275: rac-6-{[(3RS,4RS)-3-hydroxyoxan-4-yl]amino}-N-[6-(2-methylphenyl)-5-(trifluoromethyl)pyridin-2-yl]pyridine-2-sulfonamide Condition 2, LCMS: m/z 509.2 [M+H]$^+$, 3.10 min 1H NMR (400 MHz, DMSO-d6) δ 11.45 (s, 1H), 8.22 (m, 1H), 7.51 (m, 2H), 7.31 (t, J=7.5 Hz, 1H), 7.22 (m, 2H), 7.03 (m, 2H), 6.84 (m, 2H), 4.86 (m, 1H), 3.68 (m, 3H), 3.49 (m, 1H), 3.27 (m, 2H), 1.73 (m, 4H), 1.29 (m, 1H). $^{19}$F NMR (376 MHz, DMSO-d6) δ −57.06 (s).

Example 276: 6-(((3R,4R)-3-hydroxytetrahydro-2H-pyran-4-yl)amino)-N-(6-(o-tolyl)-5-(trifluoromethyl)pyridin-2-yl)pyridine-2-sulfonamide Example 275 was subjected to chiral HPLC under the following conditions: 80 g/min, 82/18 CO2/MeOH, 100 bar, 30° C., column: 21×250 mm OD-H, run time: 3.4 min stacked injections, 8.5 minute elution time. Enantiomer A cis, (−) rotation at 245 nm, Analytical method: solvents: A: CO2 (80%), B: MeOH (20%), flow rate: 2 mL/min, temp: 30° C., phase: 5 um 4.6×50 mm OD, Retention time 2.14 min. Condition 2, LCMS: m/z 509.2 [M+H]$^+$, 2.98 min. $^1$H NMR (400 MHz, DMSO-d$_6$) δ 11.45 (s, 1H), 8.22 (m, 1H), 7.51 (m, 2H), 7.31 (t, J=7.5 Hz, 1H), 7.22 (m, 2H), 7.03 (m, 2H), 6.84 (m, 2H), 4.86 (m, 1H), 3.68 (m, 3H), 3.49 (m, 1H), 3.27 (m, 2H), 1.73 (m, 4H), 1.29 (m, 1H). $^{19}$F NMR (376 MHz, DMSO-d$_6$) δ −57.06 (s).

Example 277: 6-(((3S,4S)-3-hydroxytetrahydro-2H-pyran-4-yl)amino)-N-(6-(o-tolyl)-5-(trifluoromethyl)pyridin-2-yl)pyridine-2-sulfonamide Example 275 was subjected to chiral HPLC under the following conditions: 80 g/min, 82/18 CO2/MeOH, 100 bar, 30° C., column: 21×250 mm OD-H, run time: 3.4 min stacked injections, 8.5 minute elution time. Enantiomer B (cis), (+) rotation at 245 nm, Analytical method: solvents: A: CO2 (80%), B: MeOH (20%), flow rate: 2 mL/min, temp: 30° C., phase: 5 um 4.6×50 mm OD, Retention time 2.67 min. Condition 2, LCMS: m/z 509.2 [M+H]$^+$, 3.01 min. $^1$H NMR (400 MHz, DMSO-d$_6$) δ 11.44 (s, 1H), 8.21 (m, 1H), 7.51 (m, 2H), 7.31 (t, J=7.4 Hz, 1H), 7.21 (m, 2H), 7.03 (m, 2H), 6.84 (m, 2H), 4.85 (m, 1H), 3.69 (m, 3H), 3.47 (m, 1H), 3.27 (m, 2H), 1.73 (m, 4H), 1.30 (m, 1H). $^{19}$F NMR (376 MHz, DMSO-d$_6$) δ −57.06 (s).

Example 278: N-[5-chloro-6-(5-fluoro-2-methylphenyl)pyridin-2-yl]-6-{[(3R,4R)-4-hydroxyoxan-3-yl]amino}pyridine-2-sulfonamide Condition 2, LCMS: m/z 493.2 [M+H]$^+$, 3.06 min. $^1$H NMR (400 MHz, DMSO-d$_6$) δ 11.17 (s, 1H), 7.89 (d, J=8.9 Hz, 1H), 7.51 (dd, J=7.2, 8.5 Hz, 1H), 7.43 (d, J=8.8 Hz, 1H), 7.29 (dd, J=5.8, 8.5 Hz, 1H), 7.15 (td, J=2.8, 8.6 Hz, 1H), 7.02 (m, 2H), 6.96 (m, 1H), 6.73 (d, J=8.1 Hz, 1H), 4.88 (d, J=4.6 Hz, 1H), 3.78 (dt, J=3.9, 11.5 Hz, 1H), 3.65 (dd, J=4.2, 10.9 Hz, 1H), 3.45 (m, 2H), 3.31 (m, 1H), 2.81 (dd, J=8.7, 10.7 Hz, 1H), 1.89 (m, 4H), 1.43 (m, 1H). $^{19}$F NMR (376 MHz, DMSO-d$_6$) δ −117.94 (s).

Example 279: 6-{[(3R,4R)-4-hydroxyoxan-3-yl]amino}-N-[6-(2-methylphenyl)-5-(trifluoromethyl)pyridin-2-yl]pyridine-2-sulfonamide Condition 2, LCMS: m/z 509.2 [M+H]$^+$, 2.99 min. $^1$H NMR (400 MHz, DMSO-d$_6$) δ 11.49 (s, 1H), 8.17 (d, J=8.9 Hz, 1H), 7.58 (m, 1H), 7.51 (dd, J=7.3, 8.5 Hz, 1H), 7.31 (t, J=7.3 Hz, 1H), 7.22 (m, 2H), 7.08 (d, J=7.1 Hz, 1H), 7.02 (d, J=6.9 Hz, 1H), 6.86 (d, J=8.5 Hz, 1H), 6.80 (d, J=6.4 Hz, 1H), 4.94 (m, 1H), 3.76 (m, 2H), 3.62 (m, 1H), 3.45 (m, 1H), 3.27 (m, 2H), 1.83 (m, 3H), 1.63 (m, 2H). $^{19}$F NMR (376 MHz, DMSO-d$_6$) δ −57.17 (s).

Example 280: rac-6-{[(3RS,4SR)-4-hydroxyoxan-3-yl]amino}-N-[6-(2-methylphenyl)-5-(trifluoromethyl)pyridin-2-yl]pyridine-2-sulfonamide Condition 2, LCMS: m/z 509.2 [M+H]$^+$, 2.98 min. $^1$H NMR (400 MHz, DMSO-d$_6$) δ 11.49 (s, 1H), 8.17 (d, J=8.9 Hz, 1H), 7.58 (m, 1H), 7.51 (dd, J=7.3, 8.5 Hz, 1H), 7.31 (t, J=7.3 Hz, 1H), 7.22 (m, 2H), 7.08 (d, J=7.1 Hz, 1H), 7.02 (d, J=6.9 Hz, 1H), 6.86 (d, J=8.5 Hz, 1H), 6.80 (d, J=6.4 Hz, 1H), 4.94 (m, 1H), 3.76 (m, 2H), 3.62 (m, 1H), 3.45 (m, 1H), 3.27 (m, 2H), 1.83 (m, 3H), 1.63 (m, 2H). $^{19}$F NMR (376 MHz, DMSO-d6) δ −57.17 (s).

Example 281: 6-{[(3R,4S)-4-hydroxyoxan-3-yl]amino}-N-[6-(2-methylphenyl)-5-(trifluoromethyl)pyridin-2-yl]pyridine-2-sulfonamide Example 280 was subjected to chiral HPLC under the following conditions: 80 g/min, 85/15 CO2/MeOH, 100 bar, 30° C., column: 21×250 mm OD-H, run time: 3.3 min stacked injections, 8.5 min elution time Enantiomer A (cis), (−) rotation at 245 nm, Analytical method: solvents: A: CO2 (85%), B: MeOH (15%), flow rate: 2 mL/min, temp: 30° C., phase: 5 um 4.6×50 mm OD, Retention time 2.49 min. Condition 2, LCMS: m/z 509.2 [M+H]$^+$, 2.98 min. $^1$H NMR (400 MHz, DMSO-d$_6$) δ 11.49 (s, 1H), 8.16 (m, 1H), 7.52 (m, 2H), 7.31 (t, J=7.3 Hz, 1H), 7.21 (m, 2H), 7.08 (d, J=6.7 Hz, 1H), 7.01 (d, J=7.1 Hz, 1H), 6.83 (m, 2H), 4.93 (m, 1H), 3.76 (m, 2H), 3.62 (m, 1H), 3.45 (m, 1H), 3.28 (m, 2H), 1.84 (m, 3H), 1.63 (m, 2H). $^{19}$F NMR (376 MHz, DMSO-d6) δ −57.17 (s).

Example 282: 6-{[(3S,4R)-4-hydroxyoxan-3-yl]amino}-N-[6-(2-methylphenyl)-5-(trifluoromethyl)pyridin-2-yl]pyridine-2-sulfonamide Example 280 was subjected to chiral HPLC under the following conditions: 80 g/min, 85/15 CO2/MeOH, 100 bar, 30° C., column: 21×250 mm OD-H, run time: 3.3 min stacked injections, 8.5 min elution time. Enantiomer B (cis), (+) rotation at 245 nm, Analytical method: solvents: A: CO2 (85%), B: MeOH (15%), flow rate: 2 mL/min, temp: 30° C., phase: 5 um 4.6×50 mm OD, Retention time 3.04 min. Condition 2, LCMS: m/z 509.2 [M+H]$^+$, 1H NMR (400 MHz, DMSO-d6) δ 11.49 (s, 1H), 8.16 (s, 1H), 7.53 (m, 2H), 7.31 (t, J=7.2 Hz, 1H), 7.21 (m, 2H), 7.08 (d, J=6.7 Hz, 1H), 7.01 (d, J=7.2 Hz, 1H), 6.83 (m, 2H), 4.93 (m, 1H), 3.77 (m, 2H), 3.62 (m, 1H), 3.46 (m, 1H), 3.28 (m, 2H), 1.84 (m, 3H), 1.63 (m, 2H). $^{19}$F NMR (376 MHz, DMSO-d6) δ −57.17 (s).

Example 283: N-[6-(2-methylphenyl)-5-(trifluoromethyl)pyridin-2-yl]-6-{[(1s,3s)-3-hydroxycyclobutyl]amino}pyridine-2-sulfonamide Condition 2, LCMS: m/z 479.1 [M+H]$^+$, 3.00 min. $^1$H NMR (400 MHz, Methanol-d$_4$) δ 8.08 (d, J=8.9 Hz, 1H), 7.67-7.59 (m, 1H), 7.47 (dd, J=8.5, 7.3 Hz, 1H), 7.31 (t, J=7.5 Hz, 1H), 7.21 (dd, J=16.7, 8.0 Hz, 2H), 7.12 (dd, J=7.2, 0.6 Hz, 1H), 7.08 (d, J=7.3 Hz, 1H), 6.59 (dd, J=8.5, 0.6 Hz, 1H), 3.98-3.79 (m, 1H), 3.70-3.55 (m, 1H), 3.35 (s, 2H), 2.66-2.50 (m, 2H), 1.95 (s, 3H), 1.70 (s, 2H).

Example 284: N-[6-(2-methylphenyl)-5-(trifluoromethyl)pyridin-2-yl]-6-{[(1r,3r)-3-hydroxycyclobutyl]amino}pyridine-2-sulfonamide Condition 2, LCMS: m/z 479.1 [M+H]$^+$, 3.05 min. $^1$H NMR (400 MHz, Methanol-d$_4$) δ 8.08 (d, J=8.9 Hz, 1H), 7.59 (s, 1H), 7.47 (dd, J=8.5, 7.3 Hz, 1H), 7.29 (d, J=7.5 Hz, 1H), 7.20 (dd, J=16.3, 7.7 Hz, 2H), 7.16-7.11 (m, 1H), 7.08 (d, J=7.6 Hz, 1H), 6.59 (d, J=8.4 Hz, 1H), 4.38 (t, J=6.1 Hz, 1H), 4.18 (dt, J=7.7, 3.3 Hz, 1H), 2.17 (d, J=31.2 Hz, 4H), 1.92 (s, 3H).

Example 285: N-[5-chloro-6-(2,6-dimethylphenyl)pyridin-2-yl]-6-{[(1r,3s)-3-hydroxy-3-methylcyclobutyl]amino}pyridine-2-sulfonamide Condition 2, LCMS: m/z 473.2 [M+H]$^+$, 3.10 min. $^1$H NMR (400 MHz, Methylene Chloride-d$_2$) δ 7.75 (d, J=8.9 Hz, 1H), 7.54 (t, J=7.9 Hz, 1H), 7.48 (d, J=8.7 Hz, 1H), 7.22 (dd, J=2.3, 7.3 Hz, 2H), 7.10 (d, J=7.6 Hz, 2H), 6.49 (d, J=8.5 Hz, 1H), 5.10 (s, 1H), 3.76-3.58 (m, 1H), 2.47 (ddd, J=2.7, 7.5, 9.9 Hz, 2H), 2.05-1.96 (m, 3H), 1.92 (s, 6H), 1.33 (s, 3H).

Example 286: N-[5-chloro-6-(2,6-dimethylphenyl)pyridin-2-yl]-6-{[(1s,3s)-3-hydroxycyclobutyl]amino}pyridine-2-sulfonamide Condition 2, LCMS: m/z 459.2 [M+H]$^+$, 3.05 min. $^1$H NMR (400 MHz, DMSO-d$_6$) δ 11.06 (s, 1H), 7.98 (d, J=8.8 Hz, 1H), 7.50 (dd, J=7.3, 8.4 Hz, 1H), 7.43 (d, J=8.8 Hz, 1H), 7.29 (d, J=7.0 Hz, 1H), 7.23-7.15 (m, 1H), 7.08 (d, J=7.6 Hz, 2H), 7.01-6.95 (m, 1H), 6.59 (d, J=8.2 Hz, 1H), 5.05 (d, J=6.1 Hz, 1H), 3.80-3.67 (m, 1H), 3.52-3.38 (m, 1H), 2.43 (ddt, J=3.1, 6.9, 9.5 Hz, 2H), 1.80 (s, 6H), 1.58 (qd, J=2.8, 8.7 Hz, 2H).

Example 287: N-[5-chloro-6-(2,6-dimethylphenyl)pyridin-2-yl]-6-{[(1r,3r)-3-hydroxycyclobutyl]amino}pyridine-2-sulfonamide Condition 2, LCMS: m/z 459.2 [M+H]$^+$, 3.05 min. $^1$H NMR (400 MHz, DMSO-d$_6$) δ 11.11 (s, 1H), 7.95 (d, J=8.8 Hz, 1H), 7.49 (dd, J=8.4, 7.3 Hz, 1H), 7.38-7.33 (m, 2H), 7.21-7.14 (m, 1H), 7.07 (d, J=7.6 Hz, 2H), 6.99 (d, J=6.9 Hz, 1H), 6.58 (d, J=8.4 Hz, 1H), 5.00 (d, J=5.1 Hz, 1H), 4.27-4.20 (m, 1H), 4.13-4.00 (m, 1H), 2.11-2.02 (m, 2H), 2.02-1.94 (m, 2H), 1.78 (s, 6H).

Example 288: N-[5-chloro-6-(2,6-dimethylphenyl)pyridin-2-yl]-6-{[(3S,5S)-5-(hydroxymethyl)oxolan-3-yl]oxy}pyridine-2-sulfonamide Condition 2, LCMS: m/z 490.2 [M+H]$^+$, 3.10 min. $^1$H NMR (400 MHz, DMSO-d$_6$) δ 11.41 (s, 1H), 7.86 (m, 2H), 7.50 (d, J=7.3 Hz, 1H), 7.25 (d, J=8.5 Hz, 1H), 7.17 (t, J=7.5 Hz, 1H), 7.04 (m, 3H), 5.20 (m, 1H), 4.72 (t, J=5.1 Hz, 1H), 3.82 (m, 1H), 3.74 (dd, J=4.9, 10.4 Hz, 1H), 3.63 (m, 1H), 3.39 (m, 2H), 2.26 (dt, J=7.3, 14.1 Hz, 1H), 1.74 (s, 3H), 1.70 (s, 3H), 1.59 (ddd, J=3.3, 7.1, 13.5 Hz, 1H).

Example 289: N-(5-chloro-6-(5-fluoro-2-methylphenyl)pyridin-2-yl)-6-(((3R,4S)-4-hydroxytetrahydrofuran-3-yl)oxy)pyridine-2-sulfonamide chiral HPLC under the following conditions: 80 g/min, 75/25 CO2/MeOH, 100 bar, 30° C., column: 21×250 mm Princeton DEAP, run time: 2 min stacked injections, 4.75 min elution time Analytical method: solvents: A: CO2 (80%), B: MeOH (20%), flow rate: 2 mL/min, temp: 50° C., 125 bar, phase: 3 um 2.1×100 mm Princeton DEAP, tR1.02 min. Condition 2, LCMS: m/z 480.2 [M+H]$^+$, 3.05 min. $^1$H NMR (400 MHz, DMSO-d$_6$) δ 11.44 (s, 1H), 7.98 (d, J=8.8 Hz, 1H), 7.92 (dd, J=7.4, 8.4 Hz, 1H), 7.57 (dd, J=0.6, 7.3 Hz, 1H), 7.34 (d, J=8.8 Hz, 1H), 7.30 (dd, J=5.9, 8.5 Hz, 1H), 7.16 (td, J=2.8, 8.6 Hz, 1H), 7.12 (dd, J=0.6, 8.4 Hz, 1H), 6.88 (dd, J=2.4, 9.3 Hz, 1H), 5.06 (d, J=5.6 Hz, 1H), 4.97 (q, J=5.8 Hz, 1H), 4.22 (p, J=5.2 Hz, 1H), 3.89 (dd, J=6.1, 9.2 Hz, 1H), 3.82 (dd, J=5.3, 9.0 Hz, 1H), 3.56 (dd, J=4.6, 9.0 Hz, 1H), 3.50 (dd, J=5.7, 9.2 Hz, 1H), 1.85 (s, 3H). $^{19}$F NMR (376 MHz, DMSO-d$_6$) δ −117.82 (s, 1F).

Example 290: rac-N-[5-chloro-6-(2,6-dimethylphenyl)pyridin-2-yl]-6-{[(3R,4S)-4-hydroxyoxolan-3-yl]oxy}pyridine-2-sulfonamide Condition 2, LCMS: m/z 476.2 [M+H]$^+$, 3.07 min. $^1$H NMR (400 MHz, DMSO-d$_6$) δ 11.41 (s, 1H), 7.98 (d, J=8.8 Hz, 1H), 7.90 (dd, J=7.4, 8.4 Hz, 1H), 7.54 (dd, J=0.6, 7.3 Hz, 1H), 7.31 (d, J=8.7 Hz, 1H), 7.19 (t, J=7.5 Hz, 1H), 7.09 (m, 3H), 5.07 (d, J=5.5 Hz, 1H), 4.97 (q, J=5.7 Hz, 1H), 4.26 (p, J=5.1 Hz, 1H), 3.92 (dd, J=6.1, 9.2 Hz, 1H), 3.83 (dd, J=5.3, 9.0 Hz, 1H), 3.56 (dd, J=4.6, 9.0 Hz, 1H), 3.49 (dd, J=5.7, 9.2 Hz, 1H), 1.78 (s, 3H), 1.70 (s, 3H).

Example 291: rac-6-{[(3RS,4SR)-4-hydroxyoxolan-3-yl]oxy}-N-[6-(2-methylphenyl)-5-(trifluoromethyl)pyridin-2-yl]pyridine-2-sulfonamide Condition 2, LCMS: m/z 496.2 [M+H]$^+$, 3.04 min. $^1$H NMR (400 MHz, DMSO-d$_6$) δ 11.81 (s, 1H), 8.21 (d, J=8.9 Hz, 1H), 7.91 (m, 1H), 7.56 (dd, J=0.6, 7.3 Hz, 1H), 7.47 (s, 1H), 7.32 (t, J=7.3 Hz, 1H), 7.22 (m, 2H), 7.11 (d, J=8.3 Hz, 1H), 7.05 (m, 1H), 5.07 (m, 1H), 4.95 (m, 1H), 4.21 (m, 1H), 3.82 (m, 2H), 3.54 (m, 2H), 1.79 (m, 3H). $^{19}$F NMR (376 MHz, DMSO-d$_6$) δ −57.17 (s).

Example 292: rac-N-[6-(2-methylphenyl)-5-(trifluoromethyl)pyridin-2-yl]-6-[(4-oxooxolan-3-yl)oxy]pyridine-2-sulfonamide Condition 2, LCMS: m/z 494.2 [M+H]$^+$, 3.08 min. $^1$H NMR (400 MHz, DMSO-d$_6$) δ 11.44 (s, 1H), 7.98 (d, J=8.8 Hz, 1H), 7.92 (dd, J=7.4, 8.4 Hz, 1H), 7.57 (dd, J=0.6, 7.3 Hz, 1H), 7.34 (d, J=8.8 Hz, 1H), 7.30 (dd, J=5.9, 8.5 Hz, 1H), 7.16 (td, J=2.8, 8.6 Hz, 1H), 7.12 (dd, J=0.6, 8.4 Hz, 1H), 6.88 (dd, J=2.4, 9.3 Hz, 1H), 5.06 (d, J=5.6 Hz, 1H), 4.97 (q, J=5.8 Hz, 1H), 4.22 (p, J=5.2 Hz, 1H), 3.89 (dd, J=6.1, 9.2 Hz, 1H), 3.82 (dd, J=5.3, 9.0 Hz, 1H), 3.56 (dd, J=4.6, 9.0 Hz, 1H), 3.50 (dd, J=5.7, 9.2 Hz, 1H), 1.85 (s, 3H).

Example 293: rac-6-{[(3RR,4SR)-4-hydroxy-4-methyloxolan-3-yl]oxy}-N-[6-(2-methylphenyl)-5-(trifluoromethyl)pyridin-2-yl]pyridine-2-sulfonamide Condition 2, LCMS: m/z 510.2 [M+H]$^+$, 3.07 min. $^1$H NMR (400 MHz, DMSO-d$_6$) δ 11.83 (s, 1H), 8.22 (d, J=8.9 Hz, 1H), 7.91 (dd, J=7.4, 8.3 Hz, 1H), 7.55 (d, J=7.3 Hz, 1H), 7.45 (m, 1H), 7.32 (t, J=7.4 Hz, 1H), 7.21 (m, 2H), 7.11 (d, J=8.3 Hz, 1H), 7.02 (m, 1H), 4.97 (m, 1H), 4.73 (m, 1H), 3.93 (dd, J=5.7, 9.5 Hz, 1H), 3.60 (d, J=8.5 Hz, 1H), 3.49 (d, J=8.5 Hz, 1H), 3.42 (m, 1H), 1.76 (m, 3H), 1.17 (m, 3H). $^{19}$F NMR (376 MHz, DMSO-d$_6$) δ −57.15 (m).

Example 294: 6-{[(3R,4S)-4-hydroxy-4-methyloxolan-3-yl]oxy}-N-[6-(2-methylphenyl)-5-(trifluoromethyl)pyridin-2-yl]pyridine-2-sulfonamide Example 293 was subjected to chiral HPLC under the following conditions: 80 g/min, 90/10 CO2/MeOH, 100 bar, 35° C., column: 21×250 mm IF, run time: 13 min. Enantiomer A, (−) rotation at 275 nm, Analytical method: solvents: A: CO2, B: MeOH, 5-40% in 5 min, flow rate: 2 mL/min, temp: 30° C., phase: 3 um 4.6×50 mm IF, Retention time 3.20 min. Condition 2, LCMS: m/z 510.1 [M+H]$^+$, Example 295: 6-{[(3R,4R)-4-hydroxy-4-methyloxolan-3-yl]oxy}-N-[6-(2-methylphenyl)-5-(trifluoromethyl)pyridin-2-yl]pyridine-2-sulfonamide Example 293 was subjected to chiral HPLC under the following conditions: 80 g/min, 90/10 CO2/MeOH, 100 bar, 35° C., column: 21×250 mm IF, run time: 13 min. Enantiomer B, (+) rotation at 275 nm, Analytical method: solvents: A: CO2, B: MeOH, 5-40% in 5 min, flow rate: 2 mL/min, temp: 30° C., phase: 3 um 4.6×50 mm IF, Retention time 3.45 min. Condition 2, LCMS: m/z 510.1 [M+H]$^+$, Example 296: 6-{[(3R,4S)-4-hydroxyoxolan-3-yl]oxy}-N-[6-(2-methylphenyl)-5-(trifluoromethyl)pyridin-2-yl]pyridine-2-sulfonamide Example 291 was subjected to chiral HPLC under the following conditions: 80 g/min, 78/22 CO2/MeOH, 100 bar, 30° C., column: 21×250 mm Cellulose-2, run time: 2.8 min stacked injections, 6.75 min elution time. Enantiomer A (cis), (+) rotation at 275 nm, Analytical method: solvents: A: CO2 (80%), B: MeOH (20%), flow rate: 2 mL/min, temp: 30° C., phase: 3 um 4.6×50 mm Cellulose-2, Retention time 2.17 min. Condition 2, LCMS: m/z 496.2 [M+H]$^+$, 3.01 min. $^1$H NMR (400 MHz, DMSO-d$_6$) δ 11.81 (s, 1H), 8.19 (m, 1H), 7.90 (t, J=7.2 Hz, 1H), 7.55 (d, J=7.3 Hz, 1H), 7.45 (s, 1H), 7.32 (t, J=7.3 Hz, 1H), 7.21 (m, 2H), 7.08 (m, 2H), 5.06 (m, 1H), 4.96 (m, 1H), 4.20 (m, 1H), 3.83 (m, 2H), 3.50 (m, 2H), 1.79 (m, 3H). $^{19}$F NMR (376 MHz, DMSO-d$_6$) δ −57.14 (s).

Example 297: ethyl 1-(4-(6-(N-(6-(5-fluoro-2-methylphenyl)-5-(trifluoromethyl)pyridin-2-yl)sulfamoyl)pyridin-2-yl)piperazin-1-yl)cyclopropane-1-carboxylate Purified by ISCO reverse-phase C18 chromatography [30 g Redisep GOLD C18 column, eluted with 10-100% acetonitrile/water], Condition 3, LCMS: R$_t$ 0.70 min; m/z 608.3 [M+H]$^+$. $^1$H NMR (400 MHz, DMSO-d6) δ 11.57 (s, 1H), 8.22 (d, J=8.9 Hz, 1H), 7.69 (dd, J=8.7, 7.3 Hz, 1H), 7.55 (d, J=8.7 Hz, 1H), 7.28 (dd, J=8.5, 5.8 Hz, 1H), 7.21-7.14 (m, 1H), 7.13 (d, J=7.2 Hz, 1H), 7.05 (d, J=8.7 Hz, 1H), 6.94 (d, J=7.1 Hz, 1H), 3.99 (q, J=7.1 Hz, 2H), 3.31 (s, 4H), 2.81 (s, 4H), 1.77 (s, 3H), 1.19 (q, J=3.8 Hz, 2H), 1.09 (t, J=7.1 Hz, 3H), 0.94 (q, J=3.5 Hz, 2H).

Example 298: tert-butyl 4-(6-(N-(5-chloro-6-(5-fluoro-2-methylphenyl)pyridin-2-yl)sulfamoyl)pyridin-2-yl)piperazine-1-carboxylate Condition 3, LCMS: R$_t$ 0.69 min; m/z 562.2 [M+H]$^+$. $^1$H NMR (400 MHz, DMSO-d6) δ 11.18 (s, 1H), 7.99 (d, J=8.7 Hz, 1H), 7.77-7.69 (m, 1H), 7.42 (d, J=8.6 Hz, 1H), 7.34-7.27 (m, 1H), 7.22-7.11 (m, 2H), 7.06 (d, J=8.6 Hz, 1H), 6.94-6.86 (m, 1H), 3.46-3.34 (m, 4H), 3.30-3.25 (m, 4H), 1.89 (s, 3H), 1.40 (s, 9H).

Example 299: N-(6-(5-cyano-2-methylphenyl)-5-(trifluoromethyl)pyridin-2-yl)-6-(3-hydroxy-3-methylazetidin-1-yl)pyridine-2-sulfonamide Purified by Condition 2, Mobile Phase 2. LCMS: m/z 504.1 [M+H]$^+$, 0.66 min. $^1$H NMR (300 MHz, CD$_3$OD) δ ppm 8.11 (d, J=9.0 Hz, 1H), 7.67 (dd, J=8.1, 1.8 Hz, 1H), 7.58 (t, J=8.1, 3.6 Hz, 2H), 7.48-7.40 (m, 2H), 7.19 (d, J=7.2 Hz, 1H), 6.55 (d, J=8.4 Hz, 1H), 3.83-3.75 (m, 4H), 1.99 (s, 3H), 1.47 (s, 3H).

Example 300: 1-(6-(N-(6-(5-fluoro-2-methylphenyl)-5-(trifluoromethyl)pyridin-2-yl) sulfamoyl)pyridin-2-yl)pyrrolidine-3-carboxylic Acid Purified by Condition 2, Mobile Phase 1. Condition 3, LCMS: m/z 525.2 [M+H]$^+$, 0.65 min. $^1$H NMR (400 MHz, DMSO-d6) δ ppm 8.14 (brs, 1H), 7.64 (t, J=8.0 Hz, 1H), 7.57 (brs, 1H), 7.27 (dd, J=8.4, 5.6 Hz, 1H), 7.16 (dt, J=8.8, 2.8 Hz, 1H), 7.08 (d, J=7.2 Hz, 1H), 6.97-6.95 (m, 1H), 6.68 (d, J=8.4, 1H), 3.45-3.39 (m, 2H), 3.28-3.24 (m, 2H), 3.16-3.11 (m, 1H), 2.18-2.12 (m, 1H), 2.11-2.04 (m, 1H), 1.78 (s, 3H).

Example 301: tert-butyl 1-(6-(N-(6-(o-tolyl)-5-(trifluoromethyl)pyridin-2-yl)sulfamoyl)pyridin-2-yl)-1,6-diazaspiro[3.3]heptane-6-carboxylate Condition 6, LCMS: R$_t$ 0.92 min; m/z 590.4 [M+H]$^+$. $^1$H NMR (400 MHz, Methanol-d4) δ 8.10 (d, J=8.9 Hz, 1H), 7.68-7.52 (m, 2H), 7.35-7.12 (m, 4H), 7.03 (d, J=7.2 Hz, 1H), 6.53 (d, J=8.4 Hz, 1H), 4.62 (s, 2H), 3.93 (d, J=9.6 Hz, 2H), 3.82 (t, J=7.1 Hz, 2H), 2.58 (t, J=7.1 Hz, 2H), 1.90 (s, 3H), 1.49 (s, 9H).

Example 302: 6-(4,7-diazaspiro[2.5]octan-7-yl)-N-(6-(o-tolyl)-5-(trifluoromethyl)pyridin-2-yl)pyridine-2-sulfonamide Purified by ISCO reverse-phase C18 chromatography [30 g Redisep GOLD C18 column, eluted with 10-100% acetonitrile/water]. Condition 4, LCMS: R$_t$ 1.64 min; m/z 504.1 [M+H]$^+$. $^1$H NMR (400 MHz, DMSO-d6) δ 8.15 (d, J=8.9 Hz, 1H), 7.66 (dd, J=8.7, 7.3 Hz, 1H), 7.51 (d, J=8.8 Hz, 1H), 7.31 (dd, J=7.4, 1.3 Hz, 1H), 7.27-7.17 (m, 2H), 7.09 (d, J=7.2 Hz, 1H), 7.06 (d, J=7.5 Hz, 1H), 7.00 (d, J=8.7 Hz, 1H), 3.43-3.35 (m, 2H), 3.29 (s, 2H), 2.78-2.70 (m, 2H), 1.82 (s, 3H), 0.42 (s, 2H), 0.31 (d, J=8.2 Hz, 2H).

Example 303: 6-(8-amino-5-oxa-2-azaspiro[3.4]octan-2-yl)-N-(6-(o-tolyl)-5-(trifluoromethyl)pyridin-2-yl)pyridine-2-sulfonamide Condition 4, LCMS: R$_t$ 1.64 min; m/z 520.4 [M+H]$^+$. $^1$H NMR (400 MHz, Methanol-d4) δ 8.03 (d, J=8.9 Hz, 1H), 7.65-7.52 (m, 2H), 7.35-7.09 (m, 5H), 7.06 (d, J=7.6 Hz, 1H), 6.57 (d, J=8.4 Hz, 1H), 4.27 (d, J=9.8 Hz, 1H), 4.00 (q, J=7.8 Hz, 1H), 3.87 (h, J=5.2 Hz, 3H), 3.80-3.72 (m, 1H), 3.61 (dd, J=6.6, 3.7 Hz, 1H), 2.35-2.21 (m, 1H), 1.94 (s, 4H).

Example 304: (R)-6-(1-amino-8-azaspiro[4.5]decan-8-yl)-N-(6-(o-tolyl)-5-(trifluoromethyl)pyridin-2-yl)pyridine-2-sulfonamide Condition 5, LCMS: R$_t$ 3.25 min; m/z 546.2 [M+H]$^+$. $^1$H NMR (400 MHz, Methanol-d4) δ 7.79 (dd, J=8.9, 1.4 Hz, 1H), 7.54 (ddd, J=8.3, 7.4, 0.7 Hz, 1H), 7.38 (dq, J=9.0, 1.0 Hz, 1H), 7.30-7.09 (m, 4H), 7.03 (d, J=7.6 Hz, 1H), 6.84 (d, J=8.5 Hz, 1H), 4.13-3.99 (m, 2H), 3.08-2.89 (m, 3H), 2.10 (dd, J=13.6, 6.5 Hz, 1H), 1.94 (d, J=2.2 Hz, 3H), 1.84-1.45 (m, 6H), 1.44-1.25 (m, 4H).

Example 305: N-(5-chloro-6-(5-cyano-2-methylphenyl)pyridin-2-yl)-6-(3-hydroxy-3-methylazetidin-1-yl)pyridine-2-sulfonamide Purified by Condition 2, Mobile Phase 1. Condition 3, LCMS: m/z 470.3 [M+H]$^+$, 0.61 min. $^1$H NMR (300 MHz, CD$_3$OD) δ ppm 7.84 (d, J=8.7 Hz, 1H), 7.67-7.58 (m, 2H), 7.45-7.42 (m, 2H), 7.37 (d, J=1.8 Hz, 1H), 7.22-7.19 (m, 1H), 6.56 (dd, J=8.4, 0.6 Hz, 1H), 3.85-3.76 (m, 4H), 2.11 (s, 3H), 1.48 (s, 3H).

Example 306: (S)-6-(1-amino-7-azaspiro[3.5]nonan-7-yl)-N-(6-(o-tolyl)-5-(trifluoromethyl)pyridin-2-yl)pyridine-2-sulfonamide Condition 5, LCMS: R$_t$ 3.14 min; m/z 532.2 [M+H]$^+$. $^1$H NMR (400 MHz, Methanol-d4) δ 7.84 (d, J=8.9 Hz, 1H), 7.54 (dd, J=8.6, 7.3 Hz, 1H), 7.47-7.39 (m, 1H), 7.31-7.10 (m, 4H), 7.08-7.01 (m, 1H), 6.82 (dd, J=15.2, 8.6 Hz, 1H), 4.17-3.90 (m, 2H), 3.17 (s, 1H), 2.99-2.69 (m, 2H), 2.29-2.18 (m, 1H), 1.97-1.83 (m, 5H), 1.72-1.41 (m, 5H).

Example 307: 6-((1R)-1-amino-2-(hydroxymethyl)-8-azaspiro[4.5]decan-8-yl)-N-(6-(o-tolyl)-5-(trifluoromethyl)pyridin-2-yl)pyridine-2-sulfonamide Condition 5, LCMS: R$_t$ 3.14 min; m/z 576.2 [M+H]$^+$. $^1$H NMR (400 MHz, Methanol-d4) δ 7.79 (d, J=8.9 Hz, 1H), 7.54 (dd, J=8.6, 7.3 Hz, 1H), 7.45-7.35 (m, 1H), 7.31-7.09 (m, 4H), 7.03 (d, J=7.9 Hz, 1H), 6.82 (dd, J=8.6, 2.7 Hz, 1H), 4.21-3.81 (m, 2H), 3.73-3.51 (m, 2H), 3.10-2.80 (m, 2H), 2.74 (d, J=9.1 Hz, 1H), 2.12-1.97 (m, 1H), 1.97-1.77 (m, 5H), 1.76-1.20 (m, 9H).

Example 308: N-(6-(3-cyano-2-methylphenyl)-5-(trifluoromethyl)pyridin-2-yl)-6-(3-hydroxy-3-methylazetidin-1-yl)pyridine-2-sulfonamide Purified by Condition 2, Mobile Phase 1. Condition 3, LCMS: R$_t$ 0.63 min; m/z 504.3 [M+H]$^+$. $^1$H NMR (400 MHz, CD$_3$OD) δ ppm 8.11 (d, J=9.2 Hz, 1H), 7.74-7.72 (m, 1H), 7.60-7.56 (m, 2H), 7.39-7.37 (m, 2H), 7.20 (d, J=7.2 Hz, 1H), 6.55 (d, J=8.4 Hz, 1H), 3.84-3.75 (m, 4H), 2.06 (s, 3H), 1.47 (s, 3H).

Example 309: N-(5-chloro-6-(3-cyano-2-methylphenyl)pyridin-2-yl)-6-(3-hydroxy-3-methylazetidin-1-yl)pyridine-2-sulfonamide Purified by Condition 3, Mobile Phase 2. Condition 3, LCMS: R$_t$ 0.62 min; m/z 470.3 [M+H]$^+$. $^1$H NMR (400 MHz, CD$_3$OD) δ ppm 7.85 (d, J=9.2 Hz, 1H), 7.73-7.71 (m, 1H), 7.60 (dd, J=8.4, 7.6 Hz, 1H), 7.47 (d, J=8.8 Hz, 1H), 7.41-7.39 (m, 2H), 7.21 (d, J=7.6 Hz, 1H), 6.55 (d, J=8.8 Hz, 1H), 3.84-3.76 (m, 4H), 2.18 (s, 3H), 1.48 (s, 3H).

Example 310: N-(5-chloro-6-(5-fluoro-2-methylphenyl)pyridin-2-yl)-6-(1,6-diazaspiro[3.3]heptan-1-yl)pyridine-2-sulfonamide Condition 3, LCMS: R$_t$ 0.54 min; m/z 474.3 [M+H]$^+$. $^1$H NMR (400 MHz, Methanol-d4) δ 7.69 (dd, J=8.2, 7.5 Hz, 1H), 7.46 (d, J=8.8 Hz, 1H), 7.23-7.17 (m, 2H), 7.01 (td, J=8.6, 2.8 Hz, 1H), 6.76 (d, J=8.8 Hz, 1H), 6.53-6.46 (m, 2H), 4.08 (d, J=11.4 Hz, 2H), 4.00 (s, 2H), 3.87 (t, J=6.9 Hz, 2H), 2.46 (t, J=6.9 Hz, 2H), 1.88 (s, 3H).

Example 311: N-(6-(5-cyano-2-methylphenyl)-5-(trifluoromethyl)pyridin-2-yl)-6-(piperazin-1-yl)pyridine-2-sulfonamide Purified by Condition 5. Condition 3, LCMS: m/z 503.2 [M+H]$^+$, 0.54 min. $^1$H NMR (300 MHz, CD$_3$OD) δ ppm 8.34 (brs, 1H), 8.07 (d, J=8.7 Hz, 1H), 7.73-7.68 (m, 2H), 7.43 (dd, J=8.4, 3.6 Hz, 2H), 7.34-7.32 (m, 2H), 7.06 (d, J=8.4 Hz, 1H), 3.77-3.74 (m, 4H), 3.24-3.20 (m, 4H), 1.97 (s, 3H).

Example 312: N-(5-chloro-6-(5-cyano-2-methylphenyl)pyridin-2-yl)-6-(piperazin-1-yl)pyridine-2-sulfonamide Purified by Condition 3, Mobile Phase 2. Condition 3, LCMS: R$_t$ 0.50 min; m/z 469.2 [M+H]$^+$. $^1$H NMR (300 MHz, CD$_3$OD) δ ppm 7.76 (dd, J=7.8, 1.8 Hz, 1H), 7.66 (t, J=7.5 Hz, 2H), 7.46 (d, J=1.8 Hz, 1H), 7.37 (d, J=8.1 Hz, 1H), 7.22 (d, J=7.2 Hz, 1H), 7.15 (d, J=9.0 Hz, 1H), 7.86 (d, J=8.7 Hz, 1H), 3.46 (brs, 4H), 2.93 (brs, 4H), 1.86 (s, 3H).

Example 313: 6-(1,6-diazaspiro[3.3]heptan-1-yl)-N-(6-(o-tolyl)-5-(trifluoromethyl)pyridin-2-yl)pyridine-2-sulfonamide Condition 6, LCMS: R$_t$ 0.90 min; m/z 488.4 [M+H]$^+$. $^1$H NMR (400 MHz, Methanol-d4) δ 7.71-7.63 (m, 2H), 7.31-7.24 (m, 1H), 7.20-7.12 (m, 3H), 6.91 (d, J=7.6 Hz, 1H), 6.77 (d, J=8.7 Hz, 1H), 6.48 (d, J=7.9 Hz, 1H), 4.12 (d, J=11.4 Hz, 1H), 3.99 (dd, J=11.4, 3.9 Hz, 1H), 3.91-3.77 (m, 3H), 3.70 (dd, J=11.5, 3.5 Hz, 1H), 2.54-2.32 (m, 2H), 1.65 (s, 3H)

Example 314: 6-((2R,3S)-3-hydroxy-2-methylpyrrolidin-1-yl)-N-(6-(o-tolyl)-5-(trifluoromethyl)pyridin-2-yl)pyridine-2-sulfonamide Condition 4, LCMS: R$_t$ 2.50 min; m/z 493.4 [M+H]$^+$. $^1$H NMR (400 MHz, Methanol-d4) δ 8.55 (brs, 1H), 8.04 (d, J=9.3 Hz, 1H), 7.84 (d, J=9.3 Hz, 1H), 7.58 (dd, J=9.5, 7.3 Hz, 1H), 7.29 (m, 1H), 7.24-7.19 (m, 1H), 7.18-7.14 (m, 2H), 7.11-7.02 (m, 1H), 6.62 (d, J=8.5 Hz, 1H), 4.05 (d, J=3.7 Hz, 1H), 3.94-3.88 (m, 1H), 3.44-3.38 (m, 2H), 2.24-2.18 (m, 1H), 1.93 (s, 3H), 1.99-1.86 (m, 1H), 1.01 (brs, 3H).

Example 315: 1-(6-(N-(6-(5-fluoro-2-methylphenyl)-5-(trifluoromethyl)pyridin-2-yl)sulfamoyl)pyridin-2-yl)-3-hydroxypyrrolidine-2-carboxylic Acid Condition 3, LCMS: m/z 541.3 [M+H]$^+$, 0.63 min. $^1$H NMR (300 MHz, CD$_3$OD) δ ppm 8.10 (d, J=8.7 Hz, 1H), 7.67-7.60 (m, 2H), 7.24-7.19 (m, 2H), 7.03 (dt, J=8.7, 3.0 Hz, 1H), 6.81 (d, J=7.8 Hz, 1H), 6.53 (d, J=8.1 Hz, 1H), 4.63-4.58 (m, 1H), 4.43 (brs, 1H), 3.66-3.59 (m, 1H), 3.47-3.39 (m, 1H), 2.22-2.04 (m, 2H), 1.86 (s, 3H).

Example 316: 6-{[(3S,4R)-4-hydroxyoxolan-3-yl]oxy}-N-[6-(2-methylphenyl)-5-(trifluoromethyl)pyridin-2-yl]pyridine-2-sulfonamide Example 291 was subjected to chiral HPLC under the following conditions: 80 g/min, 78/22 CO2/MeOH, 100 bar, 30° C., column: 21×250 mm Cellulose-2, run time: 2.8 min stacked injections, 6.75 min elution time. Enantiomer B, (−) rotation at 275 nm cis, Analytical method: solvents: A: CO2 (80%), B: MeOH (20%), flow rate: 2 mL/min, temp: 30° C., phase: 3 um 4.6×50 mm Cellulose-2, Retention time 2.70 min. Condition 2, LCMS: m/z 496.2 [M+H]$^+$, 1.45 min. $^1$H NMR (400 MHz, DMSO-d$_6$) δ 11.81 (s, 1H), 8.19 (m, 1H), 7.90 (t, J=7.2 Hz, 1H), 7.55 (d, J=7.3 Hz, 1H), 7.45 (s, 1H), 7.32 (t, J=7.3 Hz, 1H), 7.21 (m, 2H), 7.08 (m, 2H), 5.06 (m, 1H), 4.96 (m, 1H), 4.20 (m, 1H), 3.83 (m, 2H), 3.50 (m, 2H), 1.79 (m, 3H). $^{19}$F NMR (376 MHz, DMSO-d6) δ −57.14 (S).

Example 317: N-(6-(5-cyano-2-methylphenyl)-5-(trifluoromethyl)pyridin-2-yl)-2-(3-hydroxy-3-methylazetidin-1-yl)pyridine-4-sulfonamide Condition 3, LCMS: m/z 504.3 [M+H]$^+$, 0.62 min. $^1$H NMR (300 MHz, CD$_3$OD) δ ppm 8.13-8.08 (m, 2H), 7.73 (dd, J=8.7 Hz, 1H), 7.67-7.60 (m, 2H), 7.24-7.19 (m, 2H), 7.03 (dt, J=8.7, 3.0 Hz, 1H), 6.81 (d, J=7.8, 1.8 Hz, 1H), 7.51 (d, J=7.8 Hz, 1H), 7.45 (s, 1H), 7.17 (d, J=9.0 Hz, 1H), 6.95 (dd, J=5.4, 1.8 Hz, 1H), 6.72 (s, 1H), 3.81-3.70 (m, 4H), 1.97 (s, 3H), 1.53 (s, 3H).

Example 318: (R)—N-(5-chloro-6-(5-fluoro-2-methylphenyl)pyridin-2-yl)-2-(3-methylmorpholino)pyridine-4-sulfonamide Condition 3, LCMS: m/z 477.2 [M+H]$^+$, 0.67 min. $^1$H NMR (300 MHz, CD$_3$OD) δ ppm 8.21 (d, J=5.4 Hz, 1H), 7.83 (d, J=8.4 Hz, 1H), 7.28 (dd, J=8.4, 5.7 Hz, 1H), 7.12-7.05 (m, 3H), 6.98 (dd, J=5.1, 1.2 Hz, 1H), 6.85 (dd, J=9.3, 2.7 Hz, 1H), 4.18-4.12 (m, 1H), 3.90 (dd, J=11.1, 3.6 Hz, 1H), 3.73-3.58 (m, 3H), 3.49 (dt, J=11.7, 3.0 Hz, 1H), 2.98 (dt, J=11.7, 3.9 Hz, 1H), 1.96 (s, 3H), 1.07 (d, J=6.6 Hz, 3H).

Example 319: (R)—N-(5-chloro-6-(3-fluoro-2-methylphenyl)pyridin-2-yl)-2-(3-methylmorpholino)pyridine-4-sulfonamide Condition 3, LCMS: m/z 477.2 [M+H]$^+$, 0.67 min. $^1$H NMR (300 MHz, CD$_3$OD) δ ppm 8.21 (d, J=5.1 Hz, 1H), 7.83 (d, J=9.0 Hz, 1H), 7.27-7.22 (m, 1H), 7.16-7.09 (m, 3H), 6.98-6.93 (m, 2H), 4.11-4.15 (m, 1H), 3.90 (dd, J=11.4, 3.0 Hz, 1H), 3.73-3.58 (m, 3H), 3.53-3.44 (m, 1H), 2.98 (dt, J=12.9, 3.9 Hz, 1H), 1.87 (s, 3H), 1.07 (d, J=6.6 Hz, 3H).

Example 320: N-(6-(5-fluoro-2-methylphenyl)-5-(trifluoromethyl)pyridin-2-yl)-2-(3-hydroxy-3-methylazetidin-1-yl)pyridine-4-sulfonamide Condition 3, LCMS: m/z 497.3 [M+H]$^+$, 0.64 min. $^1$H NMR (300 MHz, CD$_3$OD) δ ppm 8.09 (s, 1H), 8.07 (d, J=3.0 Hz, 1H), 7.30 (dd, J=8.4, 5.4 Hz, 1H), 7.17-7.08 (m, 2H), 6.97 (dd, J=5.4, 1.5 Hz, 1H), 6.86-6.82 (m, 1H), 6.76 (d, J=0.6 Hz, 1H), 3.77-3.69 (m, 4H), 1.87 (s, 3H), 1.52 (s, 3H).

Example 321: (R)—N-(6-(5-fluoro-2-methylphenyl)-5-(trifluoromethyl)pyridin-2-yl)-2-(3-methylmorpholino)pyridine-4-sulfonamide Condition 3, LCMS: m/z 511.3 [M+H]$^+$, 0.67 min. $^1$H NMR (300 MHz, CD$_3$OD) δ ppm 8.20 (d, J=5.1 Hz, 1H), 8.06 (d, J=8.7 Hz, 1H), 7.29-7.23 (m, 1H), 7.20-7.08 (m, 3H), 6.98 (d, J=5.1 Hz, 1H), 6.82 (d, J=8.7 Hz, 1H), 4.23-4.12 (m, 1H), 3.91 (dd, J=11.4, 3.0 Hz, 1H), 3.74-3.46 (m, 4H), 1.86 (d, J=18.9 Hz, 3H), 1.09 (t, J=7.2 Hz, 3H).

Example 322: N-(5-chloro-6-(5-fluoro-2-methylphenyl)pyridin-2-yl)-2-(3-hydroxyazetidin-1-yl)pyridine-4-sulfonamide Condition 3, LCMS: m/z 449.1 [M+H]$^+$, 0.61 min. $^1$H NMR (400 MHz, CD$_3$OD) δ ppm 8.08 (d, J=6.0 Hz, 1H), 7.82 (d, J=8.8 Hz, 1H), 7.29 (dd, J=8.4, 6.0 Hz, 1H), 7.09-7.06 (m, 2H), 6.94 (dd, J=5.2, 1.6 Hz, 1H), 6.84 (dd, J=8.8, 2.4 Hz, 1H), 6.74 (d, J=0.8 Hz, 1H), 4.64-4.61 (m, 1H), 4.05 (t, J=8.0 Hz, 2H), 3.67 (dd, J=9.2, 4.4 Hz, 2H), 1.93 (s, 3H).

Example 323: N-(5-chloro-6-(3-fluoro-2-methylphenyl)pyridin-2-yl)-2-(3-hydroxyazetidin-1-yl)pyridine-4-sulfonamide Condition 3, LCMS: m/z 449.1 [M+H]$^+$, 0.62 min. $^1$H NMR (400 MHz, CD$_3$OD) δ ppm 8.09 (d, J=6.0 Hz, 1H), 7.82 (d, J=8.8 Hz, 1H), 7.29-7.24 (m, 1H), 7.14 (d, J=8.4 Hz, 1H), 7.07 (d, J=8.8 Hz, 1H), 6.95-6.92 (m, 2H), 6.74 (s, 1H), 4.63-4.60 (m, 1H), 4.03 (t, J=8.0 Hz, 2H), 3.67 (dd, J=9.2, 4.4 Hz, 2H), 1.86 (d, J=2.4 Hz, 3H).

Example 324: N-(6-(5-fluoro-2-methylphenyl)-5-(trifluoromethyl)pyridin-2-yl)-2-(3-hydroxyazetidin-1-yl)pyridine-4-sulfonamide Condition 3, LCMS: m/z 483.2 [M+H]$^+$, 0.62 min. $^1$H NMR (400 MHz, CD$_3$OD) δ ppm 8.08 (s, 1H), 8.06 (d, J=2.8 Hz, 1H), 7.29 (dd, J=8.0, 5.6 Hz, 1H), 7.15-7.08 (m, 2H), 6.94 (dd, J=5.6, 1.6 Hz, 1H), 6.83 (dd, J=9.2, 2.4 Hz, 1H), 6.72 (d, J=1.2 Hz, 1H), 4.67-4.62 (m, 1H), 4.08-4.00 (m, 2H), 3.70-3.64 (m, 2H), 1.82 (s, 3H).

Example 325: 2-(3-hydroxyazetidin-1-yl)-N-(5-(trifluoromethyl)-6-(2-(trifluoromethyl)phenyl)pyridin-2-yl)pyridine-2-yl)pyridine-4-sulfonamide Condition 3, LCMS: m/z 519.2 [M+H]$^+$, 0.61 min. $^1$H NMR (400 MHz, CD$_3$OD) δ ppm 8.06 (d, J=2.4 Hz, 1H), 8.05 (d, J=5.6 Hz, 1H), 7.78 (dd, J=5.6, 3.6 Hz, 1H), 7.67-7.65 (m, 2H), 7.28-7.24 (m, 2H), 6.93 (dd, J=5.2, 1.2 Hz, 1H), 6.70 (s, 1H), 4.66-4.61 (m, 1H), 4.10-4.05 (m, 2H), 3.68 (dd, J=9.2, 4.4 Hz, 2H).

Example 326: N-(6-(5-fluoro-2-methylphenyl)-5-(trifluoromethyl)pyridin-2-yl)-2-(piperazin-1-yl)pyridine-4-sulfonamide Condition 3, LCMS: m/z 496.2 [M+H]$^+$, 0.54 min. $^1$H NMR (400 MHz, CD$_3$OD) δ ppm 8.35 (brs, 1H), 8.22 (d, J=5.2 Hz, 1H), 7.99 (d, J=8.8 Hz, 1H), 7.28-7.24 (m, 2H), 7.11-7.07 (m, 3H), 6.81 (dd, J=8.8, 2.4 Hz, 1H), 3.65 (t, J=5.2 Hz, 4H), 3.22 (t, J=5.2 Hz, 4H), 1.84 (s, 3H).

Example 327: N-(5-chloro-6-(5-fluoro-2-methylphenyl)pyridin-2-yl)-2-(piperazin-1-yl)pyridine-4-sulfonamide Condition 3, LCMS: R$_t$ 0.53 min; m/z 462.2 [M+H]$^+$, 0.53 min. $^1$H NMR (400 MHz, CD$_3$OD) δ ppm 8.33 (brs, 1H), 8.26 (d, J=5.2 Hz, 1H), 7.81 (d, J=8.4 Hz, 1H), 7.31-7.28 (m, 2H), 7.11-7.06 (m, 3H), 6.83 (dd, J=9.2, 2.4 Hz, 1H), 3.66 (t, J=5.2 Hz, 4H), 3.22 (t, J=5.6 Hz, 4H), 1.96 (s, 3H).

Example 328

(R)-1-(6-(N-(6-(2-ethoxyphenyl)-5-(trifluoromethyl)pyridin-2-yl)sulfamoyl)pyridin-2-yl)-3-methylpiperidine-3-carboxylic Acid LCMS conditions 7: 1.70 min, MS for C$_{26}$H$_{28}$F$_3$N$_4$O$_5$S [M+H]$^+$ m/z=565.2, found m/z=564.9. Rotomers/atropisomers are present in the NMR spectra. $^1$H NMR (400 MHz, Chloroform-d) δ 10.10 (br. s, 2H), 8.01 (d, J=8.8 Hz, 1H), 7.76 (d, J=8.7 Hz, 1H), 7.47 (dd, J=7.2, 8.7 Hz, 1H), 7.40-7.32 (m, 1H), 7.05 (d, J=7.2 Hz, 2H), 6.93 (t, J=7.4 Hz, 1H), 6.88 (d, J=8.3 Hz, 1H), 6.77 (d, J=8.7 Hz, 1H), 4.82 (d, J=13.4 Hz, 1H), 3.88 (d, J=13.8 Hz, 3H), 2.96 (td, J=2.9, 13.3 Hz, 1H), 2.73 (d, J=13.5 Hz, 1H), 2.05 (d, J=11.7 Hz, 1H), 1.72 (m, 1H), 1.49 (m, 1H), 1.34 (td, J=4.7, 13.1 Hz, 1H), 1.16 (s, 3H), 1.08 (s, 3H). $^{19}$F NMR (376 MHz, Chloroform-d) δ −59.27 (br. s, 1F).

Example 329

(R)-3-methyl-1-(6-(N-(6-(2-propoxyphenyl)-5-(trifluoromethyl)pyridin-2-yl)sulfamoyl)pyridin-2-yl)piperidine-3-carboxylic Acid LCMS conditions 7: 1.80 min, MS for C$_{27}$H$_{30}$F$_3$N$_4$O$_5$S [M+H]$^+$ m/z=579.2, found m/z=578.9. Rotomers/atropisomers are present in the NMR spectra. $^1$H NMR (400 MHz, Chloroform-d) δ 10.16 (br. s, 1H) 8.01 (d, J=8.8 Hz, 1H), 7.77 (d, J=8.8 Hz, 1H), 7.46 (dd, J=7.2, 8.7 Hz, 1H), 7.41-7.32 (m, 1H), 7.05 (m, 2H), 6.94 (t, J=7.5 Hz, 1H), 6.88 (d, J=8.3 Hz, 1H), 6.76 (d, J=8.7 Hz, 1H), 4.86 (d, J=13.5 Hz, 1H), 3.88 (d, J=13.6 Hz, 1H), 3.79 (t, J=6.2 Hz, 2H), 2.98 (td, J=2.8, 13.3 Hz, 1H), 2.73 (d, J=13.5 Hz, 1H), 2.10-1.98 (m, 1H), 1.74 (m, 1H), 1.50 (m, 3H), 1.39-1.28 (m, 2H), 1.16 (s, 3H), 0.68 (s, 3H). $^{19}$F NMR (376 MHz, Chloroform-d) δ −59.26 (s, 1F).

Example 330

1-(6-(N-(6-(o-tolyl)-5-(trifluoromethyl)pyridin-2-yl)sulfamoyl)pyridin-2-yl)azetidine-3-carboxylic Acid LCMS conditions 7: 1.53 min, MS for C$_{22}$H$_{20}$F$_3$N$_4$O$_4$S [M+H]+ m/z=493.1; found m/z 493.1. $^1$H NMR (400 MHz, chloroform-d) 8.69 (s, 1H), 8.46 (d, J=8.8 Hz, 1H), 8.08 (d, J=8.8 Hz, 1H), 7.90-7.75 (m, 2H), 7.58-7.48 (m, 1H), 7.48-7.36 (m, 2H), 7.33-7.25 (m, 1H), 3.57 (t, J=6.0 Hz, 2H), 3.42 (s, 2H), 2.04 (s, 3H), 1.07 (m, 2H). $^{19}$F NMR (376 MHz, chloroform-d) δ −58.91 (s, 1F).

Example 331

3-((6-(N-(6-(o-tolyl)-5-(trifluoromethyl)pyridin-2-yl)sulfamoyl)pyridin-2-yl)oxy)cyclobutanecarboxylic Acid Mixture of cis/trans isomers. LCMS conditions 7: 1.56 min, MS for C$_{23}$H$_{21}$F$_3$N$_3$O$_5$S [M+H]$^+$ m/z=508.1, found m/z 508.1; MS for C$_{23}$H$_{20}$F$_3$N$_3$NaO$_5$S, [M+Na]$^+$ m/z=530.1, found m/z=530.1. $^1$H NMR (400 MHz, Chloroform-d) δ 8.78 (br. S, 1H), 8.02 (d, J=8.9 Hz, 1H), 7.78 (dd, J=7.4, 8.3 Hz, 1H), 7.69 (d, J=7.3 Hz, 1H), 7.61 (d, J=8.9 Hz, 1H), 7.41-7.33 (m, 1H), 7.27-7.18 (m, 2H), 7.12 (d, J=7.5 Hz, 1H), 6.93 (d, J=8.3 Hz, 1H), 4.90 (p, J=7.8 Hz, 1H), 2.76-2.57 (m, 3H), 2.35 (s, 2H), 2.03 (s, 3H). $^{19}$F NMR (376 MHz, Chloroform-d) δ −58.82 (s, 1F).

Example 332

(3R)-1-(6-{[6-(2-methylphenyl)-5-(trifluoromethyl)pyridin-2-yl]sulfamoyl}pyridin-2-yl)piperidine-3-carboxylic Acid LCMS conditions 7: 1.795 min; MS for C$_{24}$H$_{24}$F$_3$N$_4$O$_4$S [M+H]$^+$ m/z=521.15, found m/z=521.15. $^1$H NMR (400 MHz, DMSO-d$_6$) δ 12.40 (s, 1H), 11.58 (s, 1H), 8.14 (dd, J=9.2, 3.2 Hz, 1H), 7.67 (dd, J=8.7, 7.3 Hz, 1H), 7.49 (d, J=8.9 Hz, 1H), 7.31 (td, J=7.4, 1.4 Hz, 1H), 7.25-7.15 (m, 2H), 7.13-7.07 (m, 2H), 7.05 (d, J=7.6 Hz, 1H), 4.25-4.08 (m, 1H), 3.94-3.79 (m, 1H), 3.08-2.95 (m, 1H), 2.95-2.82 (m, 1H), 2.32-2.16 (m, 1H), 1.98-1.84 (m, 1H), 1.77 (s, 3H), 1.59-1.48 (m, 1H), 1.34-1.14 (m, 2H).

Example 333

(3S)-1-(6-{[6-(2-methylphenyl)-5-(trifluoromethyl)pyridin-2-yl]sulfamoyl}pyridin-2-yl)piperidine-3-carboxylic Acid LCMS conditions 7: 1.795 min; MS for C$_{24}$H$_{24}$F$_3$N$_4$O$_4$S [M+H]$^+$ m/z=521.15, found m/z=521.20. $^1$H NMR (400 MHz, DMSO-d$_6$) δ 12.40 (s, 1H), 11.58 (s, 1H), 8.14 (d, J=8.8 Hz, 1H), 7.67 (dd, J=8.7, 7.3 Hz, 1H), 7.49 (d, J=8.7 Hz, 1H), 7.31 (td, J=7.5, 1.4 Hz, 1H), 7.26-7.16 (m, 2H), 7.13-7.07 (m, 2H), 7.04 (d, J=7.6 Hz, 1H), 4.27-4.09 (m, 1H), 3.94-3.80 (m, 1H), 3.08-2.96 (m, 1H), 2.96-2.83 (m, 1H), 2.32-2.16 (m, 1H), 1.97-1.84 (m, 1H), 1.77 (s, 3H), 1.59-1.49 (m, 1H), 1.33-1.15 (m, 2H).

Example 334

(2S)-1-[(tert-butoxy)carbonyl]-4-(6-{[6-(2-methylphenyl)-5-(trifluoromethyl)pyridin-2-yl]sulfamoyl}pyridin-2-yl)piperazine-2-carboxylic Acid LCMS conditions 7: 1.648 min; MS for C$_{28}$H$_{31}$F$_3$N$_5$O$_6$S [M+H]$^+$ m/z=622.19, found m/z=622.30. $^1$H NMR (400 MHz, DMSO-d$_6$) δ 11.61 (s, 1H), 8.31-8.10 (m, 1H), 7.73 (dd, J=8.7, 7.3 Hz, 1H), 7.66-7.46 (m, 1H), 7.36-7.28 (m, 1H), 7.27-7.14 (m, 3H), 7.13-6.99 (m, 2H), 4.63-4.29 (m, 2H), 4.03-3.84 (m, 1H), 3.76-3.59 (m, 1H), 3.20-2.94 (m, 2H), 2.84-2.75 (m, 1H), 1.83 (s, 3H), 1.39 (d, J=15.2 Hz, 9H).

Example 335

(2S)-4-(6-{[6-(2-methylphenyl)-5-(trifluoromethyl)pyridin-2-yl]sulfamoyl}pyridin-2-yl)piperazine-2-carboxylic Acid LCMS conditions 7: 1.278 min; MS for $C_{23}H_{23}F_3N_5O_4S$ [M+H]$^+$ m/z=522.14, found m/z=522.20. $^1$H NMR (400 MHz, Methanol-d$_4$) δ 8.08 (d, J=8.9 Hz, 1H), 7.76 (dd, J=8.6, 7.4 Hz, 1H), 7.57 (d, J=8.9 Hz, 1H), 7.40 (d, J=7.3 Hz, 1H), 7.32 (td, J=7.5, 1.4 Hz, 1H), 7.27-7.13 (m, 3H), 7.05 (d, J=7.5 Hz, 1H), 4.67-4.55 (m, 1H), 4.23-4.09 (m, 2H), 3.50-3.33 (m, 3H), 3.23-3.10 (m, 1H), 1.92 (s, 3H).

Example 336

3-methyl-1-(6-{[6-(2-methylphenyl)-5-(trifluoromethyl)pyridin-2-yl]sulfamoyl}pyridin-2-yl)pyrrolidine-3-carboxylic Acid LCMS conditions 7: 1.808 min; MS for $C_{24}H_{24}F_3N_4O_4S$ [M+H]$^+$ m/z=521.15, found m/z=521.15. $^1$H NMR (400 MHz, DMSO-d$_6$) δ 12.59 (s, 1H), 11.51 (s, 1H), 8.18 (d, J=8.9 Hz, 1H), 7.66 (dd, J=8.6, 7.3 Hz, 1H), 7.63-7.52 (m, 1H), 7.32 (td, J=7.4, 1.4 Hz, 1H), 7.27-7.16 (m, 2H), 7.12-7.04 (m, 2H), 6.68 (d, J=8.5 Hz, 1H), 3.69-3.53 (m, 1H), 3.33-3.17 (m, 2H), 3.09-2.92 (m, 1H), 2.36-2.21 (m, 1H), 1.91-1.73 (m, 4H), 1.32-1.15 (m, 3H).

Example 337

3-methyl-1-(6-{[6-(2-methylphenyl)-5-(trifluoromethyl)pyridin-2-yl]sulfamoyl}pyridin-2-yl)piperidine-3-carboxylic Acid LCMS conditions 7: 1.743 min; MS for $C_{25}H_{26}F_3N_4O_4S$ [M+H]$^+$ m/z=535.16, found m/z=535.20. $^1$H NMR (400 MHz, DMSO-d$_6$) δ 12.33 (s, 1H), 11.53 (s, 1H), 8.17 (d, J=8.9 Hz, 1H), 7.65 (dd, J=8.7, 7.2 Hz, 1H), 7.59-7.45 (m, 1H), 7.36-7.27 (m, 1H), 7.26-7.17 (m, 2H), 7.13-7.00 (m, 3H), 3.87 (d, J=13.1 Hz, 1H), 3.72-3.56 (m, 1H), 3.18-3.07 (m, 1H), 3.07-2.94 (m, 1H), 2.05-1.92 (m, 1H), 1.80 (d, J=10.2 Hz, 3H), 1.51-1.31 (m, 3H), 1.03-0.97 (m, 3H).

Example 338

(2R)-1-[(tert-butoxy)carbonyl]-4-(6-{[6-(2-methylphenyl)-5-(trifluoromethyl)pyridin-2-yl]sulfamoyl}pyridin-2-yl)piperazine-2-carboxylic Acid LCMS conditions 7: 1.660 min; MS for $C_{28}H_{31}F_3N_5O_6S$ [M+H]$^+$ m/z=622.19, found m/z=622.30. $^1$H NMR (400 MHz, DMSO-d$_6$) δ 11.62 (s, 1H), 8.30-8.10 (m, 1H), 7.73 (dd, J=8.7, 7.3 Hz, 1H), 7.67-7.50 (m, 1H), 7.36-7.28 (m, 1H), 7.27-7.14 (m, 3H), 7.13-7.00 (m, 2H), 4.62-4.30 (m, 2H), 4.06-3.84 (m, 1H), 3.77-3.59 (m, 1H), 3.21-2.93 (m, 2H), 2.88-2.64 (m, 1H), 1.83 (s, 3H), 1.39 (d, J=15.3 Hz, 9H).

Example 339

(2R)-4-(6-{[6-(2-methylphenyl)-5-(trifluoromethyl)pyridin-2-yl]sulfamoyl}pyridin-2-yl)morpholine-2-carboxylic Acid LCMS conditions 7: 1.702 min; MS for $C_{23}H_{22}F_3N_4O_5S$ [M+H]$^+$ m/z=523.13, found m/z=523.10. $^1$H NMR (400 MHz, DMSO-d$_6$) δ 11.67 (s, 1H), 8.13 (d, J=8.9 Hz, 1H), 7.73 (dd, J=8.7, 7.3 Hz, 1H), 7.47 (d, J=8.8 Hz, 1H), 7.31 (td, J=7.5, 1.4 Hz, 1H), 7.26-7.16 (m, 3H), 7.11 (d, J=8.7 Hz, 1H), 7.05 (d, J=7.6 Hz, 1H), 4.18-4.06 (m, 1H), 4.06-3.95 (m, 1H), 3.93-3.84 (m, 1H), 3.71-3.57 (m, 1H), 3.57-3.46 (m, 1H), 3.19-2.99 (m, 2H), 1.78 (s, 3H).

Example 340

(1R,2S,5S)-3-(6-{[6-(2-methylphenyl)-5-(trifluoromethyl)pyridin-2-yl]sulfamoyl}pyridin-2-yl)-3-azabicyclo[3.1.0]hexane-2-carboxylic Acid LCMS conditions 7: 1.793 min; MS for $C_{24}H_{22}F_3N_4O_4S$ [M+H]$^+$ m/z=519.13, found m/z=519.10. $^1$H NMR (400 MHz, DMSO-d$_6$) δ 12.57 (s, 1H), 11.48 (s, 1H), 8.17 (d, J=8.3 Hz, 1H), 7.74-7.56 (m, 2H), 7.36-7.28 (m, 1H), 7.27-7.13 (m, 4H), 7.09 (d, J=7.5 Hz, 1H), 4.33-4.16 (m, 1H), 3.61-3.47 (m, 1H), 3.40-3.35 (m, 1H), 2.11-1.95 (m, 1H), 1.85 (s, 3H), 1.81-1.64 (m, 1H), 0.78-0.65 (m, 1H), 0.55-0.41 (m, 1H).

Example 341

(2R)-4-(6-{[6-(2-methylphenyl)-5-(trifluoromethyl)pyridin-2-yl]sulfamoyl}pyridin-2-yl)piperazine-2-carboxylic Acid LCMS conditions 7: 1.508 min; MS for $C_{23}H_{23}F_3N_5O_4S$ [M+H]$^+$ m/z=522.14, found m/z=522.10. $^1$H NMR (400 MHz, Methanol-d$_4$) δ 8.08 (d, J=8.9 Hz, 1H), 7.76 (dd, J=8.7, 7.4 Hz, 1H), 7.58 (d, J=8.8 Hz, 1H), 7.40 (d, J=7.3 Hz, 1H), 7.32 (td, J=7.5, 1.4 Hz, 1H), 7.27-7.18 (m, 2H), 7.16 (d, J=8.7 Hz, 1H), 7.05 (d, J=7.5 Hz, 1H), 4.66-4.54 (m, 1H), 4.26-4.09 (m, 2H), 3.53-3.32 (m, 3H), 3.24-3.11 (m, 1H), 1.93 (s, 3H).

Example 342

4-((6-(N-(6-(o-tolyl)-5-(trifluoromethyl)pyridin-2-yl)sulfamoyl)pyridin-2-yl)oxy)cyclohexanecarboxylic Acid Mixture (~2:1) of diastereomers. LCMS conditions 7: 1.63 min, MS for $C_{25}H_{25}F_3N_3O_5S$ [M+H]$^+$ m/z=536.1, found 536.1. $^1$H NMR (400 MHz, DMSO-d$_6$) δ 12.13 (s, 1H), 11.79 (s, 1H), 8.21 (t, J=8.3 Hz, 1H), 7.94-7.82 (m, 1H), 7.60-7.52 (m, 1H), 7.51 (dd, J=2.2, 7.3 Hz, 1H), 7.45 (s, 1H), 7.31 (t, J=7.4 Hz, 1H), 7.21 (t, J=7.8 Hz, 1H), 7.09-7.01 (m, 2H), 7.01-6.93 (m, 1H), 6.30-6.26 (m, 1H), 5.02-4.85 (m, 1H), 1.82-1.58 (m, 5H), 1.52 (m, 2H), 1.27 (m, 3H). $^{19}$F NMR (376 MHz, DMSO-d$_6$) δ −57.13 (s, 2F), −57.18 (s, 1F).

Example 343

4-methyl-1-(6-(N-(6-(2-morpholinophenyl)-5-(trifluoromethyl)pyridin-2-yl)sulfamoyl)pyridin-2-yl)piperidine-4-carboxylic Acid LCMS conditions 7: 1.60 min, MS for $C_{28}H_{31}F_3N_5O_5S$ [M+H]$^+$ m/z=606.2, found m/z=606.2. $^1$H NMR (400 MHz, Chloroform-d) δ 7.96 (d, J=9.0 Hz, 1H), 7.59 (dd, J=7.3, 8.7 Hz, 2H), 7.47-7.40 (m, 1H), 7.32 (d, J=7.2 Hz, 1H), 7.20-7.09 (m, 3H), 6.76 (d, J=8.7 Hz, 1H), 3.93 (d, J=13.5 Hz, 2H), 3.43 (s, 4H), 2.93-2.80 (m, 2H), 2.80-2.66 (m, 4H), 2.03 (d, J=13.5 Hz, 3H), 1.36 (dd, J=3.1, 12.6 Hz, 2H), 1.23 (s, 3H). $^{19}$F NMR (376 MHz, Chloroform-d) δ −58.19 (s, 1F).

Example 344

1-(6-{[6-(2-methylphenyl)-5-(trifluoromethyl)pyridin-2-yl]sulfamoyl}pyridin-2-yl)piperidine-4-carboxylic Acid LCMS conditions 7: 1.764 min; MS for $C_{24}H_{24}F_3N_4O_4S$ [M+H]$^+$ m/z=521.15, found m/z=521.10. $^1$H NMR (400 MHz, DMSO-d$_6$) δ 12.22 (s, 1H), 11.53 (s, 1H), 8.27-8.07 (m, 1H), 7.67 (t, J=8.0 Hz, 1H), 7.60-7.40 (m, 1H), 7.31 (td, J=7.4, 1.4 Hz, 1H), 7.26-7.16 (m, 2H), 7.14-6.98 (m, 3H), 4.11-3.91 (m, 2H), 2.97-2.78 (m, 2H), 2.48-2.41 (m, 1H), 1.78 (s, 3H), 1.74-1.64 (m, 2H), 1.38-1.15 (m, 2H).

Example 345

9-(6-{[6-(2-methylphenyl)-5-(trifluoromethyl)pyridin-2-yl]sulfamoyl}pyridin-2-yl)-9-azabicyclo[3.3.1]nonane-3-carboxylic Acid LCMS conditions 7: 1.843 min; MS for $C_{27}H_{28}F_3N_4O_4S$ [M+H]$^+$ m/z=561.18, found m/z=561.15. $^1$H NMR (400 MHz, DMSO-d$_6$) δ 12.13 (s, 1H), 11.52 (s, 1H), 8.18 (d, J=8.9 Hz, 1H), 7.68 (dd, J=8.7, 7.2 Hz, 1H), 7.59-7.45 (m, 1H), 7.31 (td, J=7.4, 1.4 Hz, 1H), 7.25-7.15 (m, 2H), 7.09-6.97 (m, 3H), 4.67-4.18 (m, 2H), 3.24-3.07 (m, 1H), 2.05-1.87 (m, 1H), 1.85-1.69 (m, 5H), 1.67-1.49 (m, 6H), 1.49-1.37 (m, 1H).

Example 346

8-(6-{[6-(2-methylphenyl)-5-(trifluoromethyl)pyridin-2-yl]sulfamoyl}pyridin-2-yl)-8-azabicyclo[3.2.1]octane-3-carboxylic Acid LCMS conditions 7: 1.805 min; MS for $C_{26}H_{26}F_3N_4O_4S$ [M+H]$^+$ m/z=547.16, found m/z=547.20. $^1$H NMR (400 MHz, DMSO-d$_6$) δ 12.10 (s, 1H), 11.53 (s, 1H), 8.19 (d, J=9.0 Hz, 1H), 7.69 (dd, J=8.6, 7.3 Hz, 1H), 7.65-7.50 (m, 1H), 7.31 (td, J=7.4, 1.4 Hz, 1H), 7.27-7.15 (m, 2H), 7.13-7.02 (m, 2H), 6.95 (d, J=8.6 Hz, 1H), 4.49-4.22 (m, 2H), 2.90-2.74 (m, 1H), 2.02-1.84 (m, 2H), 1.84-1.65 (m, 5H), 1.58-1.20 (m, 4H).

Example 347

(2R)-4-[(tert-butoxy)carbonyl]-1-(6-{[6-(2-methylphenyl)-5-(trifluoromethyl)pyridin-2-yl]sulfamoyl}pyridin-2-yl)piperazine-2-carboxylic Acid LCMS conditions 7: 1.703 min; MS for $C_{28}H_{31}F_3N_5O_6S$ [M+H]$^+$ m/z=622.19, found m/z=622.25.

Example 348

(3S)-1-(6-{[6-(2-methylphenyl)-5-(trifluoromethyl)pyridin-2-yl]sulfamoyl}pyridin-2-yl)pyrrolidine-3-carboxylic Acid LCMS conditions 7: 1.759 min; MS for $C_{23}H_{22}F_3N_4O_4S$ [M+H]$^+$ m/z=507.13, found m/z=507.20. $^1$H NMR (400 MHz, DMSO-d$_6$) δ 12.52 (s, 1H), 11.54 (s, 1H), 8.15 (d, J=8.5 Hz, 1H), 7.65 (dd, J=8.6, 7.3 Hz, 1H), 7.62-7.47 (m, 1H), 7.32 (td, J=7.5, 1.4 Hz, 1H), 7.27-7.16 (m, 2H), 7.13-7.01 (m, 2H), 6.69 (d, J=8.5 Hz, 1H), 3.52-3.36 (m, 2H), 3.33-3.19 (m, 2H), 3.19-3.03 (m, 1H), 2.23-2.00 (m, 2H), 1.83 (s, 3H).

Example 349

(3R)-1-(6-{[6-(2-methylphenyl)-5-(trifluoromethyl)pyridin-2-yl]sulfamoyl}pyridin-2-yl)pyrrolidine-3-carboxylic Acid LCMS conditions 7: 1.759 min; MS for $C_{23}H_{22}F_3N_4O_4S$ [M+H]$^+$ m/z=507.13, found m/z=507.10. $^1$H NMR (400 MHz, DMSO-d$_6$) δ 12.52 (s, 1H), 11.54 (s, 1H), 8.15 (d, J=8.5 Hz, 1H), 7.65 (dd, J=8.6, 7.3 Hz, 1H), 7.62-7.47 (m, 1H), 7.32 (td, J=7.5, 1.4 Hz, 1H), 7.27-7.16 (m, 2H), 7.13-7.01 (m, 2H), 6.69 (d, J=8.5 Hz, 1H), 3.52-3.36 (m, 2H), 3.33-3.19 (m, 2H), 3.19-3.03 (m, 1H), 2.23-2.00 (m, 2H), 1.83 (s, 3H).

Example 350

(2S)-4-[(tert-butoxy)carbonyl]-1-(6-{[6-(2-methylphenyl)-5-(trifluoromethyl)pyridin-2-yl]sulfamoyl}pyridin-2-yl)piperazine-2-carboxylic acid LCMS conditions 7: 1.666 min; MS for $C_{28}H_{31}F_3N_5O_6S$ [M+H]$^+$ m/z=622.19, found m/z=622.20.

Example 351

1-(6-{[6-(2-ethylphenyl)-5-(trifluoromethyl)pyridin-2-yl]sulfamoyl}pyridin-2-yl)-4-propylpiperidine-4-carboxylic acid LCMS conditions 7: 1.925 min; MS for $C_{28}H_{32}F_3N_4O_4S$ [M+H]$^+$ m/z=577.21, found m/z=577.20. $^1$H NMR (400 MHz, DMSO-d$_6$) δ 12.48 (s, 1H), 11.49 (s, 1H), 8.31-8.02 (m, 1H), 7.67 (t, J=8.0 Hz, 1H), 7.58-7.42 (m, 1H), 7.36 (td, J=7.5, 1.4 Hz, 1H), 7.29-7.24 (m, 1H), 7.20 (td, J=7.5, 1.4 Hz, 1H), 7.08 (d, J=7.2 Hz, 1H), 7.06-6.94 (m, 2H), 3.98-3.78 (m, 2H), 2.93-2.77 (m, 2H), 2.22-1.92 (m, 2H), 1.92-1.78 (m, 2H), 1.38-1.27 (m, 2H), 1.20-0.97 (m, 4H), 0.87 (t, J=7.6 Hz, 3H), 0.80 (t, J=7.2 Hz, 3H).

Example 352

1-(6-{[6-(2-ethylphenyl)-5-(trifluoromethyl)pyridin-2-yl]sulfamoyl}pyridin-2-yl)-3-propylpiperidine-3-carboxylic Acid LCMS conditions 7: 1.966 min; MS for $C_{28}H_{32}F_3N_4O_4S$ [M+H]$^+$ m/z=577.21, found m/z=577.20. $^1$H NMR (400 MHz, DMSO-d$_6$) δ 12.33 (s, 1H), 11.52 (s, 1H), 8.17 (d, J=8.9 Hz, 1H), 7.65 (dd, J=8.6, 7.3 Hz, 1H), 7.61-7.47 (m, 1H), 7.36 (td, J=7.5, 1.4 Hz, 1H), 7.28 (dd, J=7.4, 3.1 Hz, 1H), 7.21 (td, J=7.5, 1.2 Hz, 1H), 7.13-6.99 (m, 3H), 3.90 (dd, J=26.3, 13.1 Hz, 1H), 3.69 (dd, J=43.7, 12.7 Hz, 1H), 3.09 (dd, J=39.9, 13.2 Hz, 1H), 3.01-2.81 (m, 1H), 2.27-2.11 (m, 1H), 2.11-1.90 (m, 2H), 1.57-1.04 (m, 7H), 0.97-0.84 (m, 3H), 0.84-0.66 (m, 3H).

Example 353

(2R)-1-(6-{[6-(2-methylphenyl)-5-(trifluoromethyl)pyridin-2-yl]sulfamoyl}pyridin-2-yl)piperazine-2-carboxylic Acid LCMS conditions 7: 1.300 min; MS for $C_{23}H_{23}F_3N_5O_4S$ [M+H]$^+$ m/z=522.14, found m/z=522.20. $^1$H NMR (400 MHz, Methanol-d$_4$) δ 8.07 (d, J=8.9 Hz, 1H), 7.73 (dd, J=8.7, 7.4 Hz, 1H), 7.58-7.45 (m, 1H), 7.39-7.27 (m, 2H), 7.27-7.16 (m, 2H), 7.13-7.01 (m, 2H), 5.41-5.26 (m, 1H), 4.43-4.30 (m, 1H), 3.97-3.84 (m, 1H), 3.40-3.32 (m, 2H), 3.28-3.18 (m, 1H), 3.17-3.06 (m, 1H), 2.03-1.87 (m, 3H).

Example 354

(2S)-1-(6-{[6-(2-methylphenyl)-5-(trifluoromethyl)pyridin-2-yl]sulfamoyl}pyridin-2-yl)piperazine-2-carboxylic Acid LCMS conditions 7: 1.294 min; MS for $C_{23}H_{23}F_3N_5O_4S$ [M+H]$^+$ m/z=522.14, found m/z=522.20. $^1$H NMR (400 MHz, Methanol-d$_4$) δ 8.07 (d, J=9.0 Hz, 1H), 7.72 (dd, J=8.7, 7.3 Hz, 1H), 7.53 (d, J=8.9 Hz, 1H), 7.37-7.28 (m, 2H), 7.26-7.16 (m, 2H), 7.12-7.03 (m, 2H), 5.32-5.20 (m, 1H), 4.43-4.31 (m, 1H), 3.95-3.81 (m, 1H), 3.40-3.32 (m, 2H), 3.28-3.17 (m, 1H), 3.15-3.02 (m, 1H), 2.02-1.89 (m, 3H).

Example 355

(1r,3r)-3-((6-(N-(6-(o-tolyl)-5-(trifluoromethyl)pyridin-2-yl)sulfamoyl)pyridin-2-yl)amino)cyclobutanecarboxylic Acid LCMS conditions 7: 1.4 min, MS for $C_{23}H_{22}F_3N_4O_4S$ [M+H]$^+$ m/z=507.1, found m/z=507.2. $^1$H NMR (400 MHz, DMSO-d$_6$) δ 12.20 (s, 1H), 11.56 (s, 1H), 8.18 (d, J=8.9 Hz, 1H), 7.57-7.44 (m, 3H), 7.36-7.27 (m, 1H), 7.24-7.18 (m, 2H), 7.06-7.03 (m, 2H), 6.63 (d, J=8.4 Hz, 1H), 4.29-4.19 (m, 1H), 2.97-2.91 (m, 1H), 2.36-2.33 (m, 2H), 2.12-1.95 (m, 2H), 1.78 (s, 3H).

Example 356

(1s,3s)-1-methyl-3-((6-(N-(6-(o-tolyl)-5-(trifluoromethyl)pyridin-2-yl)sulfamoyl)pyridin-2-yl)amino)cyclobutanecarboxylic Acid LCMS conditions 7: 1.6 min, MS for $C_{24}H_{24}F_3N_4O_4S$ [M+H]$^+$ m/z=521.2, found m/z=521.2. $^1$H NMR (400 MHz, DMSO-d$_6$) δ 11.49 (s, 1H), 8.27 (d, J=8.9 Hz, 1H), 7.60 (d, J=7.1 Hz, 1H), 7.55 (dd, J=8.4, 7.3 Hz, 1H), 7.49 (d, J=7.2 Hz, 1H), 7.32 (t, J=7.5 Hz, 1H), 7.28-7.17 (m, 2H), 7.09-7.00 (m, 2H), 6.62 (d, J=8.5 Hz, 1H), 3.94 (h, J=8.5 Hz, 1H), 3.60 (s, 3H), 2.76-2.63 (m, 1H), 2.33-2.20 (m, 2H), 1.99-1.85 (m, 2H), 1.83 (s, 3H).

Example 357

(3R)-1-(6-{[6-(5-fluoro-2-methylphenyl)-5-(trifluoromethyl)pyridin-2-yl]sulfamoyl}pyridin-2-yl)piperidine-3-carboxylic Acid LCMS conditions 7: 1.806 min; MS for $C_{24}H_{23}F_4N_4O_4S$ [M+H]$^+$ m/z=539.14, found m/z=539.10. $^1$H NMR (400 MHz, DMSO-d$_6$) δ 12.40 (s, 1H), 11.64 (s, 1H), 8.20-8.06 (m, 1H), 7.67 (dd, J=8.7, 7.3 Hz, 1H), 7.49 (d, J=8.8 Hz, 1H), 7.26 (dd, J=8.6, 5.7 Hz, 1H), 7.17 (td, J=8.6, 2.8 Hz, 1H), 7.13-7.04 (m, 2H), 6.99-6.87 (m, 1H), 4.26-4.09 (m, 1H), 3.94-3.79 (m, 1H), 3.10-2.83 (m, 2H), 2.31-2.17 (m, 1H), 1.96-1.85 (m, 1H), 1.72 (s, 3H), 1.65-1.48 (m, 2H), 1.33-1.15 (m, 1H).

Example 358

(3R)-1-(6-{[6-(3-fluoro-2-methylphenyl)-5-(trifluoromethyl)pyridin-2-yl]sulfamoyl}pyridin-2-yl)piperidine-3-carboxylic Acid LCMS conditions 7: 1.810 min; MS for $C_{24}H_{23}F_4N_4O_4S$ [M+H]$^+$ m/z=539.14, found m/z=539.10. $^1$H NMR (400 MHz, DMSO-d$_6$) δ 12.40 (s, 1H), 11.64 (s, 1H), 8.16 (dd, J=8.9, 5.6 Hz, 1H), 7.68 (dd, J=8.7, 7.3 Hz, 1H), 7.49 (d, J=8.8 Hz, 1H), 7.31-7.17 (m, 2H), 7.14-7.05 (m, 2H), 6.92 (d, J=7.0 Hz, 1H), 4.28-4.09 (m, 1H), 3.94-3.78 (m, 1H), 3.10-2.82 (m, 2H), 2.35-2.14 (m, 1H), 1.97-1.83 (m, 1H), 1.75-1.45 (m, 5H), 1.36-1.15 (m, 1H).

Example 359

(3S)-1-(6-{[6-(5-fluoro-2-methylphenyl)-5-(trifluoromethyl)pyridin-2-yl]sulfamoyl}pyridin-2-yl)piperidine-3-carboxylic Acid LCMS conditions 7: 1.804 min; MS for $C_{24}H_{23}F_4N_4O_4S$ [M+H]$^+$ m/z=539.14, found m/z=539.20. $^1$H NMR (400 MHz, DMSO-d$_6$) δ 12.40 (s, 1H), 11.64 (s, 1H), 8.21-8.07 (m, 1H), 7.67 (dd, J=8.7, 7.3 Hz, 1H), 7.49 (d, J=8.8 Hz, 1H), 7.27 (dd, J=8.6, 5.7 Hz, 1H), 7.17 (td, J=8.7, 2.8 Hz, 1H), 7.12-7.07 (m, 2H), 6.99-6.88 (m, 1H), 4.27-4.07 (m, 1H), 3.96-3.78 (m, 1H), 3.09-2.81 (m, 2H), 2.30-2.17 (m, 1H), 1.96-1.85 (m, 1H), 1.72 (s, 3H), 1.65-1.48 (m, 2H), 1.35-1.15 (m, 1H).

Example 360

(3S)-1-(6-{[6-(3-fluoro-2-methylphenyl)-5-(trifluoromethyl)pyridin-2-yl]sulfamoyl}pyridin-2-yl)piperidine-3-carboxylic Acid LCMS conditions 7: 1.809 min; MS for $C_{24}H_{23}F_4N_4O_4S$ [M+H]$^+$ m/z=539.14, found m/z=539.15. $^1$H NMR (400 MHz, DMSO-d$_6$) δ 12.40 (s, 1H), 11.64 (s, 1H), 8.16 (dd, J=8.8, 5.6 Hz, 1H), 7.68 (dd, J=8.7, 7.3 Hz, 1H), 7.49 (d, J=8.8 Hz, 1H), 7.32-7.18 (m, 2H), 7.14-7.03 (m, 2H), 6.92 (d, J=7.1 Hz, 1H), 4.29-4.09 (m, 1H), 3.95-3.76 (m, 1H), 3.11-2.82 (m, 2H), 2.34-2.14 (m, 1H), 1.99-1.83 (m, 1H), 1.73-1.46 (m, 5H), 1.34-1.15 (m, 1H).

Example 361

1-(6-{[6-(5-fluoro-2-methylphenyl)-5-(trifluoromethyl)pyridin-2-yl]sulfamoyl}pyridin-2-yl)-3-methylpiperidine-3-carboxylic Acid LCMS conditions 7: 1.754 min; MS for $C_{25}H_{25}F_4N_4O_4S$ [M+H]$^+$ m/z=553.15, found m/z=553.20. $^1$H NMR (400 MHz, DMSO-d$_6$) δ 12.32 (s, 1H), 11.59 (s, 1H), 8.19 (d, J=8.9 Hz, 1H), 7.64 (dd, J=8.7, 7.2 Hz, 1H), 7.55 (d, J=8.8 Hz, 1H), 7.31-7.21 (m, 1H), 7.17 (td, J=8.6, 2.8 Hz, 1H), 7.11-7.02 (m, 2H), 7.00-6.88 (m, 1H), 3.87 (d, J=13.1 Hz, 1H), 3.74-3.56 (m, 1H), 3.12 (d, J=13.1 Hz, 1H), 3.09-2.94

(m, 1H), 2.05-1.92 (m, 1H), 1.75 (d, J=9.8 Hz, 3H), 1.60-1.31 (m, 3H), 1.02-0.97 (m, 3H).

Example 362

1-(6-{[6-(3-fluoro-2-methylphenyl)-5-(trifluoromethyl)pyridin-2-yl]sulfamoyl}pyridin-2-yl)-3-methylpiperidine-3-carboxylic Acid LCMS conditions 7: 1.757 min; MS for $C_{25}H_{25}F_4N_4O_4S$ [M+H]$^+$ m/z=553.15, found m/z=553.20. $^1$H NMR (400 MHz, DMSO-d$_6$) δ 12.32 (s, 1H), 11.59 (s, 1H), 8.19 (d, J=8.9 Hz, 1H), 7.65 (dd, J=8.8, 7.2 Hz, 1H), 7.59-7.47 (m, 1H), 7.30-7.17 (m, 2H), 7.08 (dd, J=8.0, 5.3 Hz, 2H), 6.98-6.87 (m, 1H), 3.86 (d, J=13.1 Hz, 1H), 3.71-3.56 (m, 1H), 3.13 (dd, J=13.1, 8.8 Hz, 1H), 3.08-2.94 (m, 1H), 2.03-1.89 (m, 1H), 1.75-1.62 (m, 3H), 1.53-1.30 (m, 3H), 1.00 (d, J=8.0 Hz, 3H).

Example 363

1-(6-(N-(6-(2-cyclobutylphenyl)-5-(trifluoromethyl)pyridin-2-yl)sulfamoyl)pyridin-2-yl)-4-methylpiperidine-4-carboxylic Acid LCMS conditions 7: 1.80 min, MS for $C_{28}H_{30}F_3N_4O_4S$ [M+H]$^+$ m/z=575.2, found m/z=575.1. $^1$H NMR (400 MHz, DMSO-d$_6$) δ 12.45 (s, 1H), 11.49 (s, 1H), 8.20 (d, J=8.9 Hz, 1H), 7.70 (dd, J=7.4, 8.6 Hz, 1H), 7.54 (d, J=8.2 Hz, 1H), 7.40 (t, J=7.5 Hz, 1H), 7.34 (d, J=7.5 Hz, 1H), 7.21 (t, J=7.4 Hz, 1H), 7.13-7.06 (m, 2H), 7.03 (d, J=7.4 Hz, 1H), 3.88-3.74 (m, 2H), 3.03 (m, 3H), 1.97-1.91 (m, 1H), 1.90-1.83 (m, 2H), 1.76 (m, 2H), 1.65-1.51 (m, 2H), 1.43 (s, 1H), 1.22-1.15 (m, 2H), 1.11 (s, 3H). $^{19}$F NMR (376 MHz, DMSO-d$_6$) δ −56.19 (s, 1F).

Example 364

(1r,4r)-4-((6-(N-(6-(o-tolyl)-5-(trifluoromethyl)pyridin-2-yl)sulfamoyl)pyridin-2-yl)amino)cyclohexanecarboxylic Acid LCMS conditions 7: 1.616 min, MS for $C_{25}H_{26}F_3N_4O_4S$ [M+H]$^+$ m/z=535.2, found m/z=535.2. $^1$H NMR (400 MHz, Methanol-d$_4$) δ 8.07 (d, J=8.9 Hz, 1H), 7.59 (dd, J=13.2, 8.9 Hz, 1H), 7.44 (ddd, J=8.5, 7.2, 1.1 Hz, 1H), 7.33-7.25 (m, 1H), 7.24-7.15 (m, 2H), 7.12-7.00 (m, 2H), 6.61-6.52 (m, 1H), 3.66-3.51 (m, 1H), 2.34-2.06 (m, 1H), 2.00-1.78 (m, 7H), 1.45 (d, J=12.3 Hz, 2H), 1.14 (t, J=14.1 Hz, 2H).

Example 365

(1r,3s)-1-methyl-3-[(6-{[6-(2-methylphenyl)-5-(trifluoromethyl)-pyridin-2-yl]sulfamoyl}pyridin-2-yl)amino]cyclobutane-1-carboxylic Acid LCMS conditions 7: 1.594 min; MS for $C_{24}H_{24}F_3N_4O_4S$ [M+H]$^+$ m/z=521.15, found m/z=521.20. $^1$H NMR (400 MHz, DMSO-d$_6$) δ 12.31 (s, 1H), 11.55 (s, 1H), 8.14 (d, J=8.9 Hz, 1H), 7.59-7.44 (m, 2H), 7.41 (d, J=6.8 Hz, 1H), 7.30 (td, J=7.5, 1.4 Hz, 1H), 7.25-7.14 (m, 2H), 7.09-6.95 (m, 2H), 6.60 (d, J=8.4 Hz, 1H), 4.22-4.04 (m, 1H), 2.72-2.55 (m, 2H), 1.84-1.58 (m, 5H), 1.28 (s, 3H).

Example 366

(R)-1-(6-(N-(6-(2-cyclobutylphenyl)-5-(trifluoromethyl)pyridin-2-yl)sulfamoyl)pyridin-2-yl)piperidine-3-carboxylic Acid LCMS conditions 7: 1.76 min, MS for $C_{27}H_{28}F_3N_4O_4S$ [M+H]$^+$ m/z=561.2, found m/z=561.2. $^1$H NMR (400 MHz, DMSO-d$_6$) δ 12.43 (s, 1H), 11.56 (s, 1H), 8.13 (dd, J=3.1, 8.9 Hz, 1H), 7.69 (t, J=8.0 Hz, 1H), 7.51 (d, J=7.6 Hz, 1H), 7.40 (t, J=7.5 Hz, 1H), 7.33 (d, J=7.7 Hz, 1H), 7.21 (t, J=7.4 Hz, 1H), 7.12 (d, J=7.9 Hz, 2H), 7.02 (d, J=7.4 Hz, 1H), 4.23 (t, J=15.4 Hz, 1H), 3.93 (t, J=12.4 Hz, 1H), 3.01 (ddd, J=5.9, 10.9, 13.6 Hz, 2H), 2.96-2.80 (m, 1H), 2.31 (ddt, J=4.3, 10.2, 14.3 Hz, 1H), 1.94 (dt, J=4.8, 9.8 Hz, 2H), 1.84-1.69 (m, 2H), 1.68-1.50 (m, 4H), 1.43 (s, 1H), 1.33-1.28 (m, 1H). $^{19}$F NMR (376 MHz, DMSO-d$_6$) δ −56.21 (d, J=6.8 Hz, 1F).

Example 367

(S)-1-(6-(N-(6-(2-cyclobutylphenyl)-5-(trifluoromethyl)pyridin-2-yl)sulfamoyl)pyridin-2-yl)piperidine-3-carboxylic Acid LCMS conditions 7: 1.77 min, MS for $C_{27}H_{28}F_3N_4O_4S$ [M+H]$^+$ m/z=561.2, found m/z=561.2. $^1$H NMR (400 MHz, DMSO-d$_6$) δ 12.43 (s, 1H), 11.56 (s, 1H), 8.13 (dd, J=3.0, 8.8 Hz, 1H), 7.69 (t, J=7.9 Hz, 1H), 7.51 (d, J=7.7 Hz, 1H), 7.40 (t, J=7.5 Hz, 1H), 7.33 (d, J=7.7 Hz, 1H), 7.21 (t, J=7.2 Hz, 1H), 7.12 (d, J=7.8 Hz, 2H), 7.02 (d, J=7.4 Hz, 1H), 4.32-4.14 (m, 1H), 3.93 (t, J=12.4 Hz, 1H), 3.01 (ddd, J=6.1, 11.1, 13.6 Hz, 2H), 2.96-2.79 (m, 1H), 2.39-2.21 (m, 1H), 1.98-1.85 (m, 2H), 1.84-1.68 (m, 2H), 1.67-1.49 (m, 4H), 1.43 (s, 1H), 1.29 (m, 1H). $^{19}$F NMR (376 MHz, DMSO-d$_6$) δ −56.21 (d, J=6.7 Hz, 1F).

Example 368

1-(6-(N-(6-(2-cyclobutylphenyl)-5-(trifluoromethyl)pyridin-2-yl)sulfamoyl)pyridin-2-yl)-3-methylpiperidine-3-carboxylic Acid LCMS conditions 7: 1.81 min, MS for $C_{28}H_{30}F_3N_4O_4S$ [M+H]$^+$ m/z=575.2, found m/z=575.2. $^1$H NMR (400 MHz, DMSO-d$_6$) δ 12.35 (s, 1H), 11.52 (s, 1H), 8.15 (d, J=8.9 Hz, 1H), 7.71-7.60 (m, 1H), 7.55 (s, 1H), 7.38 (m, 2H), 7.22 (t, J=7.4 Hz, 1H), 7.10 (m, 2H), 7.03 (t, J=7.2 Hz, 1H), 3.89 (m, 1H), 3.79-3.50 (m, 1H), 3.27-2.94 (m, 3H), 2.05-1.88 (m, 2H), 1.80 (d, J=9.1 Hz, 2H), 1.60 (d, J=7.8 Hz, 2H), 1.54-1.35 (m, 4H), 1.03 (d, J=8.2 Hz, 3H). $^{19}$F NMR (376 MHz, DMSO-d$_6$) δ −56.22 (d, J=12.0 Hz, 1F).

Example 369

(R)-1-(6-(N-(6-(2-ethylphenyl)-5-(trifluoromethyl)pyridin-2-yl)sulfamoyl)pyridin-2-yl)piperidine-3-carboxylic Acid LCMS conditions 7: 1.68 min, MS for $C_{25}H_{26}F_3N_4O_4S$ [M+H]$^+$ m/z=535.2, found m/z=535.2. $^1$H NMR (400 MHz, DMSO-d$_6$) δ 12.41 (s, 1H), 11.56 (s, 1H), 8.15 (dd, J=3.3, 8.8 Hz, 1H), 7.73-7.62 (m, 1H), 7.52 (d, J=8.1 Hz, 1H), 7.36 (t, J=7.5 Hz, 1H), 7.28 (d, J=7.6 Hz, 1H), 7.21 (t, J=7.4 Hz, 1H), 7.10 (dd, J=6.1, 7.9 Hz, 2H), 7.03 (d, J=7.5 Hz, 1H), 4.18 (t, J=11.9 Hz, 1H), 3.88 (d, J=13.0 Hz, 1H), 3.01 (m, 1H), 2.89 (q, J=10.8 Hz, 1H), 2.36-2.22 (m, 1H), 2.15 (m, 1H), 2.08-1.97 (m, 1H), 1.96-1.85 (m, 1H), 1.67-1.48 (m, 2H), 0.87 (m, 4H). $^{19}$F NMR (376 MHz, DMSO-d$_6$) δ −56.62 (s, 1F).

Example 370

(S)-1-(6-(N-(6-(2-ethylphenyl)-5-(trifluoromethyl)pyridin-2-yl)sulfamoyl)pyridin-2-yl)piperidine-3-carboxylic Acid LCMS conditions 7: 1.68 min, MS for $C_{25}H_{26}F_3N_4O_4S$ [M+H]$^+$ m/z=535.2, found m/z=535.2. $^1$H NMR (400 MHz, DMSO-d$_6$) δ 12.42 (s, 1H), 11.56 (s, 1H), 8.15 (d, J=6.0 Hz, 1H), 7.68 (dd, J=7.4, 8.6 Hz, 1H), 7.51 (d, J=7.0 Hz, 1H), 7.36 (t, J=7.5 Hz, 1H), 7.28 (d, J=7.5 Hz, 1H), 7.21 (t, J=7.4 Hz, 1H), 7.14-7.07 (m, 2H), 7.03 (d, J=7.4 Hz, 1H), 4.18 (t, J=11.9 Hz, 1H), 3.88 (d, J=13.3 Hz, 1H), 3.10-2.95 (m, 1H), 2.89 (q, J=10.9 Hz, 1H), 2.28 (d, J=10.7 Hz, 1H), 2.15 (dd, J=7.4, 14.4 Hz, 1H), 2.08-2.01 (m, 1H), 1.92 (m, 1H), 1.70-1.48 (m, 2H), 0.87 (m, 4H). $^{19}$F NMR (376 MHz, DMSO-d$_6$) δ −56.62 (s, 1F).

Example 371

1-(6-(N-(6-(2-ethylphenyl)-5-(trifluoromethyl)pyridin-2-yl)sulfamoyl)pyridin-2-yl)-3-methylpiperidine-3-carboxylic Acid LCMS conditions 7: 1.75 min, MS for $C_{26}H_{28}F_3N_4O_4S$ [M+H]+ m/z=549.2, found m/z=549.2. $^1$H NMR (400 MHz, DMSO-d$_6$) δ 12.34 (s, 1H), 11.52 (s, 1H), 8.18 (d, J=8.9 Hz, 1H), 7.71-7.61 (m, 1H), 7.56 (s, 1H), 7.37 (t, J=7.5 Hz, 1H), 7.28 (d, J=7.6 Hz, 1H), 7.22 (td, J=1.0, 7.5 Hz, 1H), 7.14-6.98 (m, 3H), 3.87 (t, J=12.7 Hz, 1H), 3.63 (m, 1H), 3.14 (m, 1H), 2.98 (d, J=8.7 Hz, 1H), 2.18 (m, 1H), 2.12-2.01 (m, 1H), 1.99 (d, J=3.7 Hz, 1H), 1.43 (m, 3H), 1.01 (d, J=12.7 Hz, 3H), 0.89 (dq, J=3.5, 7.2 Hz, 3H). $^{19}$F NMR (376 MHz, DMSO-d$_6$) δ −56.61 (s, 1F).

Example 372

4-((6-(N-(6-(o-tolyl)-5-(trifluoromethyl)pyridin-2-yl)sulfamoyl)pyridin-2-yl)amino)cyclohexanecarboxylic Acid LCMS conditions 7: 1.628 min, MS for $C_{25}H_{26}F_3N_4O_4S$ [M+H]$^+$ m/z=535.2, found m/z=534.9. $^1$H NMR (400 MHz, Methanol-d$_4$) δ 8.07 (d, J=8.9 Hz, 1H), 7.61 (d, J=8.9 Hz, 1H), 7.44 (dd, J=8.5, 7.3 Hz, 1H), 7.30 (td, J=7.5, 1.4 Hz, 1H), 7.25-7.11 (m, 2H), 7.12-6.97 (m, 2H), 6.64 (dt, J=8.6, 1.0 Hz, 1H), 3.71 (dt, J=6.9, 4.0 Hz, 1H), 2.45 (dtt, J=15.4, 7.8, 3.9 Hz, 1H), 1.92 (d, J=1.5 Hz, 5H), 1.59 (s, 6H).

Example 373

(S)-1-(6-(N-(6-(2-cyclobutylphenyl)-5-(trifluoromethyl)pyridin-2-yl)sulfamoyl)pyridin-2-yl)-3-methylpiperidine-3-carboxylic Acid LCMS conditions 7: 1.81 min, MS for $C_{28}H_{30}F_3N_4O_4S$ [M+H]$^+$ m/z=575.2, found m/z=575.2. $^1$H NMR (400 MHz, DMSO-d$_6$) δ 12.35 (s, 1H), 11.52 (s, 1H), 8.15 (d, J=8.9 Hz, 1H), 7.71-7.60 (m, 1H), 7.55 (s, 1H), 7.38 (m, 2H), 7.22 (t, J=7.4 Hz, 1H), 7.10 (m, 2H), 7.03 (t, J=7.2 Hz, 1H), 3.89 (m, 1H), 3.79-3.50 (m, 1H), 3.27-2.94 (m, 3H), 2.05-1.88 (m, 2H), 1.80 (d, J=9.1 Hz, 2H), 1.60 (d, J=7.8 Hz, 2H), 1.54-1.35 (m, 4H), 1.03 (d, J=8.2 Hz, 3H). $^{19}$F NMR (376 MHz, DMSO-d$_6$) δ −56.22 (d, J=12.0 Hz, 1F). Chiral purification conditions: isocratic 6 min run, SFC 80/20 CO$_2$/IPA eluent at 80 g/min flowrate, 35° C. column temperature, preparatory column DAICEL ChiralPak IC 21×250 mm. The (S) enantiomer has a retention time of 3.18 min.

Example 374

1-(4-(N-(6-(2-ethylphenyl)-5-(trifluoromethyl)pyridin-2-yl)sulfamoyl)pyridin-2-yl)-4-methylpiperidine-4-carboxylic Acid LCMS conditions 7: 1.69 min, MS for $C_{26}H_{28}F_3N_4O_4S$ [M+H]$^+$ m/z=549.2, found m/z=549.2. $^1$H NMR (400 MHz, DMSO-d$_6$) δ 12.47 (s, 1H), 11.86 (s, 1H), 8.22 (d, J=5.1 Hz, 1H), 8.18 (d, J=8.8 Hz, 1H), 7.39 (td, J=1.4, 7.5 Hz, 1H), 7.29 (d, J=7.6 Hz, 1H), 7.22 (td, J=1.3, 7.4 Hz, 2H), 7.05 (d, J=7.7 Hz, 1H), 7.02 (d, J=1.3 Hz, 1H), 6.87 (dd, J=1.3, 5.1 Hz, 1H), 3.81-3.62 (m, 2H), 3.01 (m, 2H), 2.19 (m, 1H), 2.10-1.99 (m, 1H), 1.93 (m, 2H), 1.31 (m, 2H), 1.16 (s, 3H), 0.86-0.82 (m, 3H). $^{19}$F NMR (376 MHz, DMSO-d$_6$) δ −56.69 (s, 1F).

Example 375

(R)-1-(6-(N-(6-(2-isopropylphenyl)-5-(trifluoromethyl)pyridin-2-yl)sulfamoyl)pyridin-2-yl)piperidine-3-carboxylic Acid LCMS conditions 7: 1.92 min, MS for $C_{26}H_{28}F_3N_4O_4S$ [M+H]$^+$ m/z=549.2, found m/z=549.1. Rotomers/atropisomers are present in the NMR spectra. $^1$H NMR (400 MHz, Chloroform-d) δ 9.80 (br. s, 1H), 8.08 (t, J=9.0 Hz, 1H), 7.87-7.73 (m, 1H), 7.53 (m, 1H), 7.48-7.31 (m, 2H), 7.24-7.16 (m, 1H), 7.15-6.96 (m, 2H), 6.79 (dd, J=2.2, 8.7 Hz, 1H), 4.45 (m, 1H), 3.61 (m, 1H), 3.55-3.31 (m, 2H), 2.55 (dt, J=4.8, 9.3 Hz, 1H), 2.32 (m, 1H), 1.86-1.73 (m, 3H), 1.43 (m, 1H), 1.16-1.02 (m, 5H), 0.79 (m, 2H). $^{19}$F NMR (376 MHz, Chloroform-d) δ −58.53 (s, 1F), −58.75 (s, 0.8F).

Example 376

(S)-1-(6-(N-(6-(2-isopropylphenyl)-5-(trifluoromethyl)pyridin-2-yl)sulfamoyl)pyridin-2-yl)piperidine-3-carboxylic Acid LCMS conditions 7: 1.90 min, MS for $C_{26}H_{28}F_3N_4O_4S$ [M+H]$^+$ m/z=549.2, found m/z=549.2. Rotomers/atropisomers are present in the NMR spectra. $^1$H NMR (400 MHz, Chloroform-d) δ 8.07 (dd, J=7.6, 8.8 Hz, 1H), 7.79 (t, J=9.5 Hz, 1H), 7.54 (m, 1H), 7.45-7.31 (m, 2H), 7.24-7.11 (m, 2H), 7.09-6.98 (m, 1H), 6.80 (dd, J=1.7, 8.7 Hz, 1H), 4.53-4.14 (m, 1H), 3.73-3.33 (m, 3H), 2.54 (m, 1H), 2.34 (m, 1H), 1.93-1.69 (m, 3H), 1.50-1.37 (m, 1H), 1.16-1.03 (m, 5H), 0.82 (d, J=6.8 Hz, 2H). $^{19}$F NMR (376 MHz, Chloroform-d) δ −58.51 (s, 1F), −58.69 (s, 0.8F).

Example 377

1-(6-(N-(6-(2-isopropylphenyl)-5-(trifluoromethyl)pyridin-2-yl)sulfamoyl)pyridin-2-yl)-3-methylpiperidine-3-carboxylic Acid LCMS conditions 7: 1.96 min, MS for $C_{27}H_{30}F_3N_4O_4S$ [M+H]$^+$ m/z=563.2, found m/z=563.2. Rotomers/atropisomers are present in the NMR spectra. $^1$H NMR (400 MHz, Chloroform-d) δ 10.22 (br. s, 1H), 8.09 (m, 1H), 7.80 (m, 1H), 7.48 (m, 1H), 7.44-7.30 (m, 2H), 7.18 m, 1H), 7.11-6.93 (m, 2H), 6.78 (m, 1H), 4.82 (m, 1H), 3.88 (m, 1H), 3.09-2.91 (m, 1H), 2.78 (m, 1H), 2.30 (m 1H), 2.02 (m, 1H), 1.83-1.67 (m, 1H), 1.47 (m, 1H), 1.43-1.32 (m, 2H), 1.17 (m, 3H), 1.14-1.03 (m, 5H), 0.69 (d, J=6.8 Hz, 1H). $^{19}$F NMR (376 MHz, Chloroform-d) δ −58.53 (s, 1F), −58.88 (s, 0.9F).

Example 378

1-(4-(N-(6-(2-cyclobutylphenyl)-5-(trifluoromethyl) pyridin-2-yl)sulfamoyl)pyridin-2-yl)-4-methylpiperidine-4-carboxylic Acid LCMS conditions 7: 1.78 min, MS for $C_{28}H_{30}F_3N_4O_4S$ [M+H]$^+$ m/z=575.2, found m/z=575.2. $^1$H NMR (400 MHz, Chloroform-d) δ 10.54 (s, 1H), 8.28 (d, J=5.1 Hz, 1H), 8.05 (d, J=9.0 Hz, 1H), 7.65 (d, J=8.9 Hz, 1H), 7.50-7.38 (m, 2H), 7.22 (td, J=1.5, 7.4 Hz, 1H), 7.11 (d, J=1.2 Hz, 1H), 7.07 (d, J=7.6 Hz, 1H), 6.93 (dd, J=1.3, 5.1 Hz, 1H), 4.12-3.92 (m, 2H), 3.15 (p, J=8.5 Hz, 1H), 3.01-2.84 (m, 2H), 2.01 (q, J=9.8, 11.6 Hz, 4H), 1.80-1.64 (m, 4H), 1.43-1.31 (m, 3H), 1.21 (s, 3H). $^{19}$F NMR (376 MHz, Chloroform-d) δ −58.30 (s, 1F).

Example 379

1-(6-(N-(6-(2-cyclopentylphenyl)-5-(trifluoromethyl)pyridin-2-yl)sulfamoyl)pyridin-2-yl)-4-methylpiperidine-4-carboxylic Acid

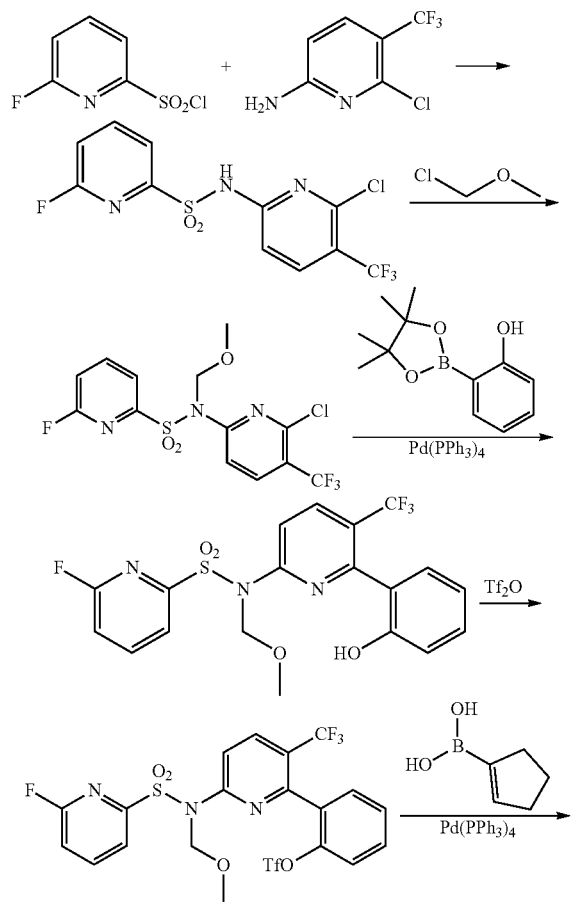

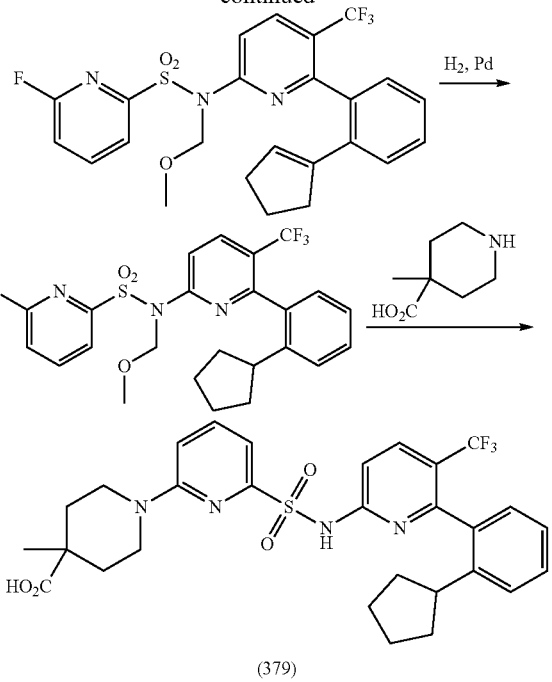

(379)

Step 1: Synthesis of N-(6-chloro-5-(trifluoromethyl) pyridin-2-yl)-6-fluoropyridine-2-sulfonamide 6-Chloro-5-(trifluoromethyl)pyridin-2-amine (1.2 g, 6.11 mmol) and sulfonyl chloride 6-fluoropyridine-2-sulfonyl chloride (1.493 g, 7.63 mmol) were dissolved in pyridine (10 mL). The resulting red solution was stirred at 20° C. for 3 days. The reaction mixture was diluted with ethyl acetate, washed with water, sat. NH$_4$Cl, 1 N HCl and brine, dried over Na$_2$SO$_4$ and concentrated. The crude product was purified by silica gel chromatography (0-40% EtOAc/hexane) to yield N-(6-chloro-5-(trifluoromethyl)pyridin-2-yl)-6-fluoropyridine-2-sulfonamide (1.05 g, 2.92 mmol, 47.9% yield). LCMS conditions 7:1.56 min, MS for $C_{11}H_7ClF_4N_3O_2S$ [M+H]$^+$ m/z=356.0, found m/z=355.9. $^1$H NMR (500 MHz, Chloroform-d) δ 8.14-8.07 (m, 1H), 8.07-8.04 (m, 1H), 7.97 (d, J=8.6 Hz, 1H), 7.79 (br. s, 1H), 7.56 (d, J=8.5 Hz, 1H), 7.23 (ddd, J=0.9, 2.6, 8.1 Hz, 1H). $^{19}$F NMR (471 MHz, Chloroform-d) −62.67 (s, 3F), −62.73 (br. s, 1F).

Step 2: Synthesis of N-(6-chloro-5-(trifluoromethyl) pyridin-2-yl)-6-fluoro-N-(methoxymethyl)pyridine-2-sulfonamide N-(6-chloro-5-(trifluoromethyl)pyridin-2-yl)-6-fluoro-pyridine-2-sulfonamide (1.02 g, 2.87 mmol) was dissolved in ACN (30 mL). The mixture was treated with powdered potassium carbonate (0.396 g, 2.87 mmol) and MOM-Cl (0.218 mL, 2.87 mmol). The mixture was stirred at 20° C. for 18 h. The reaction mixture was filtered and concentrated. The crude product was purified by silica gel chromatography (0-40% EtOAc/heptane) to yield the desired product N-(6-chloro-5-(trifluoromethyl)pyridin-2-yl)-6-fluoro-N-(methoxymethyl)pyridine-2-sulfonamide (0.98 g, 2.427 mmol, 85% yield). LCMS conditions 7: 1.69 min, MS for $C_{13}H_{11}ClF_4N_3O_3S$ [M+H]$^+$ m/z=400.0, found m/z=400.1. $^1$H NMR (500 MHz, Chloroform-d) δ 8.16 (ddd, J=0.9, 2.1, 7.5 Hz, 1H), 8.14-8.09 (m, 1H), 7.97 (d, J=8.5 Hz, 1H), 7.53 (d, J=8.4 Hz, 1H), 7.19 (ddd, J=0.9, 2.6, 7.9 Hz, 1H), 5.54 (s, 2H), 3.56 (s, 3H). $^{19}$F NMR (471 MHz, Chloroform-d) δ −62.87 (s, 3F), −64.16 (s, 1F).

Step 3: Synthesis of 6-fluoro-N-(6-(2-hydroxyphenyl)-5-(trifluoromethyl)pyridin-2-yl)-N-(methoxymethyl)pyridine-2-sulfonamide N-(6-chloro-5-(trifluoromethyl)pyridin-2-yl)-6-fluoro-N-(methoxymethyl)pyridine-2-sulfonamide (0.2 g, 0.500 mmol) and 2-(4,4,5,5-tetramethyl-1,3,2-dioxaborolan-2-yl) phenol (0.165 g, 0.750 mmol) were dissolved in dioxane (10 mL) and water (1.5 mL) and treated with sodium carbonate (0.159 g, 1.501 mmol). The mixture was degassed using argon. The catalyst tetrakis(triphenylphosphino)palladium (0) (0.058 g, 0.050 mmol) was added, the mixture was degassed again, and was stirred at 120° C. for 18 h. The mixture was cooled, the aqueous layer was discarded and enough ethyl acetate was added until all solids were dissolved. The mixture was dried over Na$_2$SO$_4$, filtered and concentrated to yield a reddish oil. The crude product was purified by silica gel chromatography (0-30% EtOAc/heptane) to yield the desired product 6-fluoro-N-(6-(2-hydroxyphenyl)-5-(trifluoromethyl)pyridin-2-yl)-N-(methoxymethyl)pyridine-2-sulfonamide (0.145 g, 0.301 mmol, 60.2% yield). LCMS conditions 7: 1.67 min, MS for C$_{19}$H$_{16}$F$_4$N$_3$O$_4$S [M+H]$^+$ m/z=458.1, found m/z=458.1. $^1$H NMR (400 MHz, DMSO-d$_6$) δ 9.39 (s, 1H), 8.26 (d, J=8.8 Hz, 1H), 8.00 (q, J=7.8 Hz, 1H), 7.77 (dd, J=1.9, 7.5 Hz, 1H), 7.53 (d, J=8.7 Hz, 1H), 7.45 (dd, J=2.0, 8.2 Hz, 1H), 7.25-7.17 (m, 1H), 6.82 (d, J=8.3 Hz, 1H), 6.77 (t, J=7.4 Hz, 1H), 6.72-6.68 (m, 1H), 5.45 (s, 2H), 3.39 (s, 3H). $^{19}$F NMR (376 MHz, DMSO-d$_6$) δ −58.03 (s, 3F), −66.28 (s, 1F).

Step 4: Synthesis of 2-(6-(6-fluoro-N-(methoxymethyl)pyridine-2-sulfonamido)-3-(trifluoromethyl)pyridin-2-yl)phenyl Trifluoromethanesulfonate 6-Fluoro-N-(6-(2-hydroxyphenyl)-5-(trifluoromethyl)pyridin-2-yl)-N-(methoxymethyl)pyridine-2-sulfonamide (0.15 g, 0.328 mmol) was dissolved in pyridine (3 mL), treated with triflic anhydride (0.078 mL, 0.459 mmol), and the mixture was stirred at 20° C. for 18 h. The mixture was diluted with water and extracted with ethyl acetate (2×25 mL). The combined extracts were washed with water, sat. NH$_4$Cl, and brine, then dried over Na$_2$SO$_4$, filtered and concentrated to yield a reddish oil. The crude product was purified by silica gel chromatography (0-40% EtOAc/heptane) to yield the desired product 2-(6-(6-fluoro-N-(methoxymethyl)pyridine-2-sulfonamido)-3-(trifluoromethyl)pyridin-2-yl)phenyl trifluoromethanesulfonate (0.13 g, 0.218 mmol, 67% yield). LCMS conditions 7: 1.83 min, MS for C$_{20}$H$_{15}$F$_7$N$_3$O$_6$S$_2$ [M+H]$^+$ m/z=590.0, found m/z=590.1. $^1$H NMR (500 MHz, Chloroform-d) δ 8.08 (d, J=8.7 Hz, 1H), 7.78-7.73 (m, 2H), 7.73-7.65 (m, 1H), 7.59-7.51 (m, 1H), 7.47 (td, J=1.2, 7.5 Hz, 1H), 7.39 (dd, J=1.8, 7.7 Hz, 1H), 7.32 (dd, J=1.1, 8.3 Hz, 1H), 7.04 (ddd, J=0.9, 2.6, 8.0 Hz, 1H), 5.64 (s, 1H), 5.51 (s, 1H), 3.53 (s, 3H). $^{19}$F NMR (471 MHz, Chloroform-d) δ −58.71 (s, 3F), −64.66 (s, 1F), −74.58 (s, 3F).

Step 5: Synthesis of N-(6-(2-(cyclopent-1-en-1-yl) phenyl)-5-(trifluoromethyl)pyridin-2-yl)-6-fluoro-N-(methoxymethyl)pyridine-2-sulfonamide 2-(6-(6-Fluoro-N-(methoxymethyl)pyridine-2-sulfonamido)-3-(trifluoromethyl)pyridin-2-yl)phenyl trifluoromethanesulfonate (0.13 g, 0.221 mmol) and cyclopent-1-en-1-ylboronic acid (0.031 g, 0.276 mmol) were dissolved in dioxane (10 mL) and water (1.5 mL) and treated with sodium carbonate (0.093 g, 0.882 mmol). The mixture was degassed using argon, tetrakis(triphenylphosphino)palladium(0) (0.025 g, 0.022 mmol) was added, the mixture was degassed again, and was stirred at 120° C. for 18 h. The mixture was cooled, the aqueous layer was discarded and the mixture was filtered. The solids were washed with more dioxane. The combined filtrate was dried over Na$_2$SO$_4$, filtered and concentrated to yield a reddish oil. The crude product was purified by silica gel chromatography (0-40% EtOAc/heptane) to yield the desired product N-(6-(2-(cyclopent-1-en-1-yl)phenyl)-5-(trifluoromethyl)pyridin-2-yl)-6-fluoro-N-(methoxymethyl)pyridine-2-sulfonamide (25 mg, 0.049 mmol, 22.34% yield). LCMS conditions 7: 1.93 min, MS for C$_{24}$H$_{22}$F$_4$N$_3$O$_3$S [M+H]$^+$ m/z=508.1, found m/z=508.2. $^1$H NMR (500 MHz, Chloroform-d) δ 7.98 (d, J=8.7 Hz, 1H), 7.73-7.63 (m, 1H), 7.57-7.46 (m, 2H), 7.41-7.31 (m, 2H), 7.19 (ddd, J=2.2, 6.5, 7.7 Hz, 1H), 6.94 (ddd, J=0.7, 2.6, 8.2 Hz, 1H), 6.90 (d, J=7.6 Hz, 1H), 5.57 (d, J=11.5 Hz, 1H), 5.48 (d, J=11.4 Hz, 1H), 5.00 (p, J=2.4 Hz, 1H), 3.58 (s, 3H), 2.36 (m, 1H), 2.27-2.09 (m, 2H), 1.87-1.60 (m, 3H). $^{19}$F NMR (471 MHz, Chloroform-d) δ −58.87 (s, 3F), −65.33 (s, 1F).

Step 6: Synthesis of N-(6-(2-cyclopentylphenyl)-5-(trifluoromethyl)pyridin-2-yl)-6-fluoro-N-(methoxymethyl)pyridine-2-sulfonamide N-(6-(2-(cyclopent-1-en-1-yl)phenyl)-5-(trifluoromethyl) pyridin-2-yl)-6-fluoro-N-(methoxymethyl)pyridine-2-sulfonamide (22 mg, 0.043 mmol) was dissolved in ethyl acetate (10 mL) and treated with palladium black on carbon (10%; 9 mg, 0.9 mmol). The mixture was degassed using argon, then hydrogen, and stirred at 20° C. for 18 h. The mixture was filtered and concentrated to yield the desired product N-(6-(2-cyclopentylphenyl)-5-(trifluoromethyl)pyridin-2-yl)-6-fluoro-N-(methoxymethyl)pyridine-2-sulfonamide (18 mg, 0.034 mmol, 77% yield). LCMS conditions 7: 2.04 min, MS for C$_{24}$H$_{24}$F$_4$N$_3$O$_3$S [M+H]$^+$ m/z=510.1, found m/z=510.2. $^1$H NMR (500 MHz, Chloroform-d) δ 7.94 (d, J=8.7 Hz, 1H), 7.56 (ddd, J=0.7, 1.9, 7.5 Hz, 1H), 7.46 (dd, J=0.8, 8.7 Hz, 1H), 7.40 (dt, J=7.5, 8.2 Hz, 1H), 7.32-7.24 (m, 2H), 7.01 (ddd, J=2.0, 6.6, 7.7 Hz, 1H), 6.85 (ddd, J=0.7, 2.6, 8.2 Hz, 1H), 6.70 (d, J=7.6 Hz, 1H), 5.51 (d, J=11.5 Hz, 1H), 5.38 (d, J=11.5 Hz, 1H), 3.49 (s, 3H), 2.42 (p, J=8.5 Hz, 1H), 1.84-1.67 (m, 2H), 1.57-1.43 (m, 4H), 1.40-1.27 (m, 2H). $^{19}$F NMR (471 MHz, Chloroform-d) δ −58.51 (s, 3F), −65.20 (s, 1F).

Step 7: Synthesis of 1-(6-(N-(6-(2-cyclopentylphenyl)-5-(trifluoromethyl)pyridin-2-yl)sulfamoyl)pyridin-2-yl)-4-methylpiperidine-4-carboxylic Acid The intermediate N-(6-(2-cyclopentylphenyl)-5-(trifluoromethyl)pyridin-2-yl)-6-fluoro-N-(methoxymethyl)pyridine-2-sulfonamide (18 mg, 0.035 mmol), methyl 4-methylpiperidine-4-carboxylate (9.52 mg, 0.053 mmol) and potassium carbonate (14.65 mg, 0.106 mmol) were dissolved/suspended in dioxane (8 mL) and the resulting mixture was stirred at 120° C. for 18 hr. The mixture was diluted with water and pH adjusted to ~1 with 1 N aq. HCl and then extracted with EtOAc (2×30 mL). The combined extracts were washed with brine, dried over Na$_2$SO$_4$, filtered and concentrated. The crude product was purified by silica gel chromatography (0-50% EtOAc/EtOH (3:1) mixture/heptane) to yield the desired title product Example 379: 1-(6-(N-(6-(2-cyclopentylphenyl)-5-(trifluoromethyl)pyridin-2-yl)sulfamoyl)pyridin-2-yl)-4-methylpiperidine-4-carboxylic acid (4 mg, 6.12 µmol, 17.31% yield). LCMS conditions 7: 1.97 min, MS for $C_{29}H_{32}F_3N_4O_4S$ [M+H]$^+$ m/z=589.2, found m/z=589.2. $^1$H NMR (400 MHz, Chloroform-d) δ 7.99 (d, J=9.0 Hz, 1H), 7.68 (d, J=8.9 Hz, 1H), 7.60 (dd, J=7.2, 8.7 Hz, 1H), 7.45-7.34 (m, 2H), 7.31 (d, J=7.2 Hz, 1H), 7.16 (td, J=1.5, 7.3 Hz, 1H), 7.04 (d, J=7.6 Hz, 1H), 6.76 (d, J=8.7 Hz, 1H), 3.95 (m, 2H), 2.85 (m, 2H), 2.44 (m, 1H), 2.01 (t, J=12.9 Hz, 2H), 1.86-1.74 (m, 3H), 1.70 (s, 3H), 1.49-1.38 (m, 5H), 1.21 (s, 3H). $^{19}$F NMR (376 MHz, Chloroform-d) δ −58.29 (s, 1F).

Example 380

1-(6-(6-(2-ethylphenyl)-5-(trifluoromethyl)pyridine-2-sulfonamido)pyridin-2-yl)-4-methylpiperidine-4-carboxylic Acid LCMS conditions 7: 1.84 min, MS for $C_{26}H_{28}F_3N_4O_4S$ [M+H]$^+$ m/z=549.2, found m/z=549.2. Rotomers/atropisomers are present in the NMR spectra. $^1$H NMR (400 MHz, Chloroform-d) δ 8.36-8.20 (m, 0.5H), 7.93 (m, 1H), 7.75-7.65 (m, 1H), 7.63-7.54 (m, 0.5H), 7.52-7.33 (m, 2.5H), 7.26-7.07 (m, 2H), 6.93 (br. s, 1H), 6.36-6.08 (m, 1H), 4.10-3.97 (m, 1H), 3.55 (m, 0.5H), 3.23 (m, 0.5H), 2.90 (m, 0.5H), 2.51 (m, 0.5H), 2.40 (m, 0.5H), 2.18 (m, 1H), 2.04 (m, 1.5H), 1.52 (m, 2.5H), 1.32-1.26 (m, 5H), 1.10 (t, J=7.6 Hz, 2H), 1.00-0.79 (m, 3H). $^{19}$F NMR (376 MHz, Chloroform-d) δ −58.38 (s, 1F), −58.31 (s, 0.74F).

Example 381

4-methyl-1-(6-(N-(6-(2-(2,2,2-trifluoroethoxy)phenyl)-5-(trifluoromethyl)pyridin-2-yl)sulfamoyl)pyridin-2-yl)piperidine-4-carboxylic Acid LCMS conditions 7: 1.84 min, MS for $C_{26}H_{25}F_6N_4O_5S$ [M+H]$^+$ m/z=619.2, found m/z=619.2. Rotomers/atropisomers are present in the NMR spectra. $^1$H NMR (400 MHz, Chloroform-d) δ 7.98 (dd, J=2.0, 8.9 Hz, 1H), 7.73 (d, J=8.8 Hz, 1H), 7.63-7.50 (m, 1H), 7.43 (td, J=2.0, 8.0 Hz, 1H), 7.31 (d, J=2.0 Hz, 1H), 7.20 (dd, J=1.7, 7.6 Hz, 1H), 7.10 (td, J=1.8, 7.4 Hz, 1H), 6.94 (d, J=8.2 Hz, 1H), 6.76 (dd, J=2.1, 8.7 Hz, 1H), 4.26 (qd, J=2.0, 8.1 Hz, 2H), 3.91 (s, 2H), 2.92 (ddd, J=2.6, 11.3, 14.0 Hz, 2H), 2.01 (d, J=13.7 Hz, 2H), 1.38-1.30 (m, 2H), 1.21 (d, J=2.0 Hz, 3H). $^{19}$F NMR (376 MHz, Chloroform-d) δ −59.12 (s, 3F), −74.04 (s, 3F).

Example 382

1-(6-(N-(6-(2-isobutoxyphenyl)-5-(trifluoromethyl)pyridin-2-yl)sulfamoyl)pyridin-2-yl)-4-methylpiperidine-4-carboxylic Acid LCMS conditions 7: 1.93 min, MS for $C_{28}H_{32}F_3N_4O_5S$ [M+H]$^+$ m/z=593.2, found m/z=593.2. Rotomers/atropisomers are present in the NMR spectra. $^1$H NMR (400 MHz, Chloroform-d) δ 7.95 (d, J=9.0 Hz, 1H), 7.64 (d, J=9.0 Hz, 1H), 7.59 (dd, J=7.3, 8.7 Hz, 1H), 7.40 (ddd, J=1.7, 7.6, 9.2 Hz, 1H), 7.31 (d, J=7.2 Hz, 1H), 7.13-7.07 (m, 1H), 6.95 (dd, J=0.9, 7.4 Hz, 1H), 6.91 (d, J=8.1 Hz, 1H), 6.74 (d, J=8.7 Hz, 1H), 3.97 (d, J=13.5 Hz, 2H), 3.64 (d, J=6.4 Hz, 2H), 2.91-2.77 (m, 2H), 2.01 (d, J=13.6 Hz, 2H), 1.84 (hept, J=6.7 Hz, 1H), 1.37-1.31 (m, 2H), 1.21 (s, 3H), 0.76 (dd, J=6.7, 11.8 Hz, 6H). $^{19}$F NMR (376 MHz, Chloroform-d) δ −58.88 (s, 1F).

Example 383

(R)-1-(6-(N-(6-(2-cyclobutylphenyl)-5-(trifluoromethyl)pyridin-2-yl)sulfamoyl)pyridin-2-yl)-3-methylpiperidine-3-carboxylic Acid LCMS conditions 7: 1.81 min, MS for $C_{28}H_{30}F_3N_4O_4S$ [M+H]$^+$ m/z=575.2, found m/z=575.2. $^1$H NMR (400 MHz, DMSO-d$_6$) δ 12.35 (s, 1H), 11.52 (s, 1H), 8.15 (d, J=8.9 Hz, 1H), 7.71-7.60 (m, 1H), 7.55 (s, 1H), 7.38 (m, 2H), 7.22 (t, J=7.4 Hz, 1H), 7.10 (m, 2H), 7.03 (t, J=7.2 Hz, 1H), 3.89 (m, 1H), 3.79-3.50 (m, 1H), 3.27-2.94 (m, 3H), 2.05-1.88 (m, 2H), 1.80 (d, J=9.1 Hz, 2H), 1.60 (d, J=7.8 Hz, 2H), 1.54-1.35 (m, 4H), 1.03 (d, J=8.2 Hz, 3H). $^{19}$F NMR (376 MHz, DMSO-d$_6$) δ −56.22. (d, J=12.0 Hz, 1F). Chiral purification conditions: isocratic 6 min run, SFC 80/20 CO$_2$/IPA eluent at 80 g/min flowrate, 35° C. column temperature, preparatory column DAICEL ChiralPak IC 21×250 mm. The (R) enantiomer has a retention time of 2.25 min.

Example 384

(R)-1-(6-(N-(6-(2-isopropylphenyl)-5-(trifluoromethyl)pyridin-2-yl)sulfamoyl)pyridin-2-yl)-3-methylpiperidine-3-carboxylic Acid LCMS conditions 7: 1.96 min, MS for $C_{27}H_{30}F_3N_4O_4S$ [M+H]$^+$ m/z=563.2, found m/z=563.2. Rotomers/atropisomers are present in the NMR spectra. $^1$H NMR (400 MHz, Chloroform-d) δ 10.22 (br. s, 1H), 8.09 (m, 1H), 7.80 (m, 1H), 7.48 (m, 1H), 7.44-7.30 (m, 2H), 7.18 m, 1H), 7.11-6.93 (m, 2H), 6.78 (m, 1H), 4.82 (m, 1H), 3.88 (m, 1H), 3.09-2.91 (m, 2H), 2.78 (m, 1H), 2.30 (m 1H), 2.02 (m, 1H), 1.83-1.67 (m, 1H), 1.47 (m, 1H), 1.43-1.32 (m, 2H), 1.17 (m, 3H), 1.14-1.03 (m, 5H), 0.69 (d, J=6.8 Hz, 1H). $^{19}$F NMR (376 MHz, Chloroform-d) δ −58.53 (s, 1F), −58.88 (s, 0.9F). Chiral purification conditions: isocratic 9 min run, HPLC 90/10 heptane/ethanol eluent at 1 mL/min flowrate, 20° C. column temperature, column 3 µm Whelk 0-1 4.6×50 mm. The (R) enantiomer has a retention time of 6.57 min.

Example 385

(S)-1-(6-(N-(6-(2-isopropylphenyl)-5-(trifluoromethyl)pyridin-2-yl)sulfamoyl)pyridin-2-yl)-3-methylpiperidine-3-carboxylic Acid LCMS conditions 7: 1.96 min, MS for $C_{27}H_{30}F_3N_4O_4S$ [M+H]$^+$ m/z=563.2, found m/z=563.2. Rotomers/atropisomers are present in the NMR spectra. $^1$H NMR (400 MHz, Chloroform-d) δ 10.22 (br. s, 1H), 8.09 (m, 1H), 7.80 (m, 1H), 7.48 (m, 1H), 7.44-7.30 (m, 2H), 7.18 m, 1H), 7.11-6.93 (m, 2H), 6.78 (m, 1H), 4.82 (m, 1H), 3.88 (m, 1H), 3.09-2.91 (m, 2H), 2.78 (m, 1H), 2.30 (m 1H), 2.02 (m, 1H), 1.83-1.67 (m, 1H), 1.47 (m, 1H), 1.43-1.32 (m, 2H), 1.17 (m, 3H), 1.14-1.03 (m, 5H), 0.69 (d, J=6.8 Hz, 1H). $^{19}$F NMR (376 MHz, Chloroform-d) δ −58.53 (s, 1F), −58.88 (s, 0.9F). Chiral purification conditions: isocratic 9 min run, HPLC 90/10 heptane/ethanol eluent at 1 mL/min flowrate, 20° C. column temperature, column 3 µm Whelk 0-1 4.6×50 mm. The (S) enantiomer has a retention time of 5.70 min.

Example 386

1-(6-(N-(6-(2-isobutoxyphenyl)-5-(trifluoromethyl)pyridin-2-yl)sulfamoyl)pyridin-2-yl)-3-methylpiperidine-3-carboxylic Acid LCMS conditions 7: 1.87 min, MS for $C_{28}H_{32}F_3N_4O_5S$ [M+H]$^+$ m/z=593.2, found m/z=593.1. Rotomers/atropisomers are present in the NMR spectra. $^1$H NMR (400 MHz, Chloroform-d) δ 8.04 (d, J=8.8 Hz, 1H), 7.80 (d, J=8.9 Hz, 1H), 7.48 (dd, J=7.2, 8.7 Hz, 1H), 7.38 (ddd, J=1.7, 7.4, 8.3 Hz, 1H), 7.09 (d, J=7.5 Hz, 1H), 7.06 (d, J=7.2 Hz, 1H), 7.00-6.92 (m, 1H), 6.89 (d, J=8.4 Hz, 1H), 6.77 (d, J=8.7 Hz, 1H), 4.93 (d, J=13.5 Hz, 1H), 3.89 (d, J=13.6 Hz, 1H), 3.63 (t, J=7.4 Hz, 2H), 3.09-2.96 (m, 1H), 2.76 (d, J=13.5 Hz, 1H), 2.13-2.03 (m, 1H), 1.86-1.72 (m, 1H), 1.56-1.48 (m, 1H), 1.37 (ddd, J=4.6, 12.4, 13.8 Hz, 2H), 1.19 (s, 3H), 0.69 (br. s, 6H). $^{19}$F NMR (376 MHz, Chloroform-d) δ −59.31 (br. s, 1F).

Example 387

1-(6-(N-(5-chloro-6-(2-ethylphenyl)pyridin-2-yl)sulfamoyl)pyridin-2-yl)-3-methylpiperidine-3-carboxylic Acid LCMS conditions 7: 1.609 min; MS for $C_{25}H_{28}ClN_4O_4S$ m/z [M+H]$^+$=515.20. $^1$H NMR (400 MHz, DMSO) δ 12.35 (s, 1H), 11.13 (s, 1H), 7.92 (d, J=8.8 Hz, 1H), 7.65 (dd, J=8.7, 7.3 Hz, 1H), 7.41 (d, J=8.8 Hz, 1H), 7.35 (td, J=7.5, 1.4 Hz, 1H), 7.31-7.27 (m, 1H), 7.24 (td, J=7.4, 1.4 Hz, 1H), 7.10-7.03 (m, 3H), 3.88 (d, J=13.1 Hz, 1H), 3.67 (d, J=10.3 Hz, 1H), 3.13 (d, J=13.1 Hz, 1H), 3.09-2.98 (m, 1H), 2.28-2.14 (m, 2H), 2.04-1.95 (m, 1H), 1.55-1.36 (m, 3H), 1.04 (s, 3H), 0.90-0.81 (m, 3H).

Example 388

1-(6-(N-(5-chloro-6-(2-isopropylphenyl)pyridin-2-yl)sulfamoyl)pyridin-2-yl)-3-methylpiperidine-3-carboxylic Acid LCMS conditions 7: 1.645 min; MS for $C_{26}H_{30}ClN_4O_4S$ m/z [M+H]$^+$=529.20. $^1$H NMR (400 MHz, DMSO) δ 12.35 (s, 1H), 11.13 (s, 1H), 7.92 (d, J=8.8 Hz, 1H), 7.65 (dd, J=8.7, 7.3 Hz, 1H), 7.45 (d, J=8.8 Hz, 1H), 7.41-7.37 (m, 2H), 7.26-7.19 (m, 1H), 7.08 (dd, J=8.0, 4.9 Hz, 2H), 7.00 (d, J=7.5 Hz, 1H), 3.88 (d, J=12.6 Hz, 1H), 3.74-3.59 (m, 1H), 3.19-2.96 (m, 2H), 2.05-1.94 (m, 1H), 1.56-1.36 (m, 3H), 1.32-1.20 (m, 1H), 1.04 (s, 6H), 0.95 (s, 3H).

Example 389

1-(6-(N-(5-chloro-6-(2-cyclobutylphenyl)pyridin-2-yl)sulfamoyl)pyridin-2-yl)-3-methylpiperidine-3-carboxylic Acid LCMS conditions 7: 1.674 min; MS for $C_{27}H_{30}ClN_4O_4S$ m/z [M+H]$^+$=541.20. $^1$H NMR (400 MHz, DMSO) δ 12.36 (s, 1H), 11.13 (s, 1H), 7.89 (d, J=8.8 Hz, 1H), 7.66 (dd, J=8.7, 7.3 Hz, 1H), 7.41-7.33 (m, 2H), 7.31 (d, J=7.6 Hz, 1H), 7.23 (td, J=7.4, 1.0 Hz, 1H), 7.09 (t, 2H), 7.04 (d, J=7.5 Hz, 1H), 3.96-3.54 (m, 2H), 3.29-2.97 (m, 4H), 2.06-1.94 (m, 1H), 1.93-1.36 (m, 8H), 1.05 (s, 3H).

Example 390

1-(6-(N-(6-(2-(tert-butyl)phenyl)-5-chloropyridin-2-yl)sulfamoyl)pyridin-2-yl)-3-methylpiperidine-3-carboxylic Acid LCMS conditions 7: 1.656 min; MS $C_{27}H_{32}ClN_4O_4S$ m/z [M+H]$^+$=543.20. $^1$H NMR (400 MHz, DMSO) δ 12.35 (s, 1H), 11.19-11.01 (m, 1H), 7.88 (d, J=8.8 Hz, 1H), 7.66-7.60 (m, 1H), 7.53 (d, J=8.0 Hz, 1H), 7.42 (dd, J=8.8, 3.9 Hz, 1H), 7.37-7.32 (m, 1H), 7.24-7.19 (m, 1H), 7.09-7.04 (m, 2H), 6.85 (ddd, J=7.6, 4.1, 1.4 Hz, 1H), 3.90 (dd, J=13.0, 6.8 Hz, 1H), 3.80-3.65 (m, 1H), 3.19-2.97 (m, 2H), 2.07-1.96 (m, 1H), 1.58-1.37 (m, 3H), 1.06 (d, J=2.0 Hz, 3H), 1.02 (d, J=1.7 Hz, 9H).

Example 391

(R)-1-(6-(N-(5-chloro-6-(2-cyclobutylphenyl)pyridin-2-yl)sulfamoyl)pyridin-2-yl)-3-methylpiperidine-3-carboxylic Acid LCMS conditions 7: 1.670 min; MS for $C_{27}H_{30}ClN_4O_4S$ [M+H]$^+$ m/z=541.06, found m/z=541.10. $^1$H NMR (400 MHz, DMSO-d$_6$) δ 12.36 (s, 1H), 11.13 (s, 1H), 7.89 (d, J=8.8 Hz, 1H), 7.67 (dd, J=8.7, 7.3 Hz, 1H), 7.41-7.33 (m, 2H), 7.31 (d, J=7.6 Hz, 1H), 7.26-7.21 (m, 1H), 7.09 (t, 2H), 7.04 (d, J=7.5 Hz, 1H), 3.97-3.55 (m, 2H), 3.28-2.96 (m, 3H), 2.06-1.93 (m, 1H), 1.93-1.36 (m, 9H), 1.05 (s, 3H).

Example 392

(R)-1-(6-(N-(5-chloro-6-(2-isopropylphenyl)pyridin-2-yl)sulfamoyl)pyridin-2-yl)-3-methylpiperidine-3-carboxylic Acid LCMS conditions 7: 1.638 min; MS for $C_{26}H_{30}ClN_4O_4S$ [M+H]$^+$ m/z=529.05, found m/z=529.15. $^1$H NMR (400 MHz, DMSO-d$_6$) δ 12.31 (s, 1H), 11.12 (s, 1H), 7.93 (d, J=8.8 Hz, 1H), 7.65 (dd, J=8.7, 7.3 Hz, 1H), 7.45 (d, J=8.7 Hz, 1H), 7.40-7.37 (m, 2H), 7.26-7.19 (m, 1H), 7.08 (dd, J=8.0, 5.1 Hz, 2H), 7.00 (d, J=7.5 Hz, 1H), 3.88 (d, J=12.7 Hz, 1H), 3.66 (s, 1H), 3.19-2.95 (m, 2H), 2.06-1.94 (m, 1H), 1.57-1.35 (m, 3H), 1.32-1.19 (m, 1H), 1.04 (s, 6H), 0.95 (s, 3H).

Example 393

(R)-1-(6-(N-(5-chloro-6-(2-ethylphenyl)pyridin-2-yl)sulfamoyl)pyridin-2-yl)-3-methylpiperidine-3-carboxylic Acid LCMS conditions 7: 1.609 min; MS for $C_{25}H_{28}ClN_4O_4S$ [M+H]$^+$ m/z=515.02, found m/z=515.20. $^1$H NMR (400 MHz, DMSO-d$_6$) δ 12.31 (s, 1H), 11.13 (s, 1H), 7.93 (d, 1H), 7.68-7.62 (m, 1H), 7.41 (d, 1H), 7.38-7.32 (m, 1H), 7.31-7.20 (m, 2H), 7.11-7.03 (m, 3H), 3.88 (d, J=13.1 Hz, 1H), 3.68 (d, J=11.5 Hz, 1H), 3.13 (d, J=13.1 Hz, 1H), 3.04 (s, 1H), 2.20 (s, 2H), 2.00 (q, J=6.4 Hz, 1H), 1.44 (dq, J=28.0, 9.3 Hz, 3H), 1.04 (s, 3H), 0.91-0.80 (m, 3H).

Example 394

(R)-1-(6-(N-(6-(2-ethylphenyl)-5-(trifluoromethyl)pyridin-2-yl)sulfamoyl)pyridin-2-yl)-3-methylpiperidine-3-carboxylic Acid LCMS conditions 7: 1.82 min, MS for $C_{26}H_{28}F_3N_4O_4S$ [M+H]$^+$ m/z=549.2, found m/z=549.1. Rotomers/atropisomers are present in the NMR spectra. $^1$H NMR (400 MHz, DMSO-d$_6$) δ 12.34 (s, 1H), 11.52 (s, 1H), 8.18 (d, J=8.9 Hz, 1H), 7.65 (ddd, J=1.9, 7.1, 9.0 Hz, 1H), 7.56 (s, 1H), 7.37 (td, J=1.4, 7.5 Hz, 1H), 7.28 (d, J=7.6 Hz, 1H), 7.22 (td, J=1.3, 7.4 Hz, 1H), 7.13-6.98 (m, 3H), 3.87 (t, J=12.7 Hz, 1H), 3.63 (m, 1H), 3.14 (m, 1H), 3.07-2.90 (m, 1H), 2.18 (m, 1H), 2.06 (m, 1H), 1.44-1.32 (m, 2H), 1.01 (m, 3H), 0.88 (m, 5H). $^{19}$F NMR (376 MHz, DMSO-d$_6$) δ −56.61 (s, 1F).

Example 395 rac-(1RS,3RS,4SR)-3-((6-(N-(6-(o-tolyl)-5-(trifluoromethyl)pyridin-2-yl)sulfamoyl)pyridin-2-yl)amino)-7-oxabicyclo[2.2.1]heptane-1-carboxylic Acid LCMS conditions 7: 1.64 min, MS for $C_{25}H_{24}F_3N_4O_5S$ [M+H]$^+$ m/z=549.1, found m/z=549.1. $^1$H NMR (400 MHz, Methanol-d$_4$) δ 8.07 (d, J=8.9 Hz, 1H), 7.57-7.42 (m, 2H), 7.32-7.28 (m, 1H), 7.25-7.13 (m, 3H), 7.06 (s, 1H), 6.68-6.59 (m, 1H), 4.24 (d, J=34.0 Hz, 1H), 3.98 (s, 1H), 2.25 (dd, J=12.9, 7.9 Hz, 1H), 1.97-1.85 (m, 3H), 1.85-1.67 (m, 3H), 1.61 (d, J=9.0 Hz, 2H).

Example 396

(R)-1-(6-(N-(6-(2-isobutoxyphenyl)-5-(trifluoromethyl)pyridin-2-yl)sulfamoyl)pyridin-2-yl)-3-methylpiperidine-3-carboxylic Acid LCMS conditions 7: 1.89 min, MS for $C_{28}H_{32}F_3N_4O_5S$ [M+H]$^+$ m/z=593.2, found m/z=593.1. Rotomers/atropisomers are present in the NMR spectra. $^1$H NMR (400 MHz, Chloroform-d) δ 10.44 (s, 1H), 8.03 (d, J=8.9 Hz, 1H), 7.81 (d, J=8.8 Hz, 1H), 7.48 (dd, J=7.2, 8.7 Hz, 1H), 7.42-7.33 (m, 1H), 7.09 (dd, J=4.3, 8.0 Hz, 2H), 6.96 (td, J=0.9, 7.5 Hz, 1H), 6.91-6.85 (m, 1H), 6.78 (d, J=8.7 Hz, 1H), 4.74 (d, J=13.4 Hz, 1H), 3.87 (d, J=13.5 Hz, 1H), 3.66-3.53 (m, 2H), 2.97 (t, J=12.6 Hz, 1H), 2.77 (d, J=13.5 Hz, 1H), 2.07 (q, J=3.6, 5.7 Hz, 1H), 1.80-1.62 (m, 2H), 1.51 (dq, J=3.6, 14.0 Hz, 1H), 1.40-1.31 (m, 2H), 1.17 (s, 3H), 0.80 (d, J=6.7 Hz, 1H), 0.70-0.53 (br. m, 6H). $^{19}$F NMR (376 MHz, Chloroform-d) δ −59.20 (s, 1F).

Example 397

1-(6-(N-(5-chloro-6-(2-isobutoxyphenyl)pyridin-2-yl)sulfamoyl)pyridin-2-yl)-4-methylpiperidine-4-carboxylic Acid LCMS conditions 7: 1.84 min, MS for $C_{27}H_{32}ClN_4O_5S$ [M+H]$^+$ m/z=559.2, found m/z=559.1. $^1$H NMR (400 MHz, Chloroform-d) δ 7.69 (d, J=8.9 Hz, 1H), 7.57 (dd, J=7.3, 8.7 Hz, 1H), 7.53 (d, J=8.9 Hz, 1H), 7.37 (td, J=1.7, 8.1 Hz, 1H), 7.29 (d, J=7.0 Hz, 1H), 7.13 (dd, J=1.7, 7.4 Hz, 1H), 6.94 (t, J=7.5 Hz, 2H), 6.73 (d, J=8.7 Hz, 1H), 3.97 (d, J=13.6 Hz, 2H), 3.67 (d, J=6.4 Hz, 2H), 2.88 (ddd, J=2.3, 11.4, 13.6 Hz, 2H), 2.03 (d, J=13.5 Hz, 2H), 1.90 (dh, J=6.7, 13.2 Hz, 1H), 1.39-1.28 (m, 3H), 1.20 (s, 3H), 0.81 (d, J=6.7 Hz, 6H).

Example 398

4-methyl-1-(6-(N-(6-(2-propylphenyl)-5-(trifluoromethyl)pyridin-2-yl)sulfamoyl)pyridin-2-yl)piperidine-4-carboxylic Acid LCMS conditions 7: 1.83 min, MS for $C_{27}H_{30}F_3N_4O_4S$ [M+H]$^+$ m/z=563.2, found m/z=563.1. Rotomers/atropisomers are present in the NMR spectra. $^1$H NMR (400 MHz, Chloroform-d) δ 10.34 (br. s, 1H), 7.90 (d, J=9.0 Hz, 1H), 7.60 (d, J=8.9 Hz, 1H), 7.51 (dd, J=7.3, 8.7 Hz, 1H), 7.28 (ddd, J=1.4, 6.2, 7.5 Hz, 1H), 7.22 (d, J=7.2 Hz, 1H), 7.12-7.06 (m, 2H), 6.98 (d, J=7.6 Hz, 1H), 6.67 (d, J=8.7 Hz, 1H), 6.62 (d, J=8.8 Hz, 1H), 3.99-3.62 (m, 2H), 2.89-2.69 (m, 2H), 2.31-2.03 (m, 2H), 2.01-1.81 (m, 3H), 1.35 (ddt, J=4.2, 7.4, 11.7 Hz, 2H), 1.28-1.22 (m, 2H), 0.85-0.74 (m, 2H), 0.66 (t, J=7.3 Hz, 3H). $^{19}$F NMR (376 MHz, Chloroform-d) δ −58.29 (br. s, 1F).

Example 399

1-(6-(N-(6-(2-chlorophenyl)-5-(trifluoromethyl)pyridin-2-yl)sulfamoyl)pyridin-2-yl)-3-methylpiperidine-3-carboxylic Acid LCMS conditions 7: 1.78 min, MS for $C_{24}H_{23}ClF_3N_4O_4S$ [M+H]$^+$ m/z=555.1, found m/z=555.1. Rotomers/atropisomers are present in the NMR spectra. $^1$H NMR (500 MHz, Chloroform-d) δ 10.42 (br. s, 1H), 8.10 (m, 1H), 7.90-7.82 (m, 1H), 7.55-7.36 (m, 3H), 7.35-7.30 (m, 1H), 7.23 (m, 1H), 7.01 (m, 1H), 6.80 (d, J=8.7 Hz, 1H), 4.89 (m, 1H), 3.93 (m, 1H), 3.14-2.97 (m, 1H), 2.85-2.72 (m, 1H), 2.07 (s, 1H), 2.02-1.88 (m, 1H), 1.82-1.68 (m, 1H), 1.48-1.32 (m, 2H), 1.19 (d, J=3.9 Hz, 3H). $^{19}$F NMR (471 MHz, Chloroform-d) δ −59.08 (s, 0.53F), −59.27 (s, 1F).

Example 400

1-(6-(N-(5-chloro-6-(2-isobutoxyphenyl)pyridin-2-yl)sulfamoyl)pyridin-2-yl)-3-methylpiperidine-3-carboxylic Acid LCMS conditions 7: 1.87 min, MS for $C_{27}H_{32}ClN_4O_5S$ [M+H]$^+$ m/z=559.2, found m/z=559.1. Rotomers/atropisomers are present in the NMR spectra. $^1$H NMR (500 MHz, Chloroform-d) δ 7.79 (d, J=8.7 Hz, 1H), 7.64 (d, J=8.7 Hz, 1H), 7.45 (dd, J=7.2, 8.7 Hz, 1H), 7.38 (ddd, J=1.8, 7.4, 8.3 Hz, 1H), 7.02 (d, J=6.9 Hz, 1H), 6.96 (t, J=7.5 Hz, 2H), 6.92 (d, J=8.2 Hz, 1H), 6.76 (d, J=8.7 Hz, 1H), 5.04 (d, J=13.5 Hz, 1H), 3.93 (d, J=12.3 Hz, 1H), 3.71-3.57 (m, 2H), 3.07 (td, J=2.8, 13.3 Hz, 1H), 2.75 (d, J=13.6 Hz, 1H), 2.05 (d, J=15.8 Hz, 1H), 1.95-1.76 (m, 2H), 1.50 (ddt, J=2.6, 4.7, 10.5 Hz, 1H), 1.39 (td, J=4.8, 13.2 Hz, 1H), 1.32 (d, J=6.3 Hz, 1H), 1.19 (s, 3H), 0.79 (dd, J=6.7, 10.8 Hz, 6H).

Example 401

3-methyl-1-(6-(N-(6-(2-propylphenyl)-5-(trifluoromethyl)pyridin-2-yl)sulfamoyl)pyridin-2-yl)piperidine-3-carboxylic Acid LCMS conditions 7: 1.87 min, MS for $C_{27}H_{30}F_3N_4O_4S$ [M+H]$^+$ m/z=563.2, found m/z=563.1. Rotomers/atropisomers are present in the NMR spectra. $^1$H NMR (500 MHz, Chloroform-d) δ 11.39-8.91 (br. s, 1H), 8.09 (m, 1H), 7.80 (t, J=8.8 Hz, 1H), 7.54-7.44 (m, 1H), 7.36 (t, J=7.5 Hz, 1H), 7.25-7.13 (m, 3H), 7.12-7.05 (m, 1H), 7.01 (t, J=6.7 Hz, 1H), 6.79 (dd, J=8.6, 4.8 Hz, 1H), 4.90-4.76 (m, 1H), 3.97-3.83 (m, 1H), 3.12-2.95 (m, 1H), 2.84-2.74 (m, 1H), 2.41-2.14 (m, 1H), 2.07-1.98 (m, 1H), 1.95 (t, J=7.9 Hz, 1H), 1.77 (m, 2H), 1.47 (dt, J=14.8, 6.6 Hz, 3H), 1.20-1.13 (m, 3H), 0.74 (m, 3H). $^{19}$F NMR (471 MHz, Chloroform-d) δ −58.56 (s, 1F), −58.50 (s, 1.13F).

Example 402

1-(6-(N-(6-(2-cyclopropylphenyl)-5-(trifluoromethyl)pyridin-2-yl)sulfamoyl)pyridin-2-yl)-3-methylpiperidine-3-carboxylic Acid LCMS conditions 7: 1.84 min, MS for $C_{27}H_{28}F_3N_4O_4S$ [M+H]$^+$ m/z=561.2, found m/z=561.1. Rotomers/atropisomers are present in the NMR spectra. $^1$H NMR (500 MHz, Chloroform-d) δ 10.17 (s, 1H), 8.09 (m, 1H), 7.80 (d, J=8.6 Hz, 1H), 7.54-7.39 (m, 1H), 7.37-7.31 (m, 1H), 7.18 (m, 1H), 7.13-7.02 (m, 2H), 6.97 (t, J=7.9 Hz, 2H), 6.79 (dd, J=8.7, 3.2 Hz, 1H), 4.78 (m, 1H), 3.90 (m, 1H), 3.11-2.94 (m, 1H), 2.79 (d, J=13.5 Hz, 1H), 2.00 (d, J=14.7 Hz, 1H), 1.89-1.65 (m, 1H), 1.56-1.46 (m, 1H), 1.42-1.35 (m, 1H), 1.17 (d, J=2.2 Hz, 3H), 1.03 (m, 1H), 0.81-0.56 (m, 2H), 0.49-0.31 (m, 2H). $^{19}$F NMR (471 MHz, Chloroform-d) δ −58.41 (s, 1F), −58.70 (s, 1.24F).

Example 403 rac-(1RS,3RS,4SR)-3-((6-(N-(6-(2-isopropylphenyl)-5-(trifluoromethyl)pyridin-2-yl)sulfamoyl)pyridin-2-yl)amino)-7-oxabicyclo[2.2.1]heptane-1-carboxylic Acid LCMS conditions 7: 1.67 min, MS for $C_{27}H_{28}F_3N_4O_5S$ [M+H]$^+$ m/z=577.2, found m/z=577.1. $^1$H NMR (400 MHz, DMSO-d$_6$) δ 11.42 (s, 1H), 8.23 (dd, J=9.0, 1.2 Hz, 1H), 7.62-7.47 (m, 2H), 7.42-7.30 (m, 3H), 7.23-7.10 (m, 1H), 7.07-6.90 (m, 2H), 6.71-6.68 (m, 1H), 4.13-4.00 (m, 1H), 3.73-3.62 (m, 1H), 2.39-2.23 (m, 1H), 2.08-2.02 (m, 1H), 1.71-1.41 (m, 4H), 1.30-1.22 (m, 1H), 1.03-0.99 (m, 3H), 0.93-0.84 (m, 3H).

Example 404 rac-(1SR,5RS,6RS,7SR)-5-propyl-2-(6-(N-(6-(o-tolyl)-5-(trifluoromethyl)pyridin-2-yl)sulfamoyl)pyridin-2-yl)-2-azabicyclo[4.2.0]octane-7-carboxylic Acid LCMS conditions 7: 1.85 min, MS for $C_{29}H_{32}F_3N_4O_4S$ [M+H]$^+$ m/z=589.2, found m/z=589.1. $^1$H NMR (400 MHz, DMSO-d$_6$) δ 12.30 (s, 1H), 11.53 (s, 1H), 8.21 (d, J=8.9 Hz, 1H), 7.69 (dd, J=8.7, 7.3 Hz, 1H), 7.58 (d, J=8.8 Hz, 1H), 7.33-7.29 (m, 1H), 7.26-7.17 (m, 2H), 7.14 (d, J=7.3 Hz, 1H), 7.05 (d, J=7.6 Hz, 1H), 6.78 (d, J=8.7 Hz, 1H), 4.53-4.35 (m, 1H), 3.62-3.58 (m, 1H), 2.84 (d, J=13.7 Hz, 1H), 2.71-2.59 (m, 1H), 2.39-2.33 (m, 2H), 2.14-2.01 (m, 1H), 1.78-1.73 (m, 3H), 1.59 (s, 1H), 1.44-1.26 (m, 3H), 1.24-1.13 (m, 2H), 1.05-1.01 (m, 1H), 0.88-0.80 (m, 3H).

Example 405

(R)-1-(6-(N-(6-(2-cyclopropylphenyl)pyridin-2-yl) sulfamoyl)pyridin-2-yl)-3-methylpiperidine-3-carboxylic Acid conditions 7: 1.491 min; MS for $C_{26}H_{29}N_4O_4S$ [M+H]$^+$ m/z=493.59, found m/z=493.20. $^1$H NMR (400 MHz, DMSO-d$_6$) δ 12.44 (s, 1H), 11.05 (s, 1H), 7.79-7.73 (m, 1H), 7.69-7.63 (m, 1H), 7.37-7.25 (m, 2H), 7.19 (t, J=6.9 Hz, 1H), 7.16-7.07 (m, 3H), 7.05 (d, J=8.7 Hz, 1H), 6.98 (d, J=7.7 Hz, 1H), 3.85 (d, J=13.1 Hz, 1H), 3.74-3.63 (m, 1H), 3.17 (d, J=13.1 Hz, 1H), 3.13-3.02 (m, 1H), 2.02-1.89 (m, 3H), 1.55-1.34 (m, 2H), 1.01 (s, 3H), 0.74-0.66 (m, 2H), 0.58-0.50 (m, 2H).

Example 406

(R)-1-(6-(N-(6-(2-cyclopropylphenyl)-5-methylpyridin-2-yl)sulfamoyl)pyridin-2-yl)-3-methylpiperidine-3-carboxylic Acid LCMS conditions 7: 1.514 min; MS for $C_{27}H_{31}N_4O_4S$ [M+H]$^+$ m/z=507.62, found m/z=507.20. $^1$H NMR (400 MHz, DMSO-d$_6$) δ 7.68-7.60 (m, 2H), 7.52-7.38 (m, 1H), 7.30 (t, J=7.3 Hz, 1H), 7.19 (t, J=7.0 Hz, 1H), 7.07 (d, J=7.2 Hz, 1H), 7.06-6.97 (m, 2H), 6.92 (d, J=7.7 Hz, 1H), 3.85 (d, J=13.1 Hz, 1H), 3.72-3.63 (m, 1H), 3.15 (d, J=13.1 Hz, 1H), 3.07 (d, J=6.1 Hz, 1H), 1.99 (d, J=4.6 Hz, 1H), 1.95 (s, 3H), 1.44 (dd, J=31.5, 11.8 Hz, 4H), 1.02 (s, 3H), 0.73-0.43 (m, 4H).

Example 407

(R)-1-(6-(N-(5-cyclopropyl-6-(2-cyclopropylphenyl) pyridin-2-yl)sulfamoyl)pyridin-2-yl)-3-methylpiperidine-3-carboxylic Acid LCMS conditions 7: 1.576 min; MS for $C_{29}H_{33}N_4O_4S$ [M+H]$^+$ m/z=533.65, found m/z=533.20. $^1$H NMR (400 MHz, DMSO-d$_6$) δ 7.64 (dd, J=8.7, 7.3 Hz, 1H), 7.52-7.34 (m, 1H), 7.33-7.24 (m, 2H), 7.19 (t, J=7.4 Hz, 1H), 7.12-6.98 (m, 3H), 6.92 (d, J=7.9 Hz, 1H), 3.86 (d, J=12.9 Hz, 1H), 3.70-3.59 (m, 1H), 3.13 (d, J=12.9 Hz, 1H), 3.08-2.96 (m, 1H), 2.03-1.92 (m, 1H), 1.53-1.33 (m, 5H), 1.02 (s, 3H), 0.81-0.44 (m, 8H).

Example 408

(R)-1-(6-(N-(6-(2-cyclopropylphenyl)-5-methoxypyridin-2-yl)sulfamoyl)pyridin-2-yl)-3-methylpiperidine-3-carboxylic Acid LCMS conditions 7: 1.516 min; MS for $C_{27}H_{31}N_4O_5S$ [M+H]$^+$ m/z=523.62, found m/z=523.20. $^1$H NMR (400 MHz, DMSO-d$_6$) δ 12.35 (s, 1H), 10.57 (s, 1H), 7.64 (dd, J=8.7, 7.3 Hz, 1H), 7.52 (d, J=9.0 Hz, 1H), 7.37 (d, J=8.9 Hz, 1H), 7.24 (td, J=7.6, 1.4 Hz, 1H), 7.13 (td, J=7.4, 1.2 Hz, 1H), 7.08-7.02 (m, 2H), 6.98 (dd, J=7.6, 1.3 Hz, 1H), 6.88 (d, J=7.7 Hz, 1H), 3.89-3.81 (m, 1H), 3.71-3.63 (m, 4H), 3.14 (d, J=13.1 Hz, 1H), 3.08-3.00 (m, 1H), 2.02-1.92 (m, 1H), 1.54-1.34 (m, 4H), 1.03 (s, 3H), 0.63-0.54 (m, 2H), 0.50-0.41 (m, 2H).

Example 409

(R)-3-methyl-1-(6-(N-(5-methyl-6-(o-tolyl)pyridin-2-yl)sulfamoyl)pyridin-2-yl)piperidine-3-carboxylic Acid LCMS conditions 7: 1.456 min; MS for $C_{25}H_{29}N_4O_4S$ [M+H]$^+$ m/z=481.58, found m/z=481.20. $^1$H NMR (400 MHz, DMSO-d$_6$) δ 7.67-7.59 (m, 2H), 7.40 (s, 1H), 7.33-7.19 (m, 3H), 7.09-6.98 (m, 3H), 3.85 (d, J=13.1 Hz, 1H), 3.72-3.62 (m, 1H), 3.15 (d, J=13.1 Hz, 1H), 3.11-3.01 (m, 1H), 2.02-1.95 (m, 1H), 1.90 (s, 6H), 1.55-1.34 (m, 3H), 1.02 (s, 3H).

Example 410

(R)-1-(6-(N-(5-methoxy-6-(o-tolyl)pyridin-2-yl)sulfamoyl)pyridin-2-yl)-3-methylpiperidine-3-carboxylic Acid LCMS conditions 7: 1.471 min; MS for $C_{25}H_{29}N_4O_5S$ [M+H]$^+$ m/z=497.58, found m/z=497.20. $^1$H NMR (400 MHz, DMSO-d$_6$) δ 12.35 (s, 1H), 10.56 (s, 1H), 7.68-7.62 (m, 1H), 7.53 (d, J=9.0 Hz, 1H), 7.36 (d, J=8.9 Hz, 1H), 7.28-7.15 (m, 3H), 7.08-7.01 (m, 3H), 3.87 (d, J=13.2 Hz, 1H), 3.73-3.65 (m, 4H), 3.14 (d, J=13.1 Hz, 1H), 3.08-3.00 (m, 1H), 2.04-1.90 (m, 4H), 1.55-1.35 (m, 3H), 1.04 (s, 3H).

Example 411

(R)-1-(6-(N-(5-cyclopropyl-6-(o-tolyl)pyridin-2-yl)sulfamoyl)pyridin-2-yl)-3-methylpiperidine-3-carboxylic Acid LCMS conditions 7: 1.526 min; MS for $C_{27}H_{31}N_4O_4S$ [M+H]$^+$ m/z=507.62, found m/z=507.20. $^1$H NMR (400 MHz, DMSO-d$_6$) δ 12.41 (s, 1H), 10.91 (s, 1H), 7.66-7.60 (m, 1H), 7.44-7.33 (m, 1H), 7.33-7.19 (m, 4H), 7.15-7.08 (m, 1H), 7.08-6.99 (m, 2H), 3.86 (d, J=13.1 Hz, 1H), 3.71-3.60 (m, 1H), 3.14 (d, J=13.1 Hz, 1H), 3.08-2.98 (m, 1H), 2.05-1.89 (m, 4H), 1.54-1.32 (m, 4H), 1.02 (s, 3H), 0.78-0.69 (m, 2H), 0.61-0.53 (m, 2H).

Example 412

(R)-3-methyl-1-(6-(N-(6-(o-tolyl)pyridin-2-yl)sulfamoyl)pyridin-2-yl)piperidine-3-carboxylic Acid LCMS conditions 7: 1.447 min; MS for $C_{24}H_{27}N_4O_4S$ [M+H]$^+$ m/z=466.55, found m/z=467.20. $^1$H NMR (400 MHz, DMSO-d$_6$) δ 12.41 (s, 1H), 11.10 (s, 1H), 7.78-7.72 (m, 1H), 7.66 (dd, J=8.7, 7.3 Hz, 1H), 7.35-7.15 (m, 5H), 7.11 (dd, J=7.2, 3.2 Hz, 1H), 7.08-6.99 (m, 2H), 3.85 (d, J=13.1 Hz, 1H), 3.72-3.63 (m, 1H), 3.16 (d, J=13.1 Hz, 1H), 3.11-3.01 (m, 1H), 2.18-2.10 (m, 3H), 2.02-1.91 (m, 1H), 1.53-1.33 (m, 3H), 1.00 (s, 3H).

Example 413

(R)-1-(6-(N-(6-(2-cyclopropylphenyl)-5-(trifluoromethyl)pyridin-2-yl)sulfamoyl)pyridin-2-yl)-3-methylpiperidine-3-carboxylic Acid LCMS conditions 7: 1.77 min; MS for $C_{27}H_{28}F_3N_4O_4S$ [M+H]$^+$ m/z=561.2, found m/z=561.1. $^1$H NMR (400 MHz, DMSO-d$_6$) δ 12.33 (s, 1H), 11.53 (s, 1H), 8.18 (d, J=8.9 Hz, 1H), 7.66 (t, J=8.1 Hz, 1H), 7.62 (d, J=6.3 Hz, 1H), 7.32 (t, J=7.7 Hz, 1H), 7.18 (t, J=7.5 Hz, 1H), 7.12-7.07 (m, 2H), 7.03 (s, 1H), 6.93 (d, J=7.9 Hz, 1H), 3.88 (d, J=13.3 Hz, 1H), 3.75-3.56 (m, 1H), 3.17-3.06 (m, 1H), 3.06-2.91 (m, 1H), 1.99 (d, J=6.7 Hz, 1H), 1.55-1.33 (m, 3H), 1.29 (d, J=7.2 Hz, 1H), 1.01 (d, J=5.7 Hz, 3H), 0.75-0.50 (m, 3H), 0.38 (d, J=17.7 Hz, 1H). $^{19}$F NMR (376 MHz, DMSO-d$_6$) δ −56.78 (s, 1F).

Example 414

1-(6-(N-(6-(2-chloro-5-methoxyphenyl)-5-(trifluoromethyl)pyridin-2-yl)sulfamoyl)pyridin-2-yl)-3-methylpiperidine-3-carboxylic Acid LCMS conditions 7: 1.73 min, MS for $C_{25}H_{25}ClF_3N_4O_5S$ [M+H]$^+$ m/z=585.1, found m/z=585.1. $^1$H NMR (400 MHz, DMSO-d$_6$) δ 12.33 (s, 1H), 11.62 (s, 1H), 8.20 (dd, J=1.7, 8.9 Hz, 1H), 7.73-7.62 (m, 2H), 7.42 (dd, J=1.8, 8.9 Hz, 1H), 7.11 (dd, J=2.0, 7.3 Hz, 2H), 7.05 (dd, J=3.0, 8.9 Hz, 2H), 6.85 (dd, J=2.6, 6.4 Hz, 1H), 3.88 (d, J=13.0 Hz, 1H), 3.64 (d, J=12.9 Hz, 1H), 3.11 (dd, J=9.1, 13.1 Hz, 1H), 3.07-2.94 (m, 1H), 1.99 (s, 2H), 1.56-1.33 (m, 3H), 1.27 (d, J=8.5 Hz, 1H), 1.01 (d, J=5.1 Hz, 3H). $^{19}$F NMR (376 MHz, DMSO-d$_6$) δ −57.48 (s, 1F).

Example 415

(3R)-3-methyl-1-(6-{[6-(2-methylphenyl)-5-(trifluoromethyl)pyridin-2-yl]sulfamoyl}pyridin-2-yl)piperidine-3-carboxylic Acid LCMS conditions 7: 1.759 min; MS for $C_{25}H_{26}F_3N_4O_4S$ [M+H]$^+$ m/z=535.16, found m/z=535.20. $^1$H NMR (400 MHz, DMSO-d$_6$) δ 12.33 (s, 1H), 11.53 (s, 1H), 8.17 (d, J=8.9 Hz, 1H), 7.64 (dd, J=8.7, 7.2 Hz, 1H), 7.60-7.44 (m, 1H), 7.35-7.27 (m, 1H), 7.27-7.16 (m, 2H), 7.11-6.99 (m, 3H), 3.87 (d, J=13.2 Hz, 1H), 3.71-3.59 (m, 1H), 3.18-3.08 (m, 1H), 3.08-2.90 (m, 1H), 1.99 (d, J=11.0 Hz, 1H), 1.80 (d, J=10.1 Hz, 3H), 1.52-1.32 (m, 3H), 1.04-0.97 (m, 3H).

Example 416

(3R)-1-(6-{[6-(5-fluoro-2-methylphenyl)-5-(trifluoromethyl)pyridin-2-yl]sulfamoyl}pyridin-2-yl)-3-methylpiperidine-3-carboxylic Acid LCMS conditions 7: 1.769 min; MS for $C_{25}H_{25}F_4N_4O_4S$ [M+H]$^+$ m/z=553.15, found m/z=553.20. $^1$H NMR (400 MHz, DMSO-d$_6$) δ 12.32 (s, 1H), 11.59 (s, 1H), 8.19 (d, J=8.9 Hz, 1H), 7.64 (dd, J=8.8, 7.2 Hz, 1H), 7.59-7.49 (m, 1H), 7.31-7.22 (m, 1H), 7.20-7.13 (m, 1H), 7.11-7.02 (m, 2H), 7.00-6.89 (m, 1H), 3.87 (d, J=13.1 Hz, 1H), 3.73-3.58 (m, 1H), 3.18-3.09 (m, 1H), 3.09-2.96 (m, 1H), 2.05-1.92 (m, 1H), 1.75 (d, J=9.7 Hz, 3H), 1.51-1.31 (m, 3H), 1.00 (d, J=5.1 Hz, 3H).

Example 417

(3R)-1-(6-{[6-(3-fluoro-2-methylphenyl)-5-(trifluoromethyl)pyridin-2-yl]sulfamoyl}pyridin-2-yl)-3-methylpiperidine-3-carboxylic Acid LCMS conditions 7: 1.770 min; MS for $C_{25}H_{25}F_4N_4O_4S$ [M+H]$^+$ m/z=553.15, found m/z=553.20. $^1$H NMR (400 MHz, DMSO-d$_6$) δ 12.29 (s, 1H), 11.59 (s, 1H), 8.19 (d, J=8.9 Hz, 1H), 7.65 (dd, J=8.7, 7.2 Hz, 1H), 7.60-7.46 (m, 1H), 7.32-7.17 (m, 2H), 7.13-7.01 (m, 2H), 6.99-6.83 (m, 1H), 3.86 (d, J=13.1 Hz, 1H), 3.72-3.57 (m, 1H), 3.19-3.08 (m, 1H), 3.08-2.94 (m, 1H), 2.05-1.90 (m, 1H), 1.74-1.61 (m, 3H), 1.52-1.32 (m, 3H), 1.00 (d, J=8.0 Hz, 3H).

Example 418

(1S,3S)-3-((6-(N-(6-(2-isopropylphenyl)-5-(trifluoromethyl)pyridin-2-yl)sulfamoyl)pyridin-2-yl)amino)cyclohexanecarboxylic Acid LCMS conditions 7: 1.76 min, MS for $C_{27}H_{30}F_3N_4O_4S$ [M+H]$^+$ m/z=563.2, found m/z=563.1. $^1$H NMR (400 MHz, Chloroform-d) δ 7.98 (d, J=9.0 Hz, 1H), 7.63 (s, 1H), 7.58-7.48 (m, 1H), 7.43 (dt, J=7.2, 12.2 Hz, 2H), 7.33-7.29 (m, 1H), 7.25-7.17 (m, 1H), 7.08 (dd, J=7.8, 11.5 Hz, 1H), 6.61-6.48 (m, 1H), 4.56 (s, 1H), 3.85-3.67 (m, 1H), 2.77-2.17 (m, 3H), 1.89 (s, 2H), 1.78 (s, 3H), 1.41 (s, 3H), 1.17-1.06 (m, 6H). $^{19}$F NMR (376 MHz, Chloroform-d) δ −58.34 (s, 1F).

Example 419

5-(6-(N-(6-(o-tolyl)-5-(trifluoromethyl)pyridin-2-yl)sulfamoyl)pyridin-2-yl)-5-azaspiro[2.4]heptane-1-carboxylic Acid LCMS conditions 7: 1.531 min; MS for $C_{25}H_{24}F_3N_4O_4S$ [M+H]$^+$ m/z=533.54, found m/z=533.10. $^1$H NMR (400 MHz, DMSO-d$_6$) δ 12.27 (s, 1H), 11.54 (s, 1H), 8.23-8.14 (m, 1H), 7.70-7.53 (m, 2H), 7.32 (t, J=7.5 Hz, 1H), 7.27-7.17 (m, 2H), 7.12-7.03 (m, 2H), 6.69-6.62 (m, 1H), 3.42-3.34 (m, 2H), 2.06-1.97 (m, 1H), 1.90-1.70 (m, 5H), 1.30-1.04 (m, 4H).

Example 420

5-(6-(N-(6-(2-cyclopropylphenyl)-5-(trifluoromethyl)pyridin-2-yl)sulfamoyl)pyridin-2-yl)-5-azaspiro[2.4]heptane-1-carboxylic Acid LCMS conditions 7: 1.571 min; MS for $C_{27}H_{26}F_3N_4O_4S$ [M+H]$^+$ m/z=559.57, found m/z=559.20. $^1$H NMR (400 MHz, Chloroform-d) δ 10.81 (s, 1H), 8.06-7.91 (m, 1H), 7.85-7.29 (m, 3H), 7.26-6.91 (m, 4H), 6.51-6.11 (m, 1H), 3.76-3.56 (m, 1H), 3.54-3.09 (m, 3H), 2.23-1.53 (m, 3H), 1.53-1.14 (m, 3H), 0.94-0.50 (m, 4H).

Example 421

(R)-1-(6-(N-(6-(2-chlorophenyl)-5-(trifluoromethyl)pyridin-2-yl)sulfamoyl)pyridin-2-yl)-3-methylpiperidine-3-carboxylic Acid LCMS conditions 7: 1.70 min, MS for $C_{24}H_{23}ClF_3N_4O_4S$ [M+H]$^+$ m/z=555.1, found m/z=555.0. Rotomers/atropisomers are present in the NMR spectra. $^1$H NMR (400 MHz, Chloroform-d) δ 9.80 (br. s, 1H), 8.10 (m, 1H), 7.87 (dd, J=3.9, 8.7 Hz, 1H), 7.58-7.30 (m, 4H), 7.26-7.04 (m, 1H), 6.86 (dd, J=7.9, 46.2 Hz, 2H), 4.89 (m, 1H), 3.93 (m, 1H), 3.03 (m, 1H), 2.77 (t, J=12.8 Hz, 1H), 2.06 (d, J=4.0 Hz, 1H), 2.02-1.88 (m, 1H), 1.44-1.34 (m, 2H), 1.18 (d, J=3.4 Hz, 4H). $^{19}$F NMR (376 MHz, Chloroform-d) δ −59.26 (s, 1F), −59.07 (s, 1.9F).

Example 422

(R)-1-(6-(N-(5-chloro-6-(2-isobutoxyphenyl)pyridin-2-yl)sulfamoyl)pyridin-2-yl)-3-methylpiperidine-3-carboxylic Acid LCMS conditions 7: 1.80 min, MS for $C_{27}H_{32}ClN_4O_5S$ [M+H]$^+$ m/z=559.2, found m/z=559.1. Rotomers/atropisomers are present in the NMR spectrum. $^1$H NMR (400 MHz, Chloroform-d) δ 7.80 (d, J=8.7 Hz, 1H), 7.64 (d, J=8.7 Hz, 1H), 7.45 (dd, J=7.2, 8.7 Hz, 1H), 7.38 (ddd, J=1.9, 7.4, 8.4 Hz, 1H), 6.96 (m, 4H), 6.76 (d, J=8.7 Hz, 1H), 5.05 (m, 1H), 3.93 (m, 1H), 3.71-3.59 (m, 2H), 3.07 (m, 1H), 2.74 (m, 1H), 2.05 (m, 1H), 1.83 (m, 2H), 1.54-1.44 (m, 2H), 1.43-1.32 (m, 2H), 1.21 (m, 1H), 0.83-0.68 (m, 6H).

Example 423

(R)-3-methyl-1-(6-(N-(6-(2-propylphenyl)-5-(trifluoromethyl)pyridin-2-yl)sulfamoyl)pyridin-2-yl)piperidine-3-carboxylic Acid LCMS conditions 7: 1.80 min, MS for $C_{27}H_{30}F_3N_4O_4S$ [M+H]$^+$ m/z=563.2, found m/z=563.1. Rotomers/atropisomers are present in the NMR spectra. $^1$H NMR (400 MHz, Chloroform-d) δ 10.2 (br. s, 1H), 8.10 (m, 1H), 7.99-7.76 (m, 1H), 7.59-7.42 (m, 1H), 7.36 (t, J=7.6 Hz, 1H), 7.24-7.12 (m, 2H), 7.08 (m, 1H), 7.03-6.92 (m, 1H), 6.83-6.69 (m, 1H), 4.97-4.84 (m, 1H), 4.00-3.80 (m, 1H), 3.04 (m, 1H), 2.86-2.71 (m, 1H), 2.27 (m, 1H), 2.09-1.86 (m, 3H), 1.80 (m, 2H), 1.46-1.31 (m, 3H), 1.18 (d, J=5.8 Hz, 3H), 0.74 (m, 3H). $^{19}$F NMR (376 MHz, Chloroform-d) δ −58.55 (s, 1F), −58.60 (s, 1F).

Example 424

(R)-1-(6-(N-(6-(2-chloro-5-methoxyphenyl)-5-(trifluoromethyl)pyridin-2-yl)sulfamoyl)pyridin-2-yl)-3-methylpiperidine-3-carboxylic Acid LCMS conditions 7: 1.70 min, MS for $C_{25}H_{25}ClF_3N_4O_5S$ [M+H]$^+$ m/z=585.1, found m/z=585.0. Rotomers/atropisomers are present in the NMR spectra. $^1$H NMR (400 MHz, Chloroform-d) δ 9.8 (br. s, 1H), 8.09 (m, 1H), 7.87 (dd, J=5.0, 8.7 Hz, 1H), 7.58-7.37 (m, 1H), 7.33 (d, J=8.9 Hz, 1H), 7.24 (d, J=8.9 Hz, 1H), 7.14-6.86 (m, 2H), 6.81 (dd, J=4.6, 8.7 Hz, 1H), 6.76 (d, J=2.7 Hz, 1H), 4.89 (m, 1H), 3.94 (m, 1H), 3.79 (d, J=10.2 Hz, 3H), 3.15-2.92 (m, 1H), 2.78 (t, J=12.7 Hz, 1H), 2.13-1.89 (m, 2H), 1.48-1.33 (m, 2H), 1.20 (d, J=2.8 Hz, 3H). $^{19}$F NMR (376 MHz, Chloroform-d) δ −59.07 (s, 1F), −59.20 (s, 2F).

Example 425

(S)-3-methyl-1-(6-(N-(6-(2-propylphenyl)-5-(trifluoromethyl)pyridin-2-yl)sulfamoyl)pyridin-2-yl)piperidine-3-carboxylic Acid LCMS conditions 7: 1.80 min, MS for $C_{27}H_{30}F_3N_4O_4S$ [M+H]$^+$ m/z=563.2, found m/z=563.1. Rotomers/atropisomers are present in the NMR spectra. $^1$H NMR (400 MHz, Chloroform-d) δ 8.08 (m, 1H), 7.88-7.76 (m, 1H), 7.55-7.38 (m, 1H), 7.39-7.31 (m, 1H), 7.17 (m, 2H), 7.11-6.92 (m, 2H), 6.75 (m, 1H), 4.82 (m, 1H), 3.97-3.78 (m, 1H), 3.13-2.89 (m, 1H), 2.82-2.63 (m, 1H), 2.42-2.10 (m, 1H), 2.01-1.86 (m, 2H), 1.81-1.61 (m, 1H), 1.54-1.41 (m, 2H), 1.38-1.29 (m, 2H), 1.15 (d, J=5.2 Hz, 3H), 0.72 (m, 3H). ¹⁹F NMR (376 MHz, Chloroform-d) δ −58.52 (s, 1F), −58.58 (s, 1.1F).

Example 426

1-(6-(N-(6-(5-chloro-2-methoxyphenyl)-5-(trifluoromethyl)pyridin-2-yl)sulfamoyl)pyridin-2-yl)-4-methylpiperidine-4-carboxylic Acid LCMS conditions 7: 1.69 min, MS for $C_{25}H_{25}ClF_3N_4O_5S$ [M+H]⁺ m/z=585.1, found m/z=585.0. ¹H NMR (400 MHz, Chloroform-d) δ 7.96 (d, J=9.0 Hz, 1H), 7.67 (d, J=8.9 Hz, 1H), 7.61 (dd, J=7.3, 8.7 Hz, 1H), 7.37 (dd, J=2.6, 8.8 Hz, 1H), 7.32 (d, J=7.2 Hz, 1H), 7.09 (d, J=2.6 Hz, 1H), 6.89 (d, J=8.9 Hz, 1H), 6.79 (d, J=8.7 Hz, 1H), 4.13-3.79 (m, 2H), 3.72 (s, 3H), 2.89 (q, J=11.1, 11.5 Hz, 2H), 2.03 (s, 2H), 1.41-1.31 (m, 3H), 1.23 (s, 3H). ¹⁹F NMR (376 MHz, Chloroform-d) δ −59.32 (s, 1F).

Example 427

1-(6-(N-(6-(5-chloro-2-isopropoxyphenyl)-5-(trifluoromethyl)pyridin-2-yl)sulfamoyl)pyridin-2-yl)-4-methylpiperidine-4-carboxylic Acid LCMS conditions 7: 1.80 min, MS for $C_{27}H_{29}ClF_3N_4O_5S$ [M+H]⁺ m/z=613.1, found m/z=613.1. Rotomers/atropisomers are present in the NMR spectra. ¹H NMR (400 MHz, Chloroform-d) δ 7.97 (d, J=9.0 Hz, 1H), 7.71 (d, J=8.9 Hz, 1H), 7.61 (dd, J=7.3, 8.7 Hz, 1H), 7.35 (dd, J=2.6, 8.9 Hz, 1H), 7.32 (d, J=7.2 Hz, 1H), 7.08 (d, J=2.6 Hz, 1H), 6.84 (dd, J=8.8, 28.0 Hz, 2H), 4.47 (dp, J=6.0, 12.1 Hz, 1H), 4.09-3.85 (m, 1H), 3.81-3.55 (m, 1H), 3.03-2.79 (m, 2H), 2.06 (d, J=11.2 Hz, 2H), 1.41-1.33 (m, 3H), 1.24 (s, 3H), 1.20 (br. s, 6H). ¹⁹F NMR (376 MHz, Chloroform-d) δ −58.96 (s, 1F).

Example 428

(3S)-3-methyl-1-(6-{[6-(2-methylphenyl)-5-(trifluoromethyl)pyridin-2-yl]sulfamoyl}pyridin-2-yl)piperidine-3-carboxylic Acid LCMS conditions 7: 1.868 min; MS for $C_{25}H_{26}F_3N_4O_4S$ [M+H]⁺ m/z=535.16, found m/z=535.20. ¹H NMR of S-isomer: ¹H NMR (400 MHz, DMSO-d₆) δ 12.31 (s, 1H), 11.53 (s, 1H), 8.17 (d, J=8.9 Hz, 1H), 7.65 (dd, J=8.8, 7.3 Hz, 1H), 7.59-7.46 (m, 1H), 7.36-7.27 (m, 1H), 7.27-7.15 (m, 2H), 7.12-7.00 (m, 3H), 3.87 (d, J=13.1 Hz, 1H), 3.72-3.54 (m, 1H), 3.19-3.07 (m, 1H), 3.07-2.91 (m, 1H), 2.07-1.91 (m, 1H), 1.80 (d, J=10.1 Hz, 3H), 1.54-1.32 (m, 3H), 1.06-0.93 (m, 3H).

Example 429

(S)-1-(6-(N-(6-(2-cyclopropylphenyl)-5-(trifluoromethyl)pyridin-2-yl)sulfamoyl)pyridin-2-yl)-3-methylpiperidine-3-carboxylic Acid LCMS conditions 7: 1.74 min, MS for $C_{27}H_{28}F_3N_4O_4S$ [M+H]⁺ m/z=563.2, found m/z=561.1. Rotomers/atropisomers are present in the NMR spectra. ¹H NMR (400 MHz, Chloroform-d) δ 8.07 (dd, J=8.8, 14.9 Hz, 1H), 7.79 (dd, J=4.3, 8.7 Hz, 1H), 7.44 (m, 1H), 7.35-7.27 (m, 1H), 7.23-7.11 (m, 1H), 7.07 (t, J=7.6 Hz, 1H), 7.03-6.90 (m, 2H), 6.82-6.69 (m, 1H), 4.70 (t, J=14.3 Hz, 1H), 3.99-3.80 (m, 1H), 3.11-2.84 (m, 1H), 2.77 (dd, J=2.1, 13.5 Hz, 1H), 1.99 (t, J=13.5 Hz, 1H), 1.84-1.56 (m, 1H), 1.54-1.28 (m, 3H), 1.14 (d, J=2.1 Hz, 3H), 1.01 (ddd, J=5.8, 8.0, 14.0 Hz, 1H), 0.77-0.52 (m, 2H), 0.47-0.26 (m, 2H). ¹⁹F NMR (376 MHz, Chloroform-d) δ −58.39 (s, 1F), −58.68 (s, 1.2F).

Example 430

1-(6-(N-(5-chloro-6-(2-cyclopropylphenyl)pyridin-2-yl)sulfamoyl)pyridin-2-yl)-4-methylpiperidine-4-carboxylic Acid LCMS conditions 7: 1.69 min, MS for $C_{26}H_{28}ClN_4O_4S$ [M+H]⁺ m/z=527.1, found m/z=527.1. ¹H NMR (400 MHz, Chloroform-d) δ 7.71 (d, J=8.9 Hz, 1H), 7.58-7.51 (m, 2H), 7.31-7.27 (m, 1H), 7.15 (td, J=1.0, 7.5 Hz, 1H), 7.07 (dd, J=1.4, 7.6 Hz, 1H), 6.95 (d, J=7.8 Hz, 1H), 6.71 (d, J=8.7 Hz, 1H), 3.93 (d, J=13.5 Hz, 2H), 2.98-2.71 (m, 2H), 1.99 (d, J=13.5 Hz, 2H), 1.52 (tt, J=5.3, 8.5 Hz, 1H), 1.36-1.28 (m, 2H), 1.17 (s, 3H), 0.66-0.57 (m, 2H), 0.53-0.45 (m, 2H).

Example 431

1-(6-(N-(5-chloro-6-(2-cyclopropylphenyl)pyridin-2-yl)sulfamoyl)pyridin-2-yl)-3-methylpiperidine-3-carboxylic Acid LCMS conditions 7: 1.73 min, MS for $C_{27}H_{30}F_3N_4O_4S$ [M+H]⁺ m/z=527.1, found m/z=527.1. ¹H NMR (400 MHz, Chloroform-d) δ 10.3 (br. s, 1H), 7.82 (d, J=8.7 Hz, 1H), 7.64 (d, J=8.8 Hz, 1H), 7.38 (s, 1H), 7.31 (td, J=1.3, 7.7 Hz, 1H), 7.19 (s, 1H), 7.01 (s, 2H), 6.92 (s, 1H), 6.74 (d, J=8.5 Hz, 1H), 4.87 (d, J=13.5 Hz, 1H), 3.90 (d, J=13.7 Hz, 1H), 3.03 (td, J=2.5, 13.4 Hz, 1H), 2.74 (d, J=13.6 Hz, 1H), 2.02-1.89 (m, 1H), 1.79 (m, 1H), 1.45 (ddt, J=2.7, 4.8, 10.6 Hz, 1H), 1.35 (m, 2H), 1.15 (s, 3H), 0.79-0.47 (m, 2H), 0.33 (br. s, 3H).

Example 432

1-(6-(N-(6-(5-chloro-2-methoxyphenyl)-5-(trifluoromethyl)pyridin-2-yl)sulfamoyl)pyridin-2-yl)-3-methylpiperidine-3-carboxylic Acid LCMS conditions 7: 1.72 min, MS for $C_{25}H_{25}ClF_3N_4O_5S$ [M+H]⁺ m/z=585.1, found m/z=585.0. Rotomers/atropisomers are present in the NMR spectra. ¹H NMR (400 MHz, Chloroform-d) δ 10.05 (br. s, 1H), 7.99 (d, J=8.9 Hz, 1H), 7.82 (d, J=8.8 Hz, 1H), 7.51 (dd, J=7.2, 8.7 Hz, 1H), 7.34 (dd, J=2.6, 8.8 Hz, 1H), 7.15-7.07 (m, 1H), 7.04 (s, 1H), 6.83 (dd, J=5.2, 8.7 Hz, 2H), 4.54 (d, J=12.2 Hz, 1H), 3.96-3.78 (m, 1H), 3.67 (br. s, 3H), 3.05-2.86 (m, 1H), 2.81 (d, J=13.4 Hz, 1H), 2.09 (d, J=13.6 Hz, 1H), 1.65 (s, 1H), 1.56-1.43 (m, 1H), 1.45-1.32 (m, 1H), 1.14 (s, 4H). ¹⁹F NMR (376 MHz, Chloroform-d) δ −58.55 (s, 1F), −59.44 (br. s, 1F).

Example 433

1-(6-(N-(6-(5-chloro-2-isopropoxyphenyl)-5-(trifluoromethyl)pyridin-2-yl)sulfamoyl)pyridin-2-yl)-3-methylpiperidine-3-carboxylic Acid LCMS conditions 7: 1.80 min, MS for $C_{27}H_{29}ClF_3N_4O_5S$ [M+H]⁺ m/z=563.2, found m/z=613.1. Rotomers/atropisomers are present in the NMR spectra. ¹H NMR (400 MHz, Chloroform-d) δ 10.05 (br. s, 1H), 8.02 (d, J=8.8 Hz, 1H), 7.81 (d, J=8.8 Hz, 1H), 7.51 (dd, J=7.3, 8.6 Hz, 1H), 7.32

(dd, J=2.6, 8.9 Hz, 1H), 7.08 (d, J=7.1 Hz, 1H), 7.05-6.92 (m, 1H), 6.83 (dd, J=3.4, 8.8 Hz, 2H), 4.63 (d, J=12.8 Hz, 1H), 4.41 (s, 1H), 3.89 (d, J=13.0 Hz, 1H), 3.05-2.93 (m, 1H), 2.84 (d, J=13.4 Hz, 1H), 2.11 (d, J=13.6 Hz, 1H), 1.73 (s, 1H), 1.55 (dt, J=3.6, 13.6 Hz, 1H), 1.47-1.35 (m, 1H), 1.34-1.29 (m, 1H), 1.18 (s, 4H), 1.12 (d, J=6.0 Hz, 5H). $^{19}$F NMR (376 MHz, Chloroform-d) δ −59.11 (br. s, 1F).

Example 434 rac-(1SR,5RS,6RS,7SR)-2-(6-(N-(3-chloro-2'-isopropyl-[2,3'-bipyridin]-6-yl)sulfamoyl)pyridin-2-yl)-5-propyl-2-azabicyclo[4.2.0]octane-7-carboxylic Acid LCMS conditions 7: 1.50 min, MS for $C_{29}H_{35}ClN_5O_4S$ [M+H]$^+$ m/z=584.2, found m/z=584.1. $^1$H NMR (400 MHz, DMSO-d$_6$) δ 12.29 (s, 1H), 11.21 (s, 1H), 8.60 (dd, J=4.8, 1.7 Hz, 1H), 8.00 (dd, J=8.8, 1.3 Hz, 1H), 7.71-7.66 (m, 1H), 7.54 (d, J=7.7 Hz, 1H), 7.48 (d, J=8.8 Hz, 1H), 7.33 (dd, J=7.9, 4.8 Hz, 1H), 7.18-7.04 (m, 1H), 6.77 (d, J=8.7 Hz, 1H), 4.43 (s, 1H), 3.67 (s, 1H), 2.93-2.87 (m, 1H), 2.70-2.54 (m, 3H), 2.39-2.35 (m, 2H), 2.21-2.07 (m, 1H), 1.81-1.57 (m, 2H), 1.49-1.14 (m, 5H), 1.12-0.77 (m, 8H).

Example 435

(3S)-1-(6-{[6-(5-fluoro-2-methylphenyl)-5-(trifluoromethyl)pyridin-2-yl]sulfamoyl}pyridin-2-yl)-3-methylpiperidine-3-carboxylic Acid LCMS conditions 7: 1.770 min; MS for $C_{25}H_{25}F_4N_4O_4S$ [M+H]$^+$ m/z=553.15, found m/z=553.15. $^1$H NMR of S-isomer: $^1$H NMR (400 MHz, DMSO-d$_6$) δ 12.31 (s, 1H), 11.59 (s, 1H), 8.19 (d, J=8.9 Hz, 1H), 7.65 (dd, J=8.7, 7.2 Hz, 1H), 7.55 (d, J=8.8 Hz, 1H), 7.31-7.22 (m, 1H), 7.17 (td, J=8.6, 2.8 Hz, 1H), 7.11-7.02 (m, 2H), 6.99-6.89 (m, 1H), 3.87 (d, J=13.1 Hz, 1H), 3.74-3.56 (m, 1H), 3.12 (d, J=13.1 Hz, 1H), 3.08-2.95 (m, 1H), 2.05-1.88 (m, 1H), 1.75 (d, J=9.7 Hz, 3H), 1.54-1.32 (m, 3H), 1.00 (d, J=5.2 Hz, 3H).

Example 436

(3S)-1-(6-{[6-(3-fluoro-2-methylphenyl)-5-(trifluoromethyl)pyridin-2-yl]sulfamoyl}pyridin-2-yl)-3-methylpiperidine-3-carboxylic Acid LCMS conditions 7: 1.805 min; MS for $C_{25}H_{25}F_4N_4O_4S$ [M+H]$^+$ m/z=553.15, found m/z=553.15. $^1$H NMR of S-isomer: $^1$H NMR (400 MHz, DMSO-d$_6$) δ 12.32 (s, 1H), 11.59 (s, 1H), 8.19 (d, J=8.9 Hz, 1H), 7.65 (dd, J=8.7, 7.2 Hz, 1H), 7.59-7.49 (m, 1H), 7.31-7.17 (m, 2H), 7.12-7.01 (m, 2H), 6.97-6.88 (m, 1H), 3.86 (d, J=13.1 Hz, 1H), 3.70-3.55 (m, 1H), 3.13 (dd, J=13.1, 8.8 Hz, 1H), 3.08-2.95 (m, 1H), 2.04-1.89 (m, 1H), 1.67 (d, J=16.0 Hz, 3H), 1.53-1.31 (m, 3H), 1.00 (d, J=8.0 Hz, 3H).

Example 437

(R)-1-(6-(N-(5-chloro-6-(2-cyclopropylphenyl)pyridin-2-yl)sulfamoyl)pyridin-2-yl)-3-methylpiperidine-3-carboxylic Acid LCMS conditions 7: 1.80 min, MS for $C_{26}H_{28}ClN_4O_4S$ [M+H]$^+$ m/z=527.1, found m/z=527.1. Rotomers/atropisomers are present in the NMR spectra. $^1$H NMR (400 MHz, Chloroform-d) δ 10.75-8.87 (br. s, 1H), 7.86 (d, J=8.7 Hz, 1H), 7.66 (d, J=8.7 Hz, 1H), 7.37 (s, 1H), 7.33 (td, J=1.3, 7.6 Hz, 1H), 7.23 (d, J=7.5 Hz, 1H), 7.14-6.98 (m, 2H), 6.93 (m, 1H), 6.75 (d, J=7.5 Hz, 1H), 5.01 (m, 1H), 3.93 (d, J=13.8 Hz, 1H), 3.18-2.98 (m, 1H), 2.75 (d, J=13.6 Hz, 1H), 2.00 (m, 1H), 1.86 (dtt, J=4.4, 8.6, 17.0 Hz, 1H), 1.47 (ddt, J=2.4, 4.9, 10.5 Hz, 1H), 1.43-1.32 (m, 2H), 1.18 (s, 4H), 0.75 (s, 1H), 0.59 (s, 1H), 0.33 (s, 1H), 0.28 (s, 1H).

Example 438 rac-(1RS,3RS,4SR)-3-((6-(N-(6-(2-cyclopropylphenyl)-5-(trifluoromethyl)pyridin-2-yl)sulfamoyl)pyridin-2-yl)amino)-7-oxabicyclo[2.2.1]heptane-1-carboxylic Acid LCMS conditions 7: 1.61 min, MS for $C_{27}H_{26}F_3N_4O_5S$ [M+H]$^+$ m/z=575.2, found m/z=575.1. $^1$H NMR (400 MHz, Methanol-d$_4$) δ 8.08 (dd, J=8.9, 2.9 Hz, 1H), 7.57-7.53 (m, 1H), 7.47 (ddd, J=8.4, 7.2, 2.5 Hz, 1H), 7.33-7.28 (m, 1H), 7.20-7.12 (m, 2H), 7.05 (dd, J=14.4, 7.5 Hz, 1H), 6.97 (dd, J=7.9, 4.2 Hz, 1H), 6.63 (dd, J=8.3, 1.5 Hz, 1H), 4.23 (dd, J=42.4, 4.0 Hz, 1H), 4.04-3.87 (m, 1H), 2.29-2.22 (m, 1H), 1.89-1.49 (m, 5H), 1.44-1.31 (m, 1H), 0.69-0.51 (m, 3H), 0.46-0.37 (m, 1H).

Example 439

5-(6-(N-(6-(5-fluoro-2-methylphenyl)-5-(trifluoromethyl)pyridin-2-yl)sulfamoyl)pyridin-2-yl)-5-azaspiro[2.5]octane-1-carboxylic Acid LCMS conditions 7: 1.538 min; MS for $C_{26}H_{25}F_4N_4O_4S$ [M+H]$^+$ m/z=565.55, found m/z=565.20. $^1$H NMR (400 MHz, Chloroform-d) δ 9.93 (s, 2H), 7.91 (d, J=8.9 Hz, 1H), 7.60 (dd, J=8.9, 0.9 Hz, 1H), 7.51 (dd, J=8.7, 7.2 Hz, 1H), 7.22 (d, J=7.2 Hz, 1H), 7.14-7.08 (m, 1H), 6.95 (td, J=8.5, 2.7 Hz, 1H), 6.76 (dd, J=8.8, 2.8 Hz, 1H), 6.69 (d, J=8.7 Hz, 1H), 3.49-3.16 (m, 4H), 1.74-1.59 (m, 2H), 1.59-1.44 (m, 4H), 1.27-1.13 (m, 2H), 0.95-0.85 (m, 2H).

Example 440

5-(6-(N-(6-(3-fluoro-2-methylphenyl)-5-(trifluoromethyl)pyridin-2-yl)sulfamoyl)pyridin-2-yl)-5-azaspiro[2.5]octane-1-carboxylic Acid LCMS conditions 7: 1.540 min; MS for $C_{26}H_{25}F_4N_4O_4S$ [M+H]$^+$ m/z=565.55, found m/z=565.20. $^1$H NMR (400 MHz, Methanol-d$_4$) δ 7.98 (d, J=8.8 Hz, 1H), 7.51 (dd, J=8.7, 7.3 Hz, 1H), 7.44 (dd, J=8.9, 4.5 Hz, 1H), 7.08 (t, J=7.9 Hz, 2H), 7.00 (ddd, J=9.7, 8.2, 1.2 Hz, 1H), 6.83 (dd, J=14.4, 8.1 Hz, 2H), 3.60-3.23 (m, 4H), 1.71 (tt, J=7.7, 3.7 Hz, 5H), 1.56-1.33 (m, 3H), 0.77 (dtd, J=25.5, 9.3, 8.0, 4.8 Hz, 2H).

Example 441

5-(6-(N-(6-(o-tolyl)-5-(trifluoromethyl)pyridin-2-yl)sulfamoyl)pyridin-2-yl)-5-azaspiro[2.5]octane-1-carboxylic Acid LCMS conditions 7: 1.521 min; MS for $C_{26}H_{26}F_3N_4O_4S$ [M+H]$^+$ m/z=547.56, found m/z=547.20. $^1$H NMR (400 MHz, Chloroform-d) δ 10.47 (s, 2H), 7.99 (d, J=9.0 Hz, 1H), 7.67 (d, J=8.9 Hz, 1H), 7.62-7.56 (m, 1H), 7.36-7.29 (m, 2H), 7.23 (dqdd, J=7.5, 6.7, 1.4, 0.7 Hz, 2H), 7.13-7.08 (m, 1H), 6.77 (dd, J=8.7, 0.6 Hz, 1H), 3.58-3.24 (m, 4H), 2.02 (s, 3H), 1.79-1.65 (m, 2H), 1.65-1.53 (m, 2H), 1.37-1.23 (m, 1H), 0.97 (d, J=6.9 Hz, 2H).

Example 442 rac-(1SR,6RS,7SR)-2-(6-(N-(6-(2-isopropylphenyl)-5-(trifluoromethyl)pyridin-2-yl)sulfamoyl)pyridin-2-yl)-2-azabicyclo[4.2.0]octane-7-carboxylic Acid LCMS conditions 7: 1.78 min, MS for $C_{28}H_{30}F_3N_4O_4S$ [M+H]$^+$ m/z=575.2, found m/z=575.1. $^1$H NMR (400 MHz, DMSO-d$_6$) δ 12.23 (s, 1H), 11.47 (s, 1H), 8.20 (d, J=8.9 Hz, 1H), 7.71-7.67 (m, 1H), 7.60 (s, 1H), 7.45-7.28 (m, 2H), 7.26-7.09 (m, 2H), 7.01-6.97 (m, 1H), 6.71 (d, J=8.7 Hz, 1H), 4.17-4.00 (m, 1H), 3.38-3.35 (m, 1H), 3.06-2.89 (m, 1H), 2.86-2.75 (m, 2H), 2.42-2.23 (m, 2H), 1.98-1.87 (m, 1H), 1.74 (d, J=9.7 Hz, 2H), 1.62-1.40 (m, 2H), 1.04-1.00 (m, 3H), 0.93-0.87 (m, 3H).

Example 443 rac-(1SR,6RS,7SR)-2-(6-(N-(6-(o-tolyl)-5-(trifluoromethyl)pyridin-2-yl)sulfamoyl)pyridin-2-yl)-2-azabicyclo[4.2.0]octane-7-carboxylic Acid LCMS conditions 7: 1.70 min, MS for $C_{26}H_{26}F_3N_4O_4S$ [M+H]$^+$ m/z=547.2, found m/z=546.9. $^1$H NMR (400 MHz, DMSO-d$_6$) δ 12.22 (s, 1H), 11.54 (s, 1H), 8.20 (d, J=8.9 Hz, 1H), 7.70 (dd, J=8.6, 7.3 Hz, 1H), 7.53 (s, 1H), 7.33-7.29 (m, 1H), 7.25-7.18 (m, 2H), 7.16 (d, J=7.2 Hz, 1H), 7.05 (d, J=7.7 Hz, 1H), 6.71 (d, J=8.6 Hz, 1H), 4.18-4.01 (m, 2H), 3.40 (s, 1H), 3.01 (s, 1H), 2.89-2.73 (m, 2H), 2.37 (s, 1H), 1.95-1.92 (m, 1H), 1.79-1.75 (m, 4H), 1.60-1.42 (m, 2H).

Example 444

1-(6-(N-(6-(2-(hydroxymethyl)phenyl)-5-(trifluoromethyl)pyridin-2-yl)sulfamoyl)pyridin-2-yl)-3-methylpiperidine-3-carboxylic Acid LCMS conditions 7: 1.62 min, MS for $C_{25}H_{26}F_3N_4O_5S$ [M+H]$^+$ m/z=551.15, found m/z=551.2, $^1$H NMR (600 MHz, DMSO-d$_6$) δ 12.32 (s, 1H), 11.52 (s, 1H), 8.14 (s, 1H), 7.63 (dd, J=8.7, 7.3 Hz, 1H), 7.59-7.49 (m, 2H), 7.43 (td, J=7.6, 1.3 Hz, 1H), 7.27 (td, J=7.5, 1.3 Hz, 1H), 7.14-7.00 (m, 3H), 4.96 (s, 1H), 4.25-3.96 (m, 2H), 3.88 (d, J=13.2 Hz, 1H), 3.60 (d, J=33.2 Hz, 1H), 3.21-2.92 (m, 2H), 1.95-1.84 (m, 1H), 1.57-1.32 (m, 2H), 1.32-1.20 (m, 1H), 1.01 (s, 3H).

Example 445

1-(6-(N-(6-(2-(2-hydroxyethyl)phenyl)-5-(trifluoromethyl)pyridin-2-yl)sulfamoyl)pyridin-2-yl)-3-methylpiperidine-3-carboxylic Acid LCMS conditions 7: 1.63 min, MS for $C_{26}H_{28}F_3N_4O_5S$ [M+H]$^+$ m/z=565.17, found m/z=565.2. $^1$H NMR (400 MHz, DMSO-d$_6$) δ 12.32 (s, 1H), 11.55 (s, 1H), 8.17 (dd, J=8.5, 6.0 Hz, 1H), 7.77-7.53 (m, 2H), 7.41-7.28 (m, 2H), 7.23 (ddd, J=7.6, 6.6, 2.1 Hz, 1H), 7.15-6.94 (m, 3H), 4.52 (s, 1H), 3.97-3.83 (m, 1H), 3.75-3.58 (m, 1H), 3.48-3.35 (m, 3H), 3.23-2.90 (m, 2H), 2.43 (t, J=7.4 Hz, 1H), 2.29 (dd, J=14.2, 7.2 Hz, 1H), 1.61-1.32 (m, 3H), 1.02 (d, J=5.3 Hz, 3H).

Example 446

7-(6-(N-(6-(o-tolyl)-5-(trifluoromethyl)pyridin-2-yl)sulfamoyl)pyridin-2-yl)-7-azaspiro[3.5]nonane-2-carboxylic Acid LCMS conditions 7: 1.74 min, MS for $C_{27}H_{28}F_3N_4O_4S$ [M+H]$^+$ m/z=561.2, found m/z=561.2. $^1$H NMR (500 MHz, DMSO-d$_6$) δ 12.03 (s, 1H), 11.49 (s, 1H), 8.19 (d, J=8.9 Hz, 1H), 7.66 (dd, J=8.7, 7.2 Hz, 1H), 7.48 (d, J=8.9 Hz, 1H), 7.31 (td, J=7.5, 1.4 Hz, 1H), 7.21 (m, 2H), 7.05 (m, 3H), 3.33 (m, 4H), 3.01 (m, 1H), 1.96 (m, 2H), 1.88 (m, 2H), 1.75 (s, 3H), 1.38 (s, 2H), 1.27 (s, 2H). $^{19}$F NMR (471 MHz, DMSO-d$_6$) δ −57.04 (s, 1F).

Example 447

(R)-1-(6-(N-(5-chloro-6-(o-tolyl)pyridin-2-yl)sulfamoyl)pyridin-2-yl)-3-methylpiperidine-3-carboxylic Acid LCMS conditions 7: 1.69 min, MS for $C_{24}H_{26}ClN_4O_4S$ [M+H]$^+$ m/z=501.1, found m/z=500.9. Rotomers/atropisomers are present in the NMR spectra. $^1$H NMR (500 MHz, Chloroform-d) δ 7.82 (d, J=8.8 Hz, 1H), 7.64 (d, J=8.8 Hz, 1H), 7.43 (dd, J=7.3, 8.6 Hz, 1H), 7.30 (td, J=1.4, 7.6 Hz, 1H), 7.19 (dd, J=4.2, 7.2 Hz, 2H), 7.02 (s, 1H), 6.91 (d, J=7.2 Hz, 1H), 6.75 (d, J=8.7 Hz, 1H), 4.97 (d, J=13.6 Hz, 1H), 3.92 (d, J=13.8 Hz, 1H), 3.05 (td, J=3.0, 13.5 Hz, 1H), 2.73 (d, J=13.6 Hz, 1H), 1.97 (d, J=13.5 Hz, 1H), 1.84 (m, 4H), 1.46 (ddt, J=2.6, 4.9, 10.6 Hz, 2H), 1.36 (td, J=4.9, 12.6, 13.1 Hz, 1H), 1.16 (s, 3H).

Example 448

(R)-1-(6-(N-(5-chloro-6-(2,6-dimethylphenyl)pyridin-2-yl)sulfamoyl)pyridin-2-yl)-3-methylpiperidine-3-carboxylic Acid LCMS conditions 7: 1.73 min, MS for $C_{25}H_{28}ClN_4O_4S$ [M+H]$^+$ m/z=515.1, found m/z=514.9. Rotomers/atropisomers are present in the NMR spectra. $^1$H NMR (500 MHz, Chloroform-d) δ 9.50 (br. s, 1H), 7.85 (d, J=8.7 Hz, 1H), 7.64 (d, J=8.7 Hz, 1H), 7.38 (dd, J=7.2, 8.7 Hz, 1H), 7.18 (t, J=7.6 Hz, 1H), 7.05 (d, J=7.6 Hz, 1H), 6.98 (d, J=7.6 Hz, 1H), 6.87-6.80 (m, 1H), 6.73 (d, J=8.7 Hz, 1H), 5.02 (d, J=13.7 Hz, 1H), 3.93 (d, J=15.9 Hz, 1H), 3.07 (td, J=2.9, 13.5 Hz, 1H), 2.71 (d, J=13.6 Hz, 1H), 1.94 (s, 3H), 1.91 (d, J=1.8 Hz, 1H), 1.82 (dtt, J=4.5, 8.8, 17.3 Hz, 1H), 1.49 (s, 3H), 1.43 (ddd, J=2.4, 5.0, 13.4 Hz, 1H), 1.36 (td, J=5.0, 12.6, 13.1 Hz, 1H), 1.32-1.27 (m, 1H), 1.16 (s, 3H).

Example 449

(R)-1-(6-(N-(6-(2-chloro-5-methoxyphenyl)-5-(trifluoromethyl)pyridin-2-yl)sulfamoyl)pyridin-2-yl)piperidine-3-carboxylic Acid LCMS conditions 7: 1.80 min, MS for $C_{27}H_{30}F_3N_4O_4S$ [M+H]$^+$ m/z=563.2, found m/z=563.1. Rotomers/atropisomers are present in the NMR spectra. $^1$H NMR (500 MHz, Chloroform-d) δ 11.22-8.54 (br. s, 1H), 8.08 (m, 1H), 7.86 (d, J=8.8 Hz, 1H), 7.62-7.45 (m, 1H), 7.33 (d, J=8.8 Hz, 1H), 7.22-6.99 (m, 2H), 6.97-6.88 (m, 1H), 6.87-6.72 (m, 2H), 4.42 (m, 1H), 3.79 (m, 3H), 3.65 (d, J=11.3 Hz, 1H), 3.59-3.36 (m, 2H), 2.63-2.50 (m, 1H), 1.98-1.91 (m, 1H), 1.90-1.78 (m, 2H), 1.48 (d, J=13.6 Hz, 1H). $^{19}$F NMR (471 MHz, Chloroform-d) δ −59.04 (s, 1F), −59.15 (s, 1.2F).

Example 450

(R)-1-(6-(N-(6-(5-chloro-2-methylphenyl)-5-(trifluoromethyl)pyridin-2-yl)sulfamoyl)pyridin-2-yl)-3-methylpiperidine-3-carboxylic Acid LCMS conditions 7: 1.80 min, MS for $C_{25}H_{25}ClF_3N_4O_4S$ [M+H]$^+$ m/z=569.1, found m/z=568.8. Rotomers/atropisomers are present in the NMR spectra. $^1$H NMR (400 MHz, Chloroform-d) δ 10.11 (br. s, 1H), 8.13-8.00 (m, 1H), 7.82 (d, J=8.8 Hz, 1H), 7.54-7.37 (m, 1H), 7.28 (dd, J=2.2, 8.2 Hz, 1H), 7.16 (m, 1H), 7.09 (s, 1H), 7.03 (t, J=8.5 Hz, 1H), 6.95 (d, J=7.4 Hz, 1H), 6.80 (t, J=7.8 Hz, 1H), 4.75 (m, 1H), 3.90 (d, J=13.1 Hz, 1H), 3.00 (m, 1H), 2.78 (d, J=13.5 Hz, 1H), 2.10-1.99 (m, 1H), 1.96 (s, 1H), 1.82-1.66 (m, 2H), 1.61 (s, 2H), 1.55-1.45 (m, 1H), 1.38 (t, J=12.7 Hz, 1H), 1.16 (d, J=4.1 Hz, 3H). $^{19}$F NMR (376 MHz, Chloroform-d) δ −58.96 (s, 1F), −59.12 (s, 1.1F).

Example 451

1-(6-(N-(6-(5-chloro-2-methylphenyl)-5-(trifluoromethyl)pyridin-2-yl)sulfamoyl)pyridin-2-yl)-4-methylpiperidine-4-carboxylic Acid LCMS conditions 7: 1.78 min, MS for $C_{25}H_{25}ClF_3N_4O_4S$ [M+H]$^+$ m/z=569.1, found m/z=568.9. Rotomers/atropisomers are present in the $^1$H NMR spectrum. $^1$H NMR (400 MHz, Chloroform-d) δ 10.47 (br. s, 1H), 7.98 (d, J=8.9 Hz, 1H), 7.65 (d, J=8.8 Hz, 1H), 7.58 (dd, J=7.3, 8.7 Hz, 1H), 7.32-7.25 (m, 3H), 7.17 (d, J=8.3 Hz, 1H), 7.06 (d, J=1.9 Hz, 1H), 6.76 (d, J=8.7 Hz, 1H), 4.12 (m, 1H), 3.86 (d, J=12.0 Hz, 1H), 2.85 (q, J=10.8 Hz, 2H), 2.01 (m, 5H), 1.37-1.28 (m, 2H), 1.20 (s, 3H). $^{19}$F NMR (376 MHz, Chloroform-d) δ −58.84 (s, 1F).

Example 452

1-(6-(N-(5-chloro-6-(o-tolyl)pyridin-2-yl)sulfamoyl)pyridin-2-yl)-3-ethylpiperidine-3-carboxylic Acid LCMS conditions 7: 1.80 min, MS for $C_{25}H_{28}ClN_4O_4S$ [M+H]$^+$ m/z=515.1, found m/z=514.9. $^1$H NMR (400 MHz, Chloroform-d) δ 10.10 (br. s, 1H), 7.81 (d, J=8.8 Hz, 1H), 7.64 (d, J=8.8 Hz, 1H), 7.43 (dd, J=7.3, 8.7 Hz, 1H), 7.30 (td, J=1.4, 7.6 Hz, 1H), 7.19 (dt, J=3.3, 7.1 Hz, 2H), 7.06 (d, J=7.6 Hz, 1H), 6.94 (d, J=7.1 Hz, 1H), 6.75 (d, J=8.7 Hz, 1H), 4.87 (d, J=13.6 Hz, 1H), 3.92 (d, J=13.7 Hz, 1H), 3.01 (td, J=2.9, 13.4 Hz, 1H), 2.75 (d, J=13.6 Hz, 1H), 2.06 (d, J=12.7 Hz, 2H), 1.91 (dq, J=7.3, 14.6 Hz, 3H), 1.77 (tdd, J=4.4, 8.8, 17.0 Hz, 2H), 1.49 (ddt, J=2.8, 4.7, 10.6 Hz, 1H), 1.33-1.27 (m, 1H), 1.23-1.11 (m, 1H), 0.76 (t, J=7.4 Hz, 3H).

Example 453

1-(6-(N-(5-chloro-6-(2,6-dimethylphenyl)pyridin-2-yl)sulfamoyl)pyridin-2-yl)-3-ethylpiperidine-3-carboxylic Acid LCMS conditions 7: 1.80 min, MS for $C_{26}H_{30}ClN_4O_4S$ [M+H]$^+$ m/z=529.2, found m/z=528.9. Rotomers/atropisomers are present in the NMR spectra. $^1$H NMR (400 MHz, Chloroform-d) δ 9.45 (br. s, 1H), 7.85 (d, J=8.7 Hz, 1H), 7.64 (d, J=8.7 Hz, 1H), 7.38 (dd, J=7.2, 8.7 Hz, 1H), 7.18 (t, J=7.6 Hz, 1H), 7.05 (d, J=7.5 Hz, 1H), 6.98 (d, J=7.6 Hz, 1H), 6.84 (d, J=7.1 Hz, 1H), 6.73 (d, J=8.7 Hz, 1H), 4.95 (d, J=13.6 Hz, 1H), 3.93 (d, J=13.8 Hz, 1H), 3.05 (td, J=2.9, 13.4 Hz, 1H), 2.72 (d, J=13.6 Hz, 1H), 2.04-1.97 (m, 2H), 1.95 (s, 3H), 1.77 (qt, J=4.4, 13.0 Hz, 1H), 1.50 (s, 3H), 1.49-1.42 (m, 1H), 1.28 (m, 2H), 1.13 (dq, J=7.4, 14.6 Hz, 1H), 0.77 (t, J=7.4 Hz, 3H).

Example 454

3-ethyl-1-(6-(N-(6-(o-tolyl)-5-(trifluoromethyl)pyridin-2-yl)sulfamoyl)pyridin-2-yl)piperidine-3-carboxylic Acid LCMS conditions 7: 1.77 min, MS for $C_{26}H_{28}F_3N_4O_4S$ [M+H]$^+$ m/z=549.2, found m/z=548.9. Rotomers/atropisomers are present in the NMR spectra. $^1$H NMR (400 MHz, Chloroform-d) δ 10.25 (br. s, 1H), 8.06 (t, J=8.9 Hz, 1H), 7.78 (d, J=8.8 Hz, 1H), 7.51-7.39 (m, 1H), 7.30 (m, 2H), 7.17 (dt, J=7.3, 16.3 Hz, 2H), 7.12-6.89 (m, 2H), 6.77 (d, J=8.7 Hz, 1H), 4.73 (d, J=13.5 Hz, 1H), 3.91 (t, J=12.5 Hz, 1H), 2.96 (m, 1H), 2.77 (d, J=13.5 Hz, 1H), 2.03 (m, 3H), 1.80 (m, 3H), 1.51 (m, 1H), 1.29 (m, 2H), 0.75 (t, J=7.4 Hz, 3H). $^{19}$F NMR (376 MHz, Chloroform-d) δ −58.79 (s, 1F), −59.13 (s, 1.2F).

Example 455

(R)-1-(6-(N-(6-(5-chloro-2-methoxyphenyl)-5-(trifluoromethyl)pyridin-2-yl)sulfamoyl)pyridin-2-yl)-3-methylpiperidine-3-carboxylic Acid LCMS conditions 7: 1.74 min, MS for $C_{25}H_{25}ClF_3N_4O_5S$ [M+H]$^+$ m/z=585.1, found m/z=584.8. Rotomers/atropisomers are present in the NMR spectra. $^1$H NMR (400 MHz, Chloroform-d) δ 9.80 (br. s, 1H), 8.01 (d, J=8.8 Hz, 1H), 7.82 (d, J=7.4 Hz, 1H), 7.50 (dd, J=7.2, 8.7 Hz, 1H), 7.34 (dd, J=2.6, 8.8 Hz, 1H), 7.06 (d, J=6.6 Hz, 2H), 6.82 (t, J=8.9 Hz, 2H), 4.74 (d, J=10.5 Hz, 1H), 3.87 (d, J=11.5 Hz, 1H), 3.66 (br. s, 3H), 3.04-2.88 (m, 1H), 2.75 (d, J=13.4 Hz, 1H), 2.09 (d, J=13.6 Hz, 1H), 1.52 (d, J=13.4 Hz, 1H), 1.36 (td, J=4.6, 13.1 Hz, 1H), 1.29 (m, 2H), 1.16 (s, 3H). $^{19}$F NMR (376 MHz, Chloroform-d) δ −59.43 (br. s, 1F), −59.58 (br. s, 1F).

Example 456

1-(6-(N-(5-chloro-6-(o-tolyl)pyridin-2-yl)sulfamoyl)pyridin-2-yl)-3-propylpiperidine-3-carboxylic Acid LCMS conditions 7: 1.80 min, MS for $C_{26}H_{30}ClN_4O_4S$ [M+H]$^+$ m/z=529.2, found m/z=528.9. $^1$H NMR (400 MHz, Chloroform-d) δ 11.29 (br. s), 9.45 (s, 1H), 7.85 (d, J=8.8 Hz, 1H), 7.66 (d, J=8.8 Hz, 1H), 7.45 (dd, J=7.3, 8.6 Hz, 1H), 7.32 (td, J=1.3, 7.5 Hz, 1H), 7.25-7.16 (m, 2H), 7.06 (d, J=7.1 Hz, 1H), 6.93 (d, J=7.1 Hz, 1H), 6.77 (d, J=8.7 Hz, 1H), 5.00 (d, J=13.6 Hz, 1H), 3.95 (d, J=13.7 Hz, 1H), 3.06 (td, J=2.7, 13.4 Hz, 1H), 2.75 (d, J=13.6 Hz, 1H), 2.06 (d, J=6.0 Hz, 1H), 1.97-1.74 (m, 5H), 1.50 (ddt, J=2.4, 4.8, 10.5 Hz, 2H), 1.34 (dd, J=5.0, 13.2 Hz, 1H), 1.10 (qd, J=2.8, 9.3, 10.7 Hz, 2H), 0.91 (t, J=6.4 Hz, 3H).

Example 457

1-(6-(N-(5-chloro-6-(2,6-dimethylphenyl)pyridin-2-yl)sulfamoyl)pyridin-2-yl)-3-propylpiperidine-3-carboxylic Acid LCMS conditions 7: 1.82 min, MS for $C_{27}H_{30}F_3N_4O_4S$ [M+H]$^+$ m/z=543.2, found m/z=542.9. Rotomers/atropisomers are present in the NMR spectra. $^1$H NMR (400 MHz, Chloroform-d) δ 11.53 (s, 1H), 9.64 (s, 1H), 7.87 (d, J=8.7 Hz, 1H), 7.66 (d, J=8.7 Hz, 1H), 7.40 (dd, J=7.2, 8.7 Hz, 1H), 7.20 (t, J=7.6 Hz, 1H), 7.07 (d, J=7.6 Hz, 1H), 7.00 (d, J=7.6 Hz, 1H), 6.86 (d, J=7.1 Hz, 1H), 6.75 (d, J=8.7 Hz, 1H), 4.99 (d, J=13.6 Hz, 1H), 3.95 (d, J=13.7 Hz, 1H), 3.07 (td, J=2.8, 13.5 Hz, 1H), 2.74 (d, J=13.6 Hz, 1H), 2.02 (d, J=13.9 Hz, 1H), 1.97 (s, 4H), 1.92 (dd, J=3.0, 10.2 Hz, 1H), 1.79 (dddd, J=4.4, 8.7, 13.0, 17.4 Hz, 1H), 1.51 (s, 3H), 1.50-1.44 (m, 1H), 1.34 (dd, J=5.0, 13.5 Hz, 2H), 1.09 (tt, J=4.6, 8.8 Hz, 2H), 0.93-0.89 (m, 3H).

Example 458

3-propyl-1-(6-(N-(6-(o-tolyl)-5-(trifluoromethyl) pyridin-2-yl)sulfamoyl)pyridin-2-yl)piperidine-3-carboxylic Acid LCMS conditions 7: 1.80 min, MS for $C_{27}H_{30}F_3N_4O_4S$ [M+H]$^+$ m/z=563.2, found m/z=562.9. Rotomers/atropisomers are present in the NMR spectra. $^1$H NMR (400 MHz, Chloroform-d) δ 10.27 (s, 1H), 8.09 (t, J=9.7 Hz, 1H), 7.81 (d, J=8.7 Hz, 1H), 7.53-7.40 (m, 1H), 7.33 (td, J=1.1, 7.5 Hz, 1H), 7.20 (dq, J=7.4, 18.1 Hz, 2H), 7.13-6.92 (m, 2H), 6.79 (d, J=8.7 Hz, 1H), 4.79 (d, J=13.2 Hz, 1H), 3.93 (t, J=13.5 Hz, 1H), 2.98 (dt, J=12.3, 26.4 Hz, 1H), 2.77 (d, J=13.5 Hz, 1H), 2.17-1.97 (m, 3H), 1.81 (dd, J=18.8, 29.7 Hz, 2H), 1.53 (s, 1H), 1.33 (d, J=6.7 Hz, 2H), 1.22-0.99 (m, 2H), 0.90 (t, J=7.1 Hz, 2H), 0.87 (t, J=7.1 Hz, 3H). $^{19}$F NMR (376 MHz, Chloroform-d) δ −58.79 (s, 1F), −59.15 (s, 1.2F).

Example 459

3-((6-(N-(6-(o-tolyl)-5-(trifluoromethyl)pyridin-2-yl) sulfamoyl)pyridin-2-yl)amino)cyclopentanecarboxylic Acid Mixture of diastereomers. LCMS conditions 7: 1.71 min, MS for $C_{24}H_{24}F_3N_4O_4S$ [M+H]$^+$ m/z=521.2, found m/z=521.2. $^1$H NMR (400 MHz, Chloroform-d) δ 7.96 (d, J=8.9 Hz, 1H), 7.66 (d, J=8.8 Hz, 1H), 7.49 (dd, J=7.4, 8.4 Hz, 1H), 7.32 (td, J=1.3, 7.5 Hz, 1H), 7.27 (d, J=7.3 Hz, 1H), 7.23 (d, J=7.2 Hz, 1H), 7.20 (d, J=7.4 Hz, 1H), 7.09 (d, J=7.5 Hz, 1H), 6.54 (d, J=8.5 Hz, 1H), 5.39 (s, 1H), 4.02 (s, 1H), 2.91-2.73 (m, 1H), 2.18-2.07 (m, 1H), 2.01 (s, 3H), 1.90 (q, J=7.4 Hz, 2H), 1.76 (qd, J=5.7, 10.4, 12.0 Hz, 2H), 1.59 (dq, J=6.6, 12.4 Hz, 1H), 1.30 (dd, J=5.0, 10.3 Hz, 1H). $^{19}$F NMR (376 MHz, Chloroform-d) δ −58.70 (s, 1F).

Example 460

3-((6-(N-(6-(o-tolyl)-5-(trifluoromethyl)pyridin-2-yl) sulfamoyl)pyridin-2-yl)amino)cyclohexanecarboxylic Acid Mixture of diastereomers. LCMS conditions 7: 1.72 min, MS for $C_{25}H_{26}F_3N_4O_4S$ [M+H]$^+$ m/z=535.1, found m/z=535.1. Rotomers/atropisomers are present in the NMR spectra. $^1$H NMR (400 MHz, Chloroform-d) δ 9.45 (br. s, 1H), 7.97 (d, J=8.9 Hz, 1H), 7.59 (d, J=8.6 Hz, 1H), 7.52 (dd, J=7.3, 8.4 Hz, 1H), 7.39-7.32 (m, 1H), 7.31-7.27 (m, 2H), 7.23 (d, J=7.6 Hz, 1H), 7.13 (d, J=7.5 Hz, 1H), 6.49 (d, J=8.4 Hz, 1H), 4.52 (s, 1H), 3.53 (d, J=6.9 Hz, 1H), 2.38 (td, J=3.6, 11.7 Hz, 1H), 2.24 (d, J=12.6 Hz, 1H), 2.05 (s, 3H), 1.96 (d, J=12.5 Hz, 2H), 1.83 (s, 1H), 1.41-1.28 (m, 4H), 1.15-0.99 (m, 1H). $^{19}$F NMR (376 MHz, Chloroform-d) δ −58.63 (s, 1F).

Example 461

(1,3-cis)-3-((6-(N-(6-(o-tolyl)-5-(trifluoromethyl) pyridin-2-yl)amino)cyclohexanecarboxylic Acid LCMS conditions 7: 1.72 min, MS for $C_{25}H_{26}F_3N_4O_4S$ [M+H]$^+$ m/z=535.2, found m/z=535.2. $^1$H NMR (400 MHz, Chloroform-d) δ 7.97 (d, J=9.0 Hz, 1H), 7.59 (d, J=8.8 Hz, 1H), 7.52 (dd, J=7.3, 8.4 Hz, 1H), 7.35 (td, J=1.2, 7.5 Hz, 1H), 7.29 (d, J=7.1 Hz, 1H), 7.26-7.24 (m, 1H), 7.22 (d, J=7.0 Hz, 1H), 7.13 (d, J=7.5 Hz, 1H), 6.49 (d, J=8.4 Hz, 1H), 4.57 (s, 1H), 3.51 (s, 1H), 2.37 (dt, J=5.8, 11.5 Hz, 1H), 2.22 (d, J=11.8 Hz, 1H), 2.04 (d, J=2.5 Hz, 3H), 1.96 (s, 2H), 1.85 (d, J=19.3 Hz, 1H), 1.42-1.28 (m, 3H), 1.05 (q, J=9.9, 10.4 Hz, 1H). $^{19}$F NMR (376 MHz, Chloroform-d) δ −58.64 (s, 1F).

Example 462

(1S,2S,4R)-7-(6-(N-(6-(o-tolyl)-5-(trifluoromethyl) pyridin-2-yl)sulfamoyl)pyridin-2-yl)-7-azabicyclo [2.2.1]heptane-2-carboxylic Acid LCMS conditions 7: 1.71 min, MS for $C_{25}H_{24}F_3N_4O_4S$ [M+H]$^+$ m/z=533.1, found m/z=533.1. Rotomers/atropisomers are present in the NMR spectra. $^1$H NMR (400 MHz, Chloroform-d) δ 9.77 (br. s, 1H), 8.00 (d, J=8.9 Hz, 1H), 7.71 (d, J=8.8 Hz, 1H), 7.65-7.57 (m, 1H), 7.42 (d, J=7.3 Hz, 1H), 7.33 (td, J=1.3, 7.5 Hz, 1H), 7.24 (d, J=8.9 Hz, 1H), 7.20 (d, J=7.4 Hz, 1H), 7.09 (d, J=7.5 Hz, 1H), 6.82 (d, J=8.4 Hz, 1H), 4.61 (br. s, 1H), 4.23 (br. s, 1H), 2.95 (q, J=7.8 Hz, 1H), 2.01 (s, 3H), 1.81 (d, J=7.4 Hz, 2H), 1.73-1.61 (m, 1H), 1.56 (d, J=7.5 Hz, 2H), 1.50-1.40 (m, 1H). $^{19}$F NMR (376 MHz, Chloroform-d) δ −58.77 (s, 1F).

Example 463

(1,3-trans)-3-((6-(N-(6-(o-tolyl)-5-(trifluoromethyl) pyridin-2-yl)sulfamoyl)pyridin-2-yl)amino)cyclohexanecarboxylic Acid LCMS conditions 7: 1.73 min, MS for $C_{25}H_{26}F_3N_4O_4S$ [M+H]$^+$ m/z=535.2, found m/z=535.2. Rotomers/atropisomers are present in the NMR spectra. $^1$H NMR (400 MHz, Chloroform-d) δ 7.99 (d, J=8.9 Hz, 1H), 7.61 (d, J=7.0 Hz, 1H), 7.58-7.49 (m, 1H), 7.37 (td, J=1.2, 7.6 Hz, 1H), 7.31 (d, J=7.2 Hz, 1H), 7.23 (d, J=7.5 Hz, 1H), 7.14 (d, J=7.3 Hz, 1H), 6.56 (d, J=8.2 Hz, 1H), 4.56 (s, 1H), 3.81-3.69 (m, 1H), 2.58 (t, J=8.9 Hz, 1H), 2.48-2.29 (m, 2H), 2.05 (s, 3H), 1.95-1.84 (m, 2H), 1.79 (d, J=10.4 Hz, 2H), 1.65 (s, 3H). $^{19}$F NMR (376 MHz, Chloroform-d) δ −58.75 (br. s, 1F).

Example 464

(3R,6S)-6-methyl-1-(6-(N-(6-(o-tolyl)-5-(trifluoromethyl)pyridin-2-yl)sulfamoyl)pyridin-2-yl)piperidine-3-carboxylic Acid LCMS conditions 7: 1.73 min, MS for $C_{25}H_{26}F_3N_4O_4S$ [M+H]$^+$ m/z=535.1, found m/z=534.9. Rotomers/atropisomers are present in the NMR spectra. $^1$H NMR (400 MHz, Chloroform-d) δ 9.31 (br. s, 1H), 7.99 (d, J=8.9 Hz, 1H), 7.75 (d, J=8.2 Hz, 1H), 7.59 (dd, J=7.3, 8.7 Hz, 1H), 7.34-7.28 (m, 2H), 7.22 (dd, J=7.3, 14.5 Hz, 2H), 7.08 (d, J=7.5 Hz, 1H), 6.78 (d, J=8.8 Hz, 1H), 4.35 (d, J=13.4 Hz, 2H), 3.00-2.85 (m, 1H), 2.41 (tt, J=4.1, 11.7 Hz, 1H), 1.99 (s, 3H), 1.97-1.88 (m, 2H), 1.80 (qd, J=4.6, 12.1 Hz, 1H), 1.68 (dd, J=3.8, 8.2 Hz, 1H), 1.65-1.57 (m, 1H), 1.07 (d, J=6.8 Hz, 3H). $^{19}$F NMR (376 MHz, Chloroform-d) δ −58.69 (s, 1F).

Example 465

(R)-1-(6-(N-(6-(2,6-dimethylphenyl)-5-(trifluoromethyl)pyridin-2-yl)sulfamoyl)pyridin-2-yl)-3-methyl-piperidine-3-carboxylic Acid LCMS conditions 7: 1.76 min, MS for $C_{26}H_{28}F_3N_4O_4S$ [M+H]$^+$ m/z=549.2, found m/z=548.9. Rotomers/atropisomers are present in the NMR spectra. $^1$H NMR (400 MHz, Chloroform-d) δ 9.92 (br. s, 1H), 8.13 (d, J=8.8 Hz, 1H), 7.82 (d, J=8.7 Hz, 1H), 7.42 (dd, J=7.2, 8.7 Hz, 1H), 7.20 (t, J=7.6 Hz, 1H), 7.06 (d, J=7.6 Hz, 1H), 6.98 (d, J=7.6 Hz, 1H), 6.90 (d, J=7.2 Hz, 1H), 6.77 (d, J=8.7 Hz, 1H), 4.98 (d, J=13.6 Hz, 1H), 3.94 (d, J=13.8 Hz, 1H), 3.08 (td, J=2.7, 13.5 Hz, 1H), 2.74 (d, J=13.6 Hz, 1H), 1.99 (m), 1.92 (s, 4H), 1.80 (m, 1H), 1.51 (s, 3H), 1.46 (dd, J=2.4, 4.9 Hz, 1H), 1.43-1.34 (m, 1H), 1.18 (s, 3H). $^{19}$F NMR (376 MHz, Chloroform-d) δ −58.56 (s, 1F).

| Ex. No. | Product |
|---|---|
| 102 | |
| 103 | |
| 104 | |
| 105 | |
| 106 | |
| 107 | |

| Ex. No. | Product |
|---|---|
| 108 | 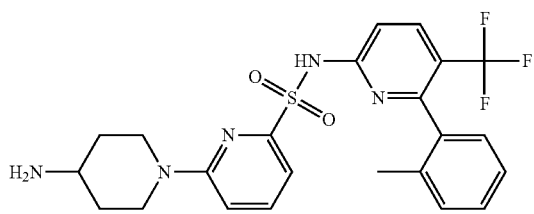 [SMILES: Cc1ccccc1-c1nc(NS(=O)(=O)c2cccc(N3CCC(N)CC3)n2)ccc1C(F)(F)F] |
| 109 | 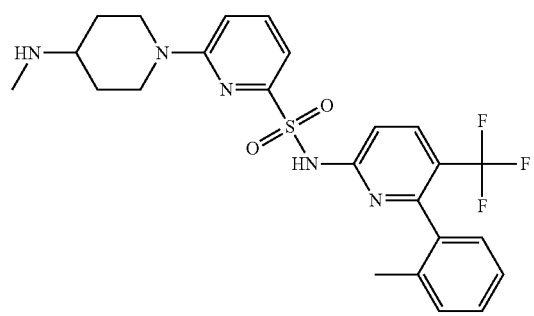 [SMILES: CNC1CCN(c2cccc(S(=O)(=O)Nc3ccc(C(F)(F)F)c(-c4ccccc4C)n3)n2)CC1] |
| 110 | 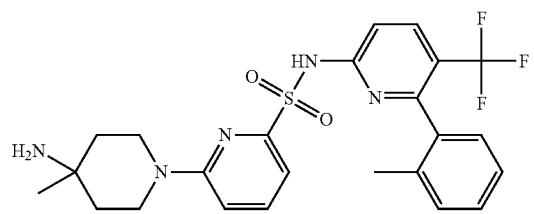 [SMILES: Cc1ccccc1-c1nc(NS(=O)(=O)c2cccc(N3CCC(C)(N)CC3)n2)ccc1C(F)(F)F] |
| 111 | 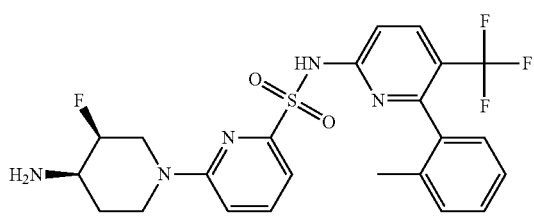 [SMILES: Cc1ccccc1-c1nc(NS(=O)(=O)c2cccc(N3CC[C@@H](N)[C@@H](F)C3)n2)ccc1C(F)(F)F] |
| 112 | 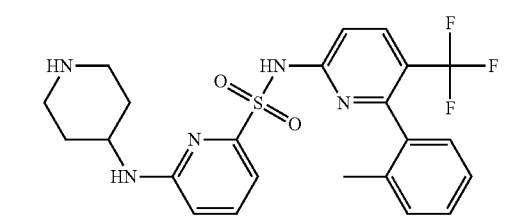 [SMILES: Cc1ccccc1-c1nc(NS(=O)(=O)c2cccc(NC3CCNCC3)n2)ccc1C(F)(F)F] |
| 113 | 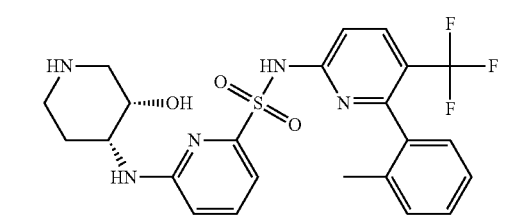 [SMILES: Cc1ccccc1-c1nc(NS(=O)(=O)c2cccc(N[C@@H]3CCNC[C@@H]3O)n2)ccc1C(F)(F)F] |

-continued
| Ex. No. | Product |
|---|---|
| 114 | 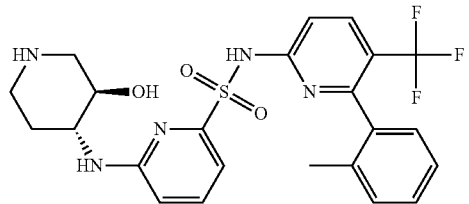 [SMILES: Cc1ccccc1-c1nc(NS(=O)(=O)c2cccc(N[C@@H]3CCNC[C@H]3O)n2)ccc1C(F)(F)F] |
| 115 | 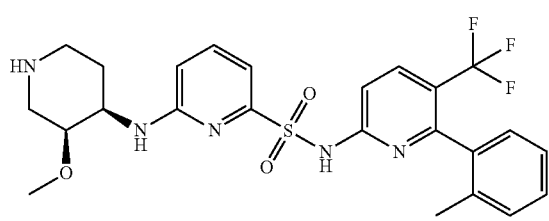 [SMILES: CO[C@H]1CNCC[C@H]1Nc1cccc(S(=O)(=O)Nc2ccc(C(F)(F)F)c(-c3ccccc3C)n2)n1] |
| 116 | 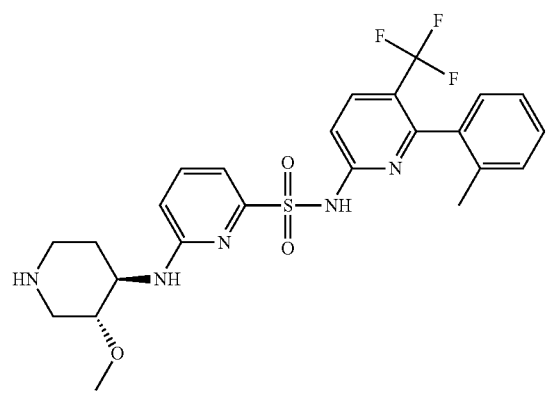 [SMILES: CO[C@@H]1CNCC[C@H]1Nc1cccc(S(=O)(=O)Nc2ccc(C(F)(F)F)c(-c3ccccc3C)n2)n1] |
| 117 | 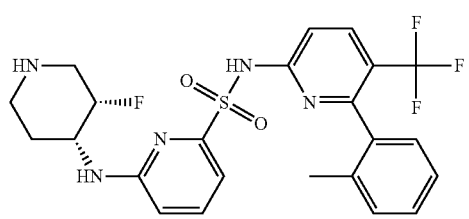 [SMILES: Cc1ccccc1-c1nc(NS(=O)(=O)c2cccc(N[C@@H]3CCNC[C@@H]3F)n2)ccc1C(F)(F)F] |
| 118 | 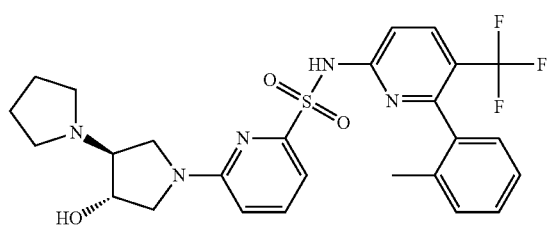 [SMILES: Cc1ccccc1-c1nc(NS(=O)(=O)c2cccc(N3C[C@H](O)[C@@H](N4CCCC4)C3)n2)ccc1C(F)(F)F] |
| 119 | 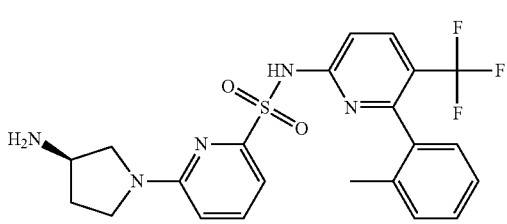 [SMILES: Cc1ccccc1-c1nc(NS(=O)(=O)c2cccc(N3CC[C@@H](N)C3)n2)ccc1C(F)(F)F] |

| Ex. No. | Product |
|---|---|
| 120 | 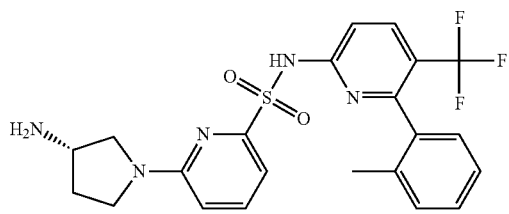 [SMILES: Cc1ccccc1-c1nc(NS(=O)(=O)c2cccc(N3CC[C@H](N)C3)n2)ccc1C(F)(F)F] |
| 121 | 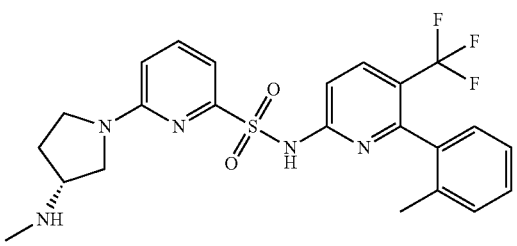 [SMILES: CN[C@@H]1CCN(c2cccc(S(=O)(=O)Nc3ccc(C(F)(F)F)c(-c4ccccc4C)n3)n2)C1] |
| 122 | 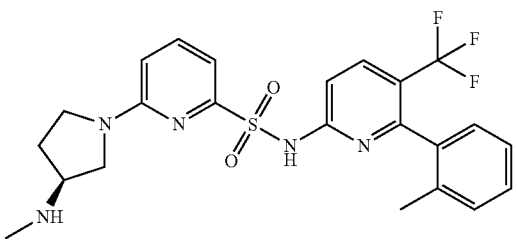 [SMILES: CN[C@H]1CCN(c2cccc(S(=O)(=O)Nc3ccc(C(F)(F)F)c(-c4ccccc4C)n3)n2)C1] |
| 123 | 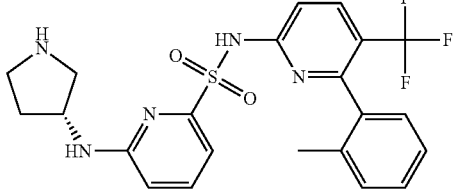 |
| 124 | 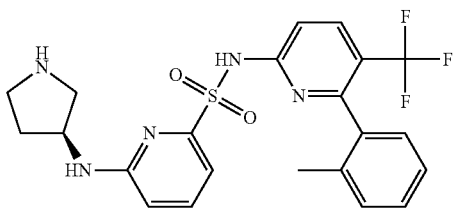 [SMILES: Cc1ccccc1-c1nc(NS(=O)(=O)c2cccc(N[C@H]3CCNC3)n2)ccc1C(F)(F)F] |
| 125 | 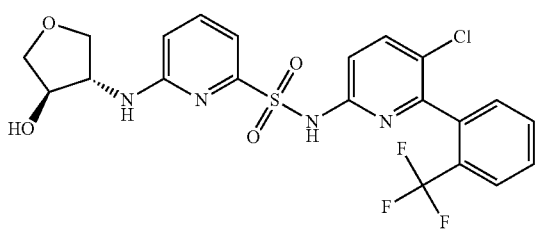 [SMILES: O=S(=O)(Nc1ccc(Cl)c(-c2ccccc2C(F)(F)F)n1)c1cccc(N[C@H]2COC[C@@H]2O)n1] |

-continued
| Ex. No. | Product |
|---|---|
| 126 | 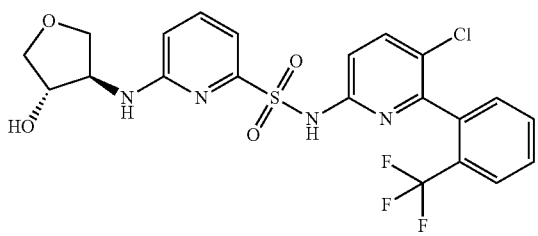 [SMILES: O=S(=O)(Nc1ccc(Cl)c(-c2ccccc2C(F)(F)F)n1)c1cccc(N[C@@H]2COC[C@H]2O)n1] |
| 127 | 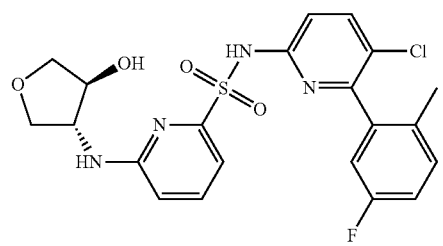 [SMILES: Cc1ccc(F)cc1-c1nc(NS(=O)(=O)c2cccc(N[C@@H]3COC[C@H]3O)n2)ccc1Cl] |
| 128 | 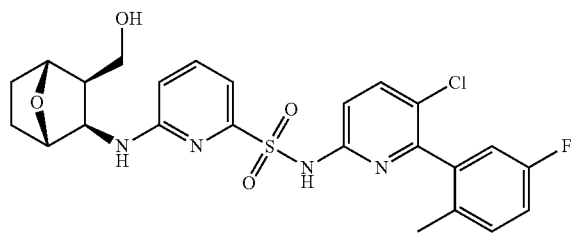 [SMILES: Cc1ccc(F)cc1-c1nc(NS(=O)(=O)c2cccc(N[C@@H]3[C@H](CO)[C@H]4CC[C@@H]3O4)n2)ccc1Cl] |
| 129 | 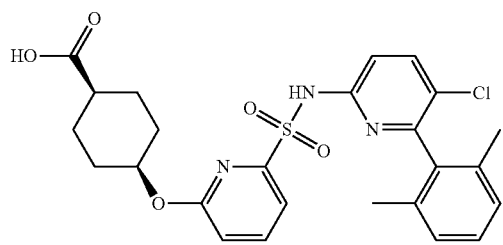 [SMILES: Cc1cccc(C)c1-c1nc(NS(=O)(=O)c2cccc(O[C@H]3CC[C@@H](C(=O)O)CC3)n2)ccc1Cl] |
| 130 | 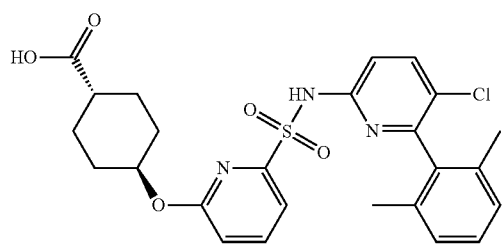 [SMILES: Cc1cccc(C)c1-c1nc(NS(=O)(=O)c2cccc(O[C@H]3CC[C@H](C(=O)O)CC3)n2)ccc1Cl] |
| 131 | 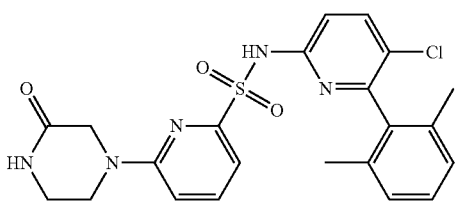 [SMILES: Cc1cccc(C)c1-c1nc(NS(=O)(=O)c2cccc(N3CCNC(=O)C3)n2)ccc1Cl] |

-continued
| Ex. No. | Product |
|---|---|
| 132 | 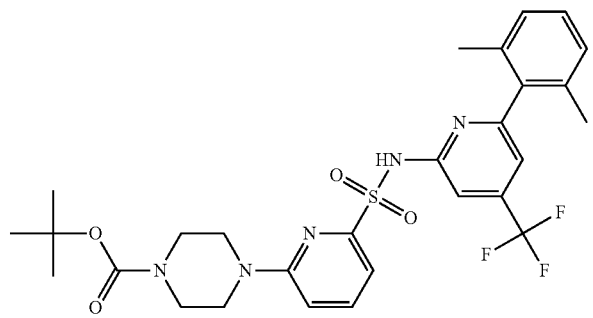 [SMILES: Cc1cccc(C)c1-c1cc(C(F)(F)F)cc(NS(=O)(=O)c2cccc(N3CCN(C(=O)OC(C)(C)C)CC3)n2)n1] |
| 133 | 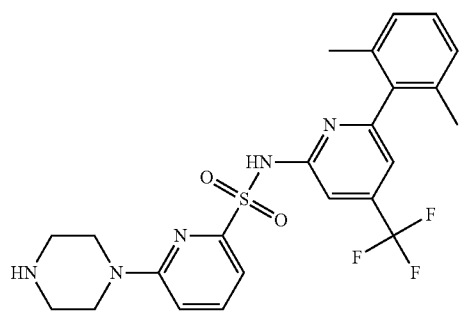 [SMILES: Cc1cccc(C)c1-c1cc(C(F)(F)F)cc(NS(=O)(=O)c2cccc(N3CCNCC3)n2)n1] |
| 134 | 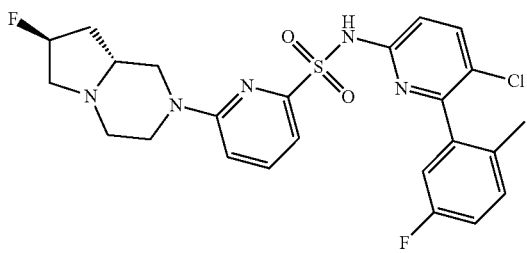 [SMILES: Cc1ccc(F)cc1-c1nc(NS(=O)(=O)c2cccc(N3CCN4C[C@@H](F)C[C@@H]4C3)n2)ccc1Cl] |
| 135 | 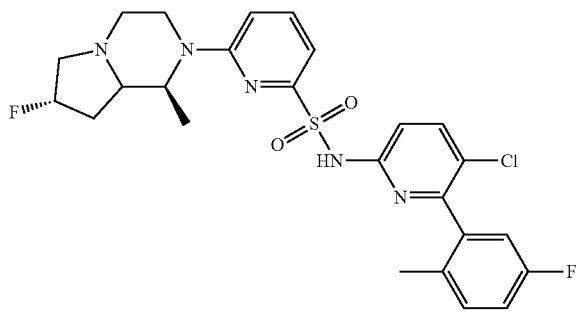 [SMILES: Cc1ccc(F)cc1-c1nc(NS(=O)(=O)c2cccc(N3CCN4C[C@@H](F)CC4[C@@H]3C)n2)ccc1Cl] |
| 136 | 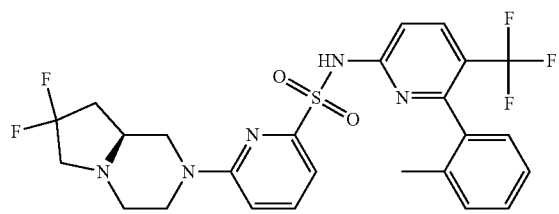 [SMILES: Cc1ccccc1-c1nc(NS(=O)(=O)c2cccc(N3CCN4CC(F)(F)C[C@H]4C3)n2)ccc1C(F)(F)F] |

| Ex. No. | Product |
|---|---|
| 137 | (chemical structure) |
| 138 | (chemical structure) |
| 139 | (chemical structure) |
| 140 | (chemical structure) |
| 141 | (chemical structure) |
| 142 | (chemical structure) |
| 143 | (chemical structure) |

-continued
| Ex. No. | Product |
|---|---|
| 144 | 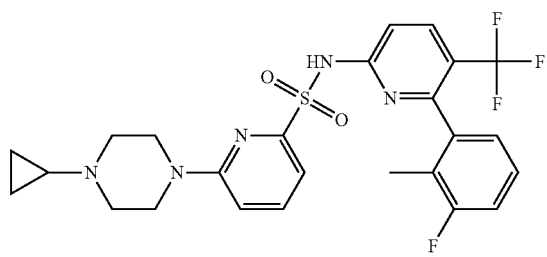 [SMILES: Cc1c(F)cccc1-c1nc(NS(=O)(=O)c2cccc(N3CCN(C4CC4)CC3)n2)ccc1C(F)(F)F] |
| 145 | 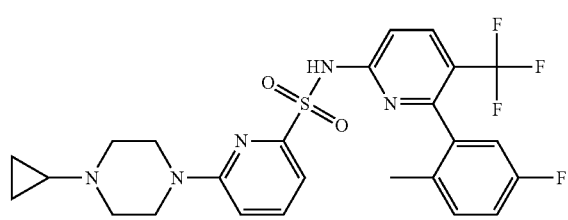 [SMILES: Cc1ccc(F)cc1-c1nc(NS(=O)(=O)c2cccc(N3CCN(C4CC4)CC3)n2)ccc1C(F)(F)F] |
| 146 | 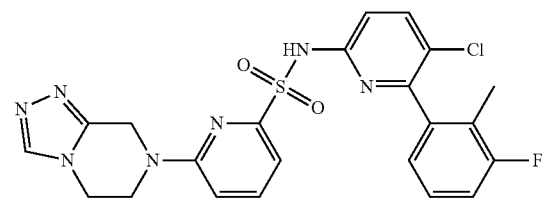 [SMILES: Cc1c(F)cccc1-c1nc(NS(=O)(=O)c2cccc(N3CCn4cnnc4C3)n2)ccc1Cl] |
| 147 | 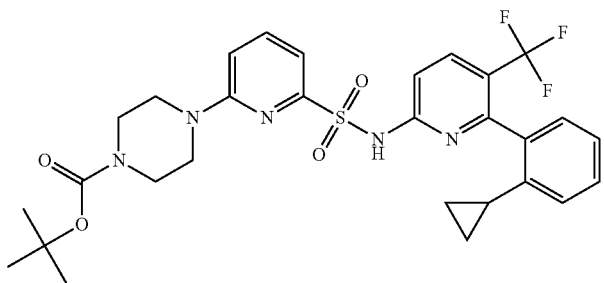 [SMILES: CC(C)(C)OC(=O)N1CCN(c2cccc(S(=O)(=O)Nc3ccc(C(F)(F)F)c(-c4ccccc4C4CC4)n3)n2)CC1] |
| 148 | 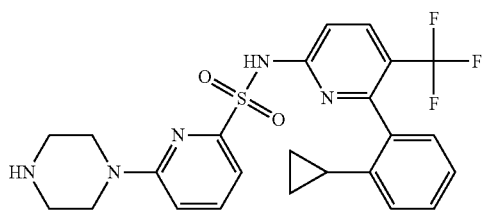 [SMILES: O=S(=O)(Nc1ccc(C(F)(F)F)c(-c2ccccc2C2CC2)n1)c1cccc(N2CCNCC2)n1] |
| 149 | 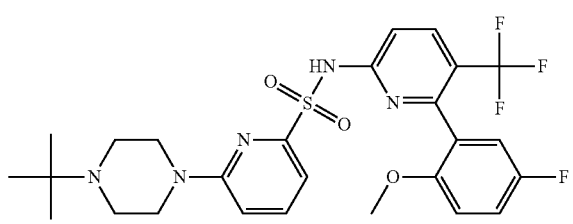 |

| Ex. No. | Product |
|---|---|
| 150 | 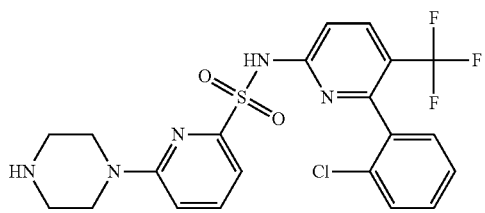 [SMILES: O=S(=O)(Nc1ccc(C(F)(F)F)c(-c2ccccc2Cl)n1)c1cccc(N2CCNCC2)n1] |
| 151 | 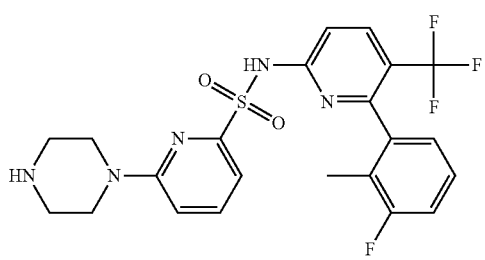 [SMILES: Cc1c(F)cccc1-c1nc(NS(=O)(=O)c2cccc(N3CCNCC3)n2)ccc1C(F)(F)F] |
| 152 | 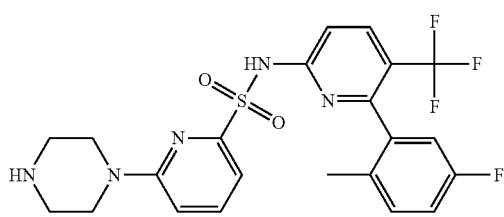 [SMILES: Cc1ccc(F)cc1-c1nc(NS(=O)(=O)c2cccc(N3CCNCC3)n2)ccc1C(F)(F)F] |
| 153 | 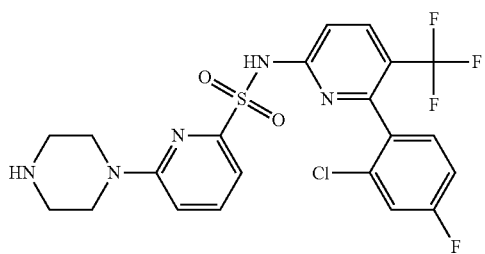 [SMILES: O=S(=O)(Nc1ccc(C(F)(F)F)c(-c2ccc(F)cc2Cl)n1)c1cccc(N2CCNCC2)n1] |
| 154 | 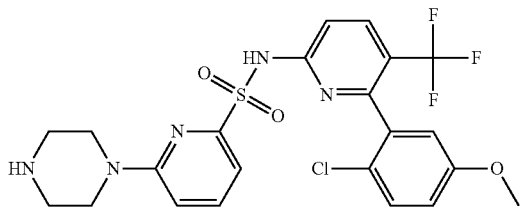 [SMILES: COc1ccc(Cl)c(-c2nc(NS(=O)(=O)c3cccc(N4CCNCC4)n3)ccc2C(F)(F)F)c1] |
| 155 | 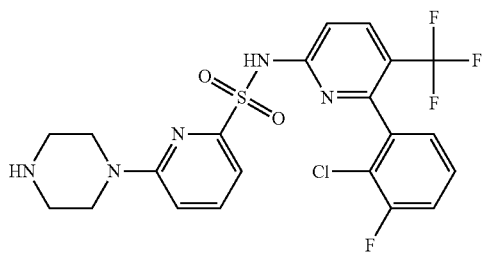 [SMILES: O=S(=O)(Nc1ccc(C(F)(F)F)c(-c2cccc(F)c2Cl)n1)c1cccc(N2CCNCC2)n1] |

-continued

| Ex. No. | Product |
|---|---|
| 156 | 6-(piperazin-1-yl)-N-(5-chloro-6-(2-chlorophenyl)pyridin-2-yl)pyridine-2-sulfonamide |
| 157 | 6-(piperazin-1-yl)-N-(6-(3,5-dichloro-4-fluorophenyl...) — structure shown |
| 158 | 6-(piperazin-1-yl)-N-(5-chloro-6-(2-chloro-5-methoxyphenyl)pyridin-2-yl)pyridine-2-sulfonamide |
| 159 | 6-(piperazin-1-yl)-N-(5-chloro-6-(2-chloro-3-fluorophenyl)pyridin-2-yl)pyridine-2-sulfonamide |
| 160 | tert-butyl 4-(6-(N-(6-(2-methylphenyl)-5-(trifluoromethyl)pyridin-2-yl)sulfamoyl)pyridin-2-yl)piperazine-1-carboxylate |
| 161 | 6-(piperazin-1-yl)-N-(6-(2-methylphenyl)-5-(trifluoromethyl)pyridin-2-yl)pyridine-2-sulfonamide |
| 162 | tert-butyl 4-(6-(N-(5-chloro-6-(2,6-dimethylphenyl)pyridin-2-yl)sulfamoyl)pyridin-2-yl)piperazine-1-carboxylate |

-continued
| Ex. No. | Product |
|---|---|
| 163 | 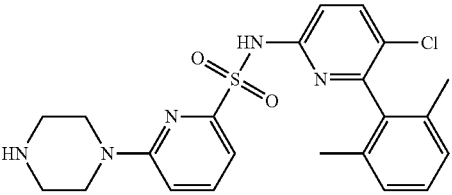 [SMILES: Cc1cccc(C)c1-c1nc(NS(=O)(=O)c2cccc(N3CCNCC3)n2)ccc1Cl] |
| 164 | 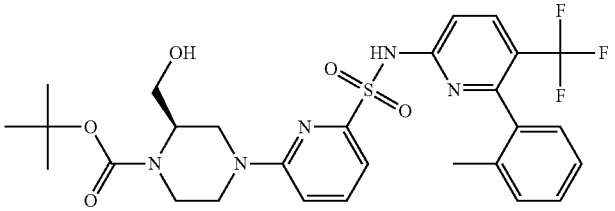 [SMILES: Cc1ccccc1-c1nc(NS(=O)(=O)c2cccc(N3CCN(C(=O)OC(C)(C)C)[C@@H](CO)C3)n2)ccc1C(F)(F)F] |
| 165 | 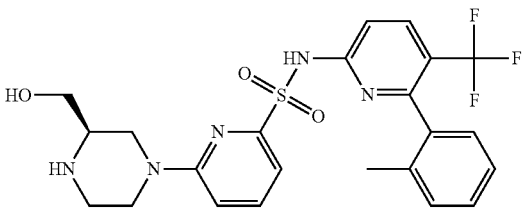 [SMILES: Cc1ccccc1-c1nc(NS(=O)(=O)c2cccc(N3CCN[C@@H](CO)C3)n2)ccc1C(F)(F)F] |
| 166 | 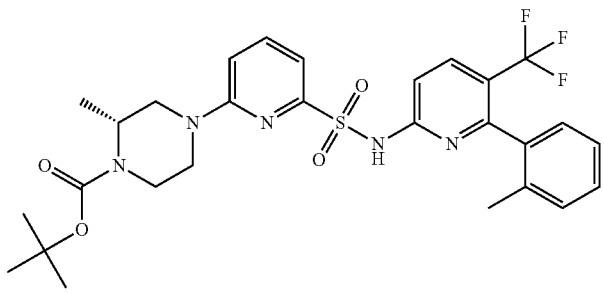 [SMILES: Cc1ccccc1-c1nc(NS(=O)(=O)c2cccc(N3CCN(C(=O)OC(C)(C)C)[C@H](C)C3)n2)ccc1C(F)(F)F] |
| 167 | 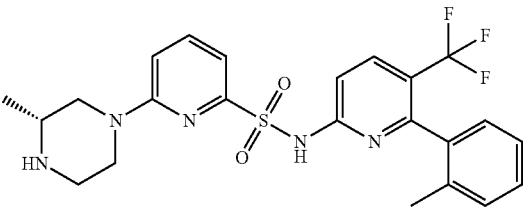 [SMILES: Cc1ccccc1-c1nc(NS(=O)(=O)c2cccc(N3CCN[C@H](C)C3)n2)ccc1C(F)(F)F] |
| 168 | 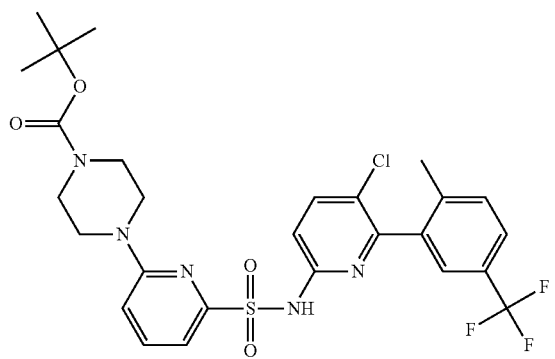 [SMILES: Cc1ccc(C(F)(F)F)cc1-c1nc(NS(=O)(=O)c2cccc(N3CCN(C(=O)OC(C)(C)C)CC3)n2)ccc1Cl] |

-continued
| Ex. No. | Product |
|---|---|
| 169 | 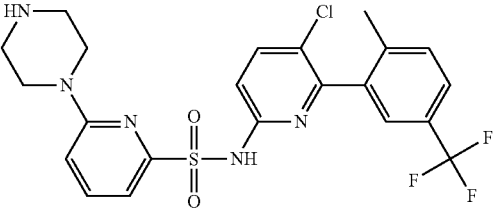 [SMILES: Cc1ccc(C(F)(F)F)cc1-c1nc(NS(=O)(=O)c2cccc(N3CCNCC3)n2)ccc1Cl] |
| 170 | 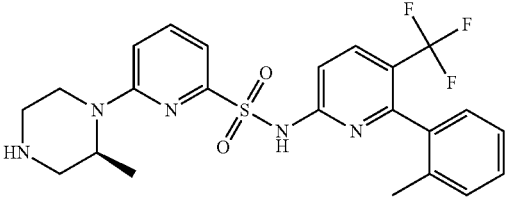 [SMILES: Cc1ccccc1-c1nc(NS(=O)(=O)c2cccc(N3CCNC[C@@H]3C)n2)ccc1C(F)(F)F] |
| 171 | 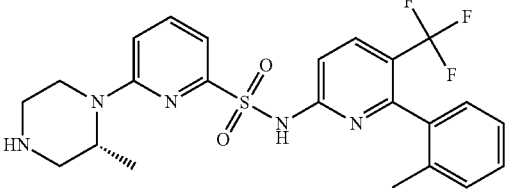 |
| 172 | 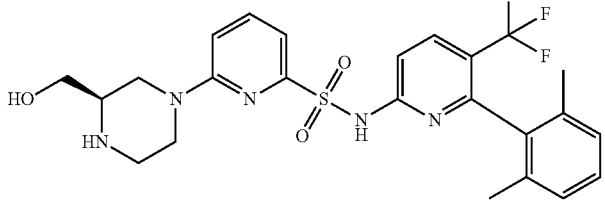 |
| 173 | 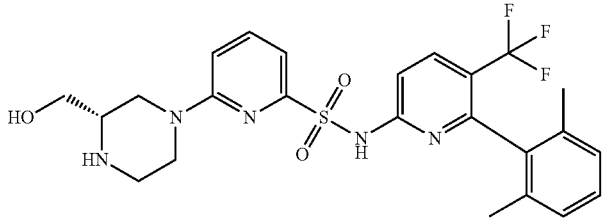 [SMILES: Cc1cccc(C)c1-c1nc(NS(=O)(=O)c2cccc(N3CCN[C@H](CO)C3)n2)ccc1C(F)(F)F] |
| 174 | 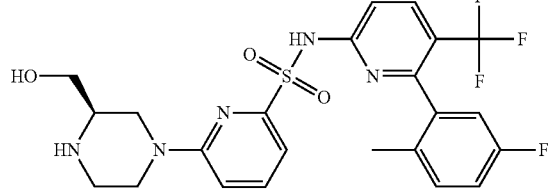 |
| 175 | 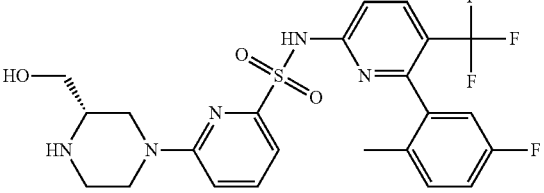 |

-continued

| Ex. No. | Product |
|---|---|
| 176 | (structure) |
| 177 | (structure) |
| 178 | (structure) |
| 179 | (structure) |
| 180 | (structure) |
| 181 | (structure) |
| 182 | (structure) |

| Ex. No. | Product |
|---|---|
| 183 | (structure) |
| 184 | (structure) |
| 185 | (structure) |
| 186 | (structure) |
| 187 | (structure) |
| 188 | (structure) |
| 189 | (structure) |

-continued

| Ex. No. | Product |
|---|---|
| 190 | (structure) |
| 191 | (structure) |
| 192 | (structure) |
| 193 | (structure) |
| 194 | (structure) |
| 195 | (structure) |
| 196 | (structure) |

-continued
| Ex. No. | Product |
|---|---|
| 197 | 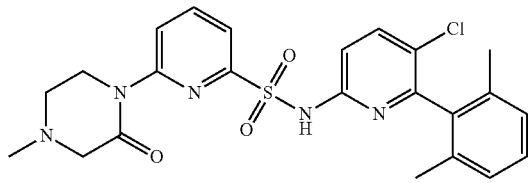 [SMILES: Cc1cccc(C)c1-c1nc(NS(=O)(=O)c2cccc(N3CCN(C)CC3=O)n2)ccc1Cl] |
| 198 | 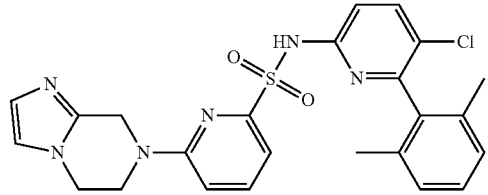 [SMILES: Cc1cccc(C)c1-c1nc(NS(=O)(=O)c2cccc(N3CCn4ccnc4C3)n2)ccc1Cl] |
| 199 | 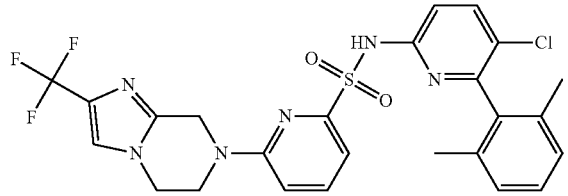 [SMILES: Cc1cccc(C)c1-c1nc(NS(=O)(=O)c2cccc(N3CCn4cc(C(F)(F)F)nc4C3)n2)ccc1Cl] |
| 200 | 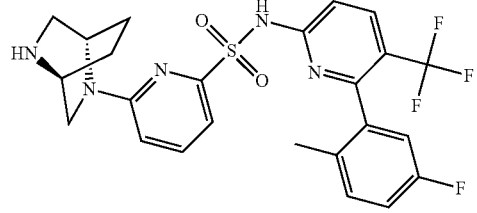 [SMILES: Cc1ccc(F)cc1-c1nc(NS(=O)(=O)c2cccc(N3C[C@@H]4CC[C@H]3CN4)n2)ccc1C(F)(F)F] |
| 201 | 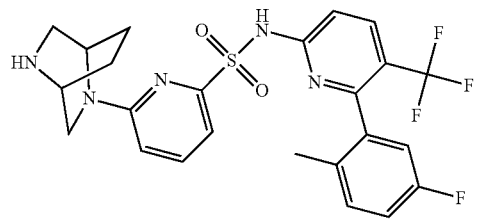 [SMILES: Cc1ccc(F)cc1-c1nc(NS(=O)(=O)c2cccc(N3CC4CCC3CN4)n2)ccc1C(F)(F)F] |
| 202 | 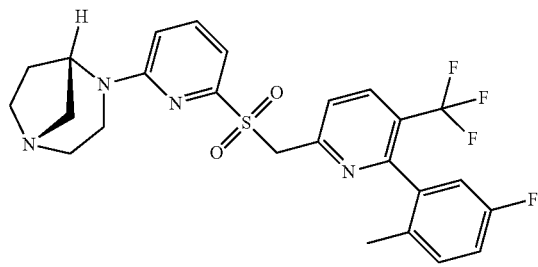 [SMILES: Cc1ccc(F)cc1-c1nc(CS(=O)(=O)c2cccc(N3CC[N@]4CC[C@H]3C4)n2)ccc1C(F)(F)F] |
| 203 | 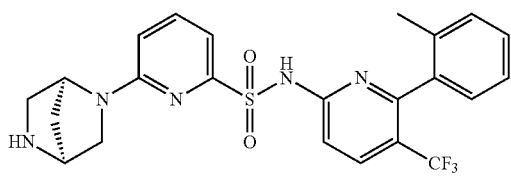 [SMILES: Cc1ccccc1-c1nc(NS(=O)(=O)c2cccc(N3C[C@@H]4C[C@H]3CN4)n2)ccc1C(F)(F)F] |

-continued
| Ex. No. | Product |
|---|---|
| 204 | 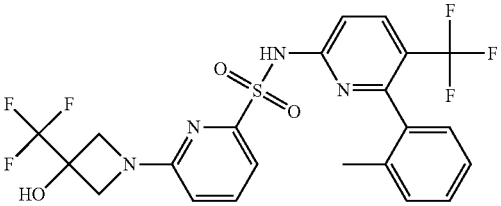 [SMILES: Cc1ccccc1-c1nc(NS(=O)(=O)c2cccc(N3CC(O)(C(F)(F)F)C3)n2)ccc1C(F)(F)F] |
| 205 | 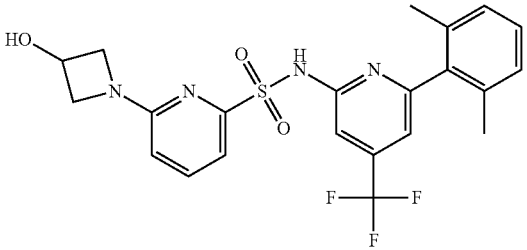 [SMILES: Cc1cccc(C)c1-c1cc(C(F)(F)F)cc(NS(=O)(=O)c2cccc(N3CC(O)C3)n2)n1] |
| 206 | 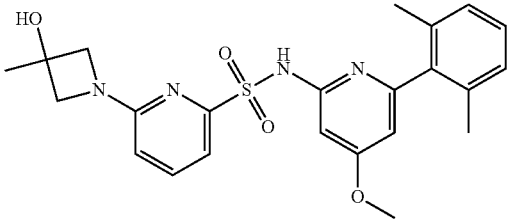 [SMILES: COc1cc(NS(=O)(=O)c2cccc(N3CC(C)(O)C3)n2)nc(-c2c(C)cccc2C)c1] |
| 207 | 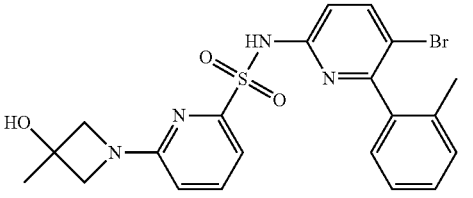 [SMILES: Cc1ccccc1-c1nc(NS(=O)(=O)c2cccc(N3CC(C)(O)C3)n2)ccc1Br] |
| 208 | 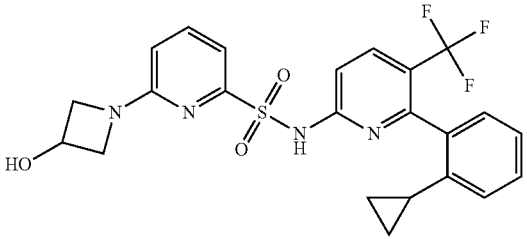 [SMILES: O=S(=O)(Nc1ccc(C(F)(F)F)c(-c2ccccc2C2CC2)n1)c1cccc(N2CC(O)C2)n1] |
| 209 | 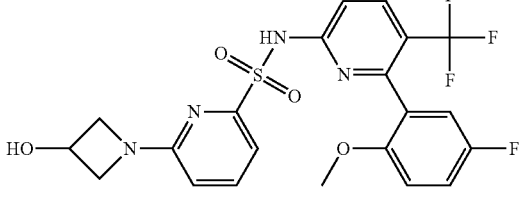 |
| 210 | 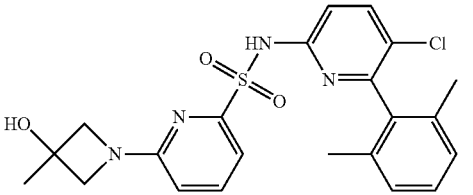 [SMILES: Cc1cccc(C)c1-c1nc(NS(=O)(=O)c2cccc(N3CC(C)(O)C3)n2)ccc1Cl] |

-continued
| Ex. No. | Product |
|---|---|
| 211 | 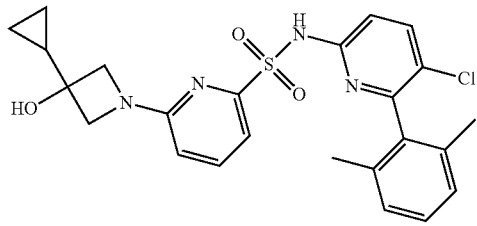 [SMILES: Cc1cccc(C)c1-c1nc(NS(=O)(=O)c2cccc(N3CC(O)(C4CC4)C3)n2)ccc1Cl] |
| 212 | 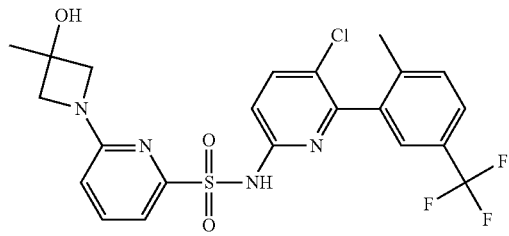 [SMILES: Cc1ccc(C(F)(F)F)cc1-c1nc(NS(=O)(=O)c2cccc(N3CC(C)(O)C3)n2)ccc1Cl] |
| 213 | 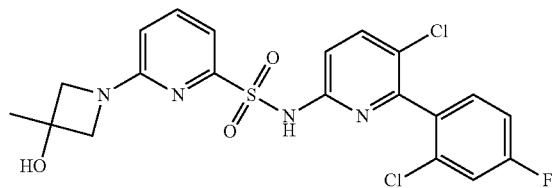 [SMILES: CC1(O)CN(c2cccc(S(=O)(=O)Nc3ccc(Cl)c(-c4ccc(F)cc4Cl)n3)n2)C1] |
| 214 | 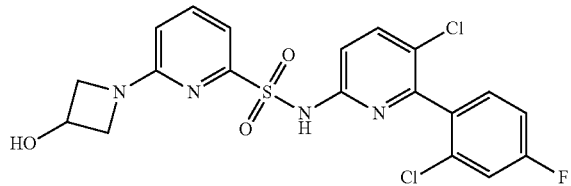 [SMILES: O=S(=O)(Nc1ccc(Cl)c(-c2ccc(F)cc2Cl)n1)c1cccc(N2CC(O)C2)n1] |
| 215 | 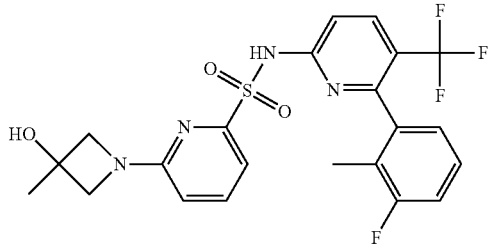 [SMILES: Cc1c(F)cccc1-c1nc(NS(=O)(=O)c2cccc(N3CC(C)(O)C3)n2)ccc1C(F)(F)F] |
| 216 | 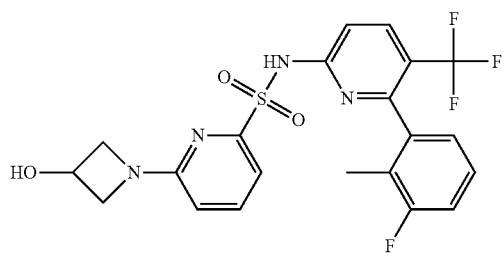 [SMILES: Cc1c(F)cccc1-c1nc(NS(=O)(=O)c2cccc(N3CC(O)C3)n2)ccc1C(F)(F)F] |

| Ex. No. | Product |
|---|---|
| 217 | (structure) |
| 218 | (structure) |
| 219 | (structure) |
| 220 | (structure) |
| 221 | (structure) |
| 222 | (structure) |

| Ex. No. | Product |
|---|---|
| 223 | (structure) |
| 224 | (structure) |
| 225 | (structure) |
| 226 | (structure) |
| 227 | (structure) |
| 228 | (structure) |

-continued
| Ex. No. | Product |
|---|---|
| 229 | 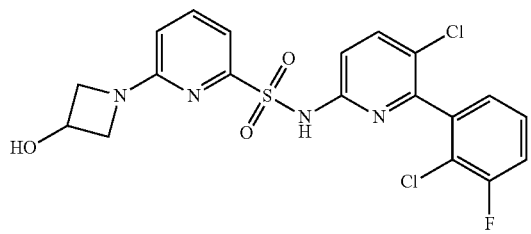 [SMILES: O=S(=O)(Nc1ccc(Cl)c(-c2cccc(F)c2Cl)n1)c1cccc(N2CC(O)C2)n1] |
| 230 | 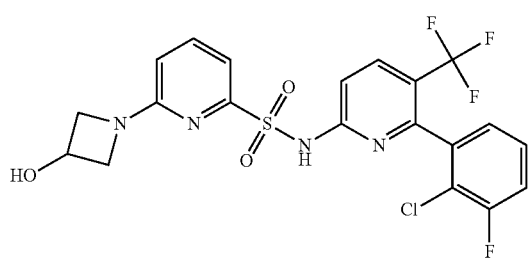 [SMILES: O=S(=O)(Nc1ccc(C(F)(F)F)c(-c2cccc(F)c2Cl)n1)c1cccc(N2CC(O)C2)n1] |
| 231 | 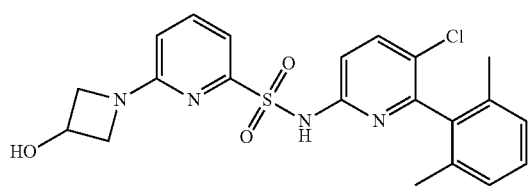 [SMILES: Cc1cccc(C)c1-c1nc(NS(=O)(=O)c2cccc(N3CC(O)C3)n2)ccc1Cl] |
| 232 | 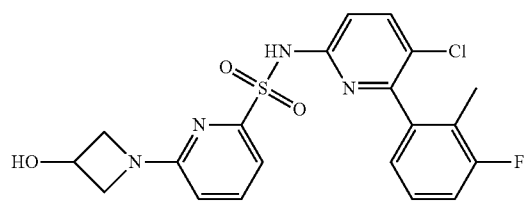 [SMILES: Cc1c(F)cccc1-c1nc(NS(=O)(=O)c2cccc(N3CC(O)C3)n2)ccc1Cl] |
| 233 | 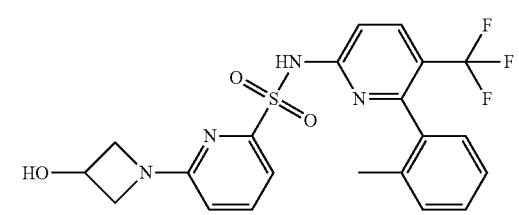 [SMILES: Cc1ccccc1-c1nc(NS(=O)(=O)c2cccc(N3CC(O)C3)n2)ccc1C(F)(F)F] |
| 234 | 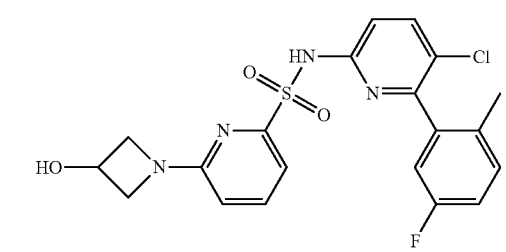 [SMILES: Cc1ccc(F)cc1-c1nc(NS(=O)(=O)c2cccc(N3CC(O)C3)n2)ccc1Cl] |

| Ex. No. | Product |
|---|---|
| 235 | 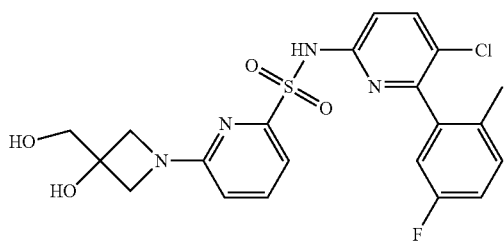 [SMILES: Cc1ccc(F)cc1-c1nc(NS(=O)(=O)c2cccc(N3CC(O)(CO)C3)n2)ccc1Cl] |
| 236 | 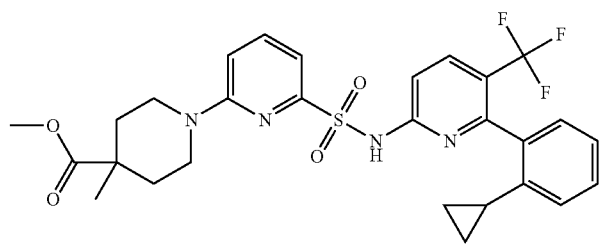 [SMILES: COC(=O)C1(C)CCN(c2cccc(S(=O)(=O)Nc3ccc(C(F)(F)F)c(-c4ccccc4C4CC4)n3)n2)CC1] |
| 237 | 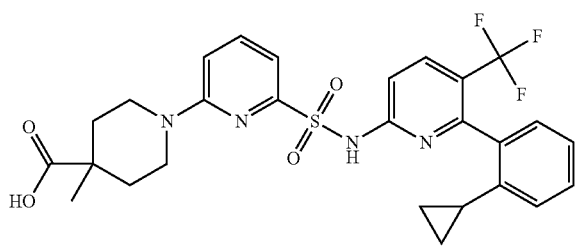 [SMILES: CC1(C(=O)O)CCN(c2cccc(S(=O)(=O)Nc3ccc(C(F)(F)F)c(-c4ccccc4C4CC4)n3)n2)CC1] |
| 238 | 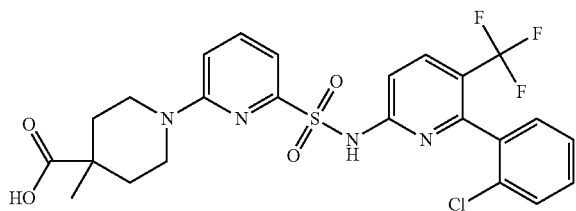 [SMILES: CC1(C(=O)O)CCN(c2cccc(S(=O)(=O)Nc3ccc(C(F)(F)F)c(-c4ccccc4Cl)n3)n2)CC1] |
| 239 | 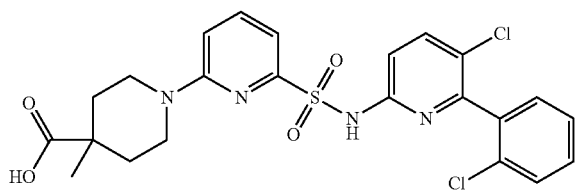 [SMILES: CC1(C(=O)O)CCN(c2cccc(S(=O)(=O)Nc3ccc(Cl)c(-c4ccccc4Cl)n3)n2)CC1] |
| 240 | 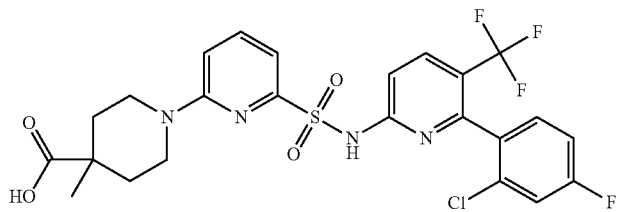 [SMILES: CC1(C(=O)O)CCN(c2cccc(S(=O)(=O)Nc3ccc(C(F)(F)F)c(-c4ccc(F)cc4Cl)n3)n2)CC1] |

-continued
| Ex. No. | Product |
|---|---|
| 241 | 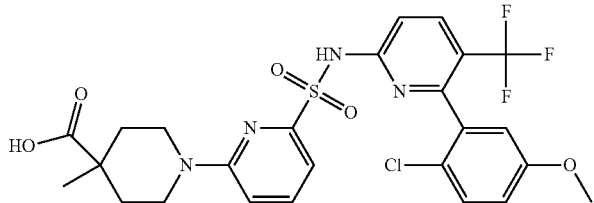 [SMILES: COc1ccc(Cl)c(-c2nc(NS(=O)(=O)c3cccc(N4CCC(C)(C(=O)O)CC4)n3)ccc2C(F)(F)F)c1] |
| 242 | 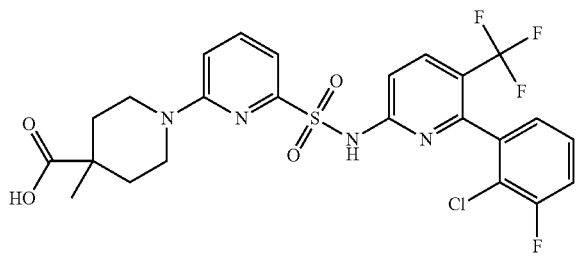 [SMILES: CC1(C(=O)O)CCN(c2cccc(S(=O)(=O)Nc3ccc(C(F)(F)F)c(-c4cccc(F)c4Cl)n3)n2)CC1] |
| 243 | 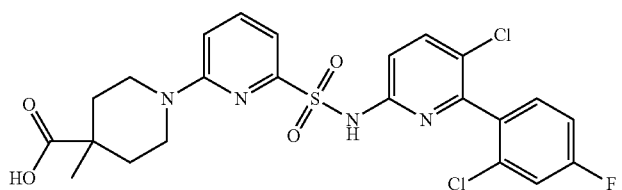 [SMILES: CC1(C(=O)O)CCN(c2cccc(S(=O)(=O)Nc3ccc(Cl)c(-c4ccc(F)cc4Cl)n3)n2)CC1] |
| 244 | 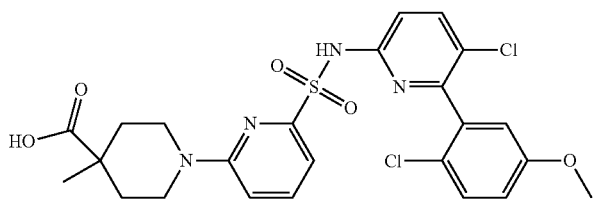 [SMILES: COc1ccc(Cl)c(-c2nc(NS(=O)(=O)c3cccc(N4CCC(C)(C(=O)O)CC4)n3)ccc2Cl)c1] |
| 245 | 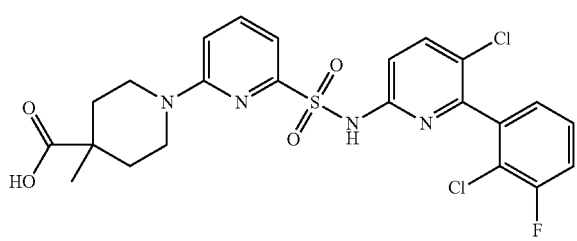 [SMILES: CC1(C(=O)O)CCN(c2cccc(S(=O)(=O)Nc3ccc(Cl)c(-c4cccc(F)c4Cl)n3)n2)CC1] |
| 246 | 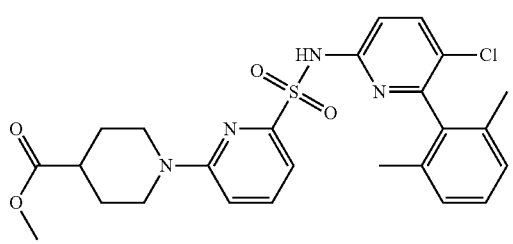 [SMILES: COC(=O)C1CCN(c2cccc(S(=O)(=O)Nc3ccc(Cl)c(-c4c(C)cccc4C)n3)n2)CC1] |
| 247 | 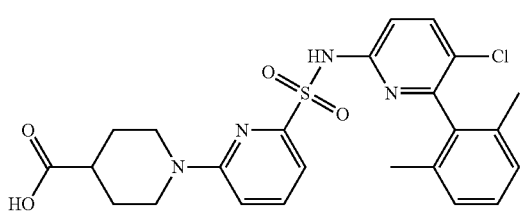 [SMILES: Cc1cccc(C)c1-c1nc(NS(=O)(=O)c2cccc(N3CCC(C(=O)O)CC3)n2)ccc1Cl] |

-continued
| Ex. No. | Product |
|---|---|
| 248 | 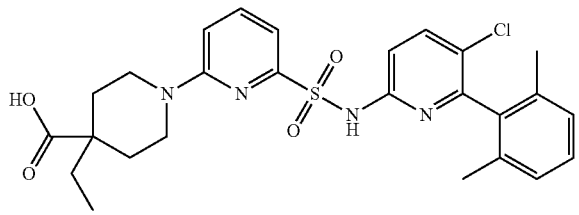 [SMILES: CCC1(C(=O)O)CCN(c2cccc(S(=O)(=O)Nc3ccc(Cl)c(-c4c(C)cccc4C)n3)n2)CC1] |
| 249 | 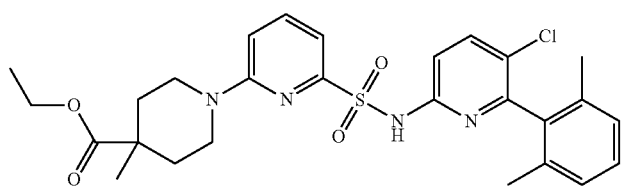 [SMILES: CCOC(=O)C1(C)CCN(c2cccc(S(=O)(=O)Nc3ccc(Cl)c(-c4c(C)cccc4C)n3)n2)CC1] |
| 250 | 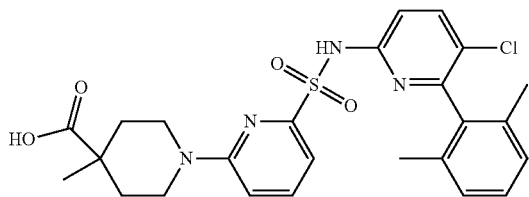 [SMILES: Cc1cccc(C)c1-c1nc(NS(=O)(=O)c2cccc(N3CCC(C)(C(=O)O)CC3)n2)ccc1Cl] |
| 251 | 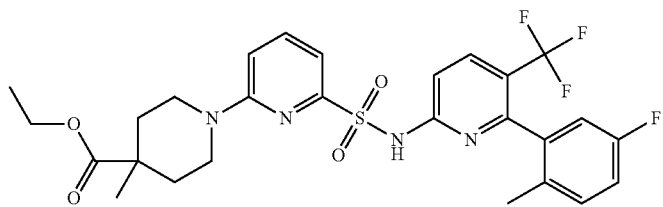 [SMILES: CCOC(=O)C1(C)CCN(c2cccc(S(=O)(=O)Nc3ccc(C(F)(F)F)c(-c4cc(F)ccc4C)n3)n2)CC1] |
| 252 | 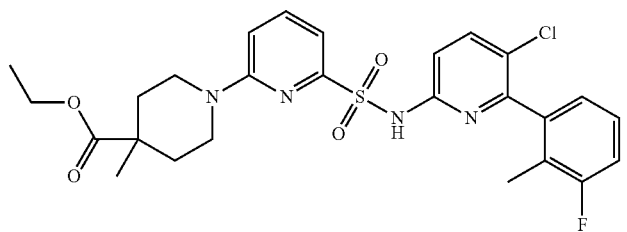 [SMILES: CCOC(=O)C1(C)CCN(c2cccc(S(=O)(=O)Nc3ccc(Cl)c(-c4cccc(F)c4C)n3)n2)CC1] |
| 253 | 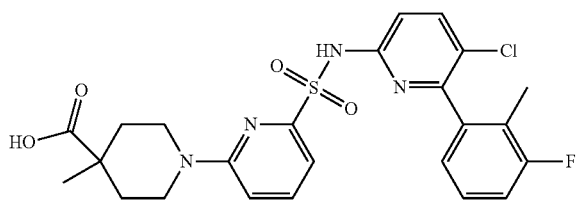 [SMILES: Cc1c(F)cccc1-c1nc(NS(=O)(=O)c2cccc(N3CCC(C)(C(=O)O)CC3)n2)ccc1Cl] |
| 254 | 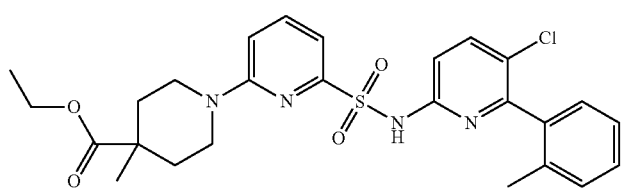 [SMILES: CCOC(=O)C1(C)CCN(c2cccc(S(=O)(=O)Nc3ccc(Cl)c(-c4ccccc4C)n3)n2)CC1] |

| Ex. No. | Product |
|---|---|
| 255 | 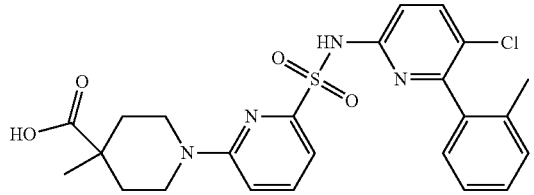 [SMILES: Cc1ccccc1-c1nc(NS(=O)(=O)c2cccc(N3CCC(C)(C(=O)O)CC3)n2)ccc1Cl] |
| 256 | 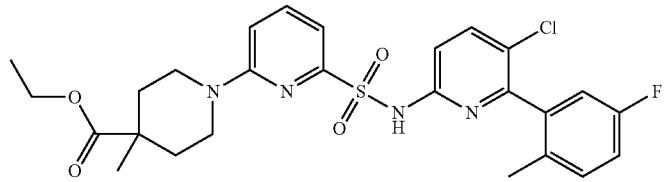 [SMILES: CCOC(=O)C1(C)CCN(c2cccc(S(=O)(=O)Nc3ccc(Cl)c(-c4cc(F)ccc4C)n3)n2)CC1] |
| 257 | 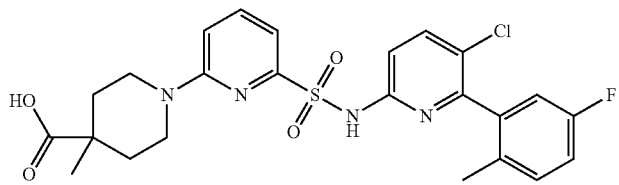 [SMILES: Cc1ccc(F)cc1-c1nc(NS(=O)(=O)c2cccc(N3CCC(C)(C(=O)O)CC3)n2)ccc1Cl] |
| 258 | 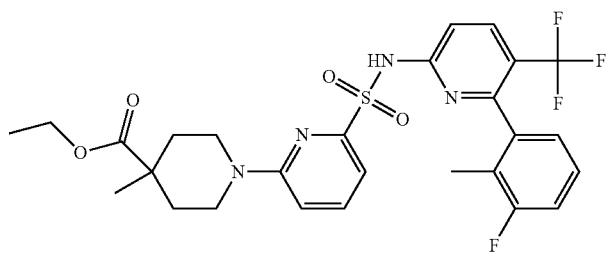 [SMILES: CCOC(=O)C1(C)CCN(c2cccc(S(=O)(=O)Nc3ccc(C(F)(F)F)c(-c4cccc(F)c4C)n3)n2)CC1] |
| 259 | 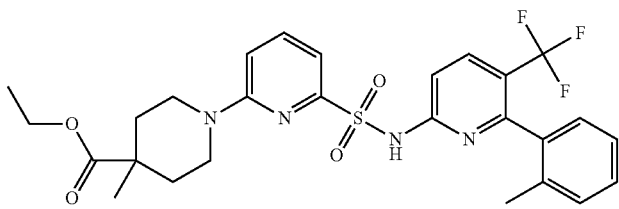 [SMILES: CCOC(=O)C1(C)CCN(c2cccc(S(=O)(=O)Nc3ccc(C(F)(F)F)c(-c4ccccc4C)n3)n2)CC1] |
| 260 | 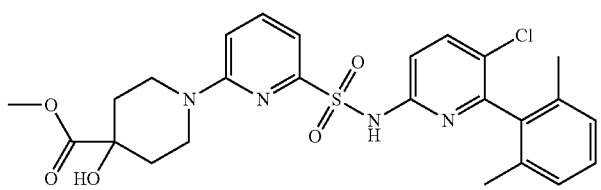 [SMILES: COC(=O)C1(O)CCN(c2cccc(S(=O)(=O)Nc3ccc(Cl)c(-c4c(C)cccc4C)n3)n2)CC1] |
| 261 | 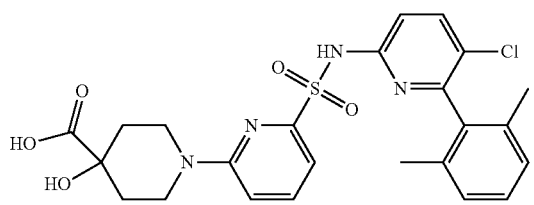 |

-continued
| Ex. No. | Product |
|---|---|
| 262 | 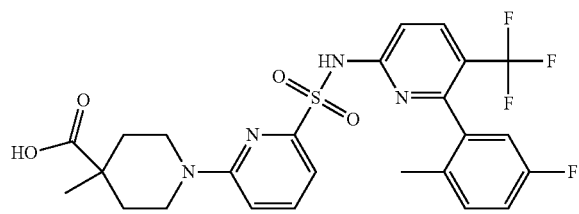 [SMILES: Cc1ccc(F)cc1-c1nc(NS(=O)(=O)c2cccc(N3CCC(C)(C(=O)O)CC3)n2)ccc1C(F)(F)F] |
| 263 | 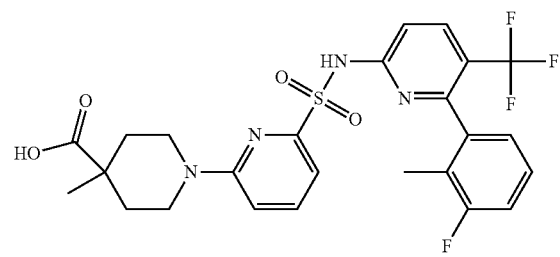 [SMILES: Cc1c(F)cccc1-c1nc(NS(=O)(=O)c2cccc(N3CCC(C)(C(=O)O)CC3)n2)ccc1C(F)(F)F] |
| 264 | 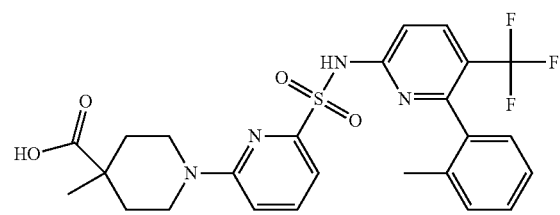 [SMILES: Cc1ccccc1-c1nc(NS(=O)(=O)c2cccc(N3CCC(C)(C(=O)O)CC3)n2)ccc1C(F)(F)F] |
| 265 | 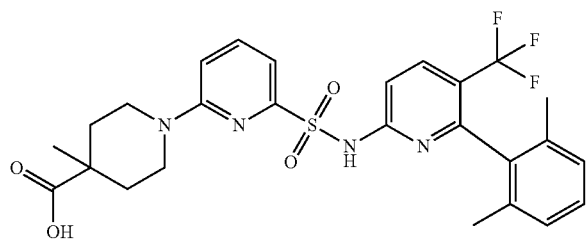 [SMILES: Cc1cccc(C)c1-c1nc(NS(=O)(=O)c2cccc(N3CCC(C)(C(=O)O)CC3)n2)ccc1C(F)(F)F] |
| 266 | 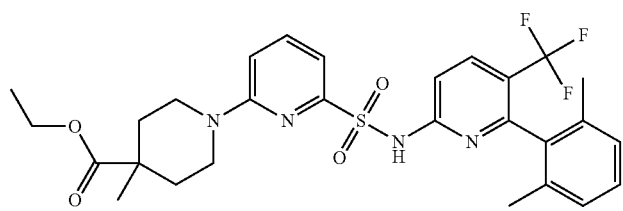 [SMILES: CCOC(=O)C1(C)CCN(c2cccc(S(=O)(=O)Nc3ccc(C(F)(F)F)c(-c4c(C)cccc4C)n3)n2)CC1] |
| 267 | 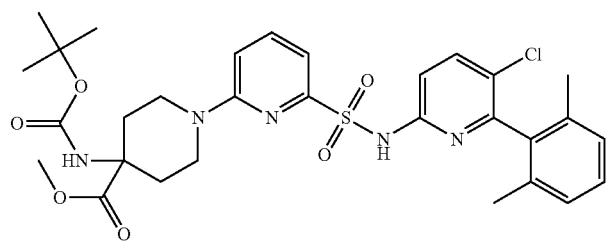 [SMILES: COC(=O)C1(NC(=O)OC(C)(C)C)CCN(c2cccc(S(=O)(=O)Nc3ccc(Cl)c(-c4c(C)cccc4C)n3)n2)CC1] |

| Ex. No. | Product |
|---|---|
| 268 | 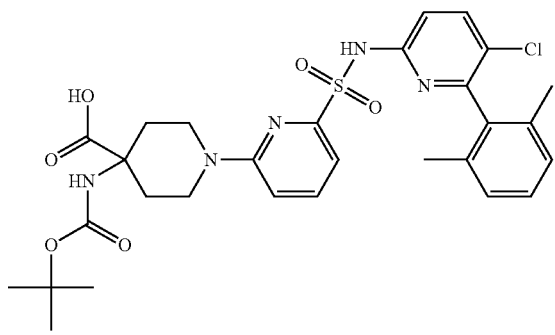 [SMILES: Cc1cccc(C)c1-c1nc(NS(=O)(=O)c2cccc(N3CCC(NC(=O)OC(C)(C)C)(C(=O)O)CC3)n2)ccc1Cl] |
| 269 | 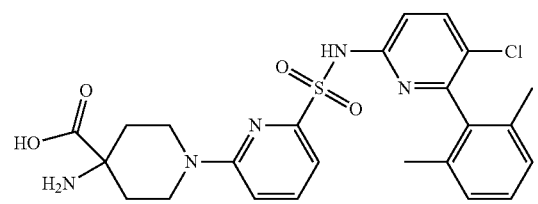 [SMILES: Cc1cccc(C)c1-c1nc(NS(=O)(=O)c2cccc(N3CCC(N)(C(=O)O)CC3)n2)ccc1Cl] |
| 270 | 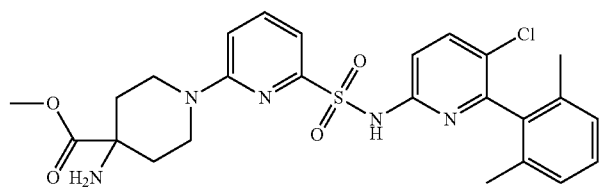 [SMILES: COC(=O)C1(N)CCN(c2cccc(S(=O)(=O)Nc3ccc(Cl)c(-c4c(C)cccc4C)n3)n2)CC1] |
| 271 | 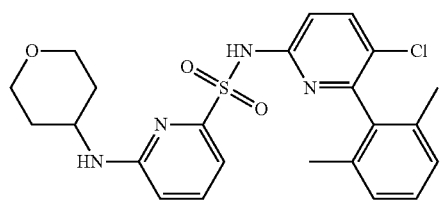 [SMILES: Cc1cccc(C)c1-c1nc(NS(=O)(=O)c2cccc(NC3CCOCC3)n2)ccc1Cl] |
| 272 | 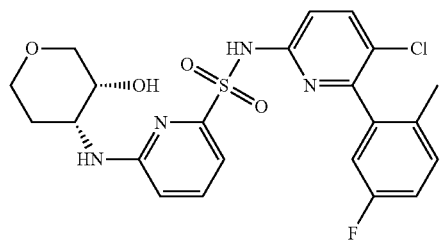 [SMILES: Cc1ccc(F)cc1-c1nc(NS(=O)(=O)c2cccc(N[C@@H]3CCOC[C@@H]3O)n2)ccc1Cl] |
| 273 | 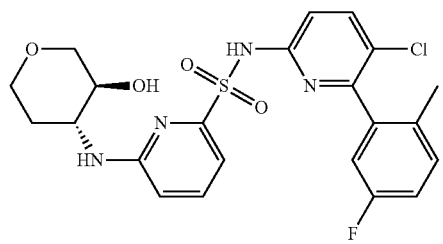 [SMILES: Cc1ccc(F)cc1-c1nc(NS(=O)(=O)c2cccc(N[C@@H]3CCOC[C@H]3O)n2)ccc1Cl] |

US 10,450,273 B2
265
266
-continued
| Ex. No. | Product |
|---|---|
| 274 | 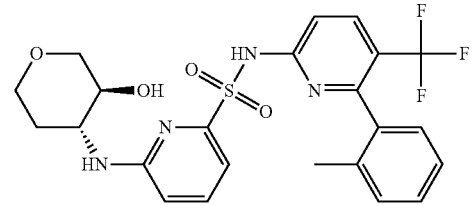 [SMILES: Cc1ccccc1-c1nc(NS(=O)(=O)c2cccc(N[C@@H]3CCOC[C@H]3O)n2)ccc1C(F)(F)F] |
| 275 | 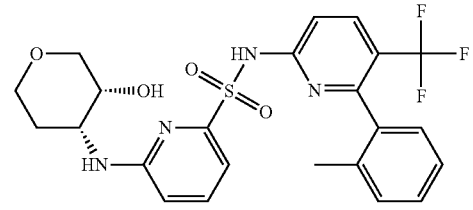 |
| 276 | 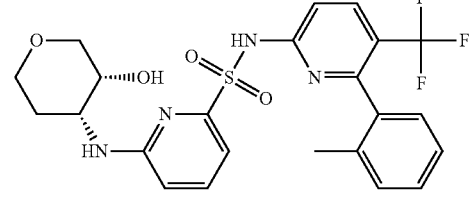 |
| 277 | 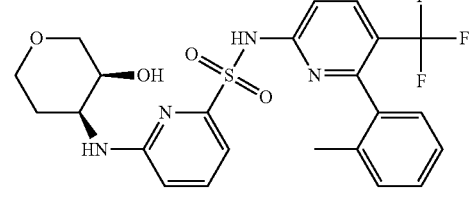 |
| 278 | 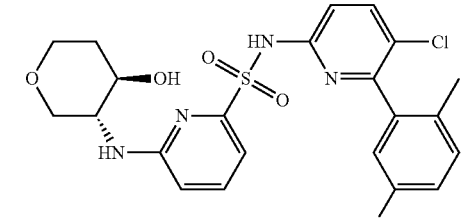 |
| 279 | 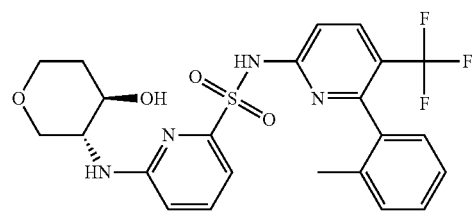 [SMILES: Cc1ccccc1-c1nc(NS(=O)(=O)c2cccc(N[C@@H]3COCC[C@H]3O)n2)ccc1C(F)(F)F] |
| 280 | 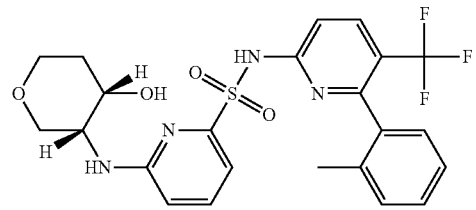 [SMILES: Cc1ccccc1-c1nc(NS(=O)(=O)c2cccc(N[C@@H]3COCC[C@@H]3O)n2)ccc1C(F)(F)F] |

-continued
| Ex. No. | Product |
|---|---|
| 281 | 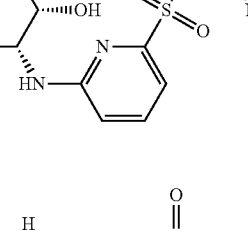 |
| 282 | 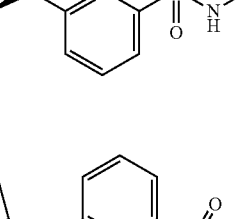 |
| 283 | 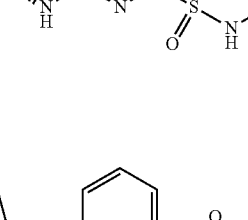 |
| 284 | 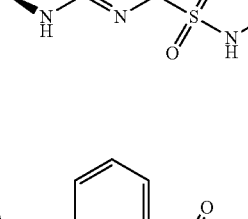 |
| 285 | 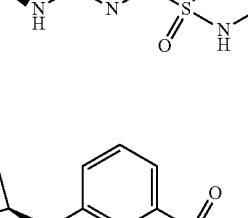 |
| 286 | 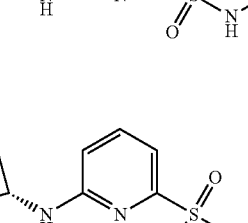 |
| 287 |  |

| Ex. No. | Product |
|---|---|
| 288 | 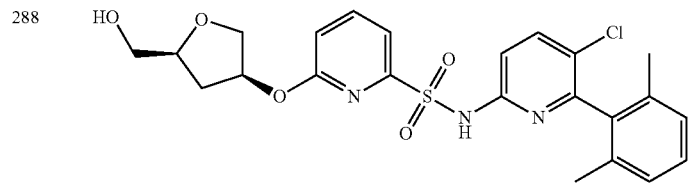 |
| 289 | 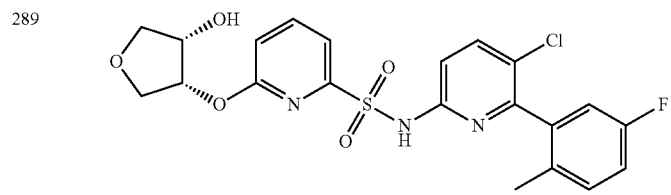 |
| 290 | 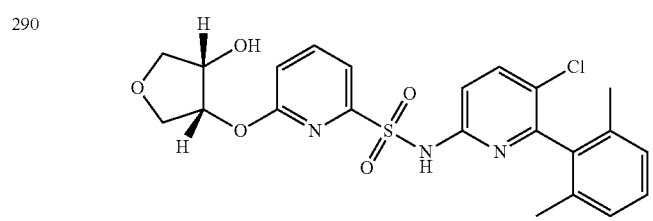 |
| 291 | 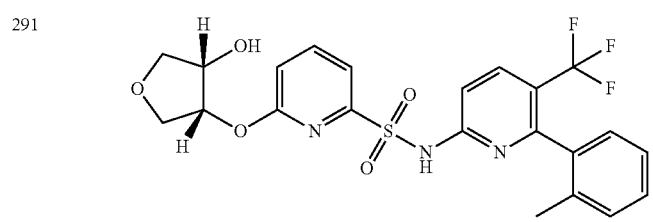 |
| 292 | 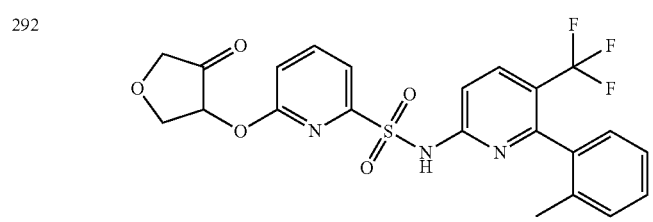 |
| 293 | 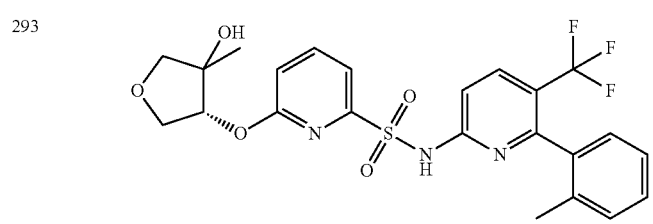 |
| 294 | 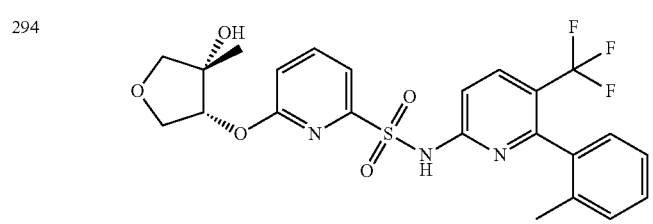 |

| Ex. No. | Product |
|---|---|
| 295 | |
| 296 | |
| 297 | |
| 298 | |
| 299 | |
| 300 | |
| 301 | |

-continued
| Ex. No. | Product |
|---|---|
| 302 | 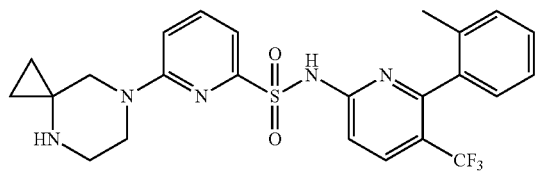 [SMILES: Cc1ccccc1-c1nc(NS(=O)(=O)c2cccc(N3CCNC4(CC4)C3)n2)ccc1C(F)(F)F] |
| 303 | 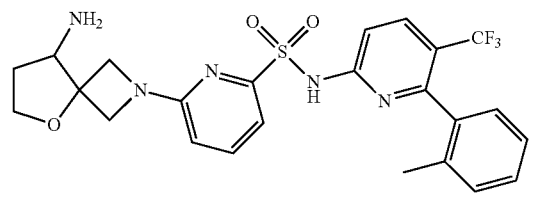 [SMILES: Cc1ccccc1-c1nc(NS(=O)(=O)c2cccc(N3CC4(C3)OCCC4N)n2)ccc1C(F)(F)F] |
| 304 | 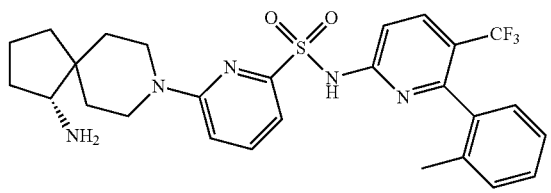 [SMILES: Cc1ccccc1-c1nc(NS(=O)(=O)c2cccc(N3CCC4(CCC[C@H]4N)CC3)n2)ccc1C(F)(F)F] |
| 305 | 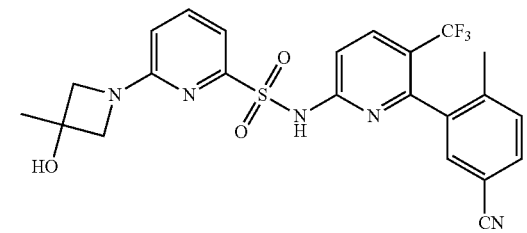 [SMILES: Cc1ccc(C#N)cc1-c1nc(NS(=O)(=O)c2cccc(N3CC(C)(O)C3)n2)ccc1C(F)(F)F] |
| 306 | 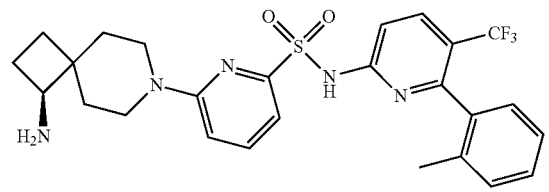 [SMILES: Cc1ccccc1-c1nc(NS(=O)(=O)c2cccc(N3CCC4(CC[C@@H]4N)CC3)n2)ccc1C(F)(F)F] |
| 307 | 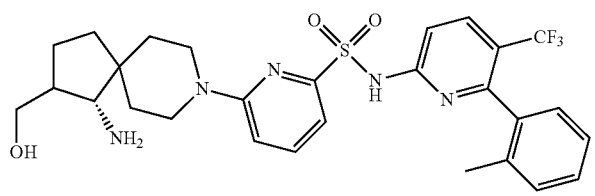 [SMILES: Cc1ccccc1-c1nc(NS(=O)(=O)c2cccc(N3CCC4(CCC(CO)[C@H]4N)CC3)n2)ccc1C(F)(F)F] |
| 308 | 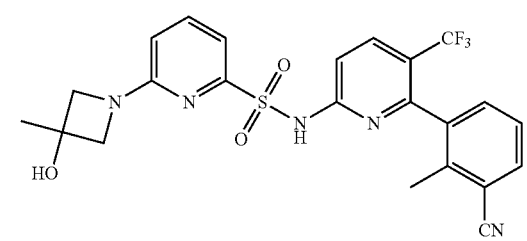 [SMILES: Cc1c(C#N)cccc1-c1nc(NS(=O)(=O)c2cccc(N3CC(C)(O)C3)n2)ccc1C(F)(F)F] |

| Ex. No. | Product |
|---|---|
| 309 | 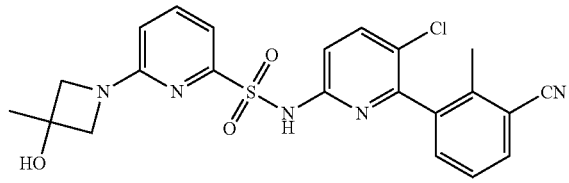 [SMILES: Cc1c(C#N)cccc1-c1nc(NS(=O)(=O)c2cccc(N3CC(C)(O)C3)n2)ccc1Cl] |
| 310 | 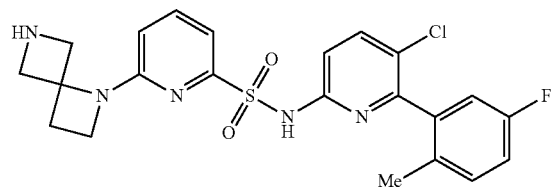 [SMILES: Cc1ccc(F)cc1-c1nc(NS(=O)(=O)c2cccc(N3CCC34CNC4)n2)ccc1Cl] |
| 311 | 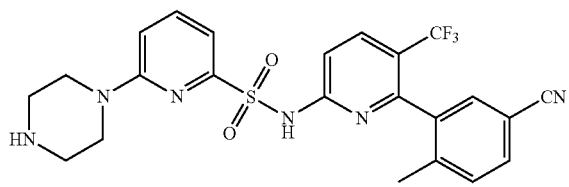 [SMILES: Cc1ccc(C#N)cc1-c1nc(NS(=O)(=O)c2cccc(N3CCNCC3)n2)ccc1C(F)(F)F] |
| 312 | 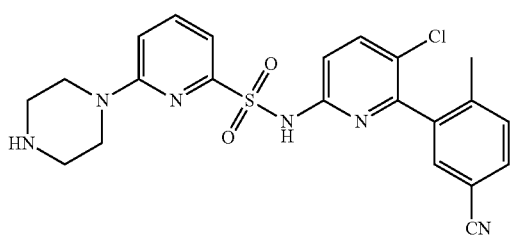 [SMILES: Cc1ccc(C#N)cc1-c1nc(NS(=O)(=O)c2cccc(N3CCNCC3)n2)ccc1Cl] |
| 313 | 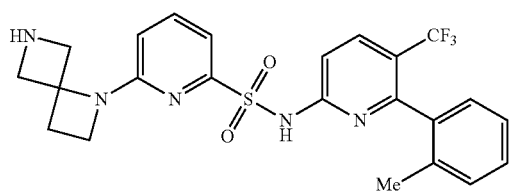 [SMILES: Cc1ccccc1-c1nc(NS(=O)(=O)c2cccc(N3CCC34CNC4)n2)ccc1C(F)(F)F] |
| 314 | 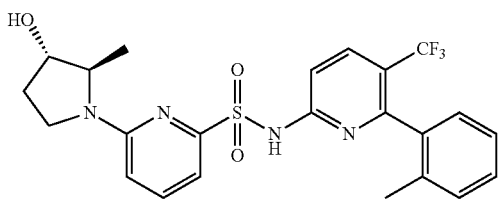 [SMILES: Cc1ccccc1-c1nc(NS(=O)(=O)c2cccc(N3CC[C@H](O)[C@H]3C)n2)ccc1C(F)(F)F] |
| 315 | 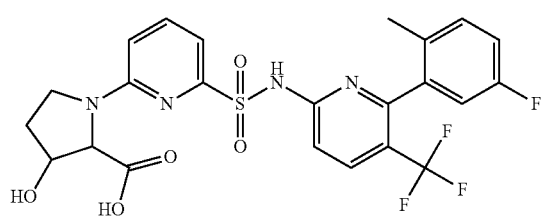 [SMILES: Cc1ccc(F)cc1-c1nc(NS(=O)(=O)c2cccc(N3CCC(O)C3C(=O)O)n2)ccc1C(F)(F)F] |

-continued
| Ex. No. | Product |
|---|---|
| 316 | 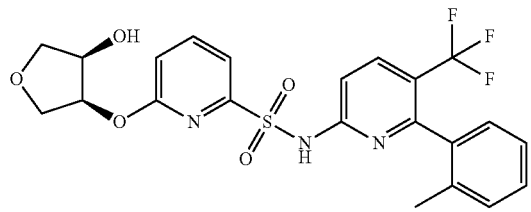 [SMILES: Cc1ccccc1-c1nc(NS(=O)(=O)c2cccc(O[C@H]3COC[C@H]3O)n2)ccc1C(F)(F)F] |
| 317 | 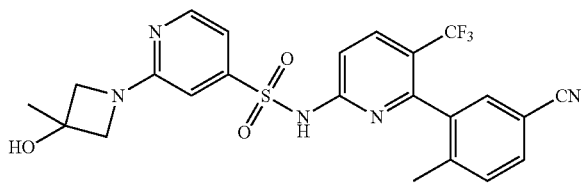 [SMILES: Cc1ccc(C#N)cc1-c1nc(NS(=O)(=O)c2ccnc(N3CC(C)(O)C3)c2)ccc1C(F)(F)F] |
| 318 | 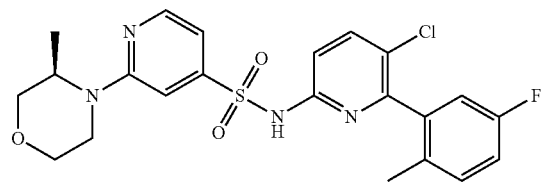 [SMILES: Cc1ccc(F)cc1-c1nc(NS(=O)(=O)c2ccnc(N3CCOC[C@H]3C)c2)ccc1Cl] |
| 319 | 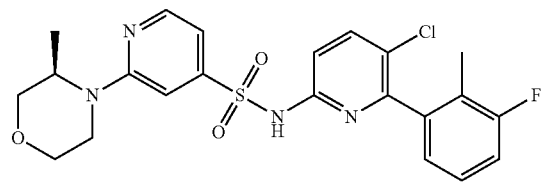 [SMILES: Cc1c(F)cccc1-c1nc(NS(=O)(=O)c2ccnc(N3CCOC[C@H]3C)c2)ccc1Cl] |
| 320 | 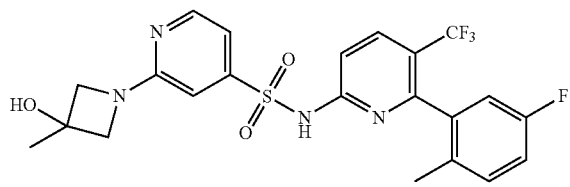 [SMILES: Cc1ccc(F)cc1-c1nc(NS(=O)(=O)c2ccnc(N3CC(C)(O)C3)c2)ccc1C(F)(F)F] |
| 321 | 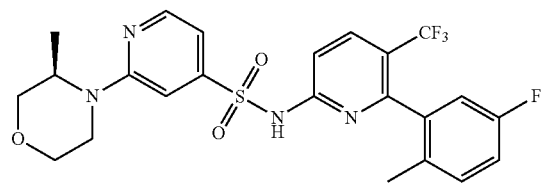 [SMILES: Cc1ccc(F)cc1-c1nc(NS(=O)(=O)c2ccnc(N3CCOC[C@H]3C)c2)ccc1C(F)(F)F] |
| 322 | 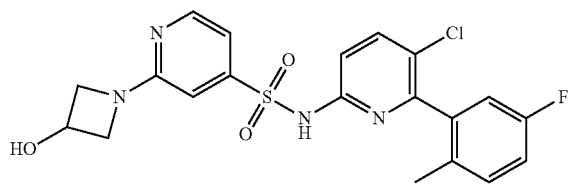 [SMILES: Cc1ccc(F)cc1-c1nc(NS(=O)(=O)c2ccnc(N3CC(O)C3)c2)ccc1Cl] |

-continued
| Ex. No. | Product |
|---|---|
| 323 | 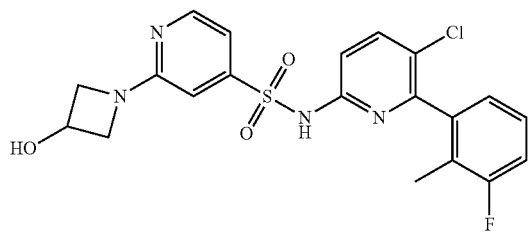 [SMILES: Cc1c(F)cccc1-c1nc(NS(=O)(=O)c2ccnc(N3CC(O)C3)c2)ccc1Cl] |
| 324 | 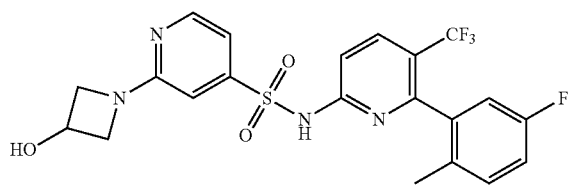 [SMILES: Cc1ccc(F)cc1-c1nc(NS(=O)(=O)c2ccnc(N3CC(O)C3)c2)ccc1C(F)(F)F] |
| 325 | 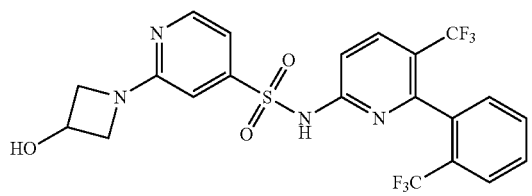 [SMILES: O=S(=O)(Nc1ccc(C(F)(F)F)c(-c2ccccc2C(F)(F)F)n1)c1ccnc(N2CC(O)C2)c1] |
| 326 | 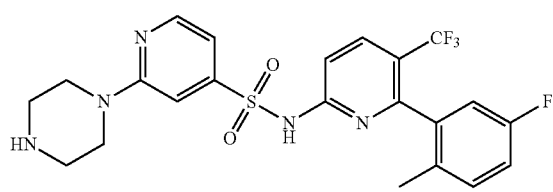 |
| 327 | 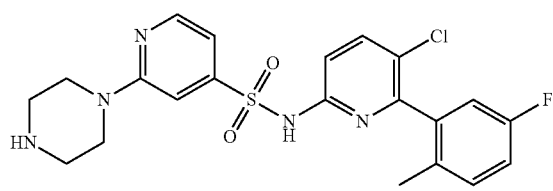 [SMILES: Cc1ccc(F)cc1-c1nc(NS(=O)(=O)c2ccnc(N3CCNCC3)c2)ccc1Cl] |
| 328 | 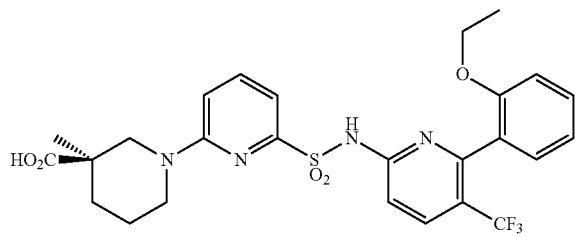 |
| 329 | 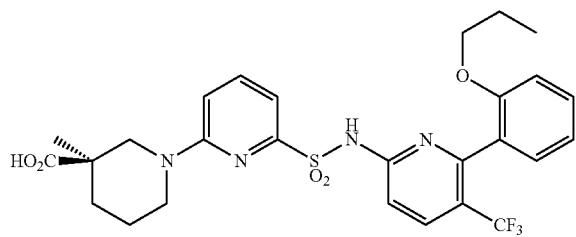 [SMILES: CCCOc1ccccc1-c1nc(NS(=O)(=O)c2cccc(N3CCC[C@@](C)(C(=O)O)C3)n2)ccc1C(F)(F)F] |

-continued
| Ex. No. | Product |
|---|---|
| 330 | 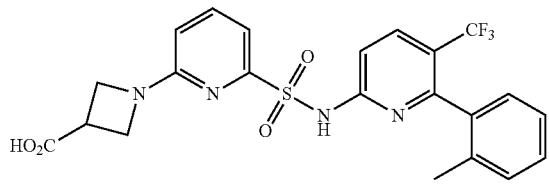 [SMILES: Cc1ccccc1-c1nc(NS(=O)(=O)c2cccc(N3CC(C(=O)O)C3)n2)ccc1C(F)(F)F] |
| 331 | 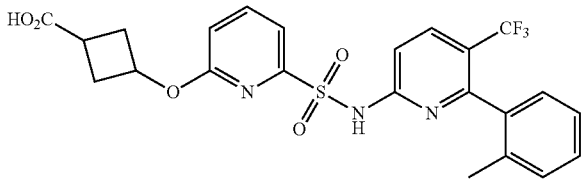 [SMILES: Cc1ccccc1-c1nc(NS(=O)(=O)c2cccc(OC3CC(C(=O)O)C3)n2)ccc1C(F)(F)F] |
| 332 | 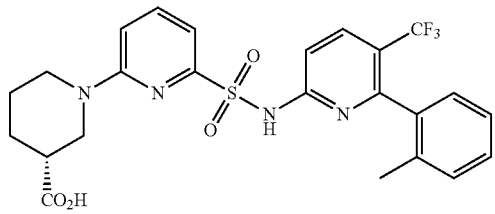 [SMILES: Cc1ccccc1-c1nc(NS(=O)(=O)c2cccc(N3CCC[C@@H](C(=O)O)C3)n2)ccc1C(F)(F)F] |
| 333 | 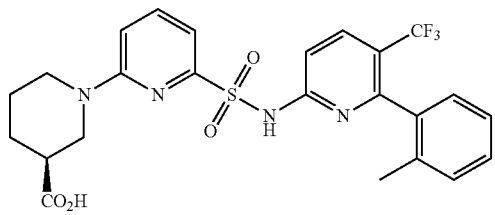 [SMILES: Cc1ccccc1-c1nc(NS(=O)(=O)c2cccc(N3CCC[C@H](C(=O)O)C3)n2)ccc1C(F)(F)F] |
| 334 | 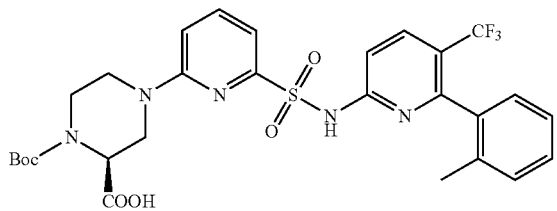 [SMILES: Cc1ccccc1-c1nc(NS(=O)(=O)c2cccc(N3CCN(C(=O)OC(C)(C)C)[C@H](C(=O)O)C3)n2)ccc1C(F)(F)F] |
| 335 | 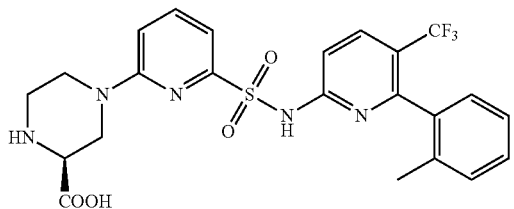 [SMILES: Cc1ccccc1-c1nc(NS(=O)(=O)c2cccc(N3CCN[C@H](C(=O)O)C3)n2)ccc1C(F)(F)F] |
| 336 | 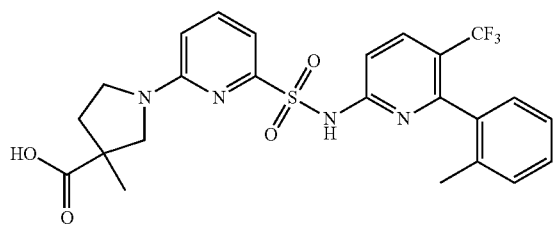 [SMILES: Cc1ccccc1-c1nc(NS(=O)(=O)c2cccc(N3CCC(C)(C(=O)O)C3)n2)ccc1C(F)(F)F] |

US 10,450,273 B2
283
-continued
| Ex. No. | Product |
|---|---|
| 337 | 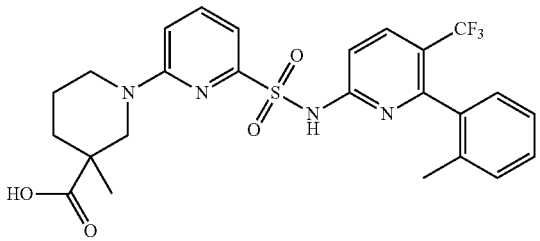 [SMILES: Cc1ccccc1-c1nc(NS(=O)(=O)c2cccc(N3CCCC(C)(C(=O)O)C3)n2)ccc1C(F)(F)F] |
| 338 | 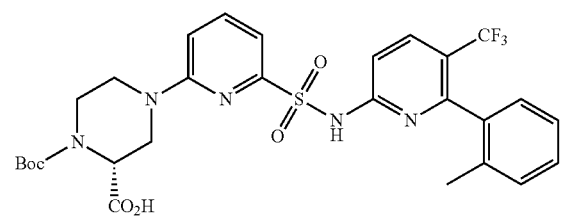 [SMILES: Cc1ccccc1-c1nc(NS(=O)(=O)c2cccc(N3CCN(C(=O)OC(C)(C)C)[C@@H](C(=O)O)C3)n2)ccc1C(F)(F)F] |
| 339 | 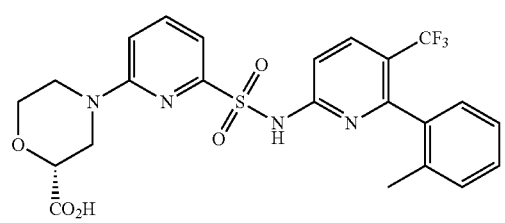 [SMILES: Cc1ccccc1-c1nc(NS(=O)(=O)c2cccc(N3CCO[C@@H](C(=O)O)C3)n2)ccc1C(F)(F)F] |
| 340 | 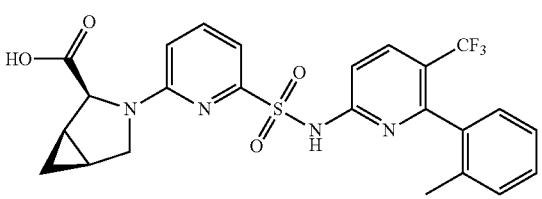 [SMILES: Cc1ccccc1-c1nc(NS(=O)(=O)c2cccc(N3C[C@H]4C[C@H]4[C@H]3C(=O)O)n2)ccc1C(F)(F)F] |
| 341 | 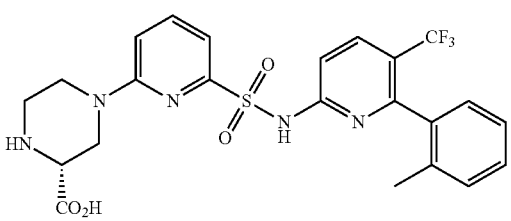 [SMILES: Cc1ccccc1-c1nc(NS(=O)(=O)c2cccc(N3CCN[C@@H](C(=O)O)C3)n2)ccc1C(F)(F)F] |
| 342 | 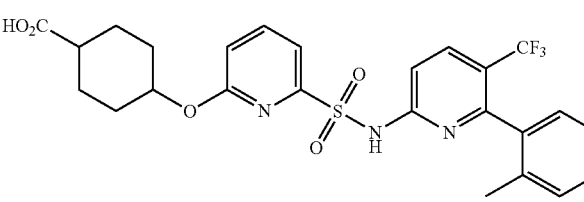 |
| 343 | 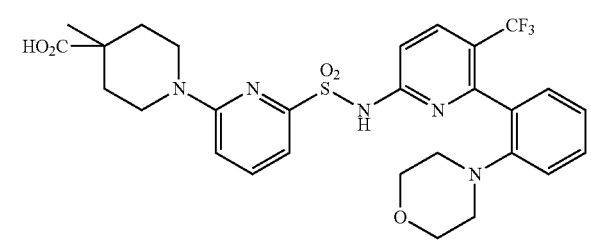 [SMILES: CC1(C(=O)O)CCN(c2cccc(S(=O)(=O)Nc3ccc(C(F)(F)F)c(-c4ccccc4N4CCOCC4)n3)n2)CC1] |
284

-continued
| Ex. No. | Product |
|---|---|
| 344 | 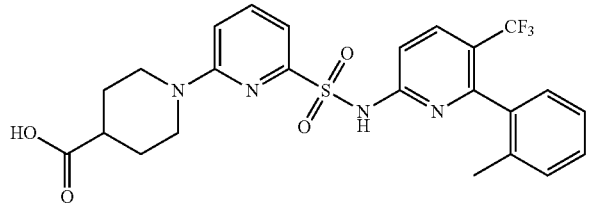 [SMILES: Cc1ccccc1-c1nc(NS(=O)(=O)c2cccc(N3CCC(C(=O)O)CC3)n2)ccc1C(F)(F)F] |
| 345 | 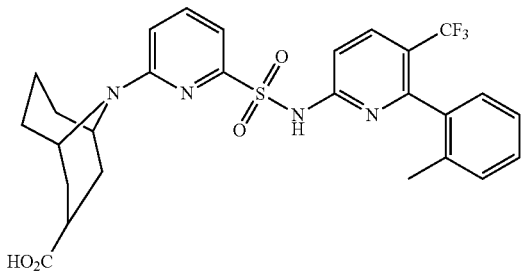 [SMILES: Cc1ccccc1-c1nc(NS(=O)(=O)c2cccc(N3C4CCCC3CC(C(=O)O)C4)n2)ccc1C(F)(F)F] |
| 346 | 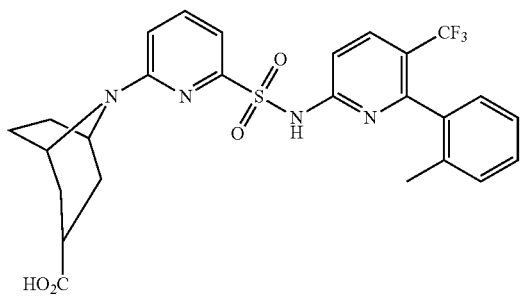 [SMILES: Cc1ccccc1-c1nc(NS(=O)(=O)c2cccc(N3C4CCC3CC(C(=O)O)C4)n2)ccc1C(F)(F)F] |
| 347 | 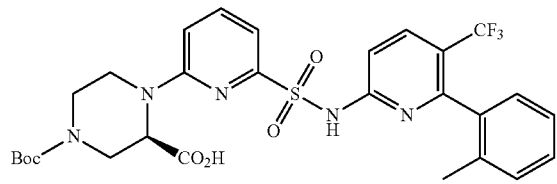 [SMILES: Cc1ccccc1-c1nc(NS(=O)(=O)c2cccc(N3CCN(C(=O)OC(C)(C)C)C[C@@H]3C(=O)O)n2)ccc1C(F)(F)F] |
| 348 | 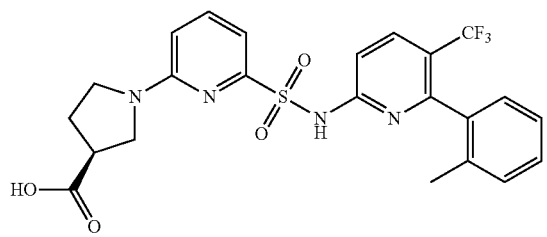 [SMILES: Cc1ccccc1-c1nc(NS(=O)(=O)c2cccc(N3CC[C@H](C(=O)O)C3)n2)ccc1C(F)(F)F] |
| 349 | 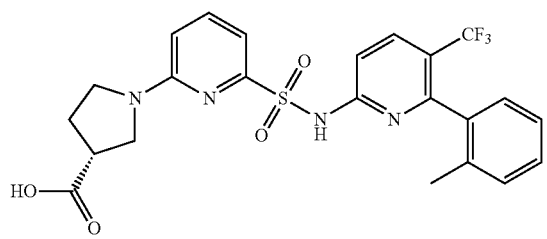 [SMILES: Cc1ccccc1-c1nc(NS(=O)(=O)c2cccc(N3CC[C@@H](C(=O)O)C3)n2)ccc1C(F)(F)F] |

-continued
| Ex. No. | Product |
|---|---|
| 350 | 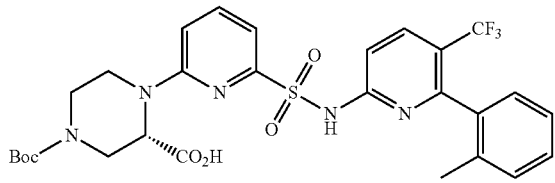 [SMILES: Cc1ccccc1-c1nc(NS(=O)(=O)c2cccc(N3CCN(C(=O)OC(C)(C)C)C[C@H]3C(=O)O)n2)ccc1C(F)(F)F] |
| 351 | 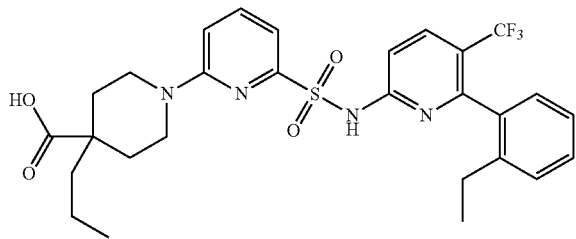 [SMILES: CCCC1(C(=O)O)CCN(c2cccc(S(=O)(=O)Nc3ccc(C(F)(F)F)c(-c4ccccc4CC)n3)n2)CC1] |
| 352 | 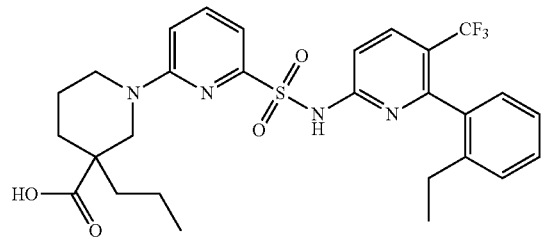 [SMILES: CCCC1(C(=O)O)CCCN(c2cccc(S(=O)(=O)Nc3ccc(C(F)(F)F)c(-c4ccccc4CC)n3)n2)C1] |
| 353 | 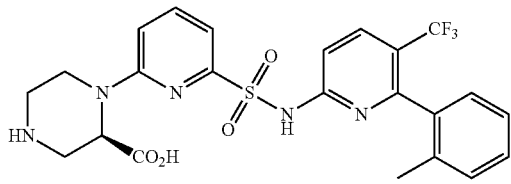 [SMILES: Cc1ccccc1-c1nc(NS(=O)(=O)c2cccc(N3CCNC[C@@H]3C(=O)O)n2)ccc1C(F)(F)F] |
| 354 | 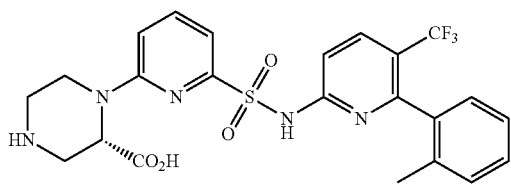 [SMILES: Cc1ccccc1-c1nc(NS(=O)(=O)c2cccc(N3CCNC[C@H]3C(=O)O)n2)ccc1C(F)(F)F] |
| 355 | 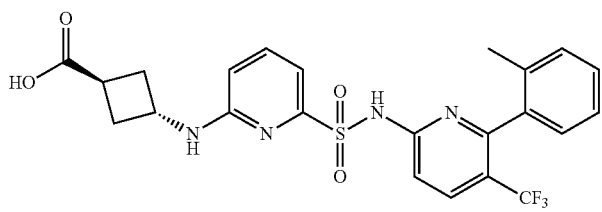 [SMILES: Cc1ccccc1-c1nc(NS(=O)(=O)c2cccc(N[C@H]3C[C@H](C(=O)O)C3)n2)ccc1C(F)(F)F] |
| 356 | 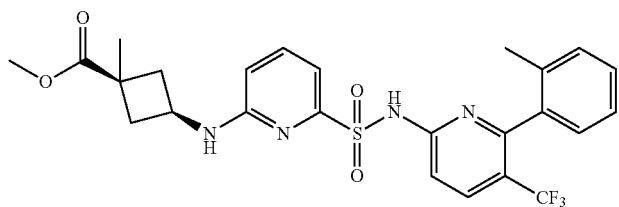 [SMILES: COC(=O)[C@]1(C)C[C@H](Nc2cccc(S(=O)(=O)Nc3ccc(C(F)(F)F)c(-c4ccccc4C)n3)n2)C1] |

| Ex. No. | Product |
|---|---|
| 357 | 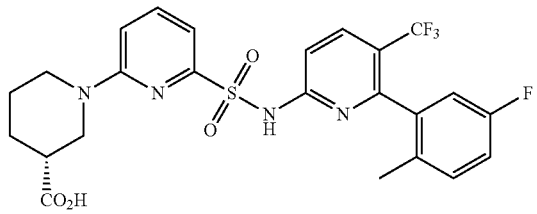 [SMILES: Cc1ccc(F)cc1-c1nc(NS(=O)(=O)c2cccc(N3CCC[C@@H](C(=O)O)C3)n2)ccc1C(F)(F)F] |
| 358 | 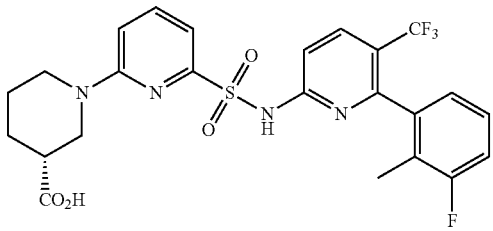 [SMILES: Cc1c(F)cccc1-c1nc(NS(=O)(=O)c2cccc(N3CCC[C@@H](C(=O)O)C3)n2)ccc1C(F)(F)F] |
| 359 | 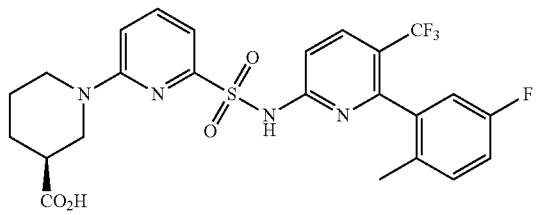 [SMILES: Cc1ccc(F)cc1-c1nc(NS(=O)(=O)c2cccc(N3CCC[C@H](C(=O)O)C3)n2)ccc1C(F)(F)F] |
| 360 | 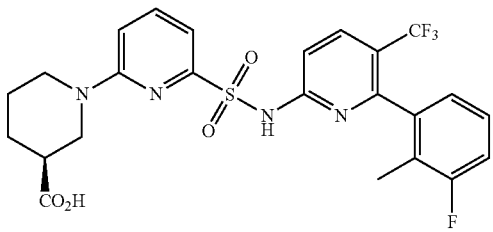 [SMILES: Cc1c(F)cccc1-c1nc(NS(=O)(=O)c2cccc(N3CCC[C@H](C(=O)O)C3)n2)ccc1C(F)(F)F] |
| 361 | 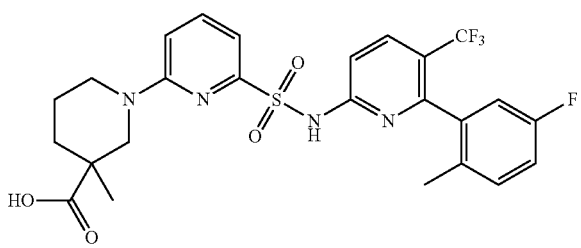 [SMILES: Cc1ccc(F)cc1-c1nc(NS(=O)(=O)c2cccc(N3CCCC(C)(C(=O)O)C3)n2)ccc1C(F)(F)F] |
| 362 | 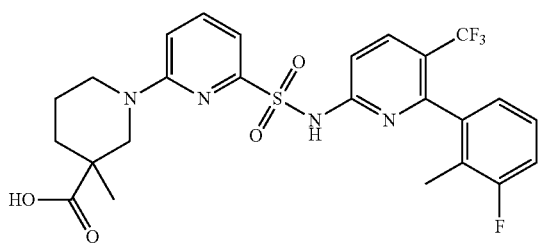 [SMILES: Cc1c(F)cccc1-c1nc(NS(=O)(=O)c2cccc(N3CCCC(C)(C(=O)O)C3)n2)ccc1C(F)(F)F] |

| Ex. No. | Product |
|---|---|
| 363 | 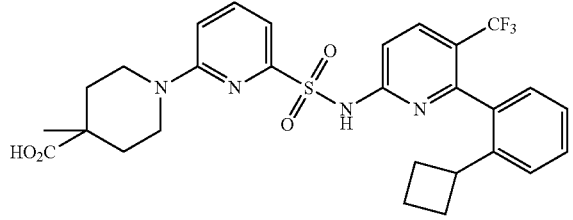 [SMILES: CC1(C(=O)O)CCN(c2cccc(S(=O)(=O)Nc3ccc(C(F)(F)F)c(-c4ccccc4C4CCC4)n3)n2)CC1] |
| 364 | 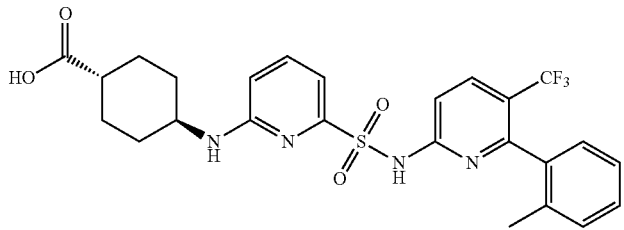 [SMILES: Cc1ccccc1-c1nc(NS(=O)(=O)c2cccc(N[C@H]3CC[C@H](C(=O)O)CC3)n2)ccc1C(F)(F)F] |
| 365 | 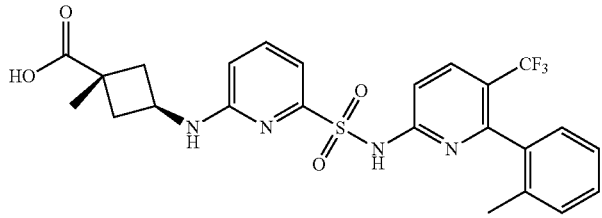 [SMILES: Cc1ccccc1-c1nc(NS(=O)(=O)c2cccc(N[C@H]3C[C@](C)(C(=O)O)C3)n2)ccc1C(F)(F)F] |
| 366 | 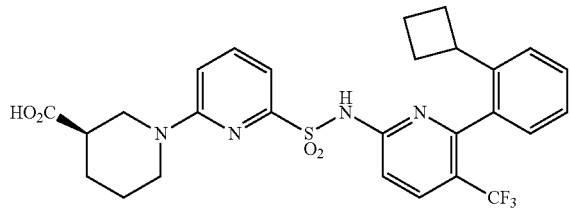 [SMILES: O=C(O)[C@@H]1CCCN(c2cccc(S(=O)(=O)Nc3ccc(C(F)(F)F)c(-c4ccccc4C4CCC4)n3)n2)C1] |
| 367 | 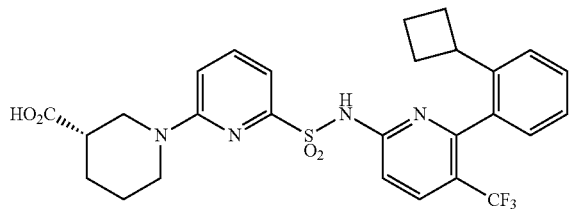 |
| 368 | 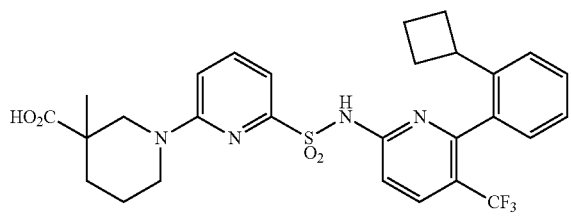 [SMILES: CC1(C(=O)O)CCCN(c2cccc(S(=O)(=O)Nc3ccc(C(F)(F)F)c(-c4ccccc4C4CCC4)n3)n2)C1] |
| 369 | 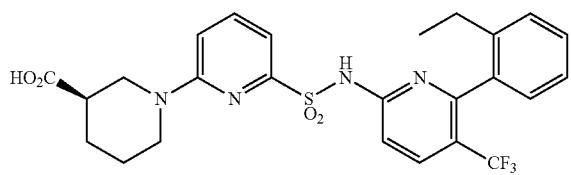 [SMILES: CCc1ccccc1-c1nc(NS(=O)(=O)c2cccc(N3CCC[C@H](C(=O)O)C3)n2)ccc1C(F)(F)F] |

-continued

| Ex. No. | Product |
|---|---|
| 370 | |
| 371 | |
| 372 | |
| 373 | |
| 374 | |
| 375 | |
| 376 | |

| Ex. No. | Product |
|---|---|
| 377 | 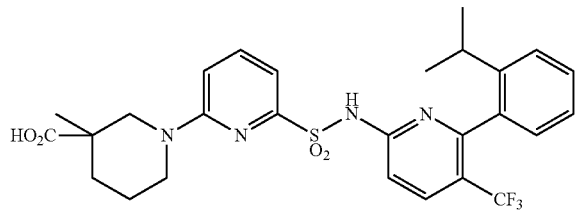 |
| 378 | 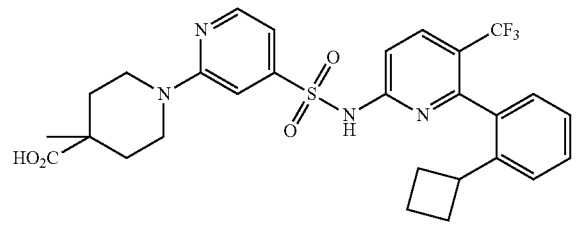 [SMILES: CC1(C(=O)O)CCN(c2cc(S(=O)(=O)Nc3ccc(C(F)(F)F)c(-c4ccccc4C4CCC4)n3)ccn2)CC1] |
| 379 | 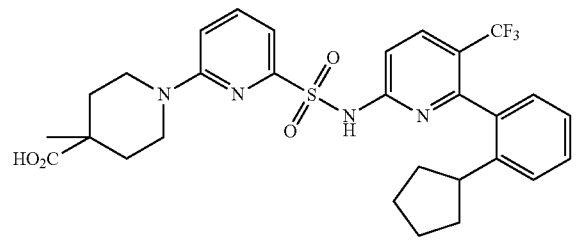 [SMILES: CC1(C(=O)O)CCN(c2cccc(S(=O)(=O)Nc3ccc(C(F)(F)F)c(-c4ccccc4C4CCCC4)n3)n2)CC1] |
| 380 | 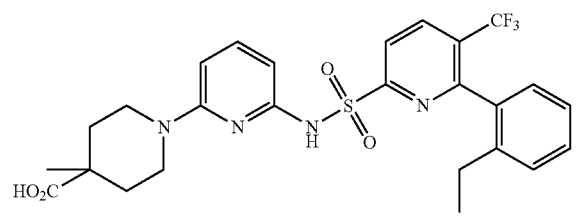 [SMILES: CCc1ccccc1-c1nc(S(=O)(=O)Nc2cccc(N3CCC(C)(C(=O)O)CC3)n2)ccc1C(F)(F)F] |
| 381 | 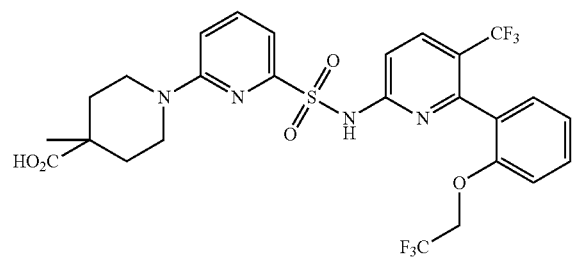 [SMILES: CC1(C(=O)O)CCN(c2cccc(S(=O)(=O)Nc3ccc(C(F)(F)F)c(-c4ccccc4OCC(F)(F)F)n3)n2)CC1] |
| 382 | 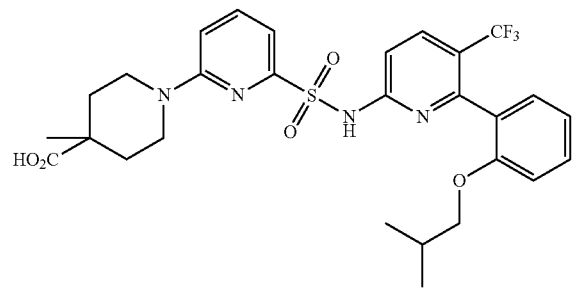 [SMILES: CC(C)COc1ccccc1-c1nc(NS(=O)(=O)c2cccc(N3CCC(C)(C(=O)O)CC3)n2)ccc1C(F)(F)F] |

| Ex. No. | Product |
|---|---|
| 383 | 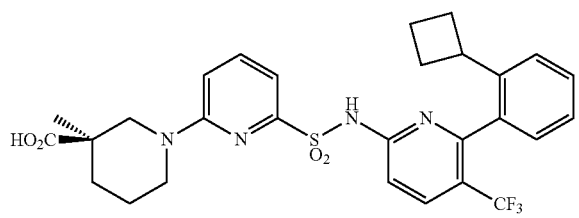 [SMILES: C[C@@]1(C(=O)O)CCCN(c2cccc(S(=O)(=O)Nc3ccc(C(F)(F)F)c(-c4ccccc4C4CCC4)n3)n2)C1] |
| 384 | 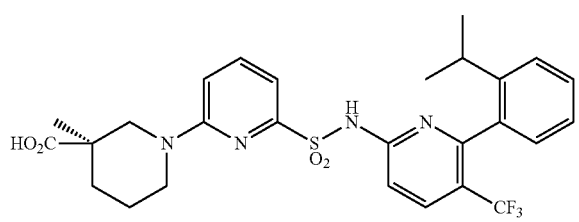 [SMILES: CC(C)c1ccccc1-c1nc(NS(=O)(=O)c2cccc(N3CCC[C@@](C)(C(=O)O)C3)n2)ccc1C(F)(F)F] |
| 385 | 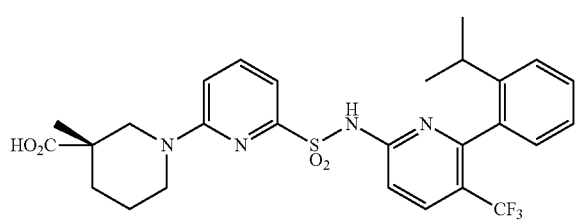 [SMILES: CC(C)c1ccccc1-c1nc(NS(=O)(=O)c2cccc(N3CCC[C@](C)(C(=O)O)C3)n2)ccc1C(F)(F)F] |
| 386 | 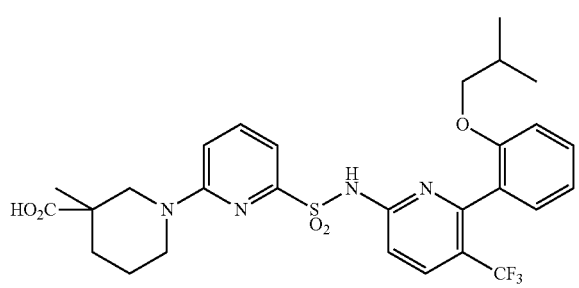 [SMILES: CC(C)COc1ccccc1-c1nc(NS(=O)(=O)c2cccc(N3CCCC(C)(C(=O)O)C3)n2)ccc1C(F)(F)F] |
| 387 | 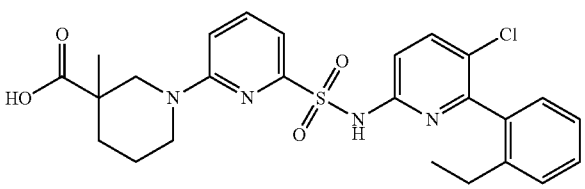 [SMILES: CCc1ccccc1-c1nc(NS(=O)(=O)c2cccc(N3CCCC(C)(C(=O)O)C3)n2)ccc1Cl] |
| 388 | 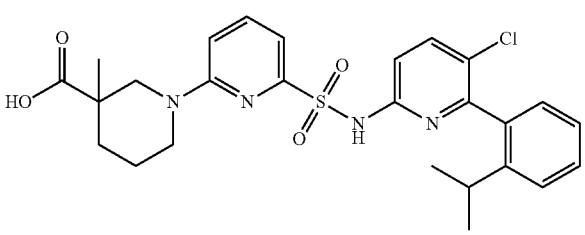 [SMILES: CC(C)c1ccccc1-c1nc(NS(=O)(=O)c2cccc(N3CCCC(C)(C(=O)O)C3)n2)ccc1Cl] |

-continued
| Ex. No. | Product |
|---|---|
| 389 | 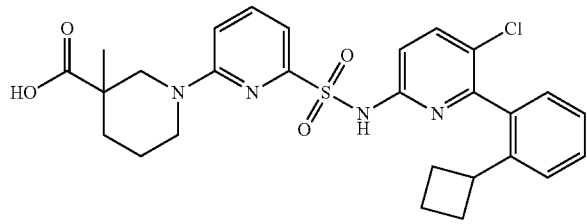 [SMILES: CC1(C(=O)O)CCCN(c2cccc(S(=O)(=O)Nc3ccc(Cl)c(-c4ccccc4C4CCC4)n3)n2)C1] |
| 390 | 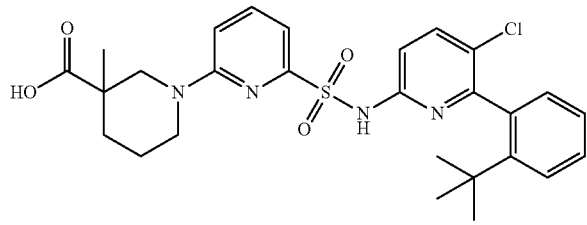 [SMILES: CC1(C(=O)O)CCCN(c2cccc(S(=O)(=O)Nc3ccc(Cl)c(-c4ccccc4C(C)(C)C)n3)n2)C1] |
| 391 | 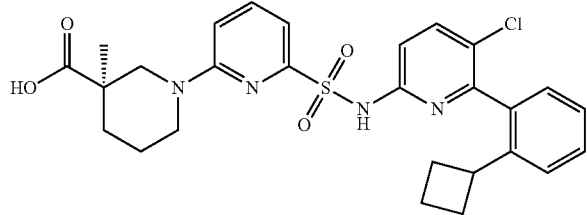 |
| 392 | 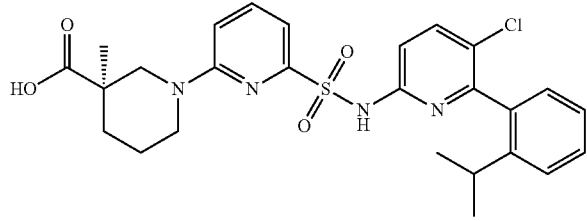 [SMILES: CC(C)c1ccccc1-c1nc(NS(=O)(=O)c2cccc(N3CCC[C@@](C)(C(=O)O)C3)n2)ccc1Cl] |
| 393 | 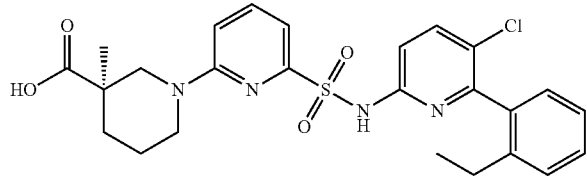 [SMILES: CCc1ccccc1-c1nc(NS(=O)(=O)c2cccc(N3CCC[C@@](C)(C(=O)O)C3)n2)ccc1Cl] |
| 394 | 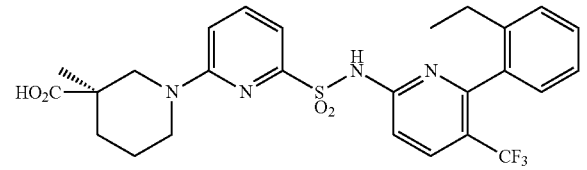 [SMILES: CCc1ccccc1-c1nc(NS(=O)(=O)c2cccc(N3CCC[C@@](C)(C(=O)O)C3)n2)ccc1C(F)(F)F] |

| Ex. No. | Product |
|---|---|
| 395 | 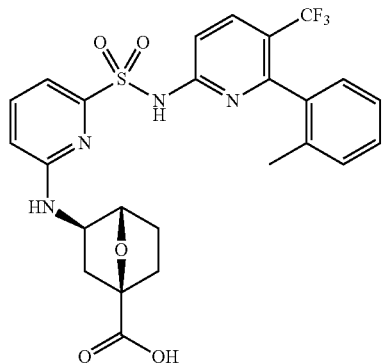 [SMILES: Cc1ccccc1-c1nc(NS(=O)(=O)c2cccc(N[C@@H]3C[C@@]4(C(=O)O)CC[C@@H]3O4)n2)ccc1C(F)(F)F] |
| 396 | 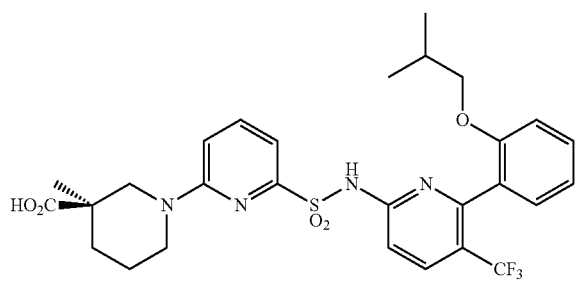 [SMILES: CC(C)COc1ccccc1-c1nc(NS(=O)(=O)c2cccc(N3CCC[C@@](C)(C(=O)O)C3)n2)ccc1C(F)(F)F] |
| 397 | 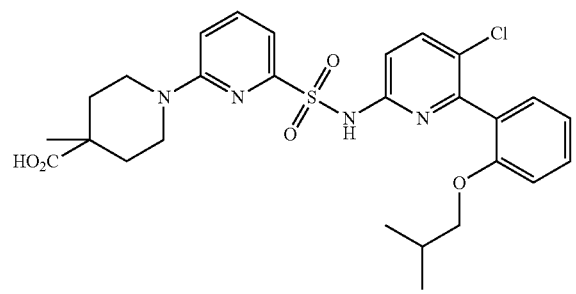 [SMILES: CC(C)COc1ccccc1-c1nc(NS(=O)(=O)c2cccc(N3CCC(C)(C(=O)O)CC3)n2)ccc1Cl] |
| 398 | 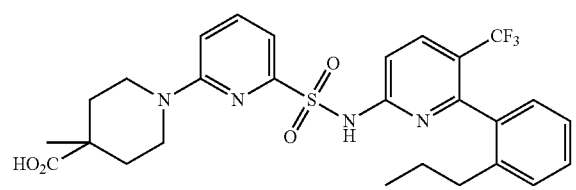 [SMILES: CCCc1ccccc1-c1nc(NS(=O)(=O)c2cccc(N3CCC(C)(C(=O)O)CC3)n2)ccc1C(F)(F)F] |
| 399 | 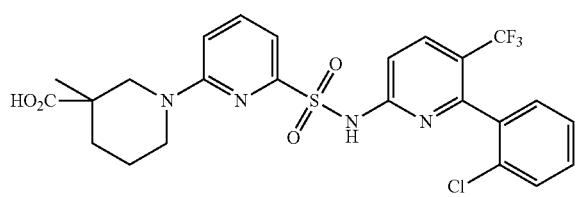 [SMILES: CC1(C(=O)O)CCCN(c2cccc(S(=O)(=O)Nc3ccc(C(F)(F)F)c(-c4ccccc4Cl)n3)n2)C1] |

-continued
| Ex. No. | Product |
|---|---|
| 400 | 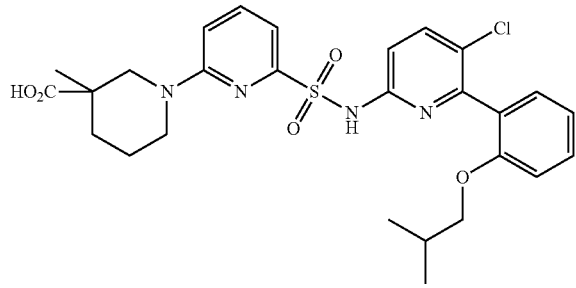 [SMILES: CC(C)COc1ccccc1-c1nc(NS(=O)(=O)c2cccc(N3CCCC(C)(C(=O)O)C3)n2)ccc1Cl] |
| 401 | 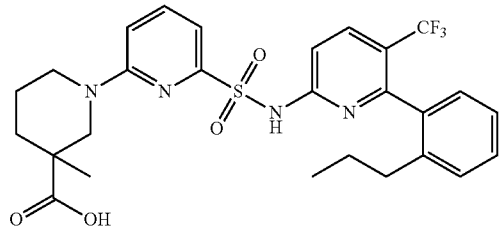 [SMILES: CCCc1ccccc1-c1nc(NS(=O)(=O)c2cccc(N3CCCC(C)(C(=O)O)C3)n2)ccc1C(F)(F)F] |
| 402 | 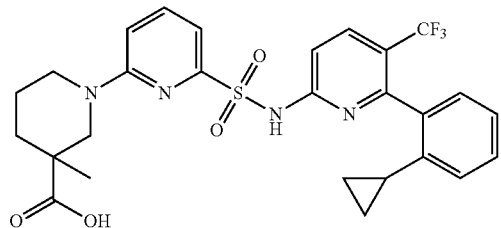 [SMILES: CC1(C(=O)O)CCCN(c2cccc(S(=O)(=O)Nc3ccc(C(F)(F)F)c(-c4ccccc4C4CC4)n3)n2)C1] |
| 403 | 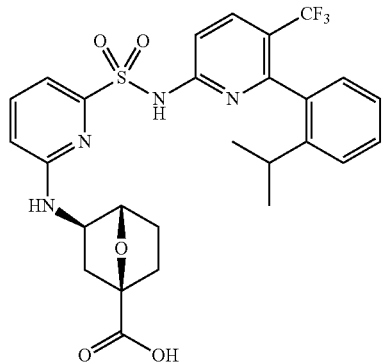 [SMILES: CC(C)c1ccccc1-c1nc(NS(=O)(=O)c2cccc(N[C@@H]3C[C@@]4(C(=O)O)CC[C@@H]3O4)n2)ccc1C(F)(F)F] |
| 404 | 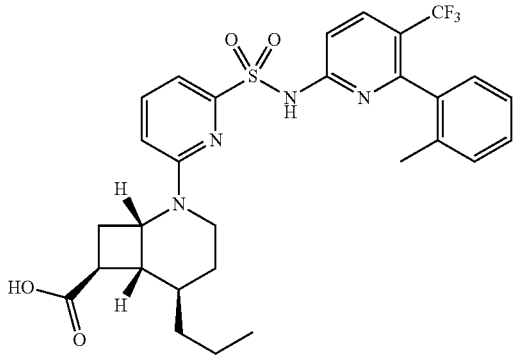 [SMILES: CCC[C@@H]1CCN(c2cccc(S(=O)(=O)Nc3ccc(C(F)(F)F)c(-c4ccccc4C)n3)n2)[C@H]2C[C@H](C(=O)O)[C@@H]12] |

| Ex. No. | Product |
|---|---|
| 405 | 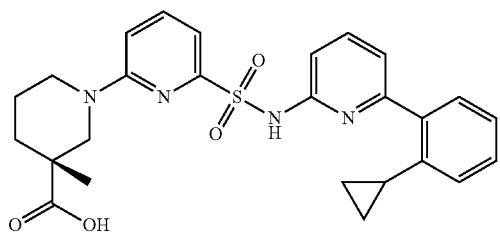 [SMILES: C[C@@]1(C(=O)O)CCCN(c2cccc(S(=O)(=O)Nc3cccc(-c4ccccc4C4CC4)n3)n2)C1] |
| 406 | 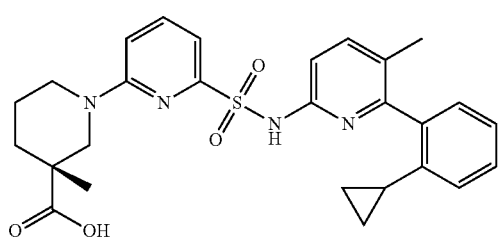 [SMILES: Cc1ccc(NS(=O)(=O)c2cccc(N3CCC[C@@](C)(C(=O)O)C3)n2)nc1-c1ccccc1C1CC1] |
| 407 | 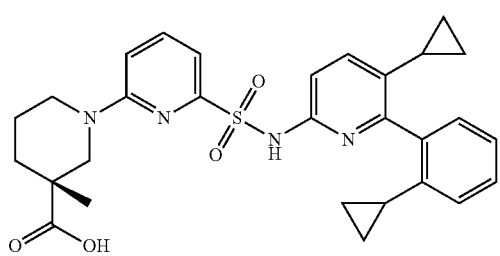 [SMILES: C[C@@]1(C(=O)O)CCCN(c2cccc(S(=O)(=O)Nc3ccc(C4CC4)c(-c4ccccc4C4CC4)n3)n2)C1] |
| 408 | 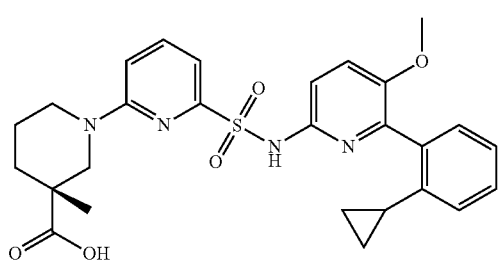 [SMILES: COc1ccc(NS(=O)(=O)c2cccc(N3CCC[C@@](C)(C(=O)O)C3)n2)nc1-c1ccccc1C1CC1] |
| 409 | 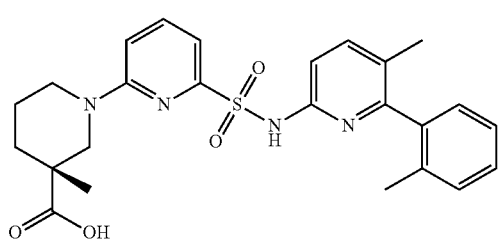 [SMILES: Cc1ccccc1-c1nc(NS(=O)(=O)c2cccc(N3CCC[C@@](C)(C(=O)O)C3)n2)ccc1C] |
| 410 | 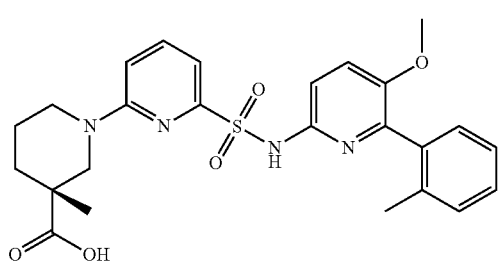 [SMILES: COc1ccc(NS(=O)(=O)c2cccc(N3CCC[C@@](C)(C(=O)O)C3)n2)nc1-c1ccccc1C] |

| Ex. No. | Product |
|---|---|
| 411 | 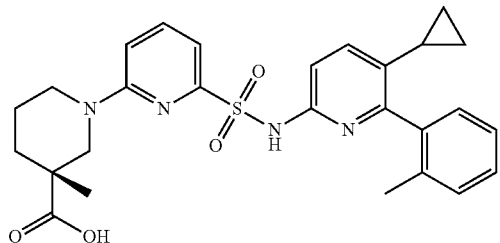 [SMILES: Cc1ccccc1-c1nc(NS(=O)(=O)c2cccc(N3CCC[C@@](C)(C(=O)O)C3)n2)ccc1C1CC1] |
| 412 | 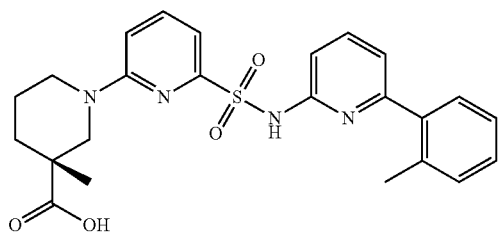 [SMILES: Cc1ccccc1-c1cccc(NS(=O)(=O)c2cccc(N3CCC[C@@](C)(C(=O)O)C3)n2)n1] |
| 413 | 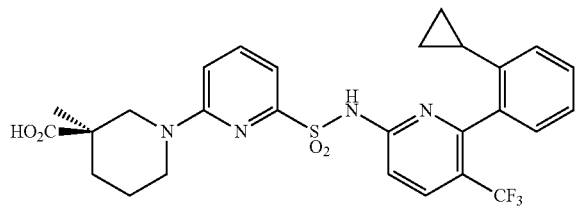 [SMILES: C[C@@]1(C(=O)O)CCCN(c2cccc(S(=O)(=O)Nc3ccc(C(F)(F)F)c(-c4ccccc4C4CC4)n3)n2)C1] |
| 414 | 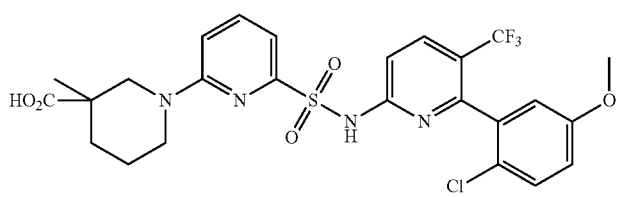 [SMILES: COc1ccc(Cl)c(-c2nc(NS(=O)(=O)c3cccc(N4CCCC(C)(C(=O)O)C4)n3)ccc2C(F)(F)F)c1] |
| 415 | 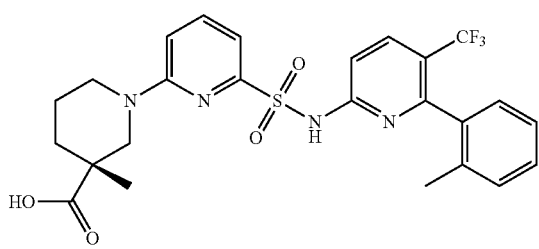 [SMILES: Cc1ccccc1-c1nc(NS(=O)(=O)c2cccc(N3CCC[C@@](C)(C(=O)O)C3)n2)ccc1C(F)(F)F] |
| 416 | 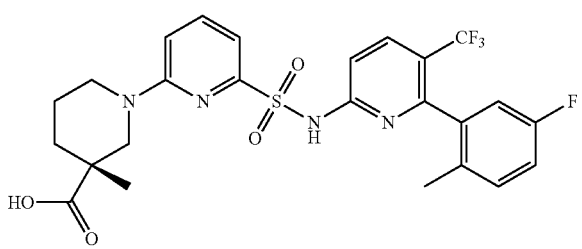 [SMILES: Cc1ccc(F)cc1-c1nc(NS(=O)(=O)c2cccc(N3CCC[C@@](C)(C(=O)O)C3)n2)ccc1C(F)(F)F] |

-continued
| Ex. No. | Product |
|---|---|
| 417 | 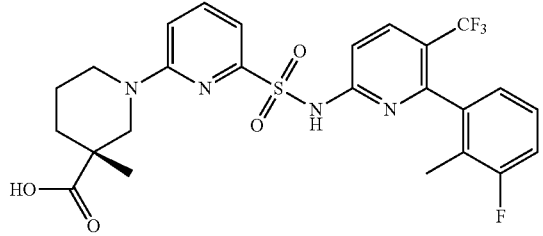 [SMILES: Cc1c(F)cccc1-c1nc(NS(=O)(=O)c2cccc(N3CCC[C@@](C)(C(=O)O)C3)n2)ccc1C(F)(F)F] |
| 418 | 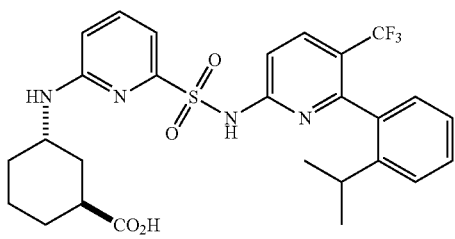 |
| 419 | 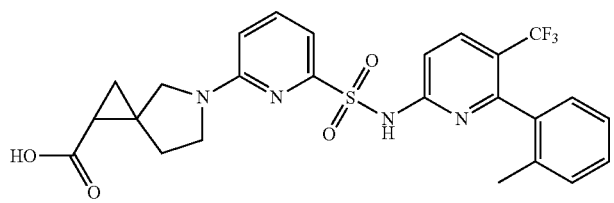 [SMILES: Cc1ccccc1-c1nc(NS(=O)(=O)c2cccc(N3CCC4(CC4C(=O)O)C3)n2)ccc1C(F)(F)F] |
| 420 | 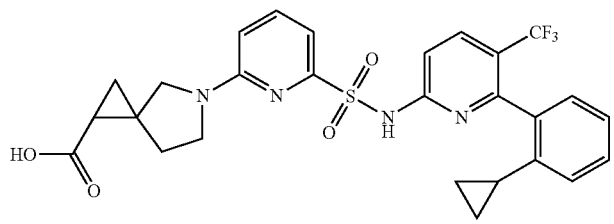 [SMILES: O=C(O)C1CC12CCN(c1cccc(S(=O)(=O)Nc3ccc(C(F)(F)F)c(-c4ccccc4C4CC4)n3)n1)C2] |
| 421 | 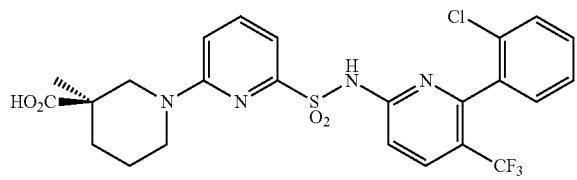 [SMILES: C[C@@]1(C(=O)O)CCCN(c2cccc(S(=O)(=O)Nc3ccc(C(F)(F)F)c(-c4ccccc4Cl)n3)n2)C1] |
| 422 | 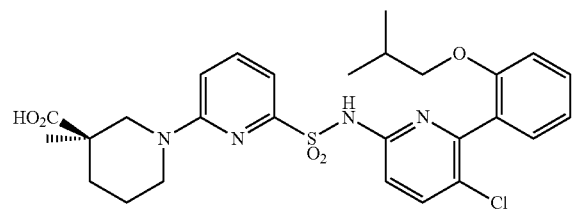 [SMILES: CC(C)COc1ccccc1-c1nc(NS(=O)(=O)c2cccc(N3CCC[C@@](C)(C(=O)O)C3)n2)ccc1Cl] |
| 423 | 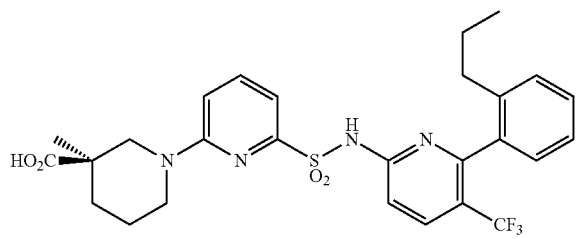 [SMILES: CCCc1ccccc1-c1nc(NS(=O)(=O)c2cccc(N3CCC[C@@](C)(C(=O)O)C3)n2)ccc1C(F)(F)F] |

| Ex. No. | Product |
|---|---|
| 424 | *(chemical structure)* |
| 425 | *(chemical structure)* |
| 426 | *(chemical structure)* |
| 427 | *(chemical structure)* |
| 428 | *(chemical structure)* |
| 429 | *(chemical structure)* |
| 430 | *(chemical structure)* |

| Ex. No. | Product |
|---|---|
| 431 | 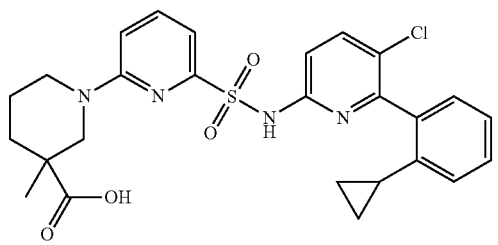 [SMILES: CC1(C(=O)O)CCCN(c2cccc(S(=O)(=O)Nc3ccc(Cl)c(-c4ccccc4C4CC4)n3)n2)C1] |
| 432 | 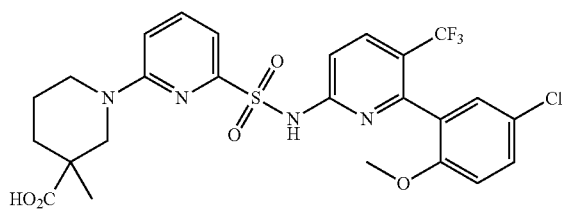 [SMILES: COc1ccc(Cl)cc1-c1nc(NS(=O)(=O)c2cccc(N3CCCC(C)(C(=O)O)C3)n2)ccc1C(F)(F)F] |
| 433 | 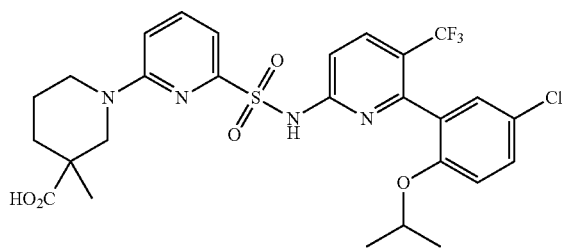 [SMILES: CC(C)Oc1ccc(Cl)cc1-c1nc(NS(=O)(=O)c2cccc(N3CCCC(C)(C(=O)O)C3)n2)ccc1C(F)(F)F] |
| 434 | 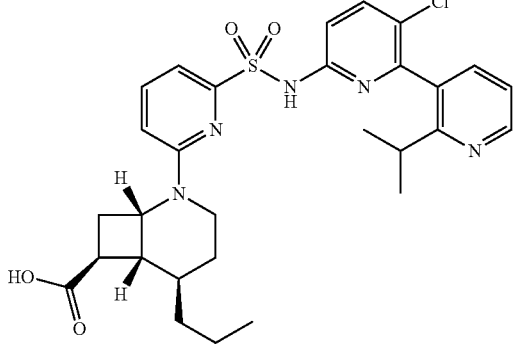 |
| 435 | 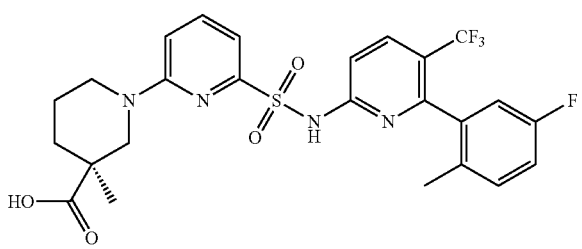 |
| 436 | 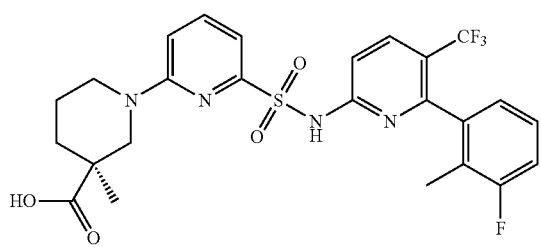 [SMILES: Cc1c(F)cccc1-c1nc(NS(=O)(=O)c2cccc(N3CCC[C@](C)(C(=O)O)C3)n2)ccc1C(F)(F)F] |

| Ex. No. | Product |
|---|---|
| 437 | 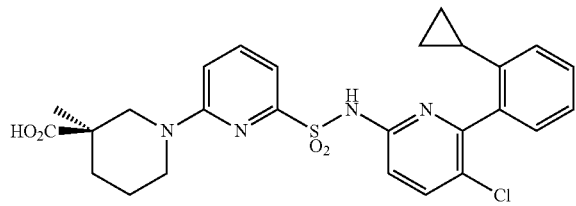 [SMILES: C[C@@]1(C(=O)O)CCCN(c2cccc(S(=O)(=O)Nc3ccc(Cl)c(-c4ccccc4C4CC4)n3)n2)C1] |
| 438 | 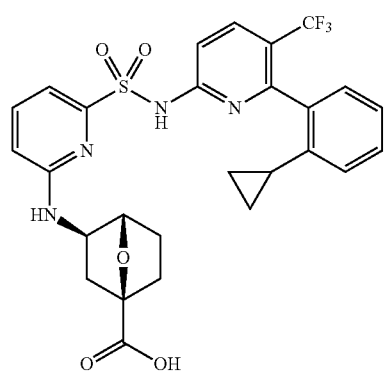 [SMILES: O=C(O)[C@]12CC[C@H](O1)[C@H](Nc1cccc(S(=O)(=O)Nc3ccc(C(F)(F)F)c(-c4ccccc4C4CC4)n3)n1)C2] |
| 439 | 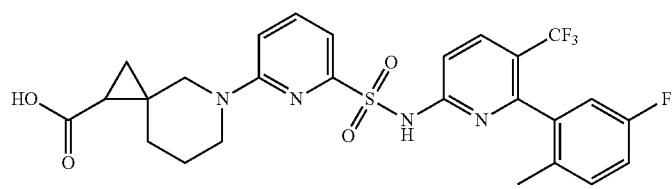 [SMILES: Cc1ccc(F)cc1-c1nc(NS(=O)(=O)c2cccc(N3CCCC4(CC4C(=O)O)C3)n2)ccc1C(F)(F)F] |
| 440 | 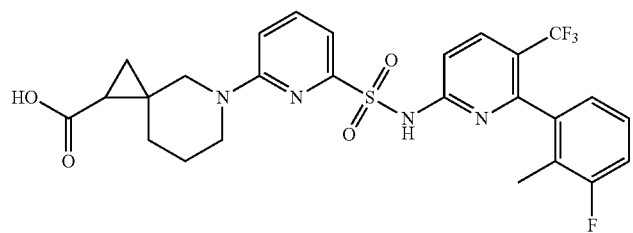 [SMILES: Cc1c(F)cccc1-c1nc(NS(=O)(=O)c2cccc(N3CCCC4(CC4C(=O)O)C3)n2)ccc1C(F)(F)F] |
| 441 | 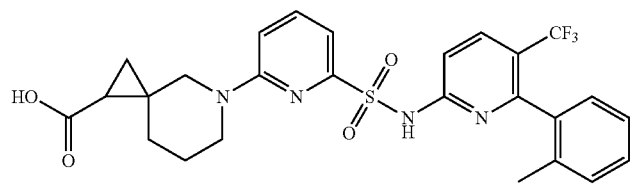 [SMILES: Cc1ccccc1-c1nc(NS(=O)(=O)c2cccc(N3CCCC4(CC4C(=O)O)C3)n2)ccc1C(F)(F)F] |
| 442 | 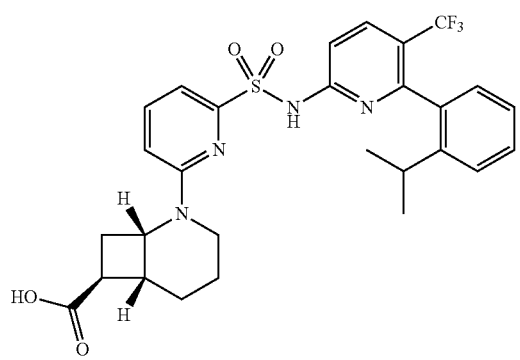 [SMILES: CC(C)c1ccccc1-c1nc(NS(=O)(=O)c2cccc(N3CCC[C@@H]4[C@@H](C(=O)O)C[C@@H]43)n2)ccc1C(F)(F)F] |

| Ex. No. | Product |
|---|---|
| 443 | 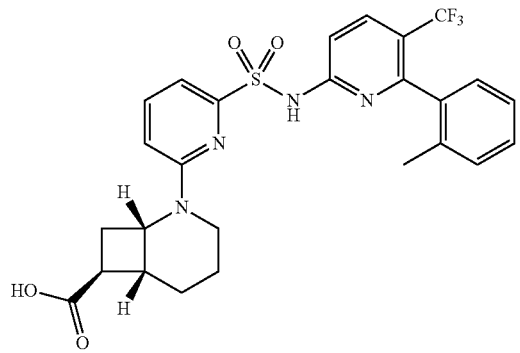 [SMILES: Cc1ccccc1-c1nc(NS(=O)(=O)c2cccc(N3CCC[C@@H]4[C@@H](C(=O)O)C[C@@H]43)n2)ccc1C(F)(F)F] |
| 444 | 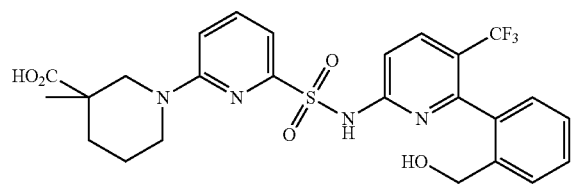 [SMILES: CC1(C(=O)O)CCCN(c2cccc(S(=O)(=O)Nc3ccc(C(F)(F)F)c(-c4ccccc4CO)n3)n2)C1] |
| 445 | 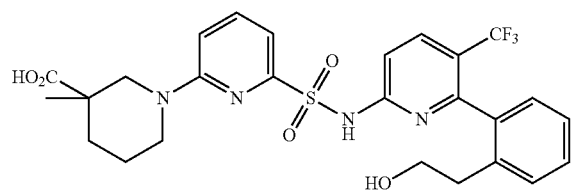 [SMILES: CC1(C(=O)O)CCCN(c2cccc(S(=O)(=O)Nc3ccc(C(F)(F)F)c(-c4ccccc4CCO)n3)n2)C1] |
| 446 | 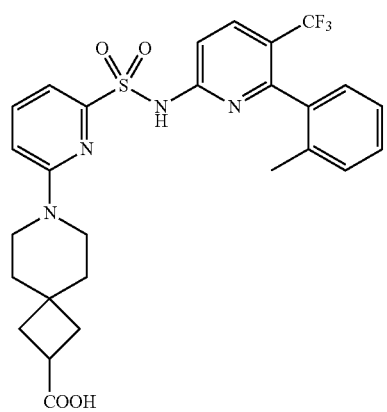 [SMILES: Cc1ccccc1-c1nc(NS(=O)(=O)c2cccc(N3CCC4(CC3)CC(C(=O)O)C4)n2)ccc1C(F)(F)F] |
| 447 | 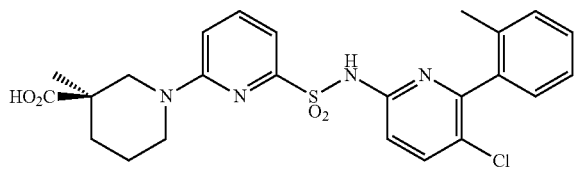 [SMILES: Cc1ccccc1-c1nc(NS(=O)(=O)c2cccc(N3CCC[C@@](C)(C(=O)O)C3)n2)ccc1Cl] |
| 448 | 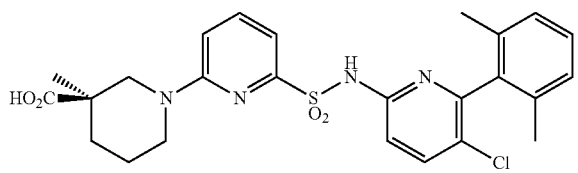 [SMILES: Cc1cccc(C)c1-c1nc(NS(=O)(=O)c2cccc(N3CCC[C@@](C)(C(=O)O)C3)n2)ccc1Cl] |

| Ex. No. | Product |
|---|---|
| 449 | |
| 450 | |
| 451 | |
| 452 | |
| 453 | |
| 454 | |
| 455 | |
| 456 | |

-continued

| Ex. No. | Product |
|---|---|
| 457 | |
| 458 | |
| 459 | |
| 460 | |
| 461 | |
| 462 | |
| 463 | |

| Ex. No. | Product |
|---|---|
| 464 | *(chemical structure)* |
| 465 | *(chemical structure)* |

Biological Assays

Measurement of delF508-CFTR-HRP Surface Expression in CFBE41o-Cells

This assay quantifies the cell surface expressions of the mutant CFTR channel using an extracellular HRP tag.

A cellular assay was developed to measure surface expression of horseradish peroxidase (HRP) tagged delF508-CFTR in the human bronchial epithelial immortalized CFBE41o-cell line (Phuan, P. W., et al, (2014) Molecular Pharmacology 86:42-51). Specifically, the HRP sequence was inserted into the fourth extracellular loop of delF508-CFTR and stably expressed in CFBE41o-cells. Cells were seeded in 384 well plate at a density of 5000 cells/well and incubated at 37° C. for 12 to 24 hours in medium (Gibco MEM #11095, 10% FBS, 10 mM HEPES, 200 mM L-Glutamine, 200 μg/mL G418, 3 μg/mL Puromycin). The delF508-CFTR-HRP expression was induced with 500 ng/mL doxycycline (Sigma D-9891, dissolved in $H_2O$ and sterile filtered) in medium and the cells were incubated at 37° C. for 48 h. Old medium was removed and fresh medium was added containing 500 ng/mL doxycycline and unknown test compound at required concentration in DMSO, not exceeding 0.5% final DMSO concentration. The highest concentration tested was 10 μM with a 10-point concentration response curve using a 3-fold dilution. After addition of compounds, the cells were incubated for 24 h at 37° C. On the final day, cells were washed four times in PBS containing 1 mM $MgCl_2$ and 0.1 mM $CaC_2$. HRP-Substrate (SuperSignal ELISA Pico, Fisher #37069) 20 μl/well was added and the luminescence signal was determined (Viewlux, Perkin Elmer). Light was emitted upon addition of exogenous HRP-Substrate only when delF508-CFTR-HRP reached the cell surface and the HRP tag was accessible to the HRP-Substrate (note: HRP-Substrate cannot cross the lipid bilayer to reach delF508-CFTR-HRP misfolded within the cell).

The median activity for the lowest concentration of the compounds on each assay plate was calculated and this value was used to normalize the signal for each well on the respective plate. Three replicates at each concentrations for every compound were run to determine one $EC_{50}$. The median value was determined and used to calculate compound activities as described below. Effective half maximal values ($EC_{50}$) were calculated for each compound by performing logistic regression on measured dose-response data points using the equation:

$$Y = \text{Bottom} + \frac{\text{Top} - \text{Bottom}}{1 + \left(\frac{X}{EC_{50}}\right)^{\text{Hill coefficient}}}$$

where "Y" is the observed activity, "Bottom" is the lowest observed value, "Top" is the highest observed value, and the "Hill coefficient" gives the largest absolute value of the slope. The curve fitting is carried out by a curve fitting program implemented at GNF using Matlab (Mathworks).

The dose response curves also were used to calculate Fold Change (FC) using the equation:

$$\text{Fold change} = \frac{\text{Top} - \text{Bottom}}{\text{Bottom}}$$

Compound efficacy relative to the reference compound 3-(6-(1-(2,2-difluorobenzo[d][1,3]dioxol-5-yl)cyclopropane-1-carboxamido)-3-methylpyridin-2-yl)benzoic acid was determined using the following formula:

$$\% \text{ Amax} = \frac{FC \text{ of test compound}}{FC \text{ of reference compound}} * 100$$

Measurement of delF508-CFTR Functional Activity in Primary Human Bronchial Epithelial Cells (HBECs) Using Multi-Transepithelial Clamp Circuit (MTECC-24) Assay This assay measures the functional activity of the CFTR channel (Chloride ion transport) in patient derived primary human bronchial epithilial cells with forskolin activation and in the presence of the CFTR corrector/potentiator combo.

Primary human delF508-CFTR bronchial epithelial cells were purchased from Asterand and cultured according to previously established methods (Fulcher et al. (2005) Methods Mol Med 107: 183-206). Briefly, vendor supplied cells were rapidly defrosted and added to a T175 flask in 50 mL growth media (Lonza BEBM media with Lonza BEGM singlequots). Media was replaced after 24 h and then cells were fed every other day until cells were 80-90% confluent, at which point cells were cryopreserved. These P1 vials were thawed at 37° C. as needed and added to T175 flasks in 50 mL growth media at $5 \times 10^5$ cells/flask. Media was replaced after 24 h, and then cells were fed every other day until 80-90% confluent. Cells were lifted with 5 mL accutase at 37° C. for 5 minutes, centrifuged at 1000 rpms for 5 min (300 g), and resuspended in differentiation media (50% BEBM in DMEM, BEGM singlequots, all trans retinoic acid ($5 \times 10^{-8}$M)). Cells were then counted and cell suspension was added to collagen coated inserts at $3 \times 10^4$ cells/insert in 0.15 mL with 0.5 mL differentiation media on the basolateral side.

Apical and basolateral media were replaced on alternate days, and following day 7 (or when confluent plus 2 days), air liquid interface was established for approximately two weeks by removal of apical media. One day prior to use on the MTECC24 system (EP-Devices, EP Design, Belgium), 0.15 mL of warmed (37° C.) PBS was added to the apical surface of the cultures and returned to humidifier (37° C., 5% $CO_2$ incubator) for 30 min before aspirating the apical surface to remove any mucus.

Compound treatments were then prepared. Compound dilutions, typically a 10 point concentration response with 1 in 3 dilution steps, were made in 100% DMSO before dilution 1 in 1000 into differentiation medium with a final DMSO concentration of 0.1% or 0.2% for the study. Compound containing medium was then transferred into the wells of a 24 well plate at 0.5 mL per well and warmed for 30 min in a 37° C. incubator prior to transferring washed inserts into the compound containing plates. Cells were incubated in compound containing medium (basolateral only) for 24 h prior to measurement in the MTECC24 system.

Following 24 hr treatment, compound dilutions were prepared again, diluted 1 in 1000 into 37° C. assay medium (F-12 Coon's modified, 20 mM HEPES pH7.4 with TRIS Base, No FCS or bicarbonate). Cells which were treated for 24 h with test compound were then transferred into plates containing 0.75 mL compound treatment in assay medium (basolateral) and 0.25 mL of the compound containing assay medium was added to the apical surface. The plates were then transferred to the heated plate compartments of the MTECC24 system for 45 min prior to measurements (this can also be done in a non-$CO_2$ 37° C. humidified incubator). Basolateral temperature should not exceed 36.5° C. and apical temperature should be approximately 35.5° C.
Modulators were Added Sequentially as Follows while the MTECC24 Instrument Recorded the Equivalent Short Circuit Current (Ieq):

| Final | Added to plate | Stock (in F12 Coons) | Approx. incubation time |
|---|---|---|---|
| 10 µM Amiloride | 25 µL Apical | 110 µM | 15 min |
| 20 µM Forskolin | 25 µL Apical | 240 µM | 15 min |
| 0.5 µM (S)-3-amino-6-methoxy-N-(3,3,3-trifluoro-2-hydroxy-2-methylpropyl)-5-(trifluoromethyl)picolinamide | 25 µL Apical/ 75 µL Basolateral | 6.5 µM | 15 min |
| 30 µM CFTRinh-172 | 25 µL Apical/ 75 µL Basolateral | 420 µM | 30 min |

Prior to dilution into F-12 medium the stocks are as follows:
Amiloride stock is 10 mM in $H_2O$
Forskolin Stock is 10 mM in 100% DMSO
(S)-3-amino-6-methoxy-N-(3,3,3-trifluoro-2-hydroxy-2-methylpropyl)-5-(trifluoromethyl)picolinamide is 0.5 mM stock in 100% DMSO
INH-172 (4-[[4-Oxo-2-thioxo-3-[3-trifluoromethyl)phenyl]-5-thiazolidinylidene]methyl]benzoic acid) stock is 30 mM in 100% DMSO The data was normalized using the median signal from wells treated with 0.1% DMSO as a baseline. Curve fitting and $EC_{50}$ calculations were performed using the following equation:

$$Y = \text{Bottom} + \frac{\text{Top} - \text{Bottom}}{1 + \left(\frac{X}{EC_{50}}\right) Hillcoefficient}$$

where "Y" is the observed activity, "Bottom" is the lowest observed value, "Top" is the highest observed value, and the "Hill coefficient" gives the largest absolute value of the slope. The curve fitting is carried out by a curve fitting program implemented at GNF using Matlab (Mathworks).

At least two replicates for every compound were run and $EC_{50}$ reported in the table are mean values.

The dose response curves also were used to calculate Fold Change (FC) using the equation:

$$\text{Fold change} = \frac{\text{Top} - \text{Bottom}}{\text{Bottom}}$$

% Amax calculations were performed using the equation:

$$\% \, Amax = \frac{FC \text{ of test compound}}{FC \text{ of reference compound}} * 100\%$$

where the test compound (added 24 h before assay) was in the presence of the potentiator (S)-3-amino-6-methoxy-N-(3,3,3-trifluoro-2-hydroxy-2-methylpropyl)-5-(trifluoromethyl)picolinamide at the time of assay. The reference compound was combination of 2 µM 3-(6-(1-(2,2-difluorobenzo[d][1,3]dioxol-5-yl)cyclopropane-1-carboxamido)-3-methylpyridin-2-yl)benzoic acid added 24 h prior to assay and 0.5 µM N-(2,4-di-tert-butyl-5-hydroxyphenyl)-4-oxo-1,4-dihydroquinoline-3-carboxamide added at the time of assay.

Activity Table

| Example No. | DelF508-CFTR-HRP $EC_{50}$ (µM) | DelF508-CFTR-HRP Amax % | MTECC24 CFHBEC-$EC_{50}$ (µM) | MTECC24 CFHBEC-Amax % |
|---|---|---|---|---|
| 1 | 1.781 | 867.1 | 0.004 | 78.9 |
| 2 | 0.967 | 724.1 | 0.008 | 75.5 |
| 3 | 1.443 | 688.1 | 0.0019 | 60.3 |
| 4 | 0.912 | 632.0 | 0.0408 | 52.0 |
| 5 | 1.149 | 628.6 | 0.003 | 97.56 |
| 6 | 1.506 | 612.2 | 0.0131 | 61.0 |
| 7 | 1.628 | 609.9 | 0.0027 | 66.8 |
| 8 | 1.36 | 607.8 | NT | NT |
| 9 | 1.516 | 596.6 | NT | NT |
| 10 | 1.533 | 591.9 | 0.0058 | 87.0 |
| 11 | 1.352 | 578.7 | 0.0136 | 94.3 |
| 12 | 1.322 | 555.3 | 0.0097 | 85.2 |
| 13 | 1.308 | 536.2 | 0.0240 | 100.1 |
| 14 | 1.352 | 523.4 | NT | NT |
| 15 | 2.299 | 520.5 | NT | NT |
| 16 | 1.012 | 519.4 | NT | NT |
| 17 | 2.091 | 509.9 | 0.0051 | 69.5 |
| 18 | 1.885 | 504.6 | 0.0079 | 65.5 |

Activity Table

| Example No. | DelF508-CFTR-HRP EC$_{50}$ (µM) | DelF508-CFTR-HRP Amax % | MTECC24 CFHBEC-EC$_{50}$ (µM) | MTECC24 CFHBEC-Amax % |
|---|---|---|---|---|
| 19 | 1.296 | 501.1 | NT | NT |
| 20 | 1.76 | 499.4 | NT | NT |
| 21 | 1.357 | 492.8 | NT | NT |
| 22 | 1.616 | 489.5 | NT | NT |
| 23 | 1.879 | 486.1 | NT | NT |
| 24 | 1.458 | 484.6 | NT | NT |
| 25 | 1.061 | 481.8 | 0.0145 | 94.2 |
| 26 | 2.204 | 450.2 | NT | NT |
| 27 | 1.716 | 430.0 | NT | NT |
| 28 | 1.384 | 429.2 | 0.0016 | 77.1 |
| 29 | 1.077 | 429.1 | NT | NT |
| 30 | 1.702 | 421.0 | NT | NT |
| 31 | 1.316 | 418.1 | NT | NT |
| 32 | 1.643 | 412.0 | NT | NT |
| 33 | 2.196 | 404.0 | NT | NT |
| 34 | 2.518 | 399.5 | 0.0116 | 58.2 |
| 35 | 2.113 | 397.7 | NT | NT |
| 36 | 2.097 | 390.2 | 0.0259 | 67.6 |
| 37 | 2.285 | 385.5 | NT | NT |
| 38 | 1.998 | 376.5 | NT | NT |
| 39 | 1.899 | 374.3 | NT | NT |
| 40 | 2.358 | 373.1 | NT | NT |
| 41 | 2.34 | 367.9 | 0.0139 | 88.8 |
| 42 | 2.263 | 367.2 | 0.0399 | 72.4 |
| 43 | 2.118 | 361.2 | 0.0633 | 54.2 |
| 44 | 1.771 | 346.5 | 0.0460 | 61.6 |
| 45 | 1.235 | 345.4 | NT | NT |
| 46 | 1.946 | 339.3 | NT | NT |
| 47 | 1.396 | 335.2 | NT | NT |
| 48 | 2.327 | 334.0 | NT | NT |
| 49 | 3.048 | 332.9 | NT | NT |
| 50 | 0.683 | 332.4 | NT | NT |
| 51 | 1.982 | 332.2 | NT | NT |
| 52 | 1.379 | 327.1 | NT | NT |
| 53 | 1.844 | 324.7 | NT | NT |
| 54 | 2.354 | 305.3 | NT | NT |
| 55 | 1.7 | 305.2 | 0.0155 | 86.7 |
| 56 | 2.579 | 301.3 | 0.0283 | 63.9 |
| 57 | 1.075 | 284.6 | 0.1184 | 72.9 |
| 58 | 1.777 | 269.7 | NT | NT |
| 59 | 1.102 | 258.0 | NT | NT |
| 60 | 2.98 | 253.1 | NT | NT |
| 61 | 2.62 | 251.1 | 0.1026 | 74.0 |
| 62 | 1.73 | 239.5 | 0.0512 | 46.1 |
| 63 | 2.687 | 225.6 | NT | NT |
| 64 | 1.959 | 223.1 | NT | NT |
| 65 | 1.536 | 220.1 | NT | NT |
| 66 | 3.072 | 214.6 | NT | NT |
| 67 | 1.844 | 214.1 | 0.1136 | 45.8 |
| 68 | 2.425 | 208.6 | NT | NT |
| 69 | 3.3 | 198.7 | NT | NT |
| 70 | 2.636 | 197.4 | NT | NT |
| 71 | 3.55 | 196.4 | NT | NT |
| 72 | 3.41 | 192.6 | NT | NT |
| 73 | 4.24 | 162.9 | 0.1345 | 64.2 |
| 74 | 2.576 | 158.4 | 0.2834 | 67.3 |
| 75 | 2.838 | 158.2 | NT | NT |
| 76 | 2.304 | 155.5 | NT | NT |
| 77 | 2.552 | 151.7 | NT | NT |
| 78 | 2.727 | 141.1 | NT | NT |
| 79 | 2.297 | 140.9 | NT | NT |
| 80 | 2.284 | 136.9 | 0.0960 | 50.7 |
| 81 | 1.982 | 126.6 | NT | NT |
| 82 | 0.942 | 124.4 | NT | NT |
| 83 | 4.11 | 115.4 | NT | NT |
| 84 | 1.537 | 110.9 | NT | NT |
| 85 | 3.68 | 110.3 | NT | NT |
| 86 | 3.53 | 107.8 | NT | NT |
| 87 | 4.1 | 93.8 | NT | NT |
| 88 | 3.78 | 92.9 | NT | NT |
| 89 | 3.86 | 91.5 | 0.0399 | 35.7 |
| 90 | 3.78 | 50.0 | NT | NT |
| 91 | 2.202 | 41.7 | NT | NT |
| 92 | 1.109 | 23.9 | NT | NT |
| 93 | 3.55 | 23.5 | NT | NT |
| 94 | 3.19 | 20.3 | NT | NT |
| 95 | 3.75 | 19.0 | NT | NT |
| 96 | 4.33 | 10.0 | NT | NT |
| 102 | 3.28 | 576.9 | 0.1361 | 54.3 |
| 103 | 2.974 | 370.2 | 0.0948 | 67.8 |
| 104 | 2.135 | 999.0 | 0.0245 | 73.4 |
| 105 | 3.19 | 309.9 | 0.2220 | 58.1 |
| 106 | 2.576 | 911.5 | 0.0795 | 106.4 |
| 107 | 1.993 | 755.6 | 0.1107 | 72.2 |
| 108 | 4.07 | 336.0 | 0.0549 | 61.4 |
| 109 | 2.682 | 331.5 | 0.1696 | 84.9 |
| 110 | 2.797 | 372.2 | 0.0280 | 65.6 |
| 111 | | | 0.0318 | 59.5 |
| 112 | 4.05 | 172.5 | 0.4950 | 55.0 |
| 113 | 4.22 | 72.0 | NT | NT |
| 114 | 3.63 | 66.2 | NT | NT |
| 115 | 3.81 | 192.0 | NT | NT |
| 116 | 3.16 | 370.5 | 0.1071 | 60.8 |
| 117 | 2.78 | 264.3 | 0.0331 | 74.7 |
| 118 | 2.601 | 491.7 | 0.0117 | 78.5 |
| 119 | 1.832 | 411.3 | 0.0553 | 70.2 |
| 120 | 2.817 | 269.6 | 0.0372 | 57.9 |
| 121 | 3.45 | 308.1 | 0.1644 | 79.6 |
| 122 | 2.689 | 384.6 | 0.0271 | 81.8 |
| 123 | 3.151 | 217.7 | 0.2384 | 85.2 |
| 124 | 4.61 | 147.6 | NT | NT |
| 125 | 1.944 | 214.8 | 0.0475 | 67.5 |
| 126 | 2.175 | 235.2 | NT | NT |
| 127 | 2.323 | 382.0 | 0.0157 | 45.4 |
| 128 | 2.24 | 729.6 | 0.0053 | 61.9 |
| 129 | 1.723 | 1030.4 | 0.0195 | 54.8 |
| 130 | 2.921 | 156.7 | 0.0841 | 37.9 |
| 131 | 2.136 | 728.7 | 0.0250 | 78.4 |
| 132 | 0.803 | 894.0 | NT | NT |
| 133 | 2.033 | 570.2 | 0.0979 | 71.2 |
| 134 | 1.98 | 905.9 | 0.0190 | 112.7 |
| 135 | 3.44 | 804.5 | 0.0130 | 95.3 |
| 136 | 1.108 | 861.5 | NT | NT |
| 137 | 1.352 | 853.5 | NT | NT |
| 138 | 0.681 | 635.7 | 0.0156 | 108.4 |
| 139 | 4.97 | 53.2 | NT | NT |
| 140 | 3.48 | 395.4 | 0.0295 | 65.3 |
| 141 | 2.015 | 938.2 | 0.0086 | 88.7 |
| 142 | 2.631 | 418.4 | 0.0052 | 63.7 |
| 143 | 2.99 | 888.4 | NT | NT |
| 144 | 1.883 | 1088.9 | 0.0020 | 80.5 |
| 145 | 1.271 | 1275.6 | 0.0050 | 90.9 |
| 146 | 4.28 | 59.1 | NT | NT |
| 147 | 0.375 | 482.5 | 0.0042 | 92.8 |
| 148 | 2.458 | 362.7 | 0.0854 | 74.1 |
| 149 | 1.746 | 289.0 | 0.0228 | 76.0 |
| 150 | 3.51 | 180.5 | 0.0973 | 64.4 |
| 151 | 3.69 | 186.8 | 0.0956 | 75.3 |
| 152 | 2.676 | 332.5 | 0.0578 | 62.5 |
| 153 | 3.8 | 158.9 | NT | NT |
| 154 | 3.46 | 395.2 | 0.2387 | 69.5 |
| 155 | 4.4 | 196.1 | NT | NT |
| 156 | 4.03 | 177.6 | NT | NT |
| 157 | 4.28 | 179.5 | NT | NT |
| 158 | 4.19 | 229.7 | 0.0935 | 76.6 |
| 159 | 4.42 | 129.6 | NT | NT |
| 160 | 0.743 | 476.0 | 0.0233 | 88.2 |
| 161 | 2.905 | 221.9 | 0.0916 | 88.2 |
| 162 | 0.666 | 662.1 | 0.0177 | 58.8 |
| 163 | 3.142 | 304.7 | 0.0590 | 64.8 |
| 164 | 1.058 | 577.7 | 0.0495 | 74.3 |
| 165 | 2.902 | 401.4 | 0.3420 | 50.8 |
| 166 | 0.744 | 1224.3 | 0.0118 | 62.4 |
| 167 | 3.71 | 316.6 | 0.0855 | 67.6 |
| 168 | 0.626 | 271.1 | NT | NT |
| 169 | 4 | 182.0 | 0.1442 | 40.5 |

Activity Table

| Example No. | DelF508-CFTR-HRP EC$_{50}$ (μM) | DelF508-CFTR-HRP Amax % | MTECC24 CFHBEC-EC$_{50}$ (μM) | MTECC24 CFHBEC-Amax % |
|---|---|---|---|---|
| 170 | 2.204 | 306.3 | 0.1743 | 63.3 |
| 171 | 2.732 | 504.9 | 0.1176 | 66.2 |
| 172 | 2.511 | 683.6 | 0.3144 | 77.0 |
| 173 | 2.369 | 682.3 | 0.0769 | 61.4 |
| 174 | 2.64 | 515.4 | 0.2074 | 57.1 |
| 175 | 3.27 | 530.1 | 0.2813 | 63.4 |
| 176 | 3.42 | 528.7 | 0.2239 | 69.8 |
| 177 | 2.809 | 447.1 | 0.2317 | 79.7 |
| 178 | 1.146 | 231.4 | 0.2087 | 66.3 |
| 179 | 2.081 | 1082.0 | 0.0316 | 91.9 |
| 180 | 1.503 | 626.9 | 0.0094 | 44.5 |
| 181 | 2.67 | 453.8 | 0.0398 | 101.5 |
| 182 | 3.22 | 485.4 | 0.0878 | 89.6 |
| 183 | 0.896 | 191.4 | 0.0749 | 67.8 |
| 184 | 0.835 | 149.2 | 0.0535 | 69.2 |
| 185 | 1.456 | 877.0 | 0.0046 | 105.5 |
| 186 | 1.187 | 1049.3 | 0.0026 | 81.5 |
| 187 | 2.562 | 633.7 | 0.0920 | 78.8 |
| 188 | 0.971 | 658.3 | NT | NT |
| 189 | 2.834 | 414.2 | 0.0317 | 79.0 |
| 190 | 3.41 | 565.3 | 0.0132 | 64.5 |
| 191 | 3.86 | 205.5 | 0.1013 | 64.4 |
| 192 | 2.521 | 279.4 | 0.0161 | 42.3 |
| 193 | 3.92 | 385.1 | 0.1780 | 81.2 |
| 194 | 3.84 | 177.3 | NT | NT |
| 195 | 3.38 | 213.2 | 0.4640 | 80.0 |
| 196 | 3.061 | 389.0 | 0.0096 | 82.4 |
| 197 | 3.65 | 499.8 | 0.0670 | 73.9 |
| 198 | 1.953 | 691.5 | NT | NT |
| 199 | 2.224 | 700.3 | 0.0383 | 87.1 |
| 200 | 3.17 | 553.1 | NT | NT |
| 201 | 2.619 | 570.5 | 0.1354 | 75.9 |
| 202 | 3.93 | 159.4 | NT | NT |
| 203 | 2.979 | 297.9 | 0.0233 | 80.9 |
| 204 | 1.727 | 943.3 | 0.0057 | 90.6 |
| 205 | 1.287 | 592.4 | 0.0018 | 66.8 |
| 206 | 3.7 | 95.9 | NT | NT |
| 207 | 2.267 | 503.4 | 0.0194 | 78.0 |
| 208 | 1.381 | 607.0 | 0.0052 | 88.1 |
| 209 | 2.7 | 231.2 | 0.1392 | 95.6 |
| 210 | 0.716 | 507.1 | 0.0022 | 68.7 |
| 211 | 1.755 | 1042.4 | 0.0086 | 71.6 |
| 212 | 1.816 | 377.7 | 0.0820 | 68.0 |
| 213 | 2.49 | 224.3 | 0.0478 | 78.0 |
| 214 | 2.034 | 255.9 | 0.0519 | 71.1 |
| 215 | 2.104 | 302.6 | 0.0047 | 66.4 |
| 216 | 1.71 | 446.1 | 0.0048 | 82.1 |
| 217 | 0.3079 | 157.1 | 0.0380 | 66.3 |
| 218 | 1.745 | 465.3 | 0.0230 | 59.5 |
| 219 | 1.599 | 711.4 | 0.0111 | 119.0 |
| 220 | 1.606 | 901.5 | 0.0032 | 58.6 |
| 221 | 1.323 | 552.0 | 0.0070 | 63.5 |
| 222 | 1.711 | 427.0 | 0.0106 | 61.1 |
| 223 | 1.918 | 426.8 | 0.0144 | 59.9 |
| 224 | 1.383 | 499.1 | 0.0049 | 63.9 |
| 225 | 2.74 | 360.8 | 0.0176 | 87.7 |
| 226 | 2.399 | 720.8 | 0.0129 | 83.5 |
| 227 | 2.67 | 402.9 | 0.0491 | 104.9 |
| 228 | 2.994 | 405.0 | 0.0381 | 87.0 |
| 229 | 4.29 | 341.3 | 0.0533 | 69.0 |
| 230 | 2.94 | 512.7 | 0.0211 | 60.6 |
| 231 | 1.157 | 465.1 | 0.0206 | 71.8 |
| 232 | 1.7 | 349.0 | 0.0319 | 72.3 |
| 233 | 1.527 | 586.5 | 0.0052 | 85.3 |
| 234 | 1.934 | 513.1 | 0.0113 | 84.0 |
| 235 | 1.975 | 202.8 | 0.1820 | 57.6 |
| 236 | 0.573 | 601.9 | NT | NT |
| 237 | 1.459 | 544.2 | 0.0043 | 55.4 |
| 238 | 3.46 | 425.8 | 0.0196 | 59.0 |
| 239 | 4.51 | 279.6 | NT | NT |
| 240 | 3.42 | 385.2 | NT | NT |
| 241 | 2.89 | 509.5 | 0.0124 | 48.9 |
| 242 | 2.92 | 468.2 | 0.0203 | 63.2 |
| 243 | 2.60 | 151.7 | NT | NT |
| 244 | 3.65 | 221.8 | NT | NT |
| 245 | 3.44 | 246.3 | 0.0431 | 48.0 |
| 246 | 1.787 | 875.3 | 0.0510 | 56.3 |
| 247 | 3.088 | 492.9 | 0.1911 | 57.0 |
| 248 | 1.608 | 568.0 | 0.0066 | 68.2 |
| 249 | 1.525 | 1104.7 | 0.0067 | 79.6 |
| 250 | 1.829 | 744.2 | 0.0110 | 59.4 |
| 251 | 1.448 | 894.2 | 0.0032 | 61.2 |
| 252 | 2.469 | 601.6 | NT | NT |
| 253 | 2.289 | 202.7 | 0.0278 | 67.1 |
| 254 | 2.586 | 620.5 | 0.0038 | 62.2 |
| 255 | 3.159 | 222.0 | 0.0104 | 55.1 |
| 256 | 2.775 | 661.9 | 0.0029 | 52.6 |
| 257 | 1.352 | 197.8 | 0.0218 | 63.0 |
| 258 | 1.39 | 827.8 | NT | NT |
| 259 | 1.566 | 801.1 | 0.0019 | 66.7 |
| 260 | 3.8 | 59.8 | NT | NT |
| 261 | 4.14 | 22.8 | NT | NT |
| 262 | 2.294 | 627.7 | 0.0140 | 81.2 |
| 263 | 2.867 | 481.1 | 0.0083 | 54.4 |
| 264 | 2.602 | 447.7 | 0.0117 | 67.2 |
| 265 | 1.828 | 879.3 | 0.0134 | 53.1 |
| 266 | 1.283 | 1404.5 | NT | NT |
| 267 | 1.256 | 887.3 | NT | NT |
| 268 | 3.73 | 103.3 | NT | NT |
| 269 | 4 | 104.6 | NT | NT |
| 270 | 1.936 | 560.8 | 0.0950 | 69.5 |
| 271 | 1.084 | 837.2 | 0.0088 | 66.6 |
| 272 | 2.313 | 806.0 | 0.0105 | 66.4 |
| 273 | 1.382 | 1065.8 | 0.0064 | 70.9 |
| 274 | 1.87 | 778.6 | 0.0033 | 77.0 |
| 275 | 1.07 | 1173.7 | 0.0015 | 77.9 |
| 276 | 3.2 | 523.1 | 0.0185 | 84.7 |
| 277 | 2.008 | 817.4 | 0.0046 | 85.1 |
| 278 | 1.098 | 1274.2 | 0.0054 | 73.4 |
| 279 | 1.193 | 1505.3 | 0.0035 | 93.7 |
| 280 | 1.96 | 844.4 | 0.0025 | 96.3 |
| 281 | 2.01 | 679.5 | 0.0037 | 85.9 |
| 282 | 1.88 | 1003.2 | 0.0024 | 69.6 |
| 283 | 1.589 | 1102.6 | 0.0008 | 84.0 |
| 284 | 2.28 | 492.8 | 0.0009 | 85.2 |
| 285 | 1.235 | 1328.1 | 0.0189 | 74.1 |
| 286 | 1.491 | 847.0 | 0.0239 | 153.1 |
| 287 | 1.407 | 383.6 | 0.0071 | 74.8 |
| 288 | 1.712 | 495.1 | 0.0341 | 69.5 |
| 289 | 2.358 | 450.0 | 0.0121 | 50.5 |
| 290 | 1.441 | 615.6 | 0.0466 | 71.4 |
| 291 | 2.5 | 496.5 | 0.0133 | 73.6 |
| 292 | 2.971 | 224.6 | NT | NT |
| 293 | 1.957 | 589.8 | 0.0220 | 78.6 |
| 294 | 2.363 | 641.4 | 0.0110 | 81.9 |
| 295 | 2.035 | 467.8 | 0.0261 | 68.7 |
| 296 | 3.22 | 254.8 | 0.0300 | 54.3 |
| 297 | | | | |
| 298 | 1.49 | 676.9 | NT | NT |
| 299 | 2.44 | 554.5 | 0.0094 | 61.7 |
| 300 | 3.27 | 625.6 | 0.0128 | 43.5 |
| 301 | 0.67 | 545.6 | NT | NT |
| 302 | 2.32 | 530.2 | 0.0183 | 74.4 |
| 303 | 3.17 | 491.2 | 0.0717 | 65.5 |
| 304 | 3.92 | 421.4 | 0.0085 | 63.4 |
| 305 | 2.63 | 312.2 | 0.0443 | 81.3 |
| 306 | 3.05 | 417.9 | 0.0315 | 88.1 |
| 307 | 3.76 | 258.8 | 0.0458 | 61.5 |
| 308 | 3.75 | 232.6 | 0.2066 | 60.7 |
| 309 | 3.79 | 194.5 | 0.2102 | 75.6 |
| 310 | 4.98 | 136.8 | NT | NT |
| 311 | 3.27 | 179.0 | 0.2199 | 61.7 |
| 312 | 3.97 | 166.6 | 0.4583 | 49.8 |
| 313 | 4.57 | 128.1 | NT | NT |
| 314 | 1.59 | 1634.22 | 0.0100 | 96.4 |
| 315 | 3.29 | 269.3 | 0.0520 | 60.9 |

Activity Table

| Example No. | DelF508-CFTR-HRP EC$_{50}$ (μM) | DelF508-CFTR-HRP Amax % | MTECC24 CFHBEC-EC$_{50}$ (μM) | MTECC24 CFHBEC-Amax % |
|---|---|---|---|---|
| 316 | NT | NT | NT | NT |
| 317 | 4.67 | 185.3 | NT | NT |
| 318 | 3.17 | 318.5 | 0.0776 | 48.7 |
| 319 | 3.48 | 194.9 | 0.0250 | 67.1 |
| 320 | 2.22 | 544.8 | 0.1256 | 74.2 |
| 321 | 1.72 | 413.2 | 0.0183 | 49.1 |
| 322 | 2.61 | 309.6 | 0.2219 | 52.6 |
| 323 | 2.77 | 252.5 | 0.1472 | 67.7 |
| 324 | 2.64 | 401.8 | 0.0479 | 49.4 |
| 325 | 2.40 | 257.3 | 0.0154 | 60.1 |
| 326 | 3.81 | 102.6 | 0.2034 | 50.5 |
| 327 | 4.26 | 92.5 | NT | NT |
| 328 | 1.79 | 1224.3 | NT | NT |
| 329 | 0.93 | 1869.6 | NT | NT |
| 330 | 2.301 | 9.1 | NT | NT |
| 331 | 1.522 | 218.5 | 0.0649 | 67.4 |
| 332 | 1.109 | 521.4 | 0.00475 | 84.0 |
| 333 | 1.954 | 427.7 | 0.0079 | 47.6 |
| 334 | 2.472 | 164.2 | NT | NT |
| 335 | 3.136 | 71.3 | NT | NT |
| 336 | 1.763 | 265.5 | NT | NT |
| 337 | 2.25 | 1082.2 | 0.002723 | 51.5 |
| 338 | 2.806 | 542.2 | NT | NT |
| 339 | 2.314 | 122.5 | NT | NT |
| 340 | 2.449 | 277.6 | NT | NT |
| 341 | 3.026 | 89.2 | NT | NT |
| 342 | 1.898 | 265.7 | 0.0802 | 85.8 |
| 343 | 2.148 | 197.1 | 0.0861 | 65.3 |
| 344 | 2.808 | 132.1 | 0.02277 | 46.7 |
| 345 | 1.331 | 557.2 | 0.0415 | 90.4 |
| 346 | 1.753 | 296.6 | NT | NT |
| 347 | 1.893 | 245.0 | NT | NT |
| 348 | 2.834 | 144.7 | NT | NT |
| 349 | 1.642 | 252.3 | NT | NT |
| 350 | 1.897 | 232.4 | NT | NT |
| 351 | 0.87 | 492.1 | 0.107 | 99.7 |
| 352 | 0.699 | 714.0 | 0.000808 | 82.2 |
| 353 | 2.799 | 118.0 | NT | NT |
| 354 | 2.738 | 154.1 | NT | NT |
| 355 | 3.69 | 139.9 | NT | NT |
| 356 | 1.513 | 553.8 | 0.00749 | 70.1 |
| 357 | 2.063 | 1024.1 | 0.0385 | 70.6 |
| 358 | 2.317 | 868.6 | 0.00402 | 57.9 |
| 359 | 1.956 | 647.9 | 0.002039 | 86.7 |
| 360 | 2.109 | 546.4 | 0.0474 | 57.5 |
| 361 | 2.079 | 1087.2 | 0.01126 | 51.9 |
| 362 | 2.005 | 1074.6 | 0.000533 | 77.9 |
| 363 | 0.705 | 615.5 | NT | NT |
| 364 | 1.593 | 230.7 | NT | NT |
| 365 | 1.888 | 165.6 | NT | NT |
| 366 | 1.342 | 1225.4 | 0.000797 | 66.9 |
| 367 | 0.928 | 808.8 | 0.001398 | 91.2 |
| 368 | 0.671 | 1232.3 | 0.000152 | 66.2 |
| 369 | 1.724 | 962.2 | NT | NT |
| 370 | 1.465 | 601.0 | 0.00085 | 105.9 |
| 371 | 1.126 | 961.9 | 0.00197 | 254.3 |
| 372 | 2.254 | 554.3 | NT | NT |
| 373 | 0.273 | 367.1 | 0.001168 | 93.1 |
| 374 | 2.78 | 233.4 | 0.1326 | 39.8 |
| 375 | 1.209 | 1030.2 | 0.000682 | 63.5 |
| 376 | 0.913 | 629.2 | NT | NT |
| 377 | 0.738 | 1477.2 | NT | NT |
| 378 | 1.355 | 271.8 | NT | NT |
| 379 | 1.081 | 645.7 | NT | NT |
| 380 | 2.656 | 42.3 | NT | NT |
| 381 | 2.506 | 284.0 | NT | NT |
| 382 | 0.711 | 503.5 | NT | NT |
| 383 | 0.498 | 1247.1 | NT | NT |
| 384 | 0.501 | 1041.9 | NT | NT |
| 385 | 0.81 | 668.0 | NT | NT |
| 386 | 0.605 | 1028.5 | NT | NT |
| 387 | 1.634 | 587.9 | NT | NT |
| 388 | 1.017 | 927.8 | NT | NT |
| 389 | 1.043 | 749.3 | NT | NT |
| 390 | 0.761 | 889.1 | NT | NT |
| 391 | 0.53 | 502.9 | NT | NT |
| 392 | 0.527 | 459.5 | NT | NT |
| 393 | 1.038 | 680.4 | NT | NT |
| 394 | 1.053 | 1331.2 | NT | NT |
| 395 | 3.65 | 64.3 | NT | NT |
| 396 | 0.845 | 1255.6 | NT | NT |
| 397 | 1.279 | 303.3 | NT | NT |
| 398 | 0.615 | 711.2 | NT | NT |
| 399 | 2.088 | 727.9 | NT | NT |
| 400 | 1.096 | 672.3 | NT | NT |
| 401 | 0.796 | 1956.7 | NT | NT |
| 402 | 0.778 | 728.9 | NT | NT |
| 403 | 2.362 | 155.3 | NT | NT |
| 404 | 0.786 | 1026.4 | NT | NT |
| 405 | 2.483 | 235.3 | NT | NT |
| 406 | 1.52 | 334.4 | NT | NT |
| 407 | 1.605 | 467.6 | NT | NT |
| 408 | 1.985 | 271.2 | NT | NT |
| 409 | 1.669 | 330.0 | NT | NT |
| 410 | 1.922 | 209.8 | NT | NT |
| 411 | 1.391 | 400.0 | NT | NT |
| 412 | 1.89 | 221.2 | NT | NT |
| 413 | 0.576 | 906.4 | NT | NT |
| 414 | 1.891 | 683.7 | NT | NT |
| 415 | 1.77 | 1593.6 | NT | NT |
| 416 | 1.896 | 1421.9 | NT | NT |
| 417 | 1.883 | 1384.8 | NT | NT |
| 418 | 1.221 | 643.6 | NT | NT |
| 419 | 2.395 | 643.9 | NT | NT |
| 420 | 1.925 | 704.9 | NT | NT |
| 421 | 2.044 | 1139.0 | NT | NT |
| 422 | 1.38 | 904.6 | NT | NT |
| 423 | 0.757 | 2390.0 | NT | NT |
| 424 | 2.019 | 1277.6 | NT | NT |
| 425 | 1.223 | 1088.4 | NT | NT |
| 426 | 2.317 | 287.3 | NT | NT |
| 427 | 0.638 | 281.8 | NT | NT |
| 428 | 1.681 | 712.9 | NT | NT |
| 429 | 0.838 | 541.2 | NT | NT |
| 430 | 1.713 | 370.0 | NT | NT |
| 431 | 1.734 | 762.8 | NT | NT |
| 432 | 1.916 | 596.1 | NT | NT |
| 433 | 0.436 | 570.8 | NT | NT |
| 434 | 2.227 | 734.4 | NT | NT |
| 435 | 2.296 | 714.3 | NT | NT |
| 436 | 1.768 | 438.3 | NT | NT |
| 437 | 1.563 | 869.0 | NT | NT |
| 438 | 1.981 | 53.4 | NT | NT |
| 439 | 2.223 | 264.0 | NT | NT |
| 440 | 2.54 | 274.4 | NT | NT |
| 441 | 2.31 | 299.0 | NT | NT |
| 442 | 1.244 | 1732.1 | NT | NT |
| 443 | 1.752 | 1161.6 | NT | NT |
| 444 | 4.06 | 47.5 | NT | NT |
| 445 | 2.664 | 94.1 | NT | NT |
| 446 | 2.115 | 278.5 | NT | NT |
| 447 | 2.407 | 1204.1 | NT | NT |
| 448 | 1.493 | 1634.9 | NT | NT |
| 449 | 2.367 | 1083.5 | NT | NT |
| 450 | 1.099 | 1773.2 | NT | NT |
| 451 | 2.675 | 846.8 | NT | NT |
| 452 | 2.358 | 990.0 | NT | NT |
| 453 | 1.594 | 1430.2 | NT | NT |
| 454 | 1.701 | 1136.1 | NT | NT |
| 455 | 1.769 | 899.2 | NT | NT |
| 456 | 1.358 | 464.6 | NT | NT |
| 457 | 0.622 | 702.0 | NT | NT |
| 458 | 1.598 | 638.7 | NT | NT |
| 459 | 2.365 | 331.5 | NT | NT |
| 460 | 1.806 | 361.5 | NT | NT |
| 461 | 1.947 | 391.6 | NT | NT |

-continued

Activity Table

| Example No. | DelF508-CFTR-HRP EC$_{50}$ (μM) | DelF508-CFTR-HRP Amax % | MTECC24 CFHBEC- EC$_{50}$ (μM) | MTECC24 CFHBEC- Amax % |
|---|---|---|---|---|
| 462 | 2.933 | 107.7 | NT | NT |
| 463 | 2.954 | 410.0 | NT | NT |
| 464 | 2.433 | 815.9 | NT | NT |
| 465 | 1.726 | 1977.5 | NT | NT |

As indicated by the test results described hereinbefore, compounds of the present invention may be useful for treating diseases, conditions and disorders through the modulation of CFTR function; consequently, the compounds of the present invention (including the compositions and processes used therein) may be used in the manufacture of a medicament for the therapeutic applications described herein. Hence, another Embodiment of the present invention is a pharmaceutical composition comprising a compound of the present invention either alone or in combination with at least one additional therapeutic agent, or a pharmaceutically acceptable salt thereof, and a pharmaceutically acceptable diluent or carrier.

The invention claimed is:

1. A compound of formula (I), or a pharmaceutically acceptable salt thereof:

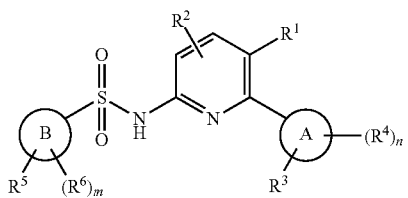

(I)

wherein:
ring A is a $C_{6-10}$aryl ring;
ring B is pyridinyl;
$R^1$ and $R^2$ are each independently hydrogen, nitrile, $C_{1-4}$alkoxy, halogen, $C_{1-4}$alkyl, halo-substituted-$C_{1-4}$alkyl, $C_{3-6}$ cycloalkyl or halo-substituted-$C_{1-4}$alkoxy;
$R^3$ and $R^4$ are each independently hydrogen, nitrile, $CD_3$, $C_{3-6}$ cycloalkyl, $C_{4-6}$ heterocycle, $C_{1-4}$alkoxy, halogen, $C_{1-4}$alkyl, halo-substituted-$C_{1-4}$alkyl, hydroxy-substituted-$C_{1-4}$alkyl or halo-substituted-$C_{1-4}$alkoxy;
n is 1 or 2;
$R^5$ is —$NR^7R^8$, —$OR^9$ or $R^{10}$;
$R^6$ is hydrogen, hydroxy, $C_{1-2}$alkyl, $C_{1-2}$alkoxy, hydroxy-substituted-$C_{1-2}$alkyl, halogen or amino;
m is 1 or 2;
$R^7$ is hydrogen, $C_{1-6}$alkyl, $C_{3-6}$ cycloalkyl, a fully or partially saturated 4 to 7-membered heterocycle, wherein said 4 to 7-membered heterocycle is optionally substituted with 1 to 4 substituents each independently selected from halogen, hydroxy, $C_{1-4}$alkyl, $C_{1-4}$alkoxy, halo-substituted-$C_{1-4}$alkyl, hydroxy-substituted-$C_{1-4}$alkyl, halo-substituted-$C_{1-4}$alkoxy, oxo, nitrile, $C_{3-6}$ cycloalkyl, $C_{4-6}$ heterocycle, $NHR^{11}$, —C(O)—$R^{13}$, —C(O)$NHR^{11}$, $C_{1-3}$alkyl-C(O)$NHR^{11}$ and —C(O)O—$R^{12}$;
$R^8$ is hydrogen or $C_{1-4}$alkyl;

$R^9$ is hydrogen, $C_{3-6}$ cycloalkyl or a fully or partially saturated 4 to 7-membered heterocycle each ring is optionally substituted with one to four substituents each independently selected from halogen, hydroxy, $C_{1-4}$alkyl, $C_{1-4}$alkoxy, halo-substituted-$C_{1-4}$alkyl, hydroxy-substituted-$C_{1-4}$alkyl, halo-substituted-$C_{1-4}$alkoxy, oxo, nitrile, $C_{3-6}$cycloalkyl, $C_{4-6}$ heterocycle, $NHR^{11}$, —C(O)—$R^{13}$, —C(O)$NHR^{11}$, $C_{1-3}$alkyl-C(O)$NHR^{11}$ and —C(O)O—$R^{12}$;
$R^{10}$ is a fully or partially saturated 4 to 10-membered heterocycle optionally substituted with one to four substituents each independently selected from halogen, hydroxy, $C_{1-4}$alkyl, $C_{1-4}$alkoxy, halo-substituted-$C_{1-4}$alkyl, hydroxy-substituted-$C_{1-4}$alkyl, halo-substituted-$C_{1-4}$alkoxy, oxo, nitrile, $C_{3-6}$ cycloalkyl, $C_{4-6}$ heterocycle, $NHR^{11}$, —C(O)—$R^{13}$, —C(O)$NHR^{11}$, $C_{1-3}$alkyl-C(O)$NHR^{11}$, —C(O)$C_{1-3}$alkyl-$NHR^{11}$ and —C(O)O—$R^{12}$, wherein said $C_{3-6}$ cycloalkyl and $C_{4-6}$ heterocycle are optionally substituted with 1 to 3 substituents each independently selected from hydroxy, halogen, amino, $C_{1-4}$alkyl, halo-substituted-$C_{1-4}$alkyl and hydroxy-substituted-$C_{1-4}$alkyl;
$R^{11}$ is hydrogen, $C_{1-4}$alkyl or $C_{0-3}$alkyl-C(O)O—$R^{14}$;
$R^{12}$ is hydrogen, $C_{1-4}$alkyl or $C_{1-3}$alkyl-C(O)—$NHR^{14}$;
$R^{13}$ is $C_{1-4}$alkyl, wherein said alkyl is optionally substituted with amino; and
$R^{14}$ is hydrogen or $C_{1-4}$alkyl.

2. The compound of claim 1 having the structure of formula (Ia), (Ib) or (Ic)), or a pharmaceutically acceptable salt thereof:

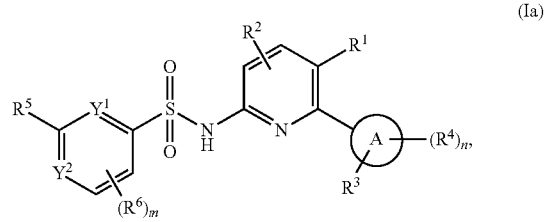

(Ia)

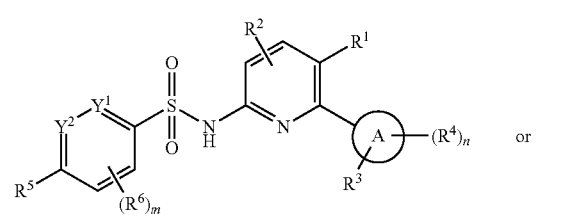

(Ib)

or

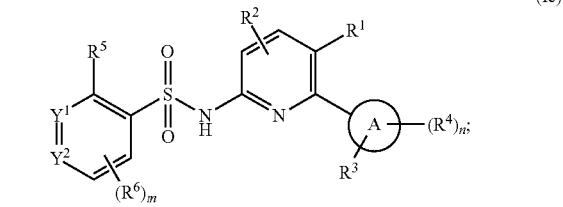

(Ic)

wherein:
at least one of $R^1$ or $R^2$ is not hydrogen;
$Y^1$ is N and $Y^2$ is $CR^6$ or $Y^2$ is N and $Y^1$ is $CR^6$.

3. The compound of claim 2, or a pharmaceutically acceptable salt thereof wherein:
$Y^1$ is N and $Y^2$ is $CR^6$.

4. The compound of claim 2, or a pharmaceutically acceptable salt thereof wherein:
$Y^1$ is $CR^6$ and $Y^2$ is N.

5. The compound of claim 1, or a pharmaceutically acceptable salt thereof wherein:
m is 1; and
n is 1.

6. The compound of claim 2 of formula (Ia), or a pharmaceutically acceptable salt thereof, wherein:
$R^1$ is hydrogen, halogen or $CF_3$;
$R^2$ is hydrogen, halogen, —$OCH_3$ or $CF_3$;
$Y^1$ is N and $Y^2$ is CH; and
ring A is phenyl.

7. The compound of claim 1, or a pharmaceutically acceptable salt thereof wherein
$R^5$ is $R^{10}$ and
$R^{10}$ is a fully or partially saturated 4 to 10-membered heterocycle optionally substituted with 1 to 4 substituents each independently selected from halogen, hydroxy, $C_{1-4}$alkyl, $C_{1-4}$alkoxy, halo-substituted-$C_{1-4}$alkyl, hydroxy-substituted-$C_{1-4}$alkyl, halo-substituted-$C_{1-4}$alkoxy, oxo, nitrile, $C_{3-6}$ cycloalkyl, $C_{4-6}$ heterocycle, $NHR^{11}$, —C(O)—$R^{13}$, —C(O)$NHR^{11}$, $C_{1-3}$alkyl-C(O)$NHR^{11}$, —C(O)$C_{1-3}$alkyl-$NHR^{11}$ and —C(O)O—$R^{12}$, wherein said $C_{3-6}$ cycloalkyl and $C_{4-6}$ heterocycle are optionally substituted with 1 to 3 substituents each independently selected from hydroxy, halogen, amino, $C_{1-4}$alkyl, halo-substituted-$C_{1-4}$alkyl and hydroxy-substituted-$C_{1-4}$alky.

8. The compound of claim 7, or a pharmaceutically acceptable salt thereof, wherein $R^{10}$ is a fully saturated 4 to 10-membered.

9. The compound of claim 7, or a pharmaceutically acceptable salt thereof, wherein $R^{10}$ is 4,5,6,7-tetrahydro-3H-imidazo[4,5-c]pyridine, 8-azabicyclo[3.2.1]octan-3-ol, octahydropyrrolo[1,2-a]pyrazine, 6-oxa-1-azaspiro[3.3]heptane, 5,6,7,8-tetrahydroimidazo[1,2-a]pyrazine, 3,8 diazabicyclo[3.2.1]octane, 8-oxa-3-azabicyclo[3.2.1]octane, 2-oxa-6-azaspiro[3.3]heptane, 1H-pyrazole, 2,6-diazaspiro[3.3]heptane, 7-azaspiro[3.5]nonane, 2,6-diazaspiro[3.4]octane, 1,6-diazaspiro[3.3]heptane, 5-oxa-2-azaspiro[3.4]octane, 2,5-diazabicyclo[2.2.1]heptane, 8-azaspiro[4.5]decane, 5-azaspiro[2.5]octane, 4,7-diazaspiro[2.5]octane, 5,6,7,8-tetrahydro-[1,2,4]triazolo[4,3-a]pyrazine or 3-azabicyclo[3.1.0]hexane; wherein $R^{10}$ is optionally substituted by 1 to 3 substituents each independently selected from amino, oxo, halogen, $C_{1-4}$alkyl, hydroxy-substituted $C_{1-4}$alkyl and halo-substituted $C_{1-4}$alkyl.

10. The compound according to claim 2 of formula (Ia), or a pharmaceutically acceptable salt thereof, wherein:
$R^1$ is F, Cl or $CF_3$;
$R^2$ is hydrogen, —$OCH_3$ or $CF_3$;
$Y^1$ is N and $Y^2$ is CH;
n is 1;
ring A is phenyl;
$R^5$ is —$NR^7R^8$; and
$R^8$ is hydrogen.

11. The compound according to claim 2 of formula (Ia), or a pharmaceutically acceptable salt thereof, wherein:
$R^1$ is F, Cl or $CF_3$;
$R^2$ is hydrogen, —$OCH_3$ or $CF_3$;
$Y^1$ is N and $Y^2$ is CH;
ring A is phenyl; and
$R^5$ is —$OR^9$.

12. The compound according to claim 1 of formula (II), or a pharmaceutically acceptable salt thereof:

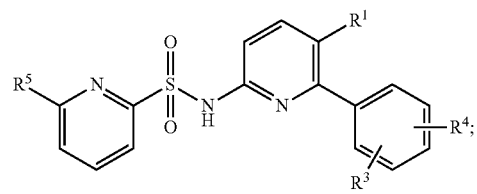

wherein:
$R^1$ is F, Cl or $CF_3$;
$R^5$ is $R^{10}$; and
$R^{10}$ is a fully or partially saturated 4 to 10-membered heterocycle optionally substituted with one to four substituents each independently selected from the group consisting of halogen, hydroxy, $C_{1-4}$alkyl, $C_{1-4}$alkoxy, halo-substituted-$C_{1-4}$alkyl, hydroxy-substituted-$C_{1-4}$alkyl, halo-substituted-$C_{1-4}$alkoxy, oxo, nitrile, $C_{3-6}$cycloalkyl, $C_{4-6}$ heterocycle, $NHR^{11}$, —C(O)—$R^{13}$, —C(O)$NHR^{11}$, $C_{1-3}$alkyl-C(O)$NHR^{11}$, —C(O)$C_{1-3}$alkyl-$NHR^{11}$ and —C(O)O—$R^{12}$; wherein said $C_{3-6}$ cycloalkyl or $C_{4-6}$ heterocycle, are optionally substituted with 1 to 3 substituents each independently selected from hydroxy, halogen, amino, $C_{1-4}$alkyl, halo-substituted-$C_{1-4}$alkyl and hydroxy-substituted-$C_{1-4}$alkyl.

13. The compound of claim 2 of formula (Ia), or a pharmaceutically acceptable salt thereof, wherein:
$R^1$ is F, Cl or $CF_3$;
$R^2$ is H;
$Y^1$ is N and $Y^2$ is CH;
n is 1;
ring A is

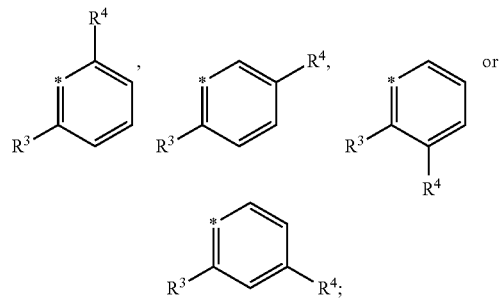

wherein * represents the carbon atom to which ring A is attached to formula (Ia);
$R^3$ and $R^4$ are each independently hydrogen, Cl, F, $CH_3$, $CD_3$, nitrile, cyclopropyl, —$OCH_3$, —$OCF_3$ or $CF_3$, where at least one of $R^3$ Or $R^4$ is not hydrogen;
$R^5$ is $R^{10}$;
$R^{11}$ is hydrogen or $C_{1-4}$alkyl;
$R^{12}$ is hydrogen or $C_{1-4}$alkyl; and
$R^{13}$ is $C_{1-4}$alkyl.

14. The compound of claim 13, or a pharmaceutically acceptable salt thereof, wherein $R^3$ is $CH_3$, $CD_3$, cyclopropyl, Cl, —$OCH_3$, —$CF_3$ or —$OCF_3$ and $R^4$ is hydrogen, Cl, —$OCH_3$, F, $CH_3$, nitrile, or —$CF_3$.

15. The compound of claim 13, or a pharmaceutically acceptable salt thereof, wherein $R^3$ is Cl, $CD_3$, or $CH_3$ and $R^4$ is hydrogen, $CH_3$, Cl or F.

16. The compound of claim 13, or a pharmaceutically acceptable salt thereof, where $R^{10}$ is

337

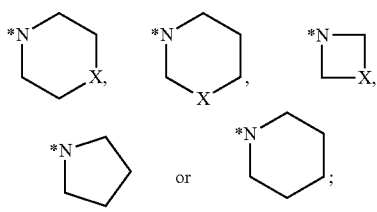

or

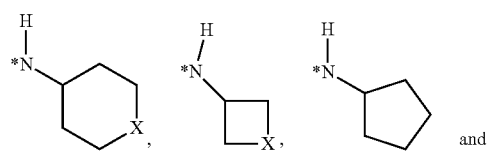

wherein *N represents the ring attachment nitrogen and X is O, C or N; wherein each $R^{10}$ ring is substituted with 1 or 2 substituents each independently selected from hydrogen, fluoro hydroxy, $C_{1-4}$alkyl, $C_{1-2}$alkoxy, halo-substituted-$C_{1-2}$alkyl, hydroxy-substituted-$C_{1-2}$alkyl, halo-substituted-$C_{1-2}$alkoxy, oxo, nitrile, $C_{3-6}$ cycloalkyl, $C_{4-6}$ heterocycle, $NHR^{11}$, —C(O)$NHR^{11}$, $C_{1-3}$alkyl-C(O)$NHR^{11}$, —C(O)$C_{1-3}$alkyl-$NHR^{11}$ and —C(O)O—$R^{12}$, wherein said $C_{3-6}$cycloalkyl and $C_{4-6}$ heterocycle are optionally substituted with 1 or 2 substituents each independently selected from hydroxy, halogen, amino, $C_{1-4}$alkyl, halo-substituted-$C_{1-4}$alkyl and hydroxy-substituted-$C_{1-4}$alkyl;

$R^{11}$ is selected from hydrogen and $C_{1-4}$alkyl; and $R^{12}$ is selected from hydrogen and $C_{1-4}$alkyl.

17. The compound of claim 2 of formula (Ia), or a pharmaceutically acceptable salt thereof:
wherein:
$R^1$ is F, Cl or $CF_3$;
$R^2$ is H;
$Y^1$ is N and $Y^2$ is CH;
n is 1;
ring A is

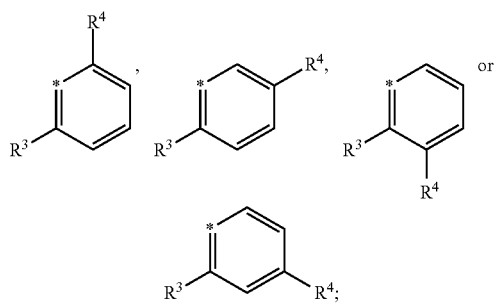

wherein * represents the carbon atom to which ring A is attached to formula (Ia);

$R^3$ is Cl, $CD_3$, or $CH_3$ and $R^4$ is hydrogen, $CH_3$, Cl or F;

$R^5$ is —$NR^7R^8$;

$R^8$ is hydrogen; —$NR^7R^8$ is selected from the group consisting of:

338

-continued

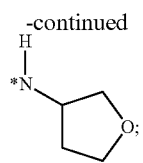

wherein *N represents the ring attachment nitrogen;
X is O, C or N;
wherein $R^7$ is substituted with 1 to 2 substituents each independently selected from hydrogen, halogen, hydroxy, $C_{1-4}$alkyl, $C_{1-4}$alkoxy, halo-substituted-$C_{1-4}$alkyl, hydroxy-substituted-$C_{1-4}$alkyl, halo-substituted-$C_{1-4}$alkoxy, oxo, nitrile, $C_{3-6}$ cycloalkyl, $C_{4-6}$ heterocycle, $NHR^{11}$, —C(O)—$R^{13}$, —C(O)$NHR^{11}$, $C_{1-3}$alkyl-C(O)$NHR^{11}$ and —C(O)O—$R^{12}$;

$R^{11}$ is selected from hydrogen and $C_{1-4}$alkyl; and
$R^{12}$ is selected from hydrogen and $C_{1-4}$alkyl.

18. The compound of claim 2 of formula (Ia), or a pharmaceutically acceptable salt thereof, wherein:
$R^1$ is F, Cl or $CF_3$;
$R^2$ is H;
$Y^1$ is N and $Y^2$ is CH;
ring A is

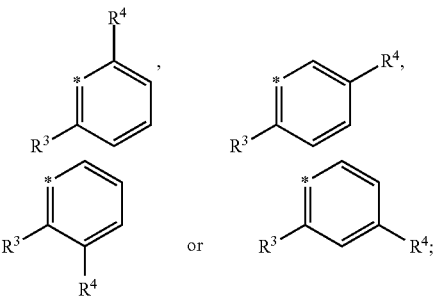

wherein * represents the carbon atom to which ring A is attached to formula (Ia);

$R^3$ and $R^4$ are each independently selected from hydrogen, Cl, F, $CH_3$, $CD_3$, nitrile, cyclopropyl, —$OCH_3$, —$OCF_3$ and $CF_3$; where at least one of $R^3$ or $R^4$ is not hydrogen;

$R^5$ is $R^{10}$;

$R^{10}$ is a heterocycle selected from the group consisting of, wherein *N represents the ring attachment nitrogen:

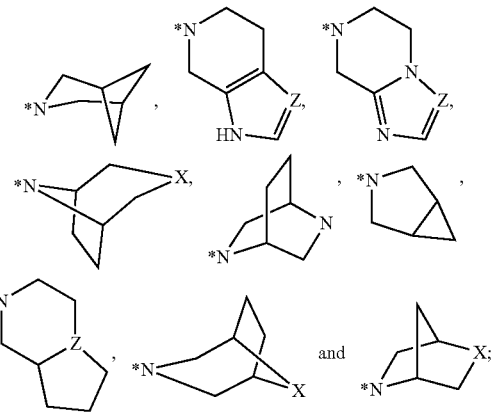

X is O, CH or N;
Z is N, or CH;
wherein said $R^{10}$ heterocycle is substituted with 1 to 2 substituents each independently selected from hydrogen, fluoro, hydroxy, $C_{1-4}$alkyl, $C_{1-2}$alkoxy, halo-substituted-$C_{1-2}$alkyl, hydroxy-substituted-$C_{1-2}$alkyl, halo-substituted-$C_{1-2}$alkoxy, oxo, nitrile, $C_{3-6}$ cycloalkyl, $C_{4-6}$ heterocycle, $NHR^{11}$, —C(O)$NHR^{11}$ and —C(O)O—$R^{12}$; wherein said $C_{3-6}$ cycloalkyl and $C_{4-6}$ heterocycle are optionally substituted with 1 or 2 substituents each independently selected from hydroxy, halogen, amino, $C_{1-4}$alkyl, halo-substituted-$C_{1-4}$alkyl and hydroxy-substituted-$C_{1-4}$alkyl;
$R^{11}$ is selected from hydrogen and $C_{1-4}$alkyl; and
$R^{12}$ is selected from hydrogen and $C_{1-4}$alkyl.

19. The compound of claim 13, or a pharmaceutically acceptable salt thereof, wherein:
$R^{10}$ is a heterocycle selected from the group consisting of, where *N represents the ring attachment nitrogen:

X is O, C or N;
wherein said $R^{10}$ heterocycle is substituted with 1 to 2 substituents each independently selected from hydrogen, fluoro, hydroxy, cyclopropyl, oxetane, $C_{1-2}$alkyl, halo-substituted-$C_{1-2}$alkyl, hydroxy-substituted-$C_{1-2}$alkyl, oxo, $NHR^{11}$, —C(O)$NHR^{11}$, $C_{13}$alkyl-C(O)$NHR^{11}$, —C(O)$C_{13}$alkyl-$NHR^{11}$ and —C(O)O—$R^{12}$;
$R^{11}$ is selected from hydrogen and $C_{1-4}$alkyl;
$R^{12}$ is selected from hydrogen and $C_{1-4}$alkyl; and
ring A is

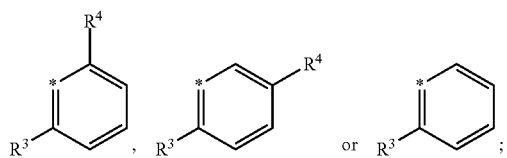

wherein * represents the carbon atom to which ring A is attached to formula (Ia);
$R^3$ is selected from Cl, $CD_3$, or $CH_3$, and $R^4$ is selected from hydrogen, $CH_3$, Cl and F.

20. The compound of claim 1, or a pharmaceutically acceptable salt thereof, where $R^3$ is $CH_3$, or Cl, and $R^4$ is hydrogen or F.

21. A The compound of claim 1, or a pharmaceutically acceptable salt thereof, selected from the group consisting of:
6-amino-N-(6-(5-fluoro-2-methylphenyl)-5-(trifluoromethyl)pyridin-2-yl)pyridine-2-sulfonamide;
6-Amino-N-(5-chloro-6-(o-tolyl)pyridin-2-yl)pyridine-2-sulfonamide;
6-amino-N-(6-(2,6-dimethylphenyl)-5-(trifluoromethyl)pyridin-2-yl)pyridine-2-sulfonamide;
6-amino-N-(5-bromo-6-(2,6-dimethylphenyl)pyridin-2-yl)pyridine-2-sulfonamide;
2-amino-N-(5-chloro-6-(2,6-dimethylphenyl)pyridin-2-yl)pyridine-4-sulfonamide;
6-amino-N-(6-(2,6-dimethylphenyl)-4-(trifluoromethyl)pyridin-2-yl)pyridine-2-sulfonamide;
6-amino-N-(5-chloro-6-(5-fluoro-2-methylphenyl)pyridin-2-yl)pyridine-2-sulfonamide;
6-amino-N-(6-(3-fluoro-2-methylphenyl)-5-(trifluoromethyl)pyridin-2-yl)pyridine-2-sulfonamide;
6-amino-N-(5-chloro-6-(2,6-dimethylphenyl)-4-(trifluoromethyl)pyridin-2-yl)pyridine-2-sulfonamide;
6-amino-N-(6-(2,6-dimethylphenyl)-5-fluoropyridin-2-yl)pyridine-2-sulfonamide;
6-amino-N-(4-chloro-6-(2,6-dimethylphenyl)pyridin-2-yl)pyridine-2-sulfonamide;
6-amino-N-(5-chloro-6-(2,6-dimethylphenyl)pyridin-2-yl)pyridine-2-sulfonamide;
6-amino-N-(5-chloro-6-(3-fluoro-2-methylphenyl)pyridin-2-yl)pyridine-2-sulfonamide;
6-amino-N-(5-chloro-6-(2-chloro-6-methylphenyl)pyridin-2-yl)pyridine-2-sulfonamide;
6-amino-N-(6-(o-tolyl)-5-(trifluoromethyl)pyridin-2-yl)pyridine-2-sulfonamide;
6-amino-N-(5-chloro-6-(5-chloro-2-cyclopropylphenyl)pyridin-2-yl)pyridine-2-sulfonamide;
6-amino-N-(6-(2-chlorophenyl)-5-(trifluoromethyl)pyridin-2-yl)pyridine-2-sulfonamide;
6-amino-N-(5-(trifluoromethyl)-6-(2-(trifluoromethyl)phenyl)pyridin-2-yl)pyridine-2-sulfonamide;
6-amino-N-(5-chloro-6-(2-cyclopropylphenyl)pyridin-2-yl)pyridine-2-sulfonamide;
6-amino-N-(5-chloro-6-(2-(methyl-d3)phenyl)pyridin-2-yl)pyridine-2-sulfonamide;
6-amino-N-(5-chloro-6-(2-cyclopropyl-5-fluorophenyl)pyridin-2-yl)pyridine-2-sulfonamide;
6-amino-N-(5-chloro-6-(o-tolyl)-4-(trifluoromethyl)pyridin-2-yl)pyridine-2-sulfonamide;
6-amino-N-(5-bromo-6-(o-tolyl)pyridin-2-yl)pyridine-2-sulfonamide;
6-amino-N-(5-chloro-6-(2-chlorophenyl)pyridin-2-yl)pyridine-2-sulfonamide;
2-amino-N-(6-(2,6-dimethylphenyl)-5-(trifluoromethyl)pyridin-2-yl)pyridine-4-sulfonamide;
2-amino-N-(5-chloro-6-(2-(methyl-d3)phenyl)pyridin-2-yl)pyridine-4-sulfonamide;
6-amino-N-(5-chloro-6-(2-cyclopropyl-4-fluorophenyl)pyridin-2-yl)pyridine-2-sulfonamide;
6-amino-N-(6-(2-cyclopropyl-4-fluorophenyl)-5-(trifluoromethyl)pyridin-2-yl)pyridine-2-sulfonamide;
6-amino-N-(5-chloro-6-(2-ethylphenyl)pyridin-2-yl)pyridine-2-sulfonamide;
6-amino-N-(5-chloro-6-(4-fluoro-2,6-dimethylphenyl)pyridin-2-yl)pyridine-2-sulfonamide;
6-amino-N-(5-chloro-6-(2-fluoro-6-methylphenyl)pyridin-2-yl)pyridine-2-sulfonamide;
6-amino-N-(5-chloro-6-mesitylpyridin-2-yl)pyridine-2-sulfonamide;
6-amino-N-(5-chloro-6-(o-tolyl)pyridin-2-yl)-3-fluoropyridine-2-sulfonamide;
6-amino-N-(5-chloro-6-(2-methyl-3-(trifluoromethyl)phenyl)pyridin-2-yl)pyridine-2-sulfonamide;
6-amino-N-(5-fluoro-6-(2-isopropylphenyl)pyridin-2-yl)pyridine-2-sulfonamide;
6-amino-5-methyl-N-(6-(o-tolyl)-5-(trifluoromethyl)pyridin-2-yl)pyridine-2-sulfonamide;
6-amino-N-(5-chloro-6-(4-fluoro-2-methylphenyl)pyridin-2-yl)pyridine-2-sulfonamide;
6-amino-N-(5-chloro-6-(6-chloro-2-fluoro-3-methylphenyl)pyridin-2-yl)pyridine-2-sulfonamide;

6-amino-N-(5-chloro-6-(2-chloro-6-fluorophenyl)pyridin-2-yl)pyridine-2-sulfonamide;
6-amino-N-(5-chloro-6-(o-tolyl)pyridin-2-yl)pyridine-3-sulfonamide;
6-amino-N-(6-(2-chloro-4-fluorophenyl)-5-(trifluoromethyl)pyridin-2-yl)pyridine-2-sulfonamide;
2-amino-N-(6-(5-fluoro-2-methylphenyl)-5-(trifluoromethyl)pyridin-2-yl)pyridine-4-sulfonamide;
6-amino-N-(5-chloro-6-(2-chloro-5-(trifluoromethyl)phenyl)pyridin-2-yl)pyridine-2-sulfonamide;
6-amino-N-(5-chloro-6-(5-fluoro-2-methylphenyl)pyridin-2-yl)pyridine-3-sulfonamide;
6-amino-N-(5-chloro-6-(2-isopropylphenyl)pyridin-2-yl)pyridine-3-sulfonamide;
2-amino-N-(5-chloro-6-(5-fluoro-2-methylphenyl)pyridin-2-yl)pyridine-4-sulfonamide;
6-amino-N-(5-chloro-6-(2,6-dimethylphenyl)pyridin-2-yl)pyridine-3-sulfonamide;
6-amino-N-(5-chloro-6-(2-(1,1-difluoroethyl)phenyl)pyridin-2-yl)pyridine-2-sulfonamide;
2-amino-N-(5-chloro-6-(2-methyl-5-(trifluoromethyl)phenyl)pyridin-2-yl)pyridine-4-sulfonamide;
6-amino-N-(5-chloro-6-(2-isopropylphenyl)pyridin-2-yl)pyridine-2-sulfonamide;
6-amino-N-(5-chloro-6-(2-methyl-5-(trifluoromethyl)phenyl)pyridin-2-yl)pyridine-2-sulfonamide;
6-amino-N-(5-chloro-6-(2-chloro-6-(trifluoromethyl)phenyl)pyridin-2-yl)pyridine-2-sulfonamide;
6-amino-N-(5-chloro-6-(2-methyl-6-(trifluoromethyl)phenyl)pyridin-2-yl)pyridine-2-sulfonamide;
6-amino-N-(5-chloro-6-(2-cyclopropylphenyl)pyridin-2-yl)pyridine-3-sulfonamide;
6-amino-N-(5-chloro-6-(2-(trifluoromethyl)phenyl)pyridin-2-yl)pyridine-2-sulfonamide;
6-amino-N-(5-chloro-6-(2-chloro-4-fluorophenyl)pyridin-2-yl)pyridine-2-sulfonamide;
2-amino-N-(5-chloro-6-(o-tolyl)pyridin-2-yl)pyridine-4-sulfonamide;
6-amino-N-(5-chloro-6-(2-chloro-6-fluoro-3-methylphenyl)pyridin-2-yl)pyridine-2-sulfonamide;
6-amino-N-(5-chloro-6-(2-(trifluoromethoxy)phenyl)pyridin-2-yl)pyridine-2-sulfonamide;
6-amino-N-(5-chloro-6-(2-fluoro-6-methylphenyl)pyridin-2-yl)pyridine-3-sulfonamide;
2-amino-N-(5-chloro-6-(2-(trifluoromethyl)phenyl)pyridin-2-yl)pyridine-4-sulfonamide;
6-amino-N-(5-chloro-6-(5-fluoro-2-methoxyphenyl)pyridin-2-yl)pyridine-2-sulfonamide;
6-amino-N-(6-(2,6-dimethylphenyl)-4-methylpyridin-2-yl)pyridine-2-sulfonamide;
2-amino-N-(6-(5-cyano-2-methylphenyl)-5-(trifluoromethyl)pyridin-2-yl)pyridine-4-sulfonamide;
6-amino-N-(5-chloro-6-(2-(difluoromethyl)phenyl)pyridin-2-yl)pyridine-2-sulfonamide;
6-amino-N-(5-cyclopropyl-6-(o-tolyl)pyridin-2-yl)pyridine-2-sulfonamide;
6-amino-N-(5-chloro-6-(3-cyano-2-methylphenyl)pyridin-2-yl)pyridine-2-sulfonamide;
6-amino-N-(6-(2,6-dimethylphenyl)pyridin-2-yl)pyridine-2-sulfonamide;
6-amino-N-(5-chloro-6-(2-fluorophenyl)pyridin-2-yl)pyridine-2-sulfonamide;
6-amino-N-(5-fluoro-6-(o-tolyl)pyridin-2-yl)pyridine-2-sulfonamide;
6-amino-N-(5-chloro-6-(4-fluoro-2-methylphenyl)pyridin-2-yl)pyridine-3-sulfonamide;
6-amino-N-(6-(2,6-dimethylphenyl)-5-methoxypyridin-2-yl)pyridine-2-sulfonamide;
6-amino-N-(5-chloro-6-(3-(trifluoromethyl)phenyl)pyridin-2-yl)pyridine-2-sulfonamide;
2-amino-N-(5-chloro-6-(2,6-dimethylphenyl)pyridin-2-yl)pyridine-3-sulfonamide;
6-amino-N-(5-methyl-6-(o-tolyl)pyridin-2-yl)pyridine-2-sulfonamide;
6-amino-N-(5-chloro-6-(2-methoxyphenyl)pyridin-2-yl)pyridine-2-sulfonamide;
6-amino-N-(6-(2-chlorophenyl)-5-methylpyridin-2-yl)pyridine-2-sulfonamide;
6-amino-N-(5-chloro-6-(2,3,6-trifluorophenyl)pyridin-2-yl)pyridine-2-sulfonamide;
6-amino-N-(5-(trifluoromethyl)-6-(3-(trifluoromethyl)phenyl)pyridin-2-yl)pyridine-2-sulfonamide;
6-amino-N-(5-chloro-6-(2,6-difluorophenyl)pyridin-2-yl)pyridine-2-sulfonamide;
6-amino-5-bromo-N-(5-chloro-6-(2,6-dimethylphenyl)pyridin-2-yl)pyridine-2-sulfonamide;
6-amino-N-(6-(2-methyl-5-(trifluoromethoxy)phenyl)-5-(trifluoromethyl)pyridin-2-yl)pyridine-2-sulfonamide;
6-amino-N-(6-(5-cyano-2-methylphenyl)-5-(trifluoromethyl)pyridin-2-yl)pyridine-2-sulfonamide;
6-amino-N-(5-chloro-6-(5-cyano-2-methylphenyl)pyridin-2-yl)pyridine-2-sulfonamide;
2-amino-N-(5-chloro-6-(5-cyano-2-methylphenyl)pyridin-2-yl)pyridine-4-sulfonamide;
6-amino-N-(5-chloro-6-(2,4,6-trifluorophenyl)pyridin-2-yl)pyridine-2-sulfonamide;
2-amino-N-(5-chloro-6-(3-cyano-2-methylphenyl)pyridin-2-yl)pyridine-4-sulfonamide;
2-amino-N-(5-chloro-6-(o-tolyl)pyridin-2-yl)pyridine-3-sulfonamide;
6-amino-N-(5-chloro-6-(2-methyl-5-(trifluoromethoxy)phenyl)pyridin-2-yl)pyridine-2-sulfonamide;
6-amino-N-(5-chloro-6-(2-cyanophenyl)pyridin-2-yl)pyridine-2-sulfonamide;
6-amino-N-(5-chloro-6-(4-cyano-2-methylphenyl)pyridin-2-yl)pyridine-2-sulfonamide;
2-amino-N-(5-chloro-6-(4-cyano-2-methylphenyl)pyridin-2-yl)pyridine-4-sulfonamide;
6-amino-N-(6-(2,6-dimethylphenyl)-3-fluoropyridin-2-yl)pyridine-2-sulfonamide;
6-amino-N-(5-chloro-6-(4-(trifluoromethyl)phenyl)pyridin-2-yl)pyridine-2-sulfonamide;
6-amino-N-(5-chloro-6-(2,6-dimethylphenyl)-3-fluoropyridin-2-yl)pyridine-2-sulfonamide;
6-amino-N-(3-chloro-6-(2,6-dimethylphenyl)pyridin-2-yl)pyridine-2-sulfonamide;
(R)-6-(3-aminopiperidin-1-yl)-N-(6-(o-tolyl)-5-(trifluoromethyl)pyridin-2-yl)pyridine-2-sulfonamide;
(S)-6-(3-aminopiperidin-1-yl)-N-(6-(o-tolyl)-5-(trifluoromethyl)pyridin-2-yl)pyridine-2-sulfonamide;
(R)-6-(piperidin-3-ylamino)-N-(6-(o-tolyl)-5-(trifluoromethyl)pyridin-2-yl)pyridine-2-sulfonamide;
(S)-6-(piperidin-3-ylamino)-N-(6-(o-tolyl)-5-(trifluoromethyl)pyridin-2-yl)pyridine-2-sulfonamide;
6-(((3R,4S)-4-methoxypiperidin-3-yl)amino)-N-(6-(o-tolyl)-5-(trifluoromethyl)pyridin-2-yl)pyridine-2-sulfonamide;
6-(6-amino-3-azabicyclo[3.1.0]hexan-3-yl)-N-(6-(o-tolyl)-5-(trifluoromethyl)pyridin-2-yl)pyridine-2-sulfonamide;
6-(4-aminopiperidin-1-yl)-N-(6-(o-tolyl)-5-(trifluoromethyl)pyridin-2-yl)pyridine-2-sulfonamide;

6-(4-(methylamino)piperidin-1-yl)-N-(6-(o-tolyl)-5-(trifluoromethyl)pyridin-2-yl)pyridine-2-sulfonamide;
6-(4-amino-4-methylpiperidin-1-yl)-N-(6-(o-tolyl)-5-(trifluoromethyl)pyridin-2-yl)pyridine-2-sulfonamide;
6-((3S,4R)-4-amino-3-fluoropiperidin-1-yl)-N-(6-(o-tolyl)-5-(trifluoromethyl)pyridin-2-yl)pyridine-2-sulfonamide;
6-(piperidin-4-ylamino)-N-(6-(o-tolyl)-5-(trifluoromethyl)pyridin-2-yl)pyridine-2-sulfonamide;
6-(((3S,4R)-3-hydroxypiperidin-4-yl)amino)-N-(6-(o-tolyl)-5-(trifluoromethyl)pyridin-2-yl)pyridine-2-sulfonamide;
6-(((3R,4R)-3-hydroxypiperidin-4-yl)amino)-N-(6-(o-tolyl)-5-(trifluoromethyl)pyridin-2-yl)pyridine-2-sulfonamide;
6-(((3S,4R)-3-methoxypiperidin-4-yl)amino)-N-(6-(o-tolyl)-5-(trifluoromethyl)pyridin-2-yl)pyridine-2-sulfonamide;
6-(((3R,4R)-3-methoxypiperidin-4-yl)amino)-N-(6-(o-tolyl)-5-(trifluoromethyl)pyridin-2-yl)pyridine-2-sulfonamide;
6-(((3S,4R)-3-fluoropiperidin-4-yl)amino)-N-(6-(o-tolyl)-5-(trifluoromethyl)pyridin-2-yl)pyridine-2-sulfonamide;
6-((3'S,4'S)-4'-hydroxy-[1 3'-bipyrrolidin]-1'-yl)-N-(6-(o-tolyl)-5-(trifluoromethyl)pyridin-2-yl)pyridine-2-sulfonamide;
(R)-6-(3-aminopyrrolidin-1-yl)-N-(6-(o-tolyl)-5-(trifluoromethyl)pyridin-2-yl)pyridine-2-sulfonamide;
(S)-6-(3-aminopyrrolidin-1-yl)-N-(6-(o-tolyl)-5-(trifluoromethyl)pyridin-2-yl)pyridine-2-sulfonamide;
(R)-6-(3-(methylamino)pyrrolidin-1-yl)-N-(6-(o-tolyl)-5-(trifluoromethyl)pyridin-2-yl)pyridine-2-sulfonamide;
(S)-6-(3-(methylamino)pyrrolidin-1-yl)-N-(6-(o-tolyl)-5-(trifluoromethyl)pyridin-2-yl)pyridine-2-sulfonamide;
(R)-6-(pyrrolidin-3-ylamino)-N-(6-(o-tolyl)-5-(trifluoromethyl)pyridin-2-yl)pyridine-2-sulfonamide;
(S)-6-(pyrrolidin-3-ylamino)-N-(6-(o-tolyl)-5-(trifluoromethyl)pyridin-2-yl)pyridine-2-sulfonamide;
N-(5-chloro-6-(2-(trifluoromethyl)phenyl)pyridin-2-yl)-6-(((3S,4R)-4-hydroxytetrahydrofuran-3-yl)amino)pyridine-2-sulfonamide;
N-(5-chloro-6-(2-(trifluoromethyl)phenyl)pyridin-2-yl)-6-(((3R,4S)-4-hydroxytetrahydrofuran-3-yl)amino)pyridine-2-sulfonamide;
N-(5-chloro-6-(5-fluoro-2-methylphenyl)pyridin-2-yl)-6-(((3R,4S)-4-hydroxytetrahydrofuran-3-yl)amino)pyridine-2-sulfonamide;
N-(5-chloro-6-(5-fluoro-2-methylphenyl)pyridin-2-yl)-6-(((1 S,2R,3R,4R)-3-(hydroxymethyl)-7-oxabicyclo[2.2.1]heptan-2-yl)amino)pyridine-2-sulfonamide;
(1s,4s)-4-((6-(N-(5-chloro-6-(2,6-dimethylphenyl)pyridin-2-yl)sulfamoyl)pyridin-2-yl)oxy)cyclohexane-1-carboxylic acid;
(1r,4r)-4-((6-(N-(5-chloro-6-(2,6-dimethylphenyl)pyridin-2-yl)sulfamoyl)pyridin-2-yl)oxy)cyclohexane-1-carboxylic acid;
N-(5-chloro-6-(2,6-dimethylphenyl)pyridin-2-yl)-6-(3-oxopiperazin-1-yl)pyridine-2-sulfonamide;
tert-butyl 4-(6-(N-(6-(2,6-dimethylphenyl)-4-(trifluoromethyl)pyridin-2-yl)sulfamoyl)pyridin-2-yl)piperazine-1-carboxylate;
N-(6-(2,6-dimethylphenyl)-4-(trifluoromethyl)pyridin-2-yl)-6-(piperazin-1-yl)pyridine-2-sulfonamide;
N-(5-chloro-6-(5-fluoro-2-methylphenyl)pyridin-2-yl)-6-((7S,8aR)-7-fluorohexahydropyrrolo[1,2-a]pyrazin-2(1H)-yl)pyridine-2-sulfonamide;
N-(5-chloro-6-(5-fluoro-2-methylphenyl)pyridin-2-yl)-6-((1 S,7S)-7-fluoro-1-methylhexahydropyrrolo[1,2-a]pyrazin-2(1H)-yl)pyridine-2-sulfonamide;
(S)-6-(7,7-difluorohexahydropyrrolo[1,2-a]pyrazin-2(1H)-yl)-N-(6-(o-tolyl)-5-(trifluoromethyl)pyridin-2-yl)pyridine-2-sulfonamide;
6-((7S,8aS)-7-fluorohexahydropyrrolo[1,2-a]pyrazin-2(1H)-yl)-N-(6-(o-tolyl)-5-(trifluoromethyl)pyridin-2-yl)pyridine-2-sulfonamide;
6-((7S,8aR)-7-fluorohexahydropyrrolo[1,2-a]pyrazin-2(1H)-yl)-N-(6-(o-tolyl)-5-(trifluoromethyl)pyridin-2-yl)pyridine-2-sulfonamide;
N-(6-(2,6-dimethylphenyl)-4-methoxypyridin-2-yl)-6-(piperazin-1-yl)pyridine-2-sulfonamide;
6-(4-(tert-butyl)piperazin-1-yl)-N-(5-chloro-6-(3-fluoro-2-methylphenyl)pyridin-2-yl)pyridine-2-sulfonamide;
N-(5-chloro-6-(3-fluoro-2-methylphenyl)pyridin-2-yl)-6-(4-cyclopropylpiperazin-1-yl)pyridine-2-sulfonamide;
6-(4-(tert-butyl)piperazin-1-yl)-N-(6-(3-fluoro-2-m ethylphenyl)-5-(trifluoromethyl)pyridin-2-yl)pyridine-2-sulfonamide;
6-(4-(tert-butyl)piperazin-1-yl)-N-(6-(5-fluoro-2-m ethylphenyl)-5-(trifluoromethyl)pyridin-2-yl)pyridine-2-sulfonamide;
6-(4-cyclopropylpiperazin-1-yl)-N-(6-(3-fluoro-2-methylphenyl)-5-(trifluoromethyl)pyridin-2-yl)pyridine-2-sulfonamide;
6-(4-cyclopropylpiperazin-1-yl)-N-(6-(5-fluoro-2-methylphenyl)-5-(trifluoromethyl)pyridin-2-yl)pyridine-2-sulfonamide;
N-(5-chloro-6-(3-fluoro-2-methylphenyl)pyridin-2-yl)-6-(5,6-dihydro-[1,2,4]triazolo[4,3-a]pyrazin-7(8H)-yl)pyridine-2-sulfonamide;
tert-butyl 4-(6-(N-(6-(2-cyclopropylphenyl)-5-(trifluoromethyl)pyridin-2-yl)sulfamoyl)pyridin-2-yl)piperazine-1-carboxylate;
N-(6-(2-cyclopropylphenyl)-5-(trifluoromethyl)pyridin-2-yl)-6-(piperazin-1-yl)pyridine-2-sulfonamide;
6-(4-(tert-butyl)piperazin-1-yl)-N-(6-(5-fluoro-2-methoxyphenyl)-5-(trifluoromethyl)pyridin-2-yl)pyridine-2-sulfonamide;
N-(6-(2-chlorophenyl)-5-(trifluoromethyl)pyridin-2-yl)-6-(piperazin-1-yl)pyridine-2-sulfonamide;
N-(6-(3-fluoro-2-methylphenyl)-5-(trifluoromethyl)pyridin-2-yl)-6-(piperazin-1-yl)pyridine-2-sulfonamide;
N-(6-(5-fluoro-2-methylphenyl)-5-(trifluoromethyl)pyridin-2-yl)-6-(piperazin-1-yl)pyridine-2-sulfonamide;
N-(6-(2-chloro-4-fluorophenyl)-5-(trifluoromethyl)pyridin-2-yl)-6-(piperazin-1-yl)pyridine-2-sulfonamide;
N-(6-(2-chloro-5-methoxyphenyl)-5-(trifluoromethyl)pyridin-2-yl)-6-(piperazin-1-yl)pyridine-2-sulfonamide;
N-(6-(2-chloro-3-fluorophenyl)-5-(trifluoromethyl)pyridin-2-yl)-6-(piperazin-1-yl)pyridine-2-sulfonamide;
N-(5-chloro-6-(2-chlorophenyl)pyridin-2-yl)-6-(piperazin-1-yl)pyridine-2-sulfonamide;
N-(5-chloro-6-(2-chloro-4-fluorophenyl)pyridin-2-yl)-6-(piperazin-1-yl)pyridine-2-sulfonamide;
N-(5-chloro-6-(2-chloro-5-methoxyphenyl)pyridin-2-yl)-6-(piperazin-1-yl)pyridine-2-sulfonamide;
N-(5-chloro-6-(2-chloro-3-fluorophenyl)pyridin-2-yl)-6-(piperazin-1-yl)pyridine-2-sulfonamide;
6-(piperazin-1-yl)-N-(6-(o-tolyl)-5-(trifluoromethyl)pyridin-2-yl)pyridine-2-sulfonamide;
tert-butyl 4-(6-(N-(6-(o-tolyl)-5-(trifluoromethyl)pyridin-2-yl)sulfamoyl)pyridin-2-yl)piperazine-1-carboxylate;

tert-butyl 4-(6-(N-(5-chloro-6-(2,6-dimethylphenyl)pyridin-2-yl)sulfamoyl)pyridin-2-yl)piperazine-1-carboxylate;
N-(5-chloro-6-(2,6-dimethylphenyl)pyridin-2-yl)-6-(piperazin-1-yl)pyridine-2-sulfonamide;
tert-butyl (R)-2-(hydroxymethyl)-4-(6-(N-(6-(o-tolyl)-5-(trifluoromethyl)pyridin-2-yl)sulfamoyl)pyridin-2-yl)piperazine-1-carboxylate;
(R)-6-(3-(hydroxymethyl)piperazin-1-yl)-N-(6-(o-tolyl)-5-(trifluoromethyl)pyridin-2-yl)pyridine-2-sulfonamide;
tert-butyl (R)-2-methyl-4-(6-(N-(6-(o-tolyl)-5-(trifluoromethyl)pyridin-2-yl)sulfamoyl)pyridin-2-yl)piperazine-1-carboxylate;
(R)-6-(3-methylpiperazin-1-yl)-N-(6-(o-tolyl)-5-(trifluoromethyl)pyridin-2-yl)pyridine-2-sulfonamide;
tert-butyl 4-(6-(N-(5-chloro-6-(2-methyl-5-(trifluoromethyl)phenyl)pyridin-2-yl)sulfamoyl)pyridin-2-yl)piperazine-1-carboxylate;
N-(5-chloro-6-(2-methyl-5-(trifluoromethyl)phenyl)pyridin-2-yl)-6-(piperazin-1-yl)pyridine-2-sulfonamide;
(S)-6-(2-methylpiperazin-1-yl)-N-(6-(o-tolyl)-5-(trifluoromethyl)pyridin-2-yl)pyridine-2-sulfonamide;
(R)-6-(2-methylpiperazin-1-yl)-N-(6-(o-tolyl)-5-(trifluoromethyl)pyridin-2-yl)pyridine-2-sulfonamide;
(R)—N-(6-(2,6-dimethylphenyl)-5-(trifluoromethyl)pyridin-2-yl)-6-(3-(hydroxymethyl)piperazin-1-yl)pyridine-2-sulfonamide;
(S)—N-(6-(2,6-dimethylphenyl)-5-(trifluoromethyl)pyridin-2-yl)-6-(3-(hydroxymethyl)piperazin-1-yl)pyridine-2-sulfonamide;
(R)—N-(6-(5-fluoro-2-methylphenyl)-5-(trifluoromethyl)pyridin-2-yl)-6-(3-(hydroxymethyl)piperazin-1-yl)pyridine-2-sulfonamide;
(S)—N-(6-(5-fluoro-2-methylphenyl)-5-(trifluoromethyl)pyridin-2-yl)-6-(3-(hydroxymethyl)piperazin-1-yl)pyridine-2-sulfonamide;
(R)—N-(6-(5-fluoro-2-methylphenyl)-5-(trifluoromethyl)pyridin-2-yl)-6-(3-methylpiperazin-1-yl)pyridine-2-sulfonamide;
(S)—N-(6-(5-fluoro-2-methylphenyl)-5-(trifluoromethyl)pyridin-2-yl)-6-(3-methylpiperazin-1-yl)pyridine-2-sulfonamide;
6-((3S,5R)-3,5-dimethylpiperazin-1-yl)-N-(6-(5-fluoro-2-methylphenyl)-5-(trifluoromethyl)pyridin-2-yl)pyridine-2-sulfonamide;
N-(6-(5-fluoro-2-methylphenyl)-5-(trifluoromethyl)pyridin-2-yl)-6-(4-methylpiperazin-1-yl)pyridine-2-sulfonamide;
6-(4-acetylpiperazin-1-yl)-N-(6-(5-fluoro-2-methylphenyl)-5-(trifluoromethyl)pyridin-2-yl)pyridine-2-sulfonamide;
6-(3,8-diazabicyclo[3.2.1]octan-3-yl)-N-(6-(o-tolyl)-5-(trifluoromethyl)pyridin-2-yl)pyridine-2-sulfonamide;
6-(4-(2-hydroxyethyl)piperazin-1-yl)-N-(6-(o-tolyl)-5-(trifluoromethyl)pyridin-2-yl)pyridine-2-sulfonamide;
2-(4-(6-(N-(6-(o-tolyl)-5-(trifluoromethyl)pyridin-2-yl)sulfamoyl)pyridin-2-yl)piperazin-1-yl)acetamide;
4-(6-(N-(6-(o-tolyl)-5-(trifluoromethyl)pyridin-2-yl)sulfamoyl)pyridin-2-yl)piperazine-1-carboxamide;
6-(4-(2,2-difluoroethyl)piperazin-1-yl)-N-(6-(o-tolyl)-5-(trifluoromethyl)pyridin-2-yl)pyridine-2-sulfonamide;
N-(6-(o-tolyl)-5-(trifluoromethyl)pyridin-2-yl)-6-(4-(2,2,2-trifuoroethyl)piperazin-1-yl)pyridine-2-sulfonamide;
6-(4-(oxetan-3-yl)piperazin-1-yl)-N-(6-(o-tolyl)-5-(trifluoromethyl)pyridin-2-yl)pyridine-2-sulfonamide;
tert-butyl 4-(6-(N-(5-chloro-6-(2,6-dimethylphenyl)pyridin-2-yl)sulfamoyl)pyridin-2-yl)-3-oxopiperazine-1-carboxylate
6-(4-methylpiperazin-1-yl)-N-(6-(o-tolyl)-5-(trifluoromethyl)pyridin-2-yl)pyridine-2-sulfonamide;
6-(3-oxopiperazin-1-yl)-N-(6-(o-tolyl)-5-(trifluoromethyl)pyridin-2-yl)pyridine-2-sulfonamide;
6-(4-glycylpiperazin-1-yl)-N-(6-(o-tolyl)-5-(trifluoromethyl)pyridin-2-yl)pyridine-2-sulfonamide;
N-(5-chloro-6-(2,6-dimethylphenyl)pyridin-2-yl)-6-(2-oxopiperazin-1-yl)pyridine-2-sulfonamide;
N-(5-chloro-6-(5-fluoro-2-methylphenyl)pyridin-2-yl)-6-(piperazin-1-yl)pyridine-2-sulfonamide;
N-[5-chloro-6-(3-fluoro-2-methylphenyl)pyridin-2-yl]-6-(piperazin-1-yl)pyridine-2-sulfonamide;
N-(5-chloro-6-(o-tolyl)pyridin-2-yl)-6-(piperazin-1-yl)pyridine-2-sulfonamide;
6-(4-methyl-3-oxopiperazin-1-yl)-N-(6-(o-tolyl)-5-(trifluoromethyl)pyridin-2-yl)pyridine-2-sulfonamide;
N-(5-chloro-6-(2,6-dimethylphenyl)pyridin-2-yl)-6-(4-methyl-2-oxopiperazin-1-yl)pyridine-2-sulfonamide;
N-(5-chloro-6-(2,6-dimethylphenyl)pyridin-2-yl)-6-(5,6-dihydroimidazo[1,2-a]pyrazin-7(8H)-yl)pyridine-2-sulfonamide;
N-(5-chloro-6-(2,6-dimethylphenyl)pyridin-2-yl)-6-(2-(trifluoromethyl)-5,6-dihydroimidazo[1,2-a]pyrazin-7(8H)-yl)pyridine-2-sulfonamide;
6-((1S,4S)-2,5-diazabicyclo[2.2.2]octan-2-yl)-N-(6-(5-fluoro-2-methylphenyl)-5-(trifluoromethyl)pyridin-2-yl)pyridine-2-sulfonamide;
6-(2,5-diazabicyclo[2.2.2]octan-2-yl)-N-(6-(5-fluoro-2-methylphenyl)-5-(trifluoromethyl)pyridin-2-yl)pyridine-2-sulfonamide;
6-((5S)-1,4-diazabicyclo[3.2.1]octan-4-yl)-N-(6-(5-fluoro-2-methylphenyl)-5-(trifluoromethyl)pyridin-2-yl)pyridine-2-sulfonamide;
6-((1S,4S)-2,5-diazabicyclo[2.2.1]heptan-2-yl)-N-(6-(o-tolyl)-5-(trifluoromethyl)pyridin-2-yl)pyridine-2-sulfonamide;
6-(3-hydroxy-3-(trifluoromethyl)azetidin-1-yl)-N-(6-(o-tolyl)-5-(trifluoromethyl)pyridin-2-yl)pyridine-2-sulfonamide;
N-(6-(2,6-dimethylphenyl)-4-(trifluoromethyl)pyridin-2-yl)-6-(3-hydroxyazetidin-1-yl)pyridine-2-sulfonamide;
N-(6-(2,6-dimethylphenyl)-4-methoxypyridin-2-yl)-6-(3-hydroxy-3-methylazetidin-1-yl)pyridine-2-sulfonamide;
N-(5-bromo-6-(o-tolyl)pyridin-2-yl)-6-(3-hydroxy-3-methylazetidin-1-yl)pyridine-2-sulfonamide;
N-(6-(2-cyclopropylphenyl)-5-(trifluoromethyl)pyridin-2-yl)-6-(3-hydroxyazetidin-1-yl)pyridine-2-sulfonamide;
N-(6-(5-fluoro-2-methoxyphenyl)-5-(trifluoromethyl)pyridin-2-yl)-6-(3-hydroxyazetidin-1-yl)pyridine-2-sulfonamide;
N-(5-chloro-6-(2,6-dimethylphenyl)pyridin-2-yl)-6-(3-hydroxy-3-methylazetidin-1-yl)pyridine-2-sulfonamide;
N-(5-chloro-6-(2,6-dimethylphenyl)pyridin-2-yl)-6-(3-cyclopropyl-3-hydroxyazetidin-1-yl)pyridine-2-sulfonamide;
N-(5-chloro-6-(2-methyl-5-(trifluoromethyl)phenyl)pyridin-2-yl)-6-(3-hydroxy-3-methylazetidin-1-yl)pyridine-2-sulfonamide;
N-(5-chloro-6-(2-chloro-4-fluorophenyl)pyridin-2-yl)-6-(3-hydroxy-3-methylazetidin-1-yl)pyridine-2-sulfonamide;

N-(5-chloro-6-(2-chloro-4-fluorophenyl)pyridin-2-yl)-6-(3-hydroxyazetidin-1-yl)pyridine-2-sulfonamide;

N-(6-(3-fluoro-2-methylphenyl)-5-(trifluoromethyl)pyridin-2-yl)-6-(3-hydroxy-3-methylazetidin-1-yl)pyridine-2-sulfonamide;

N-(6-(3-fluoro-2-methylphenyl)-5-(trifluoromethyl)pyridin-2-yl)-6-(3-hydroxyazetidin-1-yl)pyridine-2-sulfonamide;

N-(6-(4-fluoro-2-methylphenyl)-5-(trifluoromethyl)pyridin-2-yl)-6-(3-hydroxy-3-methylazetidin-1-yl)pyridine-2-sulfonamide;

N-(6-(4-fluoro-2-methylphenyl)-5-(trifluoromethyl)pyridin-2-yl)-6-(3-hydroxyazetidin-1-yl)pyridine-2-sulfonamide;

N-(6-(5-fluoro-2-methylphenyl)-5-(trifluoromethyl)pyridin-2-yl)-6-(3-hydroxy-3-methylazetidin-1-yl)pyridine-2-sulfonamide;

N-(6-(5-fluoro-2-methylphenyl)-5-(trifluoromethyl)pyridin-2-yl)-6-(3-hydroxyazetidin-1-yl)pyridine-2-sulfonamide;

N-(6-(2-chlorophenyl)-5-(trifluoromethyl)pyridin-2-yl)-6-(3-hydroxy-3-methylazetidin-1-yl)pyridine-2-sulfonamide;

N-(6-(2-chlorophenyl)-5-(trifluoromethyl)pyridin-2-yl)-6-(3-hydroxyazetidin-1-yl)pyridine-2-sulfonamide;

N-(5-chloro-6-(2-methyl-5-(trifluoromethyl)phenyl)pyridin-2-yl)-6-(3-hydroxyazetidin-1-yl)pyridine-2-sulfonamide;

6-(3-hydroxyazetidin-1-yl)-N-(5-(trifluoromethyl)-6-(2-(trifluoromethyl)phenyl)pyridin-2-yl)pyridine-2-sulfonamide;

N-(6-(2-chloro-4-fluorophenyl)-5-(trifluoromethyl)pyridin-2-yl)-6-(3-hydroxyazetidin-1-yl)pyridine-2-sulfonamide;

N-(6-(2-chloro-5-methoxyphenyl)-5-(trifluoromethyl)pyridin-2-yl)-6-(3-hydroxyazetidin-1-yl)pyridine-2-sulfonamide;

N-(5-chloro-6-(2-chlorophenyl)pyridin-2-yl)-6-(3-hydroxyazetidin-1-yl)pyridine-2-sulfonamide;

N-(5-chloro-6-(2-chloro-5-methoxyphenyl)pyridin-2-yl)-6-(3-hydroxyazetidin-1-yl)pyridine-2-sulfonamide;

N-(5-chloro-6-(2-chloro-3-fluorophenyl)pyridin-2-yl)-6-(3-hydroxyazetidin-1-yl)pyridine-2-sulfonamide;

N-(6-(2-chloro-3-fluorophenyl)-5-(trifluoromethyl)pyridin-2-yl)-6-(3-hydroxyazetidin-1-yl)pyridine-2-sulfonamide;

N-(5-chloro-6-(2,6-dimethylphenyl)pyridin-2-yl)-6-(3-hydroxyazetidin-1-yl)pyridine-2-sulfonamide;

N-(5-chloro-6-(3-fluoro-2-methylphenyl)pyridin-2-yl)-6-(3-hydroxyazetidin-1-yl)pyridine-2-sulfonamide;

6-(3-hydroxyazetidin-1-yl)-N-(6-(o-tolyl)-5-(trifluoromethyl)pyridin-2-yl)pyridine-2-sulfonamide;

N-(5-chloro-6-(5-fluoro-2-methylphenyl)pyridin-2-yl)-6-(3-hydroxyazetidin-1-yl)pyridine-2-sulfonamide;

N-(5-chloro-6-(5-fluoro-2-methylphenyl)pyridin-2-yl)-6-(3-hydroxy-3-(hydroxymethyl)azetidin-1-yl)pyridine-2-sulfonamide;

methyl 1-(6-(N-(6-(2-cyclopropylphenyl)-5-(trifluoromethyl)pyridin-2-yl)sulfamoyl)pyridin-2-yl)-4-methylpiperidine-4-carboxylate;

1-(6-(N-(6-(2-cyclopropylphenyl)-5-(trifluoromethyl)pyridin-2-yl)sulfamoyl)pyridin-2-yl)-4-methylpiperidine-4-carboxylic acid;

1-(6-(N-(6-(2-chlorophenyl)-5-(trifluoromethyl)pyridin-2-yl)sulfamoyl)pyridin-2-yl)-4-methylpiperidine-4-carboxylic acid;

1-(6-(N-(5-chloro-6-(2-chlorophenyl)pyridin-2-yl)sulfamoyl)pyridin-2-yl)-4-methylpiperidine-4-carboxylic acid;

1-(6-(N-(6-(2-chloro-4-fluorophenyl)-5-(trifluoromethyl)pyridin-2-yl)sulfamoyl)pyridin-2-yl)-4-methylpiperidine-4-carboxylic acid;

1-(6-(N-(6-(2-chloro-5-methoxyphenyl)-5-(trifluoromethyl)pyridin-2-yl)sulfamoyl)pyridin-2-yl)-4-methylpiperidine-4-carboxylic acid;

1-(6-(N-(6-(2-chloro-3-fluorophenyl)-5-(trifluoromethyl)pyridin-2-yl)sulfamoyl)pyridin-2-yl)-4-methylpiperidine-4-carboxylic acid;

1-(6-(N-(5-chloro-6-(2-chloro-4-fluorophenyl)pyridin-2-yl)sulfamoyl)pyridin-2-yl)-4-methylpiperidine-4-carboxylic acid;

1-(6-(N-(5-chloro-6-(2-chloro-5-methoxyphenyl)pyridin-2-yl)sulfamoyl)pyridin-2-yl)-4-methylpiperidine-4-carboxylic acid;

1-(6-(N-(5-chloro-6-(2-chloro-3-fluorophenyl)pyridin-2-yl)sulfamoyl)pyridin-2-yl)-4-methylpiperidine-4-carboxylic acid;

methyl 1-(6-(N-(5-chloro-6-(2,6-dimethylphenyl)pyridin-2-yl)sulfamoyl)pyridin-2-yl)piperidine-4-carboxylate;

1-(6-(N-(5-chloro-6-(2,6-dimethylphenyl)pyridin-2-yl)sulfamoyl)pyridin-2-yl)piperidine-4-carboxylic acid;

1-(6-(N-(5-chloro-6-(2,6-dimethylphenyl)pyridin-2-yl)sulfamoyl)pyridin-2-yl)-4-ethylpiperidine-4-carboxylic acid;

ethyl 1-(6-(N-(5-chloro-6-(2,6-dimethylphenyl)pyridin-2-yl)sulfamoyl)pyridin-2-yl)-4-methylpiperidine-4-carboxylate;

1-(6-(N-(5-chloro-6-(2,6-dimethylphenyl)pyridin-2-yl)sulfamoyl)pyridin-2-yl)-4-methylpiperidine-4-carboxylic acid;

ethyl 1-(6-(N-(6-(5-fluoro-2-methylphenyl)-5-(trifluoromethyl)pyridin-2-yl)sulfamoyl)pyridin-2-yl)-4-methylpiperidine-4-carboxylate;

ethyl 1-(6-(N-(5-chloro-6-(3-fluoro-2-methylphenyl)pyridin-2-yl)sulfamoyl)pyridin-2-yl)-4-methylpiperidine-4-carboxylate;

1-(6-(N-(5-chloro-6-(3-fluoro-2-methylphenyl)pyridin-2-yl)sulfamoyl)pyridin-2-yl)-4-methylpiperidine-4-carboxylic acid;

ethyl 1-(6-(N-(5-chloro-6-(o-tolyl)pyridin-2-yl)sulfamoyl)pyridin-2-yl)-4-methylpiperidine-4-carboxylate;

1-(6-(N-(5-chloro-6-(o-tolyl)pyridin-2-yl)sulfamoyl)pyridin-2-yl)-4-methylpiperidine-4-carboxylic acid;

ethyl 1-(6-(N-(5-chloro-6-(5-fluoro-2-methylphenyl)pyridin-2-yl)sulfamoyl)pyridin-2-yl)-4-methylpiperidine-4-carboxylate;

1-(6-{[5-chloro-6-(5-fluoro-2-methylphenyl)pyridin-2-yl]sulfamoyl}pyridin-2-yl)-4-methylpiperidine-4-carboxylic acid;

ethyl 1-(6-{[6-(3-fluoro-2-methylphenyl)-5-(trifluoromethyl)pyridin-2-yl]sulfamoyl}pyridin-2-yl)-4-methylpiperidine-4-carboxylate;

ethyl 4-methyl-1-(6-{[6-(2-methylphenyl)-5-(trifluoromethyl)pyridin-2-yl]sulfamoyl}pyridin-2-yl)piperidine-4-carboxylate;

methyl 1-(6-{[5-chloro-6-(2,6-dimethylphenyl)pyridin-2-yl]sulfamoyl}pyridin-2-yl)-4-hydroxypiperidine-4-carboxylate;

1-(6-{[5-chloro-6-(2,6-dimethylphenyl)pyridin-2-yl]sulfamoyl}pyridin-2-yl)-4-hydroxypiperidine-4-carboxylic acid;

1-(6-{[6-(5-fluoro-2-methylphenyl)-5-(trifluoromethyl) pyridin-2-yl]sulfamoyl}pyridin-2-yl)-4-methylpiperidine-4-carboxylic acid;
1-(6-(N-(6-(3-fluoro-2-methylphenyl)-5-(trifluoromethyl)pyridin-2-yl)sulfamoyl)pyridin-2-yl)-4-methyl-piperidine-4-carboxylic acid;
4-methyl-1-(6-(N-(6-(o-tolyl)-5-(trifluoromethyl)pyridin-2-yl)sulfamoyl)pyridin-2-yl)piperidine-4-carboxylic acid;
1-(6-{[6-(3-fluoro-2-methylphenyl)-5-(trifluoromethyl) pyridin-2-yl]sulfamoyl}pyridin-2-yl)-4-methylpiperidine-4-carboxylic acid;
4-methyl-1-(6-{[6-(2-methylphenyl)-5-(trifluoromethyl) pyridin-2-yl]sulfamoyl}pyridin-2-yl)piperidine-4-carboxylic acid;
1-(6-{[6-(2,6-dimethylphenyl)-5-(trifluoromethyl)pyridin-2-yl]sulfamoyl}pyridin-2-yl)-4-methylpiperidine-4-carboxylic acid;
ethyl 1-(6-{[6-(2,6-dimethylphenyl)-5-(trifluoromethyl) pyridin-2-yl]sulfamoyl}pyridin-2-yl)-4-methylpiperidine-4-carboxylate;
methyl 4-{[(tert-butoxy)carbonyl]amino}-1-(6-{[5-chloro-6-(2,6-dimethylphenyl)pyridin-2-yl] sulfamoyl}pyridin-2-yl)piperidine-4-carboxylate;
4-{[(tert-butoxy)carbonyl]amino}-1-(6-{[5-chloro-6-(2,6-dimethylphenyl)pyridin-2-yl]sulfamoyl}pyridin-2-yl)piperidine-4-carboxylic acid;
4-amino-1-(6-{[5-chloro-6-(2,6-dimethylphenyl)pyridin-2-yl]sulfamoyl}pyridin-2-yl)piperidine-4-carboxylic acid;
methyl 4-amino-1-(6-{[5-chloro-6-(2,6-dimethylphenyl)pyridin-2-yl]sulfamoyl}pyridin-2-yl)piperidine-4-carboxylate;
N-[5-chloro-6-(2,6-dimethylphenyl)pyridin-2-yl]-6-[(oxan-4-yl)amino]pyridine-2-sulfonamide;
rac-N-[5-chloro-6-(5-fluoro-2-methylphenyl)pyridin-2-yl]-6-{[(3R,4R)-3-hydroxyoxan-4-yl]amino}pyridine-2-sulfonamide;
N-[5-chloro-6-(5-fluoro-2-methylphenyl)pyridin-2-yl]-6-{[(3S,4R)-3-hydroxyoxan-4-yl]amino}pyridine-2-sulfonamide;
rac-6-{[(3R,4R)-3-hydroxyoxan-4-yl]amino}-N-[6-(2-methylphenyl)-5-(trifluoromethyl)pyridin-2-yl]pyridine-2-sulfonamide;
6-{[(3S,4R)-3-hydroxyoxan-4-yl]amino}-N-[6-(2-methylphenyl)-5-(trifluoromethyl)pyridin-2-yl]pyridine-2-sulfonamide;
6-{[(3R,4R)-3-hydroxyoxan-4-yl]amino}-N-[6-(2-methylphenyl)-5-(trifluoromethyl)pyridin-2-yl]pyridine-2-sulfonamide;
6-{[(3S,4S)-3-hydroxyoxan-4-yl]amino}-N-[6-(2-methylphenyl)-5-(trifluoromethyl)pyridin-2-yl]pyridine-2-sulfonamide;
N-[5-chloro-6-(5-fluoro-2-methylphenyl)pyridin-2-yl]-6-{[(3R,4R)-4-hydroxyoxan-3-yl]amino}pyridine-2-sulfonamide;
6-{[(3R,4R)-4-hydroxyoxan-3-yl]amino}-N-[6-(2-methylphenyl)-5-(trifluoromethyl)pyridin-2-yl]pyridine-2-sulfonamide;
rac-6-{[(3R,4S)-4-hydroxyoxan-3-yl]amino}-N-[6-(2-methylphenyl)-5-(trifluoromethyl)pyridin-2-yl]pyridine-2-sulfonamide;
6-{[(3R,4S)-4-hydroxyoxan-3-yl]amino}-N-[6-(2-methylphenyl)-5-(trifluoromethyl)pyridin-2-yl]pyridine-2-sulfonamide;
6-{[(3S,4R)-4-hydroxyoxan-3-yl]amino}-N-[6-(2-methylphenyl)-5-(trifluoromethyl)pyridin-2-yl]pyridine-2-sulfonamide;
N-[6-(2-methylphenyl)-5-(trifluoromethyl)pyridin-2-yl]-6-{[(1s,3s)-3-hydroxycyclobutyl]amino}pyridine-2-sulfonamide;
N-[6-(2-methylphenyl)-5-(trifluoromethyl)pyridin-2-yl]-6-{[(1r,3r)-3-hydroxycyclobutyl]amino}pyridine-2-sulfonamide;
N-[5-chloro-6-(2,6-dimethylphenyl)pyridin-2-yl]-6-{[(1r,3s)-3-hydroxy-3-methylcyclobutyl]amino}pyridine-2-sulfonamide;
N-[5-chloro-6-(2,6-dimethylphenyl)pyridin-2-yl]-6-{[(1s,3s)-3-hydroxycyclobutyl]amino}pyridine-2-sulfonamide;
N-[5-chloro-6-(2,6-dimethylphenyl)pyridin-2-yl]-6-{[(1r,3r)-3-hydroxycyclobutyl]amino}pyridine-2-sulfonamide;
N-[5-chloro-6-(2,6-dimethylphenyl)pyridin-2-yl]-6-{[(3S,5S)-5-(hydroxymethyl)oxolan-3-yl]oxy}pyridine-2-sulfonamide;
N-[5-chloro-6-(5-fluoro-2-methylphenyl)pyridin-2-yl]-6-{[(3R,4S)-4-hydroxyoxolan-3-yl]oxy}pyridine-2-sulfonamide;
rac-N-[5-chloro-6-(2,6-dimethylphenyl)pyridin-2-yl]-6-{[(3R,4S)-4-hydroxyoxolan-3-yl]oxy}pyridine-2-sulfonamide;
rac-6-{[(3RS,4SR)-4-hydroxyoxolan-3-yl]oxy}-N-[6-(2-methylphenyl)-5-(trifluoromethyl)pyridin-2-yl]pyridine-2-sulfonamide;
rac-N-[6-(2-methylphenyl)-5-(trifluoromethyl)pyridin-2-yl]-6-[(4-oxooxolan-3-yl)oxy]pyridine-2-sulfonamide;
rac-6-{[(3RR,4SR)-4-hydroxy-4-methyloxolan-3-yl]oxy}-N-[6-(2-methylphenyl)-5-(trifluoromethyl)pyridin-2-yl]pyridine-2-sulfonamide;
6-{[(3R,4R)-4-hydroxy-4-methyloxolan-3-yl]oxy}-N-[6-(2-methylphenyl)-5-(trifluoromethyl)pyridin-2-yl]pyridine-2-sulfonamide;
6-{[(3R,4S)-4-hydroxy-4-methyloxolan-3-yl]oxy}-N-[6-(2-methylphenyl)-5-(trifluoromethyl)pyridin-2-yl]pyridine-2-sulfonamide;
6-{[(3R,4S)-4-hydroxyoxolan-3-yl]oxy}-N-[6-(2-methylphenyl)-5-(trifluoromethyl)pyridin-2-yl]pyridine-2-sulfonamide;
ethyl 1-(4-(6-(N-(6-(5-fluoro-2-methylphenyl)-5-(trifluoromethyl)pyridin-2-yl)sulfamoyl)pyridin-2-yl)piperazin-1-yl)cyclopropane-1-carboxylate;
tert-butyl 4-(6-(N-(5-chloro-6-(5-fluoro-2-methylphenyl)pyridin-2-yl)sulfamoyl)pyridin-2-yl)piperazine-1-carboxylate;
N-(6-(5-cyano-2-methylphenyl)-5-(trifluoromethyl)pyridin-2-yl)-6-(3-hydroxy-3-methylazetidin-1-yl)pyridine-2-sulfonamide;
1-(6-(N-(6-(5-fluoro-2-methylphenyl)-5-(trifluoromethyl)pyridin-2-yl)sulfamoyl)pyridin-2-yl) pyrrolidine-3-carboxylic acid;
tert-butyl 1-(6-(N-(6-(o-tolyl)-5-(trifluoromethyl)pyridin-2-yl)sulfamoyl)pyridin-2-yl)-1,6-diazaspiro[3.3]heptane-6-carboxylate;
6-(4,7-diazaspiro[2.5]octan-7-yl)-N-(6-(o-tolyl)-5-(trifluoromethyl)pyridin-2-yl)pyridine-2-sulfonamide;
6-(8-amino-5-oxa-2-azaspiro[3.4]octan-2-yl)-N-(6-(o-tolyl)-5-(trifluoromethyl)pyridin-2-yl)pyridine-2-sulfonamide;
(R)-6-(1-amino-8-azaspiro[4.5]decan-8-yl)-N-(6-(o-tolyl)-5-(trifluoromethyl)pyridin-2-yl)pyridine-2-sulfonamide;

N-(5-chloro-6-(5-cyano-2-methylphenyl)pyridin-2-yl)-6-(3-hydroxy-3-methylazetidin-1-yl)pyridine-2-sulfonamide;
(S)-6-(1-amino-7-azaspiro[3.5]nonan-7-yl)-N-(6-(o-tolyl)-5-(trifluoromethyl)pyridin-2-yl)pyridine-2-sulfonamide;
6-((1R)-1-amino-2-(hydroxymethyl)-8-azaspiro[4.5]decan-8-yl)-N-(6-(o-tolyl)-5-(trifluoromethyl)pyridin-2-yl)pyridine-2-sulfonamide;
N-(6-(3-cyano-2-methylphenyl)-5-(trifluoromethyl)pyridin-2-yl)-6-(3-hydroxy-3-methylazetidin-1-yl)pyridine-2-sulfonamide;
N-(5-chloro-6-(3-cyano-2-methylphenyl)pyridin-2-yl)-6-(3-hydroxy-3-methylazetidin-1-yl)pyridine-2-sulfonamide;
N-(5-chloro-6-(5-fluoro-2-methylphenyl)pyridin-2-yl)-6-(1,6-diazaspiro[3.3]heptan-1-yl)pyridine-2-sulfonamide;
N-(6-(5-cyano-2-methylphenyl)-5-(trifluoromethyl)pyridin-2-yl)-6-(piperazin-1-yl)pyridine-2-sulfonamide;
N-(5-chloro-6-(5-cyano-2-methylphenyl)pyridin-2-yl)-6-(piperazin-1-yl)pyridine-2-sulfonamide;
6-(1,6-diazaspiro[3.3]heptan-1-yl)-N-(6-(o-tolyl)-5-(trifluoromethyl)pyridin-2-yl)pyridine-2-sulfonamide;
6-((2R,3S)-3-hydroxy-2-methylpyrrolidin-1-yl)-N-(6-(o-tolyl)-5-(trifluoromethyl)pyridin-2-yl)pyridine-2-sulfonamide;
1-(6-(N-(6-(5-fluoro-2-methylphenyl)-5-(trifluoromethyl)pyridin-2-yl)sulfamoyl)pyridin-2-yl)-3-hydroxypyrrolidine-2-carboxylic acid;
6-{[(3S,4R)-4-hydroxyoxolan-3-yl]oxy}-N-[6-(2-methylphenyl)-5-(trifluoromethyl)pyridin-2-yl]pyridine-2-sulfonamide;
N-(6-(5-cyano-2-methylphenyl)-5-(trifluoromethyl)pyridin-2-yl)-2-(3-hydroxy-3-methylazetidin-1-yl)pyridine-4-sulfonamide;
(R)—N-(5-chloro-6-(5-fluoro-2-methylphenyl)pyridin-2-yl)-2-(3-methylmorpholino)pyridine-4-sulfonamide;
(R)—N-(5-chloro-6-(3-fluoro-2-methylphenyl)pyridin-2-yl)-2-(3-methylmorpholino)pyridine-4-sulfonamide;
N-(6-(5-fluoro-2-methylphenyl)-5-(trifluoromethyl)pyridin-2-yl)-2-(3-hydroxy-3-methylazetidin-1-yl)pyridine-4-sulfonamide;
(R)—N-(6-(5-fluoro-2-methylphenyl)-5-(trifluoromethyl)pyridin-2-yl)-2-(3-methylmorpholino)pyridine-4-sulfonamide;
N-(5-chloro-6-(5-fluoro-2-methylphenyl)pyridin-2-yl)-2-(3-hydroxyazetidin-1-yl)pyridine-4-sulfonamide;
N-(5-chloro-6-(3-fluoro-2-methylphenyl)pyridin-2-yl)-2-(3-hydroxyazetidin-1-yl)pyridine-4-sulfonamide;
N-(6-(5-fluoro-2-methylphenyl)-5-(trifluoromethyl)pyridin-2-yl)-2-(3-hydroxyazetidin-1-yl)pyridine-4-sulfonamide;
2-(3-hydroxyazetidin-1-yl)-N-(5-(trifluoromethyl)-6-(2-(trifluoromethyl)phenyl)pyridin-2-yl)pyridine-4-sulfonamide;
N-(6-(5-fluoro-2-methylphenyl)-5-(trifluoromethyl)pyridin-2-yl)-2-(piperazin-1-yl)pyridine-4-sulfonamide;
N-(5-chloro-6-(5-fluoro-2-methylphenyl)pyridin-2-yl)-2-(piperazin-1-yl)pyridine-4-sulfonamide;
(R)-1-(6-(N-(6-(2-ethoxyphenyl)-5-(trifluoromethyl)pyridin-2-yl)sulfamoyl)pyridin-2-yl)-3-methylpiperidine-3-carboxylic acid;
(R)-3-methyl-1-(6-(N-(6-(2-propoxyphenyl)-5-(trifluoromethyl)pyridin-2-yl)sulfamoyl)pyridin-2-yl)piperidine-3-carboxylic acid;
1-(6-(N-(6-(o-tolyl)-5-(trifluoromethyl)pyridin-2-yl)sulfamoyl)pyridin-2-yl)azetidine-3-carboxylic acid;
3-((6-(N-(6-(o-tolyl)-5-(trifluoromethyl)pyridin-2-yl)sulfamoyl)pyridin-2-yl)oxy)cyclobutanecarboxylic acid;
(3R)-1-(6-{[6-(2-methylphenyl)-5-(trifluoromethyl)pyridin-2-yl]sulfamoyl}pyridin-2-yl)piperidine-3-carboxylic acid;
(3S)-1-(6-{[6-(2-methylphenyl)-5-(trifluoromethyl)pyridin-2-yl]sulfamoyl}pyridin-2-yl)piperidine-3-carboxylic acid;
(2S)-1-[(tert-butoxy)carbonyl]-4-(6-{[6-(2-methylphenyl)-5-(trifluoromethyl)pyridin-2-yl]sulfamoyl}pyridin-2-yl)piperazine-2-carboxylic acid;
(2S)-4-(6-{[6-(2-methylphenyl)-5-(trifluoromethyl)pyridin-2-yl]sulfamoyl}pyridin-2-yl)piperazine-2-carboxylic acid;
3-methyl-1-(6-{[6-(2-methylphenyl)-5-(trifluoromethyl)pyridin-2-yl]sulfamoyl}pyridin-2-yl)pyrrolidine-3-carboxylic acid;
3-methyl-1-(6-{[6-(2-methylphenyl)-5-(trifluoromethyl)pyridin-2-yl]sulfamoyl}pyridin-2-yl)piperidine-3-carboxylic acid;
(2R)-1-[(tert-butoxy)carbonyl]-4-(6-{[6-(2-methylphenyl)-5-(trifluoromethyl)pyridin-2-yl]sulfamoyl}pyridin-2-yl)piperazine-2-carboxylic acid;
(2R)-4-(6-{[6-(2-methylphenyl)-5-(trifluoromethyl)pyridin-2-yl]sulfamoyl}pyridin-2-yl)morpholine-2-carboxylic acid;
(1R,2S,5S)-3-(6-{[6-(2-methylphenyl)-5-(trifluoromethyl)pyridin-2-yl]sulfamoyl}pyridin-2-yl)-3-azabicyclo[3.1.0]hexane-2-carboxylic acid;
(2R)-4-(6-{[6-(2-methylphenyl)-5-(trifluoromethyl)pyridin-2-yl]sulfamoyl}pyridin-2-yl)piperazine-2-carboxylic acid;
4-((6-(N-(6-(o-tolyl)-5-(trifluoromethyl)pyridin-2-yl)sulfamoyl)pyridin-2-yl)oxy)cyclohexanecarboxylic acid;
4-methyl-1-(6-(N-(6-(2-morpholinophenyl)-5-(trifluoromethyl)pyridin-2-yl)sulfamoyl)pyridin-2-yl)piperidine-4-carboxylic acid;
1-(6-{[6-(2-methylphenyl)-5-(trifluoromethyl)pyridin-2-yl]sulfamoyl}pyridin-2-yl)piperidine-4-carboxylic acid;
9-(6-{[6-(2-methylphenyl)-5-(trifluoromethyl)pyridin-2-yl]sulfamoyl}pyridin-2-yl)-9-azabicyclo[3.3.1]nonane-3-carboxylic acid;
8-(6-{[6-(2-methylphenyl)-5-(trifluoromethyl)pyridin-2-yl]sulfamoyl}pyridin-2-yl)-8-azabicyclo[3.2.1]octane-3-carboxylic acid;
(2R)-4-[(tert-butoxy)carbonyl]-1-(6-{[6-(2-methylphenyl)-5-(trifluoromethyl)pyridin-2-yl]sulfamoyl}pyridin-2-yl)piperazine-2-carboxylic acid;
(3S)-1-(6-{[6-(2-methylphenyl)-5-(trifluoromethyl)pyridin-2-yl]sulfamoyl}pyridin-2-yl)pyrrolidine-3-carboxylic acid;
(3R)-1-(6-{[6-(2-methylphenyl)-5-(trifluoromethyl)pyridin-2-yl]sulfamoyl}pyridin-2-yl)pyrrolidine-3-carboxylic acid;
(2S)-4-[(tert-butoxy)carbonyl]-1-(6-{[6-(2-methylphenyl)-5-(trifluoromethyl)pyridin-2-yl]sulfamoyl}pyridin-2-yl)piperazine-2-carboxylic acid;
1-(6-{[6-(2-ethylphenyl)-5-(trifluoromethyl)pyridin-2-yl]sulfamoyl}pyridin-2-yl)-4-propylpiperidine-4-carboxylic acid;
1-(6-{[6-(2-ethylphenyl)-5-(trifluoromethyl)pyridin-2-yl]sulfamoyl}pyridin-2-yl)-3-propylpiperidine-3-carboxylic acid;

(2R)-1-(6-{[6-(2-methylphenyl)-5-(trifluoromethyl)pyridin-2-yl]sulfamoyl}pyridin-2-yl)piperazine-2-carboxylic acid;
(2S)-1-(6-{[6-(2-methylphenyl)-5-(trifluoromethyl)pyridin-2-yl]sulfamoyl}pyridin-2-yl)piperazine-2-carboxylic acid;
(1r,3r)-3-((6-(N-(6-(o-tolyl)-5-(trifluoromethyl)pyridin-2-yl)sulfamoyl)pyridin-2-yl)amino)cyclobutanecarboxylic acid;
(1s,3s)-1-methyl-3-((6-(N-(6-(o-tolyl)-5-(trifluoromethyl)pyridin-2-yl)sulfamoyl)pyridin-2-yl)amino)cyclobutanecarboxylic acid;
(3R)-1-(6-{[6-(5-fluoro-2-methylphenyl)-5-(trifluoromethyl)pyridin-2-yl]sulfamoyl}pyridin-2-yl)piperidine-3-carboxylic acid;
(3R)-1-(6-{[6-(3-fluoro-2-methylphenyl)-5-(trifluoromethyl)pyridin-2-yl]sulfamoyl}pyridin-2-yl)piperidine-3-carboxylic acid;
(3S)-1-(6-{[6-(5-fluoro-2-methylphenyl)-5-(trifluoromethyl)pyridin-2-yl]sulfamoyl}pyridin-2-yl)piperidine-3-carboxylic acid;
(3S)-1-(6-{[6-(3-fluoro-2-methylphenyl)-5-(trifluoromethyl)pyridin-2-yl]sulfamoyl}pyridin-2-yl)piperidine-3-carboxylic acid;
1-(6-{[6-(5-fluoro-2-methylphenyl)-5-(trifluoromethyl)pyridin-2-yl]sulfamoyl}pyridin-2-yl)-3-methylpiperidine-3-carboxylic acid;
1-(6-{[6-(3-fluoro-2-methylphenyl)-5-(trifluoromethyl)pyridin-2-yl]sulfamoyl}pyridin-2-yl)-3-methylpiperidine-3-carboxylic acid;
1-(6-(N-(6-(2-cyclobutylphenyl)-5-(trifluoromethyl)pyridin-2-yl)sulfamoyl)pyridin-2-yl)-4-methylpiperidine-4-carboxylic acid;
(1r,4r)-4-((6-(N-(6-(o-tolyl)-5-(trifluoromethyl)pyridin-2-yl)sulfamoyl)pyridin-2-yl)amino)cyclohexanecarboxylic acid;
(1r,3s)-1-methyl-3-[(6-{[6-(2-methylphenyl)-5-(trifluoromethyl)pyridin-2-yl]sulfamoyl}pyridin-2-yl)amino]cyclobutane-1-carboxylic acid;
(R)-1-(6-(N-(6-(2-cyclobutylphenyl)-5-(trifluoromethyl)pyridin-2-yl)sulfamoyl)pyridin-2-)yl)piperidine-3-carboxylic acid;
(S)-1-(6-(N-(6-(2-cyclobutylphenyl)-5-(trifluoromethyl)pyridin-2-yl)sulfamoyl)pyridin-2-yl)piperidine-3-carboxylic acid;
1-(6-(N-(6-(2-cyclobutylphenyl)-5-(trifluoromethyl)pyridin-2-yl)sulfamoyl)pyridin-2-yl)-3-methylpiperidine-3-carboxylic acid;
(R)-1-(6-(N-(6-(2-ethylphenyl)-5-(trifluoromethyl)pyridin-2-yl)sulfamoyl)pyridin-2-yl)piperidine-3-carboxylic acid;
(S)-1-(6-(N-(6-(2-ethylphenyl)-5-(trifluoromethyl)pyridin-2-yl)sulfamoyl)pyridin-2-yl)piperidine-3-carboxylic acid;
1-(6-(N-(6-(2-ethylphenyl)-5-(trifluoromethyl)pyridin-2-yl)sulfamoyl)pyridin-2-yl)-3-methylpiperidine-3-carboxylic acid;
4-((6-(N-(6-(o-tolyl)-5-(trifluoromethyl)pyridin-2-yl)sulfamoyl)pyridin-2-yl)amino)cyclohexanecarboxylic acid;
(S)-1-(6-(N-(6-(2-cyclobutylphenyl)-5-(trifluoromethyl)pyridin-2-yl)sulfamoyl)pyridin-2-yl)-3-methylpiperidine-3-carboxylic acid;
1-(4-(N-(6-(2-ethylphenyl)-5-(trifluoromethyl)pyridin-2-yl)sulfamoyl)pyridin-2-yl)-4-methylpiperidine-4-carboxylic acid;
(R)-1-(6-(N-(6-(2-isopropylphenyl)-5-(trifluoromethyl)pyridin-2-yl)sulfamoyl)pyridin-2-yl)piperidine-3-carboxylic acid;
(S)-1-(6-(N-(6-(2-isopropylphenyl)-5-(trifluoromethyl)pyridin-2-yl)sulfamoyl)pyridin-2-yl)piperidine-3-carboxylic acid;
1-(6-(N-(6-(2-isopropylphenyl)-5-(trifluoromethyl)pyridin-2-yl)sulfamoyl)pyridin-2-yl)-3-methylpiperidine-3-carboxylic acid;
1-(4-(N-(6-(2-cyclobutylphenyl)-5-(trifluoromethyl)pyridin-2-yl)sulfamoyl)pyridin-2-yl)-4-methylpiperidine-4-carboxylic acid;
1-(6-(N-(6-(2-cyclopentylphenyl)-5-(trifluoromethyl)pyridin-2-yl)sulfamoyl)pyridin-2-yl)-4-methylpiperidine-4-carboxylic acid;
1-(6-(6-(2-ethylphenyl)-5-(trifluoromethyl)pyridine-2-sulfonamido)pyridin-2-yl)-4-methylpiperidine-4-carboxylic acid;
4-methyl-1-(6-(N-(6-(2-(2,2,2-trifluoroethoxy)phenyl)-5-(trifluoromethyl)pyridin-2-yl)sulfamoyl)pyridin-2-yl)piperidine-4-carboxylic acid;
1-(6-(N-(6-(2-isobutoxyphenyl)-5-(trifluoromethyl)pyridin-2-yl)sulfamoyl)pyridin-2-yl)-4-methylpiperidine-4-carboxylic acid;
(R)-1-(6-(N-(6-(2-cyclobutylphenyl)-5-(trifluoromethyl)pyridin-2-yl)sulfamoyl)pyridin-2-yl)-3-methylpiperidine-3-carboxylic acid;
(R)-1-(6-(N-(6-(2-isopropylphenyl)-5-(trifluoromethyl)pyridin-2-yl)sulfamoyl)pyridin-2-yl)-3-methylpiperidine-3-carboxylic acid;
(S)-1-(6-(N-(6-(2-isopropylphenyl)-5-(trifluoromethyl)pyridin-2-yl)sulfamoyl)pyridin-2-yl)-3-methylpiperidine-3-carboxylic acid;
1-(6-(N-(6-(2-isobutoxyphenyl)-5-(trifluoromethyl)pyridin-2-yl)sulfamoyl)pyridin-2-yl)-3-methylpiperidine-3-carboxylic acid;
1-(6-(N-(5-chloro-6-(2-ethylphenyl)pyridin-2-yl)sulfamoyl)pyridin-2-yl)-3-methylpiperidine-3-carboxylic acid;
1-(6-(N-(5-chloro-6-(2-isopropylphenyl)pyridin-2-yl)sulfamoyl)pyridin-2-yl)-3-methylpiperidine-3-carboxylic acid;
1-(6-(N-(5-chloro-6-(2-cyclobutylphenyl)pyridin-2-yl)sulfamoyl)pyridin-2-yl)-3-methylpiperidine-3-carboxylic acid;
1-(6-(N-(6-(2-(tert-butyl)phenyl)-5-chloropyridin-2-yl)sulfamoyl)pyridin-2-yl)-3-methylpiperidine-3-carboxylic acid;
(R)-1-(6-(N-(5-chloro-6-(2-cyclobutylphenyl)pyridin-2-yl)sulfamoyl)pyridin-2-yl)-3-methylpiperidine-3-carboxylic acid;
(R)-1-(6-(N-(5-chloro-6-(2-isopropylphenyl)pyridin-2-yl)sulfamoyl)pyridin-2-yl)-3-methylpiperidine-3-carboxylic acid;
(R)-1-(6-(N-(5-chloro-6-(2-ethylphenyl)pyridin-2-yl)sulfamoyl)pyridin-2-yl)-3-methylpiperidine-3-carboxylic acid;
(R)-1-(6-(N-(6-(2-ethylphenyl)-5-(trifluoromethyl)pyridin-2-yl)sulfamoyl)pyridin-2-yl)-3-methylpiperidine-3-carboxylic acid;
rac-(1RS,3RS,4SR)-3-((6-(N-(6-(o-tolyl)-5-(trifluoromethyl)pyridin-2-yl)sulfamoyl)pyridin-2-yl)amino)-7-oxabicyclo[2.2.1]heptane-1-carboxylic acid;
(R)-1-(6-(N-(6-(2-isobutoxyphenyl)-5-(trifluoromethyl)pyridin-2-yl)sulfamoyl)pyridin-2-yl)-3-methylpiperidine-3-carboxylic acid;

1-(6-(N-(5-chloro-6-(2-isobutoxyphenyl)pyridin-2-yl)sulfamoyl)pyridin-2-yl)-4-methylpiperidine-4-carboxylic acid;

4-methyl-1-(6-(N-(6-(2-propylphenyl)-5-(trifluoromethyl)pyridin-2-yl)sulfamoyl)pyridin-2-yl)piperidine-4-carboxylic acid;

1-(6-(N-(6-(2-chlorophenyl)-5-(trifluoromethyl)pyridin-2-yl)sulfamoyl)pyridin-2-yl)-3-methylpiperidine-3-carboxylic acid;

1-(6-(N-(5-chloro-6-(2-isobutoxyphenyl)pyridin-2-yl)sulfamoyl)pyridin-2-yl)-3-methylpiperidine-3-carboxylic acid;

3-methyl-1-(6-(N-(6-(2-propylphenyl)-5-(trifluoromethyl)pyridin-2-yl)sulfamoyl)pyridin-2-yl)piperidine-3-carboxylic acid;

1-(6-(N-(6-(2-cyclopropylphenyl)-5-(trifluoromethyl)pyridin-2-yl)sulfamoyl)pyridin-2-yl)-3-methylpiperidine-3-carboxylic acid;

rac-(1RS,3RS,4SR)-3-((6-(N-(6-(2-isopropylphenyl)-5-(trifluoromethyl)pyridin-2-yl)sulfamoyl)pyridin-2-yl)amino)-7-oxabicyclo[2.2.1]heptane-1-carboxylic acid;

rac-(1SR,5RS,6RS,7SR)-5-propyl-2-(6-(N-(6-(o-tolyl)-5-(trifluoromethyl)pyridin-2-yl)sulfamoyl)pyridin-2-yl)-2-azabicyclo[4.2.0]octane-7-carboxylic acid;

(R)-1-(6-(N-(6-(2-cyclopropylphenyl)pyridin-2-yl)sulfamoyl)pyridin-2-yl)-3-methylpiperidine-3-carboxylic acid;

(R)-1-(6-(N-(6-(2-cyclopropylphenyl)-5-methylpyridin-2-yl)sulfamoyl)pyridin-2-yl)-3-methylpiperidine-3-carboxylic acid;

(R)-1-(6-(N-(5-cyclopropyl-6-(2-cyclopropylphenyl)pyridin-2-yl)sulfamoyl)pyridin-2-yl)-3-methylpiperidine-3-carboxylic acid;

(R)-3-methyl-1-(6-(N-(5-methyl-6-(o-tolyl)pyridin-2-yl)sulfamoyl)pyridin-2-yl)piperidine-3-carboxylic acid;

R)-1-(6-(N-(5-methoxy-6-(o-tolyl)pyridin-2-yl)sulfamoyl)pyridin-2-yl)-3-methylpiperidine-3-carboxylic acid;

R)-1-(6-(N-(5-methoxy-6-(o-tolyl)pyridin-2-yl)sulfamoyl)pyridin-2-yl)-3-methylpiperidine-3-carboxylic acid;

(R)-3-methyl-1-(6-(N-(6-(o-tolyl)pyridin-2-yl)sulfamoyl)pyridin-2-yl)piperidine-3-carboxylic acid;

(R)-1-(6-(N-(6-(2-cyclopropylphenyl)-5-(trifluoromethyl)pyridin-2-yl)sulfamoyl)pyridin-2-yl)-3-methylpiperidine-3-carboxylic acid;

1-(6-(N-(6-(2-chloro-5-methoxyphenyl)-5-(trifluoromethyl)pyridin-2-yl)sulfamoyl)pyridin-2-yl)-3-methylpiperidine-3-carboxylic acid;

(3R)-3-methyl-1-(6-{[6-(2-methylphenyl)-5-(trifluoromethyl)pyridin-2-yl]sulfamoyl}pyridin-2-yl)piperidine-3-carboxylic acid;

(3R)-1-(6-{[6-(5-fluoro-2-methylphenyl)-5-(trifluoromethyl)pyridin-2-yl]sulfamoyl}pyridin-2-yl)-3-methylpiperidine-3-carboxylic acid;

(3R)-1-(6-{[6-(3-fluoro-2-methylphenyl)-5-(trifluoromethyl)pyridin-2-yl]sulfamoyl}pyridin-2-yl)-3-methylpiperidine-3-carboxylic acid;

(1 S,3S)-3-((6-(N-(6-(2-isopropylphenyl)-5-(trifluoromethyl)pyridin-2-yl)sulfamoyl)pyridin-2-yl)amino)cyclohexanecarboxylic acid;

5-(6-(N-(6-(o-tolyl)-5-(trifluoromethyl)pyridin-2-yl)sulfamoyl)pyridin-2-yl)-5-azaspiro[2.4]heptane-1-carboxylic acid;

5-(6-(N-(6-(2-cyclopropylphenyl)-5-(trifluoromethyl)pyridin-2-yl)sulfamoyl)pyridin-2-yl)-5-azaspiro[2.4]heptane-1-carboxylic acid;

(R)-1-(6-(N-(6-(2-chlorophenyl)-5-(trifluoromethyl)pyridin-2-yl)sulfamoyl)pyridin-2-yl)-3-methylpiperidine-3-carboxylic acid;

(R)-1-(6-(N-(5-chloro-6-(2-isobutoxyphenyl)pyridin-2-yl)sulfamoyl)pyridin-2-yl)-3-methylpiperidine-3-carboxylic acid;

(R)-3-methyl-1-(6-(N-(6-(2-propylphenyl)-5-(trifluoromethyl)pyridin-2-yl)sulfamoyl)pyridin-2-yl)piperidine-3-carboxylic acid;

(R)-1-(6-(N-(6-(2-chloro-5-methoxyphenyl)-5-(trifluoromethyl)pyridin-2-yl)sulfamoyl)pyridin-2-yl)-3-methyl piperidine-3-carboxylic acid;

(S)-3-methyl-1-(6-(N-(6-(2-propylphenyl)-5-(trifluoromethyl)pyridin-2-yl)sulfamoyl)pyridin-2-yl)piperidine-3-carboxylic acid;

1-(6-(N-(6-(5-chloro-2-methoxyphenyl)-5-(trifluoromethyl)pyridin-2-yl)sulfamoyl)pyridin-2-yl)-4-methylpiperidine-4-carboxylic acid;

1-(6-(N-(6-(5-chloro-2-isopropoxyphenyl)-5-(trifluoromethyl)pyridin-2-yl)sulfamoyl)pyridin-2-yl)-4-methylpiperidine-4-carboxylic acid;

(3S)-3-methyl-1-(6-{[6-(2-methylphenyl)-5-(trifluoromethyl)pyridin-2-yl]sulfamoyl}pyridin-2-yl)piperidine-3-carboxylic acid;

(S)-1-(6-(N-(6-(2-cyclopropylphenyl)-5-(trifluoromethyl)pyridin-2-yl)sulfamoyl)pyridin-2-yl)-3-methylpiperidine-3-carboxylic acid;

1-(6-(N-(5-chloro-6-(2-cyclopropylphenyl)pyridin-2-yl)sulfamoyl)pyridin-2-yl)-4-methylpiperidine-4-carboxylic acid;

1-(6-(N-(5-chloro-6-(2-cyclopropylphenyl)pyridin-2-yl)sulfamoyl)pyridin-2-yl)-3-methylpiperidine-3-carboxylic acid;

1-(6-(N-(6-(5-chloro-2-methoxyphenyl)-5-(trifluoromethyl)pyridin-2-yl)sulfamoyl)pyridin-2-yl)-3-methylpiperidine-3-carboxylic acid;

1-(6-(N-(6-(5-chloro-2-isopropoxyphenyl)-5-(trifluoromethyl)pyridin-2-yl)sulfamoyl)pyridin-2-yl)-3-methylpiperidine-3-carboxylic acid;

rac-(1SR,5RS,6RS,7SR)-2-(6-(N-(3-chloro-2'-isopropyl-[2,3'-bipyridin]-6-yl)sulfamoyl)pyridin-2-yl)-5-propyl-2-azabicyclo[4.2.0]octane-7-carboxylic acid;

(3S)-1-(6-{[6-(5-fluoro-2-methylphenyl)-5-(trifluoromethyl)pyridin-2-yl]sulfamoyl}pyridin-2-yl)-3-methylpiperidine-3-carboxylic acid;

(3S)-1-(6-{[6-(3-fluoro-2-methylphenyl)-5-(trifluoromethyl)pyridin-2-yl]sulfamoyl}pyridin-2-yl)-3-methylpiperidine-3-carboxylic acid;

(R)-1-(6-(N-(5-chloro-6-(2-cyclopropylphenyl)pyridin-2-yl)sulfamoyl)pyridin-2-yl)-3-methylpiperidine-3-carboxylic acid;

rac-(1RS,3RS,4SR)-3-((6-(N-(6-(2-cyclopropylphenyl)-5-(trifluoromethyl)pyridin-2-yl)sulfamoyl)pyridin-2-yl)amino)-7-oxabicyclo[2.2.1]heptane-1-carboxylic acid;

5-(6-(N-(6-(5-fluoro-2-methylphenyl)-5-(trifluoromethyl)pyridin-2-yl)sulfamoyl)pyridin-2-yl)-5-azaspiro[2.5]octane-1-carboxylic acid;

5-(6-(N-(6-(3-fluoro-2-methylphenyl)-5-(trifluoromethyl)pyridin-2-yl)sulfamoyl)pyridin-2-yl)-5-azaspiro[2.5]octane-1-carboxylic acid;

5-(6-(N-(6-(o-tolyl)-5-(trifluoromethyl)pyridin-2-yl)sulfamoyl)pyridin-2-yl)-5-azaspiro[2.5]octane-1-carboxylic acid;

rac-(1SR,6RS,7SR)-2-(6-(N-(6-(2-isopropylphenyl)-5-(trifluoromethyl)pyridin-2-yl)sulfamoyl)pyridin-2-yl)-2-azabicyclo[4.2.0]octane-7-carboxylic acid;

rac-(1SR,6RS,7SR)-2-(6-(N-(6-(o-tolyl)-5-(trifluoromethyl)pyridin-2-yl)sulfamoyl)pyridin-2-yl)-2-azabicyclo[4.2.0]octane-7-carboxylic acid;
1-(6-(N-(6-(2-(hydroxymethyl)phenyl)-5-(trifluoromethyl)pyridin-2-yl)sulfamoyl)pyridin-2-yl)-3-methylpiperidine-3-carboxylic acid;
1-(6-(N-(6-(2-(2-hydroxyethyl)phenyl)-5-(trifluoromethyl)pyridin-2-yl)sulfamoyl)pyridin-2-yl)-3-methylpiperidine-3-carboxylic acid;
7-(6-(N-(6-(o-tolyl)-5-(trifluoromethyl)pyridin-2-yl)sulfamoyl)pyridin-2-yl)-7-azaspiro[3.5]nonane-2-carboxylic acid;
(R)-1-(6-(N-(5-chloro-6-(o-tolyl)pyridin-2-yl)sulfamoyl)pyridin-2-yl)-3-methylpiperidine-3-carboxylic acid;
(R)-1-(6-(N-(5-chloro-6-(2,6-dimethylphenyl)pyridin-2-yl)sulfamoyl)pyridin-2-yl)-3-methylpiperidine-3-carboxylic acid;
(R)-1-(6-(N-(6-(2-chloro-5-methoxyphenyl)-5-(trifluoromethyl)pyridin-2-yl)sulfamoyl)pyridin-2-yl)piperidine-3-carboxylic acid;
(R)-1-(6-(N-(6-(5-chloro-2-methylphenyl)-5-(trifluoromethyl)pyridin-2-yl)sulfamoyl)pyridin-2-yl)-3-methylpiperidine-3-carboxylic acid;
1-(6-(N-(6-(5-chloro-2-methylphenyl)-5-(trifluoromethyl)pyridin-2-yl)sulfamoyl)pyridin-2-yl)-4-methylpiperidine-4-carboxylic acid;
1-(6-(N-(5-chloro-6-(o-tolyl)pyridin-2-yl)sulfamoyl)pyridin-2-yl)-3-ethylpiperidine-3-carboxylic acid;
1-(6-(N-(5-chloro-6-(2,6-dimethylphenyl)pyridin-2-yl)sulfamoyl)pyridin-2-yl)-3-ethylpiperidine-3-carboxylic acid;
3-ethyl-1-(6-(N-(6-(o-tolyl)-5-(trifluoromethyl)pyridin-2-yl)sulfamoyl)pyridin-2-yl)piperidine-3-carboxylic acid;
(R)-1-(6-(N-(6-(5-chloro-2-methoxyphenyl)-5-(trifluoromethyl)pyridin-2-yl)sulfamoyl)pyridin-2-yl)-3-methylpiperidine-3-carboxylic acid;
1-(6-(N-(5-chloro-6-(o-tolyl)pyridin-2-yl)sulfamoyl)pyridin-2-yl)-3-propylpiperidine-3-carboxylic acid;
1-(6-(N-(5-chloro-6-(2,6-dimethylphenyl)pyridin-2-yl)sulfamoyl)pyridin-2-yl)-3-propylpiperidine-3-carboxylic acid;
3-propyl-1-(6-(N-(6-(o-tolyl)-5-(trifluoromethyl)pyridin-2-yl)sulfamoyl)pyridin-2-yl)piperidine-3-carboxylic acid;
3-((6-(N-(6-(o-tolyl)-5-(trifluoromethyl)pyridin-2-yl)sulfamoyl)pyridin-2-yl)amino)cyclopentanecarboxylic acid;
3-((6-(N-(6-(o-tolyl)-5-(trifluoromethyl)pyridin-2-yl)sulfamoyl)pyridin-2-yl)amino)cyclohexanecarboxylic acid;
(1,3-cis)-3-((6-(N-(6-(o-tolyl)-5-(trifluoromethyl)pyridin-2-yl)sulfamoyl)pyridin-2-yl)amino)cyclohexanecarboxylic acid;
(1 S,2S,4R)-7-(6-(N-(6-(o-tolyl)-5-(trifluoromethyl)pyridin-2-yl)sulfamoyl)pyridin-2-yl)-7-azabicyclo[2.2.1]heptane-2-carboxylic acid;
(1,3-trans)-3-((6-(N-(6-(o-tolyl)-5-(trifluoromethyl)pyridin-2-yl)sulfamoyl)pyridin-2-yl)amino)cyclohexanecarboxylic acid;
(3R,6S)-6-methyl-1-(6-(N-(6-(o-tolyl)-5-(trifluoromethyl)pyridin-2-yl)sulfamoyl)pyridin-2-yl)piperidine-3-carboxylic acid; and
(R)-1-(6-(N-(6-(2,6-dimethylphenyl)-5-(trifluoromethyl)pyridin-2-yl)sulfamoyl)pyridin-2-yl)-3-methylpiperidine-3-carboxylic acid.

22. A pharmaceutical composition comprising a compound of claim 1, or a pharmaceutically acceptable salt thereof, and a pharmaceutically acceptable carrier or diluent.

23. The pharmaceutical composition of claim 22, further comprising one or more additional pharmaceutical agent(s).

24. The pharmaceutical composition of claim 23, wherein the additional pharmaceutical agent(s) is selected from a mucolytic agent, nebulized hypertonic saline, bronchodilator, an antibiotic, an anti-infective agent, a CFTR modulator, and an anti-inflammatory agent.

25. The pharmaceutical composition of claim 23, wherein the additional pharmaceutical agent is a CFTR modulator.

26. The pharmaceutical composition of claim 23, wherein the additional pharmaceutical agent is a CFTR corrector.

27. The pharmaceutical composition of claim 23, wherein the additional pharmaceutical agent is a CFTR potentiator.

28. The pharmaceutical composition of claim 23, wherein the additional pharmaceutical agent is a CFTR modulator and a CFTR potentiator.

29. A method for ameliorating or alleviating a CFTR mediated disease selected from cystic fibrosis, asthma, COPD, and chronic bronchitis in a subject, comprising administering to the subject a compound of claim 1, or a pharmaceutically acceptable salt thereof.

30. The method of claim 29, wherein the CFTR mediated disease is cystic fibrosis.

31. The method of claim 29, further comprising administering to the subject one or more additional pharmaceutical agent(s) prior to, concurrent with, or subsequent to a compound of claim 1.

32. The method of claim 31, wherein the additional pharmaceutical agent(s) is selected from a mucolytic agent, nebulized hypertonic saline, bronchodilator, an antibiotic, an anti-infective agent, a CFTR modulator, and an anti-inflammatory agent.

33. The method of claim 31, wherein the additional pharmaceutical agent is a CFTR modulator.

34. The method of claim 31, wherein the additional pharmaceutical agent is a CFTR potentiator.

35. The method of claim 31, wherein the additional pharmaceutical agents are a CFTR modulator and a CFTR potentiator.

36. The method of claim 29, wherein the CFTR mediated disease is COPD.

37. A compound which is 6-amino-N-(5-chloro-6-(2,6-dimethylphenyl)pyridin-2-yl)pyridine-2-sulfonamide having the following formula

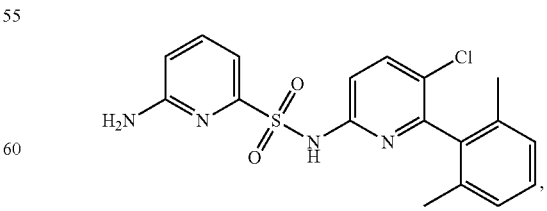

or a pharmaceutically acceptable salt thereof.

38. A compound which is 6-amino-N-(5-chloro-6-(o-tolyl)pyridin-2-yl)pyridine-2-sulfonamide having the following formula

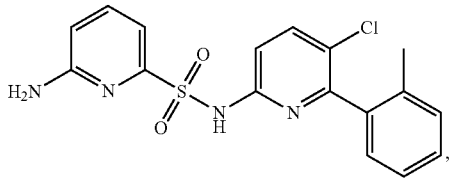 [SMILES: Cc1ccccc1-c1nc(NS(=O)(=O)c2cccc(N)n2)ccc1Cl]

or a pharmaceutically acceptable salt thereof.

39. A compound which is N-(5-chloro-6-(5-fluoro-2-methylphenyl)pyridin-2-yl)-6-(3-hydroxyazetidin-1-yl)pyridine-2-sulfonamide having the following formula

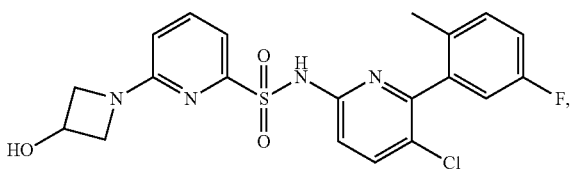 [SMILES: Cc1ccc(F)cc1-c1nc(NS(=O)(=O)c2cccc(N3CC(O)C3)n2)ccc1Cl]

or a pharmaceutically acceptable salt thereof.

40. A compound which is 4-methyl-1-(6-(N-(6-(o-tolyl)-5-(trifluoromethyl)pyridin-2-yl)sulfamoyl)pyridin-2-yl)piperidine-4-carboxylic acid having the following formula

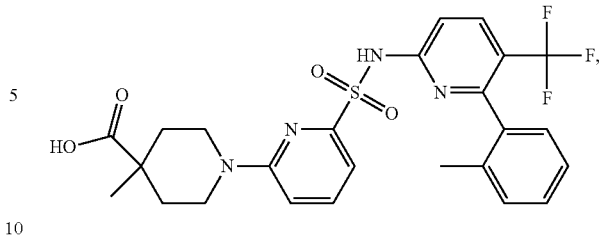

or a pharmaceutically acceptable salt thereof.

41. A compound which is 6-(piperazin-1-yl)-N-(6-(o-tolyl)-5-(trifluoromethyl)pyridin-2-yl)pyridine-2-sulfonamide having the following formula

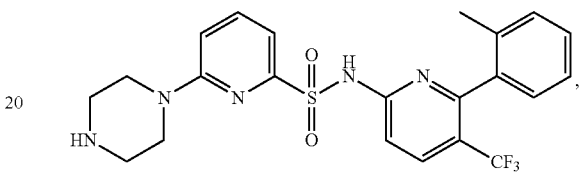

or a pharmaceutically acceptable salt thereof.

42. A method for ameliorating or alleviating a CFTR mediated disease in a subject, wherein the CFTR mediated disease is pancreatitis, comprising administering to the subject a compound of claim 1, or a pharmaceutically acceptable salt thereof.

43. The method of claim 42, wherein the CFTR mediated disease is idiopathic chronic pancreatitis, idiopathic recurrent pancreatitis, idiopathic acute pancreatitis, recurrent pancreatitis, acute pancreatitis, pancreatic insufficiency and idiopathic pancreatitis.

* * * * *